US010851367B2

(12) United States Patent
Liras et al.

(10) Patent No.: US 10,851,367 B2
(45) Date of Patent: *Dec. 1, 2020

(54) TISSUE-SPECIFIC GENOME ENGINEERING USING CRISPR-CAS9

(71) Applicants: Pfizer Inc., New York, NY (US); The Regents of the University of California, Oakland, CA (US)

(72) Inventors: Spiros Liras, Brookline, MA (US); Vincent Mascitti, Groton, CT (US); Benjamin Aaron Thuma, Old Lyme, CT (US); Jennifer A. Doudna, Berkeley, CA (US); Romain Rouet, Berkeley, CA (US)

(73) Assignees: Pfizer Inc., New York, NY (US); The Regents of the University of California, Oakland, CA (US)

( * ) Notice: Subject to any disclaimer, the term of this patent is extended or adjusted under 35 U.S.C. 154(b) by 299 days.

This patent is subject to a terminal disclaimer.

(21) Appl. No.: 15/347,339

(22) Filed: Nov. 9, 2016

(65) Prior Publication Data

US 2017/0137801 A1    May 18, 2017

Related U.S. Application Data

(60) Provisional application No. 62/254,652, filed on Nov. 12, 2015, provisional application No. 62/384,660, filed on Sep. 7, 2016.

(51) Int. Cl.
*C12N 9/22* (2006.01)
*C12N 9/96* (2006.01)
*C12N 15/90* (2006.01)
*A61K 47/54* (2017.01)

(52) U.S. Cl.
CPC .............. *C12N 9/96* (2013.01); *A61K 47/549* (2017.08); *C12N 9/22* (2013.01); *C12N 15/907* (2013.01)

(58) Field of Classification Search
CPC .......... A61K 47/549; C12N 9/22; C12N 9/96; C12N 15/90; C12N 15/907
USPC ........................................................ 514/23
See application file for complete search history.

(56) References Cited

U.S. PATENT DOCUMENTS

| | | |
|---|---|---|
| 2008/0019918 A1 | 1/2008 | Aoki et al. |
| 2014/0068797 A1 | 3/2014 | Doudna et al. |
| 2015/0031134 A1 | 1/2015 | Zhang et al. |
| 2015/0079681 A1 | 3/2015 | Zhang |

FOREIGN PATENT DOCUMENTS

| | | |
|---|---|---|
| WO | WO 2006/028129 A1 | 3/2006 |
| WO | WO 2006/120545 A1 | 11/2006 |
| WO | WO 2014/118272 A1 | 8/2014 |
| WO | WO 2015/089351 A1 | 6/2015 |

OTHER PUBLICATIONS

By Mamidyala et al, J. Am. Chem. Soc., 2012, 134, 1978-1981.*
Peters et al in Modern Methods in Carbohydrate Synthesis, Chapt. 15, p. 356, 1996, Edited by Khan et al, Harwood Academic publishers.*
Amigues et al., "Synthesis of cyclophospho-glucoses and glucitols," *Tetrahedron*, 63:10042-10053 (2007).
Clapp, "1, 2, 4-Oxadiazoles," *Advances in Heterocyclic Chemistry*, 20:65-116 (1976).
Grimmett, "Advances in Imidazole Chemistry," *Advances in Heterocyclic Chemistry*, 27:103-183 (1981).
Hetzheim et al., "Recent Advances in 1, 3, 4-Oxadiazole Chemistry," *Advances in Heterocyclic Chemistry*, 7, 183-224 (1967).
Hong et al., "Analysis and Optimization of Copper-Catalyzed Azide-Alkyne Cycloaddition for Bioconjugation," *Angewandte Chemie International Edition*, 48:9879-9883 (2009).
Jinek et al., "A Programmable Dual-RNA-Guided DNA Endonuclease in Adaptive Bacterial Immunity," *Science*, 337:816-821 (2012).
Kwon et al., "A new polyfluorene containing repeated ethylenoxy units linked to glycerol as side chains: Synthesis and application as an electron injection material in the fabrication of polymer light-emitting diodes," *Synthetic Metals*, 162(23):2163-2170 (2012).
Latorre et al., "Multifunctionalization of magnetic nanoparticles for controlled drug release: a general approach," *European Journal of Medicinal Chemistry*, 82:355-362 (2014).
Makarova et al., "An updated evolutionary classification of CRISPR-Cas systems," *Nature Reviews Microbiology*, 13:722-736 (2015).
Mamidyala, "Glycomimetic Ligands for the Human Asialoglycoprotein, Receptor," *Journal of the American Chemical Society*, 134(4):1978-1981 (2012).
Milletti, "Cell-penetrating peptides: classes, origin, and current landscape," *Drug Discovery Today*, 17: 850-860 (2012).
O'Connell et al., "Programmable RNA recognition and cleavage by CRISPR/Cas9," *Nature*, 516:263-266 (2014).
Omura et al., "Oxidation of alcohols by "activated" dimethyl sulfoxide. A preparative, steric and mechanistic study," *Tetrahedron*, 34:1651-1660 (1978).
Parikh et al., "Sulfur trioxide in the oxidation of alcohols by dimethyl sulfoxide," *Journal of the American Chemical Society*, 89:5505-5507 (1967).
Perez-Ojeda et al., "Controlled Click-Assembly of Well-Defined Hetero-Bifunctional Cubic Silsesquioxanes and Their Application in Targeted Bioimaging," *Chemistry—A European Journal*, 19(21):6630-6640 (2013).
Pinkert et al., "An Albumin Enhancer Locatted 10 KB Upstream Functions along with its Promoter to Direct Efficient, Liver-Specific Expression in Transgenic Mice," *Genes and Development*, 1(3):268-276 (1987).

(Continued)

*Primary Examiner* — Ganapathy Krishnan
(74) *Attorney, Agent, or Firm* — Arnold & Porter Kaye Scholer LLP

(57) ABSTRACT

The present application provides compounds, compositions, uses thereof for the treatment of diseases, conditions and/or disorders, and uses thereof as asialoglycoprotein receptor (ASGPR) targeting agents.

20 Claims, 19 Drawing Sheets

Specification includes a Sequence Listing.

(56) References Cited

OTHER PUBLICATIONS

Piron et al., "Synthesis of Podands with Cyanurate or Isocyanurate Cores and Terminal Triple Bonds," *Synthesis*, 10:1639-1644 (2010).
Potts, "The Chemistry of 1,2,4-Triazoles," *Chemical Reviews*, 61:87-127 (1961).
Prusty et al., "A Fluorogenic Reaction Based on Heavy-Atom Removal for Ultrasensitive DNA Detection," *Journal of the American Chemical Society*, 132(35):12197-12199 (2010).
Sander et al., "CRISPR-Cas systems for editing, regulating and targeting genomes," *Nature Biotechnology*, 32(4):347-355 (2014).
Sandstrom, "Recent Advances in the Chemistry of 1,3,4-Thiadiazoles," *Advances in Heterocyclic Chemistry*, 9:165-209 (1968).
Schaffer, "Branched-chain Higher Sugars. III. A 4-C-(Hydroxymethyl)-pentose," *Journal of the American Chemical Society*, 81:5452-5454 (1959).
Tranoy-Opalinski et al., "Design of Self-Immolative Linkers for Tumour-Activated Prodrug Therapy," *Anti-Cancer Agents in Medicinal Chemistry*, 8:618-637 (2008).
Turchi et al., "Chemistry of oxazoles," *Chemical Reviews*, 75:389-437 (1975).
Wittenberger, "Recent Developments in Tetrazole Chemistry. A Review," *Organic Preparations and Procedures International*, 26:499-531 (1994).
Al-lazikani et al., "Standard conformations for the canonical structures of immunoglobulins," *J. Molec. Biol.*, 273:927-948 (1997).
Briner et al., "Guide RNA functional modules direct Cas9 activity and orthogonality," *Molecular Cell*, 56(2):333-339 (2014).
Fu et al., "Improving CRISPR-Cas nuclease specificity using truncated guide RNAs," *Nature Biotechnology*, 32(3):279-284 (2014).
Hale et al., "Target RNA capture and cleavage by the Cmr type III-B CRISPR-Cas effector complex," *Genes & Development*, 28:2432-2443 (2014).
International Search Report dated Apr. 10, 2017, in International Patent Application No. PCT/US2016/061109.
Mali et al., "Cas9 as a versatile tool for engineering biology," Nature Methods, 10(10):957-963 (2013).
Martin et al., "Peptide-guided gene delivery," *The AAPS Journal*, 9(1):E18-E29 (2007).
Ozanne et al., "A Stabilized Formulation of IBX (SIBX) for Safe Oxidation Reactions Including a New Oxidative Demethylation of Phenolic Methyl Aryl Ethers," *Organic Letters*, 5(16):2903-2906 (2003).
Prakash et al., "Targeted delivery of antisense oligonucleotides to hepatocytes using triantennary N-acetyl galactosamine improves potency 10-fold in mice," *Nucleic Acids Res.*, 42:8796-8807 (2014).
Rittner et al., "New Basic Membrane-Destabilizing Peptides for Plasmid-Based Gene Delivery in Vitro and in Vivo," *Molecular Therapy*, 5(2):104-114 (2002).
Shaner et al., "A guide to choosing fluorescent proteins," *Nat. Methods* 2:905-909 (2005).

* cited by examiner (A)

*S. pyogenes* Cas9 (wild type) (amino acid sequence) (SEQ ID NO:848):

MDKKYSIGLDIGTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDKKHERHPIFGNIV
DEVAYHEKYPTIYHLRKKLVDSTDKADLRLIYLALAHMIKFRGHXLIEGDLNPDNSDVDKL
FIQLVQTYNQLFEENPINASGVDAKAILSARLSKSRRLENLIAQLPGEKKNGLFGNLIALSLG
LTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQ
EEFYKFIKPILEKMDGTEELLVKLNREDLLRKQRTFDNGSIPHQIHLGELHAILRRQEDFYPF
LKDNREKIEKILTFRIPYYVGPLARGNSRFAWMTRKSEETITPWNFEEVVDKGASAQSFIER
MTNFDKNLPNEKVLPKHSLLYEYFTVYNELTKVKYVTEGMRKPAFLSGEQKKAIVDLLFK
TNRKVTVKQLKEDYFKKIECFDSVEISGVEDRFNASLGTYHDLLKIIKDKDFLDNEENEDILE
DIVLTLTLFEDREMIEERLKTYAHLFDDKVMKQLKRRRYTGWGRLSRKLINGIRDKQSGKT
ILDFLKSDGFANRNFMQLIHDDSLTFKEDIQKAQVSGQGDSLHEHIANLAGSPAIKKGILQT
VKVVDELVKVMGRHKPENIVIEMARENQTTQKGQKNSRERMKRIEEGIKELGSQILKEHPV
ENTQLQNEKLYLYYLQNGRDMYVDQELDINRLSDYDVDHIVPQSFLKDDSIDNKVLTRSD
KNRGKSDNVPSEEVVKKMKNYWRQLLNAKLITQRKFDNLTKAERGGLSELDKAGFIKRQL
VETRQITKHVAQILDSRMNTKYDENDKLIREVKVITLKSKLVSDFRKDFQFYKVREINNYH
HAHDAYLNAVVGTALIKKYPKLESEFVYGDYKVYDVRKMIAKSEQEIGKATAKYFFYSNI
MNFFKTEITLANGEIRKRPLIETNGETGEIVWDKGRDFATVRKVLSMPQVNIVKKTEVQTG
GFSKESILPKRNSDKLIARKKDWDPKKYGGFDSPTVAYSVLVVAKVEKGKSKKLKSVKELL
GITIMERSSFEKNPIDFLEAKGYKEVKKDLIIKLPKYSLFELENGRKRMLASAGELQKGNELA
LPSKYVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLIHQSI
TGLYETRIDLSQLGGD

*S. pyogenes* Cas9 3NLS mCherry (amino acid sequence) (SEQ ID NO:1024):

MDKKYSIGLDIGTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDKKHERHPIFGNIV
DEVAYHEKYPTIYHLRKKLVDSTDKADLRLIYLALAHMIKFRGHXLIEGDLNPDNSDVDKL
FIQLVQTYNQLFEENPINASGVDAKAILSARLSKSRRLENLIAQLPGEKKNGLFGNLIALSLG
LTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQ
EEFYKFIKPILEKMDGTEELLVKLNREDLLRKQRTFDNGSIPHQIHLGELHAILRRQEDFYPF
LKDNREKIEKILTFRIPYYVGPLARGNSRFAWMTRKSEETITPWNFEEVVDKGASAQSFIER
MTNFDKNLPNEKVLPKHSLLYEYFTVYNELTKVKYVTEGMRKPAFLSGEQKKAIVDLLFK
TNRKVTVKQLKEDYFKKIECFDSVEISGVEDRFNASLGTYHDLLKIIKDKDFLDNEENEDILE
DIVLTLTLFEDREMIEERLKTYAHLFDDKVMKQLKRRRYTGWGRLSRKLINGIRDKQSGKT
ILDFLKSDGFANRNFMQLIHDDSLTFKEDIQKAQVSGQGDSLHEHIANLAGSPAIKKGILQT
VKVVDELVKVMGRHKPENIVIEMARENQTTQKGQKNSRERMKRIEEGIKELGSQILKEHPV
ENTQLQNEKLYLYYLQNGRDMYVDQELDINRLSDYDVDHIVPQSFLKDDSIDNKVLTRSD
KNRGKSDNVPSEEVVKKMKNYWRQLLNAKLITQRKFDNLTKAERGGLSELDKAGFIKRQL
VETRQITKHVAQILDSRMNTKYDENDKLIREVKVITLKSKLVSDFRKDFQFYKVREINNYH
HAHDAYLNAVVGTALIKKYPKLESEFVYGDYKVYDVRKMIAKSEQEIGKATAKYFFYSNI
MNFFKTEITLANGEIRKRPLIETNGETGEIVWDKGRDFATVRKVLSMPQVNIVKKTEVQTG
GFSKESILPKRNSDKLIARKKDWDPKKYGGFDSPTVAYSVLVVAKVEKGKSKKLKSVKELL

FIG. 6 (continued)

GITIMERSSFEKNPIDFLEAKGYKEVKKDLIIKLPKYSLFELENGRKRMLASAGELQKGNELA
LPSKYVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLIHQSI
TGLYETRIDLSQLGGDAYPYDVPDYASLGSGSPKKKRKVEDPKKKRKVDGIGSGSNGSSGS
VSKGEEDNMAIIKEFMRFKVHMEGSVNGHEFEIEGEGEGRPYEGTQTAKLKVTKGGPLPFA
WDILSPQFMYGSKAYVKHPADIPDYLKLSFPEGFKWERVMNFEDGGVVTVTQDSSLQDGE
FIYKVKLRGTNFPSDGPVMQKKTMGWEASSERMYPEDGALKGEIKQRLKLKDGGHYDAE
VKTTYKAKKPVQLPGAYNVNIKLDITSHNEDYTIVEQYERAEGRHSTGGMDELYKGSPKK
KRKVE

*S. pyogenes* Cas9 - mutation M1C (amino acid sequence) (SEQ ID NO:849):

CDKKYSIGLDIGTNSVGWAVITDEYKVPSKKFKVLGNTDRHSIKKNLIGALLFDSGETAEAT
RLKRTARRRYTRRKNRICYLQEIFSNEMAKVDDSFFHRLEESFLVEEDKKHERHPIFGNIVD
EVAYHEKYPTIYHLRKKLVDSTDKADLRLIYLALAHMIKFRGHFLIEGDLNPDNSDVDKLFI
QLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNT
EITKAPLSASMIKRYDEHHQDLTLLKALVRQQLPEKYKEIFFDQSKNGYAGYIDGGASQEEF
YKFIKPILEKMDGTEELLVKLNREDLLRKQRTFDNGSIPHQIHLGELHAILRRQEDFYPFLKD
NREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRK
VTVKQLKEDYFKKIECFDSVEISGVEDRFNASLGTYHDLLKIIKDKDFLDNEENEDILEDIVL
TLTLFEDREMIEEERLKTYAHLFDDKVMKQLKRRRYTGWGRLSRKLINGIRDKQSGKTILDF
LKSDGFANRNFMQLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQILKEHPVENTQ
LQNEKLYLYYLQNGRDMYVDQELDINRLSDYDVDHIVPQSFLKDDSIDNKVLTRSDKNRG
KSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAHD
AYLNAVVGTALIKKYPKLESEFVYGDYKVYDVRKMIAKSEQEIGKATAKYFFYSNIMNFFK
TEITLANGEIRKRPLIETNGETGEIVWDKGRDFATVRKVLSMPQVNIVKKTEVQTGGFSKESI
LPKRNSDKLIARKKDWDPKKYGGFDSPTVAYSVLVVAKVEKGKSKKLKSVKELLGITIME
RSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAY
NKHRDKPIREQAENIIHLFTLTNLGAPAAFKYFDTTIDRKRYTSTKEVLDATLIHQSITGLYE
TRIDLSQLGGD

*S. pyogenes* Cas9 - mutation C80S (amino acid sequence) (SEQ ID NO:1025):

MDKKYSIGLDIGTNSVGWAVITDEYKVPSKKFKVLGNTDRHSIKKNLIGALLFDSGETAEA
TRLKRTARRRYTRRKNRISYLQEIFSNEMAKVDDSFFHRLEESFLVEEDKKHERHPIFGNIVD
EVAYHEKYPTIYHLRKKLVDSTDKADLRLIYLALAHMIKFRGHFLIEGDLNPDNSDVDKLFI
QLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNT
EITKAPLSASMIKRYDEHHQDLTLLKALVRQQLPEKYKEIFFDQSKNGYAGYIDGGASQEEF
YKFIKPILEKMDGTEELLVKLNREDLLRKQRTFDNGSIPHQIHLGELHAILRRQEDFYPFLKD
NREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRK
VTVKQLKEDYFKKIECFDSVEISGVEDRFNASLGTYHDLLKIIKDKDFLDNEENEDILEDIVL
TLTLFEDREMIEEERLKTYAHLFDDKVMKQLKRRRYTGWGRLSRKLINGIRDKQSGKTILDF

FIG. 6 (continued)

LKSDGFANRNFMQLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQILKEHPVENTQ
LQNEKLYLYYLQNGRDMYVDQELDINRLSDYDVDHIVPQSFLKDDSIDNKVLTRSDKNRG
KSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAHD
AYLNAVVGTALIKKYPKLESEFVYGDYKVYDVRKMIAKSEQEIGKATAKYFFYSNIMNFFK
TEITLANGEIRKRPLIETNGETGEIVWDKGRDFATVRKVLSMPQVNIVKKTEVQTGGFSKESI
LPKRNSDKLIARKKDWDPKKYGGFDSPTVAYSVLVVAKVEKGKSKKLKSVKELLGITIME
RSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAY
NKHRDKPIREQAENIIHLFTLTNLGAPAAFKYFDTTIDRKRYTSTKEVLDATLIHQSITGLYE
TRIDLSQLGGD

*S. pyogenes* Cas9 - mutation C80S 3NLS mCherry (amino acid sequence) (SEQ ID NO:1026):

MDKKYSIGLDIGTNSVGWAVITDEYKVPSKKFKVLGNTDRHSIKKNLIGALLFDSGETAEA
TRLKRTARRRYTRRKNRISYLQEIFSNEMAKVDDSFFHRLEESFLVEEDKKHERHPIFGNIVD
EVAYHEKYPTIYHLRKKLVDSTDKADLRLIYLALAHMIKFRGHFLIEGDLNPDNSDVDKLFI
QLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNT
EITKAPLSASMIKRYDEHHQDLTLLKALVRQQLPEKYKEIFFDQSKNGYAGYIDGGASQEEF
YKFIKPILEKMDGTEELLVKLNREDLLRKQRTFDNGSIPHQIHLGELHAILRRQEDFYPFLKD
NREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRK
VTVKQLKEDYFKKIECFDSVEISGVEDRFNASLGTYHDLLKIIKDKDFLDNEENEDILEDIVL
TLTLFEDREMIEERLKTYAHLFDDKVMKQLKRRRYTGWGRLSRKLINGIRDKQSGKTILDF
LKSDGFANRNFMQLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQILKEHPVENTQ
LQNEKLYLYYLQNGRDMYVDQELDINRLSDYDVDHIVPQSFLKDDSIDNKVLTRSDKNRG
KSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAHD
AYLNAVVGTALIKKYPKLESEFVYGDYKVYDVRKMIAKSEQEIGKATAKYFFYSNIMNFFK
TEITLANGEIRKRPLIETNGETGEIVWDKGRDFATVRKVLSMPQVNIVKKTEVQTGGFSKESI
LPKRNSDKLIARKKDWDPKKYGGFDSPTVAYSVLVVAKVEKGKSKKLKSVKELLGITIME
RSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAY
NKHRDKPIREQAENIIHLFTLTNLGAPAAFKYFDTTIDRKRYTSTKEVLDATLIHQSITGLYE
TRIDLSQLGGDAYPYDVPDYASLGSGSPKKKRKVEDPKKKRKVDGIGSGSNGSSGSVSKGE
EDNMAIIKEFMRFKVHMEGSVNGHEFEIEGEGEGRPYEGTQTAKLKVTKGGPLPFAWDILS
PQFMYGSKAYVKHPADIPDYLKLSFPEGFKWERVMNFEDGGVVTVTQDSSLQDGEFIYKV
KLRGTNFPSDGPVMQKKTMGWEASSERMYPEDGALKGEIKQRLKLKDGGHYDAEVKTTY
KAKKPVQLPGAYNVNIKLDITSHNEDYTIVEQYERAEGRHSTGGMDELYKGSPKKKRKVE

*S. pyogenes* Cas9 - mutation M1C & C80S (amino acid sequence) (SEQ ID NO:850):

CDKKYSIGLDIGTNSVGWAVITDEYKVPSKKFKVLGNTDRHSIKKNLIGALLFDSGETAEAT
RLKRTARRRYTRRKNRISYLQEIFSNEMAKVDDSFFHRLEESFLVEEDKKHERHPIFGNIVDE
VAYHEKYPTIYHLRKKLVDSTDKADLRLIYLALAHMIKFRGHFLIEGDLNPDNSDVDKLFIQ
LVQTYNQLFEENPINASGVDAKAILSARLSKSRRLENLIAQLPGEKKNGLFGNLIALSLGLTP

FIG. 6 (continued)

NFKSNFDLAEDAKLQLSKDTYDDDLDNLLAQIGDQYADLFLAAKNLSDAILLSDILRVNTEI
TKAPLSASMIKRYDEHHQDLTLLKALVRQQLPEKYKEIFFDQSKNGYAGYIDGGASQEEFY
KFIKPILEKMDGTEELLVKLNREDLLRKQRTFDNGSIPHQIHLGELHAILRRQEDFYPFLKDN
REKIEKILTFRIPYYVGPLARGNSRFAWMTRKSEETITPWNFEEVVDKGASAQSFIERMTNF
DKNLPNEKVLPKHSLLYEYFTVYNELTKVKYVTEGMRKPAFLSGEQKKAIVDLLFKTNRK
VTVKQLKEDYFKKIECFDSVEISGVEDRFNASLGTYHDLLKIIKDKDFLDNEENEDILEDIVL
TLTLFEDREMIEERLKTYAHLFDDKVMKQLKRRRYTGWGRLSRKLINGIRDKQSGKTILDF
LKSDGFANRNFMQLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQILKEHPVENTQ
LQNEKLYLYYLQNGRDMYVDQELDINRLSDYDVDHIVPQSFLKDDSIDNKVLTRSDKNRG
KSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAHD
AYLNAVVGTALIKKYPKLESEFVYGDYKVYDVRKMIAKSEQEIGKATAKYFFYSNIMNFFK
TEITLANGEIRKRPLIETNGETGEIVWDKGRDFATVRKVLSMPQVNIVKKTEVQTGGFSKESI
LPKRNSDKLIARKKDWDPKKYGGFDSPTVAYSVLVVAKVEKGKSKKLKSVKELLGITIME
RSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAY
NKHRDKPIREQAENIIHLFTLTNLGAPAAFKYFDTTIDRKRYTSTKEVLDATLIHQSITGLYE
TRIDLSQLGGD

*S. pyogenes* Cas9 - mutation M1C & C80S 2NLS (amino acid sequence) (SEQ ID NO:1013):

CDKKYSIGLDIGTNSVGWAVITDEYKVPSKKFKVLGNTDRHSIKKNLIGALLFDSGETAEAT
RLKRTARRRYTRRKNRISYLQEIFSNEMAKVDDSFFHRLEESFLVEEDKKHERHPIFGNIVDE
VAYHEKYPTIYHLRKKLVDSTDKADLRLIYLALAHMIKFRGHFLIEGDLNPDNSDVDKLFIQ
LVQTYNQLFEENPINASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAILLSDILRVNTEI
TKAPLSASMIKRYDEHHQDLTLLKALVRQQLPEKYKEIFFDQSKNGYAGYIDGGASQEEFY
KFIKPILEKMDGTEELLVKLNREDLLRKQRTFDNGSIPHQIHLGELHAILRRQEDFYPFLKDN
REKIEKILTFRIPYYVGPLARGNSRFAWMTRKSEETITPWNFEEVVDKGASAQSFIERMTNF
DKNLPNEKVLPKHSLLYEYFTVYNELTKVKYVTEGMRKPAFLSGEQKKAIVDLLFKTNRK
VTVKQLKEDYFKKIECFDSVEISGVEDRFNASLGTYHDLLKIIKDKDFLDNEENEDILEDIVL
TLTLFEDREMIEERLKTYAHLFDDKVMKQLKRRRYTGWGRLSRKLINGIRDKQSGKTILDF
LKSDGFANRNFMQLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQILKEHPVENTQ
LQNEKLYLYYLQNGRDMYVDQELDINRLSDYDVDHIVPQSFLKDDSIDNKVLTRSDKNRG
KSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAHD
AYLNAVVGTALIKKYPKLESEFVYGDYKVYDVRKMIAKSEQEIGKATAKYFFYSNIMNFFK
TEITLANGEIRKRPLIETNGETGEIVWDKGRDFATVRKVLSMPQVNIVKKTEVQTGGFSKESI
LPKRNSDKLIARKKDWDPKKYGGFDSPTVAYSVLVVAKVEKGKSKKLKSVKELLGITIME
RSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAY
NKHRDKPIREQAENIIHLFTLTNLGAPAAFKYFDTTIDRKRYTSTKEVLDATLIHQSITGLYE
TRIDLSQLGGDAYPYDVPDYASLGSGSPKKKRKVEDPKKKRKVD

*S. pyogenes* Cas9 - mutation M1C & C80S 2NLS (nucleotide sequence) (SEQ ID NO:1014):
TGCGACAAGAAGTACAGCATCGGCCTGGACATCGGCACCAACTCTGTGGGCTGGGCCG
TGATCACCGACGAGTACAAGGTGCCCAGCAAGAAATTCAAGGTGCTGGGCAACACCGA

FIG. 6 (continued)

CCGGCACAGCATCAAGAAGAACCTGATCGGCGCCCTGCTGTTCGACAGCGGAGAAACA
GCCGAGGCCACCCGGCTGAAGAGAACCGCCAGAAGAAGATACACCAGACGGAAGAAC
CGGATCAGCTATCTGCAAGAGATCTTCAGCAACGAGATGGCCAAGGTGGACGACAGCT
TCTTCCACAGACTGGAAGAGTCCTTCCTGGTGGAAGAGGATAAGAAGCACGAGCGGCA
CCCCATCTTCGGCAACATCGTGGACGAGGTGGCCTACCACGAGAAGTACCCCACCATCT
ACCACCTGAGAAAGAAACTGGTGGACAGCACCGACAAGGCCGACCTGCGGCTGATCTA
TCTGGCCCTGGCCCACATGATCAAGTTCCGGGGCCACTTCCTGATCGAGGGCGACCTGA
ACCCCGACAACAGCGACGTGGACAAGCTGTTCATCCAGCTGGTGCAGACCTACAACCA
GCTGTTCGAGGAAAACCCCATCAACGCCAGCGGCGTGGACGCCAAGGCCATCCTGTCT
GCCAGACTGAGCAAGAGCAGACGGCTGGAAAATCTGATCGCCCAGCTGCCCGGCGAGA
AGAAGAATGGCCTGTTCGGCAACCTGATTGCCCTGAGCCTGGGCCTGACCCCCAACTTC
AAGAGCAACTTCGACCTGGCCGAGGATGCCAAACTGCAGCTGAGCAAGGACACCTACG
ACGACGACCTGGACAACCTGCTGGCCCAGATCGGCGACCAGTACGCCGACCTGTTTCTG
GCCGCCAAGAACCTGTCCGACGCCATCCTGCTGAGCGACATCCTGAGAGTGAACACCG
AGATCACCAAGGCCCCCCTGAGCGCCTCTATGATCAAGAGATACGACGAGCACCACCA
GGACCTGACCCTGCTGAAAGCTCTCGTGCGGCAGCAGCTGCCTGAAGTACAAAGAG
ATTTTCTTCGACCAGAGCAAGAACGGCTACGCCGGCTACATCGATGGCGGAGCCAGCC
AGGAAGAGTTCTACAAGTTCATCAAGCCCATCCTGGAAAAGATGGACGGCACCGAGGA
ACTGCTCGTGAAGCTGAACAGAGAGGACCTGCTGCGGAAGCAGCGGACCTTCGACAAC
GGCAGCATCCCCCACCAGATCCACCTGGGAGAGCTGCACGCCATTCTGCGGCGGCAGG
AAGATTTTTACCCATTCCTGAAGGACAACCGGGAAAAGATCGAGAAGATCCTGACCTT
CCGCATCCCCTACTACGTGGGCCCTCTGGCCAGGGGAAACAGCAGATTCGCCTGGATG
ACCAGAAAGAGCGAGGAAACCATCACCCCCTGGAACTTCGAGGAAGTGGTGGACAAG
GGCGCCAGCGCCCAGAGCTTCATCGAGCGGATGACCAACTTCGATAAGAACCTGCCCA
ACGAGAAGGTGCTGCCCAAGCACAGCCTGCTGTACGAGTACTTCACCGTGTACAACGA
GCTGACCAAAGTGAAATACGTGACCGAGGGAATGAGAAAGCCCGCCTTCCTGAGCGGC
GAGCAGAAAAAGCCATCGTGGACCTGCTGTTCAAGACCAACCGGAAAGTGACCGTGA
AGCAGCTGAAAGAGGACTACTTCAAGAAAATCGAGTGCTTCGACTCCGTGGAAATCTC
CGGCGTGGAAGATCGGTTCAACGCCTCCCTGGGCACATACCACGATCTGCTGAAAATTA
TCAAGGACAAGGACTTCCTGGACAATGAGGAAAACGAGGACATTCTGGAAGATATCGT
GCTGACCCTGACACTGTTTGAGGACAGAGAGATGATCGAGGAACGGCTGAAAACCTAT
GCCCACCTGTTCGACGACAAAGTGATGAAGCAGCTGAAGCGGCGGAGATACACCGGCT
GGGGCAGGCTGAGCCGGAAGCTGATCAACGGCATCCGGGACAAGCAGTCCGGCAAGA
CAATCCTGGATTTCCTGAAGTCCGACGGCTTCGCCAACAGAAACTTCATGCAGCTGATC
CACGACGACAGCCTGACCTTTAAAGAGGACATCCAGAAAGCCCAGGTGTCCGGCCAGG
GCGATAGCCTGCACGAGCACATTGCCAATCTGGCCGGCAGCCCCGCCATTAAGAAGGG
CATCCTGCAGACAGTGAAGGTGGTGGACGAGCTCGTGAAAGTGATGGGCCGGCACAAG
CCCGAGAACATCGTGATCGAAATGGCCAGAGAGAACCAGACCACCCAGAAGGGACAG
AAGAACAGCCGCGAGAGAATGAAGCGGATCGAAGAGGGCATCAAAGAGCTGGGCAGC
CAGATCCTGAAAGAACACCCCGTGGAAAACACCCAGCTGCAGAACGAGAAGCTGTACC
TGTACTACCTGCAGAATGGGCGGGATATGTACGTGGACCAGGAACTGGACATCAACCG
GCTGTCCGACTACGATGTGGACCATATCGTGCCTCAGAGCTTTCTGAAGGACGACTCCA
TCGATAACAAAGTGCTGACTCGGAGCGACAAGAACCGGGGCAAGAGCGACAACGTGC
CCTCCGAAGAGGTCGTGAAGAAGATGAAGAACTACTGGCGCCAGCTGCTGAATGCCAA
GCTGATTACCCAGAGGAAGTTCGACAATCTGACCAAGGCCGAGAGAGGCGGCCTGAGC
GAACTGGATAAGGCCGGCTTCATCAAGAGACAGCTGGTGGAAACCCGGCAGATCACAA
AGCACGTGGCACAGATCCTGGACTCCCGGATGAACACTAAGTACGACGAGAACGACAA
ACTGATCCGGGAAGTGAAAGTGATCACCCTGAAGTCCAAGCTGGTGTCCGATTTCCGG
AAGGATTTCCAGTTTTACAAAGTGCGCGAGATCAACAACTACCACCACGCCCACGACG

FIG. 6 (continued)

CCTACCTGAACGCCGTCGTGGGAACCGCCCTGATCAAAAAGTACCCTAAGCTGGAAAG
CGAGTTCGTGTACGGCGACTACAAGGTGTACGACGTGCGGAAGATGATCGCCAAGAGC
GAGCAGGAAATCGGCAAGGCTACCGCCAAGTACTTCTTCTACAGCAACATCATGAACT
TTTTCAAGACCGAGATTACCCTGGCCAACGGCGAGATCCGGAAGCGGCCTCTGATCGA
GACAAACGGCGAAACAGGCGAGATCGTGTGGGATAAGGGCCGGGACTTTGCCACCGTG
CGGAAAGTGCTGTCTATGCCCCAAGTGAATATCGTGAAAAAGACCGAGGTGCAGACAG
GCGGCTTCAGCAAAGAGTCTATCCTGCCCAAGAGGAACAGCGACAAGCTGATCGCCAG
AAAGAAGGACTGGGACCCTAAGAAGTACGGCGGCTTCGACAGCCCCACCGTGGCCTAT
TCTGTGCTGGTGGTGGCCAAAGTGGAAAAGGGCAAGTCCAAGAAACTGAAGAGTGTGA
AGAGCTGCTGGGGATCACCATCATGGAAAGAAGCAGCTTCGAGAAGAATCCCATCGA
CTTTCTGGAAGCCAAGGGCTACAAAGAAGTGAAAAAGGACCTGATCATCAAGCTGCCT
AAGTACTCCTGTTCGAGCTGGAAAACGGCCGGAAGAGAATGCTGGCCTCTGCCGGCG
AACTGCAGAAGGGAAACGAACTGGCCCTGCCCTCCAAATATGTGAACTTCCTGTACCTG
GCCAGCCACTATGAGAAGCTGAAGGGCTCCCCGAGGATAATGAGCAGAAACAGCTGT
TTGTGGAACAGCACAAACACTACCTGGACGAGATCATCGAGCAGATCAGCGAGTTCTC
CAAGAGAGTGATCCTGGCCGACGCTAATCTGGACAAGGTGCTGAGCGCCTACAACAAG
CACAGAGACAAGCCTATCAGAGAGCAGGCCGAGAATATCATCCACCTGTTTACCCTGA
CCAATCTGGGAGCCCCTGCCGCCTTCAAGTACTTTGACACCACCATCGACCGGAAGAGG
TACACCAGCACCAAAGAGGTGCTGGACGCCACCCTGATCCACCAGAGCATCACCGGCC
TGTACGAGACACGGATCGACCTGTCTCAGCTGGGAGGCGACGCCTATCCCTATGACGTG
CCCGATTATGCCAGCCTGGGCAGCGGCTCCCCCAAGAAAAAACGCAAGGTGGAAGATC
CTAAGAAAAAGCGGAAAGTGGAC

*S. pyogenes* Cas9 - mutation M1C & C80S 3NLS and mCherry (amino acid sequence) (SEQ ID NO:1015):

CDKKYSIGLDIGTNSVGWAVITDEYKVPSKKFKVLGNTDRHSIKKNLIGALLFDSGETAEAT
RLKRTARRRYTRRKNRISYLQEIFSNEMAKVDDSFFHRLEESFLVEEDKKHERHPIFGNIVDE
VAYHEKYPTIYHLRKKLVDSTDKADLRLIYLALAHMIKFRGHFLIEGDLNPDNSDVDKLFIQ
LVQTYNQLFEENPINASGVDAKAILSARLSKSRRLENLIAQLPGEKKNGLFGNLIALSLGLTP
NFKSNFDLAEDAKLQLSKDTYDDDLDNLLAQIGDQYADLFLAAKNLSDAILLSDILRVNTEI
TKAPLSASMIKRYDEHHQDLTLLKALVRQQLPEKYKEIFFDQSKNGYAGYIDGGASQEEFY
KFIKPILEKMDGTEELLVKLNREDLLRKQRTFDNGSIPHQIHLGELHAILRRQEDFYPFLKDN
REKIEKILTFRIPYYVGPLARGNSRFAWMTRKSEETITPWNFEEVVDKGASAQSFIERMTNF
DKNLPNEKVLPKHSLLYEYFTVYNELTKVKYVTEGMRKPAFLSGEQKKAIVDLLFKTNRK
VTVKQLKEDYFKKIECFDSVEISGVEDRFNASLGTYHDLLKIIKDKDFLDNEENEDILEDIVL
TLTLFEDREMIEERLKTYAHLFDDKVMKQLKRRRYTGWGRLSRKLINGIRDKQSGKTILDF
LKSDGFANRNFMQLIHDDSLTFKEDIQKAQVSGQGDSLHEHIANLAGSPAIKKGILQTVKVV
DELVKVMGRHKPENIVIEMARENQTTQKGQKNSRERMKRIEEGIKELGSQILKEHPVENTQ
LQNEKLYLYYLQNGRDMYVDQELDINRLSDYDVDHIVPQSFLKDDSIDNKVLTRSDKNRG
KSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAHD
AYLNAVVGTALIKKYPKLESEFVYGDYKVYDVRKMIAKSEQEIGKATAKYFFYSNIMNFFK
TEITLANGEIRKRPLIETNGETGEIVWDKGRDFATVRKVLSMPQVNIVKKTEVQTGGFSKESI
LPKRNSDKLIARKKDWDPKKYGGFDSPTVAYSVLVVAKVEKGKSKKLKSVKELLGITIME
RSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAY
NKHRDKPIREQAENIIHLFTLTNLGAPAAFKYFDTTIDRKRYTSTKEVLDATLIHQSITGLYE
TRIDLSQLGGDAYPYDVPDYASLGSGSPKKKRKVEDPKKKRKVDGIGSGSNGSSSGSVSKGE

FIG. 6 (continued)

EDNMAIIKEFMRFKVHMEGSVNGHEFEIEGEGEGRPYEGTQTAKLKVTKGGPLPFAWDILS
PQFMYGSKAYVKHPADIPDYLKLSFPEGFKWERVMNFEDGGVVTVTQDSSLQDGEFIYKV
KLRGTNFPSDGPVMQKKTMGWEASSERMYPEDGALKGEIKQRLKLKDGGHYDAEVKTTY
KAKKPVQLPGAYNVNIKLDITSHNEDYTIVEQYERAEGRHSTGGMDELYKGSPKKKRKVE

*S. pyogenes* Cas9 - mutation M1C & C80S 3NLS mCherry (nucleotide sequence) (SEQ ID NO:1016):

TGCGACAAGAAGTACAGCATCGGCCTGGACATCGGCACCAACTCTGTGGGCTGGGCCG
TGATCACCGACGAGTACAAGGTGCCCAGCAAGAAATTCAAGGTGCTGGGCAACACCGA
CCGGCACAGCATCAAGAAGAACCTGATCGGCGCCCTGCTGTTCGACAGCGGAGAAACA
GCCGAGGCCACCCGGCTGAAGAGAACCGCCAGAAGAAGATACACCAGACGGAAGAAC
CGGATCAGCTATCTGCAAGAGATCTTCAGCAACGAGATGGCCAAGGTGGACGACAGCT
TCTTCCACAGACTGGAAGAGTCCTTCCTGGTGGAAGAGGATAAGAAGCACGAGCGGCA
CCCCATCTTCGGCAACATCGTGGACGAGGTGGCCTACCACGAGAAGTACCCCACCATCT
ACCACCTGAGAAAGAAACTGGTGGACAGCACCGACAAGGCCGACCTGCGGCTGATCTA
TCTGGCCCTGGCCCACATGATCAAGTTCCGGGGCCACTTCCTGATCGAGGGCGACCTGA
ACCCCGACAACAGCGACGTGGACAAGCTGTTCATCCAGCTGGTGCAGACCTACAACCA
GCTGTTCGAGGAAAACCCCATCAACGCCAGCGGCGTGGACGCCAAGGCCATCCTGTCT
GCCAGACTGAGCAAGAGCAGACGGCTGGAAAATCTGATCGCCCAGCTGCCCGGCGAGA
AGAAGAATGGCCTGTTCGGCAACCTGATTGCCCTGAGCCTGGGCCTGACCCCCAACTTC
AAGAGCAACTTCGACCTGGCCGAGGATGCCAAACTGCAGCTGAGCAAGGACACCTACG
ACGACGACCTGGACAACCTGCTGGCCCAGATCGGCGACCAGTACGCCGACCTGTTTCTG
GCCGCCAAGAACCTGTCCGACGCCATCCTGCTGAGCGACATCCTGAGAGTGAACACCG
AGATCACCAAGGCCCCCCTGAGCGCCTCTATGATCAAGAGATACGACGAGCACCACCA
GGACCTGACCCTGCTGAAAGCTCTCGTGCGGCAGCAGCTGCCTGAGAAGTACAAAGAG
ATTTTCTTCGACCAGAGCAAGAACGGCTACGCCGGCTACATCGATGGCGGAGCCAGCC
AGGAAGAGTTCTACAAGTTCATCAAGCCCATCCTGGAAAAGATGGACGGCACCGAGGA
ACTGCTCGTGAAGCTGAACAGAGAGGACCTGCTGCGGAAGCAGCGGACCTTCGACAAC
GGCAGCATCCCCCACCAGATCCACCTGGGAGAGCTGCACGCCATTCTGCGGCGGCAGG
AAGATTTTTACCCATTCCTGAAGGACAACCGGGAAAAGATCGAGAAGATCCTGACCTT
CCGCATCCCCTACTACGTGGGCCCTCTGGCCAGGGGAAACAGCAGATTCGCCTGGATG
ACCAGAAAGAGCGAGGAAACCATCACCCCCTGGAACTTCGAGGAAGTGGTGGACAAG
GGCGCCAGCGCCCAGAGCTTCATCGAGCGGATGACCAACTTCGATAAGAACCTGCCCA
ACGAGAAGGTGCTGCCCAAGCACAGCCTGCTGTACGAGTACTTCACCGTGTACAACGA
GCTGACCAAAGTGAAATACGTGACCGAGGGAATGAGAAAGCCCGCCTTCCTGAGCGGC
GAGCAGAAAAAGGCCATCGTGGACCTGCTGTTCAAGACCAACCGGAAAGTGACCGTGA
AGCAGCTGAAAGAGGACTACTTCAAGAAAATCGAGTGCTTCGACTCCGTGGAAATCTC
CGGCGTGGAAGATCGGTTCAACGCCTCCCTGGGCACATACCACGATCTGCTGAAAATTA
TCAAGGACAAGGACTTCCTGGACAATGAGGAAAACGAGGACATTCTGGAAGATATCGT
GCTGACCCTGACACTGTTTGAGGACAGAGAGATGATCGAGGAACGGCTGAAAACCTAT
GCCCACCTGTTCGACGACAAAGTGATGAAGCAGCTGAAGCGGCGGAGATACACCGGCT
GGGGCAGGCTGAGCCGGAAGCTGATCAACGGCATCCGGGACAAGCAGTCCGGCAAGA
CAATCCTGGATTTCCTGAAGTCCGACGGCTTCGCCAACAGAAACTTCATGCAGCTGATC
CACGACGACAGCCTGACCTTTAAAGAGGACATCCAGAAAGCCCAGGTGTCCGGCCAGG
GCGATAGCCTGCACGAGCACATTGCCAATCTGGCCGGCAGCCCCGCCATTAAGAAGGG
CATCCTGCAGACAGTGAAGGTGGTGGACGAGCTCGTGAAAGTGATGGGCCGGCACAAG
CCCGAGAACATCGTGATCGAAATGGCCAGAGAGAACCAGACCACCCAGAAGGGACAG
AAGAACAGCCGCGAGAGAATGAAGCGGATCGAAGAGGGCATCAAAGAGCTGGGCAGC

FIG. 6 (continued)

```
CAGATCCTGAAAGAACACCCCGTGGAAAACACCCAGCTGCAGAACGAGAAGCTGTACC
TGTACTACCTGCAGAATGGGCGGGATATGTACGTGGACCAGGAACTGGACATCAACCG
GCTGTCCGACTACGATGTGGACCATATCGTGCCTCAGAGCTTTCTGAAGGACGACTCCA
TCGATAACAAAGTGCTGACTCGGAGCGACAAGAACCGGGGCAAGAGCGACAACGTGC
CCTCCGAAGAGGTCGTGAAGAAGATGAAGAACTACTGGCGCCAGCTGCTGAATGCCAA
GCTGATTACCCAGAGGAAGTTCGACAATCTGACCAAGGCCGAGAGAGGCGGCCTGAGC
GAACTGGATAAGGCCGGCTTCATCAAGAGACAGCTGGTGGAAACCCGGCAGATCACAA
AGCACGTGGCACAGATCCTGGACTCCCGGATGAACACTAAGTACGACGAGAACGACAA
ACTGATCCGGGAAGTGAAAGTGATCACCCTGAAGTCCAAGCTGGTGTCCGATTTCCGG
AAGGATTTCCAGTTTTACAAAGTGCGCGAGATCAACAACTACCACCACGCCCACGACG
CCTACCTGAACGCCGTCGTGGGAACCGCCCTGATCAAAAAGTACCCTAAGCTGGAAAG
CGAGTTCGTGTACGGCGACTACAAGGTGTACGACGTGCGGAAGATGATCGCCAAGAGC
GAGCAGGAAATCGGCAAGGCTACCGCCAAGTACTTCTTCTACAGCAACATCATGAACT
TTTTCAAGACCGAGATTACCCTGGCCAACGGCGAGATCCGGAAGCGGCCTCTGATCGA
GACAAACGGCGAAACAGGCGAGATCGTGTGGGATAAGGGCCGGGACTTTGCCACCGTG
CGGAAAGTGCTGTCTATGCCCCAAGTGAATATCGTGAAAAAGACCGAGGTGCAGACAG
GCGGCTTCAGCAAAGAGTCTATCCTGCCCAAGAGGAACAGCGACAAGCTGATCGCCAG
AAAGAAGGACTGGGACCCTAAGAAGTACGGCGGCTTCGACAGCCCCACCGTGGCCTAT
TCTGTGCTGGTGGTGGCCAAAGTGGAAAAGGGCAAGTCCAAGAAACTGAAGAGTGTGA
AAGAGCTGCTGGGGATCACCATCATGGAAAGAAGCAGCTTCGAGAAGAATCCCATCGA
CTTTCTGGAAGCCAAGGGCTACAAAGAAGTGAAAAAGGACCTGATCATCAAGCTGCCT
AAGTACTCCCTGTTCGAGCTGGAAAACGGCCGGAAGAGAATGCTGGCCTCTGCCGGCG
AACTGCAGAAGGGAAACGAACTGGCCCTGCCCTCCAAATATGTGAACTTCCTGTACCTG
GCCAGCCACTATGAGAAGCTGAAGGGCTCCCCCGAGGATAATGAGCAGAAACAGCTGT
TTGTGGAACAGCACAAACACTACCTGGACGAGATCATCGAGCAGATCAGCGAGTTCTC
CAAGAGAGTGATCCTGGCCGACGCTAATCTGGACAAGGTGCTGAGCGCCTACAACAAG
CACAGAGACAAGCCTATCAGAGAGCAGGCCGAGAATATCATCCACCTGTTTACCCTGA
CCAATCTGGGAGCCCCTGCCGCCTTCAAGTACTTTGACACCACCATCGACCGGAAGAGG
TACACCAGCACCAAAGAGGTGCTGGACGCCACCCTGATCCACCAGAGCATCACCGGCC
TGTACGAGACACGGATCGACCTGTCTCAGCTGGGAGGCGACGCCTATCCCTATGACGTG
CCCGATTATGCCAGCCTGGGCAGCGGCTCCCCCAAGAAAAAACGCAAGGTGGAAGATC
CTAAGAAAAAGCGGAAAGTGGACGGCATTGGTAGTGGGAGCAACGGCAGCAGCGGAT
CCGTGAGCAAGGGCGAGGAGGATAACATGGCCATCATCAAGGAGTTCATGCGCTTCAA
GGTGCACATGGAGGGCTCCGTGAACGGCCACGAGTTCGAGATCGAGGGCGAGGGCGA
GGGCCGCCCCTACGAGGGCACCCAGACCGCCAAGCTGAAGGTGACCAAGGGTGGCCCC
CTGCCCTTCGCCTGGGACATCCTGTCCCCTCAGTTCATGTACGGCTCCAAGGCCTACGT
GAAGCACCCCGCCGACATCCCCGACTACTTGAAGCTGTCCTTCCCCGAGGGCTTCAAGT
GGGAGCGCGTGATGAACTTCGAGGACGGCGGCGTGGTGACCGTGACCCAGGACTCCTC
CCTCCAGGACGGCGAGTTCATCTACAAGGTGAAGCTGCGCGGCACCAACTTCCCCTCCG
ACGGCCCCGTAATGCAGAAGAAGACCATGGGCTGGGAGGCCTCCTCCGAGCGGATGTA
CCCCGAGGACGGCGCCCTGAAGGGCGAGATCAAGCAGAGGCTGAAGCTGAAGGACGG
CGGCCACTACGACGCTGAGGTCAAGACCACCTACAAGGCCAAGAAGCCCGTGCAGCTG
CCCGGCGCCTACAACGTCAACATCAAGTTGGACATCACCTCCCACAACGAGGACTACA
CCATCGTGGAACAGTACGAACGCGCCGAGGGCCGCCACTCCACCGGCGGCATGGACGA
GCTGTACAAGGGGTCACCTAAGAAAAAACGAAAGTTGAG
```

*S. pyogenes* Cas9 nickase - mutation D10A (amino acid sequence) (SEQ ID NO:851):

FIG. 6 (continued)

MDKKYSIGLAIGTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDKKHERHPIFGNIV
DEVAYHEKYPTIYHLRKKLVDSTDKADLRLIYLALAHMIKFRGHFLIEGDLNPDNSDVDKL
FIQLVQTYNQLFEENPINASGVDAKAILSARLSKSRRLENLIAQLPGEKKNGLFGNLIALSLG
LTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQ
EEFYKFIKPILEKMDGTEELLVKLNREDLLRKQRTFDNGSIPHQIHLGELHAILRRQEDFYPF
LKDNREKIEKILTFRIPYYVGPLARGNSRFAWMTRKSEETITPWNFEEVVDKGASAQSFIER
MTNFDKNLPNEKVLPKHSLLYEYFTVYNELTKVKYVTEGMRKPAFLSGEQKKAIVDLLFK
TNRKVTVKQLKEDYFKKIECFDSVEISGVEDRFNASLGTYHDLLKIIKDKDFLDNEENEDILE
DIVLTLTLFEDREMIEERLKTYAHLFDDKVMKQLKRRRYTGWGRLSRKLINGIRDKQSGKT
ILDFLKSDGFANRNFMQLIHDDSLTFKEDIQKAQVSGQGDSLHEHIANLAGSPAIKKGILQT
VKVVDELVKVMGRHKPENIVIEMARENQTTQKGQKNSRERMKRIEEGIKELGSQILKEHPV
ENTQLQNEKLYLYYLQNGRDMYVDQELDINRLSDYDVDHIVPQSFLKDDSIDNKVLTRSD
KNRGKSDNVPSEEVVKKMKNYWRQLLNAKLITQRKFDNLTKAERGGLSELDKAGFIKRQL
VETRQITKHVAQILDSRMNTKYDENDKLIREVKVITLKSKLVSDFRKDFQFYKVREINNYH
HAHDAYLNAVVGTALIKKYPKLESEFVYGDYKVYDVRKMIAKSEQEIGKATAKYFFYSNI
MNFFKTEITLANGEIRKRPLIETNGETGEIVWDKGRDFATVRKVLSMPQVNIVKKTEVQTG
GFSKESILPKRNSDKLIARKKDWDPKKYGGFDSPTVAYSVLVVAKVEKGKSKKLKSVKELL
GITIMERSSFEKNPIDFLEAKGYKEVKKDLIIKLPKYSLFELENGRKRMLASAGELQKGNELA
LPSKYVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLIHQSI
TGLYETRIDLSQLGGD

*S. pyogenes* Cas9 nickase - mutation H840A (amino acid sequence) (SEQ ID NO:852):

MDKKYSIGLDIGTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDKKHERHPIFGNIV
DEVAYHEKYPTIYHLRKKLVDSTDKADLRLIYLALAHMIKFRGHFLIEGDLNPDNSDVDKL
FIQLVQTYNQLFEENPINASGVDAKAILSARLSKSRRLENLIAQLPGEKKNGLFGNLIALSLG
LTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQ
EEFYKFIKPILEKMDGTEELLVKLNREDLLRKQRTFDNGSIPHQIHLGELHAILRRQEDFYPF
LKDNREKIEKILTFRIPYYVGPLARGNSRFAWMTRKSEETITPWNFEEVVDKGASAQSFIER
MTNFDKNLPNEKVLPKHSLLYEYFTVYNELTKVKYVTEGMRKPAFLSGEQKKAIVDLLFK
TNRKVTVKQLKEDYFKKIECFDSVEISGVEDRFNASLGTYHDLLKIIKDKDFLDNEENEDILE
DIVLTLTLFEDREMIEERLKTYAHLFDDKVMKQLKRRRYTGWGRLSRKLINGIRDKQSGKT
ILDFLKSDGFANRNFMQLIHDDSLTFKEDIQKAQVSGQGDSLHEHIANLAGSPAIKKGILQT
VKVVDELVKVMGRHKPENIVIEMARENQTTQKGQKNSRERMKRIEEGIKELGSQILKEHPV
ENTQLQNEKLYLYYLQNGRDMYVDQELDINRLSDYDVDAIVPQSFLKDDSIDNKVLTRSD
KNRGKSDNVPSEEVVKKMKNYWRQLLNAKLITQRKFDNLTKAERGGLSELDKAGFIKRQL
VETRQITKHVAQILDSRMNTKYDENDKLIREVKVITLKSKLVSDFRKDFQFYKVREINNYH
HAHDAYLNAVVGTALIKKYPKLESEFVYGDYKVYDVRKMIAKSEQEIGKATAKYFFYSNI
MNFFKTEITLANGEIRKRPLIETNGETGEIVWDKGRDFATVRKVLSMPQVNIVKKTEVQTG
GFSKESILPKRNSDKLIARKKDWDPKKYGGFDSPTVAYSVLVVAKVEKGKSKKLKSVKELL
GITIMERSSFEKNPIDFLEAKGYKEVKKDLIIKLPKYSLFELENGRKRMLASAGELQKGNELA
LPSKYVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLIHQSI
TGLYETRIDLSQLGGD

FIG. 6 (continued)

*S. pyogenes* Cas9 nickase – mutations E923P & T924P (amino acid sequence) (SEQ ID NO:853):

MDKKYSIGLDIGTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDKKHERHPIFGNIV
DEVAYHEKYPTIYHLRKKLVDSTDKADLRLIYLALAHMIKFRGHFLIEGDLNPDNSDVDKL
FIQLVQTYNQLFEENPINASGVDAKAILSARLSKSRRLENLIAQLPGEKKNGLFGNLIALSLG
LTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQ
EEFYKFIKPILEKMDGTEELLVKLNREDLLRKQRTFDNGSIPHQIHLGELHAILRRQEDFYPF
LKDNREKIEKILTFRIPYYVGPLARGNSRFAWMTRKSEETITPWNFEEVVDKGASAQSFIER
MTNFDKNLPNEKVLPKHSLLYEYFTVYNELTKVKYVTEGMRKPAFLSGEQKKAIVDLLFK
TNRKVTVKQLKEDYFKKIECFDSVEISGVEDRFNASLGTYHDLLKIIKDKDFLDNEENEDILE
DIVLTLTLFEDREMIEERLKTYAHLFDDKVMKQLKRRRYTGWGRLSRKLINGIRDKQSGKT
ILDFLKSDGFANRNFMQLIHDDSLTFKEDIQKAQVSGQGDSLHEHIANLAGSPAIKKGILQT
VKVVDELVKVMGRHKPENIVIEMARENQTTQKGQKNSRERMKRIEEGIKELGSQILKEHPV
ENTQLQNEKLYLYYLQNGRDMYVDQELDINRLSDYDVDHIVPQSFLKDDSIDNKVLTRSD
KNRGKSDNVPSEEVVKKMKNYWRQLLNAKLITQRKFDNLTKAERGGLSELDKAGFIKRQL
VPPRQITKHVAQILDSRMNTKYDENDKLIREVKVITLKSKLVSDFRKDFQFYKVREINNYHH
AHDAYLNAVVGTALIKKYPKLESEFVYGDYKVYDVRKMIAKSEQEIGKATAKYFFYSNIM
NFFKTEITLANGEIRKRPLIETNGETGEIVWDKGRDFATVRKVLSMPQVNIVKKTEVQTGGF
SKESILPKRNSDKLIARKKDWDPKKYGGFDSPTVAYSVLVVAKVEKGKSKKLKSVKELLGI
TIMERSSFEKNPIDFLEAKGYKEVKKDLIIKLPKYSLFELENGRKRMLASAGELQKGNELAL
PSKYVNFLYLASHYEKLKGSPEDNEQKQLFVEQHKHYLDEIIEQISEFSKRVILADANLDKV
LSAYNKHRDKPIREQAENIIHLFTLTNLGAPAAFKYFDTTIDRKRYTSTKEVLDATLIHQSIT
GLYETRIDLSQLGGD

*Acidovorax ebreus* Cas9 (amino acid sequence) (SEQ ID NO:854):

MAQHVFGLDIGIASVGWAILGEQRIIDLGVRCFDKAETAKEGDPLNLTRRQARLLRRRLYR
RAWRLTQLSRLLKRKGLIADAKLFAKAPSYGDSAWELRRQGLDRLLTPLEWARVIYHQCK
HRGFHWTSKAEEAKADSDAEGGRVKQGLAHTKALMQAKNYRSAAEMVLAEFPDAQRNK
RGQYDKALSRVLLGEELALLFATQRRLGNPHASDFFEKLILGDGDRKSGLFWQQKPALSGA
DLLKMLGKCTFEKGEYRAPKASFSVERHVWLTRLNNLRIVVDGRSRPLNEAERQAALLLP
YQTETSKYKTLKNAFIKAGLWGDGVRFGGLAYPSQAQIDAEKTKDPEDQFLVKLPAWHEL
RKAFKAAGHEALWQQISTPALDGDPTLLDQIATVLSVYKDGAEVVQQLRQLALPEPAASIA
VLEKISFDKFSSLSLKALRRIVPLMQSGLRYDEAVAQIPEYGHHSQRIEPGAAKHLYLPPFYE
AQRKYAGKGDHIGSMQFRDDADIPRNPVVLRALNQARKVVNALIREYGSPIAVNIEMARD
LSRPLDERNKVKRAQEEFRDRNDRARSEFERDFGYKPKAAAFEKWMLYREQLGQCAYSQ
QPLDIQRVLDDHNYAQVDHALPYSRSYDDSKNNKVLVLTHENQNKGNRTAFEYLTSFPDG
EDGERWRTFVAWVQGNKAYRMAKRNRLLRKNYGVDESKGFIDRNLNDTRYICKFFKNYV
EEHLQLAARADGDTARRCVVVNGQLTAFLRARWGLTKVRGDSDRHHALDAAVVAACTH
GMVKALADYSRRKEISFLQEGFPDPETGEILNPAAFDRARQHFPEPWTHFAHELKARLFTD
DLAALREDMQRLGSYTTEDLGRLRTLFVSRAPQRRSGGAVHKETIYAQPESLKQQGGVIEK
ILLTSLKLQDFDKLLNPESNDHFVEPHRNERLYAAIRQRLEQFGGRADKAFGPDNLFHKPDK
NNQPTGPVVRSIKLVRGKQTGIPIRGGLAKNDSMLRVDIFTKAGKFHLVPVYVHHRVTGLP
NRAIVAFKDEDEWTLIDESFAFLFSVYPNDYVKVTLKKEQQSGYYSGADRSTGAMNLWAH
DRAASVGKDGLIRGIGVKTALSVEKFNVDVLGRIYLAPPETRSGLA

FIG. 6 (continued)

Acid mine drainage bacteria Ga0052161_JGI Cas9 (amino acid sequence) (SEQ ID NO:855):

MADSLSRPWRLALDVGVGSIGWAALNLKRSERSNTPGDKWVACSLLDLGVNLFDSGVED
GIPKNTARRTYKAARHRLQSVKVRKRNLRDVLVAADCLPCDSATSQRSLLKGEPRSASIAL
RDQMVPIDGDGSVAIPAVWAWRWKALRKPGQLTHHELGVILMALASARGQGFSEESDSRT
VAPLVSELQEKISRAGCTAFGDYAAEILAKSPGATIRARNAEPNFVSRQMVLGEFRAIRNAQ
TRLLSPKRWDEIENIIFDQAPLAPPRPGNCPLVKEDVRLERAHPLAQRLKIVQTLRNVRLFDA
DGAVPEDRPTQLTPDEIRKAEKFLSTRKSATAISLFKALGIKSLRSNYHGGSRAEATDLPGNE
TNVAAAREDAFGAAWAAFEPSKQRDIVELALSIRGGRTADEIRAAADTWGISIDAARAFID
MLPKGRAAYGLTATNRLLAVMLEEGLSLFDARDREYPQAAQSRKFCSLPYYAIALPDHVF
DGDPRADETATDEQRYGHVRNPIVHVALNQIRGLVNALVAEFGAPVEITVELAREISLSDDE
KKKLLKSQKERAEMRETAAATIRECGYKPSRDLIDRYVLYCGQDRRLVQGEFAEIKCVYSG
KPIESFKRLFSNDIEIDHIVPRQRSHDDSLANKVLAYRGANRNKLNRTPFEFWGHTEHWAEI
WERAEFAFRKNPKKLARFRETAAQEFTGDFASRHLNDTRYISKMTRLYLERLKGTECVYAT
RGSITGRLRKAWELAKLLPVPAAVQSLIDISRASSRDVPIELKRHDHRHHAIDAALIGLVDH
HTLQYYFEKTESQTDKRFPLPWPTFKEELAERLQGLVVRRRPEHKRGFRYQGQLVEDSRYR
LRRQNEKNVLSSRTSLIGLVIDKFGNLIPGTRSAGIQFSCKEAFESSIMRIDPTGRLITLLNWET
LQAIRNSYLTSRPGDGDSGPLERKKAEREATAFAWKSLCSRAATTAGGISSVRKKIVLEDPV
IVGPEKSAVKSAGYAFAYVIKRNVPNTRYQLFPVAMKDAETDQGPPLKPGEVVVCKLHKG
DMLSLLLESNSLSSPVYCTVQGFKSSGVLTLTTQYNAARNGGRAVNTVPEIESSDGRNAVN
KVFGTWRARIVRPTVLGRLP

Uranium mine bacteria FW106_JGI Cas9 (amino acid sequence) (SEQ ID NO:856):

MGLIIREFSMENKALEQQAAAPMVFGFDIGIASVGWTVLGPTRIIDLGVRAFDKAETAKEGE
PLNLARRTARLMRRRLRRRAWRLTKLARLLKRHGVIDEVALFMPEHPYPHSLWKLRVEAL
DRPLAAEEWARVIYHLCKHRGFHWISRAEEKKAEADSKGEGGKVKQGLAGTKRLMEDKG
YRSAAEMVLAEFPDAQRNKQGDYTKSLSRVLLGDELSLLFTRQRELGNQHATPELQLSVLG
TGDHKSGLFWAQKPALAGDALLGMLGKCTFEKSEYRAPKASFTAERHVWLTRLNNLRVV
ADGRVRPLNEQERQIALRLPYQQASDLTYKQLRAALVKAGVLPDSFRFTGLAYPNATQQS
DSKIKDPEAAPLIRIPAWQEIRLTLKKAGLETEWEGMASLAIDGKPELLDQIAWVLTVFKED
DEVRAELRKLNLPQADKMVEALLDIRFDKFHALSLKALRNIVPHMELGLRYDEACEKAGY
HHSQLFTVGAGTHRYLPPFYSKRDASGRMIFDQELDIPRNPVVLRALNQARKVINALIRHYG
PPSEVRIELARDLSRPFDERKKIQTAQDEYRERNEKEKIRFLEEFSLSGTAKGRDFEKWQLYR
EQQGKCAYSLEALDLHRLFEVGYVEIDHALPYSRSYDDSKNNKVLVLAKENRNKGNQTPY
EYLDGMENTERWRAFASFVESNKTYRVAKRSRLLRKEFGAKESSEFKERNLNDTRYICKFF
KNYVERYLQLAENSEAKRCVVVSGQLTSFLRARWGLIKVREDSDRHHALDAAVVAACSH
GMVKRLSDYARRELEKVSEGFVDMETGEIVNPAMFRQLEQHFPEPWPNFRHELEARRKID
DPASLRSEIERLGTYSSDVLQILKPLFVSRAVQRRNRGAAHKETIYSQPERLKEQGGVTQKIP
LASLTLKDIDKLIDPHRNEKLYAAIRSRLEAHGGKGDKAFPSNNPLRKPDREGNATGPIVRT
VTMVIDKLSGIPVRGGVAKNDSMLRVDVFTKAGKFHLVPVYVHHSVAKTLPDRAIVQAKD
EDEWTLIDNSFDFCFSLYPNDLIKISQKGKPPLIGYYGSCNRNTGAINLWAHDRSNAIGKNG
LIESVGVKVALNLEKFHVDVLGNIFPAPKEERRGLA

*A. sp* Cpf1 (amino acid sequence) (SEQ ID NO:857):

MTQFEGFTNLYQVSKTLRFELIPQGKTLKHIQEQGFIEEDKARNDHYKELKPIIDRIYKTYAD
QCLQLVQLDWENLSAAIDSYRKEKTEETRNALIEEQATYRNAIHDYFIGRTDNLTDAINKRH
AEIYKGLFKAELFNGKVLKQLGTVTTTEHENALLRSFDKFTTYFSGFYENRKNVFSAEDIST

FIG. 6 (continued)

AIPHRIVQDNFPKFKENCHIFTRLITAVPSLREHFENVKKAIGIFVSTSIEEVFSFPFYNQLLTQ
TQIDLYNQLLGGISREAGTEKIKGLNEVLNLAIQKNDETAHIIASLPHRFIPLFKQILSDRNTLS
FILEEFKSDEEVIQSFCKYKTLLRNENVLETAEALFNELNSIDLTHIFISHKKLETISSALCDH
WDTLRNALYERRISELTGKITKSAKEKVQRSLKHEDINLQEIISAAGKELSEAFKQKTSEILS
HAHAALDQPLPTTLKKQEEKEILKSQLDSLLGLYHLLDWFAVDESNEVDPEFSARLTGIKLE
MEPSLSFYNKARNYATKKPYSVEKFKLNFQMPTLASGWDVNKEKNNGAILFVKNGLYYL
GIMPKQKGRYKALSFEPTEKTSEGFDKMYYDYFPDAAKMIPKCSTQLKAVTAHFQTHTTPI
LLSNNFIEPLEITKEIYDLNNPEKEPKKFQTAYAKKTGDQKGYREALCKWIDFTRDFLSKYT
KTTSIDLSSLRPSSQYKDLGEYYAELNPLLYHISFQRIAEKEIMDAVETGKLYLFQIYNKDFA
KGHHGKPNLHTLYWTGLFSPENLAKTSIKLNGQAELFYRPKSRMKRMAHRLGEKMLNKK
LKDQKTPIPDTLYQELYDYVNHRLSHDLSDEARALLPNVITKEVSHEIIKDRRFTSDKFFFHV
PITLNYQAANSPSKFNQRVNAYLKEHPETPIIGIDRGERNLIYITVIDSTGKILEQRSLNTIQQF
DYQKKLDNREKERVAARQAWSVVGTIKDLKQGYLSQVIHEIVDLMIHYQAVVVLENLNFG
FKSKRTGIAEKAVYQQFEKMLIDKLNCLVLKDYPAEKVGGVLNPYQLTDQFTSFAKMGTQ
SGFLFYVPAPYTSKIDPLTGFVDPFVWKTIKNHESRKHFLEGFDFLHYDVKTGDFILHFKMN
RNLSFQRGLPGFMPAWDIVFEKNETQFDAKGTPFIAGKRIVPVIENHRFTGRYRDLYPANEL
IALLEEKGIVFRDGSNILPKLLENDDSHAIDTMVALIRSVLQMRNSNAATGEDYINSPVRDL
NGVCFDSRFQNPEWPMDADANGAYHIALKGQLLLNHLKESKDLKLQNGISNQDWLAYIQE
LRN

*L. bacterium* Cpf1 (amino acid sequence) (SEQ ID NO:858):

MSKLEKFTNCYSLSKTLRFKAIPVGKTQENIDNKRLLVEDEKRAEDYKGVKKLLDRYYLSF
INDVLHSIKLKNLNNYISLFRKKTRTEKENKELENLEINLRKEIAKAFKGNEGYKSLFKKDIIE
TILPEFLDDKDEIALVNSFNGFTTAFTGFFDNRENMFSEEAKSTSIAFRCINENLTRYISNMDI
FEKVDAIFDKHEVQEIKEKILNSDYDVEDFFEGEFFNFVLTQEGIDVYNAIIGGFVTESGEKIK
GLNEYINLYNQKTKQKLPKFKPLYKQVLSDRESLSFYGEGYTSDEEVLEVFRNTLNKNSEIF
SSIKKLEKLFKNFDEYSSAGIFVKNGPAISTISKDIFGEWNVIRDKWNAEYDDIHLKKKAVVT
EKYEDDRRKSFKKIGSFSLEQLQEYADADLSVVEKLKEIIIQKVDEIYKVYGSSEKLFDADFV
LEKSLKKNDAVVAIMKDLLDSVKSFENYIKAFFGEGKETNRDESFYGDFVLAYDILLKVDH
IYDAIRNYVTQKPYSKDKFKLYFQNPQFMGGWDKDKETDYRATILRYGSKYYLAIMDKKY
AKCLQKIDKDDVNGNYEKINYKLLPGPNKMLPKVFFSKKWMAYYNPSEDIQKIYKNGTFK
KGDMFNLNDCHKLIDFFKDSISRYPKWSNAYDFNFSETEKYKDIAGFYREVEEQGYKVSFE
SASKKEVDKLVEEGKLYMFQIYNKDFSDKSHGTPNLHTMYFKLLFDENNHGQIRLSGGAEL
FMRRASLKKEELVVHPANSPIANKNPDNPKKTTTLSYDVYKDKRFSEDQYELHIPIAINKCP
KNIFKINTEVRVLLKHDDNPYVIGIDRGERNLLYIVVVDGKGNIVEQYSLNEIINNFNGIRIKT
DYHSLLDKKEKERFEARQNWTSIENIKELKAGYISQVVHKICELVEKYDAVIALEDLNSGFK
NSRVKVEKQVYQKFEKMLIDKLNYMVDKKSNPCATGGALKGYQITNKFESFKSMSTQNGF
IFYIPAWLTSKIDPSTGFVNLLKTKYTSIADSKKFISSFDRIMYVPEEDLFEFALDYKNFSRTD
ADYIKKWKLYSYGNRIRIFRNPKKNNVFDWEEVCLTSAYKELFNKYGINYQQGDIRALLCE
QSDKAFYSSFMALMSLMLQMRNSITGRTDVDFLISPVKNSDGIFYDSRNYEAQENAILPKN
ADANGAYNIARKVLWAIGQFKKAEDEKLDKVKIAISNKEWLEYAQTSVKH

*P. macacae* Cpf1 (amino acid sequence) (SEQ ID NO:859):

MKTQHFFEDFTSLYSLSKTIRFELKPIGKTLENIKKNGLIRRDEQRLDDYEKLKKVIDEYHED
FIANILSSFSFSEEILQSYIQNLSESEARAKIEKTMRDTLAKAFSEDERYKSIFKKELVKKDIPV
WCPAYKSLCKKFDNFTTSLVPFHENRKNLYTSNEITASIPYRIVHVNLPKFIQNIEALCELQK
KMGADLYLEMMENLRNVWPSFVKTPDDLCNLKTYNHLMVQSSISEYNRFVGGYSTEDGT

FIG. 6 (continued)

KHQGINEWINIYRQRNKEMRLPGLVFLHKQILAKVDSSSFISDTLENDDQVFCVLRQFRKLF
WNTVSSKEDDAASLKDLFCGLSGYDPEAIYVSDAHLATISKNIFDRWNYISDAIRRKTEVLM
PRKKESVERYAEKISKQIKKRQSYSLAELDDLLAHYSEESLPAGFSLLSYFTSLGGQKYLVS
DGEVILYEEGSNIWDEVLIAFRDLQVILDKDFTEKKLGKDEEAVSVIKKALDSALRLRKFFD
LLSGTGAEIRRDSSFYALYTDRMDKLKGLLKMYDKVRNYLTKKPYSIEKFKLHFDNPSLLS
GWDKNKELNNLSVIFRQNGYYYLGIMTPKGKNLFKTLPKLGAEEMFYEKMEYKQIAEPML
MLPKVFFPKKTKPAFAPDQSVVDIYNKKTFKTGQKGFNKKDLYRLIDFYKEALTVHEWKL
FNFSFSPTEQYRNIGEFFDEVREQAYKVSMVNVPASYIDEAVENGKLYLFQIYNKDFSPYSK
GIPNLHTLYWKALFSEQNQSRVYKLCGGGELFYRKASLHMQDTTVHPKGISIHKKNLNKK
GETSLFNYDLVKDKRFTEDKFFFHVPISINYKNKKITNVNQMVRDYIAQNDDLQIIGIDRGE
RNLLYISRIDTRGNLLEQFSLNVIESDKGDLRTDYQKILGDREQERLRRQEWKSIESIKDLK
DGYMSQVVHKICNMVVEHKAIVVLENLNLSFMKGRKKVEKSVYEKFERMLVDKLNYLVV
DKKNLSNEPGGLYAAYQLTNPLFSFEELHRYPQSGILFFVDPWNTSLTDPSTGFVNLLGRIN
YTNVGDARKFFDRFNAIRYDGKGNILFDLDLSRFDVRVETQRKLWTLTTFGSRIAKSKKSG
KWMVERIENLSLCFLELFEQFNIGYRVEKDLKKAILSQDRKEFYVRLIYLFNLMMQIRNSDG
EEDYILSPALNEKNLQFDSRLIEAKDLPVDADANGAYNVARKGLMVVQRIKRGDHESIHRI
GRAQWLRYVQEGIVE

*P. disiens* Cpf1 (amino acid sequence) (SEQ ID NO:860):

MENYQEFTNLFQLNKTLRFELKPIGKTCELLEEGKIFASGSFLEKDKVRADNVSYVKKEIDK
KHKIFIEETLSSFSISNDLLKQYFDCYNELKAFKKDCKSDEEEVKKTALRNKCTSIQRAMRE
AISQAFLKSPQKKLLAIKNLIENVFKADENVQHFSEFTSYFSGFETNRENFYSDEEKSTSIAYR
LVHDNLPIFIKNIYIFEKLKEQFDAKTLSEIFENYKLYVAGSSLDEVFSLEYFNNTLTQKGIDN
YNAVIGKIVKEDKQEIQGLNEHINLYNQKHKDRRLPFFISLKKQILSDREALSWLPDMFKND
SEVIKALKGFYIEDGFENNVLTPLATLLSSLDKYNLNGIFIRNNEALSSLSQNVYRNFSIDEAI
DANAELQTFNNYELIANALRAKIKKETKQGRKSFEKYEEYIDKKVKAIDSLSIQEINELVEN
YVSEFNSNSGNMPRKVEDYFSLMRKGDFGSNDLIENIKTKLSAAEKLLGTKYQETAKDIFK
KDENSKLIKELLDATKQFQHFIKPLLGTGEEADRDLVFYGDFLPLYEKFEELTLLYNKVRNR
LTQKPYSKDKIRLCFNKPKLMTGWVDSKTEKSDNGTQYGGYLFRKKNEIGEYDYFLGISSK
AQLFRKNEAVIGDYERLDYYQPKANTIYGSAYEGENSYKEDKKRLNKVIIAYIEQIKQTNIK
KSIIESISKYPNISDDDKVTPSSLLEKIKKVSIDSYNGILSFKSFQSVNKEVIDNLLKTISPLKNK
AEFLDLINKDYQIFTEVQAVIDEICKQKTFIYFPISNVELEKEMGDKDKPLCLFQISNKDLSFA
KTFSANLRKKRGAENLHTMLFKALMEGNQDNLDLGSGAIFYRAKSLDGNKPTHPANEAIK
CRNVANKDKVSLFTYDIYKNRRYMENKFLFHLSIVQNYKAANDSAQLNSSATEYIRKADD
LHIIGIDRGERNLLYYSVIDMKGNIVEQDSLNIIRNNDLETDYHDLLDKREKERKANRQNWE
AVEGIKDLKKGYLSQAVHQIAQLMLKYNAIIALEDLGQMFVTRGQKIEKAVYQQFEKSLV
DKLSYLVDKKRPYNELGGILKAYQLASSITKNNSDKQNGFLFYVPAWNTSKIDPVTGFTDL
LRPKAMTIKEAQDFFGAFDNISYNDKGYFEFETNYDKFKIRMKSAQTRWTICTFGNRIKRK
KDKNYWNYEEVELTEEFKKLFKDSNIDYENCNLKEEIQNKDNRKFFDDLIKLLQLTLQMRN
SDDKGNDYIISPVANAEGQFFDSRNGDKKLPLDADANGAYNIARKGLWNIRQIKQTKNDK
KLNLSISSTEWLDFVREKPYL mCherry sequence (SEQ ID NO:915), wherein the initial methionine between brackets was not used for direct fusion to Cas9, but for independent expression:

(M)VSKGEEDNMAIIKEFMRFKVHMEGSVNGHEFEIEGEGEGRPYEGTQTAKLKVTKGGPL
PFAWDILSPQFMYGSKAYVKHPADIPDYLKLSFPEGFKWERVMNFEDGGVVTVTQDSSLQ

FIG. 6 (continued)

DGEFIYKVKLRGTNFPSDGPVMQKKTMGWEASSERMYPEDGALKGEIKQRLKLKDGGHY
DAEVKTTYKAKKPVQLPGAYNVNIKLDITSHNEDYTIVEQYERAEGRHSTGGMDELYK

*S. pyogenes* Cas9 null - mutation D10A& H840A (amino acid sequence) (SEQ ID NO:1027):

MDKKYSIGLAIGTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDKKHERHPIFGNIV
DEVAYHEKYPTIYHLRKKLVDSTDKADLRLIYLALAHMIKFRGHFLIEGDLNPDNSDVDKL
FIQLVQTYNQLFEENPINASGVDAKAILSARLSKSRRLENLIAQLPGEKKNGLFGNLIALSLG
LTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQ
EEFYKFIKPILEKMDGTEELLVKLNREDLLRKQRTFDNGSIPHQIHLGELHAILRRQEDFYPF
LKDNREKIEKILTFRIPYYVGPLARGNSRFAWMTRKSEETITPWNFEEVVDKGASAQSFIER
MTNFDKNLPNEKVLPKHSLLYEYFTVYNELTKVKYVTEGMRKPAFLSGEQKKAIVDLLFK
TNRKVTVKQLKEDYFKKIECFDSVEISGVEDRFNASLGTYHDLLKIIKDKDFLDNEENEDILE
DIVLTLTLFEDREMIEERLKTYAHLFDDKVMKQLKRRRYTGWGRLSRKLINGIRDKQSGKT
ILDFLKSDGFANRNFMQLIHDDSLTFKEDIQKAQVSGQGDSLHEHIANLAGSPAIKKGILQT
VKVVDELVKVMGRHKPENIVIEMARENQTTQKGQKNSRERMKRIEEGIKELGSQILKEHPV
ENTQLQNEKLYLYYLQNGRDMYVDQELDINRLSDYDVDAIVPQSFLKDDSIDNKVLTRSD
KNRGKSDNVPSEEVVKKMKNYWRQLLNAKLITQRKFDNLTKAERGGLSELDKAGFIKRQL
VETRQITKHVAQILDSRMNTKYDENDKLIREVKVITLKSKLVSDFRKDFQFYKVREINNYH
HAHDAYLNAVVGTALIKKYPKLESEFVYGDYKVYDVRKMIAKSEQEIGKATAKYFFYSNI
MNFFKTEITLANGEIRKRPLIETNGETGEIVWDKGRDFATVRKVLSMPQVNIVKKTEVQTG
GFSKESILPKRNSDKLIARKKDWDPKKYGGFDSPTVAYSVLVVAKVEKGKSKKLKSVKELL
GITIMERSSFEKNPIDFLEAKGYKEVKKDLIIKLPKYSLFELENGRKRMLASAGELQKGNELA
LPSKYVNFLYLASHYEKLKGSPEDNEQKQLFVEQHKHYLDEIIEQISEFSKRVILADANLDK
VLSAYNKHRDKPIREQAENIIHLFTLTNLGAPAAFKYFDTTIDRKRYTSTKEVLDATLIHQSI
TGLYETRIDLSQLGGD

TISSUE-SPECIFIC GENOME ENGINEERING USING CRISPR-CAS9

RELATED APPLICATIONS

This application claims the benefit of and priority from U.S. Provisional Patent Applications 62/254,652, filed Nov. 12, 2015, and 62/384,660, filed Sep. 7, 2016. Each of the foregoing applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 7, 2016, is named PCFC-989-101_SL.txt and is 8,027,538 bytes in size.

FIELD OF THE INVENTION

The present invention relates to compounds, compositions and uses thereof as gene targeting agents.

BACKGROUND

Considerable attention has been devoted to developing reagents and methods for delivering bioactive agents to particular tissues, cells, and/or subcellular locations. For example, delivery of large molecules, such as an antisense or RNAi molecules or proteins, is difficult as such compounds are generally not able to penetrate cell membranes; when they can, they can often lack of selectivity for the tissue of interest and therefore increase risk of off-target pharmacology and present serious safety concerns. Furthermore, selective drug delivery to targeted delivery sites is often a challenge because molecules that are cell permeable are often not selective. One solution to cell diffusion and targeted delivery is drug conjugation to targeting agents.

In the context of gene therapy, most gene editing agents have often been delivered via plasmid DNA encapsulated in viral-derived vectors such as adeno viruses and adeno-associated viruses. Unfortunately, this type of approach has been plagued with serious issues for the patients mainly i) increased risk of insertional mutagenesis, ii) increased risks of hepatotoxicity upon interaction of viral vector with Kupffer cells and iii) only transient pharmacological benefit for the patient triggered by immunogenic response against the treated cells. As a result, there remains a need to find more effective and safer ways to deliver gene editing agents. Attempts thus far have been elusive and in this context, delivering gene editing agents in the form of the protein, and not its DNA or RNA, represent an immense therapeutic opportunity.

Targeting agents often enhance pharmaceutical attributes including pharmacokinetics and pharmacodynamics. Targeting agents allow the drug payload attached to the targeting agent to be efficiently distributed to and up-taken by specific cells. Certain sugars, such as galactose, N-acetyl galactosamine, and other galactose derivatives including those described by M. G. Finn and V. Mascitti et al. in the Journal of the American Chemical Society, 134, 1978 (2012) have been used as targeting agents for hepatocytes due to the binding to asialoglycoprotein receptors (ASGPR) that are present on the surface of hepatocytes.

As a further issue for drug delivery, in receptor mediated endocytosis mechanisms, endosomal uptake pathway is known to be a rate-limiting barrier for delivering bioactive agents to the target subcellular locations. Bioactive molecules often get trapped in the endosomal vesicles and degraded in the lysosomal compartment. Various reagents, such as chloroquine, polyethyleneimine [PEI], certain highly charged cationic compounds, fusogenic peptides, and inactivated adenoviruses, have been developed that are intended to quickly disrupt the endosome in order to minimize the amount of time that a delivered bioactive agent spends in the endosome-like environment. However, these agents often lack of generality and present suboptimal ability to promote endosomal escape of the cargo and are associated with various disadvantages, including toxicity problems.

Consequently, a versatile and biocompatible cell delivery system would be important for the clinical success of gene targeting and the delivery of therapeutic agents.

SUMMARY OF THE INVENTION

One aspect of the present invention provides compounds of Formula (A-1), (A-2), or (A-3):

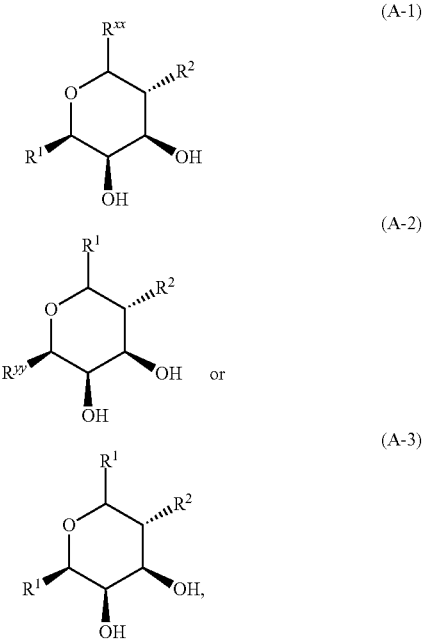

or a pharmaceutically acceptable salt thereof,
wherein:
$R^{xx}$ is —H, -alkyl, -cycloalkyl, -alkenyl, -alkynyl, -aryl, -heteroaryl, —$OR^5$, —$N(R^4)$—$R^5$, —$SR^5$, wherein a —$CH_2$— group of said $R^{xx}$ may each be independently replaced with a heteroatom group selected from —O—, —S—, —$N(R^4)$— and wherein a —$CH_3$ of said $R^{xx}$ may be replaced with a heteroatom group selected from —$N(R^4)_2$, —$OR^4$, and —$S(R^4)$ wherein the heteroatom groups are separated by at least 2 carbon atoms, and wherein the alkyl, cycloalkyl, alkenyl and alkynyl may each be independently substituted with one or more halo atoms;
$R^{yy}$ is —CN, —$CH_2$—CN, —C≡CH, —$CH_2$—$N_3$, —$CH_2$—$NH_2$, —$CH_2$—$N(R^4)$—$S(O)_2$—$R^5$, —$CH_2$—$CO_2H$, —$CO_2H$, —$CH_2$—OH, —$CH_2$—SH, —CH=CH—$R^5$, —$CH_2$—$R^5$, —$CH_2$—S—$R^5$, —CH₂—N(R⁴)—R⁵, —CH₂—N(R⁴)—C(O)—R⁵, —CH₂—N(R⁴)—C(O)—O—R⁵, —CH₂—N(R⁴)—C(O)—N(R⁴)—R⁵, —CH₂—O—R⁵, —CH₂—O—C(O)—R⁵, —CH₂—O—C(O)—N(R⁴)—R⁵, —CH₂—O—C(O)—O—R⁵, —CH₂—S(O)—R⁵, —CH₂—S(O)₂—R⁵, —CH₂—S(O)₂—N(R⁴)—R⁵, —C(O)—NH₂, —C(O)—O—R⁵, —C(O)—N(R⁴)—R⁵, or aryl or heteroaryl, wherein the aryl or heteroaryl is optionally substituted with R⁵;

each R¹ is independently —CN, —CH₂—CN, —C≡CH, —CH₂—N₃, —CH₂—NH₂, —CH₂—N(R⁴)—S(O)₂—R⁵, —CH₂—CO₂H, —CO₂H, —CH₂—OH, —CH₂—SH, —CH=CH—R⁵, —CH₂—R⁵, —CH₂—S—R⁵, —CH₂—N(R⁴)—R⁵, —CH₂—N(R⁴)—C(O)—R⁵, —CH₂—N(R⁴)—C(O)—O—R⁵, —CH₂—N(R⁴)—C(O)—N(R⁴)—R⁵, —CH₂—O—R⁵, —CH₂—O—C(O)—R⁵, —CH₂—O—C(O)—N(R⁴)—R⁵, —CH₂—O—C(O)—O—R⁵, —CH₂—S(O)—R⁵, —CH₂—S(O)₂—R⁵, —CH₂—S(O)₂—N(R⁴)—R⁵, —C(O)—NH₂, —C(O)—O—R⁵, —C(O)—N(R⁴)—R⁵, or aryl or heteroaryl, wherein the aryl or heteroaryl is optionally substituted with R⁵, or R¹ is —Z—X—Y, —Z—Y, —X—Y, —Z—X⁺Y⁻, —Z—X⁻Y⁺, —X⁻Y⁺, or —Y;

X is a linker;

X⁺ is a positively charged linker;

X⁻ is a negatively charged linker;

Y is a ribonucleoprotein or endonuclease comprising a site-directed modifying polypeptide, or Y is a site-directed modifying polypeptide, or Y is Cas9 ribonucleoprotein, or Y is a Cas9 protein, or Y is a single guide RNA sequence (sgRNA) or Y is a dual guide RNA sequence comprising a CRISPR RNA (crRNA) and a trans-activating crRNA (tracrRNA);

Y⁺ is a positively charged ribonucleoprotein or endonuclease comprising a site-directed modifying polypeptide, or Y⁺ a positively charged site-directed modifying polypeptide, or Y⁺ is a positively charged Cas9 protein;

Y⁻ is a negatively charged ribonucleoprotein or endonuclease comprising a site-directed modifying polypeptide, or Y⁻ is a negatively charged site-directed modifying polypeptide, or Y⁻ is a negatively charged Cas9 ribonucleoprotein, or Y⁻ is a negatively charged sgRNA, or Y⁻ is a negatively charged dual guide RNA sequence comprising a CRISPR RNA (crRNA) and a trans-activating crRNA (tracrRNA);

Z is absent or is —C≡C—, —CH=CH—, —CH₂—, —CH₂—O—, —C(O)—N(R⁴)—, —CH₂—S(O)—, —CH₂—S(O)₂—, —CH₂—S(O)₂—N(R⁴)—, —C(O)—O—, —CH₂—N(R⁴)—, —CH₂—N(R⁴)—C(O)—, —CH₂—N(R⁴)—S(O)₂—, —CH₂—N(R⁴)—C(O)—O—, —CH₂—N(R⁴)—C(O)—N(R⁴)—, —CH₂—O—C(O)—, —CH₂—O—C(O)—N(R⁴)—, —CH₂—O—C(O)—O—, or aryl or heteroaryl, wherein the aryl or heteroaryl is optionally substituted with R⁵;

R² is —OH, —N₃, —N(R³)₂, —N(R³)—C(O)—R³, —N(R³)—C(O)—N(R³)₂, —N(R³)—C(O)—OR³, —N(R³)—S(O)₂—R³, tetrazole, or triazole, wherein the tetrazole and triazole are optionally substituted with R³;

each R³ is independently —H, halo-substituted (C₁-C₅)alkyl, halo substituted (C₃-C₆)cycloalkyl, (C₃-C₆)cycloalkyl, —(C₁-C₅)alkenyl, —(C₁-C₅)alkynyl, halo substituted —(C₁-C₅)alkenyl, or halo substituted —(C₁-C₅)alkynyl, wherein a —CH₂— group of the alkyl or cycloalkyl may each be independently replaced with a heteroatom group selected from —O—, —S—, and —N(R⁴)— and —CH₃ of the alkyl may each be independently replaced with a heteroatom group selected from —N(R⁴)₂, —OR⁴, and —S(R⁴) wherein the heteroatom groups are separated by at least 2 carbon atoms;

each R⁴ is independently —H, —(C₁-C₂₀)alkyl, —(C₁-C₂₀)alkenyl, —(C₁-C₂₀)alkynyl, or (C₃-C₆)cycloalkyl wherein one to six —CH₂— groups of the alkyl or cycloalkyl separated by at least two carbon atoms may each be independently replaced with a heteroatom independently selected from —O—, —S—, or —N(R⁴)—, and —CH₃ of the alkyl may each be independently replaced with a heteroatom group selected from —N(R⁴)₂, —OR⁴, and —S(R⁴) wherein the heteroatom groups are separated by at least 2 carbon atoms; and wherein the alkyl, alkenyl, alkynyl, and cycloalkyl may be substituted with halo atoms;

each R⁵ is independently —H, (C₃-C₂₀)cycloalkyl, —(C₁-C₆₀)alkenyl, —(C₁-C₆₀)alkynyl, or (C₁-C₆₀)alkyl wherein one to six —CH₂— groups of the cycloalkyl or one to 20 —CH₂— groups of the alkyl may each be independently replaced with heteroatoms independently selected from —O—, —S—, and —N(R⁴)— wherein the heteroatoms are separated by at least two carbon atoms, and —CH₃ of the alkyl may each be independently replaced with a heteroatom group selected from —N(R⁴)₂, —OR⁴, and —S(R⁴) wherein the heteroatom groups are separated by at least 2 carbon atoms; and wherein the alkyl, alkenyl, alkynyl, and cycloalkyl may be substituted with halo atoms.

Another aspect of the present invention provides a compound of Formula (B):

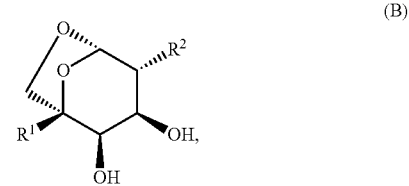

(B)

or a pharmaceutically acceptable salt thereof,
wherein:

R¹ is —Z—X—Y, —Z—Y, —X—Y, —Z—X⁺Y⁻, —X⁺Y⁻, —Z—X⁻Y⁺, —X⁻Y⁺, or —Y;

X is a linker;

X⁺ is a positively charged linker;

X⁻ is a negatively charged linker;

Y is a ribonucleoprotein or endonuclease comprising a site-directed modifying polypeptide, or Y is a site-directed modifying polypeptide, or Y is Cas9 ribonucleoprotein, or Y is a Cas9 protein, or Y is a single guide RNA sequence (sgRNA) or Y is a dual guide RNA sequence comprising a CRISPR RNA (crRNA) and a trans-activating crRNA (tracrRNA);

Y⁺ is a positively charged ribonucleoprotein or endonuclease comprising a site-directed modifying polypeptide, or Y⁺ a positively charged site-directed modifying polypeptide, or Y⁺ is a positively charged Cas9 protein;

Y⁻ is a negatively charged ribonucleoprotein or endonuclease comprising a site-directed modifying polypeptide, or Y⁻ is a negatively charged site-directed modifying polypeptide, or Y⁻ is a negatively charged Cas9 ribonucleoprotein, or Y⁻ is a negatively charged sgRNA, or Y⁻ is a negatively charged dual guide RNA sequence comprising a CRISPR RNA (crRNA) and a trans-activating crRNA (tracrRNA);

Z is absent or is —C≡C—, —C=CH—, —CH$_2$—, —CH$_2$—O—, —C(O)—N(R$^4$)—, —CH$_2$—S—, —CH$_2$—S(O)—, —CH$_2$—S(O)$_2$—, —CH$_2$—S(O)$_2$—N(R$^4$)—, —C(O)—O—, —CH$_2$—N(R$^4$)—, —CH$_2$—N(R$^4$)—C(O)—, —CH$_2$—N(R$^4$)—S(O)$_2$—, —CH$_2$—N(R$^4$)—C(O)—O—, —CH$_2$—N(R$^4$)—C(O)—N(R$^4$)—, —CH$_2$—O—C(O)—, —CH$_2$—O—C(O)—N(R$^4$)—, —CH$_2$—O—C(O)—O—, or aryl or heteroaryl, wherein the aryl or heteroaryl is optionally substituted with R$^5$;

R$^2$ is —OH, —N$_3$, —N(R$^3$)$_2$, —N(R$^3$)—C(O)—R$^3$, —N(R$^3$)—C(O)—N(R$^3$)$_2$, —N(R$^3$)—C(O)—OR$^3$, —N(R$^3$)—S(O)$_2$—R$^3$, tetrazole, or triazole, wherein the tetrazole and triazole are optionally substituted with R$^3$;

each R$^3$ is independently —H, halo-substituted (C$_1$-C$_5$)alkyl, halo substituted (C$_3$-C$_6$)cycloalkyl, —(C$_1$-C$_5$)alkenyl, —(C$_1$-C$_5$)alkynyl, halo substituted —(C$_1$-C$_5$)alkenyl, halo substituted —(C$_1$-C$_5$)alkynyl, or (C$_3$-C$_6$) cycloalkyl, wherein a —CH$_2$— group of the alkyl or cycloalkyl may each be independently replaced with a heteroatom group selected from —O—, —S—, and —N(R$^4$)— and —CH$_3$ of the alkyl may each be independently replaced with a heteroatom group selected from —N(R$^4$)$_2$, —OR$^4$, and —S(R$^4$) wherein the heteroatom groups are separated by at least 2 carbon atoms;

each R$^4$ is independently —H, —(C$_1$-C$_{20}$)alkyl, —(C$_1$-C$_{20}$) alkenyl, —(C$_1$-C$_{20}$)alkynyl, or (C$_3$-C$_6$)cycloalkyl wherein one to six —CH$_2$— groups of the alkyl or cycloalkyl separated by at least two carbon atoms may each be independently replaced with a heteroatom independently selected from —O—, —S—, or —N(R$^4$)—, and —CH$_3$ of the alkyl may each be independently replaced with a heteroatom group selected from —N(R$^4$)$_2$, —OR$^4$, and —S(R$^4$) wherein the heteroatom groups are separated by at least 2 carbon atoms; and wherein the alkyl, alkenyl, alkynyl, and cycloalkyl may be substituted with halo atoms;

each R$^5$ is independently —H, (C$_3$-C$_{20}$)cycloalkyl, —(C$_1$-C$_{60}$)alkenyl, —(C$_1$-C$_{60}$)alkynyl, or (C$_1$-C$_{60}$)alkyl wherein one to six —CH$_2$— groups of the cycloalkyl or one to 20 —CH$_2$— groups of the alkyl may each be independently replaced with heteroatoms independently selected from —O—, —S—, and —N(R$^4$)— wherein the heteroatoms are separated by at least two carbon atoms, and —CH$_3$ of the alkyl may each be independently replaced with a heteroatom group selected from —N(R$^4$)$_2$, —OR$^4$, and —S(R$^4$) wherein the heteroatom groups are separated by at least 2 carbon atoms; and wherein the alkyl, alkenyl, alkynyl, and cycloalkyl may be substituted with halo atoms.

Another aspect of the present invention includes a method for treating a liver disease or condition or a liver modulated disease or condition in a subject, including, but not limited to, hereditary angioedema, familial tyrosinemia type I, Alagille syndrome, Alpha-1-antitrypsin deficiency, Bile acid synthesis and metabolism defects, Biliary Atresia, Cystic Fibrosis liver disease, Idiopathic neonatal hepatitis, Mitochondrial hepatopathies, Progressive familial intrahepatic cholestasis, Primary sclerosing cholangitis, Transthyretin amyloidosis, Hemophilia, Homozygous familial hypercholesterolemia, familial chylomicronemia, hyperlipidemia, steatohepatitis, non-alcoholic steatohepatitis (NASH), non-alcoholic fatty liver disease (NAFLD), hyperglycemia like Type II diabetes mellitus, and diseases involving abnormally high hepatic glucose production similar to Type II diabetes mellitus, comprising the administration of an effective amount of a compound or composition described herein. In some embodiments, the disease or condition is hyperlipidemia, non-alcoholic steatohepatitis (NASH), or non-alcoholic fatty liver disease (NAFLD).

Another aspect of the present invention provides a method for selectively modulating transcription of a target DNA in a liver cell of a subject, said DNA being associated with a liver disease or condition or a liver modulated disease or condition in a subject, such as, but are not limited to hereditary angioedema, familial tyrosinemia type I, Alagille syndrome, Alpha-1-antitrypsin deficiency, Bile acid synthesis and metabolism defects, Biliary Atresia, Cystic Fibrosis liver disease, Idiopathic neonatal hepatitis, Mitochondrial hepatopathies, Progressive familial intrahepatic cholestasis, Primary sclerosing cholangitis, Transthyretin amyloidosis, Hemophilia, Homozygous familial hypercholesterolemia, familial chylomicronemia, hyperlipidemia, steatohepatitis, non-alcoholic steatohepatitis (NASH), non-alcoholic fatty liver disease (NAFLD), hyperglycemia like Type II diabetes mellitus, and diseases involving abnormally high hepatic glucose production similar to Type II diabetes mellitus, comprising the administration of an effective amount of a compound or composition described herein.

Another aspect of the present invention includes a method for editing a nucleic acid molecule encoding a protein associated with a liver disease or condition or a liver modulated disease or condition in a subject, such as, but are not limited to hereditary angioedema, familial tyrosinemia type I, Alagille syndrome, Alpha-1-antitrypsin deficiency, Bile acid synthesis and metabolism defects, Biliary Atresia, Cystic Fibrosis liver disease, Idiopathic neonatal hepatitis, Mitochondrial hepatopathies, Progressive familial intrahepatic cholestasis, Primary sclerosing cholangitis, Transthyretin amyloidosis, Hemophilia, Homozygous familial hypercholesterolemia, familial chylomicronemia, hyperlipidemia, steatohepatitis, non-alcoholic steatohepatitis (NASH), non-alcoholic fatty liver disease (NAFLD), hyperglycemia like Type II diabetes mellitus, and diseases involving abnormally high hepatic glucose production similar to Type II diabetes mellitus, comprising the administration of an effective amount of a compound or composition described herein.

Another aspect of the present invention includes a method for modulating the expression of level of at least one gene product associated with a liver disease or condition or a liver modulated disease or condition, such as, but are not limited to hereditary angioedema, familial tyrosinemia type I, Alagille syndrome, Alpha-1-antitrypsin deficiency, Bile acid synthesis and metabolism defects, Biliary Atresia, Cystic Fibrosis liver disease, Idiopathic neonatal hepatitis, Mitochondrial hepatopathies, Progressive familial intrahepatic cholestasis, Primary sclerosing cholangitis, Transthyretin amyloidosis, Hemophilia, Homozygous familial hypercholesterolemia, familial chylomicronemia, hyperlipidemia, steatohepatitis, non-alcoholic steatohepatitis (NASH), non-alcoholic fatty liver disease (NAFLD), hyperglycemia like Type II diabetes mellitus, and diseases involving abnormally high hepatic glucose production similar to Type II diabetes mellitus, comprising the administration of an effective amount of a compound or composition described herein.

Another aspect of the present invention provides a composition comprising a ribonucleoprotein described herein (e.g., a RNP comprising a site-directed modifying polypeptide described herein, such as a Cas9 RNP or a Cpf1 RNP) and an endosomal escape agent. In some embodiments, the ribonucleoprotein (e.g., a RNP comprising a site-directed modifying polypeptide described herein, such as a Cas9 RNP or a Cpf1 RNP) or the endosomal escape agent is conjugated to an antibody. In some embodiments, the ribonucleoprotein (e.g., a RNP comprising a site-directed modifying polypeptide described herein, such as a Cas9 RNP or a Cpf1 RNP) is modified to include glycosylation sites. In some embodiments, the ribonucleoprotein (e.g., a RNP comprising a site-directed modifying polypeptide described herein, such as a Cas9 RNP or a Cpf1 RNP) is modified to include transduction or translocation domains.

Another aspect of the present invention provides a composition comprising a Cas9 ribonucleoprotein and an endosomal escape agent. In some embodiments, the Cas9 ribonucleoprotein or the endosomal escape agent is conjugated to an antibody. In some embodiments, the Cas9 ribonucleoprotein is modified to include glycosylation sites. In some embodiments, the Cas9 ribonucleoprotein is modified to include transduction or translocation domains.

Another aspect of the present invention includes pharmaceutical compositions comprising (i) a composition comprising a Cas9 ribonucleoprotein and an endosomal escape agent, as described herein; and (ii) a pharmaceutically acceptable excipient, diluent, or carrier.

Another aspect of the present invention provides a composition comprising a Cpf1 ribonucleoprotein and an endosomal escape agent. In some embodiments, the Cpf1 ribonucleoprotein or the endosomal escape agent is conjugated to an antibody. In some embodiments, the Cpf1 ribonucleoprotein is modified to include glycosylation sites. In some embodiments, the Cpf1 ribonucleoprotein is modified to include transduction or translocation domains.

Another aspect of the present invention includes pharmaceutical compositions comprising (i) a composition comprising a Cpf1 ribonucleoprotein and an endosomal escape agent, as described herein; and (ii) a pharmaceutically acceptable excipient, diluent, or carrier.

Another aspect of the present invention includes a method for treating a disease or condition selected from, but not limited to, blood disorders, cell dysregulation or oncology diseases and disorders, inflammation and immune related diseases, metabolic, liver, kidney and protein diseases and disorders, muscular or skeletal diseases, neurological and neuronal diseases and disorders, and ocular diseases and disorders, comprising the administration of a composition comprising a ribonucleoprotein described herein (e.g., a RNP comprising a site-directed modifying polypeptide described herein, such as a Cas9 RNP or a Cpf1 RNP) and an endosomal escape agent described herein.

Another aspect of the present invention includes a method for selectively modulating transcription of a target DNA in a subject, said DNA being associated with a disease or condition selected from, but not limited to, blood disorders, cell dysregulation or oncology diseases and disorders, inflammation and immune related diseases, metabolic, liver, kidney and protein diseases and disorders, muscular or skeletal diseases, neurological and neuronal diseases and disorders, and ocular diseases and disorders, comprising the administration of a composition comprising a ribonucleoprotein described herein (e.g., a RNP comprising a site-directed modifying polypeptide described herein, such as a Cas9 RNP or a Cpf1 RNP) and an endosomal escape agent described herein.

Another aspect of the present invention includes a method for editing a nucleic acid molecule encoding a protein associated with a disease or condition selected from, but not limited to, blood disorders, cell dysregulation or oncology diseases and disorders, inflammation and immune related diseases, metabolic, liver, kidney and protein diseases and disorders, muscular or skeletal diseases, neurological and neuronal diseases and disorders, and ocular diseases and disorders, comprising the administration of a composition comprising a ribonucleoprotein described herein (e.g., a RNP comprising a site-directed modifying polypeptide described herein, such as a Cas9 RNP or a Cpf1 RNP) and an endosomal escape agent described herein.

Another aspect of the present invention includes a method for modulating the expression level of at least one gene product associated with a disease or condition selected from, but not limited to, blood disorders, cell dysregulation or oncology diseases and disorders, inflammation and immune related diseases, metabolic, liver, kidney and protein diseases and disorders, muscular or skeletal diseases, neurological and neuronal diseases and disorders, and ocular diseases and disorders, comprising the administration of a composition comprising a ribonucleoprotein described herein (e.g., a RNP comprising a site-directed modifying polypeptide described herein, such as a Cas9 RNP or a Cpf1 RNP) and an endosomal escape agent described herein Another aspect of the present invention provides a method for site-specific endonucleolytic cleavage of a single-stranded RNA (ssRNA), comprising the administration of a compound, a RNP, or a composition described herein, in the presence of a protospacer adjacent motif (PAM)-presenting oligonucleotides (PAMmer).

Another aspect of the present invention provides a method for site-specific endonucleolytic cleavage of a single-stranded RNA (ssRNA), comprising the administration of a compound or RNP, which comprises a CRISPR/Cas Type III-B Cmr complex, or a composition thereof, as described herein.

It is to be understood that both the foregoing general description and the following detailed description are exemplary and explanatory only and are not restrictive of the invention, as claimed.

BRIEF DESCRIPTION OF THE DRAWINGS

FIG. 6 provides exemplary Cas9, Cas9 construct, RNP, RNP construct and Cpf1 sequences.

DETAILED DESCRIPTION

Definitions

Figure 1:
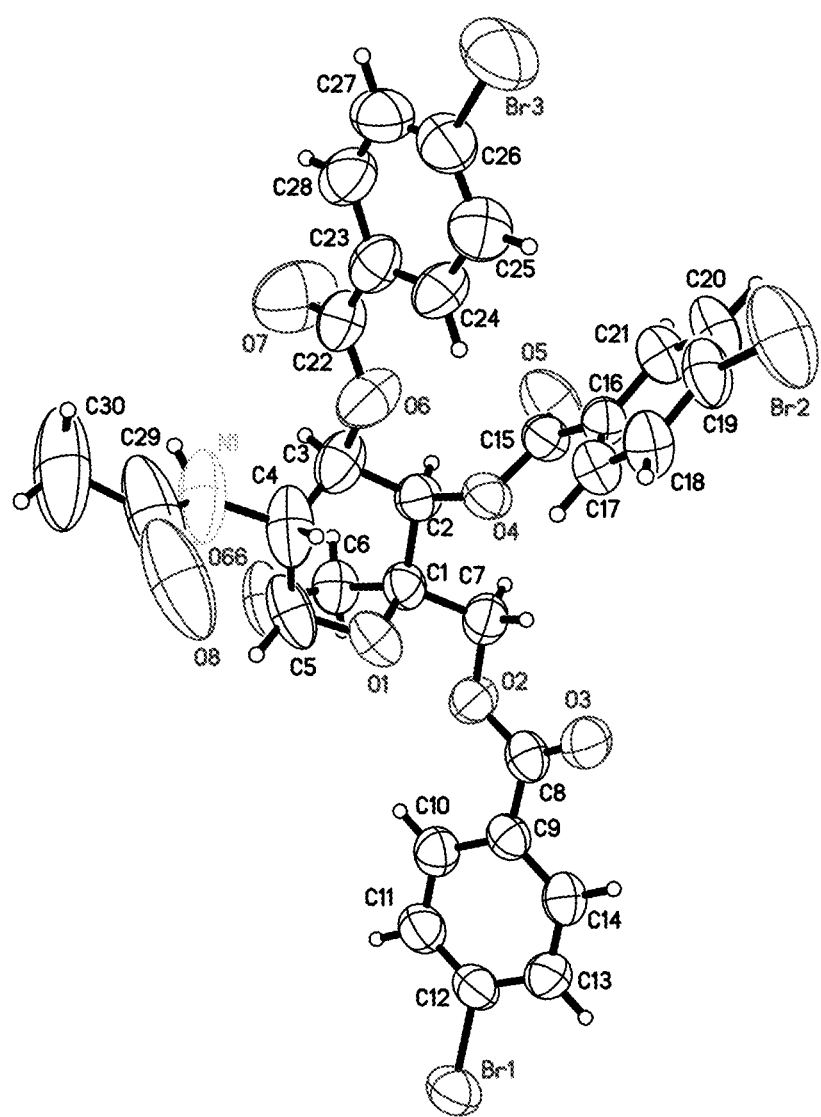
FIG. 1 represents the refined crystal structure for the compound 23 which was plotted using the SHELXTL plotting package with ellipsoids drawn at 50% confidence level.

The present invention may be understood even more readily by reference to the following detailed description of exemplary embodiments of the invention and the examples included therein.

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present invention are generally performed, unless otherwise indicated, according to conventional methods well known in the art and as described in various general and more specific references that are cited and discussed throughout this specification. See, e.g. "Principles of Neural Science," McGraw-Hill Medical, New York, N.Y. (2000); Motulsky, "Intuitive Biostatistics," Oxford University Press, Inc. (1995); Lodish et al., "Molecular Cell Biology, 4th ed.," W. H. Freeman & Co., New York (2000); Griffiths et al., "Introduction to Genetic Analysis, 7th ed.," W. H. Freeman & Co., N.Y. (1999); and Gilbert et al., "Developmental Biology, 6th ed.," Sinauer Associates, Inc., Sunderland, Mass. (2000).

Chemistry terms used herein are used according to conventional usage in the art, as exemplified by "The McGraw-Hill Dictionary of Chemical Terms," Parker S., Ed., McGraw-Hill, San Francisco, Calif. (1985).

All of the publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to". "Including" and "including but not limited to" are used interchangeably.

Each embodiment of the invention described herein may be taken alone or in combination with one or more other embodiments of the invention.

The term "agent" is used herein to denote a chemical compound (such as an organic or inorganic compound (including, such as, a compound of the present invention), a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents which are known with respect to structure, and those which are not known with respect to structure.

A "patient," "subject," or "individual" are used interchangeably and refer to either a human or a non-human animal. These terms include mammals, such as humans, primates, livestock animals (including bovine, porcine, etc.), companion animals (e.g., canine, feline, etc.) and rodents (e.g., mice and rats).

Before the present compounds, compositions and methods are disclosed and described, it is to be understood that this invention is not limited to specific synthetic methods of making that may of course vary. It is also to be understood that the terminology used herein is for the purpose of describing particular embodiments only and is not intended to be limiting. The plural and singular should be treated as interchangeable, other than the indication of number:

As used herein, the term "alkyl" refers to a hydrocarbon radical of the general formula $C_nH_{2n+1}$. The alkane radical may be straight or branched. For example, the term "($C_1$-$C_6$)alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, alkylsulfonyl, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoroethyl, 1,1-difluoroethyl and the like).

Similarly, "alkylene" refers to a divalent hydrocarbon radical of the general formula $C_nH_{2n}$ which may be straight or branched.

The term "alkenyl" refers to a univalent unsaturated hydrocarbon radical having one or more carbon-carbon double bonds. The alkenyl moiety may be straight or branched. Exemplary alkenyl groups include ethylenyl. "Alkenylene" as used herein refers to a divalent unsaturated hydrocarbon radical having one or more carbon-carbon double bonds and which may be straight or branched.

The term "alkynyl" refers to a univalent unsaturated hydrocarbon radical having one or more carbon-carbon triple bonds. The alkynyl moiety may be straight or branched.

"Alkynylene" as used herein refers to a divalent unsaturated hydrocarbon radical having one or more carbon-carbon triple bonds which may be straight or branched.

The term "aryl" means a carbocyclic aromatic system containing one, two or three rings wherein such rings may be fused. If the rings are fused, one of the rings must be fully unsaturated and the fused ring(s) may be fully saturated, partially unsaturated or fully unsaturated. The term "fused" means that a second ring is present (i.e., attached or formed) by having two adjacent atoms in common (i.e., shared) with the first ring. The term "fused" is equivalent to the term "condensed". The term "aryl" embraces aromatic radicals such as benzyl, phenyl, naphthyl, tetrahydronaphthyl, indanyl, biphenyl, benzo[b][1,4]oxazin-3(4H)-onyl, 2,3-dihydro-1H indenyl, and 1,2,3,4-tetrahydronaphthalenyl.

The term "cycloalkyl" refers to nonaromatic rings that are fully hydrogenated and may exist as a single ring, bicyclic ring or a spiro ring. Unless specified otherwise, the carbocyclic ring is generally a 3- to 20-membered ring. For example, cycloalkyl include groups such as cyclopropyl, cyclobutyl, cyclopentyl, cyclohexyl, cyclohexenyl, norbornyl (bicyclo[2.2.1]heptyl), bicyclo[2.2.2]octyl, and the like.

The term "heteroaryl" means an aromatic carbocyclic system containing one, two, three or four heteroatoms selected independently from oxygen, nitrogen and sulfur and having one, two or three rings wherein such rings may be fused, wherein fused is defined above. The term "heteroaryl" includes but is not limited to furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridiazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

The term "drug delivery system" refers to a means of delivering a therapeutically effective amount of a ligand and includes, but is not limited to polymers such as PEG (Poly(ethylene glycol) methyl ether), PEG-PLA (Poly(ethylene glycol) methyl ether-poly(D,L lactide)), PEG-PLGA (Poly(ethylene glycol) methyl ether-poly(lactide-co-glycolide)), and PEG-PCL (Poly(ethylene glycol)-poly(ε-caprolactone) methyl ether), Quantum Dots (Q dots), liposomes, immuno-liposomes, micelles, nanoparticles, and nanogels. Exemplary drug delivery systems are described in Tiwari, G., "Drug Delivery Systems: an Updated Review", Int J Pharm Investig 2 (1) p. 2-11 (January 2012), which is incorporated herein by reference for all purposes.

The term "small molecule" means an organic compound having a molecular weight between 100 and 2,000 daltons, including but not limited to synthetic compounds and natural products.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv) and domain antibodies), and fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) that contain hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al, 1997, J. Molec. Biol. 273:927-948). As used herein, a CDR may refer to CDRs defined by either approach or by a combination of both approaches.

As known in the art a "constant region" of an antibody refers to the constant region of the antibody light chain or the constant region of the antibody heavy chain, either alone or in combination.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

As used herein, "pharmaceutically acceptable carrier" or "pharmaceutical acceptable excipient" includes any material which, when combined with an active ingredient, allows the ingredient to retain biological activity and is non-reactive with the subject's immune system.

Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy, 20th Ed., Mack Publishing, 2000).

The term "compounds of the present invention" (unless specifically identified otherwise) refer to compounds of any of the Formulas described herein, and all enantiomers, tautomers and isotopically labeled compounds thereof. Hydrates and solvates of the compounds of the present invention are considered compositions of the present invention, wherein the compound is in association with water or solvent, respectively. The compounds may also exist in one or more crystalline states, i.e. as co-crystals, polymorphs, or they may exist as amorphous solids. All such forms are encompassed by the claims.

The term "linker" is a chemical group that connects one or more other chemical groups via at least one covalent bond. The linker may include one or more spacing groups including, but not limited to alkylene, alkenylene, alkynylene, alkyl, alkenyl, alkynyl, alkoxy, aryl, heteroaryl, aralkyl, aralkenyl, aralkynyl and the like. The linker may be charge neutral, charge positive or charge negative. In addition, the linker may be cleavable such that the linker's covalent bond that connects the linker to another chemical group within the linker or that bonds to the ligand may be broken or cleaved under certain conditions (see for example H. Bruyere, et al., "Tuning the pH Sensitivities of Orthoester based compounds for Drug Delivery Applications by Simple Chemical Modification", Bioorganic and Medicinal Chemistry Letters, 20, 2200 (2010) and A. A. Kislukhin et al., "Degradable Conjugates from Oxanorbornadiene Reagents", Journal of the American Chemical Society, 134, 6491 (2012). These conditions include pH, temperature, salt concentration, a catalyst, or an enzyme. (G. M. Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chemistry, 13, 855 (2002), G. Leriche et al., "Cleavable Linkers in Chemical Biology", Bioorganic and Medicinal Chemistry, 20, 571 (2012), C. P. R. Hackenberger et al., "Chemoselective Ligation and Modification Strategies for Peptides and Proteins", Angewandte Chemie International Edition, 47, 10030 (2008); D. M. Patterson et al., "Finding the Right (Bioorthogonal) Chemistry", ACS Chemical Biology, 9, 592 (2014); C. A. Blencowe et al., "Self-immolative Linkers in Polymeric Delivery Systems", Polymer Chemistry, 2, 773 (2011). The disclosures of the above publications are incorporated herein by reference in their entireties for all purposes.

In some embodiments, the linker is cleavable under intracellular conditions, such that the cleavage of the linker releases the ligand unit from the compound of Formulae A and B in the intracellular environment. In some embodiments, the linker is cleavable by a cleaving agent that is present in the intracellular environment (e.g. within a lysosome or endosome or caveolus). One example of a cleavable linker is an enzymatically cleaved linker i.e., a peptidyl linker that is cleaved by an intracellular peptidase or protease enzyme, including but not limited to, a lysosomal or endosomal protease. In some embodiments, the peptidyl linker is at least two amino acids long or at least three amino acids long. Enzymatic cleaving agents include cathepsins B and D and plasmin, all of which are known to hydrolyze dipeptide drug derivatives resulting in the release of active drug inside the target cells (see Dubowchik, Gene M. et al., Cathepsin B-Labile Dipeptide Linkers for Lysosomal Release of Doxorubicin, Bioconjugate Chem. 2002, 13, 855-869). Such linkers include peptides and dipeptides including those described in the above publications which are incorporated herein by reference in their entireties for all purposes.

Other cleavable linkers may be cleaved by nucleophilic/basic reagents, reducing reagents, photo-irradiation, and electrophilic/acidic reagents. See, e.g., Leriche, Geoffray, et al., Cleavable Linkers in Chemical Biology, Bioorganic & Medicinal Chemistry 20 (2012) 571-582.

In yet another embodiment, the linker unit is not cleavable and the drug is released by the compound of Formulae A and B by degradation. This process is often referred to as self-immolative elimination, which works by cyclization or electronic cascade reactions driven by entropy and thermodynamics. One example of a noncleavable linker is a polysubstituted, electron-rich aromatic species with an amino or hydroxyl group or other electron-donating group that is conjugated to a leaving group at a benzylic position (see Blencowe, Christopher A. et al., Self-immolative Linkers in Polymeric Delivery Systems, Polymer Chemistry, 2011, 2, 773-790). Self-immolative elimination linkers include, but are not limited to, aniline based linkers, N-hydroxyaniline based linkers, phenol based linkers, 1,8 elimination based linkers, cyclization based linkers (i.e., hydroxyl based linkers, amino based linkers and thiol based linkers), polymer-dendron conjugates, and polymer conjugates (i.e., N-(2-hydroxypropyl)-methacrylamide (HPMA) polymer conjugates, poly-ethylene glycol (PEG) polymer conjugates) (see I. Tranoy-Opalinski, et al., Design of Self-Immolative Linkers for Tumour-Activated Prodrug Therapy, Anti-Cancer Agents in Medicinal Chemistry, 2008, 8, 618-637; Blencowe, Christopher A. et al., Self-immolative Linkers in Polymeric Delivery Systems, Polymer Chemistry, 2011, 2, 773-790).

Typically, the linker is not substantially cleaved in the extracellular environment. As used herein, "not substantially cleaved in the extracellular environment" in the context of a linker means that no more than 20%, typically no more than about 15%, more typically no more than about 10%, and even more typically no more than about 5%, no more than about 3%, or no more than about 1% of the linkers in a sample of compound of Formulae A and B which includes the X—Y group, are cleaved when the compound is present in an extracellular environment (e.g., plasma). Whether a linker is not substantially cleaved in the extracellular environment can be determined for example by incubating the compound with plasma for a predetermined time period up to 24 hours (e.g. 2, 4, 8, 16 or 24 hours) and then quantitating the amount of free ligand present in the plasma.

The linker may be a monovalent, bivalent or trivalent branched linker. In one embodiment, the linker is a disulfide bridge. In another embodiment, the linker is any of structures L1-L10, which show the linkage to Y and Z (wherein Y and Z represent groups as presented in the summary):

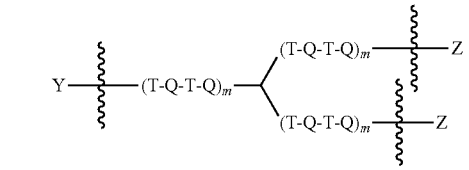
L1

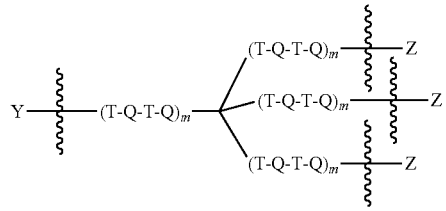
L2

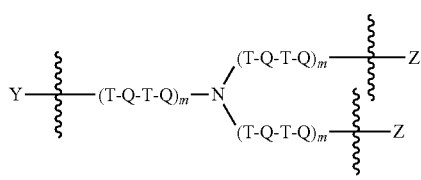
L3

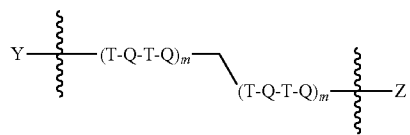
L4

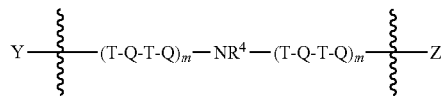
L5

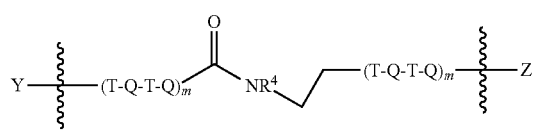
L6

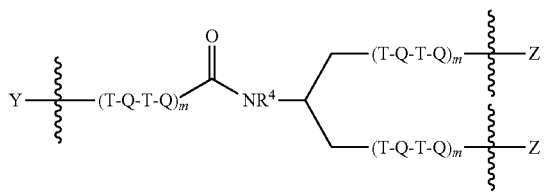
L7

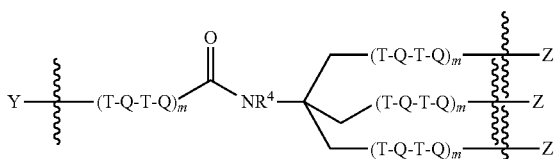
L8

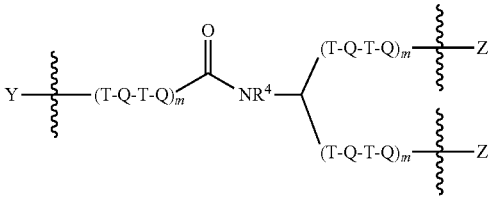
L9

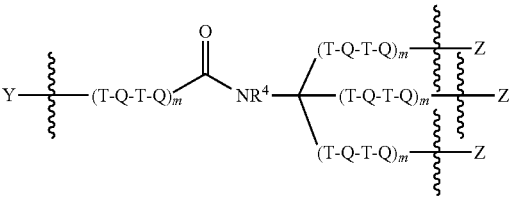
L10 wherein each T is independently absent or is alkylene, alkenylene, or alkynylene, wherein one or more —$CH_2$— groups of the alkylene, alkenylene, or alkynylene may each independently be replaced with a heteroatom group independently selected from —O—, —S—, and —N($R^4$)— wherein the heteroatom groups are separated by at least 2 carbon atoms, wherein said alkylene, alkenylene, and alkynylene may each be independently substituted with one or more halo atoms;

each Q is independently absent or is C(O), C(O)—$NR^4$, $NR^4$—C(O), O—C(O)—$NR^4$, $NR^4$—C(O)—O, —$CH_2$—, a heteroaryl, or a heteroatom group selected from O, S, S—S, S(O), S(O)$_2$, and $NR^4$, wherein at least two carbon atoms separate the heteroatom groups O, S, S—S, S(O), S(O)$_2$ and $NR^4$ from any other heteroatom group;

each $R^4$ is independently —H, —($C_1$-$C_{20}$)alkyl, or ($C_3$-$C_6$) cycloalkyl wherein one to six —$CH_2$— groups of the alkyl or cycloalkyl separated by at least two carbon atoms may be replaced with —O—, —S—, or —N($R^4$)—, and —$CH_3$ of the alkyl may be replaced with a heteroatom group selected from —N($R^4$)$_2$, —$OR^4$, and —S($R^4$) wherein the heteroatom groups are separated by at least 2 carbon atoms; and wherein the alkyl and cycloalkyl may be substituted with halo atoms; and each m is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. Each T and each Q of each (T-Q-T-Q) is independently selected.

In one embodiment, Q is a heteroaryl selected from 1H-1,2,3-triazolyl, pyridinyl, and 1,2,3,4-tetrazolyl.

The linker length could be adjusted by the value of n to optimize accessibility to the target molecule. In some cases, the optimal length of the linker could be designed by analyzing the drug-target interaction site or the space needed to adequately cleave the compound of Formulas (A) and (B).

By "genetically derived material" is meant to include proteins, endonucleases, and CRISPR/Cas from class I, II, or III (e.g., a Cas9 protein), plasmids (e.g., a plasmid that encodes the Cas9 protein or a cas9 protein and a guide sequence), RNA sequences such as mRNA, siRNA sequences and Cas9 ribonucleoproteins.

A "site-directed modifying polypeptide" as used herein refers to a CRISPR/Cas endonuclease or a derivative thereof (from class I, II, or III). In some embodiments, the site-directed modifying polypeptide is a Class 2 CRISPR/Cas endonuclease or a derivative thereof. In some embodiments, the site-directed modifying polypeptide is a type II CRISPR/Cas endonuclease, such as Cas9, or a derivative thereof. In some embodiments, the site-directed modifying polypeptide is a type V CRISPR/Cas endonuclease, such as Cpf1, or a derivative thereof. In some embodiments, the site-directed modifying polypeptide is a type III CRISPR/Cas endonuclease. In some embodiments, the site-directed modifying polypeptide is a Type III-B Cmr complex, e.g., a Type III-B Cmr complex derived from *Pyrococcus furiosus*, *Sulfolobus solfataricus*, or *Therms thermophilus*. See, e.g., Hale, C. R. et al. *Genes & Development*, 2014, 28:2432-2443, and Makarova K. S. et al. *Nature Reviews Microbiology*, 2015, 13, 1-15.

A "derivative" refers to any polypeptide having a substantially identical amino acid sequence to the naturally occurring polypeptide, in which one or more amino acids have been modified at side groups of the amino acids. The term "derivative" shall also include any polypeptide which has one or more amino acids deleted from, added to, or substituted from the natural polypeptide sequence, but which retains a substantial amino acid sequence homology to the natural sequence. A substantial sequence homology is any homology greater than 50 percent. "Derivative" shall also include fusion Cas9-fluorescent polypeptide fusion proteins such as Cas9/mcherry, Cas9/transient domains, Cas9/endosomal escape agent and Cas9/NLS. "Derivative" shall also include fusion Cpf1-fluorescent polypeptide fusion proteins such as Cpf1/mcherry, Cpf1/transient domains, Cpf1/endosomal escape agent and Cpf1/NLS. Moreover, "derivative" shall also include mutations such as glycosylation site mutations on the polypeptide.

A "ribonucleoprotein" or "RNP" or "RNP construct" refers to an association that combines ribonucleic acid (RNA) and protein. In some embodiments, a ribonucleoprotein comprises a site-directed modifying polypeptide as described herein. In some embodiments, the ribonucleoprotein comprises a Cas9 protein. In some embodiments, the ribonucleoprotein comprises a Cpf1 protein.

A "Cas9 ribonucleoprotein" or "Cas9 RNP" or "Cas9 RNP construct" may comprise two linked or associated elements: (1) a first element comprising a recognition element comprising either a dual guide RNA sequence comprising a CRISPR RNA (crRNA) and a trans-activating crRNA (tracrRNA), or a single guide RNA sequence (sgRNA), wherein when expressed, the guide sequence directs sequence-specific binding of the Cas9 ribonucleoprotein to a target sequence, and the first element optionally comprises one or more endosomal escape agents and (2) a second element comprising a Cas9 construct wherein the Cas9 construct comprises a Cas9 protein and optionally one or more nuclear localization sequences (NLSs) and optionally one or more fluorescent proteins, and one or more endosomal escape agents; wherein said first element is associated with said second element. Wherein when the present compounds of formula A-1, A-2, A-3 or B are present, said compounds are conjugated to either the first or second element of the RNP construct.

A "Cpf1 ribonucleoprotein" comprising: (1) a first element comprising a recognition element comprising a guide sequence, wherein when expressed, the guide sequence directs sequence-specific binding of the Cpf1 ribonucleoprotein to a target sequence, and the first element optionally comprises one or more endosomal escape agents, and (2) a second element comprising a Cpf1 construct wherein the Cpf1 construct comprises a Cpf1 protein and optionally one or more nuclear localization sequences (NLSs) and optionally one or more fluorescent proteins, and one or more endosomal escape agents; wherein said first element is associated with said second element. Wherein when the present compounds of formula A-1, A-2, A-3 or B are present, said compounds are conjugated to either the first or second element of the RNP construct.

In some embodiments of a ribonucleoprotein, the guide sequence directs sequence-specific binding of the ribonucleoprotein to a target sequence in a cell. The cell may be eukaryotic or prokaryotic. In some embodiments, the second element comprises about 1, 2, 3, 4, 5, 6, 7, 8, 9, or 10 NLSs at or near the amino-terminus, the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies.

A "guide RNA sequence" is any polynucleotide sequence having sufficient complementarity with a target polynucleotide sequence to hybridize with the target sequence and direct sequence-specific binding of a ribonucleoprotein described herein to the target sequence. In some embodiments, a "guide RNA sequence" is any polynucleotide sequence having (i) a portion with sufficient complementarity with a target polynucleotide sequence to hybridize with the target sequence and (ii) a portion that binds to and directs a site-directed modifying protein (e.g., Cas9, cpf1, etc., as described herein) to the target sequence. See, e.g., Jinek et al., Science 2012; Briner et al., Mol. Cell 2014. Exemplary Cas9 proteins, Cas9 guide RNA sequences, plasmids, and ribonucleoproteins are described in US20140068797, published on Mar. 6, 2014; US2015031134, published on Jan. 29, 2015; and US2015079681, published on Mar. 19, 2015, all of which are incorporated herein in their entireties for all purposes.

In some embodiments, the guide sequence comprises at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 nucleotides where the degree of complementarity between the guide sequence and its corresponding target sequence, when optimally aligned using a suitable alignment algorithm, is about or more than about 50%, 60%, 70%, 75%, 80%, 85%, 86%, 87%, 88%, 89%, 90%, 91%, 92%, 93%, 94%, 95%, 96%, 97%, 98%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net).

Cas9 protein may be derived from *S. aureus, S. pneumoniae, S. pyogenes, S. thermophilus, N. meningitidis* or *A. ebreus*. In some embodiments, the Cas9 protein exhibits conserved architecture having an HNH homing endonuclease domain and a split RuvC/RNaseH endonuclease domain whereby each Cas9 protein shares 4 primary motifs: motifs 1, 2, and 4, which are RuvC like motifs and motif 3, which is an HNH motif. For *Streptococcus pyogenes* (SEQ ID No:8), motifs 1 is SEQ ID NO:260, motif 2 is SEQ ID NO:261, motif 3 is SEQ ID NO:262, and motif 4 is SEQ ID NO:263. Therefore, by "Cas9 protein sequence" or "Cas9 protein" is meant a polypeptide which comprises an amino acid sequence having at least 4 motifs within the sequence which have at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to the motifs 1, 2, 3, and 4 of the Cas9 amino acid sequence of any of SEQ ID NOs:260-263, or to the corresponding portions in any of the amino acid sequences set forth in SEQ ID NOs:1-829. In another embodiment, the Cas9 amino acid sequence is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to the amino acids at positions 7 to 166 or 731 to 1003 of SEQ ID NO:8 or the corresponding amino acids of those set forth in SEQ ID NOs:1-7, 9-829.

In some embodiments, the Cas9 protein is selected from: *S. pyogenes* Cas9 (wild type) (SEQ ID NO:848), *S. pyogenes* Cas9-mutation M1C (SEQ ID NO:849), *S. pyogenes* Cas9-mutation M1C & C80S (SEQ ID NOs:850), *S. pyogenes* Cas9 nickase-mutation D10A (SEQ ID NO:851), *S. pyogenes* Cas9 nickase-mutation H840A (SEQ ID NO:852), *S. pyogenes* Cas9 nickase-mutations E923P & T924P (SEQ ID NO:853), *Acidovorax ebreus* Cas9 (SEQ ID NO:854), Acid mine drainage bacteria Ga0052161_JGI Cas9 (SEQ ID NO:855), *S. pyogenes* Cas9 null-mutation D10A& H840A (SEQ ID NO:1027), and Uranium mine bacteria FW106_JGI Cas9 (SEQ ID NO:856).

Cpf1 protein may be derived from *A. sp.*, *L. bacterium*, *P. macacae*, and *P. disiens*. In some embodiments, the Cpf1 protein is selected from, but is not limited to, A. sp Cpf1 (SEQ ID NO:857), *L. bacterium* Cpf1 (SEQ ID NO:858), *P. macacae* Cpf1 (SEQ ID NO:859), *P. disiens* Cpf1 (SEQ ID NO:860). In some embodiments, A Cpf1 protein can comprise an amino acid sequence having at least 75%, at least 80%, at least 85%, at least 90%, at least 95%, at least 98%, at least 99%, or 100%, amino acid sequence identity to any one of SEQ ID NOs:857-860.

"Nuclear localization sequence" (NLS) refers to an amino acid sequence which assists the ribonucleoprotein of the present invention, e.g., a Cas-9 ribonucleoprotein to enter the nucleus of a eukaryotic cell. Consequently, an NLS typically comprises one or more short sequences of positively charged lysines or arginines exposed on the protein surface. Exemplary NLSs include, but are not limited to, an NLS sequence derived from: the NLS of the SV40 virus large T-antigen, having the amino acid sequence PKK-KRKV (SEQ ID NO: 830); the NLS from nucleoplasmin (e.g. the nucleoplasmin bipartite NLS with the sequence KRPAATKKAGQAKKKK (SEQ ID NO: 831); the c-myc NLS having the amino acid sequence PAAKRVKLD (SEQ ID NO: 832) or RQRRNELKRSP (SEQ ID NO: 833); the hRNPA1 M9 NLS having the sequence NQSSNFGPMKG-GNFGGRSSGPYGGGGQYFAKPRNQGGY (SEQ ID NO: 834); the sequence RMRIXFKNKGKDTAELRRRRVEVS-VELRKAKKDEQILKRRNV (wherein X is any amino acid) (SEQ ID NO: 835) of the IBB domain from importin-alpha; the sequences VSRKRPRP (SEQ ID NO: 836) and PPKKARED (SEQ ID NO: 837) of the myoma T protein; the sequence PQPKKKPL (SEQ ID NO: 838) of human p53; the sequence SALIKKKKKMAP (SEQ ID NO: 839) of mouse c-abl IV; the sequences DRLRR (SEQ ID NO: 840) and PKQKKRK (SEQ ID NO: 841) of the influenza virus NS1; the sequence RKLKKKIKKL (SEQ ID NO: 842) of the Hepatitis virus delta antigen; the sequence REKK-KFLKRR (SEQ ID NO: 843) of the mouse Mx1 protein; the sequence KRKGDEVDGVDEVAKKKSKK (SEQ ID NO: 844) of the human poly(ADP-ribose) polymerase; the sequence RKCLQAGMNLEARKTKK (SEQ ID NO: 845) of the steroid hormone receptors (human) glucocorticoid; the sequence MAPKKKRKVGIHRGVP (SEQ ID NO:1035); and the sequence PKKKRKVEDPKKKRKVD (SEQ ID NO:1036).

"Cas9 construct Y1C80S-3N-m" or "Y1C80S-3N-m" as used herein refers to *S. pyogenes* Cas9-mutation M1C & C80S (amino acid sequence)—3NLS and mCherry (SEQ ID NO:1015).

"Cas9 construct Y1C80S-2N" or "Y1C80S-2N" as used herein refers to *S. pyogenes* Cas9-mutation M1C & C80S (amino acid sequence)—2NLS (SEQ ID NO:1013).

"Cas9 construct Y53aASGPRL" or "Y53aASGPRL" as used herein refers to *S. pyogenes* Cas9-mutation M1C & C80S (amino acid sequence)—3NLS and mCherry (SEQ ID NO:1015) labeled with two copies of fragment 53a (using compound 53 as reactant, see experimental part for further details), at cysteines position 1 and 574 (addition of 2×2165 Da) via formation of disulfide bond with S atom of cysteine:

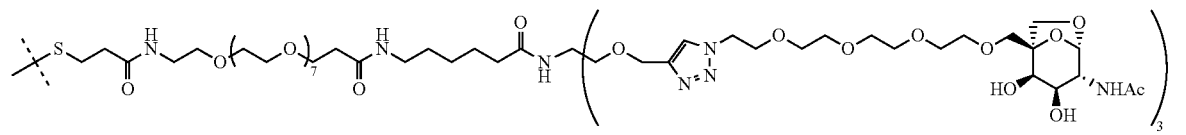

50

"RNP construct Y53aASGPRL-RNP-EMX1" or "Y53aASGPRL-RNP-EMX1" as used herein refers to a RNP construct prepared by co-incubation of (1) Cas9 construct Y53aASGPRL, and (2) EMX1 single guide sgRNA sequence (SEQ ID NO: 907), at a molar ratio of 1:1.2.

"RNP construct Y1C80S-3N-m-RNP-EMX1" or "Y1C80S-3N-m-RNP-EMX1" as used herein refers to a RNP construct prepared by co-incubation of (1) Cas9 construct Y1C80S-3N-m, and (2) EMX1 single guide sgRNA sequence (SEQ ID NO: 907), at a molar ratio of 1:1.2.

"RNP construct Y53aASGPRL-RNP-PCS4" or "Y53aASGPRL-RNP-PCS4" as used herein refers to a RNP construct prepared by co-incubation of (1) Cas9 construct Y53aASGPRL, and (2) sgRNA targeting the PCSK9 exons 4&5 locus (SEQ ID NO:906), at a molar ratio of 1:1.2.

"RNP construct Y53aASGPRL-RNP-PCS1" or "Y53aASGPRL-RNP-PCS1" as used herein refers to a RNP construct prepared by co-incubation of (1) Cas9 construct Y53aASGPRL, and (2) sgRNA targeting the PCSK9 gene (SEQ ID NO:896), at a molar ratio of 1:1.2.

An "endosomal escape agent" as used herein refers to an agent that facilitates an agent, such as compounds, DNA, siRNA, polypeptides, or ribonucleoproteins, to escape the cell endosome. Endosomal escape agents for use in the present invention include, but are not limited to, a lysosomotropic agent, a cell penetrating peptide, a fusogenic peptide, an endosomolytic peptide, a pore forming agent, and a proton sponge agent. Lysosomotropic agents are weak bases that can penetrate in lysosome as protonated form and increase the intracellular pH. Cell penetrating peptides (CPPs) are a class of diverse peptides, typically with 5-30 amino acids, that can cross the cellular membrane. Fusogenic peptides are short peptides that destabilize the phospholipid membrane. Pore-forming agents are agents, such as peptides, that induce pore formation through the membrane thereby disrupting endosome. Proton sponge agents are agents having multiple proton acceptor sites that disrupt the endosome by osmolytic action. An endosomolytic peptide may be a polyanionic peptide or peptidomimetic, or a peptide having a neutral or near neutral charge at physiological pH which shows pH-dependent membrane lytic activity and promotes endosomal lysis or leakage. In certain embodiments, the endosomolytic peptide assumes its active conformation at endosomal pH. The "active" conformation is that conformation in which the endosomolytic component promotes lysis of the endosome and/or transport of the modular composition of the invention, or its components, from the endosome to the cytoplasm of the cell.

In some embodiments, the endosomal escape agent is associated with the RNP construct. In other embodiments, the endosomal escape agent is conjugated to the first or second element of the RNP construct. In further embodiments, the endosomal escape agent is conjugated to the compound of formula A-1, A-2, A-3 or B.

Compounds

One aspect of the present invention includes compounds of Formula (A-1), (A-2), or (A-3):

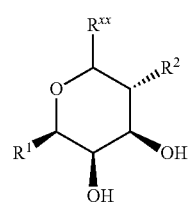

(A-1)

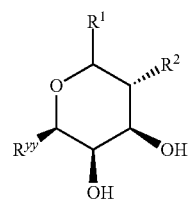

(A-2)

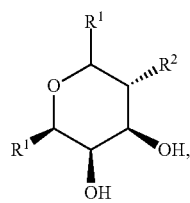

(A-3)

or a pharmaceutically acceptable salt thereof, as described in the summary.

In some embodiments of a compound of Formula (A-1), (A-2), or (A-3), the site-directed modifying polypeptide is a Cas9 protein or a Cpf1 protein. In some embodiments of a compound of Formula (A-1), (A-2), or (A-3), Y is a Cas9 ribonucleoprotein, a Cas9 protein, a single guide RNA sequence (sgRNA) or a dual guide RNA sequence comprising a CRISPR RNA (crRNA) and a trans-activating crRNA (tracrRNA); $Y^+$ is a positively charged Cas9 protein; and $Y^-$ is a negatively charged Cas9 ribonucleoprotein, a negatively charged sgRNA, or a negatively charged dual guide RNA sequence comprising a CRISPR RNA (crRNA) and a trans-activating crRNA (tracrRNA).

Another aspect of the present invention provides a compound of Formula (B):

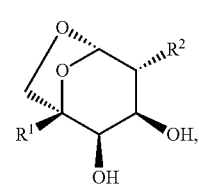

(B)

or a pharmaceutically acceptable salt thereof, as described in the summary.

In some embodiments of a compound of Formula (B), the site-directed modifying polypeptide is a Cas9 protein or a Cpf1 protein. In some embodiments of a compound of Formula (B), Y is a Cas9 ribonucleoprotein, a Cas9 protein, a single guide RNA sequence (sgRNA) or a dual guide RNA sequence comprising a CRISPR RNA (crRNA) and a trans-activating crRNA (tracrRNA); $Y^+$ is a positively charged Cas9 protein; and $Y^-$ is a negatively charged Cas9 ribonucleoprotein, a negatively charged sgRNA, or a negatively charged dual guide RNA sequence comprising a CRISPR RNA (crRNA) and a trans-activating crRNA (tracrRNA).

In some embodiments of a compound of Formula (A-1), (A-2), (A-3) or (B), $R^2$ is —NH—C(O)—$CH_3$.

In some embodiments of a compound of Formula (A-1), (A-2), (A-3) or (B), $R^1$ is —Z—$X^+Y^-$. In some embodiments, $R^1$ is —Z—$X^-Y^+$. In some embodiments, $R^1$ is —Z—X—Y. In some embodiments, $R^1$ is —Z—X—Y that is selected from the group consisting of L1-L10:

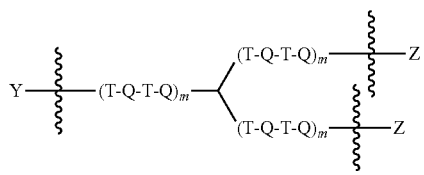

L1

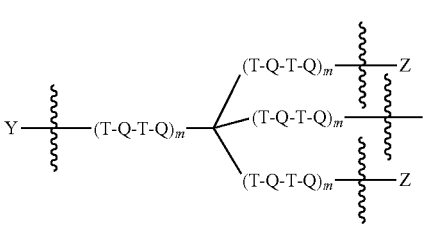

L2

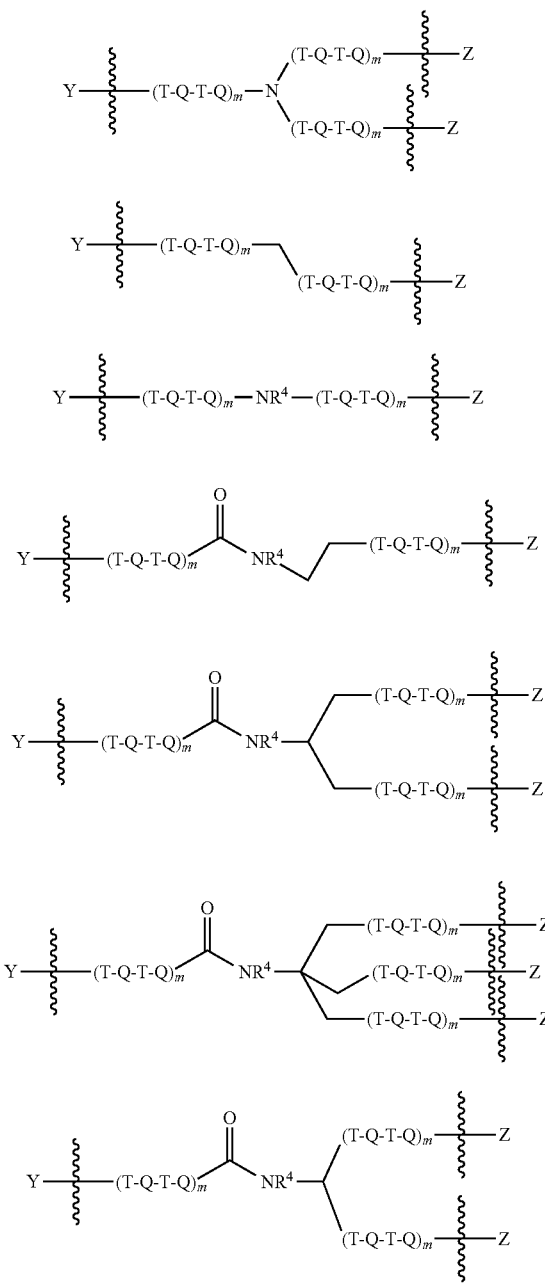

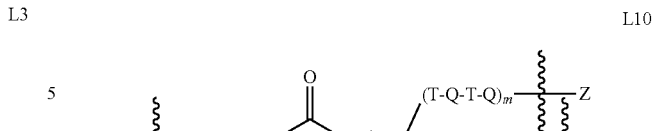

wherein each T is independently absent or is (C₁-C₁₀) alkylene, (C₂-C₁₀) alkenylene, or (C₂-C₁₀) alkynylene, wherein one or more carbon groups of said T may each independently be replaced with a heteroatom group independently selected from —O—, —S—, and —N(R⁴)— wherein the heteroatom groups are separated by at least 2 carbon atoms, wherein said alkylene, alkenylene, and alkynylene may each be independently substituted with one or more halo atoms;

each Q is independently absent or is C(O), C(O)—NR⁴, NR⁴—C(O), O—C(O)—NR⁴, NR⁴—C(O)—O, —CH₂—, a heteroaryl, or a heteroatom group selected from O, S, S—S, S(O), S(O)₂, and NR⁴, wherein at least two carbon atoms separate the heteroatom groups O, S, S—S, S(O), S(O)₂ and NR⁴ from any other heteroatom group;

each R⁴ is independently —H, —(C₁-C₂₀)alkyl, —(C₁-C₂₀) alkenyl, —(C₁-C₂₀)alkynyl, or (C₃-C₆)cycloalkyl wherein one to six —CH₂— groups of the alkyl or cycloalkyl separated by at least two carbon atoms may be replaced with —O—, —S—, or —N(R⁴)—, and —CH₃ of the alkyl may be replaced with a heteroatom group selected from —N(R⁴)₂, —OR⁴, and —S(R⁴) wherein the heteroatom groups are separated by at least 2 carbon atoms; and wherein the alkyl, alkenyl, alkynyl, and cycloalkyl may be substituted with halo atoms; and each m is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In some embodiments, Q is independently a heteroaryl selected from 1H-1,2,3-triazolyl, pyridinyl, and 1,2,3,4-tetrazolyl.

In some embodiments of a compound of Formula (A-1), (A-2), (A-3) or (B), X, X⁺, or X⁻ comprises a disulfide bond.

Another aspect of the present invention provides a compound of Formula (C-1), (C-2), (C-3) or (C4):

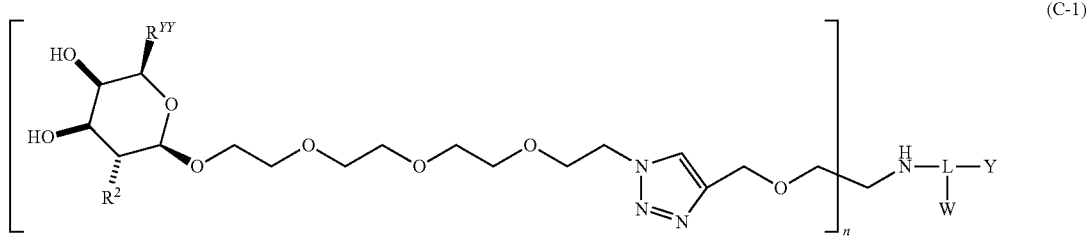

(C-1)

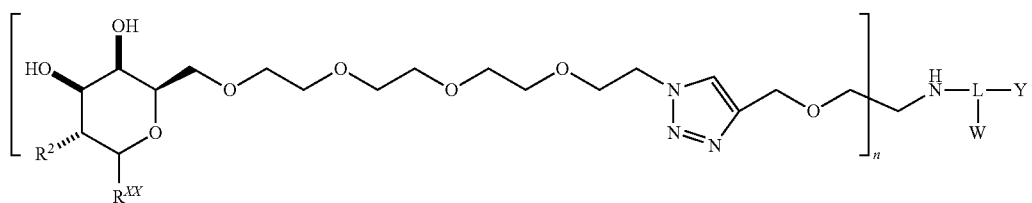

(C-2)

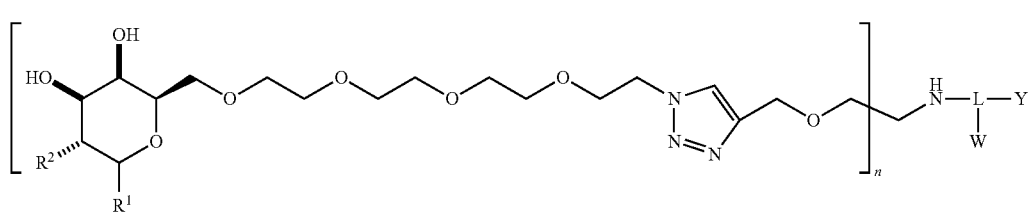

(C-3)

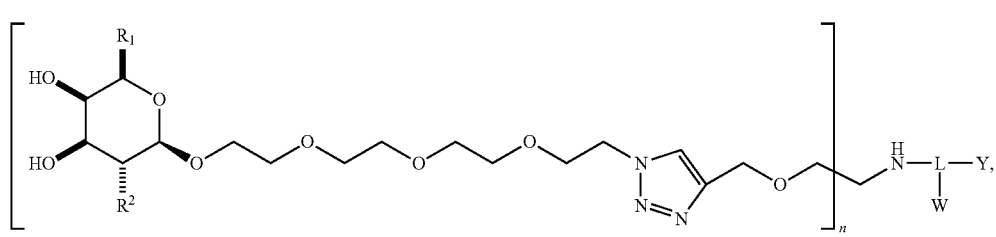

(C-4)

or a pharmaceutical acceptable salt thereof,
wherein:
n is 1, 2, or 3;
W is absent or a peptide;
L is -(T-Q-T-Q)$_m$-, wherein:
each T is independently absent or is (C$_1$-C$_{10}$) alkylene, (C$_2$-C$_{10}$) alkenylene, or (C$_2$-C$_{10}$) alkynylene, wherein one or more carbon groups of said T may each independently be replaced with a heteroatom group independently selected from —O—, —S—, and —N(R$^4$)— wherein the heteroatom groups are separated by at least 2 carbon atoms, wherein said alkylene, alkenylene, and alkynylene may each be independently substituted with one or more halo atoms;
each Q is independently absent or is C(O), C(O)—NR$^4$, NR$^4$—C(O), O—C(O)—NR$^4$, NR$^4$—C(O)—O, —CH$_2$—, a heteroaryl, or a heteroatom group selected from O, S, S—S, S(O), S(O)$_2$, and NR$^4$, wherein at least two carbon atoms separate the heteroatom groups O, S, S—S, S(O), S(O)$_2$ and NR$^4$ from any other heteroatom group;

each R$^4$ is independently —H, —(C$_1$-C$_{20}$)alkyl, —(C$_1$-C$_{20}$) alkenyl, —(C$_1$-C$_{20}$)alkynyl, or (C$_3$-C$_6$)cycloalkyl wherein one to six —CH$_2$— groups of the alkyl or cycloalkyl separated by at least two carbon atoms may be replaced with —O—, —S—, or —N(R$^4$)—, and —CH$_3$ of the alkyl may be replaced with a heteroatom group selected from —N(R$^4$)$_2$, —OR$^4$, and —S(R$^4$) wherein the heteroatom groups are separated by at least 2 carbon atoms; and wherein the alkyl, alkenyl, alkynyl, and cycloalkyl may be substituted with halo atoms;

each m is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40; and the other moieties are as defined in Formula (A-1), (A-2) or (A-3).

Another aspect of the present invention provides a compound of Formula (D-1) or (D-2):

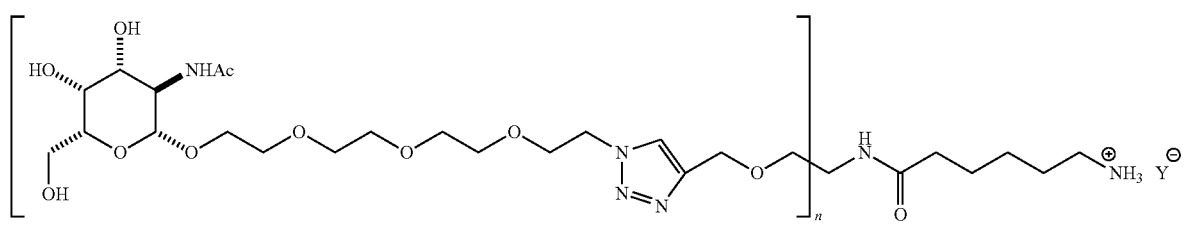

(D-1)

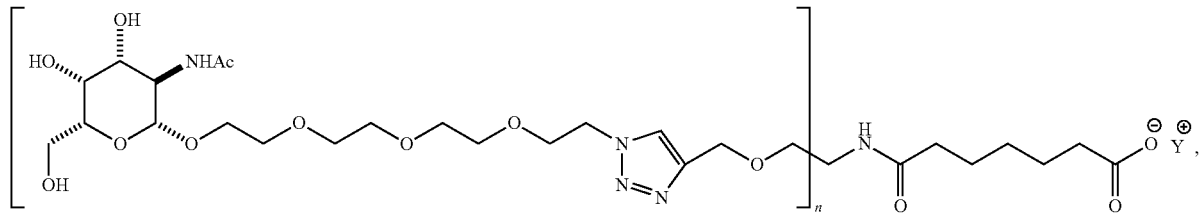

or a pharmaceutically acceptable salt thereof,
wherein Y is as defined in Formula (A-1), (A-2) or (A-3).

Another aspect of the present invention provides a compound of Formula (E):

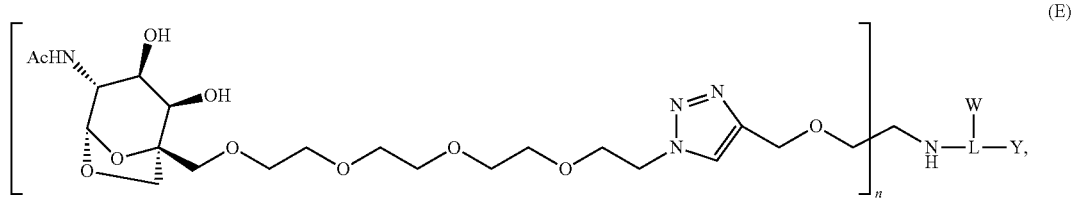

or a pharmaceutically acceptable salt thereof,
wherein:
n is 1, 2 or 3;
W is absent or is a peptide;
L is -(T-Q-T-Q)$_m$-, wherein:
each T is independently absent or is ($C_1$-$C_{10}$) alkylene, ($C_2$-$C_{10}$) alkenylene, or ($C_2$-$C_{10}$) alkynylene, wherein one or more carbon groups of said T may each independently be replaced with a heteroatom group independently selected from —O—, —S—, and —N($R^4$)— wherein the heteroatom groups are separated by at least 2 carbon atoms, wherein said alkylene, alkenylene, alkynylene, may each independently be substituted by one or more halo atoms;
each Q is independently absent or is C(O), C(O)—$NR^4$, $NR^4$—C(O), O—C(O)—$NR^4$, $NR^4$—C(O)—O, —$CH_2$—, a heteroaryl, or a heteroatom group selected from O, S, S—S, S(O), S(O)$_2$, and $NR^4$, wherein at least two carbon atoms separate the heteroatom groups O, S, S—S, S(O), S(O)$_2$ and $NR^4$ from any other heteroatom group;
each $R^4$ is independently —H, —($C_1$-$C_{20}$)alkyl, —($C_1$-$C_{20}$) alkenyl, —($C_1$-$C_{20}$)alkynyl, or ($C_3$-$C_6$)cycloalkyl wherein one to six —$CH_2$— groups of the alkyl or cycloalkyl separated by at least two carbon atoms may be replaced with —O—, —S—, or —N($R^4$)—, and —$CH_3$ of the alkyl may be replaced with a heteroatom group selected from —N($R^4$)$_2$, —$OR^4$, and —S($R^4$) wherein the heteroatom groups are separated by at least 2 carbon atoms; and wherein the alkyl, alkenyl, alkynyl, and cycloalkyl may be substituted with halo atoms;

each m is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40; and
the other moieties are as defined in Formula (B).

Another aspect of the present invention provides a compound of Formula (F-1) or (F-2):

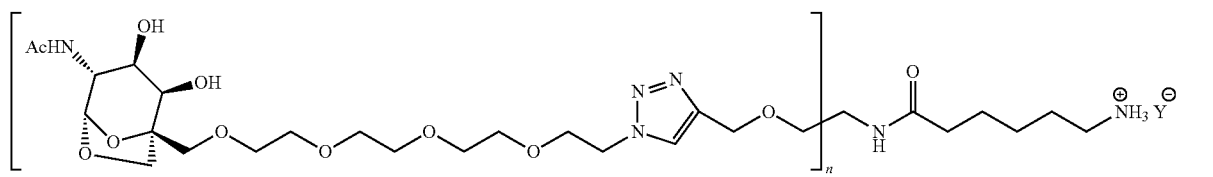

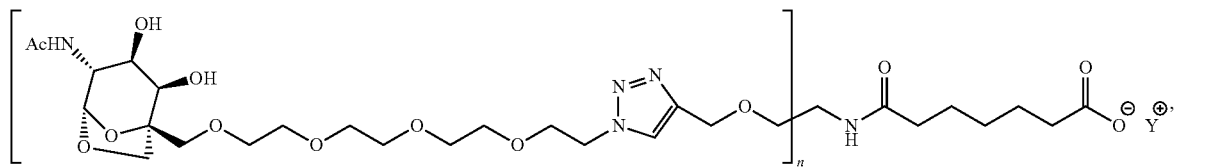

or a pharmaceutically acceptable salt thereof, and Y is as defined in Formula (B).

In some embodiments of a compound of Formula (C-1), (C-2), (C-3), (C4), (D-1), (D-2), (E), (F-1), or (F-2), n is 1. In some embodiments, n is 2. In some embodiments, n is 3.

In some embodiments of a compound of Formula (E), the compound is:

that comprises an endosomolytic peptide or a nuclear localization peptide. In some embodiments, the endosomolytic peptide may be a polyanionic, peptidomimetic or a peptide having a neutral or near-neutral charge at physiological pH, which shows pH-dependent membrane lytic activity and leads to endosome lysis or leakage. In certain embodiments, the endosomolytic peptide assumes its active conformation

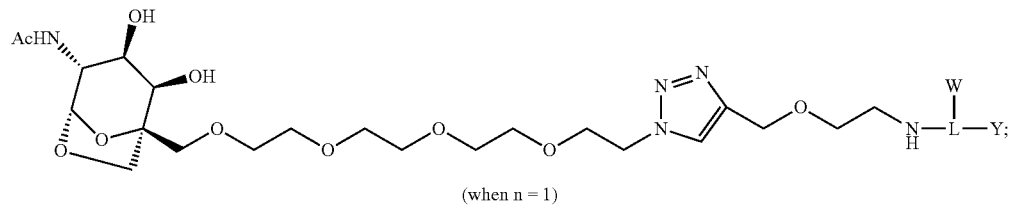
(E-1)
(when n = 1)

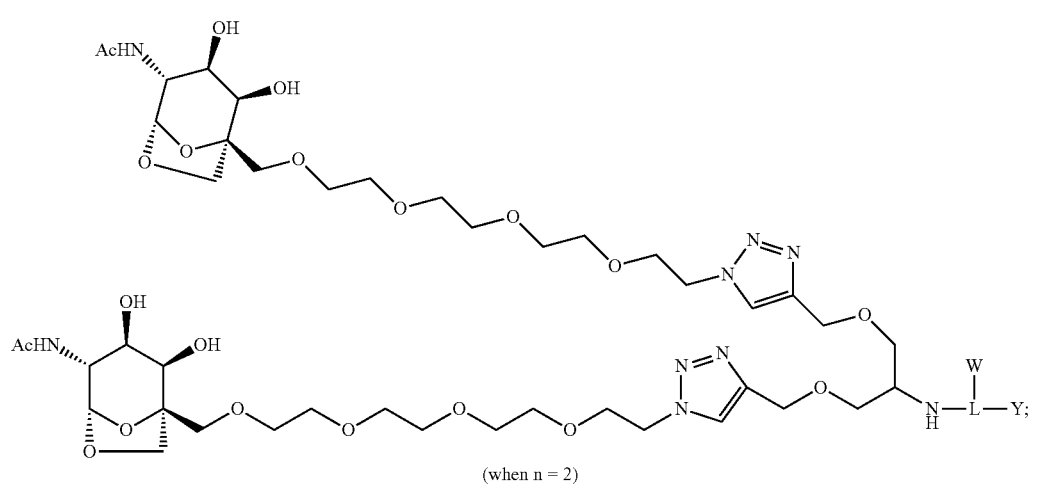
(E-2)
(when n = 2)

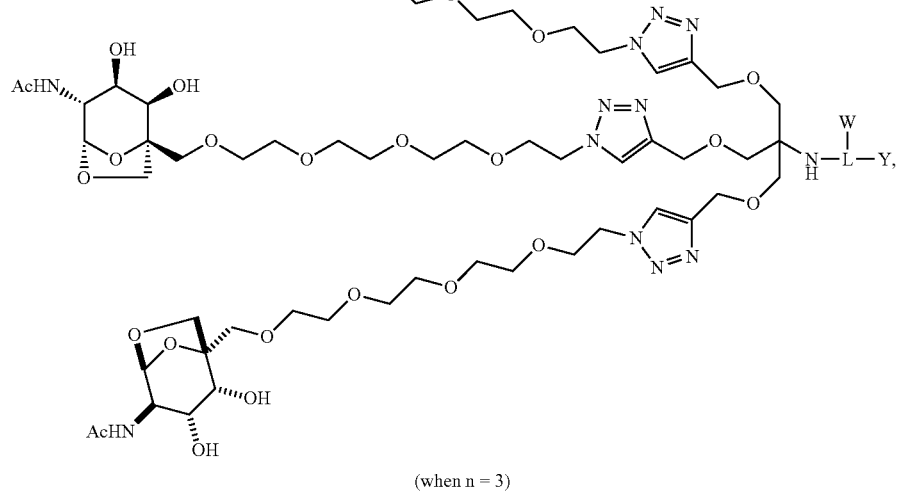
(E-3)
(when n = 3)

or a pharmaceutically acceptable salt thereof.

In some embodiments of a compound of the present invention, W is absent. In some embodiments, W is a peptide at endosomal pH. The "active" conformation is that conformation in which the endosomolytic component promotes lysis of the endosome and/or transport of the modular composition of the invention, or its components, from the endosome to the cytoplasm of the cell. See, e.g., Martin M. E. et al. Peptide-guided gene delivery, the AAPS Journal, 2007, 9(1), article 3.

In some embodiments, W is a peptide that comprises an endosomolytic histidine-rich peptide selected from, but not limited to, CHK$_6$HC (SEQ ID NO: 861); H5WYG (SEQ ID NO: 1029), GLFHAIAHFIHGGWHGLIHGWYG (SEQ ID NO: 862); and derivatives thereof.

In some embodiments, W is a peptide that comprises a fusogenic peptide selected from, but not limited to, an influenza HA-2 peptide, ppTG21 (SEQ ID NO: 1012); Aurein 1.2, GLFDIIKKIAESF (SEQ ID NO: 1023); GLF-GAIAGFIENGWEGMIDGWYG (SEQ ID NO: 863); melittin, GIGAVLKVLTTGLPALISWIKRKRQQ (SEQ ID NO: 864); tat (48-60), GRKKRRQRRRPPQ (SEQ ID NO: 865); penetratin, RQIKIWFQNRRMKWKK (SEQ ID NO: 866); transportan, GWTLNSAGYLLGKINLKALAALAKKIL (SEQ ID NO: 867); GALA peptide, WEAALAEALAEA-LAEHLAEALAEALEALAA (SEQ ID NO: 868); KALA peptide, WEAKLAKALAKALAKHLAKALAKALKA-CEA (SEQ ID NO: 869); JST-1, GLFEALLELLESLWELL-LEA (SEQ ID NO: 870); ppTG1, GLFKALLKLLK-SLWKLLLKA (SEQ ID NO: 871); ppTG20, GLFRALLRLLRSLWRLLLRA (SEQ ID NO: 872); and derivatives thereof.

In some embodiments, W is a peptide that comprises a proteasome peptide with Gly-Ala repeat, such as CWK$_{18}$(GA)$_4$ (SEQ ID NO: 873).

In some embodiments, W is a peptide that comprises a monopartite NLS including, but not limited to, the SV40 T antigen, PKKKRKV (SEQ ID NO: 830); the SV40 Vp3, KKKRK (SEQ ID NO: 874); the Adenovirus Ela, KRPRP (SEQ ID NO: 875); the human c-myc, PAAKRVKLD (SEQ ID NO: 832), RQRRNELKRSP (SEQ ID NO: 833); and derivatives thereof. In some embodiments, the peptide comprises a bipartite NLS including, but not limited to, nucleoplasmin, KRPAATKKAGQAKKKK (SEQ ID NO: 831); Xenopus N1, VRKKRKTEEESPLKDKDAKKSKQE (SEQ ID NO: 876); mouse FGF3, RLRRDAGGRGGVYEHLG-GAPRRRK (SEQ ID NO: 877); PARP, KRKGDEVDGV-DECAKKSKK (SEQ ID NO: 878), and derivatives thereof. In some embodiments, the peptide comprises a nonclassical NLS such as M9 peptide, NQSSNFGPMKGGNFGGRSS-GPYGGGGQYFAKPRNQGGY (SEQ ID NO: 834).

In some embodiments, W is a peptide that comprises a cellular targeting peptide selected from, but not limited to, RGD peptide, ICRRARGDNPDDRCT (SEQ ID NO: 1037); integrin binding peptide, PLAEIDGIELTY (SEQ ID NO: 1038); secretin, HSDGTFTSELSRLRDSARLQRLLQGLV (SEQ ID NO: 879); GE7 (from EGF), NPVVGYIGER-PQYRDL (SEQ ID NO: 880); neurotensin, ELYENK-PRRPYIL (SEQ ID NO: 881); LOX-1 binding peptide, LSIPPKA (SEQ ID NO: 882), FQTPPQL (SEQ ID NO: 883), LTPATAI (SEQ ID NO: 884); or derivatives thereof.

In some embodiments of a compound of the present invention, Y is a Cas9 ribonucleoprotein. In some embodiments, Y is a Cas9 ribonucleoprotein comprising: (1) a first element comprising a recognition element comprising either a dual guide RNA sequence comprising a CRISPR RNA (crRNA) and a trans-activating crRNA (tracrRNA), or a single guide RNA sequence (sgRNA), wherein when expressed, the guide sequence directs sequence-specific binding of the Cas9 ribonucleoprotein to a target sequence, and (2) a second element comprising a Cas9 protein and optionally one or more nuclear localization sequences (NLSs); wherein said first element is associated with said second element. In some embodiments, the target sequence is a eukaryotic cell target sequence. In other embodiments, the target sequence is a prokaryotic cell target sequence.

In some embodiments, the tracrRNA, the crRNA or the sgRNA used herein each may be optionally independently chemically modified. Suitable chemical modifications include modifications to the backbone, modifications to the base, and modifications to the sugar. Exemplary chemical modifications include, but are not limited to, use of phosphorothioate linkages (e.g., replacing one non-bridging oxygen atom on the backbone phosphate between two ribonucleotides with a sulphur atom creates a phosphorothioate (PS) linkage); use of boranophosphate linkages (e.g., the introduction of a boron atom in place of one of the non-bridging oxygen atoms to create a boron-phosphorous linkage); use of locked nucleic acid (LNA) nucleotides which contain a methylene bridge between the 2' and 4' carbons of the ribose ring; chemical modifications at the 2'-position of the ribose sugar (e.g., use of RNA analogs include 2'-O-methyl RNA, 2'-O-methoxyethyl (2'-MOE) RNA, and 2'-fluoro RNA); modification at the 4'-thio position by introducing a sulphur atom in place of oxygen attached to the 4' carbon of the ribose ring; introduction of ribo-difluorotoluyl (rF) nucleotides; and introduction of PNA or morpholino monomers.

In some embodiments, the first element of the Cas9 ribonucleoprotein comprises a dual guide RNA sequence comprising a CRISPR RNA (crRNA) and a trans-activating crRNA (tracrRNA), wherein the remainder of the compound is linked to said Cas9 ribonucleoprotein via one or more interactions each independently to the tracrRNA or to the crRNA, where the tracrRNA or the crRNA may optionally be chemically modified. In some embodiments, the tracrRNA and the crRNA are assembled to form a dual-RNA guide. In some embodiments, the tracrRNA-crRNA dual-RNA guide has the degree of complementarity between the dual RNA-guide and its corresponding target sequence, when optimally aligned using a suitable alignment algorithm, is at least 50%, 60%, 70%, 75%, 80%, 85%, 86%, 87%, 88%, 89%, 90%, 91%, 92%, 93%, 94%, 95%, 96%, 97%, 98%, 99%, or 100%.

In some embodiments of a Cas9 ribonucleoprotein, the tracrRNA comprises a sequence that is at least about 75 percent, at least about 80 percent, at least about 85 percent, at least about 90 percent, at least about 95 percent, at least about 96 percent, at least about 97 percent, at least about 98 percent, at least about 99 percent or 100 percent nucleotide sequence identity to the sequence of: CAGCAUAG-CAAGUUAAAAUAAGGCUAGUCCGUUAUCAAC-UUGAAAAAGUGGCACC GAGUCGGUGCUUUU (SEQ ID NO:1028), wherein said sequence optionally contains 2'-O-methyl or 2'-F modification at any one or more of the first 3 bases, wherein said tracrRNA may be optionally further modified. In some embodiments of a Cas9 ribonucleoprotein, the tracrRNA comprises a sequence that is at least about 75 percent, at least about 80 percent, at least about 85 percent, at least about 90 percent, at least about 95 percent, at least about 96 percent, at least about 97 percent, at least about 98 percent, at least about 99 percent or 100 percent nucleotide sequence identity to the sequence of: CAGCAUAGCAAGUUAAAAUAAGGCUAGUC-CGUUAUCAACUUGAAAAAGUGGCACC GAGUCG-GUGCUUUU (SEQ ID NO:1028), wherein said sequence optionally contains 2'-O-methyl or 2'-F modifications at the first 3 bases, wherein said tracrRNA may be optionally further modified.

In some embodiments of a Cas9 ribonucleoprotein, the crRNA comprises a sequence that is at least about 75 percent, at least about 80 percent, at least about 85 percent, at least about 90 percent, at least about 95 percent, at least about 96 percent, at least about 97 percent, at least about 98 percent, at least about 99 percent or 100 percent nucleotide sequence identity to a sequence selected from:

```
PCSK9 crRNA sequence 1:
                                    (SEQ ID NO: 885)
GGUGCUAGCCUUGCGUUCCGGUUUUAGAGCUAUGCUG,
optionally containing 2'-O-methyl or 2'-F
modification at any one or more of the first 3 of
the last 4 bases (GCU);

PCSK9 crRNA sequence 2:
                                    (SEQ ID NO: 886)
CGUGCUCGGGUGCUUCGGCCGUUUUAGAGCUAUGCUG,
optionally containing 2'-O-methyl or 2'-F
modification at any one or more of the first 3 of
the last 4 bases (GCU);

PCSK9 crRNA sequence 3:
                                    (SEQ ID NO: 887)
GCCGUCCUCCUCGGAACGCAGUUUUAGAGCUAUGCUG,
optionally containing 2'-O-methyl or 2'-F
modification at any one or more of the first 3 of
the last 4 bases (GCU);

PCSK9 crRNA sequence 4:
                                    (SEQ ID NO: 888)
GGACGAGGACGGCGACUACGGUUUUAGAGCUAUGCUG, optionally
containing 2'-O-methyl or 2'-F modification at any
one or more of the first 3 of the last 4 bases
(GCU);

PCSK9 crRNA sequence 5:
                                    (SEQ ID NO: 889)
ACCACCGGGAAAUCGAGGGCGUUUUAGAGCUAUGCUG,
optionally containing 2'-O-methyl or 2'-F
modification at any one or more of the first 3 of
the last 4 bases (GCU);

PCSK9 crRNA sequence 6:
                                    (SEQ ID NO: 890)
CGACUUCGAGAAUGUGCCCGGUUUUAGAGCUAUGCUG,
optionally containing 2'-O-methyl or 2'-F
modification at any one or more of the first 3 of
the last 4 bases (GCU);

PCSK9 crRNA sequence 7:
                                    (SEQ ID NO: 891)
GAGUGACCACCGGGAAAUCGGUUUUAGAGCUAUGCUG,
optionally containing 2'-O-methyl or 2'-F
modification at any one or more of the first 3 of
the last 4 bases (GCU);

PCSK9 crRNA sequence 8:
                                    (SEQ ID NO: 892)
CUCGGGCACAUUCUCGAAGUGUUUUAGAGCUAUGCUG, optionally
containing 2'-O-methyl or 2'-F modification at any
one or more of the first 3 of the last 4 bases
(GCU);

PCSK9 crRNA sequence 9:
                                    (SEQ ID NO: 893)
GGAAGCCAGGAAGAAGGCCAGUUUUAGAGCUAUGCUG,
optionally containing 2'-O-methyl or 2'-F
modification at any one or more of the first 3 of
the last 4 bases (GCU);

PCSK9 crRNA sequence 10:
                                    (SEQ ID NO: 894)
UCUUUGCCCAGAGCAUCCCGGUUUUAGAGCUAUGCUG,
optionally containing 2'-O-methyl or 2'-F
modification at any one or more of the first 3 of
the last 4 bases (GCU);
and PCSK9 crRNA sequence 11:
                                    (SEQ ID NO: 895)
CUAGGAGAUACACCUCCACCGUUUUAGAGCUAUGCUG,
optionally containing 2'-O-methyl or 2'-F
modification at any one or more of the first 3 of
the last 4 bases (GCU);
``` wherein said crRNA may optionally be further chemically modified.

In some embodiments of a Cas9 ribonucleoprotein, the crRNA comprises a sequence that is at least about 75 percent, at least about 80 percent, at least about 85 percent, at least about 90 percent, at least about 95 percent, at least about 96 percent, at least about 97 percent, at least about 98 percent, at least about 99 percent or 100 percent nucleotide sequence identity to a sequence selected from:

```
PCSK9 crRNA sequence 1:
                                    (SEQ ID NO: 885)
GGUGCUAGCCUUGCGUUCCGGUUUUAGAGCUAUGCUG,
optionally containing 2'-O-methyl or 2'-F
modifications at the first 3 of the last 4 bases
(GCU);

PCSK9 crRNA sequence 2:
                                    (SEQ ID NO: 886)
CGUGCUCGGGUGCUUCGGCCGUUUUAGAGCUAUGCUG,
optionally containing 2'-O-methyl or 2'-F
modifications at the first 3 of the last 4 bases
(GCU);

PCSK9 crRNA sequence 3:
                                    (SEQ ID NO: 887)
GCCGUCCUCCUCGGAACGCAGUUUUAGAGCUAUGCUG,
optionally containing 2'-O-methyl or 2'-F
modifications at the first 3 of the last 4 bases
(GCU);

PCSK9 crRNA sequence 4:
                                    (SEQ ID NO: 888)
GGACGAGGACGGCGACUACGGUUUUAGAGCUAUGCUG,
optionally containing 2'-O-methyl or 2'-F
modifications at the first 3 of the last 4 bases
(GCU);

PCSK9 crRNA sequence 5:
                                    (SEQ ID NO: 889)
ACCACCGGGAAAUCGAGGGCGUUUUAGAGCUAUGCUG,
optionally containing 2'-O-methyl or 2'-F
modifications at the first 3 of the last 4 bases
(GCU);

PCSK9 crRNA sequence 6:
                                    (SEQ ID NO: 890)
CGACUUCGAGAAUGUGCCCGGUUUUAGAGCUAUGCUG,
optionally containing 2'-O-methyl or 2'-F
modifications at the first 3 of the last 4 bases
(GCU);

PCSK9 crRNA sequence 7:
                                    (SEQ ID NO: 891)
GAGUGACCACCGGGAAAUCGGUUUUAGAGCUAUGCUG,
optionally containing 2'-O-methyl or 2'-
modifications a the first 3 of the last 4 bases
(GCU);

PCSK9 crRNA sequence 8:
                                    (SEQ ID NO: 892)
CUCGGGCACAUUCUCGAAGUGUUUUAGAGCUAUGCUG,
optionally containing 2'-O-methyl or 2'-F
modifications at the first 3 of the last 4 bases
(GCU);

PCSK9 crRNA sequence 9:
                                    (SEQ ID NO: 893)
GGAAGCCAGGAAGAAGGCCAGUUUUAGAGCUAUGCUG,
optionally containing 2'-O-methyl or 2'-F
modifications at the first 3 of the last 4 bases
```

```
PCSK9 crRNA sequence 10:
                                  (SEQ ID NO: 894)
UCUUUGCCCAGAGCAUCCCGGUUUUAGAGCUAUGCUG,
optionally containing 2'-O-methyl or 2'-F
modifications at the first 3 of the last 4 bases
(GCU);
and PCSK9 crRNA sequence 11:
                                  (SEQ ID NO: 895)
CUAGGAGAUACACCUCCACCGUUUUAGAGCUAUGCUG,
optionally containing 2'-O-methyl or 2'-F
modifications at the first 3 of the last 4 bases
(GCU);
``` wherein said crRNA may optionally be further chemically modified.

In some embodiments, the first element of the Cas9 ribonucleoprotein comprises a single guide RNA sequence (sgRNA), wherein the remainder of the compound is linked to said Cas9 ribonucleoprotein via one or more interactions to the sgRNA. In some embodiments, the sgRNA comprises 20 or more nucleotides. In some embodiments, the sgRNA comprises at least 8 nucleotides.

In some embodiments of a Cas9 ribonucleoprotein, the degree of complementarity between the sgRNA and its corresponding target sequence, when optimally aligned using a suitable alignment algorithm, is at least 50%, 60%, 70%, 75%, 80%, 85%, 86%, 87%, 88%, 89%, 90%, 91%, 92%, 93%, 94%, 95%, 96%, 97%, 98%, 99%, or 100%.

In some embodiments of a Cas9 ribonucleoprotein, said sgRNA has at least about 75 percent, at least about 80 percent, at least about 85 percent, at least about 90 percent, at least about 95 percent, at least about 96 percent, at least about 97 percent, at least about 98 percent, at least about 99 percent or 100 percent nucleotide sequence identity to the sequence selected from the group consisting of:

```
PCSK9 single guide RNA sequence 1:
                                  (SEQ ID NO: 896)
GGUGCUAGCCUUGCGUUCCGGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

PCSK9 single guide RNA sequence 2:
                                  (SEQ ID NO: 897)
CGUGCUCGGGUGCUUCGGCCGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

PCSK9 single guide RNA sequence 3:
                                  (SEQ ID NO: 898)
GCCGUCCUCCUCGGAACGCAGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

PCSK9 guide RNA sequence 4:
                                  (SEQ ID NO: 899)
GGACGAGGACGGCGACUACGGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUU;

PCSK9 single guide RNA sequence 5:
                                  (SEQ ID NO: 900)
ACCACCGGGAAAUCGAGGGCGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

PCSK9 single guide RNA sequence 6:
                                  (SEQ ID NO: 901)
CGACUUCGAGAAUGUGCCCGGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

PCSK9 single guide RNA sequence 7:
                                  (SEQ ID NO: 902)
GAGUGACCACCGGGAAAUCGGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

PCSK9 single guide RNA sequence 8:
                                  (SEQ ID NO: 903)
CUCGGGCACAUUCUCGAAGUGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

PCSK9 single guide RNA sequence 9:
                                  (SEQ ID NO: 904)
GGAAGCCAGGAAGAAGGCCAGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

PCSK9 single guide RNA sequence 10:
                                  (SEQ ID NO: 905)
UCUUUGCCCAGAGCAUCCCGGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

PCSK9 single guide RNA sequence 11:
                                  (SEQ ID NO: 906)
CUAGGAGAUACACCUCCACCGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

EMX1 single guide RNA sequence:
                                  (SEQ ID NO: 907)
GUCACCUCCAAUGACUAGGGGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

ROSA26 single guide RNA sequence:
                                  (SEQ ID NO: 908)
CGAACCCUACACAUUCAACGGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;
``` wherein said sequence is optionally chemically modified.

In some embodiments of a compound of the present invention, Y is a Cpf1 ribonucleoprotein. In some embodiments, Y is a Cpf1 ribonucleoprotein comprising: (1) a first element comprising a recognition element comprising a guide sequence, wherein when expressed, the guide sequence directs sequence-specific binding of the Cpf1 ribonucleoprotein to a target sequence, and (2) a second element comprising a Cpf1 protein and optionally one or more nuclear localization sequences (NLSs); wherein said first element is associated with said second element. In some embodiments, the target sequence is a eukaryotic cell target sequence. In some embodiments, the target sequence is a prokaryotic cell target sequence.

In some embodiments, a Cpf1 ribonucleoprotein comprises a crRNA, said crRNA comprising a sequence that is at least about 75 percent, at least about 80 percent, at least about 85 percent, at least about 90 percent, at least about 95 percent, at least about 96 percent, at least about 97 percent, at least about 98 percent, at least about 99 percent or 100 percent nucleotide sequence identity to a sequence selected from:

```
EMX1 crRNA sequence (Asp Cpf1):
                                (SEQ ID NO: 909)
UAAUUUCUACUCUUGUAGAUUCAUCUGUGCCCCUCCCUCCCUG;

EMX1 crRNA sequence (Lba Cpf1):
                                (SEQ ID NO: 910)
UAAUUUCUACUCUAAGUAGAUUCAUCUGUGCCCCUCCCUCCCUG;

PCSK9 crRNA sequence 12 (Asp Cpf1):
                                (SEQ ID NO: 911)
UAAUUUCUACUCUUGUAGAUCCCAGAGCAUCCCGUGGAACCUG;

PCSK9 crRNA sequence 12 (Lba Cpf1):
                                (SEQ ID NO: 912)
UAAUUUCUACUCUAAGUAGAUCCCAGAGCAUCCCGUGGAACCUG;

PCSK9 crRNA sequence 13 (Asp Cpf1):
                                (SEQ ID NO: 913)
UAAUUUCUACUCUUGUAGAUCCGGUGGUCACUCUGUAUGCUGG;
and PCSK9 crRNA sequence 13 (Lba Cpf1):
                                (SEQ ID NO: 914)
UAAUUUCUACUCUAAGUAGAUCCGGUGGUCACUCUGUAUGCUGG,
``` wherein said sequence is optionally chemically modified.

In some embodiments of a compound described herein, Y is a Type III-B Cmr complex, e.g., a Type III-B Cmr complex derived from *Pyrococcus furiosus, Sulfolobus solfataricus,* and *Therms thermophilus*. In some embodiments, the Cmr proteins suitable for use herein include but are not limited to those described in Hale, C. R. et al. *Genes & Development,* 2014, 28:2432-2443, and Makarova K. S. et al. *Nature Reviews Microbiology,* 2015, 13, 1-15.

In some embodiments of a compound described herein, Y further comprises a fluorescent probe. In some embodiments, the fluorescent probe comprises the mCherry sequence (SEQ ID NO:915). Other suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

In some embodiments, Y comprises one or more NLSs. In some embodiments, Y comprises one or more NLSs, each being independently selected from, but are not limited to, an NLS sequence derived from: the NLS of the SV40 virus large T-antigen, having the amino acid sequence PKKKRKV (SEQ ID NO: 830); the NLS from nucleoplasmin (e.g. the nucleoplasmin bipartite NLS with the sequence KRPAATKKAGQAKKKK (SEQ ID NO: 831); the c-myc NLS having the amino acid sequence PAAKRVKLD (SEQ ID NO: 832) or RQRRNELKRSP (SEQ ID NO: 833); the hRNPA1 M9 NLS having the sequence NQSSNFGPMKG-GNFGGRSSGPYGGGGQYFAKPRNQGGY (SEQ ID NO: 834); the sequence RMRIXFKNKGKDTAELRRRRVEVS-VELRKAKKDEQILKRRNV, wherein X is any amino acid (SEQ ID NO: 835) of the IBB domain from importin-alpha; the sequences VSRKRPRP (SEQ ID NO: 836) and PPK-KARED (SEQ ID NO: 837) of the myoma T protein; the sequence PQPKKKPL (SEQ ID NO: 838) of human p53; the sequence SALIKKKKKMAP (SEQ ID NO: 839) of mouse c-abl IV; the sequences DRLRR (SEQ ID NO: 840) and PKQKKRK (SEQ ID NO: 841) of the influenza virus NS1; the sequence RKLKKKIKKL (SEQ ID NO: 842) of the Hepatitis virus delta antigen; the sequence REKKKFLKRR (SEQ ID NO: 843) of the mouse Mx1 protein; the sequence KRKGDEVDGVDEVAKKKSKK (SEQ ID NO: 844) of the human poly(ADP-ribose) polymerase; the sequence RKCLQAGMNLEARKTKK (SEQ ID NO: 845) of the steroid hormone receptors (human) glucocorticoid; the sequence MAPKKKRKVGIHRGVP (SEQ ID NO:1035); and the sequence PKKKRKVEDPKKKRKVD (SEQ ID NO:1036). In the embodiments where Y comprises two or more NLSs, there may optionally be an intervening amino acid sequence between each two NLSs. Such intervening sequences may comprise one or more amino acid residues. In some embodiments, Y comprises two NLSs, each comprising the amino acid sequence PKKKRKV (SEQ ID NO: 830). Y comprises three NLSs, each comprising the amino acid sequence PKKKRKV (SEQ ID NO: 830).

In some embodiments of a compound of the present invention, Y comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to a Cas9 protein derived from *S. aureus, S. pneumoniae, S. pyogenes, S. thermophilus, S. Aureus, N. meningitidis* or *A. ebreus*. See, e.g., Hou et al, PNAS 2013. In some embodiments, Y comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to a Type II Cas9 protein. In some embodiments, Y comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to the amino acids at positions 7 to 166 or 731 to 1003 of SEQ ID NO:8 or the corresponding amino acids of those set forth in SEQ ID NOs:1-7, 9-829. In some embodiments, Y comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to the amino acids at positions 7 to 166 or 731 to 1003 of SEQ ID NO:8. In some embodiments, Y comprises a Cas9 protein having at least 4 motifs within the sequence which have at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to the motifs 1, 2, 3, and 4 of the Cas9 amino acid sequence of any of SEQ ID NOs: 260-263.

In some embodiments, Y comprises a Type II-C Cas9 protein. In some embodiments, Y comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to a sequence selected from: *S. pyogenes* Cas9 (wild type) (SEQ ID NO:848), *S. pyogenes* Cas9-mutation M1C (SEQ ID NO:849), *S. pyogenes* Cas9-mutation M1C & C80S (SEQ ID NO:850), *S. pyogenes* Cas9 nickase-mutation D10A (SEQ ID NO:851), *S. pyogenes* Cas9 nickase-mutation H840A (SEQ ID NO:852), *S. pyogenes* Cas9 nickase-mutations E923P & T924P (SEQ ID NO:853), *Acidovorax ebreus* Cas9 (SEQ ID NO:854), Acid mine drainage bacteria Ga0052161_JGI Cas9 (SEQ ID NO:855), *S. pyogenes* Cas9 null-mutation D10A& H840A (SEQ ID NO:1027), and Uranium mine bacteria FW106_JGI Cas9 (SEQ ID NO:856).

In some embodiments of a Cas9 protein suitable for use herein, the Cas9 protein sequence may be modified such as being codon-optimized for expression in a eukaryotic cell or to include modifications to the sequence to impact its function. In some embodiments, the Cas9 protein sequence directs cleavage of one or two strands of DNA at the location of the target sequence such as with a Cas9 nickase (i.e., Cas9-D10A) used in combination with guide sequence(s), e.g., two guide sequences, which target respectively sense and antisense strands of the DNA target thereby allowing both strands to be nicked and resulting in non-homologous end-joining. Cas9-D10A with a single guide RNA sequence can create indels. However, in other embodiments, the Cas9 protein sequence lacks DNA strand cleavage activity such as with selective use of catalytically inactive Cas (dCas) domains. In other embodiments, the Cas9 protein sequence is modified to allow covalent linkage to the Cas9 protein or Cas9 ribonucleoprotein, including lysine, glutamine, and cysteine residue modifications. In yet other embodiments, the Cas9 ribonucleoprotein is capable of directing the cleavage of RNA strands as described in O'Connell, Mitchell R., et al., Programmable RNA recognition and cleavage by CRISPR/Cas9, *Nature*, 2014, 516, p 263-266.

In another embodiment the Cas9 protein has mutated residues, such as solvent exposed lysines or arginines residues (not involved in either catalytic activity, binding of DNA, or binding of RNA) mutated to hystidines, Cysteins, or glutamines.

Modifications of the Cas9 protein sequence can include a D10A (aspartate to alanine at amino acid position 10 of SEQ ID NO: 8) mutation (or the corresponding mutation of any of the proteins set forth as SEQ ID NOs: 1-829) that can cleave the complementary strand of the target DNA but has reduced ability to cleave the non-complementary strand of the target DNA (thus resulting in a single strand break instead of a double strand break). Another modification is a H840A (histidine to alanine at amino acid position 840 of SEQ ID NO: 8) mutation (or the corresponding mutation of any of the proteins set forth as SEQ ID NOs:1-829) that can cleave the non-complementary strand of the target DNA but has reduced ability to cleave the complementary strand of the target DNA (thus resulting in a single strand break instead of a double strand break). The use of the D10A or H840A variant of Cas9 (or the corresponding mutations in any of the proteins set forth as SEQ ID NOs: 1-829) can alter the expected biological outcome because the non-homologous end joining is much more likely to occur when double strand breaks are present as opposed to single strand breaks.

Other residues can be mutated to also inactivate a particular nuclease from motif 1, 2, 3, or 4. As non-limiting examples, residues D10, G12, G17, E762, H840, N854, N863, H982, H983, A984, D986, and/or A987 (or the corresponding mutations of any of the proteins set forth as SEQ ID NOs: 1-829) can be modified. Mutations can include substitutions, additions, and deletions, or any combination thereof. In some instances, the mutation converts the mutated amino acid to another amino acid, such as alanine. Other modifications include a base modification, a backbone modification, and/or an internucleoside linkage modification.

In some embodiments of a compound of the present invention, Y is Y1C80S-3N-m or Y1C80S-2N. In some embodiments, Y is Y1C80S-3N-m-RNP-EMX1. In some embodiments, the compound is Y53aASGPRL. In some embodiments, the compound is Y53aASGPRL-RNP-EMX1, Y53aASGPRL-RNP-PCS4 or Y53aASGPRL-RNP-PCS1.

In some embodiments of a compound of the present invention, Y comprises a Cpf1 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to a Cpf1 protein derived from A. sp., *L. bacterium*, *P. macacae*, and *P. disiens*. In some embodiments, Y comprises a Cpf1 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to a Cpf1 protein selected from, but is not limited to, A. sp Cpf1 (SEQ ID NO:857), *L. bacterium* Cpf1 (SEQ ID NO:858), *P. macacae* Cpf1 (SEQ ID NO:859), *P. disiens* Cpf1 (SEQ ID NO:860).

In some embodiments, the compounds of the present invention further comprise an endosomal escape agent. In some embodiments of a compound of the present invention, the Y moiety of the compound further comprises an endosomal escape agent. In some embodiments, the endosomal escape agent is linked to the remainder of the compound via one or more covalent bonds. In some endosomal embodiments, the endosomal escape agent is associated with the remainder of the compound, e.g., via electrostatic interactions. In some embodiments, the endosomal escape agent is co-incubated with a compound of the present invention.

Suitable endosomal escape agents for use in the present invention include, but are not limited to, a lysosomotropic agent, a cell penetrating peptide, a fusogenic peptide, an endosomolytic peptide, a pore forming agent, and a proton sponge agent.

Lysosomotropic agents are weak bases that can penetrate in lysosome as protonated form and increase the intracellular pH. Suitable lysosomotropic agents for use in the present application include, but are not limited to chlorpromazine, amantadine, 4-aminoquinoline, amiodarone, amodiaquine, azithromycin, chloroquine, clindamycin, N-(3-[(2,4-dinitrophenyl)-amino]-propyl)-N-(3-aminopropyl-methylamine) dihydrochloride (DAMP), imipramine, methylamine, monensin, monodansylcadaverine, NH$_4$Cl, perhexilene, phenylalanine methyl ester, primaquine, quinacrine, suramin, thioridazine, tilorone, tributylamine, ketotifen fumarate, glycerol, and sucrose. In some embodiments, the lysosomotropic agent is chloroquine, glycerol or sucrose.

Cell penetrating peptides (CPPs) are a class of diverse peptides, typically with 5-30 amino acids, that can cross the cellular membrane. In some embodiments, suitable CPPs for use herein include cationic CPPs, amphipathic CPPs, and hydrophobic CPPs. Suitable CPPs for use herein include, but are not limited to, CPPs derived from heparin-, RNA-, and DNA-binding proteins such as those listed in Table 1, CPPs derived from signal peptides such as those listed in Table 2, CPPs derived from antimicrobial peptides such as those listed in Table 3, CPPs derived from viral proteins such as those listed in Table 4, CPPs derived from various natural proteins such as those listed in Table 5, and designed CPPs and CPPs derived from peptide libraries such as those listed in Table 6. See, e.g., Milletti, F. *Drug Discovery Today*, Volume 17, Numbers 15/16, 2012, 850-860.

TABLE 1

CPPs derived from heparan-, RNA- and DNA-binding proteins

CPPs derived from heparan binding proteins

| | |
|---|---|
| RKKRRRESRKKRRRES (SEQ ID NO: 916) | DPV3 |
| GRPRESGKKRKRKRLKP (SEQ ID NO: 917) | DPV6 |
| GKRKKKGKLGKKRDP (SEQ ID NO: 918) | DPV7 |
| GKRKKKGKLGKKRPRSR (SEQ ID NO: 919) | DPV7b |
| RKKRRRESRRARRSPRHL (SEQ ID NO: 920) | DPV3/10 |
| SRRARRSPRESGKKRKRKR (SEQ ID NO: 921) | DPV10/6 |
| VKRGLKLRHVRPRVTRMDV (SEQ ID NO: 922) | DPV1047 |
| SRRARRSPRHLGSG (SEQ ID NO: 923) | DPV10 |
| LRRERQSRLRRERQSR (SEQ ID NO: 924) | DPV15 |
| GAYDLRRRERQSRLRRRERQSR (SEQ ID NO: 925) | DPV15b |

CPPs derived from RNA binding proteins

| | |
|---|---|
| RKKRRQRRR (SEQ ID NO: 926) | HIV-1 Tat |
| RRRRNRTRRNRRRVR (SEQ ID NO: 927) | FHV coat |
| TRQARRNRRRRWRERQR (SEQ ID NO: 928) | HIV-1 Rev |
| TRRQRTRRARRNR (SEQ ID NO: 929) | HTLV-II Rex |
| KMTRAQRRAAARRNRWTAR (SEQ ID NO: 930) | BMV Gag |
| NAKTRRHERRRKLAIER (SEQ ID NO: 931) | P22 N |
| MDAQTRRRERRAEKQAQWKAAN (SEQ ID NO: 932) | λN(1-22) |
| TAKTRYKARRAELIAERR (SEQ ID NO: 933) | φ21N(12-29) |
| TRRNKRNRIQEQLNRK (SEQ ID NO: 934) | Yeast PrP6 |

TABLE 1-continued

CPPs derived from heparan-, RNA- and DNA-binding proteins

CPPs derived from DNA binding proteins

| | |
|---|---|
| PRRRRSSSRPVRRRRRPRVSRRRRRRGGRRRR (SEQ ID NO: 935) | Protamine 1 |
| Leucine zipper RIKAERKRMRNRIAASKSRKRKLERIAR (SEQ ID NO: 936) | Human cJun |
| KRRIRRERNKMAAAKSRNRRRELTDT (SEQ ID NO: 937) | Human cFos |
| Transcription factors KRARNTEAARRSRARKLQRMKQ (SEQ ID NO: 938) | Yeast GCN4 |
| Homeoproteins RQIKIWFQNRRMKWKK (SEQ ID NO: 866) | Penetratin |
| RVIRVWFQNKRCKDKK (SEQ ID NO: 939) | Islet-1 |
| SKRTRQTYTRYQTLELEKEFHFNRYITRRRRIDIANALSLSERQIKIWFQNRRMKSKKDR (SEQ ID NO: 940) | Fushi-tarazu |
| SQIKIWFQNKRAKIKK (SEQ ID NO: 941) | Engrailed-2 |
| RQVTIWFQNRRVKEKK (SEQ ID NO: 942) | HoxA-13 |
| KQINNWFINQRKRHWK (SEQ ID NO: 943) | Knotted-1 |
| RHIKIWFQNRRMKWKK (SEQ ID NO: 1039) | PDX-1 |

TABLE 2

CPPs derived from signal peptides.

Amphipathic (I): signal peptide + NLS

| | |
|---|---|
| MGLGLHLLVLAAALQGAKKKRKV (SEQ ID NO: 944) | Ig(v) |
| MVKSKIGSWILVLFVAMWSDVGLCKKRPKP (SEQ ID NO: 945) | BPrPp(1-30) |
| MANLGYWLLALFVTMWTDVGLCKKRPKP (SEQ ID NO: 946) | MPrPp(1-28) |

Hydrophobic: signal peptide alone

| | |
|---|---|
| AAVLLPVLLAAP (SEQ ID NO: 947) | K-FGF |

TABLE 3

CPPs derived from antimicrobial peptides.

Pro-rich

| | |
|---|---|
| RRIRPRPPRRLPRPRPRPLPFPRPG (SEQ ID NO: 948) | Bac7 |
| VDKGSYLPRPTPPRPIYNRN (SEQ ID NO: 949) | Pyrrhocoricin |

Amphipathic

| | |
|---|---|
| KCFQWQRNMRKVRGPPVSCIKR (SEQ ID NO: 950) | Human lactoferrin (19-40) |
| TRSSRAGLQWPVGRVHRLLRK (SEQ ID NO: 951) | Buforin 2 |

TABLE 3-continued

CPPs derived from antimicrobial peptides.

| Sequence | Name |
|---|---|
| GIGAVLKVLTTGLPALISWIKRKRQQ (SEQ ID NO: 864) | Melittin |
| GIGKWLHSAKKFGKAFVGEIMNS (SEQ ID NO: 952) | Magainin 2 |
| LLGDFFRKSKEKIGKEFKRIVQRIKDFLRNLVPRTESC (SEQ ID NO: 953) | LL-37 |
| RGGRLSYSRRRFSTSTGR (SEQ ID NO: 954) | SynB1 |
| YKQCHKKGGKKGSG (SEQ ID NO: 955) | Crotamine |
| ALWKTLLKKVLKAPKKKRKV (SEQ ID NO: 956) | S413-PVrev |
| HARIKPTFRRLKWKYKGKFW (SEQ ID NO: 957) | L-2 |

TABLE 4

CPPs derived from viral proteins.

| Sequence | Name |
|---|---|
| TKRRITPKDVIDVRSVTTEINT (SEQ ID NO: 958) | Inv3 |
| *Amphipathic* | |
| RQGAARVTSWLGRQLRIAGKRLEGRSK (SEQ ID NO: 959) | E$^{rns}$ |
| NAATATRGRSAASRPTQRPRAPARSASRPRRPVQ (SEQ ID NO: 960) | VP22 |
| RHSRIGIIQQRRTRNG (SEQ ID NO: 961) | HIV-1 VPR 77-92 |
| KLIKGRTPIKFGKADCDRPPKHSQNGMGK (SEQ ID NO: 962) | Ribotoxin2 L3 loop |
| PLSSIFSRIGDP (SEQ ID NO: 963) | PreS2-TLM |
| *Amphipathic (β-sheet)* | |
| DPKGDPKGVTVTVTVTVTGKGDPKPD (SEQ ID NO: 964) | VT5 |

TABLE 5

CPPs derived from various natural proteins.

| Sequence | Name |
|---|---|
| *Cationic* | |
| RRIPNRRPRR (SEQ ID NO: 965) | HRSV |
| RLRWR (SEQ ID NO: 966) | AIP6 |
| *Amphipathic (I)* | |
| MVRRFLVTLRIRRACGPPRVRV (SEQ ID NO: 967) | ARF(1-22) |
| MVTVLFRRLRIRRACGPPRVRV (SEQ ID NO: 968) | M918 |
| LLIILRRRIRKQAHAHSK (SEQ ID NO: 969) | pVEC |
| *Amphipathic (helical)* | |
| LSTAADMQGVVTDGMASG (SEQ ID NO: 970) | Azurin p18 |
| LSTAADMQGVVTDGMASGLDKDYLKPDD (SEQ ID NO: 971) | Azurin p28 |
| KFHTFPQTAIGVGAP (SEQ ID NO: 972) | hCT18-32 |
| *Hydrophobic* | |
| VPTLK (SEQ ID NO: 973); PMLKE (SEQ ID NO: 1030), VPALR (SEQ ID NO: 1031), VSALK (SEQ ID NO: 1032), IPALK (SEQ ID NO: 1033) | Bip |
| PFVYLI (SEQ ID NO: 974) | C105Y |
| PIEVCMYREP (SEQ ID NO: 975) | FGF12 |

TABLE 6

Designed CPPs and CPPs derived from peptide libraries.
Designed

| Sequence | Name |
|---|---|
| *Cationic* | |
| R8 (SEQ ID NO: 1040), R9 (SEQ ID NO: 1041), R10 (SEQ ID NO: 1042), R12 (SEQ ID NO: 976) | Polyarginine |
| *Amphipathic (cationic)* | |
| KETWWETWWTEWSQPKKRKV (SEQ ID NO: 977) | Pep-1 |
| GLAFLGFLGAAGSTMGAWSQPKKRKV (SEQ ID NO: 978) | MPG |
| *Amphipathic (cationic)* | |
| GWTLNSAGYLLGKINLKALAALAKKIL (SEQ ID NO: 867) | Transportan |
| AGYLLGHINLHHLAHLAibHHIL (SEQ ID NO: 979) | TH |
| KLALKALKALKAALKLA (SEQ ID NO: 980) | MAP |
| RRWWRRWRR (SEQ ID NO: 981) | W/R |
| GLWRALWRLLRSLWRLLWRA (SEQ ID NO: 982) | CADY |
| LIRLWSHLIHIWFQNRRLKWKKK (SEQ ID NO: 983) | EB-1 |
| *Amphipathic (cationic)* | |
| WEAALAEALAEALAEHLAEALAEALEALAA (SEQ ID NO: 868) | GALA |
| WEAKLAKALAKALAKHLAKALAKALKACEA (SEQ ID NO: 869) | KALA |
| LKTLTETLKELTKTLTEL (SEQ ID NO: 984) | MAP12 |
| *Amphipathic (zero-charge)* | |
| QLALQLALQALQAALQLA (SEQ ID NO: 1034) | MAP17 |
| *Amphipathic (Proline-rich)* | |
| (PPR)3 (SEQ ID NO: 1043), (PPR)4 (SEQ ID NO: 1044), (PPR)5 (SEQ ID NO: 1045), (PPR)6 (SEQ ID NO: 985) | (PPR)n |
| (PRR)3 (SEQ ID NO: 1046), (PRR)4 (SEQ ID NO: 1047), (PRR)5 (SEQ ID NO: 1048), (PRR)6 (SEQ ID NO: 986) | (PRR)n |
| GPSQPTYPGDDAPVRDLIRFYRDLQRYLNVVTRHRY (SEQ ID NO: 987) | aPP4R1 |

TABLE 6-continued

Designed CPPs and CPPs derived from peptide libraries.
Designed

| Sequence | Name |
|---|---|
| GPSQPTYPGDDAPVRDLIRFYRDLRRYLNVVTRHRY (SEQ ID NO: 988) | aPP5R1 |
| GPSQPTYPGDDAPVRDLRRFYRDLRRYLNVVTRHRY (SEQ ID NO: 989) | aPP6R1 |
| G($P_L$XX)$_n P_L$, where $P_L$ is a proline-based mimic of leucine, and X is a proline-based mimic of lysine or arginine (SEQ ID NO: 990) | PoliProline-based |
| VRLPPPVRLPPPVRLPPP (SEQ ID NO: 991) | SAP |
| VELPPPVELPPPVELPPP (SEQ ID NO: 992) | SAP(E) |

Peptide libraries
Support-vector machine model

| Sequence | Name |
|---|---|
| FKIYDKKVRTRVVKH (SEQ ID NO: 993) | SVM1 |
| RASKRDGSWVKKLHRILE (SEQ ID NO: 994) | SVM2 |
| KGTYKKKLMRIPLKGT (SEQ ID NO: 995) | SVM3 |
| LYKKGPAKKGRPPLRGWFH (SEQ ID NO: 996) | SVM4 |
| HSPIIPLGTRFVCHGVT (SEQ ID NO: 997) | SVM5 |
| YTAIAWVKAFIRKLRK (SEQ ID NO: 998) | YTA2 |
| IAWVKAFIRKLRKGPLG (SEQ ID NO: 999) | YTA4 |

Plasmid display
Amphipathic

| Sequence | Name |
|---|---|
| RLSGMNEVLSFRWL (SEQ ID NO: 1000) | SG3 |

Phage display
Hydrophobic

| Sequence | Name |
|---|---|
| SDLWEMMMVSLACQY (SEQ ID NO: 1001) | Pep-7 |
| VTWTPQAWFQWV (SEQ ID NO: 1002) | |
| GSPWGLQHHPPRT (SEQ ID NO: 1003) | 439a |
| GPFHFYQFLFPPV (SEQ ID NO: 1004) | 435b |
| TSPLNIHNGQKL (SEQ ID NO: 1005) | HN-1 |

Other

| Sequence | Name |
|---|---|
| CAYHRLRRC (SEQ ID NO: 1006) | |

Phylomer library
Cationic

| Sequence | Name |
|---|---|
| RCGRASRCRVRWMRRRRI (SEQ ID NO: 1007) | BEN_1079 |

Other

| Sequence | Name |
|---|---|
| PYSRPHVQLWYPNRESCRSLIRSLGP (SEQ ID NO: 1008) | BEN_0805 |

Peptide arrays
Hydrophobic

| Sequence | Name |
|---|---|
| PLILLRLLRGQF (SEQ ID NO: 1009) | Pept1 |
| PLIYLRLLRGQF (SEQ ID NO: 1010) | Pept2 |
| KLWMRWYSPTTRRYG (SEQ ID NO: 1011) | IVV-14 |

Fusogenic peptides are short peptides that destabilize the phospholipid membrane. In some embodiments, a fusogenic peptide comprises 20-30 amino acids. They primarily elicit endosomal escape by two main mechanisms: membrane fusion and pore formation. Suitable fusogenic peptides for use herein include, but are not limited to, an influenza HA-2 peptide, GLFGAIAGFIENGWEGMIDGWYG (SEQ ID NO: 863); melittin, GIGAVLKVLTTGLPAL-ISWIKRKRQQ (SEQ ID NO: 864); tat (48-60), GRK-KRRQRRRPPQ (SEQ ID NO: 865); penetratin, RQIKIW-FQNRRMKWKK (SEQ ID NO: 866); transportan, GWTLNSAGYLLGKINLKALAALAKKIL (SEQ ID NO: 867); GALA peptide, WEAALAEALAEALAEHLAEA-LAEALEALAA (SEQ ID NO: 868); KALA peptide, WEAKLAKALAKALAKHLAKALAKALKACEA (SEQ ID NO: 869); JST-1, GLFEALLELLESLWELLLEA (SEQ ID NO: 870); ppTG1, GLFKALLKLLKSLWKLLLKA (SEQ ID NO: 871); ppTG20, GLFRALLRLL-RSLWRLLLRA (SEQ ID NO: 872); and derivatives thereof. In some embodiments, the endosomal escape agent comprises a KALA peptide, WEAKLAKALAKALAKHLAKA-LAKALKACEA (SEQ ID NO: 869).

In some embodiments, the endosomal escape agent an endosomolytic histidine-rich peptide selected from, but not limited to, CHK$_6$HC (SEQ ID NO:861); HSWYG (SEQ ID NO: 1029), GLFHAIAHFIHGGWHGLIHGWYG (SEQ ID NO:862); and derivatives thereof. In some embodiments, the endosomal escape agent comprises a HSWYG (SEQ ID NO: 1029), or GLFHAIAHFIHGGWHGLIHGWYG (SEQ ID NO:862) peptide.

In some embodiments, the endosomal escape agent is a synthetic peptide. In some embodiments, the endosomal escape agent is peptide ppTG21: GLFHALL-HLLHSLWHLLLHA (SEQ ID NO: 1012), having the structure:

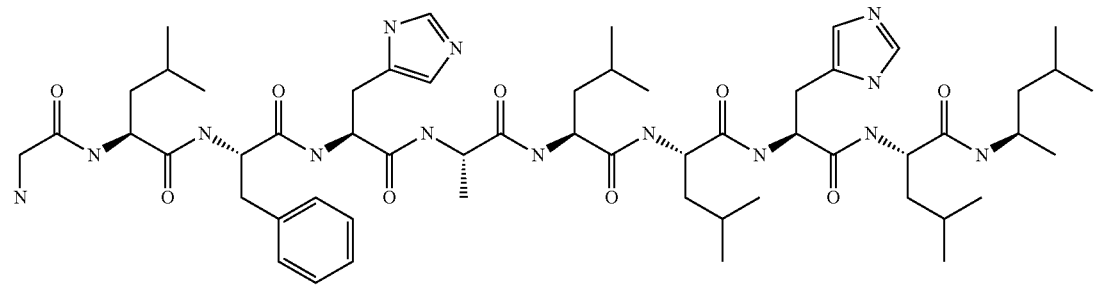

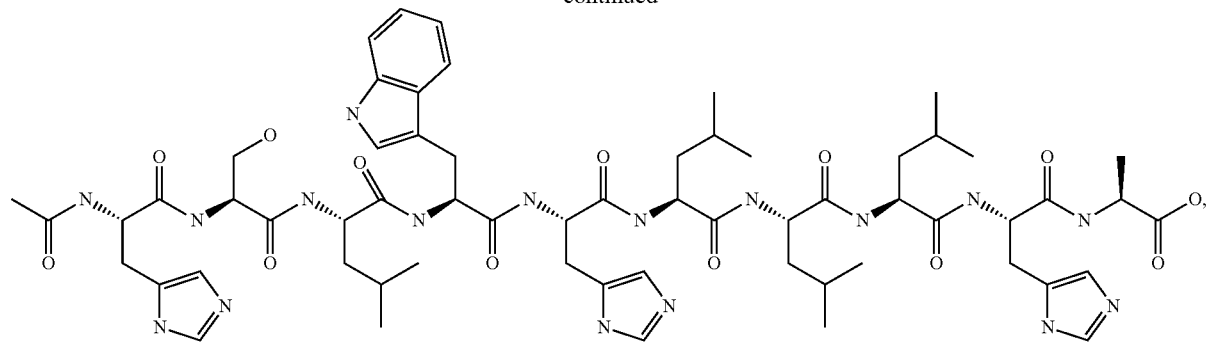

wherein the hydrogen atoms are omitted from the peptide structure for clarity of view.

See Rittner, Karola, et al., New Basic Membrane-Destabilizing Peptides for Plasmid-Based Gene Delivery in Vitro and in Vivo, MOLECULAR THERAPY 5(2) 104-114 (2002).

Pore-forming agents are agents, such as peptides, that induce pore formation through the membrane thereby disrupting endosome. Suitable pore-forming agents for use herein include, but are not limited to, cecropin (insects), magainin, CPF 1, PGLa, Bombinin BLP-1 (all three from amphibians), melittin (bees), seminalplasmin (bovine), indolicidin, bactenecin (both from bovine neutrophils), tachyplesin 1 (crabs), protegrin (porcine leukocytes), and defensins (from human, rabbit, bovine, fungi, and plants), Gramicidin A and gramicidin S (*Bacillus brevis*), the lantibiotics such as nisin (*Lactococcus lactis*), androctonin (scorpion), cardiotoxin I (cobra), caerin (frog litoria splendida), dermaseptin (frog). Viral peptides have also been shown to have pore-forming activity, examples include hemagglutinin subunit HA-2 (influenza virus), E1 (Semliki forest virus), F1 (Sendai and measles viruses), gp41 (HIV), gp32 (SIV), and vp1 (Rhino, polio, and coxsackie viruses). In some embodiments, the endosomal escape agent is a vp1 peptide derived from rhino virus. In some embodiments, the endosomal escape agent is the mellitin peptide derived from bee venom, or a masked analog thereof.

Proton sponge agents are agents having multiple proton acceptor sites that disrupt the endosome by osmolytic action. In some embodiments, the proton sponge agent suitable for use herein comprises a plurality of proton acceptor sites having pKa values between physiological and lysosomal pH. In some embodiments, the proton sponge agent suitable for use herein comprises a plurality of proton acceptor sites having pKa values within the range of 4 to 7, which endosomal lysing component is polycationic at pH 4. In some embodiments, the endosomal escape agent is a proton sponge agent selected from imidazole-containing compounds such as compounds or peptides comprising one or more histidine, histamine, vinylimidazole, or combinations thereof. In some embodiments, the suitable proton sponge agents for use herein include polymers have one or more secondary or tertiary amines and exhibit pKa values between physiological and lysosomal pH. In some embodiments, the proton sponge agents suitable for use herein include, but are not limited to polymers such as plyethylenimines, plyamidoamine dendrimers, PEG-oligo(glutamic acid)-PEI; poly (L-histidines); chloroquine, methylamine, ammonium chloride.

In another embodiment, a compound describe is capable of binding to a receptor present on a hepatocyte. In another embodiment, the receptor present on a hepatocyte is an asialoglycoprotein receptor.

Preparation Methods

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key synthetic intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg or NPg) include acetyl, trifluoroacetyl, t-butoxycarbonyl (BOC), benzyloxycarbonyl (CBz), 9-fluorenylmethyleneoxycarbonyl (Fmoc), and phthalimide (Pht). A "hydroxy-protecting group" refers to a substituent of a hydroxy group that blocks or protects the hydroxy functionality. Suitable hydroxyl-protecting groups (O-Pg) include for example, allyl, acetyl (Ac), silyl (like trimethylsily (TMS) or tert-butyldimethylsilyl (TBS)), benzyl (Bn), para-methoxybenzyl (PMB), trityl (Tr), para-bromobenzoyl, para-nitrobenzoyl and the like (benzylidene, cyclic ketals, orthoesters, orthoamides for protection of 1,2- or 1,3-diols). The need for such protection is readily determined by one skilled in the art. For a general description of protecting groups and their use, see T. W. Greene, Protective Groups in Organic Synthesis, John Wiley & Sons, New York, 1991.

Scheme 1 outlines the general procedures one could use to provide compounds of the present invention. In step 1 of Scheme 1, synthetic intermediate (I-a), that can be prepared by procedures described by H. Paulsen and M. Paal in Carbohydrate Research, 135, 53 (1984), is persylilated under classical conditions [using trimethylsilyl chloride and pyridine at room temperature (about 23° C.)] followed by selective cleavage of the trimethyl silyl group protecting the primary alcohol (by treatment under basic conditions such as potassium carbonate in an alcoholic solvent like methanol at a temperature ranging from about −10 degrees Celsius to room temperature) to reveal primary alcohol intermediate (I-b). In step 2 of Scheme 1, the additional hydroxymethylene group found in intermediate (I-c) can be introduced onto the glycoside by means of a Parikh-Doering oxidation described by J. R. Parikh and William v. E. Doering in Journal of the American Chemical Society, 89, 5505-5507 (1967) followed by treatment with a formaldehyde source (e.g., solution of formaldehyde in water, solid paraformaldehyde) in the presence of an alkali metal hydroxide (e.g., sodium hydroxide, sodium alkoxide) in water or in an alcoholic solvent at a temperature ranging from about room temperature to about 60 degrees Celsius. This is referred to as an aldol-Cannizzaro reaction. Modifications of this process known to those of skill in the art may also be used. For example, other oxidants, like stabilized 2-iodoxybenzoic acid described by Ozanne, A. et al. in Organic Letters, 5, 2903 (2003), the Swern oxidation described in Kanji Omura and Daniel Swern in Tetrahedron, 34, 1651 (1978), as well as other oxidants known by those skilled in the art can also be used. The aldol Cannizzaro sequence has been described by Robert Schaffer in the Journal of The American Chemical Society, 81, 5452 (1959) and Amigues, E. J., et al., in Tetrahedron, 63, 10042 (2007). Experimental conditions of step 2 in Scheme 1 also promote cleavage of the trimethylsilyl groups protecting the secondary alcohols. In step 3 of Scheme 1, intermediate (I-c) is treated with an organic or inorganic acid (e.g., sulfuric acid) or an acidic resin in a solvent like water at a temperature ranging from about room temperature to about 100 degrees Celsius to produce compound (1). In step 4 of Scheme 1, compound (1) can be treated with a reducing agent known to reduce azido groups to the corresponding amine (e.g., transition-metal mediated catalytic hydrogenation, use of triphenylphosphine in water under classical experimental conditions well known by those skilled in the art). Subsequent treatment in presence of an acylating agent (e.g., acetic anhydride or acetyl chloride in presence of pyridine or triethylamine in a solvent such as dichloromethane or tetrahydrofuran at a temperature ranging from 0 to 80 degrees Celsius) provides compound (2). In step 5 of Scheme 1, treatment of compound (2) in presence of an alkoxide (e.g., sodium methoxide) in a solvent, or mixture of solvents, such as an alcoholic solvent or tetrahydrofuran at a temperature ranging from about 0 to room temperature provides compound (3). Furthermore, the compounds thus obtained can then be easily functionalized to other claimed compounds from the present invention using well known protective and functional groups manipulation sequences known by those skilled in the art. Thus, in steps 6 and 7 of Scheme 1, secondary hydroxyl groups in compounds (1) and (3) respectively can be further protected by a suitable protecting group (e.g., as a cyclic ketal upon treatment with 2,2-dimethoxypropane under acidic conditions in a solvent such as N,N-dimethylformamide at a temperature ranging from about room temperature to about 90 degrees Celsius) to access intermediates such as (I-d) and (I-e). In turn, using synthetic transformations and functional and protecting groups manipulations well known by those skilled in the art, (I-d) and (I-e) are primed for further functionalization and derivatization of the primary hydroxyl group to link the desired linker X and ligand Y of interest to produce the XY-containing compounds claimed in the present invention. Removal of the protecting groups (e.g., Pg), using reagents and conditions well known to those skilled in the art (e.g., in the case where the two Pg form a cyclic ketal such as an acetonide, it can be removed under acidic conditions using an acid such as acetic acid in a solvent or mixture of solvents such as acetic acid, an alcoholic solvent, water, tetrahydrofuran at a temperature ranging from room temperature to about 80 degrees Celsius), to reveal the secondary hydroxyl groups leads to XY-containing compounds claimed in the present invention. For example, alkylation of the primary hydroxyl group in (I-e) can lead to, after protecting group manipulation and removal, the corresponding ether-linked XY-containing compounds claimed in this invention. Ester-linked, carbonate-linked and carbamate-linked XY-containing compounds claimed in the present invention can also be conveniently accessed from (3) or intermediate (I-e) using the appropriate reactants and reagents well known by those skilled in the art. Conversion of the primary hydroxyl group in (I-e) to the corresponding triflate (III-e-1) followed by nucleophilic displacement with the appropriate nucleophile can lead to, after protecting group manipulation and removal, the corresponding ether- and thioether-linked XY-containing compounds claimed in this invention. Oxidation of the thioether intermediate can also lead to the corresponding sulfoxide- and sulfone-linked XY-containing compounds claimed in this invention. In addition, displacement of the primary triflate in (III-e-1) by potassium thioacetate followed by thioester hydrolysis can provide the corresponding thiol (III-e-2) which provides compound (IV-e-1) after protecting group manipulation and removal; further alkylation of the thiol (III-e-2) and protecting group manipulation and removal can also produce thioether-linked XY-containing compounds claimed in this invention. (III-e-2) can also be converted to the corresponding sulfonyl chloride and treated with the appropriate amine to produce, after protecting group manipulation and removal, sulfonamide linked XY-containing compounds of the present invention. Displacement of the primary triflate (III-e-1) with sodium azide can also produce the corresponding azide-containing compound (III-e-3) which after protecting group manipulation and removal provides compound (IV-e-2). Reduction of compound (III-e-3) can produce the corresponding primary amine (III-e-4) primed for further functionalization (e.g., amide bond formation, reductive amination, sulfonamide formation, urea formation, carbamate formation, etc.) to link the XY substituent and produce compounds claimed in this invention after protecting group manipulation and removal. (III-e-4) can also produce compound (IV-e-3) of the present invention after protecting group manipulation and removal. Treatment of the above azide intermediate (III-e-3) with an alkyne or nitrile containing reagent or synthetic intermediate followed by protecting group manipulation and removal under conditions well known by those skilled in the art can also produce a triazole- or tetrazole-linked XY-containing compounds claimed in this invention, respectively. Oxidation of the primary hydroxyl group in (I-e) to the corresponding aldehyde (III-e-5) followed by reductive amination, under classical conditions known to those skilled in the art, with the appropriate amine, or olefination (such as Wittig-, Horner-Wadsworth-Emmons-, Petterson, Julia-type and modification thereof) followed by reduction of the olefin formed (using for instance a metal mediated catalytic hydrogenation or a diimide mediated reduction well known by those skilled in the art), can lead to the desired nitrogen- or carbon-linked X-Y-containing compounds claimed in this invention after functional group manipulation and protecting group manipulation and removal, respectively. Conversion of the aldehyde (III-e-5) to the corresponding alkyne (III-e-6) (using a Corey-Fuchs type reaction or using a Seyferth-Gilbert type reagent) followed by protecting group manipulation and removal can lead to compound (IV-e-4). In turn, treatment of alkyne (III-e-6) or (IV-e-4) with an azide containing reagent or synthetic intermediate followed by protecting group manipulation and removal under conditions well known by those skilled in the art can also produce a triazole-linked XY-containing compounds claimed in this invention. Alkyne (III-e-6) can also serve as a useful synthetic intermediate to access other compounds claimed in this invention upon treatment with the appropriate reagents under metal mediated cross couplings known to those skilled in the art (such as a Sonogashira-type reaction). Oxidation of the primary hydroxyl group in (I-e) to the corresponding acid (III-e-7) provides, using synthetic transformations well known by those skilled in the art, access to ester- and amide-linked XY-containing compound claimed in this invention, after protecting group removal. Protecting group manipulation and removal in (III-e-7) also provides readily access to compound (IV-e-5). Conversion of (IV-e-5) or (III-e-7) to the corresponding primary amide under conditions well known by those skilled in the art directly provides compound (IV-e-6) or compound (III-e-8) which after protecting group manipulation and removal gives (IV-e-6). In addition, dehydration of the amide functionality in (III-e-8) can provide the corresponding nitrile (III-e-9) which after functional group manipulation and removal provides compound (IV-e-7). Displacement of the primary triflate (III-e-1) with a cyanide anion can also produce the corresponding nitrile-containing compound (III-e-10) which after protecting group manipulation and removal provides compound (IV-e-8). In turn, hydrolysis of the nitrile in (IV-e-8) or (III-e-10) can provide directly access to acid (IV-e-9) or to (III-e-11) which after protecting group manipulation and removal provides (IV-e-9). Alkyne containing compounds such as (III-e-6)/(IV-e-4), primary amide containing compounds such as (III-e-8)/(IV-e-6), nitrile containing compounds such as (III-e-9)/(IV-e-7)/(III-e-10)/(IV-e-8), acid containing compound such as (III-e-7)/(IV-e-5)/(III-e-11)/(IV-e-9), aldehyde containing compounds such as (III-e-5) can also be further functionalized and reacted with the appropriate reagent and synthetic intermediate under conditions well known by those skilled in the art (and summarized in J. A. Joule and K. Mills, Heterocyclic Chemistry, 5$^{th}$ edition, Wiley Ed., (2010); J. J. Li, Name Reactions in heterocyclic chemistry, Wiley, (2005); M. R. Grimmett Advances in Heterocyclic Chemistry, 27, 241, (1981); I. G. Turchi et al., Chemical Reviews, 75, 389, (1975); K. T. Potts, Chemical Reviews, 61, 87, (1961); R. H. Wiley, Organic Reactions, 6, 367, (1951); L. B. Clapp, Advances in Heterocyclic Chemistry, 20, 65, (1976); A. Hetzheim et al., Advances in Heterocyclic Chemistry, 7, 183, (1967); J. Sandstrom, Advances in Heterocyclic Chemistry, 9, 165, (1968); S. J. Wittenberger, Organic Preparations and Procedures International, 26, 499, (1994); M. G. Finn et al., Angewandte Chemie International Edition, 48, 9879, (2009)) to produce additional 5 and 6 membered ring (such as isoxazole, isothiazole, pyrazole, oxazole, thiazole, imidazole, 1,2,4-oxadiazole, 1,2,4-thiadiazole, 1,2,4-triazole, 1,3,4-oxadiazole, 1,3,4-thiadiazole, tetrazole, 1,2,3-triazole) linked XY-containing compounds claimed in this invention. Aryl ring-linked XY-containing compounds claimed in this invention can also be accessed from alkynes such as (III-e-6) and (IV-e-4), or a heterosubstituted analogue of these alkynes (i.e., by replacing the alkyne hydrogen in (III-e-6)/(IV-e-4) by OR$^4$, N(R$^4$)$_2$, SR$^4$; these compounds can be accessed using conditions and reagents known to those skilled in the art), via a benzannulation reaction known from those skilled in the art (such as a Danheiser-type or Dotz-type benzannulation).

Similar chemistry described above for compounds (3) and (I-e) can also be applied to compound (1) and intermediate (I-d) to provide additional compounds claimed in the present invention. See examples section for further details.

Scheme 1.

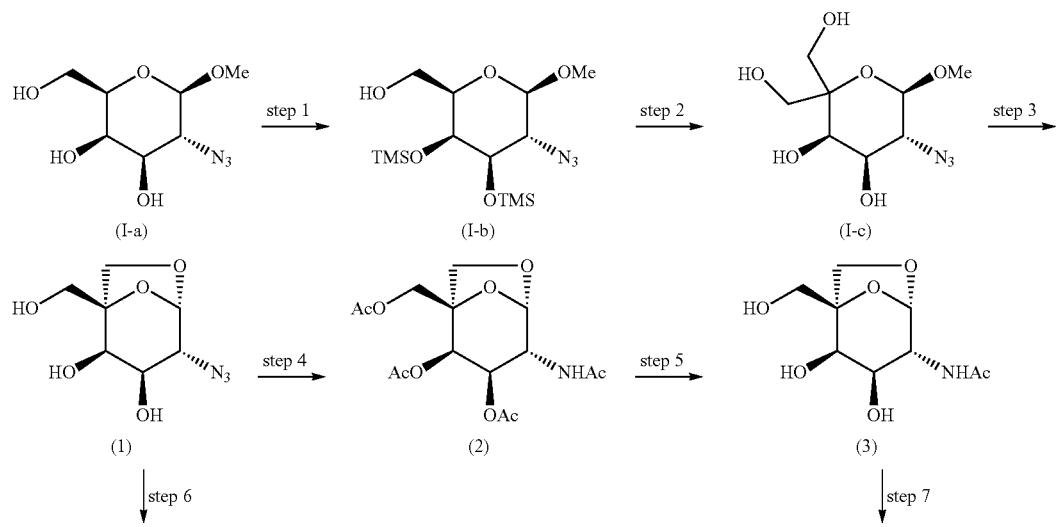

53
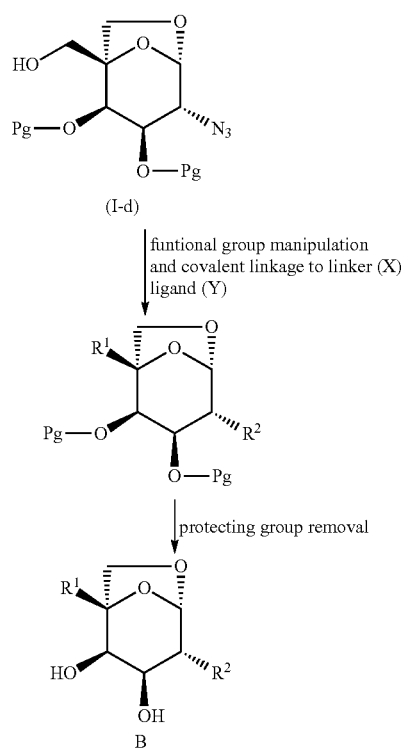
(I-d)
↓ funtional group manipulation and covalent linkage to linker (X) ligand (Y)
↓ protecting group removal
B
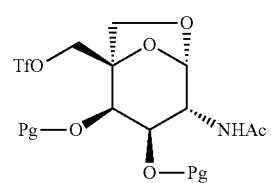 (III-e-1)
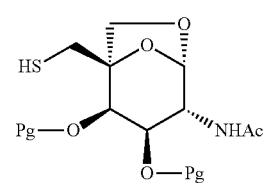 (III-e-2)
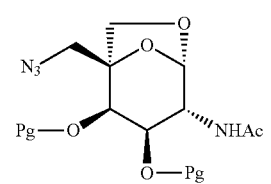 (III-e-3)
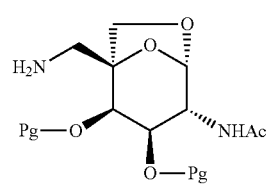 (III-e-4)
-continued
54
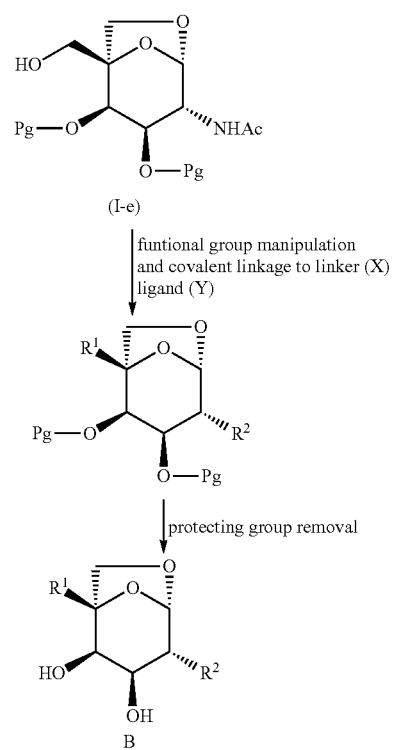
(I-e)
↓ funtional group manipulation and covalent linkage to linker (X) ligand (Y)
↓ protecting group removal
B
-continued
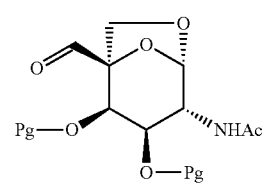 (III-e-5)
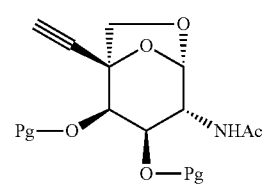 (III-e-6)
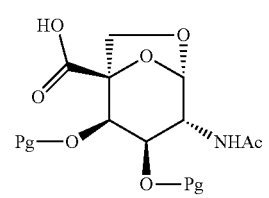 (III-e-7)
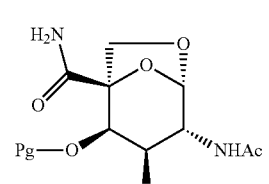 (III-e-8)

-continued

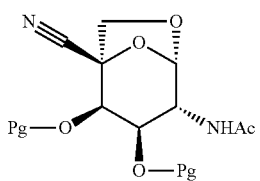
(III-e-9)

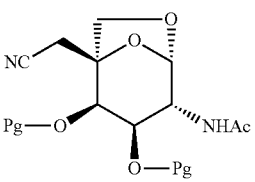
(III-e-10)

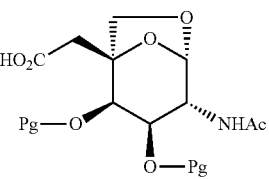
(III-e-11)

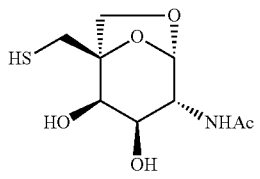
(IV-e-1)

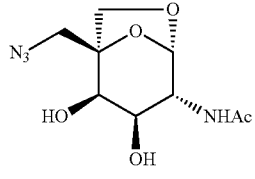
(IV-e-2)

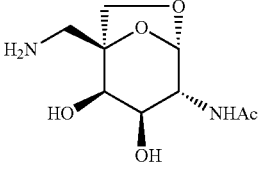
(IV-e-3)

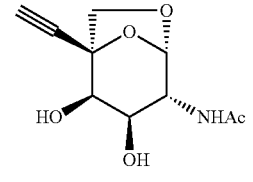
(IV-e-4)

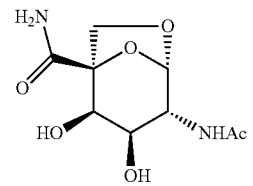
(IV-e-6)

-continued

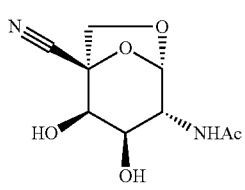
(IV-e-7)

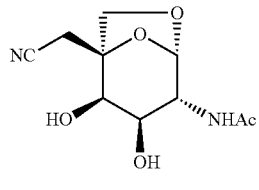
(IV-e-8)

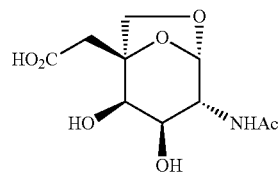
(IV-e-9)

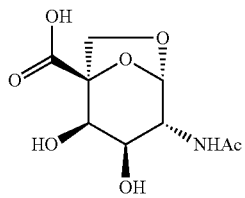
(IV-e-5)

The use of trifluoroacetic anhydride in step 4 of Scheme 1 can also provide access to N-((1S,2R,3R,4R,5S)-2,3-dihydroxy-1-(hydroxymethyl)-6,8-dioxabicyclo[3.2.1]octan-4-yl)-2,2,2-trifluoroacetamide, compound (24).

Particularly when $R^1$ contains an aliphatic-, PEG-derived chain, PEG-derived oligo- or polymer, compounds of the present invention can be further functionalized, reacted, and formulated under conditions known to those skilled in the art to access additional compounds claimed in the present invention that can be used and incorporated in the formulation of hepatoselective drug delivery systems such as Biodegradable PLGA-b-PEG polymeric nanoparticles (see, Erica Locatelli et al., Journal of Nanoparticle Research, 14, 1316, (2012)) and lipid based platforms such as liposomes, lipid nanoparticles, stable nucleic acids lipid nanoparticles (see, Sara Falsini et al., Journal of Medicinal Chemistry, 57, 1138 (2014)).

Diastereomeric mixtures can be separated into their individual diastereoisomers on the basis of their physical chemical differences by methods well known to those skilled in the art, such as by chromatography and/or fractional crystallization, distillation, sublimation. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC (high pressure liquid chromatography) column.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons. The equilibrium between closed and opened form of some intermediates (and/or mixtures of intermediates) is reminiscent of the process of mutarotation involving aldoses, known by those skilled in the art.

Scheme 3 provides exemplary Cas9 modifications in preparing the compounds of the present invention, wherein each occurrence of n, o, p, q, or r is an integer independently selected from 0 to 50.

Scheme 4 provides exemplary processes for linking a Cas9 protein or a Cas9 ribonucleoprotein to one or more other moieties via disulfide linkages, wherein each occurrence of n is an integer independently selected from 0 to 50. A person with ordinary skill in the art would appreciate that the disulfide linkages depicted herein may be replaced by other suitable linkages.

"ASGPRL" or "ASGPrL" refer to as a ligand, or dendrimer thereof, for the asialoglycoprotein receptor, such as compounds described in the present invention.

Scheme 4.

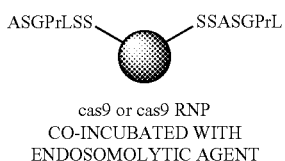

cas9 or cas9 RNP
CO-INCUBATED WITH
ENDOSOMOLYTIC AGENT

Scheme 3.

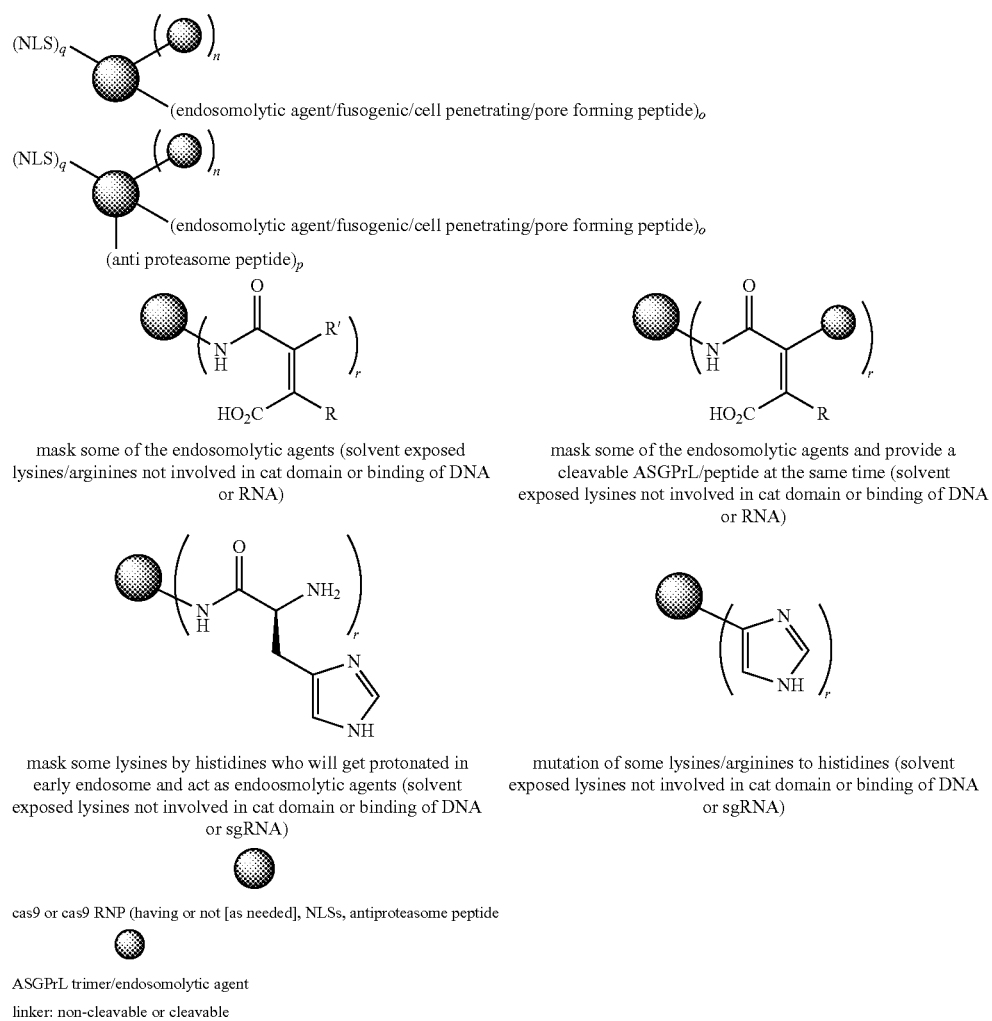

-continued

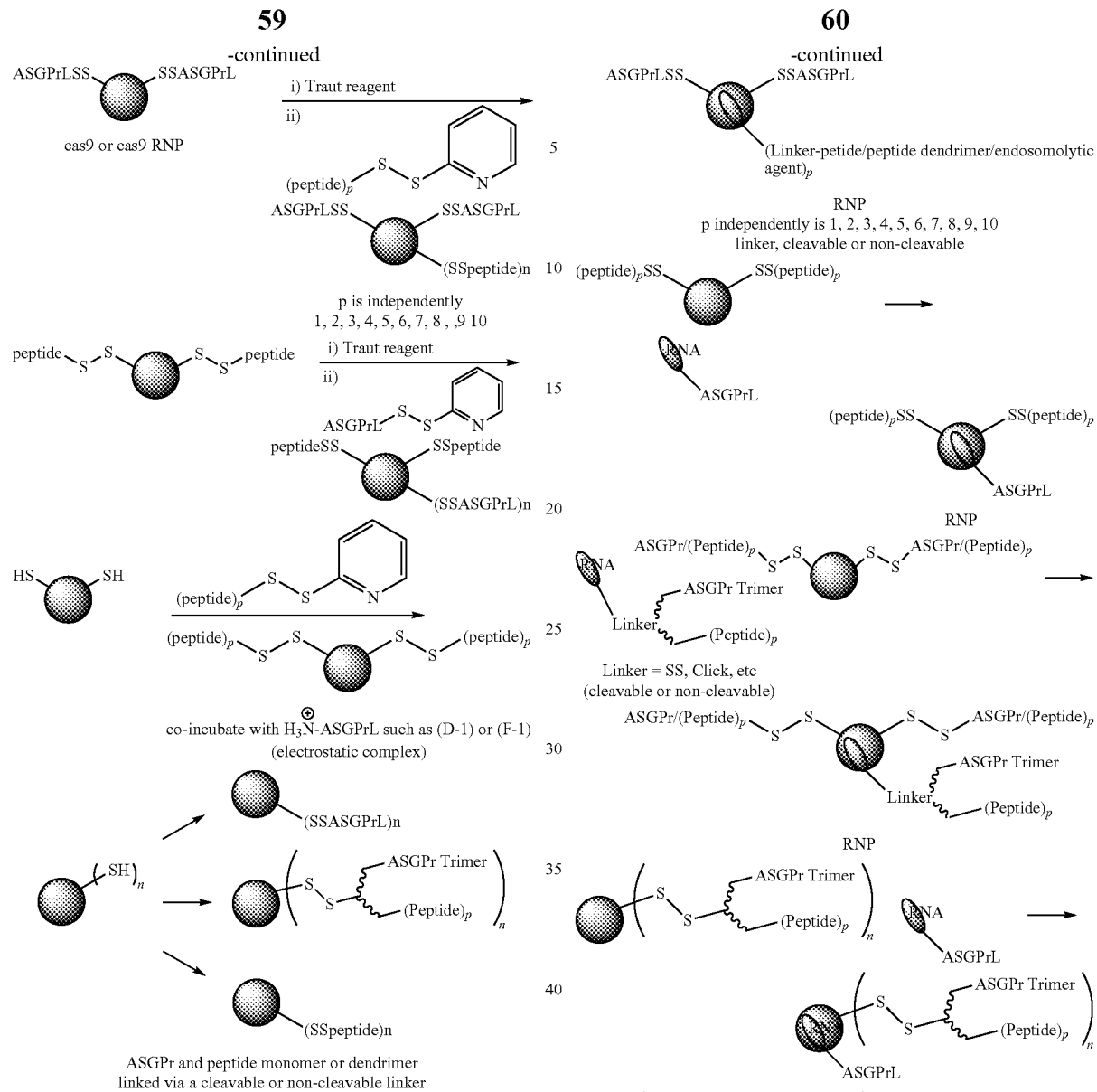

Scheme 5 provides exemplary processes for preparing Cas9 ribonucleoproteins where the RNA is associated with the Cas9 protein via electrostatic interactions, wherein each occurrence of n is an integer independently selected from 0 to 50.

Scheme 5.

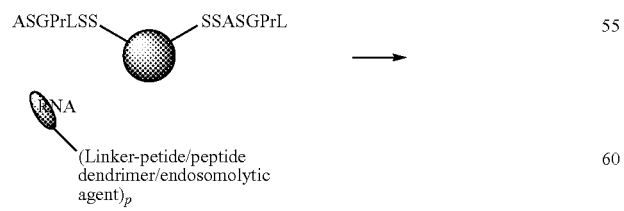

Scheme 6 provides exemplary syntheses of the linker of type L1-L10 wherein Z is peptide ppTG21 and wherein the hydrogen atoms are omitted from the peptide structures for clarity of view. A person with ordinary skill in the art would readily appreciate that the peptide ppTG21 may be replaced with any suitable small molecule such as ASGPrL or an endoosmolytic agent, or a peptide as described herein.

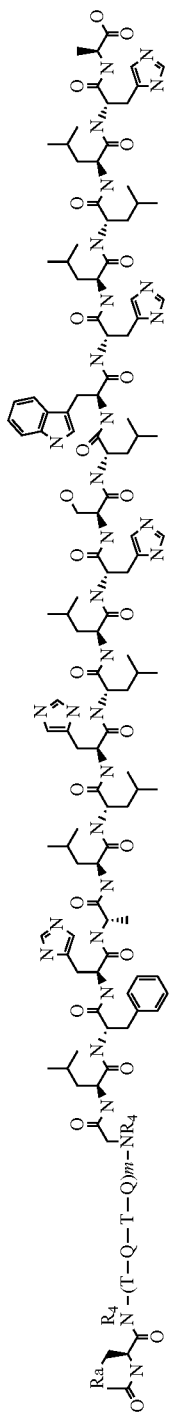
Scheme 6

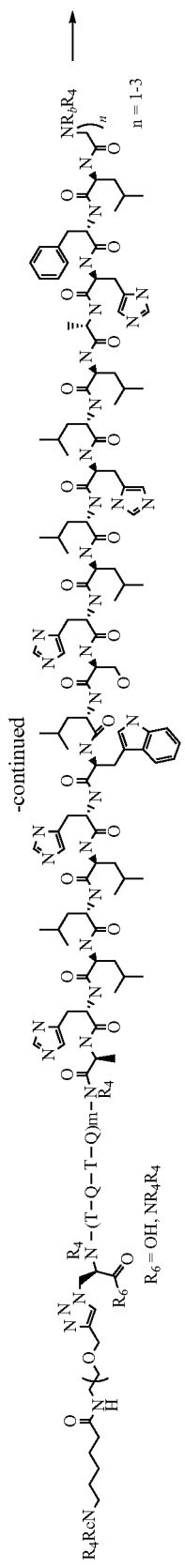
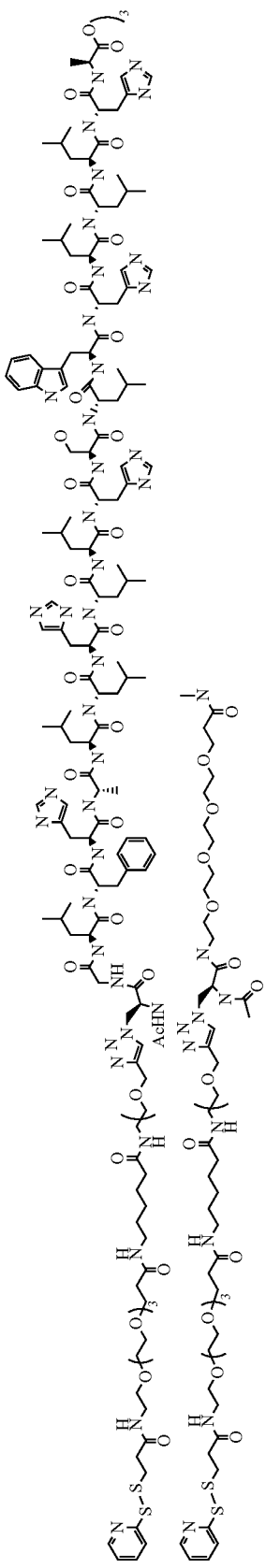
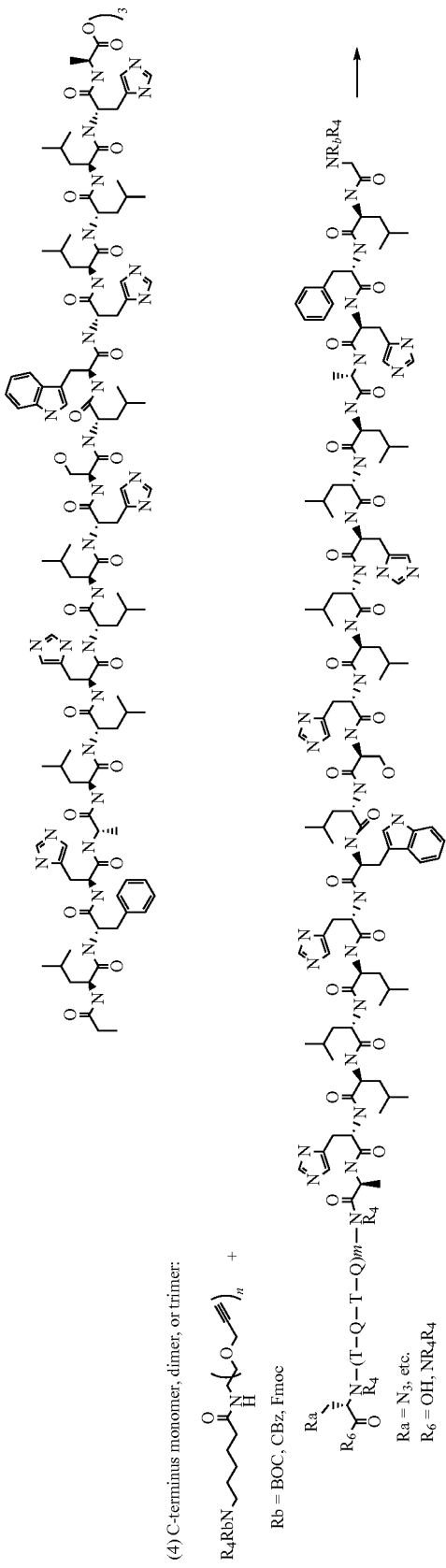
(3) N-terminus Examples:
Representative N-terminus examples:
(4) C-terminus monomer, dimer, or trimer:

-continued
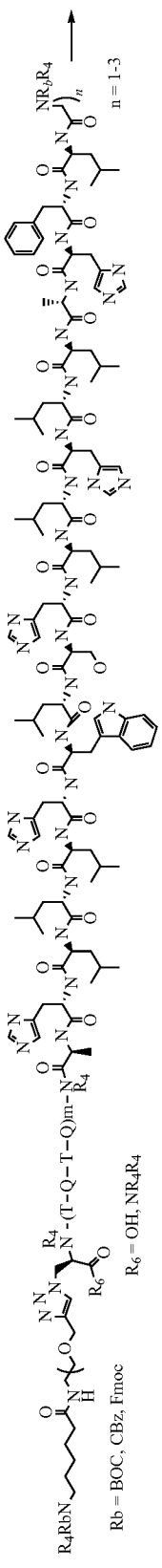
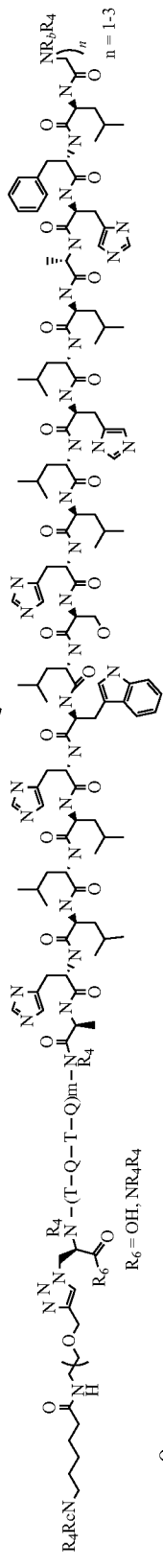
(5) N-terminus Examples:
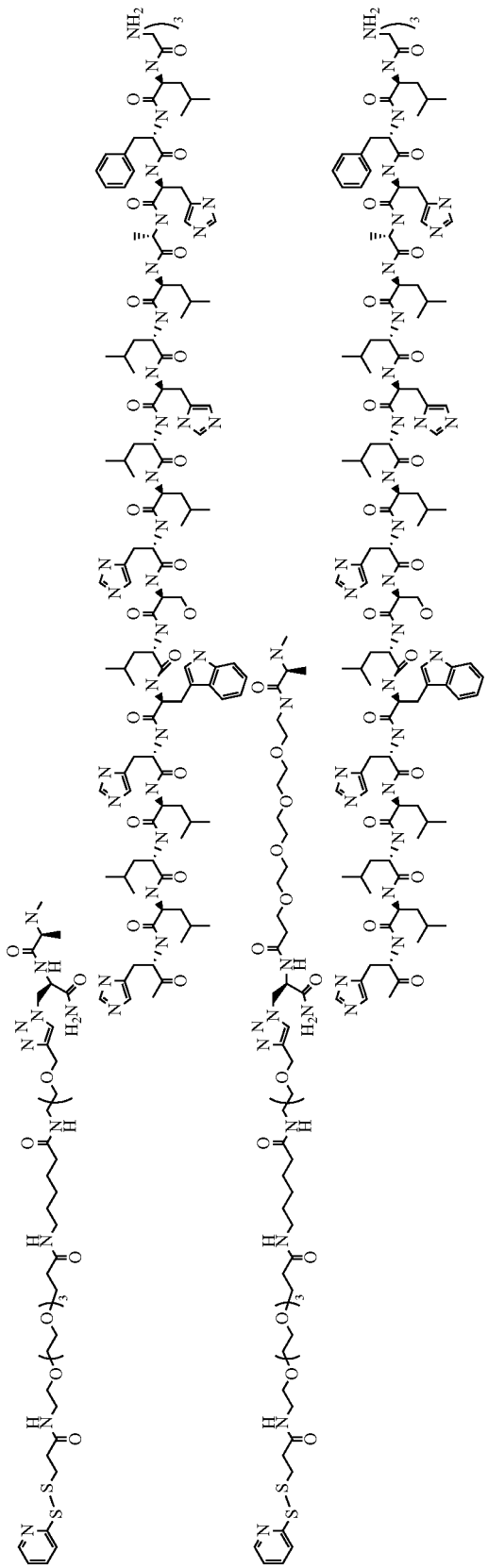
(6) General process for preparing ASGPRL-peptide conjugates

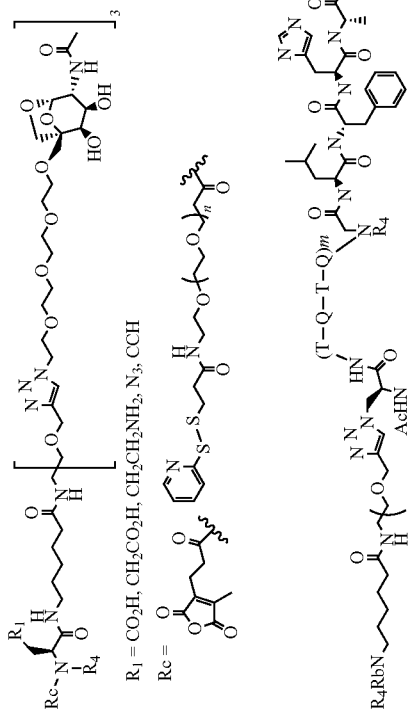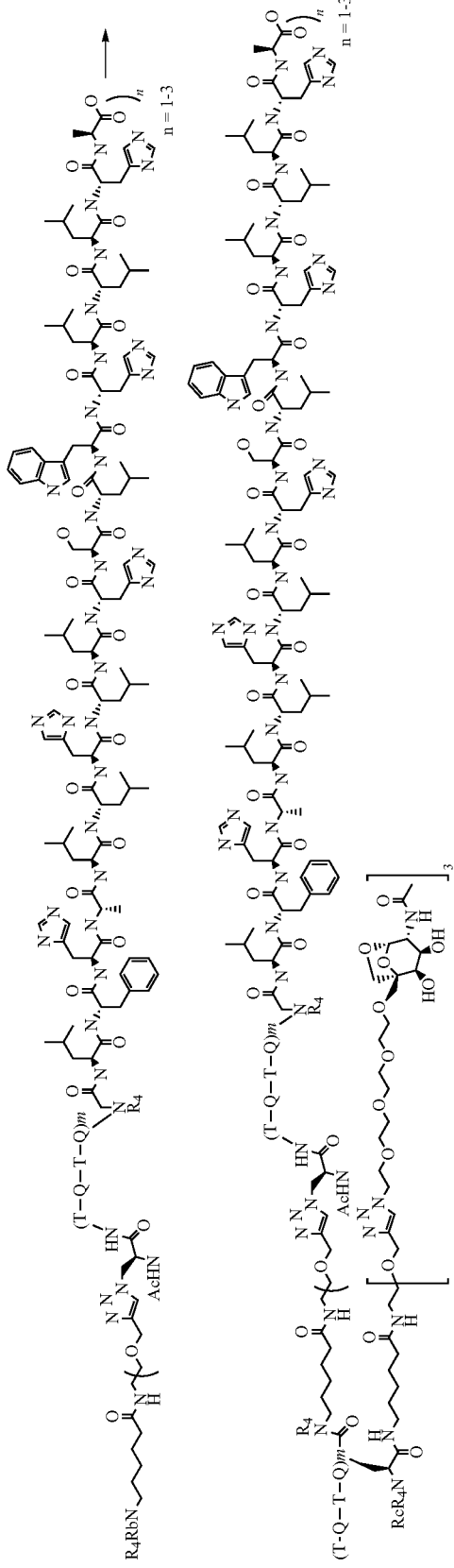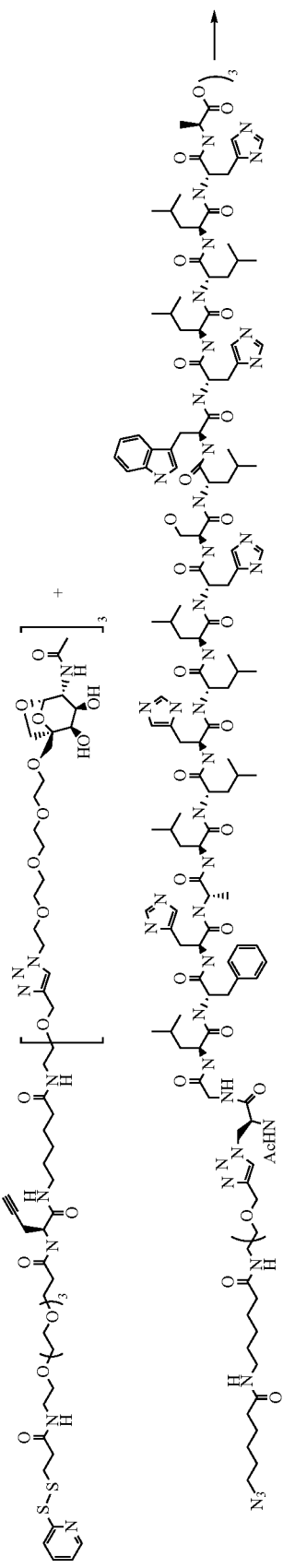

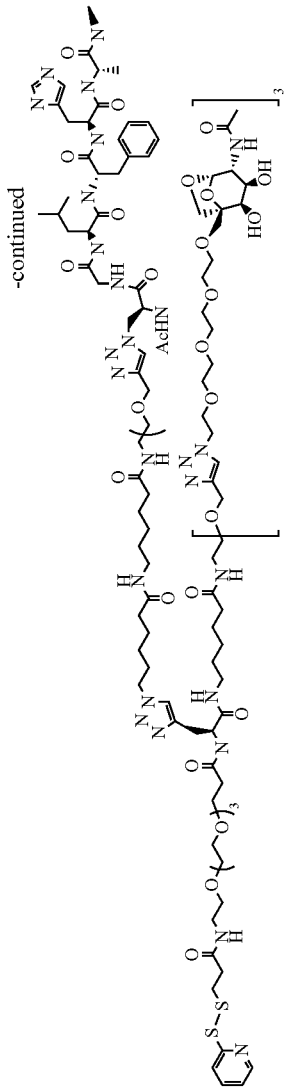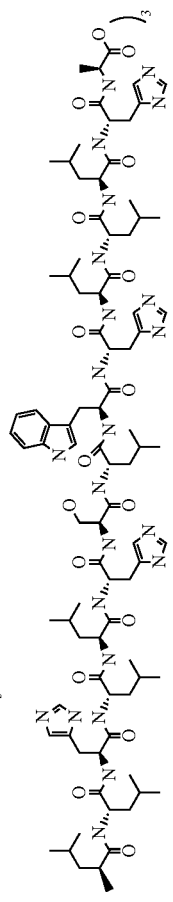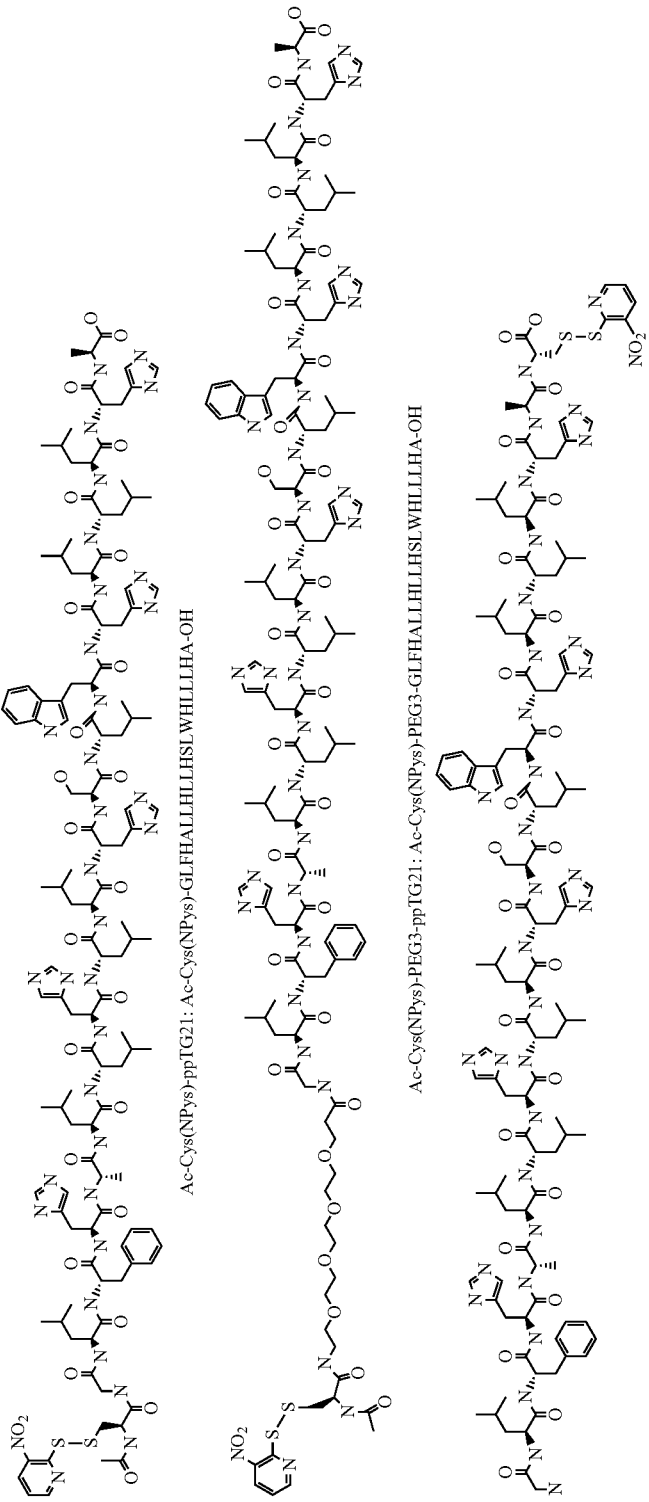
(8) Exemplary ppTG21 and derivative structures (SEQ ID NOS 1049-1051, respectively, in order of appearance):
Ac-Cys(NPys)-ppTG21: Ac-Cys(NPys)-GLFHALLHLLHSLWHLLLHA-OH
Ac-Cys(NPys)-PEG3-ppTG21: Ac-Cys(NPys)-PEG3-GLFHALLHLLHSLWHLLLHA-OH
ppTG21-Cys(NPys)-OH: GLFHALLHLLHSLWHLLLHA-Cys(NPys)-OH (9) Exemplary ASGPr ligand structures:
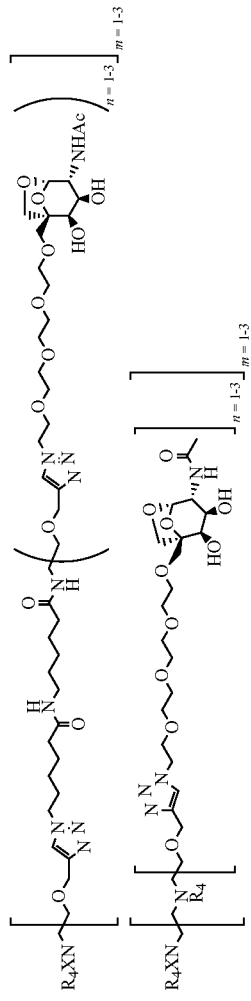

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of the present invention (e.g., those labeled with $^{3}$H and $^{14}$C) are useful in compound and/or substrate tissue distribution assays. Tritiated (i.e., $^{3}$H) and carbon-14 (i.e., $^{14}$C) isotopes are particularly preferred for their ease of preparation and detectability. Further, substitution with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Endosomal Escape Agent-Containing Compositions

Another aspect of the present invention provides a composition comprising a compound described herein and an endosomal escape agent described herein. In some embodiments of such a composition, the compound is co-incubated with the endosomal escape agent to form the composition.

Another aspect of the present invention provides a composition comprising a ribonucleoprotein described herein (e.g., a RNP comprising a site-directed modifying polypeptide, such as a Cas9 RNP or a Cpf1 RNP) and an endosomal escape agent described herein. In some embodiments of such a composition, the ribonucleoprotein (e.g., a RNP comprising a site-directed modifying polypeptide, such as a Cas9 RNP or a Cpf1 RNP) is co-incubated with the endosomal escape agent to form the composition. In some embodiments, the ribonucleoprotein (e.g., a RNP comprising a site-directed modifying polypeptide, such as a Cas9 RNP or a Cpf1 RNP) or the endosomal escape agent is conjugated to an antibody or a fragment thereof. In some embodiments, the ribonucleoprotein (e.g., a RNP comprising a site-directed modifying polypeptide, such as a Cas9 RNP or a Cpf1 RNP) is modified to include glycosylation sites. In some embodiments, the ribonucleoprotein (e.g., a RNP comprising a site-directed modifying polypeptide, such as a Cas9 RNP or a Cpf1 RNP) is modified to include transduction or translocation domains.

Pharmaceutical Compositions and Modes of Administration

Compounds and compositions of the present invention are useful for treating diseases, conditions and/or disorders; therefore, another embodiment of the present invention is a pharmaceutical composition comprising a therapeutically effective amount of a compound, or an endosomal escape agent containing composition, of the present invention and a pharmaceutically acceptable excipient, diluent or carrier. The compounds of the present invention (including the compositions and processes used therein) may also be used in the manufacture of a medicament for the therapeutic applications described herein.

The pharmaceutical compositions of this invention may be in liquid solutions (e.g., injectable and infusible solutions). The preferred form depends on the intended mode of administration and therapeutic application. Typical pharmaceutical compositions are in the form of injectable or infusible solutions, such as pharmaceutical compositions similar to those used for passive immunization of humans. One mode of administration is parenteral (e.g., intravenous, subcutaneous, intraperitoneal, intramuscular, intradermal, and intrasternally) or by infusion techniques, in the form of sterile injectable liquid or olagenous suspensions. As will be appreciated by the skilled artisan, the route and/or mode of administration will vary depending upon the desired results. In a preferred embodiment, the compound or composition is administered by intravenous infusion or injection. In another preferred embodiment, the compound or composition is administered by intramuscular or subcutaneous injection.

Therapeutic pharmaceutical compositions typically are sterile and stable under the conditions of manufacture and storage.

The pharmaceutical composition can be formulated as a solution, microemulsion, dispersion, or liposome. Sterile injectable solutions can be prepared by incorporating the compound of the present invention in the required amount in an appropriate diluent with one or a combination of ingredients enumerated above, as required, followed by sterilization (e.g., filter sterilization). Generally, dispersions are prepared by incorporating the active compound into a sterile vehicle that contains a basic dispersion medium and the required other ingredients from those enumerated above. Such suspensions may be formulated according to the known art using those suitable dispersing of wetting agents and suspending agents or other acceptable agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed, including synthetic mono- or diglycerides. In addition, n−3 polyunsaturated fatty acids may find use in the preparation of injectables.

In the case of sterile powders for the preparation of sterile injectable solutions, the preferred methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants.

Prolonged absorption of injectable pharmaceutical compositions can be brought about by including in the pharmaceutical composition an agent that delays absorption, for example, monostearate salts and gelatin or by formulating the pharmaceutical composition into prolonged absorption forms such as, depots, liposomes, polymeric microspheres, polymeric gels, and implants.

Other methods for administration of the compound of the present invention described herein include dermal patches that release the medications directly into a subject's skin. Such patches can contain the compound of the present invention in an optionally buffered, liquid solution, dissolved and/or dispersed in an adhesive, or dispersed in a polymer.

The compound may be administered once, but may also be administered multiple times. For example, the compound may be administered from once daily to once every six months or longer. The administering may be on a schedule such as three times daily, twice daily, once daily, once every two days, once every three days, once weekly, once every two weeks, once every month, once every two months, once every three months, once every six months, once a year, and once every two years.

The compound may also be administered continuously via a minipump. The compound may be administered at the site of the diseased body part or at a site distant from the site of the diseased body part. The compound may be administered once, at least twice or for at least the period of time until the disease is treated, palliated or cured. The compound generally may be administered for as long as the disease is present. The compound typically would be administered as part of a pharmaceutical composition as described supra.

The pharmaceutical compositions of the invention may include a therapeutically effective amount or a prophylactically effective amount of compound of the invention. In preparing the pharmaceutical composition, the therapeutically effective amount of the compound present in the pharmaceutical composition can be determined, for example, by taking into account the desired dose volumes and mode(s) of administration, the nature and severity of the condition to be treated, and the age and size of the subject.

Exemplary, non limiting dose ranges for administration of the pharmaceutical compositions of the present invention to a subject are from about 0.01 mg/kg to about 200 mg/kg (expressed in terms of milligrams (mg) of compound of Formula (A) or (B) administered per kilogram (kg) of subject weight), from about 0.1 mg/kg to about 100 mg/kg, from about 1.0 mg/kg to about 50 mg/kg, from about 5.0 mg/kg to about 20 mg/kg, or about 15 mg/kg. For purposes of the present invention, an average human subject weighs about 70 kg. Ranges intermediate to any of the dosages cited herein, e.g., about 0.02 mg/kg-199 mg/kg, are also intended to be part of this invention. For example, ranges of values using a combination of any of the recited values as upper and/or lower limits are intended to be included.

Dosage regimens can also be adjusted to provide the optimum desired response (e.g., a therapeutic or prophylactic response) by administering several divided doses to a subject over time or the dose can be proportionally reduced or increased as indicated by the exigencies of the therapeutic situation. It is especially advantageous to formulate parenteral pharmaceutical compositions in dosage unit form for ease of administration and uniformity of dosage.

Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound or portion and the particular therapeutic or prophylactic effect to be achieved, and (b) the limitations inherent in the art of compounding such an antibody for the treatment of sensitivity in individuals.

The liquid pharmaceutical compositions of the present invention can be prepared as unit dosage forms. For example, a unit dosage per vial may contain from 1 to 1000 milliliters (mls) of different concentrations of the compound of Formula (A) or (B). In other embodiments, a unit dosage per vial may contain about 1 ml, 2 ml, 3 ml, 4 ml, 5 ml, 6 ml, 7 ml, 8 ml, 9 ml, 10 ml, 15 ml, 20 ml, 30 ml, 40 ml, 50 ml or 100 ml of different concentrations of the compound of Formula (A) or (B). If necessary, these preparations can be adjusted to a desired concentration by adding a sterile diluent to each vial. The liquid pharmaceutical compositions of the present invention can also be prepared as unit dosage forms in sterile bags or containers, which are suitable for connection to an intravenous administration line or catheter.

Another typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of Formula (A) or (B). The term "solvate" refers to a molecular complex of a compound represented by Formula (A) or (B) (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. The crystalline forms may also exist as complexes with other innocuous small molecules, such as L-phenylalanine, L-proline, L-pyroglutamic acid and the like, as co-crystals or solvates or hydrates of the co-crystalline material. The solvates, hydrates and co-crystalline compounds may be prepared using procedures described in PCT Publication No.

WO 08/002824, incorporated herein by reference, or other procedures well-known to those of skill in the art.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Methods

Compounds and compositions of the present application are useful in treating a variety of diseases or conditions. In some embodiments, the compounds and compositions described herein are useful in treating a liver disease or condition or a liver modulated disease or condition in a subject including, but not limited to, hereditary angioedema, familial tyrosinemia type I, Alagille syndrome, Alpha-1-antitrypsin deficiency, Bile acid synthesis and metabolism defects, Biliary Atresia, Cystic Fibrosis liver disease, Idiopathic neonatal hepatitis, Mitochondrial hepatopathies, Progressive familial intrahepatic cholestasis, Primary sclerosing cholangitis, Transthyretin amyloidosis, Hemophilia, Homozygous familial hypercholesterolemia, familial chylomicronemia, hyperlipidemia, steatohepatitis, non-alcoholic steatohepatitis (NASH), non-alcoholic fatty liver disease (NAFLD), hyperglycemia like Type II diabetes mellitus, and diseases involving abnormally high hepatic glucose production similar to Type II diabetes mellitus.

Compounds and compositions of the present application are useful in selectively modulating transcription of a target DNA in a liver cell of a subject, said DNA being associated with a liver disease or condition or a liver modulated disease or condition in a subject, such as, but are not limited to hereditary angioedema, familial tyrosinemia type I, Alagille syndrome, Alpha-1-antitrypsin deficiency, Bile acid synthesis and metabolism defects, Biliary Atresia, Cystic Fibrosis liver disease, Idiopathic neonatal hepatitis, Mitochondrial hepatopathies, Progressive familial intrahepatic cholestasis, Primary sclerosing cholangitis, Transthyretin amyloidosis, Hemophilia, Homozygous familial hypercholesterolemia, familial chylomicronemia, hyperlipidemia, steatohepatitis, non-alcoholic steatohepatitis (NASH), non-alcoholic fatty liver disease (NAFLD), hyperglycemia like Type II diabetes mellitus, and diseases involving abnormally high hepatic glucose production similar to Type II diabetes mellitus, comprising the administration of an effective amount of a compound or composition described herein. In some embodiments, target DNA is the PCSK9 gene.

Compounds and compositions of the present application are useful in editing a nucleic acid molecule encoding a protein associated with a liver disease or condition or a liver modulated disease or condition in a subject, such as, but are not limited to hereditary angioedema, familial tyrosinemia type I, Alagille syndrome, Alpha-1-antitrypsin deficiency, Bile acid synthesis and metabolism defects, Biliary Atresia, Cystic Fibrosis liver disease, Idiopathic neonatal hepatitis, Mitochondrial hepatopathies, Progressive familial intrahepatic cholestasis, Primary sclerosing cholangitis, Transthyretin amyloidosis, Hemophilia, Homozygous familial hypercholesterolemia, familial chylomicronemia, hyperlipidemia, steatohepatitis, non-alcoholic steatohepatitis (NASH), non-alcoholic fatty liver disease (NAFLD), hyperglycemia like Type II diabetes mellitus, and diseases involving abnormally high hepatic glucose production similar to Type II diabetes mellitus, comprising the administration of an effective amount of a compound or composition described herein.

Compounds and compositions of the present application are useful in modulating the expression of level of at least one gene product associated with a liver disease or condition or a liver modulated disease or condition in a subject, such as, but are not limited to hereditary angioedema, familial tyrosinemia type I, Alagille syndrome, Alpha-1-antitrypsin deficiency, Bile acid synthesis and metabolism defects, Biliary Atresia, Cystic Fibrosis liver disease, Idiopathic neonatal hepatitis, Mitochondrial hepatopathies, Progressive familial intrahepatic cholestasis, Primary sclerosing cholangitis, Transthyretin amyloidosis, Hemophilia, Homozygous familial hypercholesterolemia, familial chylomicronemia, hyperlipidemia, steatohepatitis, non-alcoholic steatohepatitis (NASH), non-alcoholic fatty liver disease (NAFLD), hyperglycemia like Type II diabetes mellitus, and diseases involving abnormally high hepatic glucose production similar to Type II diabetes mellitus, comprising the administration of an effective amount of a compound or composition described herein. In some embodiments, said method modulates the level of low-density lipoproteins (LDLs). In some embodiments, said method modulates the level of cholesterol in the blood of said subject. In some embodiments, said method reduces the blood cholesterol level in said subject.

In some embodiments, the disease or condition targeted by the methods or use described herein is hyperlipidemia, non-alcoholic steatohepatitis (NASH), or non-alcoholic fatty liver disease (NAFLD). In some embodiments, said subject is human.

Compositions comprising a ribonucleoprotein described herein (e.g., a RNP comprising a site-directed modifying polypeptide described herein, such as a Cas9 RNP or a Cpf1 RNP) and an endosomal escape agent described herein are useful in treating a disorder or disease in a subject. In some embodiments, said subject is human. In some embodiments, the disorder or disease is selected from, but is not limited to, blood disorders, cell dysregulation or oncology diseases and disorders, inflammation and immune related diseases, metabolic, liver, kidney and protein diseases and disorders, muscular or skeletal diseases, neurological and neuronal diseases and disorders, and ocular diseases and disorders. In some embodiments, the blood disorder or disease is selected from, but is not limited to, anemia, bare lymphocyte syndrome, bleeding disorders, deficiency in Factor H and Factor H-like 1, V, VIII, VII, X, XI, XII, XIIIA, or XIIIB, Fanconi anemia, hemophagocytic lymphohistiocytosis disorders, hemophilia A or B, hemorrhagic disorders, leukocyde deficiencies and disorders, sickle cell anemia (HBB) and thalassemia. In some embodiments, the cell dysregulation and oncology disease or disorder is selected from, but is not limited to, B-cell non-Hodgkin lymphoma and Leukemia. In some embodiments, the inflammation and immune-related disease is selected from, but is not limited to AIDS, autoimmune lymphoproliferative syndrome, combined immunodeficiency, HIV susceptibility or infection, severe combined immunodeficiencies. In some embodiments, the metabolic, liver, kidney or protein disease is selected from, but is not limited to amyloid neuropathy, amyloidosism, cirrhosis, cystic fibrosis, glycogen storage diseases, hepatic adenoma, hepatic failure, hepatic lipase deficiency, hepatoblastoma, cancer and carcinomas, medullary cystic kidney disease, phenylketonuria, polycystic kidney and hepatic disease. In some embodiments, the muscular or skeletal disease is selected from, but is not limited to Becker muscular dystrophy, Duchenne Muscular Dystrophy, Emery-Dreifuss muscular dystrophy, facioscapulohumeral muscular dystrophy, muscular dystrophy, osteopetrosis, muscular atrophy. In some embodiments, the neurological and neuronal disease or disorder is selected from, but is not limited to ALS, Alzheimer disease, autism; Fragile X Syndrome, Huntington's disease and disease like disorders, Parkinson disease, Rett syndrome, Schizophrenia, secretase related disorders, and trinucleotide repeat disorders. In some embodiments, the ocular disease or disorder is selected from, but is not limited to, age-related macular degeneration, cataract, corneal clouding and dystrophy, cornea plana congenital, glaucoma, leber congenital amaurosis, and macular dystrophy.

In some embodiments, the disorder or disease is selected from, but is not limited to, neoplasia, age-related macular degeneration, CNS disorders (such as schizophrenia or bipolar, Alzheimer's Disease, Parkinson's Disease and autism), trinucleotide repeat disorders, Fragile X Syndrome, secretase related disorders, prion-related disorders, ALS, and substance addition.

Compositions comprising a ribonucleoprotein described herein (e.g., a RNP comprising a site-directed modifying polypeptide, such as a Cas9 RNP or a Cpf1 RNP) and an endosomal escape agent described herein are useful in modulating a cellular function in a subject. In some embodiments, the cellular signaling is selected, but is not limited to, PI3K/AKT Signaling, ERK/MAPK Signaling, Glucocorticoid Receptor Signaling, Axonal Guidance Signaling, Ephrin Receptor Signaling, Actin Cytoskeleton Signaling, Huntington's Disease Signaling, Apoptosis Signaling, B Cell Receptor Signaling, Leukocyte Extravasation Signaling, Integrin Signaling, Acute Phase Response Signaling, PTEN Signaling, p53 Signaling, Aryl Hydrocarbon Receptor Signaling, Xenobiotic Metabolism Signaling, SAPK/JNK Signaling, PPAr/RXR Signaling, NF-KB Signaling, Neuregulin Signaling, Wnt & beta catenin Signaling, Insulin Receptor Signaling, IL-6 Signaling, Hepatic Cholestasis, IGF-1 Signaling, NRF2-mediated Oxidative Stress Response, Hepatic Fibrosis/Hepatic Stellate Cell Activation, PPAR Signaling, Fc Epsilon RI Signaling, G-Protein Coupled Receptor Signaling, Inositol Phosphate Metabolism, PDGF Signaling, VEGF Signaling, Natural Killer Cell Signaling, Cell Cycle: G1/S Checkpoint Regulation, T Cell Receptor Signaling, Death Receptor Signaling, FGF Signaling, GM-CSF Signaling, Amyotrophic Lateral Sclerosis Signaling, JAK/Stat Signaling, Nicotinate and Nicotinamide Metabolism, Chemokine Signaling, IL-2 Signaling, Synaptic Long Term Depression, Estrogen Receptor Signaling, Protein Ubiquitination Pathway, IL-10 Signaling, VDR/RXR Activation, TGF-beta Signaling, Toll-like Receptor Signaling, p38 MAPK Signaling, Neurotrophin/TRK Signaling, FXR/RXR Activation, Synaptic Long Term Potentiation, Calcium Signaling, EGF Signaling, Hypoxia Signaling in the Cardiovascular System, LPS/IL-1 Mediated Inhibition of RXR Function, LXR/RXR Activation, Amyloid Processing, IL-4 Signaling, Cell Cycle: G2/M DNA Damage Checkpoint Regulation, Nitric Oxide Signaling in the Cardiovascular System, Purine Metabolism, cAMP-mediated Signaling, Mitochondrial Dysfunction, Notch Signaling, Endoplasmic Reticulum Stress Pathway, Pyrimidine Metabolism, Parkinson's Signaling, Cardiac & Beta Adrenergic Signaling, Glycolysis/Gluconeogenesis, Interferon Signaling, Sonic Hedgehog Signaling, Glycerophospholipid Metabolism, Phospholipid Degradation, Tryptophan Metabolism, Lysine Degradation, Nucleotide Excision Repair Pathway, Starch and Sucrose Metabolism, Aminosugars Metabolism, Arachidonic Acid Metabolism, Circadian Rhythm Signaling, Coagulation System, Dopamine Receptor Signaling, Glutathione Metabolism, Glycerolipid Metabolism, Linoleic Acid Metabolism, Methionine Metabolism, Pyruvate Metabolism, Arginine and Proline Metabolism, Eicosanoid Signaling, Fructose and Mannose Metabolism, Galactose Metabolism, Stilbene, Coumarine and Lignin Biosynthesis, Antigen Presentation Pathway, Biosynthesis of Steroids, Butanoate Metabolism, Citrate Cycle, Fatty Acid Metabolism, Glycerophospholipid Metabolism, Histidine Metabolism, Inositol Metabolism, Metabolism of Xenobiotics by Cytochrome p450, Methane Metabolism, Phenylalanine Metabolism, Propanoate Metabolism, Selenoamino Acid Metabolism, Sphingolipid Metabolism, Aminophosphonate Metabolism, Androgen and Estrogen Metabolism, Ascorbate and Aldarate Metabolism, Bile Acid Biosynthesis, Cysteine Metabolism, Fatty Acid Biosynthesis, Glutamate Receptor Signaling, NRF2-mediated Oxidative Stress Response, Pentose Phosphate Pathway, Pentose and Glucuronate Interconversions, Retinol Metabolism, Riboflavin Metabolism, Tyrosine Metabolism, Ubiquinone Biosynthesis, Valine, Leucine and Isoleucine Degradation, Glycine, Serine and Threonine Metabolism, Lysine Degradation, Pain/Taste, Pain, Mitochondrial Function, and Developmental Neurology.

Compositions comprising a ribonucleoprotein (e.g., a RNP comprising a site-directed modifying polypeptide, such as a Cas9 RNP or a Cpf1 RNP) and an endosomal escape agent, as described herein, are useful in selectively modulating transcription of a target DNA in a subject, said DNA being associated with a disease or disorder as described herein. In some embodiments, the target DNA is associated with neoplasia, said DNA being selected from PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc.

In some embodiments, the target DNA is associated with age-related macular degeneration, said DNA being selected from Abcr; Ccl2; Cc2; cp (ceruloplasmin); Timp3; cathepsinD; Vldlr; Ccr2.

In some embodiments, the target DNA is associated with a CNS disorder, said DNA being selected from Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b; 5-HTT (Slc6a4); COMT; DRD (Drd1a); SLC6A3; DAOA; DTNBP1; Dao (Dao1); Mecp2; BZRAP1; MDGA2; Sema5A; Neurexin 1; Fragile X (FMR2 (AFF2); FXR1; FXR2; Mglur5); E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP; x-Synuclein; DJ-1; LRRK2; Parkin; PINK1.

In some embodiments, the target DNA is associated with trinucleotide repeat disorders, said DNA being selected from HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP—global instability); VLDLR (Alzheimer's); Atxn7; Atxn10.

In some embodiments, the target DNA is associated with Fragile X Syndrome, said DNA being selected from FMR2; FXR1; FXR2; mGLUR5.

In some embodiments, the target DNA is associated with secretase related disorders, said DNA being selected from APH-1 (alpha and beta); Presenilin (Psen1); nicastrin (Ncstn); PEN-2; Nos1; Parp1; Nat1; Nat2.

In some embodiments, the target DNA is associated with prion-related disorders, said DNA being Prp.

In some embodiments, the target DNA is associated with ALS, said DNA being selected from SOD1; ALS2; STEX; FUS; TARDBP; VEGF (VEGF-a; VEGF-b; VEGF-c).

In some embodiments, the target DNA is associated with addiction, said DNA being selected from Prkce (alcohol); Drd2; Drd4; ABAT (alcohol); GRIA2; Grm5; Grin1; Htr1b; Grin2a; Drd3; Pdyn; Gria1 (alcohol).

In some embodiments, the target DNA is associated with inflammation, said DNA being selected from IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1.

In some embodiments, the target DNA is associated with blood and coagulation diseases and disorders, said DNA being selected from CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT, TAPBP, TPSN, TAP2, ABCB3, PSF2, RING11, MHC2TA, C2TA, RFX5, RFXAP, RFX5, TBXA2R, P2RX1, P2X1, HF1, CFH, HUS, MCFD2, F7, F10, F11, F12, HAF, F13A1, F13A, F13B, FANCA, FACA, FA1, FA, FAA, FAAP95, FAAP90, F1134064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596, PRF1, HPLH2, UNC13D, MUNC13-4, HPLH3, HLH3, FHL3, F8, F8C, HEMA, F9, HEMB, PI, ATT, F5, ITGB2, CD18, LCAMB, LAD, EIF2B1, EIF2BA, EIF2B2, EIF2B3, EIF2B5, LVWM, CACH, CLE, EIF2B4, HBB, HBA2, HBB, HBD, LCRB, HBA1.

In some embodiments, the target DNA is associated with cell dysregulation and oncology diseases and disorders, said DNA being selected from BCL7A, BCL7, TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN.

In some embodiments, the target DNA is associated with inflammation and immune related diseases and disorders, said DNA being selected from KIR3DL1, NKAT3, NKB1, AMB11, KIR3DS1, IFNG, CXCL12, SDF1, TNFRSF6, APT1, FAS, CD95, ALPS1A, IL2RG, SCIDX1, SCIDX, IMD4, CCL5, SCYA5, D17S136E, TCP228, IL10, CSIF, CMKBR2, CCR2, CMKBR5, CCCKR5 (CCR5), CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI, IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1, JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4).

In some embodiments, the target DNA is associated with metabolic, liver, kidney and protein diseases and disorders, said DNA being selected from TTR, PALB, APOA1, APP, AAA, CVAP, AD1, GSN, FGA, LYZ, TTR, PALB, KRT18, KRT8, CIRH1A, NAIC, TEX292, KIAA1988, CFTR, ABCC7, CF, MRP7, SLC2A2, GLUT2, G6PC, G6PT, G6PT1, GAA, LAMP2, LAMPB, AGL, GDE, GBE1, GYS2, PYGL, PFKM, TCF1, HNF1A, MODY3, SCOD1, SCO1, LIPC, CTNNB1, PDGFRL, PDGRL, PRLTS, AXIN1, AXIN, CTNNB1, TP53, P53, LFS1, IGF2R, MPRI, MET, CASP8, MCH5, UMOD, HNFJ, FJHN, MCKD2, ADMCKD2, PAH, PKU1, QDPR, DHPR, PTS, FCYT, PKHD1, ARPKD, PKD1, PKD2, PKD4, PKDTS, PRKCSH, G19P1, PCLD, SEC63.

In some embodiments, the target DNA is associated with muscular/skeletal diseases and disorders, said DNA being selected from DMD, BMD, MYF6, DMD, BMD, LMNA, LMN1, EMD2, FPLD, CMD1A, HGPS, LGMD1B, LMNA, LMN1, EMD2, FPLD, CMD1A, FSHMD1A, FSHD1A, FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1, LRP5, BMND1, LRP7, LR3, OPPG, VBCH2, CLCN7, CLC7, OPTA2, OSTM1, GL, TCIRG1, TIRC7, OC116, OPTB1, VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1.

In some embodiments, the target DNA is associated with neurological and neuronal diseases and disorders, said DNA being selected from SOD1, ALS2, STEX, FUS, TARDBP, VEGF (VEGF-a, VEGF-b, VEGF-c, APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3, Mecp2, BZRAP1, MDGA2, Sema5A, Neurexin 1, GLO1, MECP2, RTT, PPMX, MRX16, MRX79, NLGN3, NLGN4, KIAA1260, AUTSX2, FMR2, FXR1, FXR2, mGLUR5, HD, IT15, PRNP, PRIP, JPH3, JP3, HDL2, TBP, SCA17, NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2, MECP2, RTT, PPMX, MRX16, MRX79, CDKL5, STK9, MECP2, RTT, PPMX, MRX16, MRX79, x-Synuclein, DJ-1, Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1), APH-1 (alpha and beta), Presenilin (Psen1), nicastrin, (Ncstn), PEN-2, Nos1, Parp1, Nat1, Nat2, HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP—global instability), VLDLR (Alzheimer's), Atxn7, Atxn10.

In some embodiments, the target DNA is associated with ocular diseases and disorders, said DNA being selected from Abcr, Ccl2, Cc2, cp (ceruloplasmin), Timp3, cathepsinD, Vldlr, Ccr2, CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1, APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD, KERA, CNA2, MYOC, TIGR, GLC1A, JOAG, GPOA, OPTN, GLC1E, FIP2, HYPL, NRP, CYP1B1, GLC3A, OPA1, NTG, NPG, CYP1B1, GLC3A, CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3, ELOVL4, ADMD, STGD2, STGD3, RDS, RP7, PRPH2, PRPH, AVMD, AOFMD, VMD2.

Compositions comprising a ribonucleoprotein (e.g., a RNP comprising a site-directed modifying polypeptide, such as a Cas9 RNP or a Cpf1 RNP) and an endosomal escape agent, as described herein, are useful in selectively modulating transcription of a target DNA in a subject, said DNA being associated with a cellular function as described herein.

In some embodiments, the target DNA is associated with PI3K/AKT Signaling, said DNA being selected from PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1.

In some embodiments, the target DNA is associated with ERK/MAPK Signaling, said DNA being selected from PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK.

In some embodiments, the target DNA is associated with Glucocorticoid Receptor Signaling, said DNA being selected from RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1.

In some embodiments, the target DNA is associated with Axonal Guidance Signaling, said DNA being selected from PRKCE; ITGAM; ROCK1; ITGA5; CXCR4; ADAM12; IGF1; RAC1; RAP1A; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA.

In some embodiments, the target DNA is associated with Ephrin Receptor Signaling, said DNA being selected from PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK.

In some embodiments, the target DNA is associated with Actin Cytoskeleton Signaling, said DNA being selected from ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK.

In some embodiments, the target DNA is associated with Huntington's Disease Signaling, said DNA being selected from PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3.

In some embodiments, the target DNA is associated with Apoptosis Signaling, said DNA being selected from PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1.

In some embodiments, the target DNA is associated with B Cell Receptor Signaling, said DNA being selected from RAC1; PTEN; LYN; ELK1; MAPK1; RAC2; PTPN11; AKT2; IKBKB; PIK3CA; CREB1; SYK; NFKB2;

CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1.

In some embodiments, the target DNA is associated with Leukocyte Extravasation Signaling, said DNA being selected from ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9.

In some embodiments, the target DNA is associated with Integrin Signaling, said DNA being selected from ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3.

In some embodiments, the target DNA is associated with Acute Phase Response Signaling, said DNA being selected from IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6.

In some embodiments, the target DNA is associated with PTEN Signaling, said DNA being selected from ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1.

In some embodiments, the target DNA is associated with p53 Signaling, said DNA being selected from PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3.

In some embodiments, the target DNA is associated with Aryl Hydrocarbon Receptor Signaling, said DNA being selected from HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1.

In some embodiments, the target DNA is associated with Xenobiotic Metabolism Signaling, said DNA being selected from PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1.

In some embodiments, the target DNA is associated with SAPK/JNK Signaling, said DNA being selected from PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK.

In some embodiments, the target DNA is associated with PPAr/RXR Signaling, said DNA being selected from PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ.

In some embodiments, the target DNA is associated with NF-KB Signaling, said DNA being selected from IRAK1; EIF2AK2; EP300; INS; MYD88; PRKCZ: TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4: PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1.

In some embodiments, the target DNA is associated with Neuregulin Signaling, said DNA being selected from ERBB4; PRKCE; ITGAM; ITGA5: PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1.

In some embodiments, the target DNA is associated with Wnt & Beta catenin Signaling, said DNA being selected from CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2: ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2.

In some embodiments, the target DNA is associated with Insulin Receptor Signaling, said DNA being selected from PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1;

FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1.

In some embodiments, the target DNA is associated with IL-6 Signaling, said DNA being selected from HSPB1; TRAF6; MAPKAPK2; ELK1; MAPK1; PTPN11; IKBKB; FOS; NFKB2: MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6.

In some embodiments, the target DNA is associated with Hepatic Cholestasis, said DNA being selected from PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6.

In some embodiments, the target DNA is associated with IGF-1 Signaling, said DNA being selected from IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1.

In some embodiments, the target DNA is associated with NRF2-mediated Oxidative Stress Response, said DNA being selected from PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1.

In some embodiments, the target DNA is associated with Hepatic Fibrosis/Hepatic Stellate Cell Activation, said DNA being selected from EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9.

In some embodiments, the target DNA is associated with PPAR Signaling, said DNA being selected from EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1.

In some embodiments, the target DNA is associated with Fc Epsilon RI Signaling, said DNA being selected from PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA.

In some embodiments, the target DNA is associated with G-Protein Coupled Receptor Signaling, said DNA being selected from PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA.

In some embodiments, the target DNA is associated with Inositol Phosphate Metabolism, said DNA being selected from PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK.

In some embodiments, the target DNA is associated with PDGF Signaling, said DNA being selected from EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2.

In some embodiments, the target DNA is associated with VEGF Signaling, said DNA being selected from ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA.

In some embodiments, the target DNA is associated with Natural Killer Cell Signaling, said DNA being selected from PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA.

In some embodiments, the target DNA is associated with Cell Cycle: G1/S Checkpoint Regulation, said DNA being selected from HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6.

In some embodiments, the target DNA is associated with T Cell Receptor Signaling, said DNA being selected from RAC1; ELK1; MAPK1; IKBKB; CBL; PIK3CA; FOS; NFKB2; PIK3CB; PIK3C3; MAPK8; MAPK3; KRAS; RELA, PIK3C2A; BTK; LCK; RAF1; IKBKG; RELB, FYN; MAP2K2; PIK3R1; CHUK; MAP2K1; NFKB1; ITK; BCL10; JUN; VAV3.

In some embodiments, the target DNA is associated with Death Receptor Signaling, said DNA being selected from CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3.

In some embodiments, the target DNA is associated with FGF Signaling, said DNA being selected from RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF.

In some embodiments, the target DNA is associated with GM-CSF Signaling, said DNA being selected from LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1.

In some embodiments, the target DNA is associated with Amyotrophic Lateral Sclerosis Signaling, said DNA being selected from BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3.

In some embodiments, the target DNA is associated with JAK/Stat Signaling, said DNA being selected from PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1.

In some embodiments, the target DNA is associated with Nicotinate and Nicotinamide Metabolism, said DNA being selected from PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK.

In some embodiments, the target DNA is associated with Chemokine Signaling, said DNA being selected from CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA.

In some embodiments, the target DNA is associated with IL-2 Signaling, said DNA being selected from ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3.

In some embodiments, the target DNA is associated with Synaptic Long Term Depression, said DNA being selected from PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA.

In some embodiments, the target DNA is associated with Estrogen Receptor Signaling, said DNA being selected from TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2.

In some embodiments, the target DNA is associated with Protein Ubiquitination Pathway, said DNA being selected from TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3.

In some embodiments, the target DNA is associated with IL-10 Signaling, said DNA being selected from TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6.

In some embodiments, the target DNA is associated with VDR/RXR Activation, said DNA being selected from PRKCE; EP300; PRKCZ; RXRA; GADD45A; HES1; NCOR2; SP1; PRKC1; CDKN1B; PRKD1; PRKCD; RUNX2; KLF4; YY1; NCOA3; CDKN1A; NCOA2; SPP1; LRP5; CEBPB; FOXO1; PRKCA.

In some embodiments, the target DNA is associated with TGF-beta Signaling, said DNA being selected from EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5.

In some embodiments, the target DNA is associated with Toll-like Receptor Signaling, said DNA being selected from IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN.

In some embodiments, the target DNA is associated with p38 MAPK Signaling, said DNA being selected from HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1.

In some embodiments, the target DNA is associated with Neurotrophin/TRK Signaling, said DNA being selected from NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; and ATF4.

In some embodiments, the target DNA is associated with FXR/RXR Activation, said DNA being selected from INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; and FOXO1.

In some embodiments, the target DNA is associated with Synaptic Long Term Potentiation, said DNA being selected from PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; and PRKCA.

In some embodiments, the target DNA is associated with Calcium Signaling, said DNA being selected from RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; and HDAC6.

In some embodiments, the target DNA is associated with EGF Signaling, said DNA being selected from ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; and STAT1.

In some embodiments, the target DNA is associated with Hypoxia Signaling in the Cardiovascular System, said DNA being selected from EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; and HSP90AA1.

In some embodiments, the target DNA is associated with LPS/IL-1 Mediated Inhibition of RXR Function, said DNA being selected from IRAK1; MYD88; TRAF6; PPARA; RXRA; ABCA1, MAPK8; ALDH1A1; GSTP1; MAPK9; ABCB1; TRAF2; TLR4; TNF; MAP3K7; NR1H2; SREBF1; JUN; and IL1R1.

In some embodiments, the target DNA is associated with LXR/RXR Activation, said DNA being selected from FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; and MMP9.

In some embodiments, the target DNA is associated with Amyloid Processing, said DNA being selected from PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; and APP.

In some embodiments, the target DNA is associated with IL-4 Signaling, said DNA being selected from AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; and RPS6KB1.

In some embodiments, the target DNA is associated with Cell Cycle: G2/M DNA Damage Checkpoint Regulation, said DNA being selected from EP300; PCAF; BRCA1; GADD45A; PLK1; BTRC; CHEK1; ATR; CHEK2; YWHAZ; TP53; CDKN1A; PRKDC; ATM; SFN; and CDKN2A.

In some embodiments, the target DNA is associated with Nitric Oxide Signaling in the Cardiovascular System, said DNA being selected from KDR; FLT1; PGF; AKT2; PIK3CA; PIK3CB; PIK3C3; CAV1; PRKCD; NOS3; PIK3C2A; AKT1; PIK3R1; VEGFA; AKT3; and HSP90AA1.

In some embodiments, the target DNA is associated with Purine Metabolism, said DNA being selected from NME2; SMARCA4; MYH9; RRM2; ADAR; EIF2AK4; PKM2; ENTPD1; RAD51; RRM2B; TJP2; RAD51C; NT5E; POLD1; and NME1.

In some embodiments, the target DNA is associated with cAMP-mediated Signaling, said DNA being selected from RAP1A; MAPK1; GNAS; CREB1; CAMK2A; MAPK3; SRC; RAF1; MAP2K2; STAT3; MAP2K1; BRAF; and ATF4.

In some embodiments, the target DNA is associated with Mitochondrial Dysfunction, said DNA being selected from SOD2; MAPK8; CASP8; MAPK10; MAPK9; CASP9; PARK7; PSEN1; PARK2; APP; and CASP3.

In some embodiments, the target DNA is associated with Notch Signaling, said DNA being selected from HES1; JAG1; NUMB; NOTCH4; ADAM17; NOTCH2; PSEN1; NOTCH3; NOTCH1; and DLL4.

In some embodiments, the target DNA is associated with Endoplasmic Reticulum Stress Pathway, said DNA being selected from HSPA5; MAPK8; XBP1; TRAF2; ATF6; CASP9; ATF4; EIF2AK3; and CASP3.

In some embodiments, the target DNA is associated with Pyrimidine Metabolism, said DNA being selected from NME2; AICDA; RRM2; EIF2AK4; ENTPD1; RRM2B; NT5E; POLD1; and NME1.

In some embodiments, the target DNA is associated with Parkinson's Signaling, said DNA being selected from UCHL1; MAPK8; MAPK13; MAPK14; CASP9; PARK7; PARK2; and CASP3.

In some embodiments, the target DNA is associated with Cardiac & Beta Adrenergic Signaling, said DNA being selected from GNAS; GNAQ; PPP2R1A; GNB2L1; PPP2CA; PPP1CC; and PPP2R5C.

In some embodiments, the target DNA is associated with Glycolysis/Gluconeogenesis, said DNA being selected from HK2; GCK; GPI; ALDH1A1; PKM2; LDHA; and HK1.

In some embodiments, the target DNA is associated with Interferon Signaling, said DNA being selected from IRF1; SOCS1; JAK1; JAK2; IFITM1; STAT1; and IFIT3.

In some embodiments, the target DNA is associated with Sonic Hedgehog Signaling, said DNA being selected from ARRB2; SMO; GLI2; DYRK1A; GLI1; GSK3B; and DYRK1B.

In some embodiments, the target DNA is associated with Glycerophospholipid Metabolism, said DNA being selected from PLD1; GRN; GPAM; YWHAZ; SPHK1; and SPHK2.

In some embodiments, the target DNA is associated with Phospholipid Degradation, said DNA being selected from PRDX6; PLD1; GRN; YWHAZ; SPHK1; and SPHK2.

In some embodiments, the target DNA is associated with Tryptophan Metabolism, said DNA being selected from SIAH2; PRMT5; NEDD4; ALDH1A1; CYP1B1; and SIAH1.

In some embodiments, the target DNA is associated with Lysine Degradation, said DNA being selected from SUV39H1; EHMT2; NSD1; SETD7; and PPP2R5C.

In some embodiments, the target DNA is associated with Nucleotide Excision Repair Pathway, said DNA being selected from ERCC5; ERCC4; XPA; XPC; and ERCC1.

In some embodiments, the target DNA is associated with Starch and Sucrose Metabolism, said DNA being selected from UCHL1; HK2; GCK; GPI; and HK1.

In some embodiments, the target DNA is associated with Aminosugars Metabolism, said DNA being selected from NQO1; HK2; GCK; and HK1.

In some embodiments, the target DNA is associated with Arachidonic Acid Metabolism, said DNA being selected from PRDX6; GRN; YWHAZ; and CYP1B1.

In some embodiments, the target DNA is associated with Circadian Rhythm Signaling, said DNA being selected from CSNK1E; CREB1; ATF4; and NR1D1.

In some embodiments, the target DNA is associated with Coagulation System, said DNA being selected from BDKRB1; F2R; SERPINE1; and F3.

In some embodiments, the target DNA is associated with Dopamine Receptor Signaling, said DNA being selected from PPP2R1A; PPP2CA; PPP1CC; and PPP2R5C.

In some embodiments, the target DNA is associated with Glutathione Metabolism, said DNA being selected from IDH2; GSTP1; ANPEP; and IDH1.

In some embodiments, the target DNA is associated with Glycerolipid Metabolism, said DNA being selected from ALDH1A1; GPAM; SPHK1; and SPHK2.

In some embodiments, the target DNA is associated with Linoleic Acid Metabolism, said DNA being selected from PRDX6; GRN; YWHAZ; and CYP1B1.

In some embodiments, the target DNA is associated with Methionine Metabolism, said DNA being selected from DNMT1; DNMT3B; AHCY; and DNMT3A.

In some embodiments, the target DNA is associated with Pyruvate Metabolism, said DNA being selected from GLO1; ALDH1A1; PKM2; and LDHA.

In some embodiments, the target DNA is associated with Arginine and Proline Metabolism, said DNA being selected from ALDH1A1; NOS3; and NOS2A.

In some embodiments, the target DNA is associated with Eicosanoid Signaling, said DNA being selected from PRDX6; GRN; and YWHAZ.

In some embodiments, the target DNA is associated with Fructose and Mannose Metabolism, said DNA being selected from HK2; GCK; and HK1.

In some embodiments, the target DNA is associated with Galactose Metabolism, said DNA being selected from HK2; GCK; and HK1.

In some embodiments, the target DNA is associated with Stilbene, Coumarine and Lignin Biosynthesis, said DNA being selected from PRDX6; PRDX1; and TYR.

In some embodiments, the target DNA is associated with Antigen Presentation Pathway, said DNA being selected from CALR; and B2M.

In some embodiments, the target DNA is associated with Biosynthesis of Steroids, said DNA being selected from NQO1; and DHCR7.

In some embodiments, the target DNA is associated with Butanoate Metabolism, said DNA being selected from ALDH1A1; and NLGN1.

In some embodiments, the target DNA is associated with Citrate Cycle, said DNA being selected from IDH2; and IDH1.

In some embodiments, the target DNA is associated with Fatty Acid Metabolism, said DNA being selected from ALDH1A1; and CYP1B1.

In some embodiments, the target DNA is associated with Glycerophospholipid Metabolism, said DNA being selected from PRDX6; and CHKA.

In some embodiments, the target DNA is associated with Histidine Metabolism, said DNA being selected from PRMT5; and ALDH1A1.

In some embodiments, the target DNA is associated with Inositol Metabolism, said DNA being selected from ERO1L; and APEX1.

In some embodiments, the target DNA is associated with Metabolism of Xenobiotics by Cytochrome p450, said DNA being selected from GSTP1; and CYP1B1.

In some embodiments, the target DNA is associated with Methane Metabolism, said DNA being selected from PRDX6; and PRDX1.

In some embodiments, the target DNA is associated with Phenylalanine Metabolism, said DNA being selected from PRDX6; and PRDX1.

In some embodiments, the target DNA is associated with Propanoate Metabolism, said DNA being selected from ALDH1A1; and LDHA.

In some embodiments, the target DNA is associated with Selenoamino Acid Metabolism, said DNA being selected from PRMT5; and AHCY.

In some embodiments, the target DNA is associated with Sphingolipid Metabolism, said DNA being selected from SPHK1; and SPHK2.

In some embodiments, the target DNA is associated with Aminophosphonate Metabolism, said DNA being selected from PRMT5.

In some embodiments, the target DNA is associated with Androgen and Estrogen Metabolism, said DNA being PRMT5.

In some embodiments, the target DNA is associated with Ascorbate and Aldarate Metabolism, said DNA being ALDH1A1.

In some embodiments, the target DNA is associated with Bile Acid Biosynthesis, said DNA being ALDH1A1.

In some embodiments, the target DNA is associated with Cysteine Metabolism, said DNA being LDHA.

In some embodiments, the target DNA is associated with Fatty Acid Biosynthesis, said DNA being FASN.

In some embodiments, the target DNA is associated with Glutamate Receptor Signaling, said DNA being GNB2L1.

In some embodiments, the target DNA is associated with NRF2-mediated Oxidative Stress Response, said DNA being PRDX1.

In some embodiments, the target DNA is associated with Pentose Phosphate Pathway, said DNA being GPI.

In some embodiments, the target DNA is associated with Pentose and Glucuronate Interconversions, said DNA being UCHL1.

In some embodiments, the target DNA is associated with Retinol Metabolism, said DNA being ALDH1A1.

In some embodiments, the target DNA is associated with Riboflavin Metabolism, said DNA being TYR.

In some embodiments, the target DNA is associated with Tyrosine Metabolism, said DNA being selected from PRMT5, and TYR.

In some embodiments, the target DNA is associated with Ubiquinone Biosynthesis, said DNA being PRMT5.

In some embodiments, the target DNA is associated with Valine, Leucine and Isoleucine Degradation, said DNA being ALDH1A1.

In some embodiments, the target DNA is associated with Lysine Degradation, said DNA being ALDH1A1.

In some embodiments, the target DNA is associated with Glycine, Serine and Threonine Metabolism, said DNA being CHKA.

In some embodiments, the target DNA is associated with Pain or Taste, said DNA being selected from TRPM5; TRPA1; TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; and Prkar2a.

In some embodiments, the target DNA is associated with Mitochondrial Function, said DNA being selected from AIF; CytC; SMAC (Diablo); Aifm-1; and Aifm-2.

In some embodiments, the target DNA is associated with Developmental Neurology, said DNA being selected from BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln.

Another aspect of the present invention provides a method for site-specific endonucleolytic cleavage of a single-stranded RNA (ssRNA), comprising the administration of a compound, a RNP, or a composition described herein, in the presence of a protospacer adjacent motif (PAM)-presenting oligonucleotides (PAMmer). Suitable PAMmers for use in the present invention include but are not limited to those described in O'Connell, M. R. et al. *Nature*, 2014, 516 (7530): 263-6.

Another aspect of the present invention provides a method for site-specific endonucleolytic cleavage of a single-stranded RNA (ssRNA), comprising the administration of a compound or RNP, which comprises a CRISPR/Cas Type III-B Cmr complex, or a composition thereof, as described herein. In some embodiments, the Type III-B Cmr complex may be derived from *Pyrococcus furiosus*, *Sulfolobus solfataricus*, or *Thermus thermophilus*. In some embodiments, the Cmr proteins suitable for use herein include but are not limited to those described in Hale, C. R. et al. *Genes & Development*, 2014, 28:2432-2443, and Makarova K. S. et al. *Nature Reviews Microbiology*, 2015, 13, 1-15.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), AstraZeneca Pharmaceuticals (London, England), and Accela ChemBio (San Diego, Calif.).

General Experimental Procedures

NMR spectra were recorded on a Varian Unity™ 400 (available from Varian Inc., Palo Alto, Calif.) at room temperature at 400 MHz for proton. Chemical shifts are expressed in parts per million (delta) relative to residual solvent as an internal reference. The peak shapes are denoted as follows: s, singlet; d, doublet; dd, doublet of doublet; t, triplet; q, quartet; m, multiplet; bs or br.s., broad singlet; 2s, two singlets; br.d., broad doublet. In some cases only representative ¹H NMR peaks are given. Column chromatography was performed with either Baker™ silica gel (40 micron; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.). MPLC (medium pressure liquid chromatography) was performed using a Biotage™ SP purification system or a Combiflash® Companion® from Teledyne™ Isco™; Biotage™ SNAP cartridge KPsil or Redisep Rf silica (from Teledyne™ Isco™) under low nitrogen pressure were used. Except where otherwise noted, all reactions were run under an inert atmosphere of nitrogen gas using anhydrous solvents. Also, except where otherwise noted, all reactions were run at room temperature (~23° C.). When doing TLC (thin layer chromatography), $R_f$ is defined as the ratio of the distance traveled by the compound divided by the distance traveled by the eluent. $R_t$ (retention time). H-Cube® Continuous-flow Hydrogenation Reactor: A bench-top standalone hydrogenation reactor, combining continuous-flow microchemistry with endogenous on-demand hydrogen generation and a disposable catalyst cartridge system.

LC/MS TOF (ESI):

All data were gathered on an Agilent 1100 LC with MSD TOF (Agilent model G1969A) mass spec detectors running with electrospray spray ionization source. The LC instrument includes a binary pump (Agilent model G1312A) with upper pressure limit of 400 bar attached to autosampler (Agilent model G1313A) which uses external try for sample submission. The column compartment (Agilent model G1316A) which is attached to diode array (Agilent model G1315A). The instrument acquisition and data handling was done with Agilent MassHunter TOF/Q-TOF B.02 (B11285) Patches 1.2.3. Elution Conditions: Column: No column was used. Flow Injection: Injection Volume: 1.0 microL; Flow Rate: 0.5 mL/min. Run Time: 1.0 min; Solvent: Methanol (0.1% formic acid and 0.05% ammonium formate). TOF Conditions: Ionization Source: Electrospray spray ionization source in Positive Mode; Gas Temp: 325 C; Drying Gas: 6 L/min; Nebulizer: 50 psg; VCap: 3500V; Mass Range 110-100 m/z; Acquisition Rate: 0.99 spectra/s: Acquisition Time; 1012.8 ms/spectrum. All solvents were of HPLC Chromasolv grade, from Sigma Aldrich (St. Louis, Mo.). A majority of the chemicals and buffers were purchased from Sigma Aldrich, all 97% in purity or higher.

Method C 1.5 minute run LRMS (low resolution mass spectroscopy): Waters Acquity HSS T3, 2.1 mm×50 mm, C18, 1.7 µm; Mobile Phase: A: 0.1% formic acid in water (v/v); Mobile phase B: 0.1% formic acid in acetonitrile (v/v); Flow-1.25 ml/minute; Initial conditions: A—95%: B—5%; hold at initial from 0.0-0.1 minute; Linear Ramp to A—5%:B—95% over 0.1-1.0 minute; hold at A—5%:B—95% from 1.0-1.1 minute; return to initial conditions 1.1-1.5 minute.

Method C 3.0 minute run LRMS (low resolution mass spectroscopy): Waters Acqity HSS T3, 2.1 mm×50 mm, C18, 1.7 µm; Mobile Phase: A: 0.1% formic acid in water (v/v); Mobile phase B: 0.1% formic acid in acetonitrile (v/v); Flow-1.25 ml/minute; Initial conditions: A—95%: B—5%; hold at initial from 0.0-0.1 minute; Linear Ramp to A—5%:B—95% over 0.1-2.6 minute; hold at A—5%:B—95% from 2.6-2.95 minute; return to initial conditions 2.95-3.0 minute.

Procedures ((2R,3S,4R,5R,6R)-5-azido-6-methoxy-3,4-bis ((trimethylsilyl)oxy)tetrahydro-2H-pyran-2-yl) methanol (I-b)

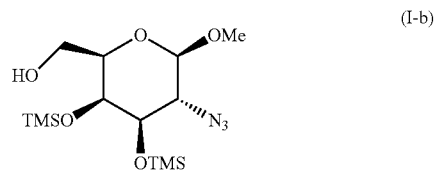

(2R,3R,4R,5R,6R)-5-azido-2-(hydroxymethyl)-6-methoxytetrahydro-2H-pyran-3,4-diol (I-a) (5 g, 23 mmol) was dissolved in anhydrous pyridine (100 mL) and trimethylsilyl chloride (17.5 mL, 139 mmol) was added. The reaction mixture was stirred for 12 hours at room temperature and then pyridine was evaporated. The residue was taken up in ethyl acetate/water. The aqueous phase was extracted once with ethyl acetate and the combined organic layers were washed with water, a saturated aqueous solution of sodium chloride, dried over magnesium sulfate, filtered and concentrated to give 9.9 g (98% yield) of the corresponding per-silylated compound as a yellow oil. The material was used in the next step without any further purification. To a solution of the above per-silylated compound (9.71 g, 22.3 mmol) in anhydrous methanol (45 mL) cooled to 0 degrees Celsius was added 9.06 mL of a solution of potassium carbonate in methanol (0.032M). The reaction mixture was stirred at 0° C. for 1 hour and then neutralized by the addition of 17 microL of acetic acid. The solvent was evaporated and the residue was dissolved in ethyl acetate. Water was added and the aqueous phase was extracted twice with ethyl acetate. The combined organic layers were washed with brine, dried over magnesium sulfate, filtered and concentrated. The crude material was purified by flash chromatography (30% ethyl acetate/hexanes) over silica gel to afford 6.77 g (84%) of (I-b) as an oil. $[\alpha]_D$ 7 (c 1, chloroform); ¹H NMR (400 MHz, CHLOROFORM-d) delta ppm 0.14 (s, 9H), 0.20 (s, 9H), 1.80 (br. s., 1H), 3.36-3.42 (m, 1H), 3.45 (dd, J=7.3, 4.6 Hz, 1H), 3.54 (dd, J=10.0, 8.0 Hz, 1H), 3.59 (s, 3H), 3.65 (dd, J=11.3, 4.7 Hz, 1H), 3.77 (d, J=2.7 Hz, 1H), 3.87 (dd, J=11.2, 7.3 Hz, 1H), 4.14 (d, J=8.0 Hz, 1H); ¹³C NMR (100 MHz, CHLOROFORM-d) delta ppm 0.27 (3C), 0.6 (3C), 57.3, 62.6, 64.0, 71.1, 73.7, 75.2, 103.4; HRMS (ESI) calcd for $C_{13}H_{29}N_3O_5Si_2$ (m/z) [M+Na]⁺386.1538, found 386.1539.

(3R,4R,5R,6R)-5-azido-2,2-bis(hydroxymethyl)-6-methoxytetrahydro-2H-pyran-3,4-diol (I-c)

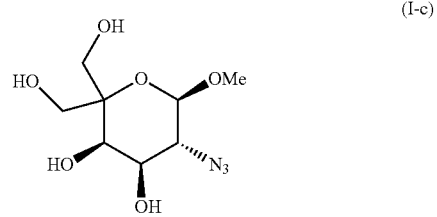 [SMILES: CO[C@@H]1OC(CO)(CO)[C@H](O)[C@H](O)[C@H]1N=[N+]=[N-]]

(I-b) (7.73 g, 21.3 mmol) was dissolved in dichloromethane (70 mL). Dimethyl sulfoxide (10.6 mL, 150 mmol) and triethylamine (9 mL, 60 mmol) were added and the reaction mixture was cooled to 0 degrees Celsius. Sulfur trioxide pyridine complex (10.2 g, 64 mmol) was added and the mixture was stirred at 0 degrees Celsius for 1 hour and then warmed up to room temperature over 30 minutes. The reaction was quenched with a saturated solution of sodium chloride and diluted with dichloromethane. The aqueous phase was extracted 3 times with dichloromethane and the combined organic layers were washed with a saturated aqueous solution of sodium chloride, dried over magnesium sulfate, filtered and concentrated to afford the corresponding aldehyde. The aldehyde was dissolved in anhydrous ethanol (106 mL) and paraformaldehyde powder (40.3 g, 425 mmol) followed by sodium ethoxide 21% wt solution in ethanol (16 mL, 42.5 mmol) were added. The reaction mixture was stirred at room temperature for 12 hours and then ethanol was evaporated. To the crude mixture was added methanol and the solid was filtered and thoroughly rinsed with methanol. To the filtrate containing the desired product was added silica gel and methanol was evaporated. The resulting dry load was dried under high vacuum and loaded on a column. The crude material was purified by flash chromatography (10% methanol/dichloromethane) over silica gel to give 3.03 g of (I-c) as a colorless oil (57% over 2 steps). $[\alpha]_D$ −20 (c 1.25, methanol); $^1$H NMR (400 MHz, METHANOL-$d_4$) delta ppm 3.46 (dd, J=10.2, 8.1 Hz, 1H), 3.51 (s, 3H), 3.64-3.80 (m, 5H), 3.80-3.83 (m, 1H), 4.54 (d, J=8.0 Hz, 1H); $^{13}$C NMR (100 MHz, METHANOL-$d_4$) delta ppm 57.2, 61.2, 63.6, 65.9, 69.9, 71.2, 80.9, 101.2; HRMS (ESI) calcd for $C_8H_{15}N_3O_6$ (m/z) [M+Na]$^+$ 272.0853, found 272.0856.

N-((3aR,4S,7S,8R,8aR)-4-(hydroxymethyl)-2,2-dimethylhexahydro-4,7-epoxy[1,3]dioxolo[4,5-d]oxepin-8-yl)acetamide (I-e-1)

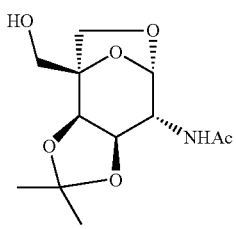

(I-e-1)

To a solution of compound (3) (230 mg, 0.986 mmol) in 6.6 mL of dimethylformamide was added 2,2-dimethoxypropane (0.8 mL, 6 mmol) followed by (+/−)-camphor-10-sulphonic acid (101 mg, 0.435 mmol). The reaction mixture was stirred at 70 degrees Celsius for 24 hours, cooled down to room temperature and then methanol was added (1.2 mL). The reaction mixture was stirred at room temperature for 30 minutes and then neutralized with triethylamine (56 microL). The solvent was evaporated and the residue was coevaporated 3 times with toluene. The crude material was purified by flash chromatography (15/1 ethyl acetate/methanol) over silica gel to afford compound (I-e-1) as a white solid (246 mg, 91% yield). m.p.: 164.7-166.0° C.; $[\alpha]_D$ 147 (c 1, methanol); $^1$H NMR (400 MHz, METHANOL-$d_4$) delta ppm 1.34 (s, 3H), 1.48 (s, 3H), 1.98 (s, 3H), 3.77 (d, J=7.8 Hz, 1H), 3.83 (d, J=7.8 Hz, 1H), 3.86 (d, J=11.6 Hz, 1H), 3.90 (d, J=11.3 Hz, 1H), 3.91-3.94 (m, 1H), 4.14-4.19 (m, 1H), 4.29 (d, J=6.0 Hz, 1H), 5.23 (d, J=2.0 Hz, 1H); $^{13}$C NMR (100 MHz, METHANOL-$d_4$) delta ppm 22.7, 26.9, 28.5, 56.8, 61.9, 70.2, 76.1, 76.6, 83.0, 102.6, 112.5, 173.6; HRMS (ESI) calcd for $C_{12}H_{19}NO_6$ (m/z) [M+H]$^+$ 274.1285, found 274.1274.

(1S,2R,3R,4R,5S)-4-azido-1-(hydroxymethyl)-6,8-dioxabicyclo[3.2.1]octane-2,3-diol (1)

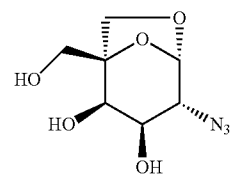

(1)

The tetra-ol (I-c) (3 g, 12 mmol) was dissolved in water (40 mL) and concentrated sulfuric acid (6.7 mL) was added. The reaction mixture was stirred at 100 degrees Celsius for 40 hours, cooled to room temperature, and then neutralized by the addition of concentrated ammonium hydroxide. Water was evaporated and methanol was added to the resulting mixture. The solid was filtered and thoroughly rinsed with methanol. To the filtrate containing the desired product was added silica gel and methanol was evaporated. The resulting dry load was dried under high vacuum and loaded on a column. The crude material was purified by flash chromatography (10% methanol/dichloromethane) over silica gel to give 2.2 g (84%) of (1) as a colorless oil. $[\alpha]_D$ 160 (c 1.1, methanol); $^1$H NMR (400 MHz, METHANOL-$d_4$) delta ppm 3.35 (dd, J=9.2, 1.6 Hz, 1H), 3.70 (d, J=8.2 Hz, 1H), 3.76 (d, J=8.0 Hz, 1H), 3.80 (d, J=11.3 Hz, 1H), 3.83-3.89 (m, 2H), 3.90 (d, J=11.5 Hz, 1H), 5.32 (d, J=1.4 Hz, 1H); $^{13}$C NMR (100 MHz, METHANOL-$d_4$) delta ppm 61.9, 66.1, 69.5, 69.6, 71.0, 85.3, 102.7; HRMS (ESI) calcd for $C_7H_{11}N_3O_5$ (m/z) [M+Na]$^+$ 240.0591, found 240.0596.

(1R,2R,3R,4R,5S)-4-acetamido-1-(acetoxymethyl)-6,8-dioxabicyclo[3.2.1]octane-2,3-diyl diacetate (2)

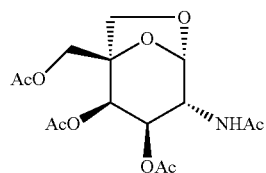

(2)

In a round bottom flask, compound (1) (1.93 g, 8.9 mmol) was dissolved in ethanol (45 mL) and the system was flushed with nitrogen. Lindlar catalyst (1.89 g, 0.9 mmol) was added and the system was flushed with nitrogen and then with hydrogen. The reaction mixture was stirred at room temperature under an atmosphere of hydrogen (using a balloon) for 24 hours. The palladium was filtered using a nylon membrane and thoroughly rinsed with methanol and then water. Solvent was evaporated and the residue was dissolved in water and lyophilized. The resulting crude material was then dissolved in pyridine (40 mL) and acetic anhydride was added (9 mL, 100 mmol). The reaction mixture was stirred at room temperature for 48 hours and the pyridine was evaporated. The residue was dissolved in ethyl acetate and washed with a saturated solution of sodium bicarbonate. The aqueous phase was extracted twice with ethyl acetate and then the combined organic layers were washed with a saturated aqueous solution of sodium chloride, dried over magnesium sulfate, filtered and evaporated. The crude material was purified by flash chromatography (3% methanol/dichloromethane) over silica gel to give (2) (3.19 g, quant.). $[\alpha]_D$ 75 (c 1, chloroform); $^1$H NMR (400 MHz, METHANOL-d$_4$) delta ppm 1.95 (s, 3H), 1.95 (s, 3H), 2.04 (s, 3H), 2.15 (s, 3H), 3.75 (d, J=8.6 Hz, 1H), 4.06 (d, J=8.6 Hz, 1H), 4.13 (d, J=11.6 Hz, 1H), 4.20 (d, J=10.6 Hz, 1H), 4.46 (d, J=11.3 Hz, 1H), 5.13 (dd, J=10.4, 4.4 Hz, 1H), 5.35 (d, J=1.0 Hz, 1H), 5.38 (d, J=4.3 Hz, 1H); $^{13}$C NMR (100 MHz, METHANOL-d$_4$) delta ppm 20.6, 20.7 (2C), 22.6, 53.3, 63.0, 68.9, 69.1, 70.3, 82.6, 103.0, 171.8, 171.9, 172.1, 173.8; HRMS (ESI) calcd for $C_{15}H_{21}NO_9$ (m/z) [M+H]$^+$ 360.1289, found 360.1290.

N-((1S,2R,3R,4R,5S)-2,3-dihydroxy-1-(hydroxymethyl)-6,8-dioxabicyclo[3.2.1]octan-4-yl)acetamide (3)

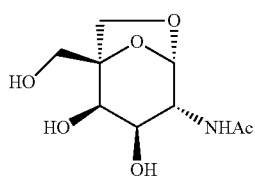

(3)

Compound (2) (3.19 g, 8.88 mmol) was dissolved in tetrahydrofuran (50 mL) and sodium methoxide 0.5M in methanol (100 mL, 50 mmol) was added. The reaction mixture was stirred at room temperature for 12 hours and then neutralized by the addition of H$^+$ Amberlyte™ IR-120 resin. The resin was filtered and solvent was evaporated to give 1.71 g of (3) as a white solid (83%). m.p.: 175.7-176.1° C.; $[\alpha]_D$ 164 (c 1, methanol); $^1$H NMR (400 MHz, METHANOL-d$_4$) delta ppm 1.99 (s, 3H), 3.68 (d, J=8.1 Hz, 1H), 3.70-3.73 (m, 1H), 3.75 (d, J=7.8 Hz, 1H), 3.81 (d, J=11.3 Hz, 1H), 3.87 (d, J=4.3 Hz, 1H), 3.92 (d, J=11.3 Hz, 1H), 3.95 (dd, J=9.9, 1.1 Hz, 1H), 5.22 (d, J=1.3 Hz, 1H); $^{13}$C NMR (100 MHz, METHANOL-d$_4$) delta ppm 22.7, 56.4, 62.1, 69.2, 69.3, 70.6, 85.1, 102.8, 174.1; HRMS (ESI) calcd for $C_9H_{15}NO_6$ (m/z) [M+H]$^+$ 234.0972, found 234.0974.

benzyl (4-((2-((1-(1-(((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)methoxy)ethyl)amino)-4-oxobutyl) carbamate (4), benzyl (4-((1,3-bis((1-(1-(((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)methoxy)propan-2-yl)amino)-4-oxobutyl)carbamate (5), benzyl (4-((1,3-bis((1-(((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)methoxy)-2-(((1-(1-(((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)methoxy)methyl)propan-2-yl)amino)-4-oxobutyl)carbamate (6)

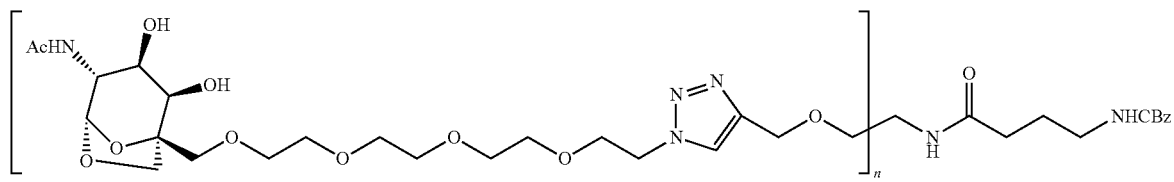

n = 1-3
(4) n = 1
(5) n = 2
(6) n = 3

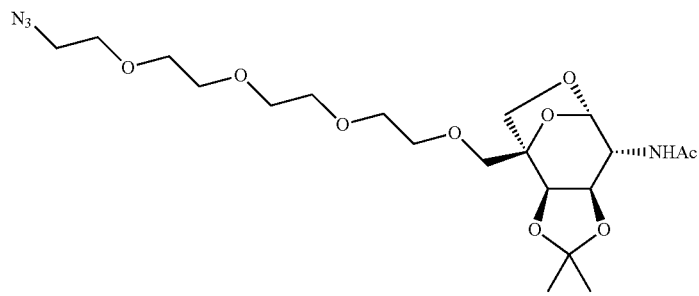

(I-e-2)

In a microwave vial was dissolved compound (I-e-1) (50 mg, 0.18 mmol) in 1 mL of dichloromethane. 12.5M aqueous sodium hydroxide (0.5 mL) was added followed by 15-crown-5-ether (5 microL, 0.02 mmol) and 1-azido-2-(2-(2-(2-iodoethoxy)ethoxy)ethoxy)ethane (described in J. Am. Chem. Soc. 132, 1523 (2010)) (301 mg, 0.915 mmol). The reaction mixture was vigorously stirred at 55° C. for 24 hours. The organic phase was removed and dried over magnesium sulfate, filtered and concentrated. The crude material was purified by flash chromatography (5% methanol/ethyl acetate) over silica gel to afford compound (I-e-2) as an oil (52 mg, 60% yield). $[\alpha]_D$ 74 (c 1, chloroform); $^1$H NMR (400 MHz, METHANOL-$d_4$) delta ppm 1.34 (s, 3H), 1.49 (s, 3H), 1.98 (s, 3H), 3.37 (t, J=4.9 Hz, 2H), 3.62-3.71 (m, 14H), 3.75-3.80 (m, 2H), 3.86 (d, J=8.1 Hz, 1H) 3.90-3.97 (m, 2H), 4.12-4.19 (m, 1H), 4.31 (d, J=5.8 Hz, 1H), 5.23 (d, J=2.0 Hz, 1H); $^{13}$C NMR (100 MHz, METHANOL-$d_4$) delta ppm 22.7, 26.9, 28.5, 51.9, 56.7, 70.9, 71.1, 71.3, 71.6, 71.7, 71.8, 71.81, 71.82, 72.7, 76.1, 76.5, 82.1, 102.4, 112.4, 173.6; HRMS (ESI) calcd for $C_{20}H_{34}N_4O_9$ (m/z) [M+H]$^+$ 475.2399, found 475.2386.

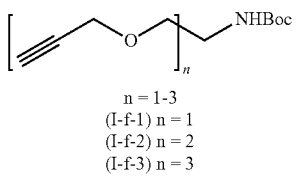

n = 1-3
(I-f-1) n = 1
(I-f-2) n = 2
(I-f-3) n = 3

Intermediate (I-f-1) is known and is described in WO06120545.

Intermediate (I-f-2) can be synthesized as follow: To a solution of Boc-serinol (1000 mg, 5.1 mmol) in tetrahydrofuran (21 mL) was added at room temperature tetrabutylammonium iodide (287 mg, 0.76 mmol), sodium iodide (153 mg, 1.02 mmol) and propargyl bromide (1.8 mL, 16 mmol, 80% in toluene). Potassium hydroxide (569 mg, 10.1 mmol) was added portion wise over 30 minutes and then the mixture was stirred at room temperature for 16 hours. The reaction mixture was diluted with ethyl acetate and water. The aqueous phase was extracted once with ethyl acetate. The combined organic layers were dried over magnesium sulfate, filtered and concentrated. The crude material was purified by flash chromatography (30% ethyl acetate/hexanes) over silica gel to afford compound (I-f-2) as an oil (530 mg, 39% yield). $^1$H NMR (400 MHz, CHLOROFORM-d/TMS) delta ppm 1.44 (s, 9H), 2.44 (t, J=2.4 Hz, 2H), 3.53-3.67 (m, 4H), 3.92 (br. s., 1H), 4.16 (d, J=2.5 Hz, 4H), 4.90 (br. s., 1H); $^{13}$C NMR (100 MHz, CHLOROFORM-d/TMS) delta ppm 28.4 (3C), 49.5, 58.5 (2C), 68.6 (2C), 74.6 (2C), 77.2, 79.5 (2C), 155.4; HRMS (ESI) calcd for $C_{14}H_{21}NO_4$ (m/z) [M+H]$^+$ 268.1543, found 268.1536.

Intermediate (I-f-3) is known and is described in R. Roy et al. J. Org. Chem. 73, 5602 (2008).

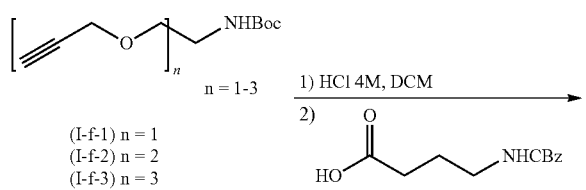

(I-f-1) n = 1
(I-f-2) n = 2
(I-f-3) n = 3

1) HCl 4M, DCM
2) PyBOP, DIPEA dioxane/DMF

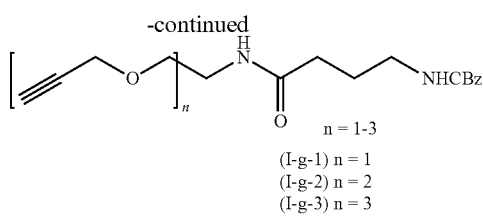

n = 1-3
(I-g-1) n = 1
(I-g-2) n = 2
(I-g-3) n = 3

Compound (I-f-1), (I-f-2), or (I-f-3) (1 equiv.) was dissolved in dichloromethane (0.2M) and hydrogen chloride 4M in dioxane (5 to 10 equiv.) was added. The reaction mixture was stirred at room temperature for 2-3 hours and then the solvent was evaporated. The residue was dried under high vacuum for 1 hour. The resulting intermediate was used in the next step without any further purification. The above resulting intermediate (1 equiv.) and 4-(((benzyloxy)carbonyl)amino)butanoic acid (1 equiv.) were dissolved in a mixture of dioxane and dimethylformamide (0.09M, 3:1). (Benzotriazol-1-yloxy)tripyrrolidinophosphonium hexafluorophosphate (1.2 equiv.) was added followed by N,N-diisopropylethylamine (5 equiv.). The reaction mixture was stirred at room temperature for 16 hours. Dichloromethane and water were added and the aqueous phase was extracted twice with dichloromethane. The combined organic layers were dried over magnesium sulfate, filtered and concentrated. The crude material was dissolved in a minimum amount of toluene, loaded on a column and purified by flash chromatography over silica gel.

Intermediate (I-g-1): Purification conditions: 100% ethyl acetate, quantitative, oil. $^1$H NMR (400 MHz, CHLOROFORM-d/TMS) delta ppm 1.80-1.91 (m, 2H), 2.24 (t, J=7.1 Hz, 2H), 2.46 (t, J=2.3 Hz, 1H), 3.22-3.31 (m, 2H), 3.43-3.51 (m, 2H), 3.56-3.64 (m, 2H), 4.16 (d, J=2.3 Hz, 2H), 5.07 (br. s., 1H), 5.10 (s, 2H), 6.09 (br. s., 1H), 7.28-7.42 (m, 5H); $^{13}$C NMR (100 MHz, CHLOROFORM-d/TMS) delta ppm 25.9, 33.7, 39.1, 40.5, 58.3, 66.7, 68.7, 74.8, 79.4, 128.1, 128.5 (4C), 136.6, 156.7, 172.5; HRMS (ESI) calcd for $C_{17}H_{22}N_2O_4$ (m/z) [M+H]$^+$ 319.1652, found 319.1646.

Intermediate (I-g-2): Purification conditions: 70% ethyl acetate/hexanes, 65 mg, oil (76% yield), oil. $^1$H NMR (400 MHz, CHLOROFORM-d/TMS) delta ppm 1.79-1.91 (m, 2H), 2.24 (t, J=7.1 Hz, 2H), 2.44 (t, J=2.4 Hz, 2H), 3.20-3.29 (m, 2H), 3.54-3.69 (m, 4H), 4.16 (d, J=1.5 Hz, 4H), 4.22-4.33 (m, 1H), 5.10 (br. s, 3H), 6.04 (d, J=7.8 Hz, 1H), 7.28-7.42 (m, 5H); $^{13}$C NMR (100 MHz, CHLOROFORM-d/TMS) delta ppm 25.8, 33.7, 40.4, 48.2, 58.4 (2C), 66.6, 68.3 (2C), 74.7 (2C), 79.4 (2C), 128.1, 128.5 (4C), 136.6, 156.6, 172.2; HRMS (ESI) calcd for $C_{21}H_{26}N_2O_5$ (m/z) [M+H]$^+$ 387.1914, found 387.1904.

Intermediate (I-g-3): Purification conditions: 70% ethyl acetate/hexanes, 42 mg, oil (60% yield). $^1$H NMR (400 MHz, CHLOROFORM-0 delta ppm 1.76-1.88 (m, 2H), 2.21 (t, J=7.1 Hz, 2H), 2.44 (t, J=2.3 Hz, 3H), 3.18-3.30 (m, 2H), 3.84 (s, 6H), 4.14 (d, J=2.3 Hz, 6H), 5.10 (s, 2H), 5.12 (br. s., 1H), 5.89 (br. s., 1H), 7.28-7.40 (m, 5H); $^{13}$C NMR (100 MHz, CHLOROFORM-d/TMS) delta ppm 25.7, 34.3, 40.3, 58.6 (3C), 59.2, 66.6, 68.5 (3C), 74.6 (3C), 79.5 (3C), 128.1, 128.5 (4C), 136.6, 156.6, 172.6; HRMS (ESI) calcd for $C_{25}H_{30}N_2O_6$ (m/z) [M+H]$^+$ 455.2177, found 455.2167.

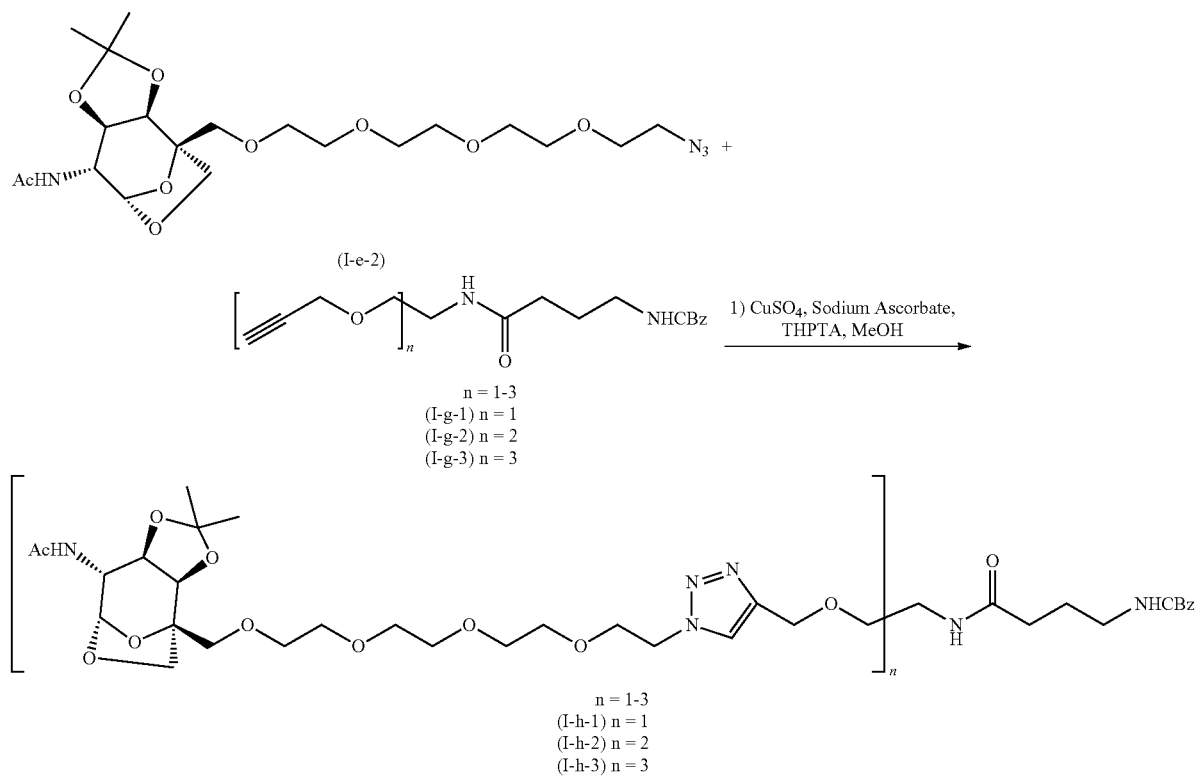

Intermediate (I-h-1):

tris(3-hydroxypropyltriazolylmethyl)amine (THPTA; see M. G. Finn et al. in Angewandte Chemie International Edition 48, 9879 (2009)) (2 mg, 0.005 mmol) and copper sulfate (1 mg, 0.004 mmol) were dissolved in water (50 microL) and then added to a solution of (I-e-2) (42 mg, 0.089 mmol) and alkyne (I-g-1) (40 mg, 0.125 mmol) in methanol (0.9 mL). Then sodium ascorbate (1.8 mg, 0.009 mmol), dissolved in water (30 microL), was added and the reaction mixture was stirred at room temperature for 24 hours. Solvent was evaporated and the crude material was purified by flash chromatography (5%-10% methanol in dichloromethane) over silica gel to afford the desired compound (I-h-1) as an oil (54 mg, 76% yield); $[\alpha]_D$ 48.2 (c 0.54, methanol); $^1$H NMR (400 MHz, METHANOL-d$_4$) delta ppm 1.33 (s, 3H), 1.48 (s, 3H), 1.70-1.83 (m, 2H), 1.98 (s, 3H), 2.21 (t, J=7.4 Hz, 2H), 3.13 (t, J=6.9 Hz, 2H), 3.37 (t, J=5.4 Hz, 2H), 3.51-3.70 (m, 14H), 3.71-3.95 (m, 7H), 4.15 (t, J=6.5 Hz, 1H), 4.29 (d, J=5.8 Hz, 1H), 4.56 (t, J=5.0 Hz, 2H), 4.60 (s, 2H), 5.06 (s, 2H), 5.22 (d, J=1.8 Hz, 1H), 7.25-7.38 (m, 5H), 8.01 (s, 1H); $^{13}$C NMR (100 MHz, METHANOL-d$_4$) delta ppm 22.7, 27.0, 27.4, 28.5, 34.4, 40.5, 41.4, 51.6, 56.7, 62.4, 64.9, 67.5, 70.0, 70.5, 70.8, 71.1, 71.5, 71.6, 71.65, 71.7, 71.73, 72.6, 73.8, 76.2, 76.5, 82.1, 102.4, 112.4, 126.1, 129.0, 129.1, 129.6, 138.6, 146.1, 159.0, 173.6, 175.7; HRMS (ESI) calcd for $C_{37}H_{56}N_6O_{13}$ (m/z) [M+H]$^+$ 793.3978, found 793.3959.

Intermediate (I-h-2)

THPTA (22 mg, 0.051 mmol) and copper sulfate (2.5 mg, 0.01 mmol) were dissolved in water (70 microL) and then added to a solution of (I-e-2) (48 mg, 0.1 mmol) and alkyne (I-g-2) (20 mg, 0.051 mmol) in methanol (1 mL). Then sodium ascorbate (4 mg, 0.02 mmol), dissolved in water (30 microL), was added and the reaction mixture was stirred at room temperature for 72 hours. Solvent was evaporated and the residue was taken up in dichloromethane and a saturated aqueous solution of ammonium chloride. The aqueous phase was extracted three times with dichloromethane. The combined organic layers were dried over magnesium sulfate, filtered and concentrated. The crude material was used in the next step without any further purification.

Intermediate (I-h-3)

THPTA (34 mg, 0.079 mmol) and copper sulfate (4 mg, 0.016 mmol) were dissolved in water (200 microL) and then added to a solution of (I-e-2) (50 mg, 0.1 mmol) and alkyne (I-g-3) (24 mg, 0.053 mmol) in methanol (1 mL). Then sodium ascorbate (6.5 mg, 0.032 mmol), dissolved in water (30 microL), was added and the reaction mixture was stirred at room temperature for 72 hours. Solvent was evaporated and the residue was taken up in dichloromethane and a saturated aqueous solution of ammonium chloride. The aqueous phase was extracted three times with dichloromethane. The combined organic layers were dried over magnesium sulfate, filtered and concentrated. The crude material was used in the next step without any further purification.

General Procedure for Acetonide Removal:

Compound (I-h-1), (I-h-2), or (I-h-3) (0.030-0.068 mmol) was dissolved in a mixture of acetic acid, methanol and water (1.6-1.8 mL, 0.5 mL, 0.5 mL respectively) and stirred at 70° C. for 24 hours. Solvent was evaporated and the residue was co-evaporated twice with toluene. The crude material was purified by flash chromatography over silica gel.

(4):

Purification conditions: 10% methanol in dichloromethane, 43.3 mg, oil (85% yield). $[\alpha]_D$ 45 (c 1, methanol); $^1$H NMR (400 MHz, METHANOL-d$_4$) delta ppm 1.72-1.83 (m, 2H), 1.99 (s, 3H), 2.22 (t, J=7.4 Hz, 2H), 3.13 (t, J=6.8 Hz, 2H), 3.37 (t, J=5.4 Hz, 2H), 3.52-3.79 (m, 20H), 3.85-4.00 (m, 3H), 4.57 (t, J=5.0 Hz, 2H), 4.61 (s, 2H), 5.07 (s, 2H), 5.21 (s, 1H), 7.24-7.41 (m, 5H), 8.02 (s, 1H); $^{13}$C NMR (100 MHz, METHANOL-d$_4$) delta ppm 22.8, 27.4, 34.4, 40.4, 41.4, 51.6, 56.4, 64.9, 67.5, 69.0, 70.0, 70.1, 70.4, 70.5, 71.4, 71.5 (2C), 71.6, 71.65, 71.7, 72.5, 84.3, 102.6, 126.0, 129.0 (2C), 129.1, 129.6 (2C), 138.6, 145.8, 159.0, 174.0, 175.8; HRMS (ESI) calcd for C$_{34}$H$_{52}$N$_6$O$_{13}$ (m/z) [M+H]$^+$ 753.3665, found 753.3679.

(5):

Purification conditions: 20% methanol in dichloromethane, 25 mg, oil (20% yield over 2 steps). [α]$_D$ 56 (c 1.25, methanol); $^1$H NMR (400 MHz, METHANOL-d$_4$) delta ppm 1.72-1.81 (m, 2H), 1.99 (s, 6H), 2.23 (t, J=7.5 Hz, 2H), 3.13 (t, J=6.9 Hz, 2H), 3.50-3.80 (m, 36H), 3.85-3.91 (m, 6H), 3.92-4.00 (m, 4H), 4.13-4.25 (m, 1H), 4.52-4.63 (m, 8H), 5.07 (s, 2H), 5.21 (d, J=1.3 Hz, 2H), 7.23-7.40 (m, 5H), 8.01 (s, 2H); $^{13}$C NMR (100 MHz, METHANOL-d$_4$) delta ppm 22.6 (2C), 27.2, 34.2, 41.2, 50.2, 51.4 (2C), 56.2 (2C), 65.0 (2C), 67.3, 68.8 (2C), 69.9 (2C), 70.0 (2C), 70.2 (2C), 70.3 (2C), 71.2 (2C), 71.3 (4C), 71.4 (2C), 71.5 (2C), 71.52

5.21 (d, J=1.3 Hz, 3H), 7.24-7.40 (m, 5H), 7.98 (s, 3H); HRMS (ESI) calcd for C$_{76}$H$_{120}$N$_{14}$O$_{33}$ (m/z) [M+2H]$^+$/2 879.4144, found 879.4148.

N-(2-((1-(1-(((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)methoxy)ethyl)-4-aminobutanamide (7), 4-amino-N-{1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]propan-2-yl}butanamide (8), 4-amino-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)butanamide (9)

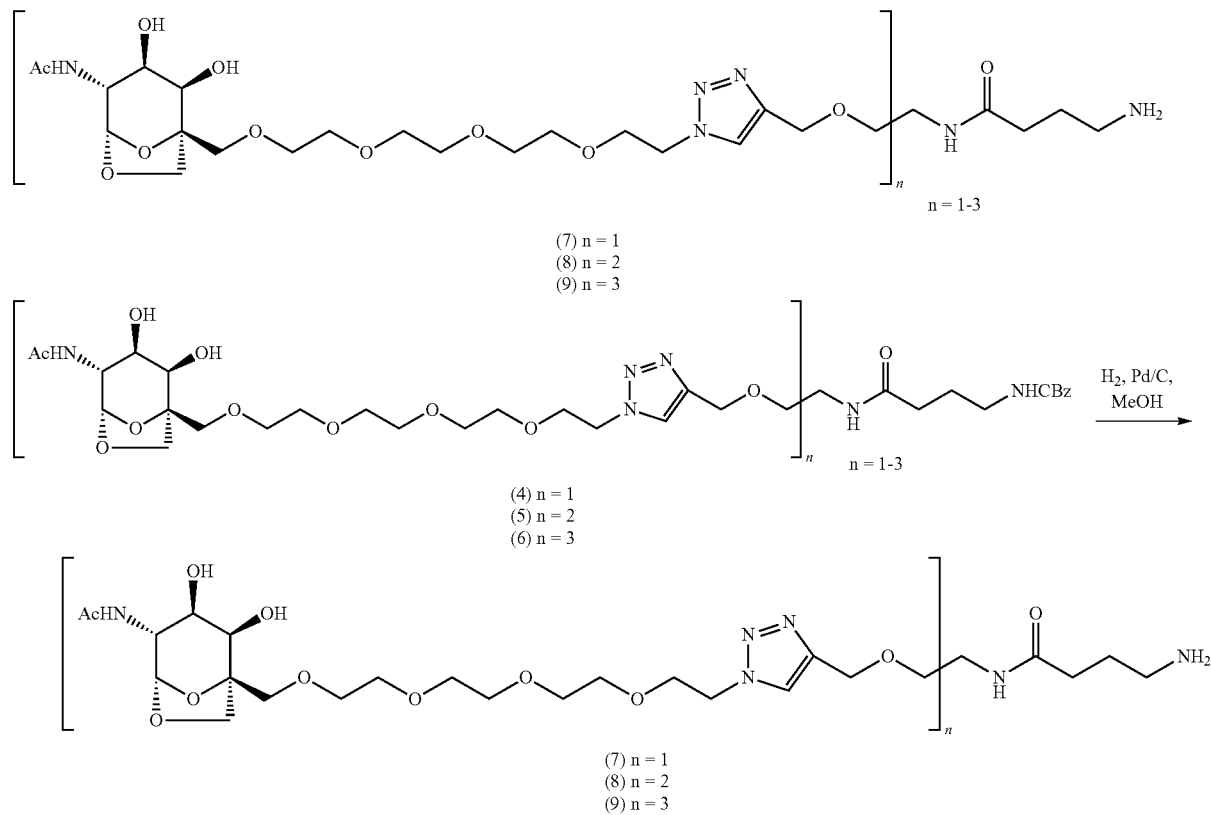

(7) n = 1
(8) n = 2
(9) n = 3

(4) n = 1
(5) n = 2
(6) n = 3

(7) n = 1
(8) n = 2
(9) n = 3

(2C), 72.3 (2C), 84.1 (2C), 102.4 (2C), 125.8 (2C), 128.8 (2C), 128.9, 129.4 (2C), 138.4, 145.6 (2C), 158.8, 173.8 (2C), 175.3; HRMS (ESI) calcd for C$_{55}$H$_{86}$N$_{10}$O$_{23}$ (m/z) [M+H]$^+$ 1255.5940, found 1255.5925.

(6):

Purification conditions: 20% methanol in dichloromethane, 31 mg, oil (18% yield over 2 steps). [α]$_D$ 53 (c 1, methanol); $^1$H NMR (400 MHz, METHANOL-d$_4$) delta ppm 1.65-1.78 (m, 2H), 1.98 (s, 9H), 2.19 (t, J=7.3 Hz, 2H), 3.11 (t, J=6.8 Hz, 2H), 3.51-3.80 (m, 54H), 3.86-3.91 (m, 9H), 3.91-3.99 (m, 6H), 4.51-4.63 (m, 12H), 5.06 (s, 2H), In a round bottom flask, compound (4), (5), or (6) (1 equiv.) was dissolved in methanol (0.01M) and the flask was flushed with nitrogen. Palladium on carbon (10%, 0.7 equiv.) was added and the flask was flushed with nitrogen and then with hydrogen. The reaction mixture was stirred at room temperature for 12-24 hours under an atmosphere of hydrogen (a balloon filled with hydrogen was used). The palladium was filtered using a 0.45 microm PTFE Acrodisc Cr and rinsed once with methanol. Solvent was evaporated.

(7):

25.5 mg, oil, 76% yield; $[\alpha]_D$ 57.6 (c 1.25, methanol); $^1$H NMR (400 MHz, METHANOL-$d_4$) delta ppm 1.70-1.81 (m, 2H), 1.99 (s, 3H), 2.24 (t, J=7.4 Hz, 2H), 2.67 (t, J=6.8 Hz, 2H), 3.36-3.41 (m, 2H), 3.51-3.80 (m, 19H), 3.84-4.01 (m, 4H), 4.59 (t, J=5.2 Hz, 2H), 4.61 (s, 2H), 5.21 (s, 1H), 8.03 (s, 1H); $^{13}$C NMR (100 MHz, METHANOL-$d_4$) delta ppm 22.8, 29.6, 34.5, 40.4, 42.0, 51.6, 56.4, 64.9, 69.0, 70.0, 70.1, 70.5, 70.6, 71.4, 71.5 (2C), 71.6, 71.66, 71.7, 72.5, 84.3, 102.6, 126.0, 145.8, 174.1, 175.9; HRMS (ESI) calcd for $C_{26}H_{46}N_6O_{11}$ (m/z) $[M+H]^+$ 619.3297, found 619.3278.

(8):

The crude material was dissolved in 0.5 mL methanol/water (50:50) and injected on a HPLC column. Preparative high-performance liquid chromatography (HPLC) was performed using a Waters XBridge BEH C18 OBD Prep Column, 130 Å, 5 microm, 19 mm×100 mm (Waters, part number 186002978), eluting with a linear slope gradient at 17 mL/min flow rate. Solvent gradient: acetonitrile/water/trifluoroacetic acid (2:98:0.1) to (22:58:0.1) in 40 min. Collected fractions were analyzed by analytical LCMS, and the fractions at 25.7-27.3 minutes judged as having adequate purity were pooled and evaporated to afford 10.7 mg of (8) as an oil, 49% yield; $[\alpha]_D$ 56 (c 1, methanol); $^1$H NMR (500 MHz, METHANOL-$d_4$) delta ppm 1.86-1.95 (m, 2H), 1.99 (s, 6H), 2.37 (t, J=7.0 Hz, 2H), 2.96 (t, J=7.4 Hz, 2H), 3.50-3.80 (m, 36H), 3.84-4.00 (m, 10H), 4.17-4.26 (m, 1H), 4.57-4.62 (m, 8H), 5.21 (s, 2H), 8.03 (s, 2H); $^{13}$C NMR (100 MHz, METHANOL-$d_4$) delta ppm 22.8 (2C), 29.2, 34.5, 41.8, 50.4, 51.6 (2C), 56.4 (2C), 65.1 (2C), 69.0 (2C), 70.1 (2C), 70.3 (2C), 70.5 (2C), 70.6 (2C), 71.4 (2C), 71.5 (4C), 71.6 (2C), 7.67, (2C), 71.7 (2C), 72.5 (2C), 84.3 (2C), 102.6 (2C), 126.1 (2C), 145.8 (2C), 174.1 (2C), 175.6; HRMS (ESI) calcd for $C_{47}H_{80}N_{10}O_{21}$ (m/z) $[M+H]^+$ 1121.5572, found 1121.5558.

(9):

The crude material was dissolved in 0.5 mL methanol/water (50:50), and injected on HPLC column. Preparative high-performance liquid chromatography (HPLC) was performed using a Waters XBridge BEH C18 OBD Prep Column, 130 Å, 5 microm, 19 mm×100 mm (Waters, part number 186002978), eluting with a linear slope gradient at 17 mL/min flow rate. Solvent gradient: acetonitrile/water/trifluoroacetic acid (2:98:0.1) to (22:58:0.1) in 40 min. Collected fractions were analyzed by analytical LCMS, and the fractions at 30.3-32.0 minutes judged as having adequate purity were pooled and evaporated to afford 15 mg of (9) as an oil, 63% yield; $[\alpha]_D$ 59.1 (c 1.1, methanol); $^1$H NMR (500 MHz, METHANOL-$d_4$) delta ppm 1.84-1.92 (m, 2H), 2.00 (s, 9H), 2.31-2.38 (m, 2H), 2.97 (t, J=7.3 Hz, 2H), 3.54-3.80 (m, 54H), 3.86-3.93 (m, 9H), 3.93-4.00 (m, 6H), 4.57 (s, 6H), 4.60 (t, J=4.9 Hz, 6H), 5.22 (s, 3H), 8.02 (s, 3H); HRMS (ESI) calcd for $C_{68}H_{114}N_{14}O_{31}$ (m/z) $[M+H]^+$ 1623.7847, found 1623.7803.

(10), (11), and (12); Alexa Fluor® 647 Conjugates

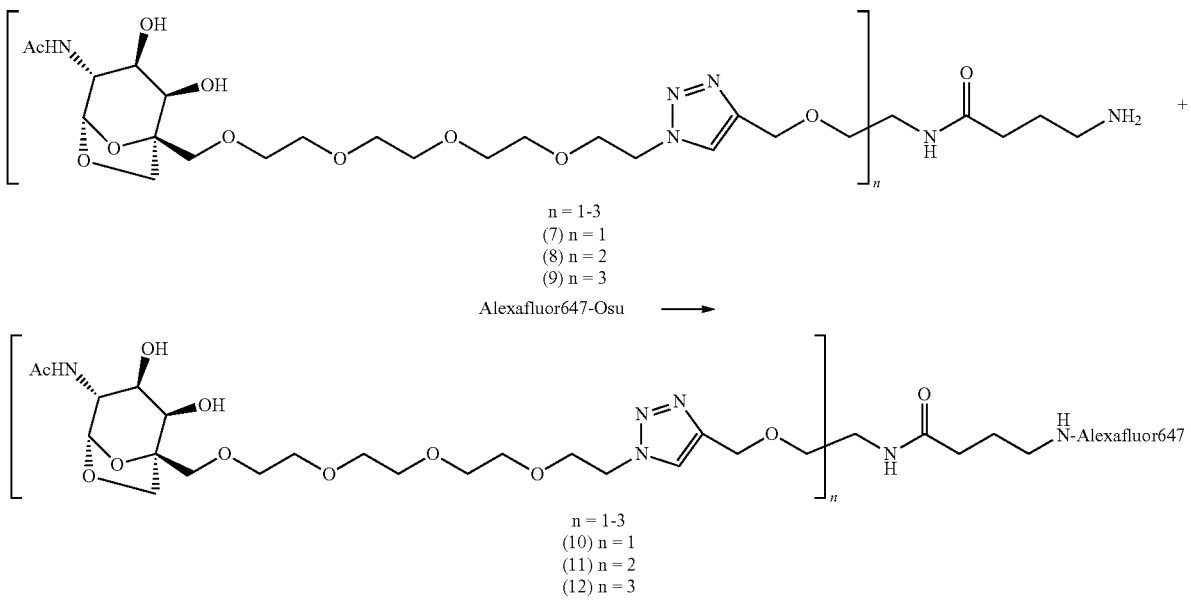

n = 1-3
(7) n = 1
(8) n = 2
(9) n = 3

Alexafluor647-Osu → n = 1-3
(10) n = 1
(11) n = 2
(12) n = 3

Alexa Fluor® 647 carboxylic acid succinimidyl ester was from Invitrogen (Catalog NumberA-20106). The molecular weight was reported by Invitrogen to be ~1250. The Alexa647 labeled compound molecular weight was estimated based on the found $[M+H]^+$ of 955.07 of Alexa Fluor 647 carboxylic acid succinimidyl ester from LCMS. Extinction coefficient for $\lambda_{max}$ 650 is ~270000±20000, which varies from batch to batch.

General Procedure for HPLC Purification:

Preparative high-performance liquid chromatography (HPLC) was performed using a Waters XBridge BEH C18 OBD Prep Column, 130 Å, 5 microm, 19 mm×100 mm (Waters, part number 186002978), eluting with a linear slope gradient at 17 mL/min flow rate. Solvent gradient: acetonitrile/water/trifluoroacetic acid (2:98:0.1) to (22:78:0.1) in 40 min. Collected fractions were analyzed by analytical LCMS, and those judged as having adequate purity were pooled and evaporated.

(10):

To a solution of compound (7) (3.0 mg, 4.8 micromol) in dimethyl sulfoxide (200 microL) were added Alexa Fluor® 647 carboxylic acid succinimidyl ester (5.0 mg, 4 micromol) and N,N-diisopropylethylamine (10 microL, 10 equiv.). The reaction mixture was shaken at room temperature for 1 hour and then directly purified by preparative HPLC. Collected fractions were analyzed by analytical LCMS, and those judged as having adequate purity were pooled ($R_t$=22.7-24 minutes). 3.2 mg of (10) was obtained (55% yield). The solution was aliquoted and evaporated in a vacuum centrifuge, and the product was stored at 4° C. MS (ESI) calcd (m/z) for [M+H]$^+$ ~1456, found 1456.82.

(11):

To a solution of compound (8) (6.0 mg, 5 micromol) in dimethyl sulfoxide (200 microL) were added Alexa Fluor® 647 carboxylic acid succinimidyl ester (5.0 mg, 4 micromol) and N,N-diisopropylethylamine (10 microL, 10 equiv.). The reaction mixture was shaken at room temperature for 1 hour and then directly purified by preparative HPLC. Collected fractions were analyzed by analytical LCMS, and those judged as having adequate purity were pooled ($R_t$=25.3-26.7 minutes). 4.8 mg of (11) was obtained (62% yield). The solution was aliquoted and evaporated in a vacuum centrifuge, and the product was stored at 4° C. MS (ESI) calcd (m/z) for [M+H]$^+$ ~1958, found 1958.74.

(12):

To a solution of compound (9) (9.8 mg, 6 micromol) in dimethyl sulfoxide (200 microL) were added Alexa Fluor® 647 carboxylic acid succinimidyl ester (5.0 mg, 4.8 micromol) and N,N-diisopropylethylamine (10 microL, 10 equiv.). The reaction mixture was shaken at room temperature for 1 hour and then directly purified by preparative HPLC. Collected fractions were analyzed by analytical LCMS, and those judged as having adequate purity were pooled ($R_t$=27.7 minutes). 5.2 mg of (12) was obtained (52% yield). The solution was aliquoted and evaporated in a vacuum centrifuge, and the product was stored at 4° C. MS (ESI) calcd (m/z) for [M+H]$^+$ ~2460, found 2461.18.

4-amino-N-[1,31-bis(1-{[(1S,2R,3R,4R,5S)-4-(acetylamino)-2,3-dihydroxy-6,8-dioxabicyclo[3.2.1]oct-1-yl]methyl}-1H-1,2,3-triazol-4-yl)-2,6,10,14,18,22,26,30-octaoxahentriacontan-16-yl]butanamide (13) and 4-amino-N-{1,31-bis(1-{[(1S,2R,3R,4R,5S)-4-(acetylamino)-2,3-dihydroxy-6,8-dioxabicyclo[3.2.1]oct-1-yl]methyl}-1H-1,2,3-triazol-4-yl)-16-[15-(1-{[(1S,2R,3R,4R,5S)-4-(acetylamino)-2,3-dihydroxy-6,8-dioxabicyclo[3.2.1]oct-1-yl]methyl}-1H-1,2,3-triazol-4-yl)-2,6,10,14-tetraoxapentadec-1-yl]-2,6,10,14,18,22,26,30-octaoxahentriacontan-16-yl}butanamide (14)

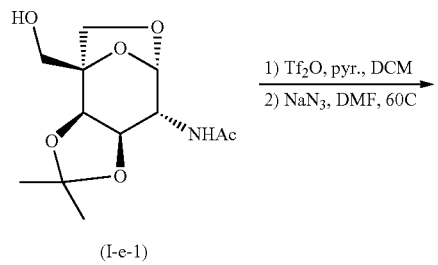

(I-e-1)

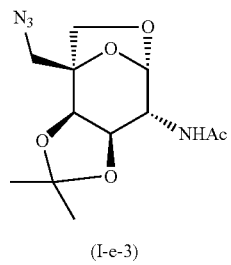

(I-e-3)

Compound (I-e-1) (247 mg, 0.904 mmol) was dissolved in dichloromethane (15 mL) and pyridine was added (1.46 mL, 18.1 mmol). The reaction mixture was cooled at −20° C. and trifluoromethanesulfonic anhydride (0.23 mL, 1.4 mmol) in dichloromethane (0.6 mL) was added dropwise and the mixture was stirred while allowing warming to 0 degrees C. over 50 minutes. The reaction mixture was diluted with dichloromethane and washed with an aqueous solution of 1M hydrogen chloride, a saturated aqueous solution of sodium bicarbonate and a saturated aqueous solution of sodium chloride. The organic phase was dried over magnesium sulfate, filtered and concentrated. The crude material was used in the next step without any further purification. Sodium azide (270 mg, 4.1 mmol) was added to a solution of the above triflate in dimethylformamide (4.1 mL). The reaction mixture was stirred at 60° C. for 16 hours. Solvent was evaporated and the crude material was purified by flash chromatography (15/1 ethyl acetate/methanol) over silica gel to afford the desired compound (I-e-3) as a yellow oil (227 mg, 92% yield). [α]$_D$ 127 (c 1, methanol); $^1$H NMR (500 MHz, CHLOROFORM-d) delta ppm 1.34 (s, 3H), 1.53 (s, 3H), 2.00 (s, 3H), 3.67 (d, J=12.7 Hz, 1H), 3.72 (d, J=7.8 Hz, 1H), 3.74 (d, J=7.8 Hz, 1H), 3.75 (d, J=12.7 Hz, 1H), 4.02-4.10 (m, 2H), 4.11 (d, J=5.9 Hz, 1H), 5.35 (d, J=2.4 Hz, 1H), 5.95 (d, J=8.8 Hz, 1H); $^{13}$C NMR (125 MHz, CHLOROFORM-d) delta ppm 23.2, 26.2, 27.7, 51.0, 54.2, 69.3, 74.8, 76.1, 80.6, 101.2, 111.6, 170.1; HRMS (ESI) calcd for $C_{12}H_{18}N_4O_5$ (m/z) [M+H]$^+$ 299.1350, found 299.1344.

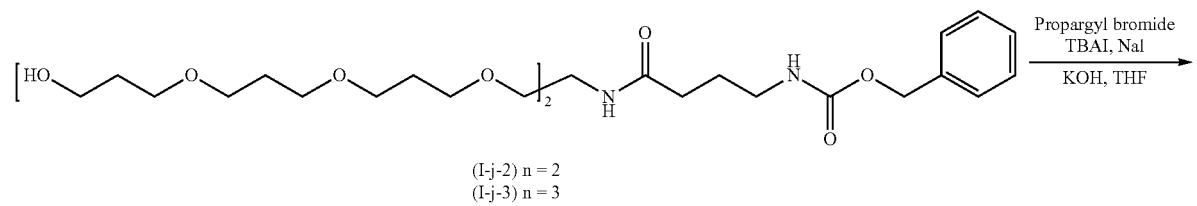

(I-j-2) n = 2
(I-j-3) n = 3

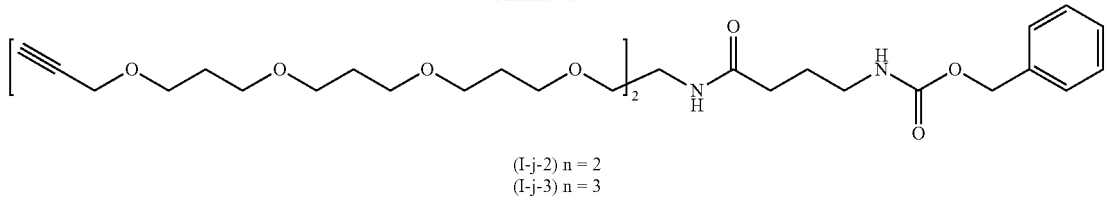

(I-j-2) n = 2
(I-j-3) n = 3

Compound (I-j-2) and (I-j-3) could be made starting from propargyl bromide, (I-i-2) (commercially available from Dalton Pharma; DC-001760) and (I-i-3) (B. Ernst et al. in Bioorganic & Medicinal Chemistry, 16, 5216 (2008)) respectively, following the same procedure described for the formation of compound (I-f-2).

Compound (I-j-2): Purification conditions: 20% ethyl acetate/hexanes, 85 mg, oil (8% yield); $^1$H NMR (400 MHz, CHLOROFORM-d/TMS) delta ppm 1.77-1.90 (m, 14H), 2.23 (t, J=7.1 Hz, 2H), 2.43 (t, J=2.3 Hz, 2H), 3.20-3.29 (m, 20H), 2.18 (t, J=6.9 Hz, 2H), 2.43 (t, J=2.4 Hz, 3H), 3.23 (q, J=6.3 Hz, 2H), 3.40-3.53 (m, 30H), 3.59 (t, J=6.3 Hz, 6H), 3.67 (s, 6H), 4.13 (d, J=2.3 Hz, 6H), 5.08 (s, 2H), 5.27 (br. s., 1H), 5.85 (s, 1H), 7.27-7.40 (m, 5H); $^{13}$C NMR (100 MHz, CHLOROFORM-d/TMS) delta ppm 25.7, 29.7 (3C), 29.9 (3C), 30.0 (3C), 34.4, 40.4, 58.1 (3C), 59.8, 66.5, 67.1 (3C), 67.6 (3C), 67.7 (3C), 67.8 (3C), 67.82 (3C), 68.4 (3C), 69.1 (3C), 74.2 (3C), 79.9 (3C), 128.0, 128.4 (4C), 136.6, 156.6, 172.3; HRMS (ESI) calcd for $C_{52}H_{84}N_2O_{15}$ (m/z) [M+H]$^+$ 977.5944, found 977.5943.

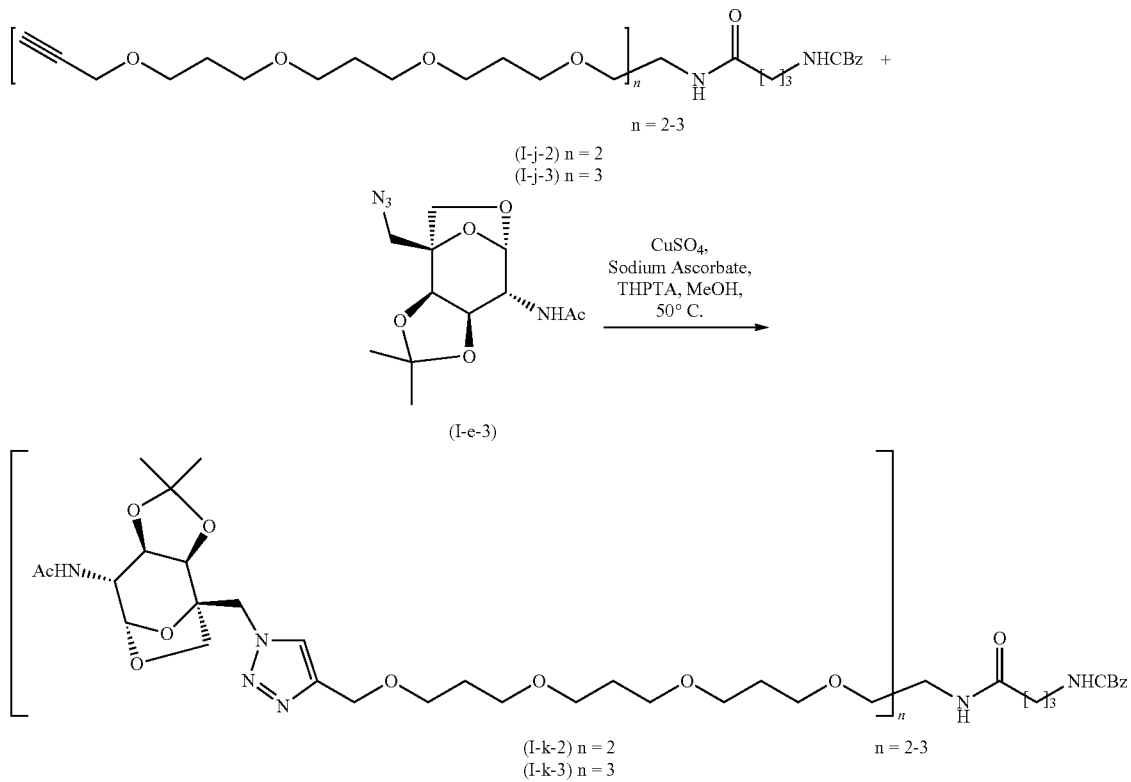

(I-j-2) n = 2
(I-j-3) n = 3

(I-e-3)

(I-k-2) n = 2
(I-k-3) n = 3
n = 2-3

2H), 3.39-3.55 (m, 24H), 3.60 (t, J=6.3 Hz, 4H), 4.13 (d, J=2.5 Hz, 4H), 4.15-4.24 (m, 1H), 5.09 (s, 2H), 5.16 (br. s., 1H), 6.05 (d, J=8.1 Hz, 1H), 7.28-7.41 (m, 5H); $^{13}$C NMR (100 MHz, CHLOROFORM-d/TMS) delta ppm 25.8, 29.8 (2C), 29.9 (2C), 30.0 (2C), 33.7, 40.4, 48.5, 58.1 (2C), 66.6, 67.2 (2C), 67.6 (2C), 67.7 (2C), 67.8 (2C), 67.9 (2C), 68.3 (2C), 69.0 (2C), 74.2 (2C), 79.9 (2C), 128.1, 128.5 (4C), 136.6, 156.6, 172.1; HRMS (ESI) calcd for $C_{39}H_{62}N_2O_{11}$ (m/z) [M+H]$^+$ 735.4426, found 735.4424.

Compound (I-j-3): Purification conditions: 85% ethyl acetate/hexanes, 32.6 mg, oil, (71% yield); $^1$H NMR (400 MHz, CHLOROFORM-d/TMS) delta ppm 1.75-1.90 (m, Compound (I-k-2):

THPTA (22.6 mg, 0.052 mmol) and copper sulfate (2.5 mg, 0.01 mmol) were dissolved in water (200 microL) and then added to a solution of (I-e-3) (45 mg, 0.152 mmol) and (I-j-2) (51 mg, 0.069 mmol) in methanol (1.1 mL). Then sodium ascorbate (4.2 mg, 0.021 mmol), dissolved in water (100 microL), was added and the reaction mixture was stirred at 50 degrees Celsius for 24 hours. Solvent was evaporated and the crude material was purified by flash chromatography (5% methanol in dichloromethane) over silica gel to afford the desired compound (I-k-2) as an oil (72 mg, 78% yield). $^1$H NMR (400 MHz, METHANOL-d$_4$)

delta ppm 1.34 (s, 6H), 1.52 (s, 6H), 1.73-1.86 (m, 12H), 1.97 (s, 6H), 2.24 (t, J=7.4 Hz, 2H), 3.15 (t, J=6.8 Hz, 2H), 3.43-3.54 (m, 22H), 3.58 (t, J=6.3 Hz, 4H), 3.86 (d, J=8.1 Hz, 2H), 3.97 (dd, J=6.2, 1.9 Hz, 2H), 4.11-4.23 (m, 5H), 4.58 (s, 4H), 4.78 (s, 6H), 4.91 (d, J=14.1 Hz, 2H), 4.98 (d, J=14.4 Hz, 2H), 5.07 (s, 2H), 5.24 (d, J=1.8 Hz, 2H), 7.25-7.40 (m, 5H), 7.99 (s, 2H); $^{13}$C NMR (100 MHz, METHANOL-$d_4$) delta ppm 22.7 (2C), 26.8 (2C), 27.5, 28.4 (2C), 31.1 (4C), 31.2 (2C), 34.5, 41.4, 50.6, 51.0 (2C), 56.3 (2C), 64.8 (2C), 67.5 (2C), 68.7 (2C), 68.8 (2C), 68.9 (3C), 69.0 (2C), 69.4 (2C), 69.7 (2C), 70.9 (2C), 76.3 (2C), 76.6 (2C), 81.5 (2C), 102.5 (2C), 112.8 (2C), 127.2 (2C), 129.0 (2C), 129.1, 129.6 (2C), 138.6, 146.3 (2C), 159.0, 173.5 (2C), 175.5; HRMS (ESI) calcd for $C_{63}H_{98}N_{10}O_{21}$ (m/z) [M+H]$^+$ 1331.6981, found 1331.6971.
Compound (I-k-3):

chromatography (10% methanol in dichloromethane) over silica gel to afford the desired compound (I-k-3) as an oil (43.5 mg, 70% yield). $^1$H NMR (400 MHz, METHANOL-$d_4$) delta ppm 1.33 (s, 9H), 1.52 (s, 9H), 1.71-1.87 (m, 18H), 1.97 (s, 9H), 2.20 (t, J=7.3 Hz, 2H), 3.15 (t, J=6.8 Hz, 2H), 3.43-3.52 (m, 28H), 3.58 (t, J=6.3 Hz, 6H), 3.67 (s, 6H), 3.86 (d, J=8.3 Hz, 3H), 3.97 (dd, J=6.0, 1.8 Hz, 3H), 4.14-4.22 (m, 5H), 4.58 (s, 6H), 4.78 (s, 8H), 4.91 (d, J=14.6 Hz, 3H), 4.97 (d, J=14.6 Hz, 3H), 5.07 (s, 2H), 5.24 (d, J=2.0 Hz, 3H), 7.26-7.38 (m, 5H), 7.98 (s, 3H); $^{13}$C NMR (100 MHz, METHANOL-$d_4$) delta ppm 22.7 (3C), 26.9 (3C), 27.7, 28.4 (3C), 31.1 (3C), 31.2 (3C), 31.3 (3C), 35.2, 41.3, 51.0 (3C), 56.3 (3C), 61.8, 64.9 (3C), 67.5 (3C), 68.7 (3C), 68.8 (3C), 68.9 (3C), 69.0 (4C), 69.6 (3C), 69.7 (3C), 70.0 (3C), 76.3 (3C), 76.6 (3C), 81.5 (3C), 102.5 (3C), 112.8 (3C), 127.2 (3C), 129.0 (2C), 129.1, 129.7 (2C), 138.6, 146.4 (3C), 159.0, 173.5 (3C), 175.6; HRMS (ESI) calcd for $C_{88}H_{138}N_4O_{30}$ (m/z) [M+H]$^+$ 1871.9776, found 1871.9713.

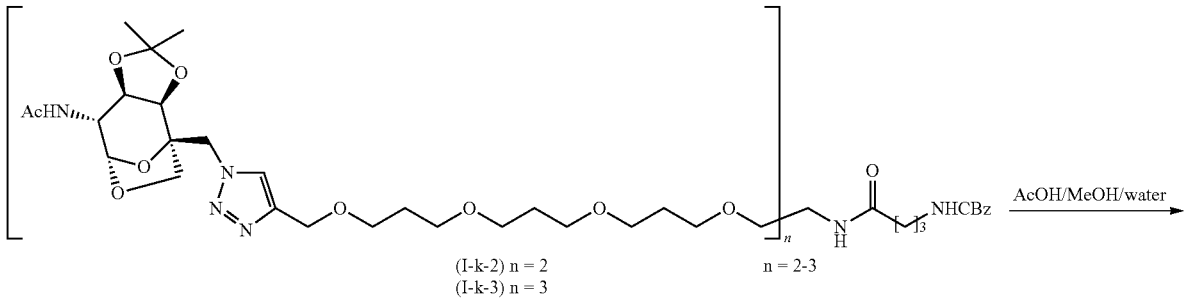

(I-k-2) n = 2
(I-k-3) n = 3
n = 2-3

AcOH/MeOH/water →

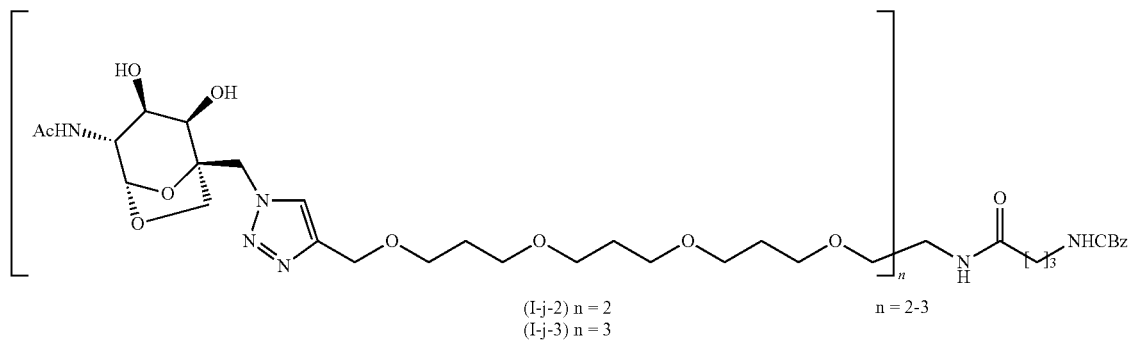

(I-j-2) n = 2
(I-j-3) n = 3
n = 2-3

THPTA (16 mg, 0.037 mmol) and copper sulfate (1.7 mg, 0.007 mmol) were dissolved in water (100 microL) and then added to a solution of (I-e-3) (32.5 mg, 0.109 mmol) and (I-j-3) (32 mg, 0.033 mmol) in methanol (1.1 mL). Then sodium ascorbate (3 mg, 0.015 mmol), dissolved in water (100 microL), was added and the reaction mixture was stirred at 50 degrees Celsius for 24 hours. Solvent was evaporated and the crude material was purified by flash Compound (I-k-2) or (I-k-3) (0.068 mmol) was dissolved in a mixture of acetic acid, methanol and water (2.5-3 mL, 0.6-0.9 mL, 0.6-0.9 mL respectively) and stirred at 70 degrees Celsius for 24 hours. Solvent was evaporated and the residue was co-evaporated twice with toluene. The crude material obtained was used in the next step without any further purification.

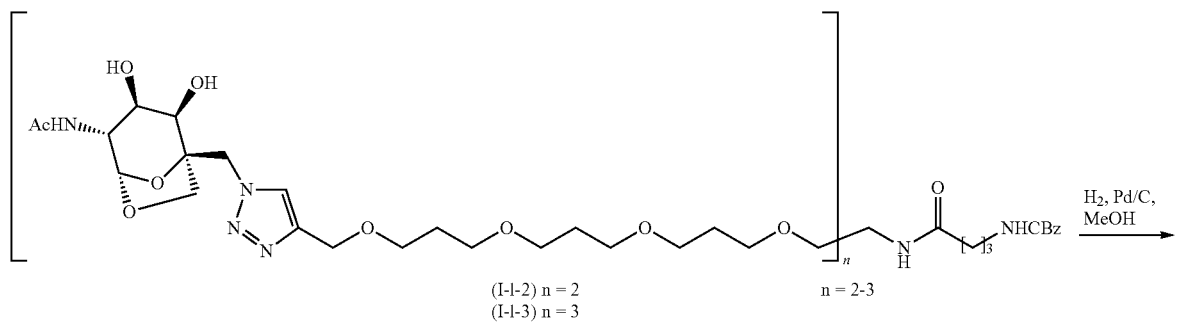

(I-l-2) n = 2
(I-l-3) n = 3 n = 2-3

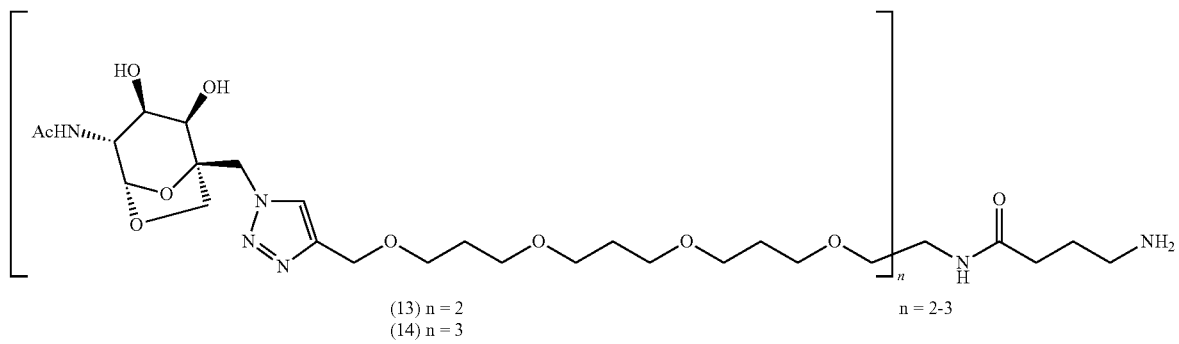

(13) n = 2
(14) n = 3 n = 2-3

In a round bottom flask, compound (I-l-2) or (I-l-3) (1 equiv.) was dissolved in methanol (0.01M) and the flask was flushed with nitrogen. Palladium on carbon (10%, 0.7 equiv.) was added and the flask was flushed with nitrogen and then with hydrogen. The reaction mixture was stirred at room temperature for 24 hours under an atmosphere of hydrogen (a balloon filled with hydrogen was used). The palladium was filtered using a 0.45 microm PTFE Acrodisc Cr and rinsed once with methanol. Solvent was evaporated.

(13):

The crude material was dissolved in 0.5 mL methanol/water (50:50) and injected on a HPLC column. Preparative high-performance liquid chromatography (HPLC) was performed using a Waters XBridge BEH C18 OBD Prep Column, 130 Å, 5 microm, 19 mm×100 mm (Waters, part number 186002978), eluting with a linear slope gradient at 17 mL/min flow rate. Solvent gradient: acetonitrile/water/trifluoroacetic acid (2:98:0.1) to (22:58:0.1) in 40 min. Collected fractions were analyzed by analytical LCMS, and the fractions at 34.7-35.6 minutes judged as having adequate purity were pooled and evaporated to afford 12.8 mg of (13) as an oil, (17% yield over 2 steps); $^1$H NMR (500 MHz, METHANOL-$d_4$) delta ppm 1.73-1.87 (m, 12H), 1.88-1.96 (m, 2H), 1.98 (s, 6H), 2.39 (t, J=7.0 Hz, 2H), 2.98 (t, J=7.4 Hz, 2H), 3.42 (d, J=8.5 Hz, 2H), 3.45-3.55 (m, 24H), 3.59 (t, J=6.3 Hz, 4H), 3.71-3.75 (m, 4H), 3.77 (d, J=8.3 Hz, 2H), 3.96-4.02 (m, 2H), 4.13-4.20 (m, 1H), 4.58 (s, 4H), 4.91-4.95 (m, 4H), 5.20 (d, J=1.5 Hz, 2H), 7.98 (s, 2H); HRMS (ESI) calcd for $C_{49}H_{84}N_{10}O_{19}$ (m/z) [M+H]$^+$ 1117.5987, found 1117.5977.

(14):

The crude material was dissolved in 0.5 mL methanol/water (50:50) and injected on a HPLC column. Preparative high-performance liquid chromatography (HPLC) was performed using a Waters XBridge BEH C18 OBD Prep Column, 130 Å, 5 microm, 19 mm×100 mm (Waters, part number 186002978), eluting with a linear slope gradient at 17 mL/min flow rate. Solvent gradient: acetonitrile/water/trifluoroacetic acid (2:98:0.1) to (42:58:0.1) in 40 min. Collected fractions were analyzed by analytical LCMS, and the fractions at 24.7-25.6 minutes judged as having adequate purity were pooled and evaporated to afford 5.5 mg of (14) as an oil (10% yield over 2 steps); $^1$H NMR (500 MHz, METHANOL-$d_4$) delta ppm 1.75-1.86 (m, 18H), 1.87-1.94 (m, 2H), 1.98 (s, 9H), 2.37 (t, J=6.8 Hz, 2H), 2.98 (t, J=7.4 Hz, 2H), 3.43 (d, J=8.5 Hz, 3H), 3.46-3.53 (m, 31H), 3.59 (t, J=6.3 Hz, 6H), 3.68 (s, 6H), 3.72-3.76 (m, 5H), 3.77 (d, J=8.3 Hz, 3H), 3.97-4.02 (m, 3H), 4.59 (s, 6H), 4.90-4.96 (m, 6H), 5.20 (d, J=1.2 Hz, 3H) 7.98 (s, 3H); HRMS (ESI) calcd for $C_{71}H_{120}N_{14}O_{28}$ (m/z) [M+H]$^+$ 1617.8469, found 1617.8415.

(15) and (16); Alexa Fluor® 647 (AF647) Conjugates

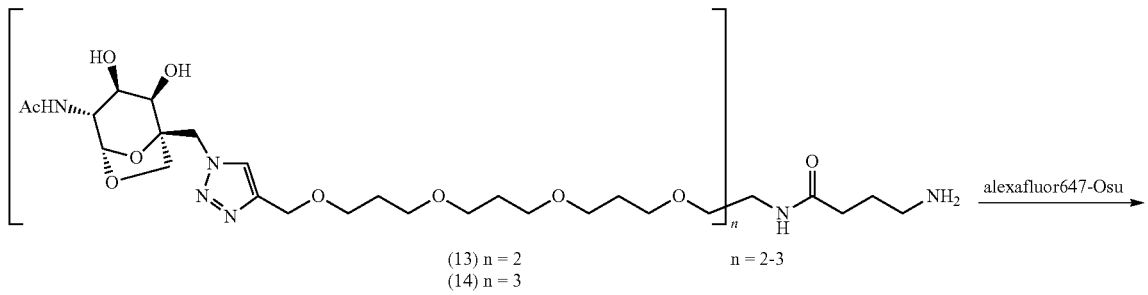

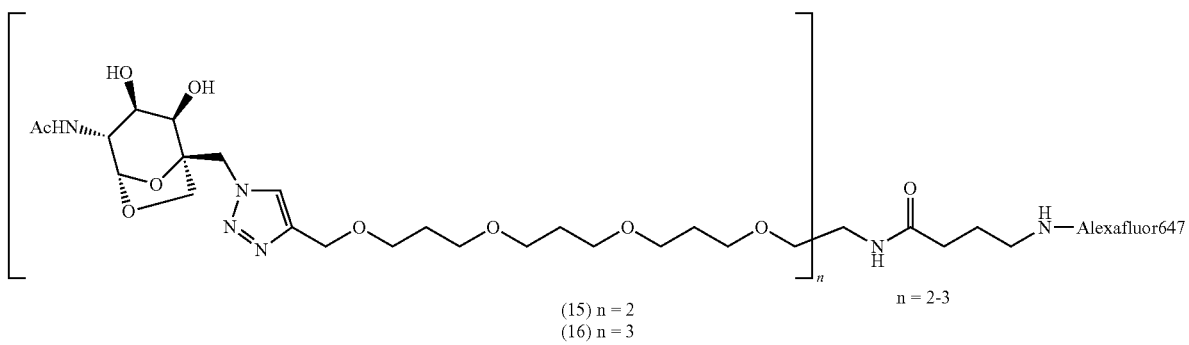

Alexa Fluor® 647 carboxylic acid succinimidyl ester was from Invitrogen (Catalog NumberA-20106). The molecular weight was reported by Invitrogen to be ~1250. The Alexa647 labeled compound molecular weight was estimated based on the found [M+H]$^+$ of 955.07 of Alexa Fluor 647 carboxylic acid succinimidyl ester from LCMS. Extinction coefficient for $\lambda_{max}$ 650 is ~270000±20000, which varies from batch to batch.

General Procedure for HPLC Purification:

Preparative high-performance liquid chromatography (HPLC) was performed using a Waters XBridge BEH C18 OBD Prep Column, 130 Å, 5 microm, 19 mm×100 mm (Waters, part number 186002978), eluting with a linear slope gradient at 17 mL/min flow rate. Solvent gradient: acetonitrile/water/trifluoroacetic acid (2:98:0.1) to (22:78:0.1) in 40 min. Collected fractions were analyzed by analytical LCMS, and those judged as having adequate purity were pooled and evaporated.

(15):

To a solution of compound (13) (4.5 mg, 4 micromol) in dimethyl sulfoxide (200 microL) were added Alexa Fluor® 647 carboxylic acid succinimidyl ester (5.0 mg, 4 micromol) and N,N-diisopropylethylamine (10 microL, 10 equiv.). The reaction mixture was shaken at room temperature for 1 hour and then directly purified by preparative HPLC. Collected fractions were analyzed by analytical LCMS, and those judged as having adequate purity were pooled ($R_t$=37.3-39 minutes). 4.0 mg of (15) was obtained (50% yield). The solution was aliquoted and evaporated in a vacuum centrifuge, and the product was stored at 4 degrees Celsius. MS (ESI) calcd (m/z) for [M+H]$^+$~1955, found 1955.32.

(16):

To a solution of compound (14) (5.2 mg, 3.2 micromol) in dimethyl sulfoxide (200 microL) were added Alexa Fluor® 647 carboxylic acid succinimidyl ester (5.0 mg, 4 micromol) and N,N-diisopropylethylamine (10 microL, 10 equiv.). The reaction mixture was shaken at room temperature for 1 hour and then directly purified by preparative HPLC. Collected fractions were analyzed by analytical LCMS, and those judged as having adequate purity were pooled ($R_t$=24.3-25.3 minutes). 4.0 mg of (16) was obtained (51% yield). The solution was aliquoted and evaporated in a vacuum centrifuge, and the product was stored at 4° C. MS (ESI) calcd (m/z) for [M+H]$^+$~2455, found 2456.90.

General Alkylation/Deprotection Conditions to Access (17)-(21):

To a solution of (I-e-1) in dichloromethane was added the desired iodoalkyl, tetrabutylammonium hydrogen sulfate, and 12.5M sodium hydroxide aqueous solution. The reaction mixture was allowed to stir overnight at room temperature, was diluted with water and dichloromethane and the aqueous phase was extracted two additional times with dichloromethane. The combined organic layers were washed with an aqueous solution of 1M hydrochloric acid, water, dried over magnesium sulfate, filtered and concentrated under reduced pressure. The resulting material can be either carried on crude to the next reaction or purified using flash chromatography over silica gel. The resulting material was dissolved in a mixture of acetic acid/methanol/water (3:1:1 v/v) and the solution was heated to 60-70 degrees Celsius overnight. The reaction mixture was concentrated under reduced pressure, co-evaporated two times with toluene and the crude material was purified by flash chromatography over silica gel or reverse phase chromatography.

N-[(1S,2R,3R,4R,5S)-1-(ethoxymethyl)-2,3-dihydroxy-6,8-dioxabicyclo[3.2.1]oct-4-yl]acetamide (17)

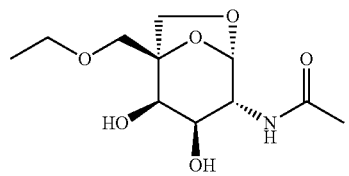

(17)

(17) was synthesized as described in the general procedure above using iodoethane (20 equiv.). The crude product was dissolved in methanol and to which was added activated charcoal. The mixture was stirred for 15 minutes, filtered and concentrated under reduced pressure. The crude material was purified by flash chromatography over silica gel eluting with ethyl acetate/methanol (15:1). The fractions containing the desired product were collected and concentrated under reduced pressure. To the crude material was added ethyl acetate/methanol (15:1) which resulted in a precipitate that was filtered yielding 9.1 mg (32% yield) of the desired product as a solid. $^1$H NMR (400 MHz, METHANOL-$d_4$) delta ppm 5.23 (d, J=1.5 Hz, 1H), 3.97 (dd, J=9.7, 1.4 Hz, 1H), 3.94 (d, J=9.3 Hz, 1H), 3.88 (d, J=4.3 Hz, 1H), 3.79 (d, J=8.1 Hz, 1H), 3.73 (dd, J=9.8, 4.3 Hz, 1H), 3.66 (d, J=8.1 Hz, 1H), 3.60 (d, J=9.6 Hz, 1H), 3.59 (dq, J=9.6, 7.1 Hz, 1H), 3.55 (dq, J=9.6, 7.1 Hz, 1H), 2.00 (s, 3H), 1.19 (t, J=6.9 Hz, 3H). LCMS (APCI) m/z: 262.1 [M+H] (100%).

N-[(1S,2R,3R,4R,5S)-2,3-dihydroxy-1-(propoxymethyl)-6,8-dioxabicyclo[3.2.1]oct-4-yl]acetamide (18)

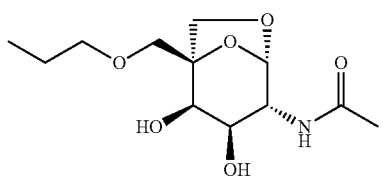

(18)

(18) was synthesized as described in the general procedure above using iodopropane (20 equiv.). The crude product was purified using flash chromatography over silica gel eluting with ethyl acetate/methanol (15:2) yielding 13.9 mg (80% yield) of the desired product as an oil. $^1$H NMR (400 MHz, METHANOL-$d_4$) delta ppm 5.23 (d, J=1.5 Hz, 1H), 3.97 (dd, J=9.7, 1.4 Hz, 1H), 3.95 (d, J=9.6 Hz, 1H), 3.89 (d, J=4.3 Hz, 1H), 3.79 (d, J=7.8 Hz, 1H), 3.73 (dd, J=9.8, 4.3 Hz, 1H), 3.66 (d, J=8.1 Hz, 1H), 3.59 (d, J=9.3 Hz, 1H), 3.49 (dt, 6.5 Hz, 1H), 3.46 (dt, 6.5 Hz, 1H), 2.01 (s, 3H), 1.60 (qt, J=7.4, 6.5 Hz, 2H), 0.94 (t, J=7.4 Hz, 3H). LCMS (APCI) m/z: 276.2 [M+H] (100%).

N-[(1S,2R,3R,4R,5S)-1-(butoxymethyl)-2,3-dihydroxy-6,8-dioxabicyclo[3.2.1]oct-4-yl]acetamide (19)

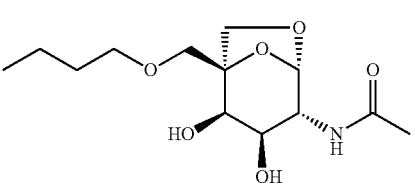

(19)

(19) was synthesized as described in the general procedure above using iodobutane (20 equiv.). The desired crude product was purified using flash chromatography over silica gel eluting with ethyl acetate/methanol (15:1) yielding 18 mg (100% yield) of the desired product as an oil. $^1$H NMR (400 MHz, METHANOL-$d_4$) delta ppm 5.23 (d, J=1.3 Hz, 1H), 3.97 (dd, J=9.6, 1.3 Hz, 1H), 3.94 (d, J=9.6 Hz, 1H), 3.88 (d, J=4.3 Hz, 1H), 3.79 (d, J=7.8 Hz, 1H), 3.73 (dd, J=9.8, 4.3 Hz, 1H), 3.66 (d, J=7.8 Hz, 1H), 3.59 (d, J=9.3 Hz, 1H), 3.54 (dt, 6.5 Hz, 1H), 3.50 (dt, 6.5 Hz, 1H), 2.00 (s, 3H), 1.52-1.61 (m, 2H), 1.34-1.45 (m, 2H), 0.95 (t, J=7.3 Hz, 3H). LCMS (APCI) m/z: 290.2 [M+H] (100%).

N-{(1S,2R,3R,4R,5S)-2,3-dihydroxy-1-[(pentyloxy)methyl]-6,8-dioxabicyclo[3.2.1]oct-4-yl}acetamide (20)

(20)

(20) was synthesized as described in the general procedure above using iodopentane (20 equiv.). The desired crude product was purified using flash chromatography over silica gel eluting with ethyl acetate/methanol (15:1) yielding 17 mg (68% yield) of the desired product as an oil. $^1$H NMR (400 MHz, METHANOL-$d_4$) delta ppm 5.23 (d, J=1.5 Hz, 1H), 3.97 (dd, J=9.8, 1.3 Hz, 1H), 3.94 (d, J=9.6 Hz, 1H), 3.88 (d, J=4.3 Hz, 1H), 3.79 (d, J=8.1 Hz, 1H), 3.73 (dd, J=9.8, 4.3 Hz, 1 H), 3.66 (d, J=8.1 Hz, 1H), 3.59 (d, J=9.6 Hz, 1H), 3.53 (dt, 6.5 Hz, 1H), 3.49 (dt, 6.5 Hz, 1H), 2.01 (s, 3H), 1.53-1.63 (m, 2H), 1.29-1.41 (m, 4H), 0.89-0.97 (m, 3H). LCMS (APCI) m/z: 304.1 [M+H] (100%).

N-{(1S,2R,3R,4R,5S)-1-[(hexyloxy)methyl]-2,3-dihydroxy-6,8-dioxabicyclo[3.2.1]oct-4-yl}acetamide (21)

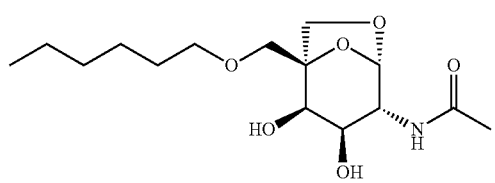

(21)

(21) was synthesized as described in the general procedure above using iodohexane (20 equiv.). The desired crude product was purified using flash chromatography over silica gel eluting with ethyl acetate/methanol (15:1) yielding 56 mg of product as an oil. This material was repurified using reverse phase chromatography yielding 7.1 mg (15% yield) of the desired product as a solid. $^1$H NMR (400 MHz, METHANOL-$d_4$) delta ppm 5.23 (d, J=1.5 Hz, 1H), 3.96 (dd, J=10.1, 1.3 Hz, 1H), 3.94 (d, J=9.6 Hz, 1H), 3.88 (d, J=4.3 Hz, 1H), 3.79 (d, J=7.8 Hz, 1H), 3.73 (dd, J=9.8, 4.3 Hz, 1H), 3.66 (d, J=8.1 Hz, 1H), 3.59 (d, J=9.6 Hz, 1H), 3.53 (dt, 6.5 Hz, 1H), 3.49 (dt, J=9.3, 6.5 Hz, 1H), 2.00 (s, 3H), 1.53-1.62 (m, 2H), 1.27-1.50 (m, 6H), 0.89-0.97 (m, 3H). LCMS (APCI) m/z: 318.1 [M+H] (100%).

N-[(1S,2R,3R,4R,5S)-2,3-dihydroxy-1-(2,5,8,11,14-pentaoxapentadec-1-yl)-6,8-dioxabicyclo[3.2.1]oct-4-yl]acetamide (22)

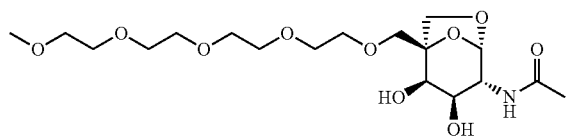

(22)

To a solution of (I-e-1) in dichloromethane (3 mL) was added pyridine (0.3 mL, 4 mmol), the mixture was cooled to −20 degrees Celsius, and trifluoromethanesulfonic anhydride (0.047 mL, 0.28 mmol) in dichloromethane (0.6 mL) was added. The reaction mixture was allowed to warm to −10 degrees Celsius over 1 hour, was diluted with dichloromethane and successively washed with an aqueous solution of 1M hydrochloric acid, saturated sodium bicarbonate aqueous solution, brine, dried over magnesium sulfate, filtered, and concentrated under reduced pressure to afford the desired crude material which was used in the next step without further purification. To a solution of 2,5,8,11-tetraoxatridecan-13-ol (207 mg, 0.994 mmol) in N,N-dimethylformamide cooled to 0 degrees Celsius was added sodium hydride (39.9 mg, 1.0 mmol) and the reaction mixture was stirred for 10 minutes. The above crude ((3aR,4R,7S,8R,8aR)-8-acetamido-2,2-dimethyltetrahydro-4,7-epoxy[1,3]dioxolo[4,5-d]oxepin-4(5H)-yl)methyl trifluoromethanesulfonate in N,N-dimethylformamide (0.5 mL) was added dropwise and the reaction mixture was allowed to stir for 25 minutes at 0 degrees Celsius. The reaction was quenched with methanol and the reaction mixture was allowed to stir for 5 minutes. The resulting mixture was then concentrated under reduced pressure and the residue obtained was dissolved in dichloromethane and washed with water. The aqueous layer was extracted two additional times with dichloromethane. The combined organic layers were washed with water and concentrated under reduced pressure. The crude material was purified by flash chromatography over silica gel eluting with ethyl acetate/methanol (15:2) yielding 85 mg (100%) of the desired product. A solution of N-((3aR,4S,7S,8R,8aR)-2,2-dimethyl-4-(2,5,8,11,14-pentaoxapentadecyl)hexahydro-4,7-epoxy[1,3]dioxolo[4,5-d]oxepin-8-yl)acetamide (85 mg, 0.18 mmol) in a mixture of acetic acid/methanol/water (3.9:1.3:1.3 v/v) was heated to 70 degrees Celsius overnight. The reaction mixture was concentrated under reduced pressure, the resulting crude material co-evaporated two times with toluene and purified by flash chromatography over silica gel eluting with 10% methanol/dichloromethane yielding 15 mg of the desired product (22) as an oil. $^1$H NMR (400 MHz, METHANOL-$d_4$) delta ppm 5.22 (d, J=1.3 Hz, 1H), 3.96 (d, J=9.6 Hz, 1H), 3.95 (dd, J=9.9, 1.3 Hz, 1H), 3.89 (d, J=4.3 Hz, 1H), 3.78 (d, J=8.1 Hz, 1H), 3.59-3.74 (m, 17H), 3.53-3.56 (m, 2H), 3.36 (s, 3H), 1.99 (s, 3H). LCMS (APCI) m/z: 424.2 [M+H] (13%), 441.3 [M+NH$_4$] (100%).

(1R,2R,3R,4R,5S)-4-acetamido-1-(((4-bromobenzoyl)oxy)methyl)-6,8-dioxabicyclo[3.2.1]octane-2,3-diyl bis(4-bromobenzoate) (23)

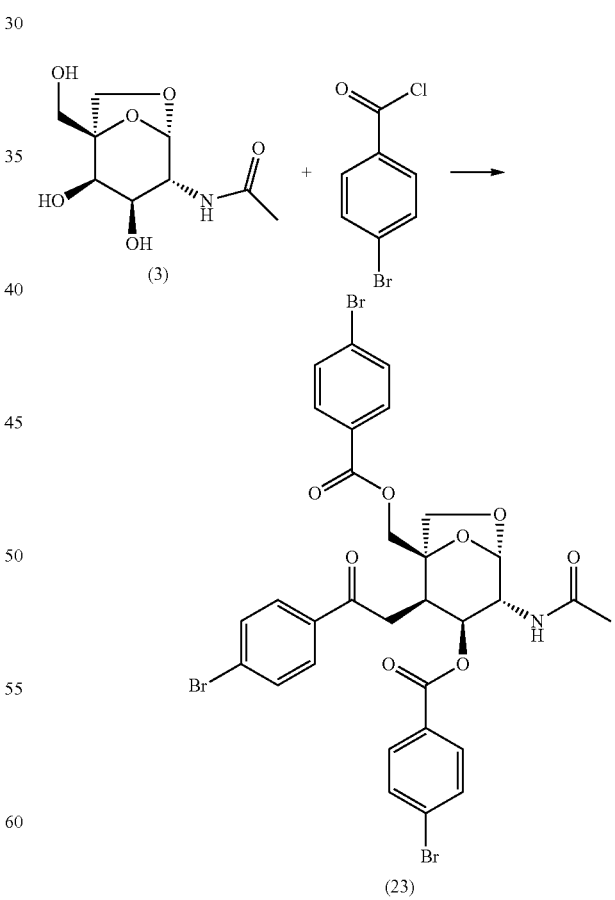

To a solution of (3) (9 mg) in anhydrous N,N-dimethylformamide (500 microL) cooled at room temperature were added N,N-diisopropylethylamine (34 microL) and 4-(dimethylamino)pyridine (4.3 mg) followed by p-bromobenzoyl chloride (44 mg), and the resulting mixture was stirred at room temperature for 4.5 h. Water was added, the resulting mixture extracted three times with ethyl acetate, and the combined organic phase was successively washed with 0.5 M aqueous hydrochloric acid solution and brine. The organic phase was dried over magnesium sulfate, filtered, and concentrated, and the crude material was purified by flash chromatography over silica gel, eluting with a gradient of 0-100% ethyl acetate in heptane, to afford 23 mg of product (23) (80% yield). 1H NMR (400 MHz, CDCl3): delta (ppm) 7.89-7.95 (m, 2H), 7.78-7.84 (m, 2H), 7.54-7.66 (m, 6H), 7.41-7.46 (m, 2H), 5.87 (d, J=8.8 Hz, 1H), 5.80 (d, J=4.3 Hz, 1H), 5.60 (d, J=1.1 Hz, 1H), 5.44 (dd, J=10.2, 4.5 Hz, 1H), 4.54-4.64 (m, 3H), 4.15 (d, J=8.6 Hz, 1H), 3.93 (d, J=8.6 Hz, 1H), 1.95 (s, 3H). $^{13}$C NMR (101 MHz, CDCl3) delta ppm 170.6, 165.6, 165.0, 164.9, 132.1, 131.9, 131.8, 131.4, 131.2, 131.2, 129.3, 129.0, 128.9, 127.7, 127.5, 127.4, 101.8, 81.6, 69.5, 68.8, 68.4, 62.5, 52.7, 23.2. Single crystals were obtained by vapor diffusion technique using methanol and heptane as solvents. Single crystal X-Ray analysis: Data collection was performed on a Bruker APEX diffractometer at room temperature. Data collection consisted of 3 omega scans and low angle and three at high angle; each with 0.5 step. In addition, 2 phi scans were collected to improve the quality of the absorption correction. Structure is a non-merohedrial twin; refined by ignoring the second domain. The structure was solved by direct methods using SHELX software suite (see SHELXTL, Version 5.1, Bruker AXS, 1997) in the space group P2(1). The structure was subsequently refined by the full-matrix least squares method. All non-hydrogen atoms were found and refined using anisotropic displacement parameters. The hydrogen atom located on nitrogen was placed in this position and constrained in reasonable position. The remaining hydrogen atoms were placed in calculated positions and were allowed to ride on their carrier atoms. The final refinement included isotropic displacement parameters for all hydrogen atoms. Analysis of the absolute structure using likelihood methods (R. W. W. Hooft et al. J. Appl. Cryst., 41, 96-103 (2008)) was performed using PLATON (A. L. Spek, J. Appl. Cryst., 36, 7-13 (2003)). The results indicate that the absolute structure has been correctly assigned. The method calculates that the probability that the structure is correct is 100.0. The Hooft parameter is reported as 0.036 with an esd of 0.013. Additionally, the Flack parameter is 0.03 with and esd of 0.04. The final R-index was 5.6%. A final difference Fourier revealed no missing or misplaced electron density. Pertinent crystal, data collection and refinement are summarized in table 1 and FIG. 1.

TABLE 1

Crystal data and structure refinement for (23).

| | |
|---|---|
| Empirical formula | C15 H12 Br1.50 N0.50 O4.50 |
| Formula weight | 391.12 |
| Temperature | 296(2) K |
| Wavelength | 1.54178 Å |
| Crystal system | Monoclinic |
| Space group | P2(1) |
| Unit cell dimensions | a = 12.5748(9) Å    α = 90°. |
| | b = 5.6465(4) Å    β = 97.453(4)°. |
| | c = 21.2806(16) Å    γ = 90°. |
| Volume | 1498.23(19) Å3 |
| Z | 4 |
| Density (calculated) | 1.734 Mg/m3 |
| Absorption coefficient | 5.476 mm-1 |
| F(000) | 776 |

TABLE 1-continued

Crystal data and structure refinement for (23).

| | |
|---|---|
| Crystal size | 0.37 × 0.22 × 0.15 mm3 |
| Theta range for data collection | 2.09 to 68.30°. |
| Index ranges | −13 <= h <= 15, −5 <= k <= 6, −24 <= l <= 24 |
| Reflections collected | 8050 |
| Independent reflections | 4408 [R(int) = 0.0247] |
| Completeness to theta = 68.30° | 93.9% |
| Absorption correction | Empirical |
| Refinement method | Full-matrix least-squares on F2 |
| Data/restraints/parameters | 4408/32/389 |
| Goodness-of-fit on F2 | 1.031 |
| Final R indices [I > 2sigma(I)] | R1 = 0.0563, wR2 = 0.1658 |
| R indices (all data) | R1 = 0.0589, wR2 = 0.1701 |
| Absolute structure parameter | 0.04(3) |
| Largest diff. peak and hole | 0.949 and −0.685 e.Å−3 |

(1S,2R,3R,4R,5S)-4-azido-2,3-bis(benzyloxy)-1-[(benzyloxy)methyl]-6,8-dioxabicyclo[3.2.1]octane (I-m-1)

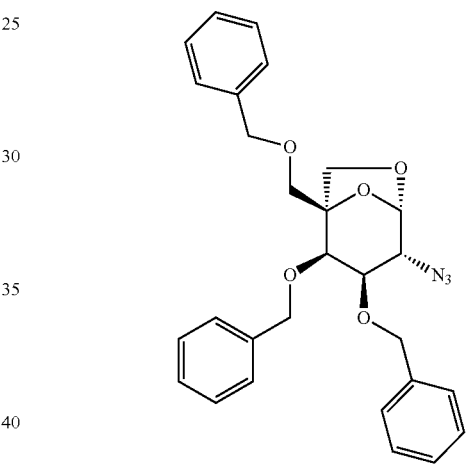

To a solution of (1S,2R,3R,4R,5S)-4-azido-1-(hydroxymethyl)-6,8-dioxabicyclo[3.2.1]octane-2,3-diol (1) (445 mg, 2.05 mmol) in N,N-dimethylformamide (5 mL) was added sodium hydride (60% dispersion in mineral oil, 410 mg, 10.2 mmol) at room temperature. The reaction became very thick and would not stir well. An additional 5 mL N,N-dimethylformamide was added and the reaction was stirred for 30 minutes at room temperature before the addition of benzylbromide (1.23 mL, 10.2 mmol) drop wise. The reaction was allowed to stir overnight at room temperature. The following morning the reaction was quenched with water and extracted with ethyl acetate three times. The combined organic layer was washed with water, brine, dried over sodium sulfate, filtered and concentrated under reduced pressure. The crude material was purified using the CombiFlash Rf (RediSep 40 g silica gel column) and eluting with a gradient of 0-30% ethyl acetate/heptane yielding the title compound (890.0 mg, 89.1%). Method C: 3 minute run LRMS [M+Na=510]. $^1$H NMR (METHANOL-d$_4$) δ: 7.07-7.52 (m, 15H), 5.31 (s, 1H), 4.81 (d, J=5.1 Hz, 1H), 4.78 (d, J=5.5 Hz, 1H), 4.68-4.74 (m, 1H), 4.47-4.51 (m, 1H), 4.46 (d, J=6.6 Hz, 1H), 4.35-4.42 (m, 1H), 4.12 (d, J=3.9 Hz, 1H), 3.87-3.91 (m, 2H), 3.86 (d, J=8.2 Hz, 1H), 3.62 (d, J=8.2 Hz, 1H), 3.58 (d, J=9.4 Hz, 1H), 3.46 (d, J=8.6 Hz, 1H)

(1S,2R,3R,4R,5S)-2,3-bis(benzyloxy)-1-[(benzyloxy)methyl]-6,8-dioxabicyclo[3.2.1]octan-4-amine (1-n-1)

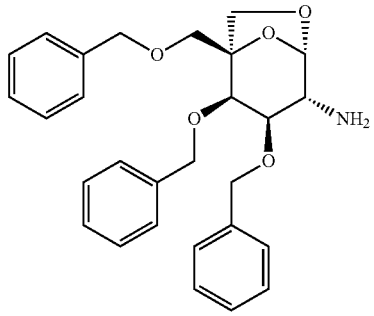 [SMILES: N[C@H]1[C@H]2OC[C@](COCc3ccccc3)(O2)[C@H](OCc2ccccc2)[C@@H]1OCc1ccccc1]

A mixture of (1S,2R,3R,4R,5S)-4-azido-2,3-bis(benzyloxy)-1-[(benzyloxy)methyl]-6,8-dioxabicyclo[3.2.1]octane (I-m-1) (310 mg, 0.64 mmol), triphenylphosphine (334 mg, 1.27 mmol), water (92 mg, 5.1 mmol), and tetrahydrofuran (10 mL) was stirred at 65° C. for 16 hours. The reaction mixture was concentrated under reduced pressure and the residue was loaded on a silica gel column. Chromatography eluting with a gradient from 20% to 80% of ethyl acetate in heptane gave the title product as a colorless gum (210 mg, 72%). $^1$H NMR (CHLOROFORM-d) δ: 7.20-7.37 (m, 15H), 5.29 (d, J=1.2 Hz, 1H), 4.90 (d, 11.5 Hz, 1H), 4.79 (d, J=11.5 Hz, 1H), 4.57 (d, J=11.7 Hz, 1H), 4.56 (d, J=12.1 Hz, 1H), 4.43 (d, J=12.1 Hz, 1H), 4.39 (d, J=11.7 Hz, 1H), 3.97 (d, J=3.9 Hz, 1H), 3.90 (d, J=9.0 Hz, 1H), 3.69 (d, J=8.2 Hz, 1H), 3.59 (d, J=8.2 Hz, 1H), 3.42 (d, J=8.6 Hz, 1H), 3.37 (dd, J=9.4, 3.5 Hz, 1H), 3.07 (dd, J=9.4, 1.2 Hz, 1H); $^{13}$C NMR (CHLOROFORM-d) δ: 131.8, 131.6, 131.5, 128.2, 128.2, 128.1, 128.1, 128.0, 127.7, 127.6, 127.6, 127.4, 103.5, 82.6, 80.3, 74.5, 73.3, 73.1, 72.2, 69.9, 69.3, 55.1; LCMS (ES+): 1.18 min, 484.2 (M+Na)$^+$.

N-{(1S,2R,3R,4R,5S)-2,3-bis(benzyloxy)-1-[(benzyloxy)methyl]-6,8-dioxabicyclo[3.2.1]oct-4-yl}acetamide (I-n-2)

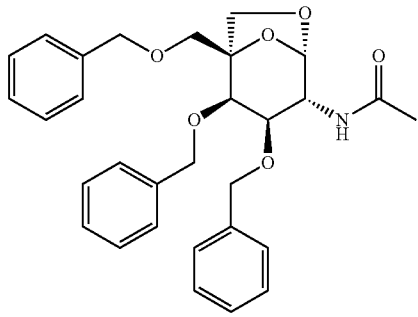

To a stirred mixture of (1S,2R,3R,4R,5S)-2,3-bis(benzyloxy)-1-[(benzyloxy)methyl]-6,8-dioxabicyclo[3.2.1]octan-4-amine (1-n-1) (25 mg, 0.054 mmol), pyridine (43 mg, 0.54 mmol), and 2-methyl-tetrahydrofuran (1 mL) was added acetic anhydride (46 mg, 0.43 mmol) in one portion at room temperature. The reaction mixture was stirred at room temperature for 16 hours and partitioned between ethyl acetate and water. The organic extract was washed with brine, dried over anhydrous magnesium sulfate, and concentrated under reduced pressure. The residue was purified on a silica gel column, eluting with a gradient from 20% to 60% of ethyl acetate in heptane to obtain the title product as a white solid (20 mg, 73%). $^1$H NMR (CHLOROFORM-d) δ: 7.24-7.43 (m, 15H), 5.35 (d, J=1.2 Hz, 1H), 5.06 (d, J=8.6 Hz, 1H), 4.96 (d, J=11.3 Hz, 1H), 4.74 (d, J=12.5 Hz, 1H), 4.58 (d, J=11.3 Hz, 1H), 4.42 (d, J=12.5 Hz, 1H), 4.40 (s, 2H), 4.30-4.36 (m, 1H), 4.04 (d, J=3.9 Hz, 1H), 3.96 (d, J=8.6 Hz, 1H), 3.67-3.70 (m, 1H), 3.58-3.61 (m, 1H), 3.41-3.47 (m, 2H), 1.87 (s, 3H); $^{13}$C NMR (CHLOROFORM-d) δ: 170.0, 138.2, 137.8, 137.4, 128.7, 128.5, 128.4, 128.3, 128.3, 128.2, 128.1, 128.0, 127.8, 101.6, 82.8, 75.7, 75.0, 73.8, 73.2, 71.5, 70.1, 69.5, 53.5, 23.3; LCMS (ES+): 1.87 min, 526.3 (M+Na)$^+$.

N-{(1S,2R,3R,4R,5S)-2,3-bis(benzyloxy)-1-[(benzyloxy)methyl]-6,8-dioxabicyclo[3.2.1]oct-4-yl}-2,2,2-trifluoroacetamide (1-n-3)

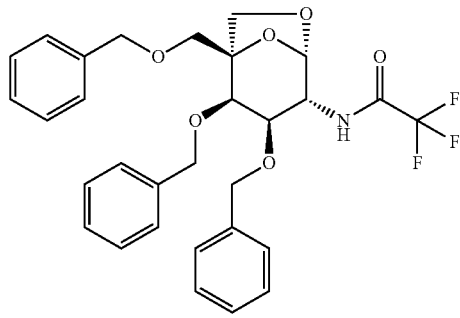 [SMILES: O=C(N[C@H]1[C@H]2OC[C@](COCc3ccccc3)(O2)[C@H](OCc2ccccc2)[C@@H]1OCc1ccccc1)C(F)(F)F]

To a stirred mixture of (1S,2R,3R,4R,5S)-2,3-bis(benzyloxy)-1-((benzyloxy)methyl)-6,8-dioxabicyclo[3.2.1]octan-4-amine (1-n-1) (75 mg, 0.16 mmol), pyridine (129 mg, 1.62 mmol), and 2-methyl-tetrahydrofuran (1 mL) was added trifluoroacetic anhydride (102 mg, 0.49 mmol) in one portion at room temperature. The reaction mixture was stirred at room temperature for 16 hours and partitioned between ethyl acetate and water. The organic extract was washed with brine, dried over anhydrous magnesium sulfate, and concentrated under reduced pressure. The residue was purified on a silica gel column, eluting with a gradient from 10% to 40% of ethyl acetate in heptane to obtain the title product as a white solid (60 mg, 66%). $^1$H NMR (CHLOROFORM-d) δ: 7.25-7.42 (m, 15H), 5.91 (d, J=8.6 Hz, 1H), 5.35 (d, J=1.2 Hz, 1H), 4.95 (d, J=11.3 Hz, 1H), 4.72 (d, J=12.5 Hz, 1H), 4.58 (d, J=11.3 Hz, 1H), 4.41 (s, 2H), 4.40 (d, J=12.5 Hz, 1H), 4.36 (t, J=9.8 Hz, 1H), 4.08 (d, J=3.9 Hz, 1H), 3.96 (d, J=9.0 Hz, 1H), 3.68-3.72 (m, 1H), 3.60-3.63 (m, 1H), 3.50 (dd, J=10.0, 3.7 Hz, 1H), 3.45 (d, J=8.6 Hz, 1H); $^{13}$C NMR (CHLOROFORM-d) δ: 137.9, 137.1, 136.1, 128.9, 128.5, 128.5, 128.4, 128.4, 128.1, 128.1, 128.1, 127.9, 100.6, 83.0, 75.0, 74.9, 73.8, 72.7, 71.4, 70.3, 69.2, 54.1; $^{19}$F NMR (CHLOROFORM-d) δ: −75.7 (s); LCMS (ES−): 2.11 min, 556.2 (M−H)$^−$.

N-{(1S,2R,3R,4R,5S)-2,3-bis(benzyloxy)-1-[(benzyloxy)methyl]-6,8-dioxabicyclo[3.2.1]oct-4-yl}methanesulfonamide (1-n-4)

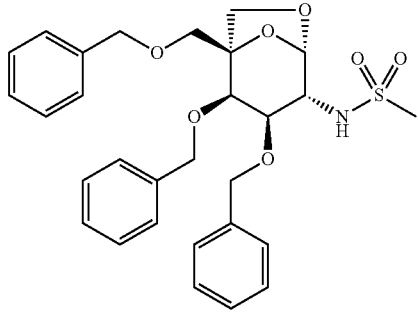 [SMILES: CS(=O)(=O)N[C@H]1[C@H]2OC[C@](COCc3ccccc3)(O2)[C@H](OCc2ccccc2)[C@@H]1OCc1ccccc1]

To a stirred mixture of (1S,2R,3R,4R,5S)-2,3-bis(benzyloxy)-1-((benzyloxy)methyl)-6,8-dioxabicyclo[3.2.1]octan-4-amine (1-n-1) (50 mg, 0.11 mmol), triethylamine (0.100 mL, 0.72 mmol), and 2-methyl-tetrahydrofuran (1 mL) was added methanesulfonyl chloride (0.025 mL, 0.33 mmol) drop wise at 0° C. The reaction mixture was stirred at room temperature for 16 hours and partitioned between ethyl acetate and saturated aqueous sodium bicarbonate. The organic extract was washed with water, brine, dried over anhydrous magnesium sulfate, and concentrated under reduced pressure. The residue was purified on a silica gel column, eluting with a gradient from 10% to 50% of ethyl acetate in heptane to obtain the title product as a white solid (58 mg, 65%). $^1$H NMR (CHLOROFORM-d) δ: 7.22-7.41 (m, 15H), 5.43 (d, J=1.2 Hz, 1H), 4.93 (d, J=11.3 Hz, 1H), 4.79 (d, J=11.7 Hz, 1H), 4.62 (br.s., 1H), 4.56 (d, J=11.7 Hz, 1H), 4.54 (d, J=11.3 Hz, 1H), 4.41 (d, J=12.1 Hz, 1H), 4.37 (d, J=12.1 Hz, 1H), 4.05 (d, J=3.9 Hz, 1H), 3.92 (d, J=8.6 Hz, 1H), 3.74 (d, J=8.6 Hz, 1H), 3.68-3.72 (m, 1H), 3.62 (d, J=8.6 Hz, 1H), 3.54 (dd, J=10.0, 3.7 Hz, 1H), 3.44 (d, J=9.0 Hz, 1H), 2.90 (s, 3H); $^{13}$C NMR (CHLOROFORM-d) δ: 138.0, 137.3, 137.2, 128.7(2), 128.5(2), 128.4(2), 128.3, 128.1(2), 128.1, 127.9(2), 127.8(2), 102.7, 82.9, 77.2, 77.1, 75.0, 73.7, 73.5, 72.8, 70.2, 69.3, 57.7, 41.2; LCMS (ES–): 1.97 min, 538.3 (M–H)⁻.

N-{(1S,2R,3R,4R,5S)-2,3-bis(benzyloxy)-1-[(benzyloxy)methyl]-6,8-dioxabicyclo[3.2.1]oct-4-yl}propanamide (1-n-5)

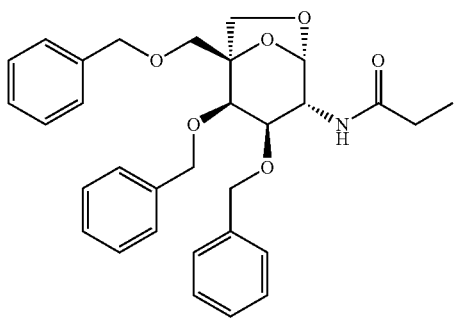 [SMILES: CCC(=O)N[C@H]1[C@H]2OC[C@](COCc3ccccc3)(O2)[C@H](OCc2ccccc2)[C@@H]1OCc1ccccc1]

To a stirred mixture of propionic acid (23 mg, 0.31 mmol) in tetrahydrofuran (1 mL) was added 1,1'-carbonyldiimidazole (33 mg, 0.20 mmol) in one portion at room temperature and the clear solution was stirred at room temperature for 3 hours. Triethylamine (0.028 mL, 0.20 mmol) and (1S,2R,3R,4R,5S)-2,3-bis(benzyloxy)-1-((benzyloxy)methyl)-6,8-dioxabicyclo[3.2.1]octan-4-amine (1-n-1) (47 mg, 0.10 mmol) were added in one portion at room temperature. The reaction mixture was stirred at room temperature for 16 hours and partitioned between ethyl acetate (3 mL), brine (2 mL), and water (2 mL). The organic extract was washed with brine, dried over anhydrous magnesium sulfate, and concentrated under reduced pressure. The residue was purified on a silica gel column, eluting with a gradient from 10% to 50% of ethyl acetate in heptane to obtain the title product as a white solid (43 mg, 82%). $^1$H NMR (CHLOROFORM-d) δ: 7.03-7.58 (m, 15H), 5.35 (s, 1H), 5.09 (d, J=8.2 Hz, 1H), 4.95 (d, J=11.3 Hz, 1H), 4.72 (d, J=12.1 Hz, 1H), 4.57 (d, J=11.3 Hz, 1H), 4.43 (d, J=12.1 Hz, 1H), 4.39 (s, 2H), 4.31-4.38 (m, 1H), 4.04 (d, J=3.9 Hz, 1H), 3.95 (d, J=9.0 Hz, 1H), 3.68 (d, J=8.2 Hz, 1H), 3.59 (d, J=8.2 Hz, 1H), 3.44-3.49 (m, 1H), 3.44 (d, J=8.6 Hz, 1H), 2.08 (q, J=7.4 Hz, 2H), 1.11 (t, J=7.6 Hz, 3H); $^{13}$C NMR (CHLOROFORM-d) δ: 173.5, 138.1, 137.8, 137.4, 128.6, 128.5, 128.3, 128.3, 128.2, 128.1, 128.0, 128.0, 127.7, 101.6, 82.7, 75.7, 74.9, 73.7, 73.2, 71.5, 70.1, 69.4, 53.3, 29.6, 9.5; LCMS (ES–): 1.94 min, 516.4 (M–H)⁻; LCMS (AP+): 1.94 min, 518.5 (M+H)⁺.

N-{(1S,2R,3R,4R,5S)-2,3-bis(benzyloxy)-1-[(benzyloxy)methyl]-6,8-dioxabicyclo[3.2.1]oct-4-yl}-3,3,3-trifluoropropanamide (1-n-6)

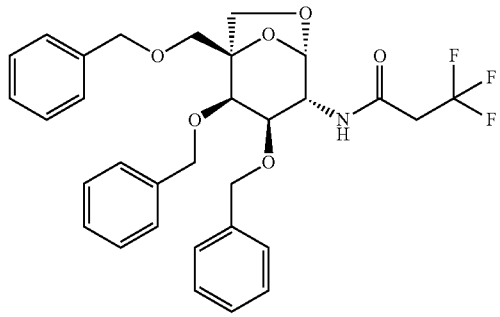 [SMILES: O=C(CC(F)(F)F)N[C@H]1[C@H]2OC[C@](COCc3ccccc3)(O2)[C@H](OCc2ccccc2)[C@@H]1OCc1ccccc1]

To a stirred mixture of 3,3,3-trifluoropropionic acid (39 mg, 0.31 mmol) in tetrahydrofuran (1 mL) was added 1,1'-carbonyldiimidazole (33 mg, 0.20 mmol) in one portion at room temperature and the clear solution was stirred at room temperature for 3 hours. Triethylamine (0.028 mL, 0.20 mmol) and (1S,2R,3R,4R,5S)-2,3-bis(benzyloxy)-1-((benzyloxy)methyl)-6,8-dioxabicyclo[3.2.1]octan-4-amine (1-n-1) (47 mg, 0.10 mmol) were added in one portion at room temperature. The reaction mixture was stirred at room temperature for 16 hours and partitioned between ethyl acetate (3 mL), brine (2 mL), and water (2 mL). The organic extract was washed with brine, dried over anhydrous magnesium sulfate, and concentrated under reduced pressure. The residue was subjected to chromatography on a silica gel column, eluting with a gradient from 10% to 50% of ethyl acetate in heptane to obtain the title product as a white solid (40 mg, 69%). $^1$H NMR (CHLOROFORM-d) δ: 7.24-7.42 (m, 15H), 5.37 (d, J=8.6 Hz, 1H), 5.35 (d, J=1.6 Hz, 1H), 4.95 (d, J=11.3 Hz, 1H), 4.71 (d, J=12.1 Hz, 1H), 4.56 (d, J=11.3 Hz, 1H), 4.45 (d, J=12.1 Hz, 1H), 4.40 (s, 2H), 4.35-4.40 (m, 1H), 4.05 (d, J=3.5 Hz, 1H), 3.95 (d, J=8.6 Hz, 1H), 3.71 (d, J=8.2 Hz, 1H), 3.61 (d, J=8.2 Hz, 1H), 3.50 (dd, J=10.0, 3.7 Hz, 1H), 3.45 (d, J=8.6 Hz, 1H), 2.92 (q, J=10.5 Hz, 2H); $^{13}$C NMR (CHLOROFORM-d) δ: 162.3, 138.0, 137.6, 137.3, 128.7, 128.5, 128.4, 128.3, 128.3, 128.2, 128.0, 128.0, 127.8, 101.1, 82.8, 75.8, 75.0, 73.7, 73.2, 71.9, 70.2, 69.3, 54.0, 41.7; $^{19}$F NMR (CHLOROFORM-d) δ: −62.8 (s); LCMS (ES−): 2.05 min, 570.3 (M−H)$^-$.

N-{(1S,2R,3R,4R,5S)-2,3-bis(benzyloxy)-1-[(benzyloxy)methyl]-6,8-dioxabicyclo[3.2.1]oct-4-yl}-2,2-difluoroacetamide (1-n-7)

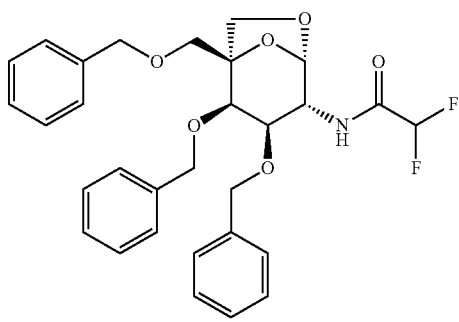 [SMILES: O=C(N[C@H]1[C@H]2OC[C@](COCc3ccccc3)(O2)[C@H](OCc2ccccc2)[C@@H]1OCc1ccccc1)C(F)F]

To a stirred mixture of difluoroacetic acid (29 mg, 0.31 mmol) in N,N-dimethylformamide (1 mL) was added 1,1'-carbonyldiimidazole (33 mg, 0.20 mmol) in one portion at room temperature and the clear solution was stirred at room temperature for 3 hours. Triethylamine (0.028 mL, 0.20 mmol) and (1S,2R,3R,4R,5S)-2,3-bis(benzyloxy)-1-((benzyloxy)methyl)-6,8-dioxabicyclo[3.2.1]octan-4-amine (1-n-1) (47 mg, 0.10 mmol) were added in one portion at room temperature. The reaction mixture was stirred at room temperature for 16 h and partitioned between ethyl acetate (3 mL), brine (2 mL), and water (2 mL). The organic extract was washed with brine, dried over anhydrous magnesium sulfate, and concentrated. The residue was subjected to chromatography on a silica gel column, eluting with a gradient from 10% to 50% of ethyl acetate in heptane to obtain the title product as a white solid (32 mg, 58%). $^1$H NMR (CHLOROFORM-d) δ: 7.14-7.47 (m, 15H), 6.02 (d, J=8.6 Hz, 1H), 5.83 (t, J=54.2 Hz, 1H), 5.35 (s, 1H), 4.96 (d, J=11.3 Hz, 1H), 4.73 (d, J=12.5 Hz, 1H), 4.58 (d, J=11.3 Hz, 1H), 4.45 (d, J=12.1 Hz, 1H), 4.41 (s, 2H), 4.34-4.40 (m, 1H), 4.08 (d, J=3.9 Hz, 1H), 3.96 (d, J=9.0 Hz, 1H), 3.67-3.75 (m, 1H), 3.59-3.65 (m, 1H), 3.53 (dd, J=9.8, 3.9 Hz, 1H), 3.46 (d, J=8.6 Hz, 1H); $^{13}$C NMR (CHLOROFORM-d) δ: 162.6, 138.0, 137.3, 128.8, 128.5, 128.4, 128.3, 128.1, 128.0, 127.8, 108.3 (t, J=253.1 Hz), 100.9, 82.9, 75.3, 75.0, 73.8, 72.9, 71.6, 70.2, 69.3, 53.5; $^{19}$F NMR (CHLOROFORM-d) δ: −126.1 (d, J=53.1 Hz); LCMS (ES−): 2.05 min, 538.2 (M−H)$^-$.

tert-butyl {(1S,2R,3R,4R,5S)-2,3-bis(benzyloxy)-1-[(benzyloxy)methyl]-6,8-dioxabicyclo[3.2.1]oct-4-yl}carbamate (I-n-8)

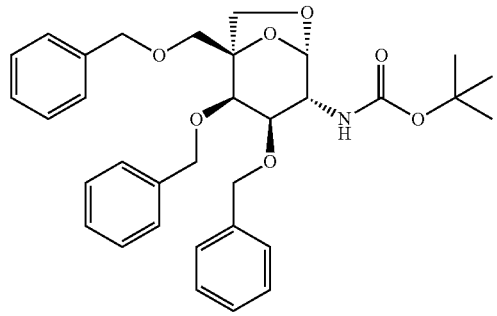 [SMILES: CC(C)(C)OC(=O)N[C@H]1[C@H]2OC[C@](COCc3ccccc3)(O2)[C@H](OCc2ccccc2)[C@@H]1OCc1ccccc1]

To a stirred mixture of (1S,2R,3R,4R,5S)-2,3-bis(benzyloxy)-1-((benzyloxy)methyl)-6,8-dioxabicyclo[3.2.1]octan-4-amine (1-n-1) (120 mg, 0.26 mmol) and N,N-dimethylaminopyridine (DMAP) (6.4 mg, 0.052 mmol), and tetrahydrofuran (2 mL) was added di-tert-butyl dicarbonate (113 mg, 0.52 mmol) in one portion at room temperature. The reaction mixture was stirred at room temperature for 16 hours and concentrated under reduced pressure. The residue was purified on a silica gel column, eluting with a gradient from 10% to 40% of ethyl acetate in heptane to obtain the title product as a white solid (104 mg, 71%). $^1$HNMR (CHLOROFORM-d) δ: 7.17-7.45 (m, 15H), 5.35 (s, 1H), 4.97 (d, J=11.3 Hz, 1H), 4.74 (d, J=12.1 Hz, 1H), 4.57 (d, J=11.3 Hz, 2H), 4.47 (d, J=7.0 Hz, 1H), 4.39 (s, 2H), 4.09 (br. s., 1H), 4.01 (d, J=3.9 Hz, 1H), 3.93 (d, J=9.0 Hz, 1H), 3.63-3.71 (m, 1H), 3.54-3.62 (m, 1H), 3.38-3.48 (m, 2H), 1.47 (s, 9H); $^{13}$C NMR (CHLOROFORM-d) δ: 155.2, 138.2, 137.8, 137.4, 128.5, 128.4, 128.3, 128.3, 128.0, 127.9, 127.8, 127.7, 102.2, 82.8, 79.4, 74.8, 73.7, 73.4, 72.0, 70.0, 69.4, 54.6, 31.9, 28.4; LCMS (AP+): 2.25 min, 462.2 (M-Boc+H)$^+$.

N-[(1S,2R,3R,4R,5S)-2,3-dihydroxy-1-(hydroxymethyl)-6,8-dioxabicyclo[3.2.1]oct-4-yl]propanamide (25)

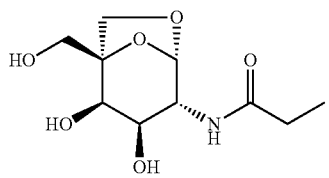 [SMILES: CCC(=O)N[C@H]1[C@H]2OC[C@](CO)(O2)[C@H](O)[C@@H]1O]

A mixture of N-((1S,2R,3R,4R,5S)-2,3-bis(benzyloxy)-1-((benzyloxy)methyl)-6,8-dioxabicyclo[3.2.1]octan-4-yl) propionamide (1-n-5) (42 mg, 0.081 mmol), 1-methyl-1,4-cyclohexadiene (0.093 mL, 0.81 mmol), 10% Pd on activated carbon (20 mg), and 2-propanol (2.5 mL) was stirred at 80° C. for 3 hours. Water (0.2 ml) was added and the whole mixture was loaded on silica gel and dried on a rotary evaporator. The material was purified on a silica gel column eluting with a gradient from 4% to 15% of methanol in dichloromethane gave the title compound as a colorless gum (12 mg, 60%). $^1$H NMR (METHANOL-d$_4$) δ: 5.21 (d, J=1.6 Hz, 1H), 3.95 (dd, J=10.1, 1.2 Hz, 1H), 3.92 (d, J=11.3

Hz, 1H), 3.87 (d, J=3.9 Hz, 1H), 3.81 (d, J=11.3 Hz, 1H), 3.75 (d, J=8.2 Hz, 1H), 3.71-3.76 (m, 2H), 3.68 (d, J=8.2 Hz, 1H), 3.35 (s, 1H), 2.26 (q, J=7.4 Hz, 2H), 1.13 (t, J=7.4 Hz, 3H); $^{13}$C NMR (METHANOL-d$_4$) δ: 177.7, 102.6, 84.9, 70.4, 69.1, 69.0, 61.9, 56.0, 30.0, 10.3; LCMS (AP+): 0.25 min, 248.2 (M+H)$^+$.

N-[(1S,2R,3R,4R,5S)-2,3-dihydroxy-1-(hydroxymethyl)-6,8-dioxabicyclo[3.2.1]oct-4-yl]-2,2,2-trifluoroacetamide (24)

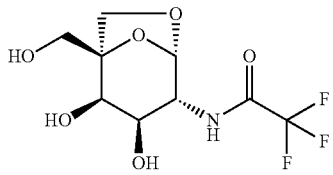 [SMILES: O=C(N[C@H]1[C@H]2OC[C@](CO)(O2)[C@H](O)[C@@H]1O)C(F)(F)F]

A mixture of N-((1S,2R,3R,4R,5S)-2,3-bis(benzyloxy)-1-((benzyloxy)methyl)-6,8-dioxabicyclo[3.2.1]octan-4-yl)-2,2,2-trifluoroacetamide (1-n-3) (20 mg, 0.036 mmol), 1-methyl-1,4-cyclohexadiene (0.093 mL, 0.81 mmol), 10% Pd on activated carbon (20 mg), and 2-propanol (2.5 mL) was stirred at 80° C. for 3 hours. Water (0.2 ml) was added and the whole mixture was loaded on silica gel and dried on a rotary evaporator. The material was purified on a silica gel column, eluting with a gradient from 4% to 15% of methanol in dichloromethane gave the title compound as a colorless gum (7.2 mg, 69%). $^1$H NMR (METHANOL-d$_4$) δ: 5.25 (d, J=1.2 Hz, 1H), 4.02 (d, J=8.6 Hz, 1H), 3.90 (d, J=7.0 Hz, 1H), 3.88-3.95 (m, 2H), 3.82 (d, J=11.7 Hz, 1H), 3.78 (d, J=7.8 Hz, 1H), 3.71 (d, J=7.8 Hz, 1H), 3.35 (s, 1H); $^{13}$C NMR (METHANOL-d$_4$) δ: 159.8, 102.3, 85.5, 70.8, 69.7, 68.4, 62.2, 57.4; $^{19}$F NMR (CHLOROFORM-d) δ: −77.0 (s); LCMS (AP+): 0.42 min, 288.2 (M+H)$^+$.

N-[(1S,2R,3R,4R,5S)-2,3-dihydroxy-1-(hydroxymethyl)-6,8-dioxabicyclo[3.2.1]oct-4-yl]methanesulfonamide (26)

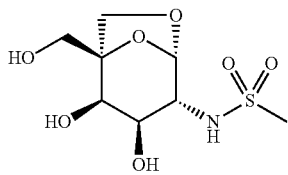

A mixture of N-((1S,2R,3R,4R,5S)-2,3-bis(benzyloxy)-1-((benzyloxy)methyl)-6,8-dioxabicyclo[3.2.1]octan-4-yl)methanesulfonamide (1-n-4) (19 mg, 0.035 mmol), 1-methyl-1,4-cyclohexadiene (0.093 mL, 0.81 mmol), 10% Pd on activated carbon (20 mg), and 2-propanol (2.5 mL) was stirred at 80° C. for 3 hours. Water (0.2 ml) was added and the whole mixture was loaded on silica gel and dried on a rotary evaporator. The material was purified on a silica gel column, eluting with a gradient from 4% to 15% of methanol in dichloromethane gave the title compound as a colorless gum (6.4 mg, 68%). $^1$H NMR (METHANOL-d$_4$) δ: 5.26 (d, J=1.6 Hz, 1H), 3.91 (d, J=11.3 Hz, 1H), 3.87 (d, J=4.3 Hz, 1H), 3.80 (d, J=11.3 Hz, 1H), 3.73 (d, J=7.8 Hz, 1H), 3.68 (d, J=7.8 Hz, 1H), 3.66-3.71 (m, 1H), 3.37 (dd, J=9.8, 1.6 Hz, 1H), 3.35 (s, 1H), 3.04 (s, 3H); $^{13}$C NMR (METHANOL-d$_4$) δ: 104.6, 85.1, 70.9, 69.8, 69.3, 62.0, 60.2, 41.7; LCMS (ES−): 0.15 min, 268.0 (M−H)$^−$.

N-[(1S,2R,3R,4R,5S)-2,3-dihydroxy-1-(hydroxymethyl)-6,8-dioxabicyclo[3.2.1]oct-4-yl]-2,2-difluoroacetamide (27)

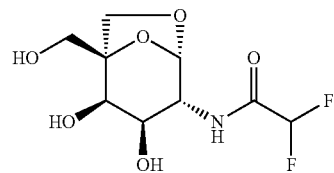 [SMILES: O=C(N[C@H]1[C@H]2OC[C@](CO)(O2)[C@H](O)[C@@H]1O)C(F)F]

To a solution of N-{(1S,2R,3R,4R,5S)-2,3-bis(benzyloxy)-1-[(benzyloxy)methyl]-6,8-dioxabicyclo[3.2.1]oct-4-yl}-2,2-difluoroacetamide (1-n-7) (32.0 mg, 0.059 mmol) in 2-propanol (1.0 mL) and tetrahydrofuran (0.5 mL) in a 5 mL microwave vial was added 1-methyl-1,4-cyclohexadiene (0.2 mL, 2 mmol) followed by the addition of 10% Palladium on carbon (50% wet wt/wt, 20.0 mg, 0 mmol). The vial was sealed and heated to 80° C. for 4 hours. After 4 hours, the TLC (10% methanol/dichloromethane) showed that the reaction was not complete but there was formation of the desired product. An additional 1-methyl-1,4-cyclohexadiene (0.2 mL mg, 2 mmol) was added and the reaction was resealed and heated to 80° C. overnight (18 hours). After 22 total hours, the reaction was diluted with methanol and filtered through a Life Sciences Acrodisc 25 mm syringe filter. The filtrate was concentrated under reduced pressure. The crude material was purified using the CombiFlash Rf (RediSep 4 g silica gel column) and eluting with a gradient of 0-20% methanol/dichloromethane yielding the title compound as a solid (5.0 mg, SOLID, 31%). Method C: 3 minute run LRMS [M+Na=292]. $^1$H NMR (METHANOL-d$_4$) δ: 6.06 (t, J=54.2 Hz, 1H), 5.25 (s, 1H), 4.02 (d, J=9.4 Hz, 1H), 3.92 (d, J=11.7 Hz, 1H), 3.84-3.90 (m, 2H), 3.81 (d, J=11.7 Hz, 1H), 3.78 (d, J=8.2 Hz, 1H), 3.70 (d, J=8.2 Hz, 1H)

N-[(1S,2R,3R,4R,5S)-2,3-dihydroxy-1-(hydroxymethyl)-6,8-dioxabicyclo[3.2.1]oct-4-yl]-3,3,3-trifluoropropanamide (28)

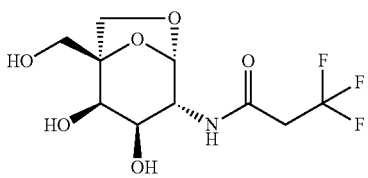 [SMILES: O=C(CC(F)(F)F)N[C@H]1[C@H]2OC[C@](CO)(O2)[C@H](O)[C@@H]1O]

To a solution of N-{(1S,2R,3R,4R,5S)-2,3-bis(benzyloxy)-1-[(benzyloxy)methyl]-6,8-dioxabicyclo[3.2.1]oct-4-yl}-3,3,3-trifluoropropanamide (1-n-6) (40.0 mg, 0.070 mmol) in 2-propanol (1.0 mL) and tetrahydrofuran (0.5 mL) in a 5 mL microwave vial was added 1-methyl-1,4-cyclohexadiene (0.2 mL, 1.75 mmol) followed by the addition of 10% palladium on carbon (50% wet wt/wt., 20.0 mg, 0 mmol). The vial was sealed and heated to 80° C. for 4 hours. After 4 hours, the reaction was diluted with methanol and filtered through a Life Sciences Acrodisc 25 mm syringe filter. The filtrate was concentrated under reduced pressure. The crude material was purified using the CombiFlash Rf (RediSep 4 g silica gel column) and eluting with a gradient of 0-20% methanol/dichloromethane yielding the title compound as a solid (15.3 mg, 73%). LRMS [M+1=302]. $^1$H NMR (METHANOL-d$_4$) δ: 5.23 (s, 1H), 3.99 (d, J=9.8 Hz, 1H), 3.92 (d, J=11.3 Hz, 1H), 3.87 (d, J=4.3 Hz, 1H), 3.81 (d, J=11.3 Hz, 1H), 3.76 (d, J=8.2 Hz, 1H), 3.71-3.74 (m, 1H), 3.69 (d, J=8.2 Hz, 1H), 3.22 (qd, J=10.7, 2.5 Hz, 2H)

N-{(1S,2R,3R,4R,5S)-2,3-bis(benzyloxy)-1-[(benzyloxy)methyl]-6,8-dioxabicyclo[3.2.1]oct-4-yl}-N-methylacetamide (I-o-1)

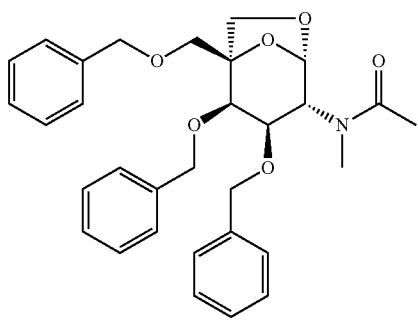 [SMILES: CC(=O)N(C)[C@H]1[C@H]2OC[C@](COCc3ccccc3)(O2)[C@H](OCc2ccccc2)[C@@H]1OCc1ccccc1]

To a stirred mixture of N-((1S,2R,3R,4R,5S)-2,3-bis(benzyloxy)-1-((benzyloxy)methyl)-6,8-dioxabicyclo[3.2.1]octan-4-yl)acetamide (I-n-2) (19 mg, 0.038 mmol) and N,N-dimethylformamide (1.5 mL) was added sodium hydride (60% suspension in mineral oil) in one portion at room temperature and the mixture was stirred for 30 minutes. Iodomethane (16 mg, 0.11 mmol) was added in one portion at room temperature. The reaction mixture was stirred at room temperature for 16 hours and partitioned between ethyl acetate (3 mL), brine (2 mL), and water (2 mL). The organic extract was washed with brine, dried over anhydrous magnesium sulfate, and concentrated under reduced pressure. The residue was purified on a silica gel column, eluting with a gradient from 10% to 50% of ethyl acetate in heptane to obtain the title product as a colorless gum (19 mg, 97%). Mixture of rotamers (3:1). Rotamer 1: $^1$H NMR (CHLOROFORM-d) δ: 7.21-7.43 (m, 15H), 5.37 (s, 1H), 4.93 (d, J=10.9 Hz, 1H), 4.65 (d, J=11.7 Hz, 1H), 4.54 (d, J=11.3 Hz, 1H), 4.50 (d, J=11.7 Hz, 1H), 4.37-4.45 (m, 2H), 4.15 (d, J=9.8 Hz, 1H), 4.09 (d, J=3.5 Hz, 1H), 3.93 (d, J=8.6 Hz, 1H), 3.85 (dd, J=10.1, 3.5 Hz, 1H), 3.78 (d, J=8.2 Hz, 1H), 3.64 (d, J=8.2 Hz, 1H), 3.45 (d, J=8.6 Hz, 1H), 2.80 (s, 3H), 2.19 (s, 3H); rotomer2: $^1$H NMR (CHLOROFORM-d) δ: 7.21-7.43 (m, 15H), 5.27 (s, 1H), 5.12 (d, J=10.9 Hz, 1H), 4.94-4.98 (m, 1H), 4.74 (d, J=12.1 Hz, 1H), 4.56 (d, J=11.7 Hz, 1H), 4.46 (d, J=11.3 Hz, 1H), 4.37-4.46 (m, 2H), 4.14-4.17 (m, 1H), 3.97 (d, J=8.6 Hz, 1H), 3.82-3.89 (m, 2H), 3.79 (d, J=8.2 Hz, 1H), 3.60-3.63 (m, 1H), 2.71 (s, 3H), 2.08 (s, 3H); $^{13}$C NMR (CHLOROFORM-d) δ: 172.2, 138.0, 137.3, 137.2, 128.6, 128.5, 128.5, 128.4, 128.1, 128.0, 127.9, 127.9, 127.9, 127.8, 103.2, 83.2, 75.2, 74.1, 73.8, 73.7, 73.0, 72.4, 70.1, 69.2, 61.2, 28.0, 22.2; LCMS (AP+): 1.99 min, 518.0 (M+H)$^+$.

N-{(1S,2R,3R,4R,5S)-2,3-bis(benzyloxy)-1-[(benzyloxy)methyl]-6,8-dioxabicyclo[3.2.1]oct-4-yl}-N-methylmethanesulfonamide (I-o-2)

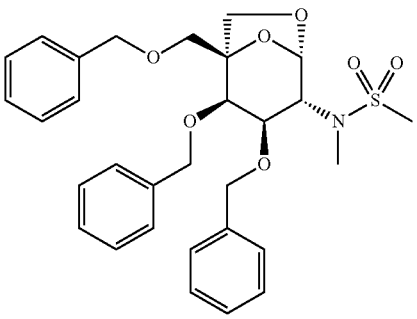

To a stirred mixture of N-((1S,2R,3R,4R,5S)-2,3-bis(benzyloxy)-1-((benzyloxy)methyl)-6,8-dioxabicyclo[3.2.1]octan-4-yl)methanesulfonamide (1-n-4) (19 mg, 0.035 mmol) and N,N-dimethylformamide (1.5 mL) was added sodium hydride (60% suspension in mineral oil) in one portion at room temperature and the mixture was stirred for 30 min. Iodomethane (16 mg, 0.11 mmol) was added in one portion at room temperature. The reaction mixture was stirred at room temperature for 16 hours and partitioned between ethyl acetate (3 mL), brine (2 mL), and water (2 mL). The organic extract was washed with brine, dried over anhydrous magnesium sulfate, and concentrated under reduced pressure. The residue was purified on a silica gel column, eluting with a gradient from 10% to 50% of ethyl acetate in heptane to obtain the title product as a colorless gum (11 mg, 56%). $^1$H NMR (CHLOROFORM-d) δ: 7.25-7.39 (m, 15H), 5.39 (d, J=0.8 Hz, 1H), 4.93 (d, J=11.7 Hz, 1H), 4.80 (d, J=11.3 Hz, 1H), 4.58 (d, J=11.3 Hz, 1H), 4.45 (d, J=11.7 Hz, 1H), 4.43 (d, J=11.7 Hz, 1H), 4.41 (d, J=11.7 Hz, 1H), 4.21 (d, J=3.5 Hz, 1H), 4.18 (d, J=10.5 Hz, 1H), 3.98 (d, J=8.6 Hz, 1H), 3.87 (dd, J=10.5, 3.9 Hz, 1H), 3.82 (d, J=8.6 Hz, 1H), 3.62 (d, J=8.2 Hz, 1H), 3.45 (d, J=9.0 Hz, 1H), 2.83 (s, 3H), 2.68 (s, 3H); $^{13}$C NMR (CHLOROFORM-d) δ: 138.1, 137.3, 136.8, 128.7, 128.5, 128.4, 128.4, 128.1, 128.1, 128.0, 127.8, 104.6, 82.9, 74.9, 73.8, 73.5, 73.3, 71.6, 70.3, 69.4, 59.7, 37.5, 29.5; LCMS (AP+): 2.08 min, 575.8 (M+Na)$^+$.

tert-butyl {(1S,2R,3R,4R,5S)-2,3-bis(benzyloxy)-1-[(benzyloxy)methyl]-6,8-dioxabicyclo[3.2.1]oct-4-yl}methylcarbamate (I-o-3)

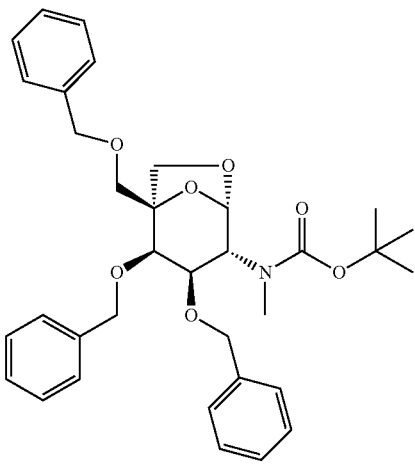 [SMILES: CN(C(=O)OC(C)(C)C)[C@H]1[C@H]2OC[C@](COCc3ccccc3)(O2)[C@H](OCc2ccccc2)[C@@H]1OCc1ccccc1]

To a stirring solution of tert-butyl {(1S,2R,3R,4R,5S)-2,3-bis(benzyloxy)-1-[(benzyloxy)methyl]-6,8-dioxabicyclo[3.2.1]oct-4-yl}carbamate (I-n-8) (100 mg, 0.178 mmol) in N,N-dimethylformamide (1.5 mL) was added sodium hydride (60% dispersion in mineral oil, 8.55 mg, 0.214 mmol) at room temperature. The reaction was stirred for 1 hour before the addition of iodomethane (0.055 mL, 0.89 mmol). The reaction was allowed to stir overnight at room temperature. After 24 hours, the reaction was quenched with water and extracted three times ethyl acetate. The combined organic layers were washed with water, brine, dried over sodium sulfate, filtered and concentrated under reduced pressure. The crude material was purified using the CombiFlash Rf (RediSep 12 g silica gel column) and eluting with a gradient of 0-100% ethyl acetate/dichloromethane yielding the title compound (78 mg, 76%). Method C: 3 minute run LRMS [M+Na=598]. $^1$H NMR (compound is a mixture of two rotamers ~1:1)

Rotamer 1: $^1$H NMR (METHANOL-$d_4$) δ: 7.08-7.48 (m, 15H), 5.26 (s, 1H), 4.83-4.90 (m, 1H), 4.73 (d, J=11.7 Hz, 1H), 4.47-4.58 (m, 3H), 4.36-4.47 (m, 2H), 4.21 (d, J=3.5 Hz, 1H), 3.98 (dd, J=10.7, 3.3 Hz, 1H), 3.92 (d, J=8.2 Hz, 2H), 3.61 (d, J=7.8 Hz, 1H), 3.47 (dd, J=8.6, 3.9 Hz, 1H), 2.75 (s, 3H), 1.42 (s, 9H)

Rotamer 2: $^1$H NMR (METHANOL-$d_4$) δ: 7.08-7.48 (m, 15H), 5.21 (s, 1H), 4.83-4.90 (m, 1H), 4.73 (d, J=11.7 Hz, 1H), 4.47-4.58 (m, 3H), 4.36-4.47 (m, 2H), 4.21 (d, J=3.5 Hz, 1H), 3.98 (dd, J=10.7, 3.3 Hz, 1H), 3.92 (d, J=8.2 Hz, 2H), 3.61 (d, J=7.8 Hz, 1H), 3.47 (dd, J=8.6, 3.9 Hz, 1H), 2.70 (s, 3H), 1.44-1.52 (m, 9H)

N-[(1S,2R,3R,4R,5S)-2,3-dihydroxy-1-(hydroxymethyl)-6,8-dioxabicyclo[3.2.1]oct-4-yl]-N-methylacetamide (29)

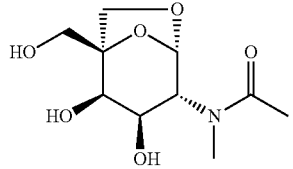

A mixture of N-((1S,2R,3R,4R,5S)-2,3-bis(benzyloxy)-1-((benzyloxy)methyl)-6,8-dioxabicyclo[3.2.1]octan-4-yl)-N-methylacetamide (I-o-1) (19 mg, 0.037 mmol), 1-methyl-1,4-cyclohexadiene (0.093 mL, 0.81 mmol), 10% Pd on activated carbon (20 mg), and 2-propanol (2.5 mL) was stirred at 80° C. for 3 hours. Water (0.2 ml) was added and the whole mixture was loaded on silica gel and dried on a rotary evaporator. The material was purified on a silica gel column, eluting with a gradient from 4% to 15% of methanol in dichloromethane gave the title compound as a colorless gum (4.3 mg, 47%). $^1$H NMR (mixture of rotomers ~1:1)

Rotamer 1: $^1$H NMR (METHANOL-$d_4$) δ: 5.20 (s, 1H), 4.65 (d, J=10.5 Hz, 1H), 4.02-4.09 (m, 1H), 3.89-3.98 (m, 2H), 3.84 (s, 1H), 3.78-3.82 (m, 1H), 3.68 (s, 1H), 3.11 (s, 3H), 2.15 (s, 3H)

Rotamer 2: $^1$H NMR (METHANOL-$d_4$) δ: 5.37 (s, 1H), 4.02-4.09 (m, 1H), 3.89-3.98 (m, 3H), 3.84-3.87 (m, 1H), 3.79-3.83 (m, 1H), 3.71 (d, J=8.2 Hz, 1H), 2.98 (s, 3H), 2.15 (s, 3H)

$^{13}$C NMR (METHANOL-$d_4$) δ: 175.4, 104.6, 85.8, 71.3, 69.7, 66.2, 62.3, 59.1, 28.8, 22.7; LCMS (ES-): 0.41 min, 246.2 (M-H)$^-$.

N-[(1S,2R,3R,4R,5S)-2,3-dihydroxy-1-(hydroxymethyl)-6,8-dioxabicyclo[3.2.1]oct-4-yl]-N-methylmethanesulfonamide (30)

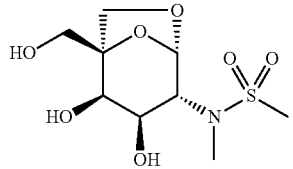 [SMILES: CN([C@H]1[C@H]2OC[C@](CO)(O2)[C@H](O)[C@@H]1O)S(C)(=O)=O]

A mixture of N-((1S,2R,3R,4R,5S)-2,3-bis(benzyloxy)-1-((benzyloxy)methyl)-6,8-dioxabicyclo[3.2.1]octan-4-yl)-N-methylmethanesulfonamide (I-o-2) (11 mg, 0.020 mmol), 1-methyl-1,4-cyclohexadiene (0.093 mL, 0.81 mmol), 10% Pd on activated carbon (20 mg), and 2-propanol (2.5 mL) was stirred at 80° C. for 3 hours. Water (0.2 ml) was added and the whole mixture was loaded on silica gel and dried on a rotary evaporator. Chromatography on a silica gel column, eluting with a gradient from 4% to 15% of methanol in dichloromethane gave the title compound as a colorless gum (2.9 mg, 51%). $^1$H NMR (METHANOL-$d_4$) δ: 5.26 (d, J=1.2 Hz, 1H), 4.00-4.05 (m, 1H), 3.92-3.96 (m, 1H), 3.89-3.91 (m, 1H), 3.84 (d, J=1.2 Hz, 1H), 3.77-3.83 (m, 2H), 3.68 (d, J=7.8 Hz, 1H), 3.35 (s, 3H), 2.93 (s, 3H); $^{13}$C NMR (METHANOL-d$_4$) δ: 106.1, 85.5, 71.5, 69.7, 65.9, 62.6, 62.2, 37.8, 30.4; LCMS (ES-): 0.42 min, 282.0 (M-H)$^-$.

tert-butyl [(1S,2R,3R,4R,5S)-2,3-dihydroxy-1-(hydroxymethyl)-6,8-dioxabicyclo[3.2.1]oct-4-yl]methylcarbamate (31)

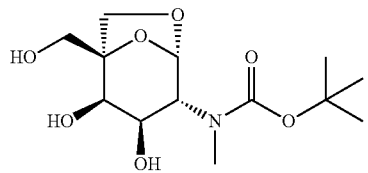 [SMILES: CN(C(=O)OC(C)(C)C)[C@H]1[C@H]2OC[C@](CO)(O2)[C@H](O)[C@@H]1O]

To a solution of tert-butyl {(1S,2R,3R,4R,5S)-2,3-bis(benzyloxy)-1-[(benzyloxy)methyl]-6,8-dioxabicyclo[3.2.1]oct-4-yl}methylcarbamate (I-o-3)(75 mg, 0.13 mmol) in 2-propanol (1.0 mL) and tetrahydrofuran (0.5 mL) in a 5 mL microwave vial was added 1-methyl-1,4-cyclohexadiene (0.18 mL, 1.56 mmol) followed by the addition of 10% palladium on carbon (50% wet wt/wt., 20.0 mg). The vial was sealed and heated to 80° C. for 4 hours. After 4 hours, the TLC (10% methanol/dichloromethane) showed that the reaction was not complete but there was formation of the desired product. An additional 1-methyl-1,4-cyclohexadiene (0.18 mL, 1.6 mmol) was added and the reaction was resealed and heated to 80° C. overnight (18 hours). After 22 total hours, the reaction was diluted with methanol and filtered through a Life Sciences Acrodisc 25 mm syringe filter. The filtrate was concentrated under reduced pressure. The crude material was purified using the CombiFlash Rf (RediSep 4 g silica gel column) and eluting with a gradient of 0-20% methanol/dichloromethane yielding the title compound (29.0 mg, 73%) as a solid. Method C: 3 minute run LRMS [M+Na=328]. Compound is a mixture of two rotamers ~1:1:

Rotamer 1: $^1$H NMR (METHANOL-d$_4$) δ: 5.22 (br. s., 1H), 4.19 (d, J=10.6 Hz, 1H), 4.00 (d, J=10.6 Hz, 1H), 3.90-3.95 (m, 2H), 3.77-3.82 (m, 2H), 3.67 (d, J=7.6 Hz, 1H), 2.94 (s, 3H), 1.47 (s, 9H)

Rotamer 2: $^1$H NMR (METHANOL-d$_4$) δ: 5.21 (br. s., 1H), 4.05-4.10 (m, 1H), 4.00 (d, J=10.6 Hz, 1H), 3.90-3.95 (m, 2H), 3.77-3.82 (m, 2H), 3.67 (d, J=7.6 Hz, 1H), 2.94 (s, 3H), 1.47 (s, 9H) (1S,2R,3R,4R,5S)-1-(hydroxymethyl)-4-(methylamino)-6,8-dioxabicyclo[3.2.1]octane-2,3-diol hydrochloride (32)

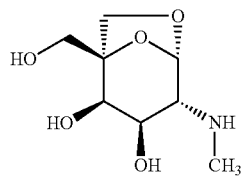

To a solution of tert-butyl [(1S,2R,3R,4R,5S)-2,3-dihydroxy-1-(hydroxymethyl)-6,8-dioxabicyclo[3.2.1]oct-4-yl]methylcarbamate (31) (25.3 mg, 0.0829 mmol) in dichloromethane (5.0 mL) was added 4.0M hydrogen chloride in dioxane (0.518 mL, 2.07 mmol) and the reaction was allowed to stir for 48 hours at room temperature. After 48 hours, the reaction was concentrated under reduced pressure. The crude material was washed with ethyl acetate (5 mL) which created a solid and diluted with heptane (10 mL) and concentrated under reduced pressure yielding the title compound as a solid (30.0 mg, 130%). Method C: 3 minute run LRMS [M+1=206]. $^1$H NMR (METHANOL-d$_4$) δ: 5.63 (s, 1H), 3.90-3.97 (m, 3H), 3.84 (s, 2H), 3.78 (d, J=8.2 Hz, 1H), 3.10-3.20 (m, 1H), 2.84 (s, 3H)

N-[(1S,2R,6R,7R,8S)-4,4-dimethyl-1-(15-phenyl-2,5,8,11,14-pentaoxapentadec-1-yl)-3,5,9,11-tetraoxatricyclo[6.2.1.0~2,6~]undec-7-yl]acetamide (I-e-3)

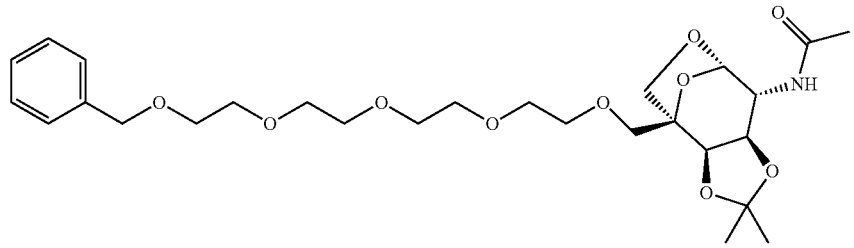 [SMILES: CC(=O)N[C@H]1[C@H]2OC[C@](COCCOCCOCCOCCOCc3ccccc3)(O2)[C@@H]2OC(C)(C)O[C@H]12]

To a solution of N-[(1S,2R,6R,7R,8S)-1-(hydroxymethyl)-4,4-dimethyl-3,5,9,11-tetraoxatricyclo[6.2.1.0~2,6~]undec-7-yl]acetamide (I-e-1) (1200 mg, 4.39 mmol) and 13-iodo-1-phenyl-2,5,8,11-tetraoxatridecane

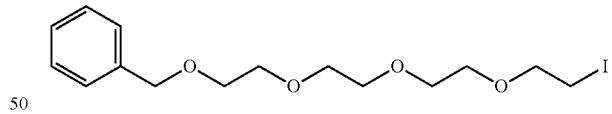

(see Synthetic Metals, 162(23), 2163-2170; 2012; 7000 mg, 17.76 mmol) in dichloromethane (30.0 mL) was added tetrabutylammonium hydrogen sulfate (2290 mg, 6.60 mmol) followed by the addition of 12.5M Sodium hydroxide aqueous (30.0 mL, 380 mmol). The reaction was allowed to stir at room temperature for 64 hours. After 64 hours, the reaction was diluted with water and dichloromethane. The layers were separated and the aqueous layer was extracted two additional times with dichloromethane. The combined organic layers were washed with 1N hydrochloric acid, dried over magnesium sulfate, filtered and concentrated under reduced pressure. The resulting crude material was added ethyl acetate (50 mL) and stirred for 30 minutes. The resulting precipitate was filtered. The filtrate was concentrated under reduced pressure. The crude material was purified using the CombiFlash Rf (ISCO RediSep Gold 80 g silica gel column) and eluting with a gradient of 0-100% ethyl acetate/heptane immediately followed by eluting with a gradient of 0-20% methanol/dichloromethane yielding the title compound (1267 mg, 53.5%). Method C: 1.5 minute run LRMS [M+Na=562]. $^1$H NMR (METHANOL-d$_4$) δ: 7.13-7.45 (m, 5H), 5.22 (d, J=1.6 Hz, 1H), 4.55 (s, 2H), 4.30 (d, J=5.9 Hz, 1H), 4.15 (t, J=6.4 Hz, 1H), 3.89-3.97 (m, 2H), 3.85 (d, J=7.8 Hz, 1H), 3.73-3.79 (m, 2H), 3.58-3.71 (m, 16H), 1.98 (s, 3H), 1.48 (s, 3H), 1.33 (s, 3H)

N-[(1S,2R,3R,4R,5S)-2,3-dihydroxy-1-(15-phenyl-2,5,8,11,14-pentaoxapentadec-1-yl)-6,8-dioxabicyclo[3.2.1]oct-4-yl]acetamide (33)

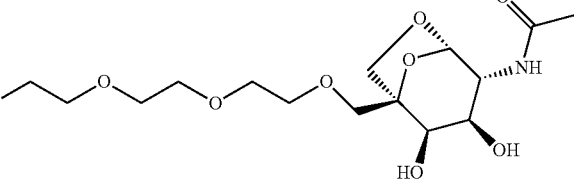

A solution of N-[(1S,2R,6R,7R,8S)-4,4-dimethyl-1-(15-phenyl-2,5,8,11,14-pentaoxapentadec-1-yl)-3,5,9,11-tetraoxatricyclo[6.2.1.0~2,6~]undec-7-yl]acetamide (I-e-3) (60.0 mg, 0.11 mmol) in acetic acid (4.0 mL), methanol (1.0 mL) and water (1.0 mL) was heated to 70° C. overnight. After 18 hours, the reaction was cooled to room temperature and concentrated under reduced pressure. The crude material was diluted with toluene and concentrated under reduced pressure. The crude material was diluted with toluene a second time and concentrated under reduced pressure. The crude material was purified using the CombiFlash Rf (RediSep 4 g Gold silica gel column) and eluting with a gradient of 0-20% methanol/dichloromethane yielding the title compound as a gum (42.5 mg, 77%). Method C: 3 minute run LRMS [M+1=500]. $^1$H NMR (METHANOL-d$_4$) δ: 7.14-7.45 (m, 5H), 5.21 (s, 1H), 4.55 (s, 2H), 3.92-4.01 (m, 2H), 3.88 (d, J=4.3 Hz, 1H), 3.77 (d, J=7.8 Hz, 1H), 3.70 (dd, J=9.8, 3.9 Hz, 1H), 3.58-3.68 (m, 18H), 1.98 (s, 3H)

N-[(1S,2R,6R,7R,8S)-1-(13-azido-2,5,8,11-tetraoxatridec-1-yl)-4,4-dimethyl-3,5,9,11-tetraoxatricyclo[6.2.1.0~2,6~]undec-7-yl]acetamide (I-e-2)

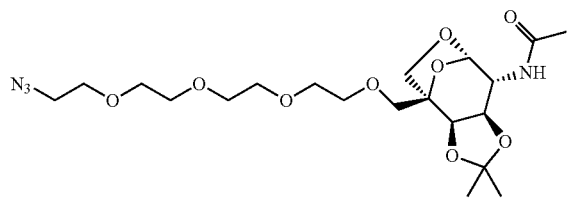 [SMILES: CC(=O)N[C@H]1[C@H]2OC[C@](COCCOCCOCCOCCN=[N+]=[N-])(O2)[C@@H]2OC(C)(C)O[C@H]12]

To a stirred solution of N-[(1S,2R,6R,7R,8S)-1-(hydroxymethyl)-4,4-dimethyl-3,5,9,11-tetraoxatricyclo[6.2.1.0~2,6~]undec-7-yl]acetamide (I-e-1) (10.0 g, 36.59 mmol, 1.0 eq) in N,N-dimethylformamide (200 ml) was added potassium hydroxide (8.21 g, 146.37 mmol, 4 eq) at 5° C. (ice/water). After addition, the reaction mixture was stirred at 5° C. for 30 min. Then 1-azido-2-{2-[2-(2-iodoethoxy)ethoxy]ethoxy}ethane (36.13 g, 109.78 mmol, 3.0 eq) was added to the reaction mixture at 5° C. (ice/water). The reaction mixture was stirred at 5° C. (ice/water) for 30 minutes and the reaction mixture was heated to 27° C. and stirred at 27° C. for 18 hours. After 18 hours, the reaction mixture was poured into ice/water and extracted three times with dichloromethane (400 ml). The combined organic layers were washed three times with water (400 ml), brine (500 ml), dried over sodium sulfate, filtered and concentrated to give crude product. The crude product was purified by silica gel chromatography eluted with dichloromethane:methanol=100:1-40:1 to the title compound (10.0 g, 57.6%) as colorless oil. Method C: 3 minute run LRMS [M+45 (formic acid)=519]. $^1$H NMR (METHANOL-d$_4$) δ: 5.23 (d, J=2.0 Hz, 1H), 4.31 (d, J=5.9 Hz, 1H), 4.16 (t, J=6.6 Hz, 1H), 3.93-3.97 (m, 1H), 3.90-3.93 (m, J=2.0 Hz, 1H), 3.86 (d, J=7.8 Hz, 1H), 3.78 (d, J=3.9 Hz, 1H), 3.75 (d, J=1.6 Hz, 1H), 3.61-3.71 (m, 14H), 3.37 (t, J=4.9 Hz, 2H), 1.98 (s, 3H), 1.49 (s, 3H), 1.34 (s, 3H)

N-[(1S,2R,3R,4R,5S)-1-(13-azido-2,5,8,11-tetraoxatridec-1-yl)-2,3-dihydroxy-6,8-dioxabicyclo[3.2.1]oct-4-yl]acetamide (34)

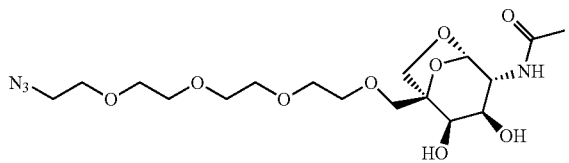 [SMILES: CC(=O)N[C@H]1[C@H]2OC[C@](COCCOCCOCCOCCN=[N+]=[N-])(O2)[C@H](O)[C@@H]1O]

A solution of N-[(1S,2R,6R,7R,8S)-1-(13-azido-2,5,8,11-tetraoxatridec-1-yl)-4,4-dimethyl-3,5,9,11-tetraoxatricyclo[6.2.1.0~2,6~]undec-7-yl]acetamide (I-e-2) (82.0 mg, 0.17 mmol) in acetic acid (6.0 mL), methanol (1.45 mL) and water (1.45 mL) was heated to 70° C. overnight. After 18 hours, the reaction was cooled to room temperature and concentrated under reduced pressure. The crude material was diluted with toluene and concentrated under reduced pressure. The crude material was diluted with toluene a second time and concentrated under reduced pressure. The crude material was purified using the CombiFlash Rf (RediSep 4 g Gold silica gel column) and eluting with a gradient of 0-20% methanol/dichloromethane yielding the title compound as an oil (43.3 mg, 58%). Method C: 3 minute run LRMS [M−1=433]. $^1$H NMR (METHANOL-d$_4$) δ: 5.21 (d, J=0.8 Hz, 1H), 3.98 (d, J=9.8 Hz, 1H), 3.94 (d, J=9.8 Hz, 1H), 3.89 (d, J=4.3 Hz, 1H), 3.78 (d, J=7.8 Hz, 1H), 3.72 (dd, J=10.1, 4.3 Hz, 1H), 3.61-3.69 (m, 16H), 3.38 (t, J=4.9 Hz, 2H), 1.99 (s, 3H)

141

N-[(1S,2R,6R,7R,8S)-4,4-dimethyl-1-(2,5,8,11-tetraoxatetradec-13-en-1-yl)-3,5,9,11-tetraoxatricyclo[6.2.1.0~2,6~]undec-7-yl]acetamide (I-e-4)

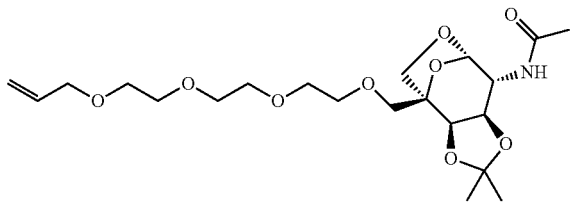 [SMILES: C=CCOCCOCCOCCOC[C@@]12CO[C@@H](O1)[C@H](NC(C)=O)[C@H]1OC(C)(C)O[C@H]12]

To a solution of N-[(1S,2R,6R,7R,8S)-1-(hydroxymethyl)-4,4-dimethyl-3,5,9,11-tetraoxatricyclo[6.2.1.0~2,6~]undec-7-yl]acetamide (I-e-1) (50.0 mg, 0.18 mmol) and 3-{2-[2-(2-iodoethoxy)ethoxy]ethoxy}prop-1-ene

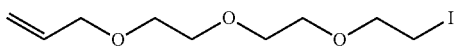

(see Organic Letters, 5(11), 1887-1890; 2003, 139.0 mg, 0.463 mmol) in dichloromethane (1.5 mL) was added tetrabutylammonium hydrogen sulfate (95.3 mg, 0.275 mmol) followed by the addition of 12.5M sodium hydroxide aqueous (0.75 mL, 9.4 mmol). The reaction was allowed to stir at room temperature overnight. After 18 hours, the reaction was diluted with water and dichloromethane. The layers were separated and the aqueous layer was extracted two additional times with dichloromethane. The combined organic layers were washed with 1N hydrochloric acid, water, dried over magnesium sulfate, filtered and concentrated under reduced pressure. The resulting crude material was diluted with ethyl acetate (5 mL) and the resulting precipitate was stirred at room temperature for 30 minutes. The precipitate was filtered and the filter cake was washed with ethyl acetate (2×5 mL). The filtrate was concentrated under reduced pressure. The crude material was purified using the CombiFlash Rf (ISCO RediSep Gold 4 g silica gel column) and eluting with a gradient of 0-100% ethyl acetate/heptane. The column was then eluted with a gradient of 0-20% methanol/dichloromethane yielding the title compound (13.6 mg, 17%). Method C: 1.5 minute run LRMS [M+Na=468]. $^1$H NMR (METHANOL-d$_4$) δ: 5.92 (ddt, J=16.8, 10.9, 5.7 Hz, 1H), 5.28 (dd, J=17.4, 1.4 Hz, 1H), 5.23 (d, J=1.6 Hz, 1H), 5.16 (dd, J=10.3, 1.0 Hz, 1H), 4.31 (d, J=5.9 Hz, 1H), 4.15 (t, J=6.4 Hz, 1H), 4.02 (d, J=5.5 Hz, 2H), 3.89-3.97 (m, 2H), 3.86 (d, J=7.8 Hz, 1H), 3.73-3.80 (m, 2H), 3.56-3.72 (m, 12H), 1.98 (s, 3H), 1.49 (s, 3H), 1.34 (s, 3H).

N-[(1S,2R,3R,4R,5S)-2,3-dihydroxy-1-(2,5,8,11-tetraoxatetradec-13-en-1-yl)-6,8-dioxabicyclo[3.2.1]oct-4-yl]acetamide (35)

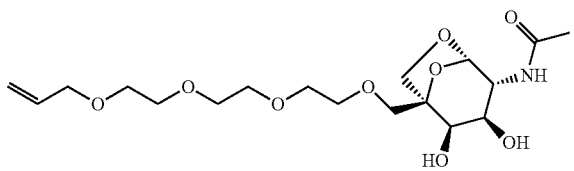 [SMILES: C=CCOCCOCCOCCOC[C@@]12CO[C@@H](O1)[C@H](NC(C)=O)[C@@H](O)[C@H]2O]

142

A solution of N-[(1S,2R,6R,7R,8S)-4,4-dimethyl-1-(2,5,8,11-tetraoxatetradec-13-en-1-yl)-3,5,9,11-tetraoxatricyclo[6.2.1.0~2,6~]undec-7-yl]acetamide (I-e-4) (13.0 mg, 0.029 mmol) in acetic acid (1.0 mL), methanol (0.25 mL) and water (0.25 mL) was heated to 70° C. overnight. After 18 hours, the reaction was cooled to room temperature and concentrated under reduced pressure. The crude material was diluted with toluene and concentrated under reduced pressure. The crude material was diluted with toluene a second time and concentrated under reduced pressure. The crude material was purified using the CombiFlash Rf (RediSep 4 g Gold silica gel column) and eluting with a gradient of 0-20% methanol/dichloromethane yielding the title compound (6.5 mg, 55%). Method C: 3 minute run LRMS [M+1=406]. $^1$H NMR (METHANOL-d$_4$) δ: 5.80-6.09 (m, 1H), 5.28 (dd, J=17.2, 1.6 Hz, 1H), 5.21 (d, J=0.8 Hz, 1H), 5.16 (dd, J=10.5, 1.2 Hz, 1H), 4.02 (d, J=5.5 Hz, 2H), 3.98 (d, J=9.8 Hz, 1H), 3.95 (d, J=10.1 Hz, 1H), 3.89 (d, J=3.9 Hz, 1H), 3.78 (d, J=8.2 Hz, 1H), 3.71 (dd, J=10.0, 4.5 Hz, 1H), 3.57-3.68 (m, 14H), 1.99 (s, 3H).

N-[(1S,2R,6R,7R,8S)-4,4-dimethyl-1-(2,5,8,11-tetraoxatetradec-13-yn-1-yl)-3,5,9,11-tetraoxatricyclo[6.2.1.0~2,6~]undec-7-yl]acetamide (I-e-5)

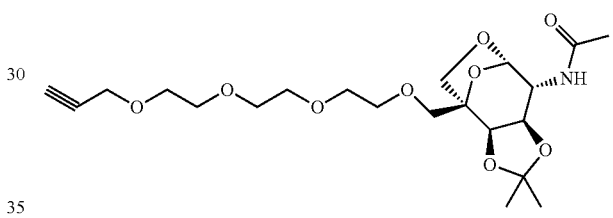

To a solution of N-[(1S,2R,6R,7R,8S)-4,4-dimethyl-1-(15-phenyl-2,5,8,11,14-pentaoxapentadec-1-yl)-3,5,9,11-tetraoxatricyclo[6.2.1.0~2,6~]undec-7-yl]acetamide (I-e-1) (100.0 mg, 0.366 mmol) and 3-{2-[2-(2-iodoethoxy)ethoxy]ethoxy}prop-1-yne

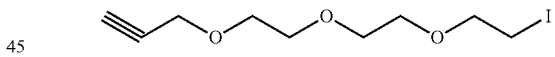

(see Synthesis, (10), 1639-1644; 2010, 425.0 mg, 1.43 mmol) in dichloromethane (3 mL) was added tetrabutylammonium hydrogen sulfate (191 mg, 0.550 mmol) followed by the addition of 12.5M sodium hydroxide aqueous (1.5 mL, 19 mmol). The reaction was allowed to stir at room temperature overnight. After 18 hours, the reaction was diluted with water and dichloromethane. The layers were separated and the aqueous layer was extracted two additional times with dichloromethane. The combined organic layers were washed with 1N hydrochloric acid, water, dried over magnesium sulfate, filtered and concentrated under reduced pressure. The resulting crude material was diluted with ethyl acetate (20 mL) and the resulting precipitate was stirred at room temperature for 30 minutes. The precipitate was filtered and the filter cake was washed with ethyl acetate (2×15 mL). The filtrate was concentrated under reduced pressure. The crude material was purified using the CombiFlash Rf (ISCO RediSep Gold 12 g silica gel column) and eluting with a gradient of 0-100% ethyl acetate/heptane. The column was then eluted with a gradient of 0-20% methanol/dichloromethane yielding the title compound (70.0 mg, 43%). Method C: 1.5 minute run LRMS [M+Na=466]. $^1$H NMR (METHANOL-$d_4$) δ: 5.23 (d, J=1.6 Hz, 1H), 4.31 (d, J=5.9 Hz, 1H), 4.19 (d, J=2.3 Hz, 2H), 4.16 (t, J=6.4 Hz, 1H), 3.90-3.97 (m, 2H), 3.86 (d, J=7.8 Hz, 1H), 3.74-3.79 (m, 2H), 3.60-3.72 (m, 12H), 2.85 (t, J=2.3 Hz, 1H), 1.98 (s, 3H), 1.49 (s, 3H), 1.34 (s, 3H)

N-[(1S,2R,3R,4R,5S)-2,3-dihydroxy-1-(2,5,8,11-tetraoxatetradec-13-yn-1-yl)-6,8-dioxabicyclo[3.2.1]oct-4-yl]acetamide (36)

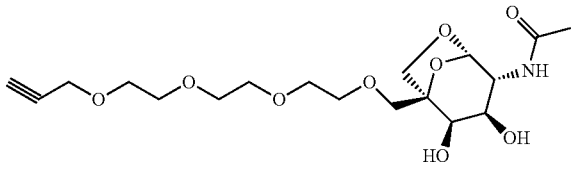 [SMILES: C#CCOCCOCCOCCOC[C@@]12CO[C@@H](O1)[C@H](NC(C)=O)[C@@H](O)[C@H]2O]

A solution of N-[(1S,2R,6R,7R,8S)-4,4-dimethyl-1-(2,5,8,11-tetraoxatetradec-13-yn-1-yl)-3,5,9,11-tetraoxatricyclo[6.2.1.0~2,6~]undec-7-yl]acetamide (I-e-5) (70.0 mg, 0.16 mmol) in acetic acid (4.0 mL), methanol (1.0 mL), and water (1.0 mL) was heated to 70° C. overnight. After 18 hours, the reaction was cooled to room temperature and concentrated under reduced pressure. The crude material was diluted with toluene and concentrated under reduced pressure. The crude material was diluted with toluene a second time and concentrated under reduced pressure. The crude material was purified using the CombiFlash Rf (RediSep 4 g Gold silica gel column) and eluting with a gradient of 0-20% methanol/dichloromethane yielding the title compound as a gum (57.6 mg, 90%). Method C: 3 minute run LRMS [M+1=404]. $^1$H NMR (METHANOL-$d_4$) δ: 5.22 (s, 1H), 4.19 (d, J=1.8 Hz, 2H), 3.98 (d, J=10.0 Hz, 1H), 3.94 (d, J=10.0 Hz, 1H), 3.89 (d, J=4.1 Hz, 1H), 3.78 (d, J=8.2 Hz, 1H), 3.71 (dd, J=10.0, 4.1 Hz, 1H), 3.60-3.69 (m, 14H), 2.86 (s, 1H), 1.99 (s, 3H)

N-[(1S,2R,3R,4R,5S)-1-(13-amino-2,5,8,11-tetraoxatridec-1-yl)-2,3-dihydroxy-6,8-dioxabicyclo[3.2.1]oct-4-yl]acetamide (37)

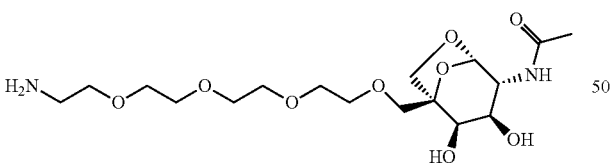

A solution of N-[(1S,2R,3R,4R,5S)-1-(13-azido-2,5,8,11-tetraoxatridec-1-yl)-2,3-dihydroxy-6,8-dioxabicyclo[3.2.1]oct-4-yl]acetamide (34) (40.0 mg, 0.092 mmol) in ethanol (2 mL) was passed through the H-cube (conditions: catalyst (10% palladium on carbon (30×4 mm), flow rate: 1 mL/min., temperature: room temperature, pressure=Full $H_2$). After passing through the H-cube, the solution was collected and concentrated under reduced pressure yielding the title compound as a gum (17.2 mg, 46%). Method C: 3 minute run LRMS [M+1=409]. $^1$H NMR (METHANOL-$d_4$) δ: 5.21 (s, 1H), 3.92-4.00 (m, 2H), 3.89 (d, J=3.9 Hz, 1H), 3.78 (d, J=8.2 Hz, 1H), 3.69-3.74 (m, 1H), 3.61-3.69 (m, 14H), 3.56 (t, J=5.1 Hz, 2H), 2.85 (t, J=5.1 Hz, 2H), 1.99 (s, 3H)

N-[(1S,2R,3R,4R,5S)-2,3-dihydroxy-1-(13-hydroxy-2,5,8,11-tetraoxatridec-1-yl)-6,8-dioxabicyclo[3.2.1]oct-4-yl]acetamide (38)

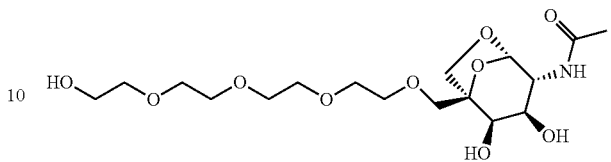

N-[(1S,2R,3R,4R,5S)-2,3-dihydroxy-1-(15-phenyl-2,5,8,11,14-pentaoxapentadec-1-yl)-6,8-dioxabicyclo[3.2.1]oct-4-yl]acetamide (33) (43 mg, 0.086 mmol) was dissolved in methanol (2 mL) was passed through the H-cube (conditions: catalyst (20% palladium hydroxide carbon (30×4 mm), flow rate: 1 mL/min., temperature: 60 C, pressure=Full $H_2$). After passing through the H-cube, the solution was collected and concentrated under reduced pressure yielding the title compound (32.2 mg, 91%). $^1$H NMR (METHANOL-$d_4$) δ: 5.21 (s, 1H), 3.98 (d, J=9.4 Hz, 1H), 3.95 (d, J=10.1 Hz, 1H), 3.89 (d, J=4.3 Hz, 1H), 3.78 (d, J=8.2 Hz, 1H), 3.71 (dd, J=9.8, 4.3 Hz, 1H), 3.61-3.69 (m, 16H), 3.54-3.59 (m, 2H), 1.99 (s, 3H). $^{13}$C NMR (METHANOL-$d_4$) δ: 174.1, 102.6, 84.3, 73.8, 72.5, 71.7, 71.7(2), 71.6, 71.5, 71.4, 70.5, 70.2, 69.0, 62.4, 56.4, 22.7

N-[(1S,2R,6R,7R,8S)-1-(13-hydroxy-2,5,8,11-tetraoxatridec-1-yl)-4,4-dimethyl-3,5,9,11-tetraoxatricyclo[6.2.1.0~2,6~]undec-7-yl]acetamide (I-e-6)

N-[(1S,2R,6R,7R,8S)-4,4-dimethyl-1-(15-phenyl-2,5,8,11,14-pentaoxapentadec-1-yl)-3,5,9,11-tetraoxatricyclo[6.2.1.0~2,6~]undec-7-yl]acetamide (I-e-3) (2.897 g, 5.37 mmol) was dissolved in methanol (150 mL) was passed through the H-cube (conditions: catalyst (10% palladium on carbon (30×4 mm), flow rate: 1 mL/min., temperature: 60° C., pressure=Full $H_2$). After passing through the H-cube, the solution was collected and concentrated under reduced pressure yielding the title compound as a gum (2.5 g, 100%). Method C: 1.5 minute run LRMS [M+1=450]. $^1$H NMR (METHANOL-$d_4$) δ: 5.23 (d, J=1.6 Hz, 1H), 4.31 (d, J=5.9 Hz, 1H), 4.16 (t, J=6.4 Hz, 1H), 3.89-3.97 (m, 2H), 3.86 (d, J=7.8 Hz, 1H), 3.74-3.80 (m, 2H), 3.60-3.71 (m, 14H), 3.53-3.59 (m, 2H), 1.98 (s, 3H), 1.49 (s, 3H), 1.34 (s, 3H)

N-[(1S,2R,6R,7R,8S)-4,4-dimethyl-1-(13-oxo-2,5,8,11-tetraoxatridec-1-yl)-3,5,9,11-tetraoxatricyclo[6.2.1.0~2,6~]undec-7-yl]acetamide (I-e-6a)

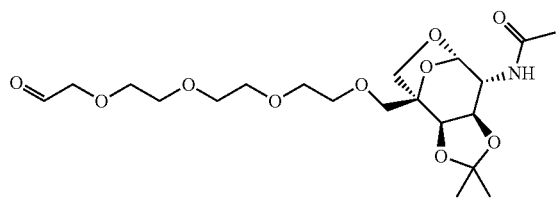 [SMILES: CC(=O)N[C@H]1[C@H]2OC[C@](COCCOCCOCCOCC=O)(O2)[C@@H]2OC(C)(C)O[C@H]12]

To a solution of N-[(1S,2R,6R,7R,8S)-1-(13-hydroxy-2,5,8,11-tetraoxatridec-1-yl)-4,4-dimethyl-3,5,9,11-tetraoxatricyclo[6.2.1.0~2,6~]undec-7-yl]acetamide (I-e-6) (175 mg, 0.389 mmol) in dichloromethane (5.0 mL) was added Dess-Martin reagent (354 mg, 0.584 mmol) which resulted in a mixture. After ~30 minutes, the reaction became almost homogeneous. After 3 hours, the reaction mixture was diluted with dichloromethane and filtered through a plug of celite and washed with dichloromethane. The filtrate was concentrated under reduced pressure. The crude material was purified using the CombiFlash Rf (RediSep 24 g gold silica gel column) and eluting with a gradient of 0-20% methanol/dichloromethane. The tubes containing the desired product were concentrated under reduced pressure. The resulting material was diluted with dichloromethane (4 mL) and diluted with ethyl ether (10 mL) which resulted in a white precipitate. The solution was decanted and the solid was diluted with dichloromethane (2 mL) and ethyl ether (8 mL) and decanted a second time. The decanted solution was passed through a Life Science Acrodisc 25 mm syringe filter with 0.45 um Nylon membrane. The collected solution was concentrated under reduced pressure yielding the title compound as a gum (65.0 mg, 37%). Method C: 3 minute run LRMS [M+1=448]. $^1$H NMR (CHLOROFORM-d) δ: 9.74 (s, 1H), 5.63 (d, J=9.0 Hz, 1H), 5.34 (d, J=1.6 Hz, 1H), 4.23 (d, J=5.9 Hz, 1H), 4.17 (s, 2H), 4.09-4.15 (m, 1H), 4.01 (t, J=6.2 Hz, 1H), 3.97 (d, J=10.1 Hz, 1H), 3.77-3.85 (m, 3H), 3.68-3.76 (m, 5H), 3.61-3.68 (m, 7H), 2.03 (s, 3H), 1.56 (s, 3H), 1.36 (s, 3H).

1-[(1S,2R,3R,4R,5S)-4-(acetylamino)-2,3-dihydroxy-6,8-dioxabicyclo[3.2.1]oct-1-yl]-2,5,8,11-tetraoxatridecan-13-oic acid (38A)

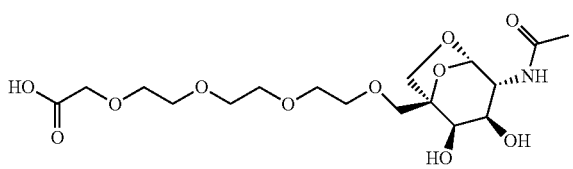 [SMILES: CC(=O)N[C@H]1[C@H]2OC[C@](COCCOCCOCCOCC(=O)O)(O2)[C@H](O)[C@@H]1O]

To a solution of N-[(1S,2R,6R,7R,8S)-4,4-dimethyl-1-(13-oxo-2,5,8,11-tetraoxatridec-1-yl)-3,5,9,11-tetraoxatricyclo[6.2.1.0~2,6~]undec-7-yl]acetamide (I-e-6a) (60.0 mg, 0.13 mmol) in tetrahydrofuran/t-butanol (1.5 mL/1.5 mL) was treated with 2-methyl-2-butene (1.0 mL) followed by a solution of sodium chlorite (169.4 mg, 2.01 mmol) and sodium phosphate (250.0 mg, 2.58 mmol) (monobasic and monohydrate, 250 mg, 2.58 mmol) in water (1.5 mL) via glass pipet. The reaction was allowed to stir at room temperature for 24 hours. After 24 hours, the reaction mixture was poured into water and extracted with ethyl acetate (three times). The organic layer was discarded. The aqueous layers were concentrated under reduced pressure and the resulting crude was dissolved in methanol (10 mL) and dichloromethane (100 mL) and the resulting mixture was filtered. The filtrate was concentrated under reduced pressure. The resulting material was dissolved in methanol (5 mL) and dichloromethane (50 mL) and the resulting mixture was filtered. The filtrate was purified using the CombiFlash Rf (RediSep 4 g silica gel column) and eluting with a gradient of 0-100% methanol/dichloromethane yielding the title compound as a gum as a sodium salt (40 mg, None, 67%). LRMS [M+1=424]; $^1$H NMR (METHANOL-d$_4$) δ: 5.24 (s, 1H), 4.14 (s, 2H), 3.97 (d, J=10.1 Hz, 2H), 3.90 (d, J=3.9 Hz, 1H), 3.81 (d, J=7.8 Hz, 1H), 3.63-3.77 (m, 15H), 2.01 (s, 3H)

1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl methanesulfonate (I-e-7)

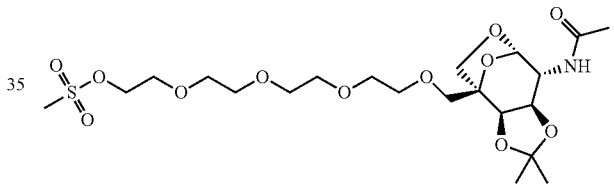

To a solution of 1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl methanesulfonate (I-e-6) (1117 mg, 2.49 mmol) in dichloromethane (12.4 mL) was added triethylamine (1.05 mL, 7.45 mmol) and cooled to 0° C. using an ice bath followed by the addition of methane sulfonyl chloride (0.232 mL, 2.98 mmol). The reaction was allowed to warm slowly to room temperature and stirred at room temperature for 1.5 hours. After 1.5 hours, the reaction was quenched with water and extracted. The layers were separated and the aqueous layer was extracted an additional time with dichloromethane. The combined organic layers were washed with brine, dried over magnesium sulfate, filtered and concentrated under reduced pressure yielding the title compound which was carried on crude (1300.0 mg, 99.2%). Method C: 3 minute run LRMS [M+Na=550]. $^1$H NMR (METHANOL-d$_4$) δ: 5.23 (d, J=2.0 Hz, 1H), 4.34-4.40 (m, 2H), 4.31 (d, J=5.9 Hz, 1H), 4.15 (t, J=6.4 Hz, 1H), 3.89-3.97 (m, 2H), 3.86 (d, J=7.8 Hz, 1H), 3.72-3.81 (m, 4H), 3.59-3.71 (m, 12H), 3.11 (s, 3H), 1.98 (s, 3H), 1.48 (s, 3H), 1.34 (s, 3H)

S-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}ethanethioate (I-e-8)

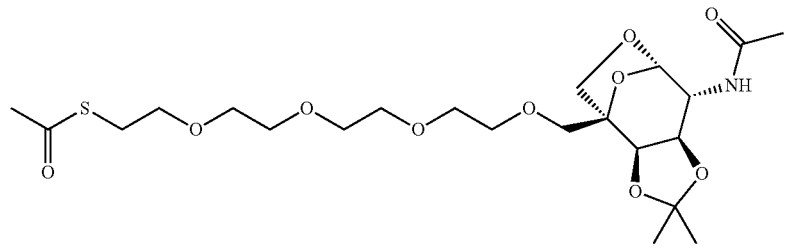 [SMILES: CC(=O)N[C@H]1[C@H]2OC[C@](COCCOCCOCCOCCSC(C)=O)(O2)[C@@H]2OC(C)(C)O[C@H]12]

To a solution of 1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-ylmethanesulfonate (I-e-7) (125.0 mg, 0.237 mmol) in N,N-dimethylformamide (2 mL) was added potassium thioacetate (135 mg, 1.18 mmol) and the reaction was stirred at room temperature for 64 hours. After 64 hours, the reaction was diluted with water and extracted with ethyl acetate three times. The combined organic layers washed with brine, dried over sodium sulfate, filtered and concentrated under reduced pressure. The crude material was purified using the CombiFlash Rf (RediSep 4 g silica gel column) and eluting with a gradient of 0-20% methanol/dichloromethane yielding the title compound as a gum (95.2 mg, 79.2%). Method C: 3 minute run LRMS [M+Na=530]. $^1$H NMR (METHANOL-$d_4$) δ: 5.23 (d, J=1.6 Hz, 1H), 4.31 (d, J=5.9 Hz, 1H), 4.16 (t, J=6.4 Hz, 1H), 3.90-3.97 (m, 2H), 3.86 (d, J=7.8 Hz, 1H), 3.74-3.79 (m, 2H), 3.55-3.72 (m, 14H), 3.08 (t, J=6.6 Hz, 2H), 2.32 (s, 3H), 1.98 (s, 3H), 1.49 (s, 3H), 1.34 (s, 3H)

S-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}ethanethioate (39)

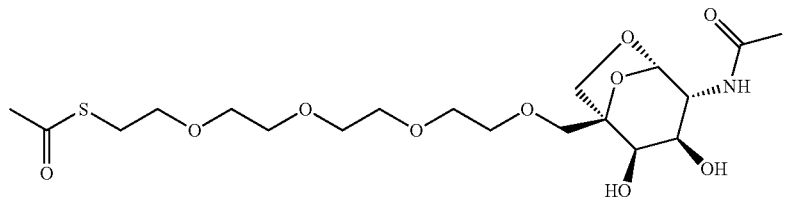 [SMILES: CC(=O)N[C@H]1[C@H]2OC[C@](COCCOCCOCCOCCSC(C)=O)(O2)[C@H](O)[C@@H]1O]

A solution of S-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}ethanethioate (I-e-8) (81.0 mg, 0.16 mmol) in acetic acid (6.0 mL), methanol (1.45 mL) and water (1.45 mL) was heated to 70° C. overnight. After 18 hours, the reaction was cooled to room temperature and concentrated under reduced pressure. The crude material was diluted with toluene and concentrated under reduced pressure. The crude material was diluted with toluene a second time and concentrated under reduced pressure. The crude material was purified using the CombiFlash Rf (RediSep 4 g Gold silica gel column) and eluting with a gradient of 0-20% methanol/dichloromethane yielding the title compound as a gum (53.7 mg, 72%). Method C: 3 minute run LRMS [M+1=468]. $^1$H NMR (METHANOL-$d_4$) δ: 5.23 (s, 1H), 4.00 (d, J=9.8 Hz, 1H), 3.97 (d, J=9.8 Hz, 1H), 3.91 (d, J=4.3 Hz, 1H), 3.80 (d, J=7.8 Hz, 1H), 3.73 (dd, J=10.1, 4.3 Hz, 1H), 3.63-3.70 (m, 14H), 3.60 (t, J=6.6 Hz, 2H), 3.10 (t, J=6.4 Hz, 2H), 2.34 (s, 3H), 2.01 (s, 3H)

N-{(1S,2R,3R,4R,5S)-2,3-dihydroxy-1-[13-(pyridin-2-yldisulfanyl)-2,5,8,11-tetraoxatridec-1-yl]-6,8-dioxabicyclo[3.2.1]oct-4-yl}acetamide (40)

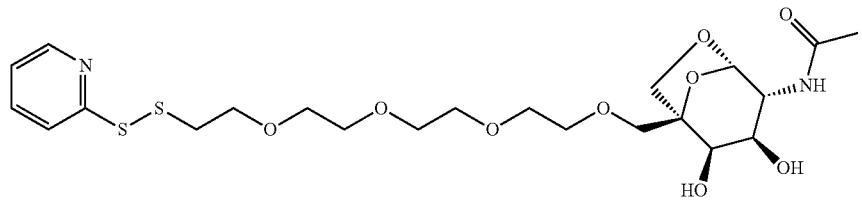 [SMILES: CC(=O)N[C@H]1[C@H]2OC[C@](COCCOCCOCCOCCSSc3ccccn3)(O2)[C@H](O)[C@@H]1O]

To a solution of S-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl} ethanethioate (39) (50 mg, 0.11 mmol) in methanol (3 mL) followed by the addition of a 0.5M sodium methoxide solution in methanol (1.28 mL, 0.642 mmol) and the reaction was allowed to stir for 45 minutes at room temperature. After 45 minutes, acetic acid (42 mg, 0.70 mmol, 0.040 mL) was added and stirred for 10 minutes. The methanol solution was then added drop wise to a stirring solution of 2,2'-disulfanediyldipyridine (35.3 mg, 0.160 mmol) in a mixture of methanol (2 mL) and acetic acid (1 mL). The reaction was allowed to stir for 2 hours at room temperature. After 2 hours, the reaction was concentrated under reduced pressure. The crude material was purified using the CombiFlash Rf (RediSep Gold 4 g silica gel column) and eluting with a gradient of 0-20% methanol/dichloromethane yielding the title compound (31.4 mg, 55%). Method C: 3 minute run LRMS [M+Na=557]. $^1$H NMR (METHANOL-$d_4$) δ: 8.39 (d, J=4.3 Hz, 1H), 7.94 (d, J=8.2 Hz, 1H), 7.83 (td, J=7.8, 1.6 Hz, 1H), 7.22 (dd, J=6.8, 5.3 Hz, 1H), 5.21 (s, 1H), 3.92-4.00 (m, 2H), 3.88 (d, J=4.3 Hz, 1H), 3.77 (d, J=7.8 Hz, 1H), 3.71 (t, J=6.0 Hz, 3H), 3.59-3.67 (m, 12H), 3.52-3.58 (m, 2H), 3.02 (t, J=6.0 Hz, 2H), 1.99 (s, 3H) tert-butyl {1,3-bis(prop-2-yn-1-yloxy)-2-[(prop-2-yn-1-yloxy)methyl]propan-2-yl}carbamate (I-f-3)

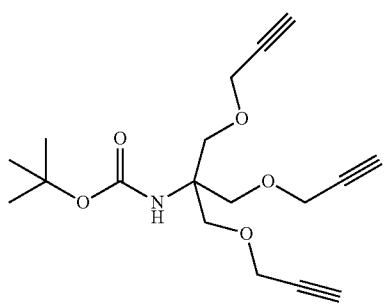 [SMILES: C#CCOCC(COCC#C)(COCC#C)NC(=O)OC(C)(C)C]

See Journal of Organic Chemistry, 73(14), 5602-5605; 2008 for synthesis of (I-f-3).

1,3-bis(prop-2-yn-1-yloxy)-2-[(prop-2-yn-1-yloxy)methyl]propan-2-amine hydrochloric acid (I-p-1)

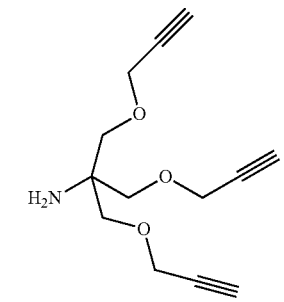 [SMILES: C#CCOCC(N)(COCC#C)COCC#C]

To a solution of tert-butyl {1,3-bis(prop-2-yn-1-yloxy)-2-[(prop-2-yn-1-yloxy)methyl]propan-2-yl}carbamate (I-f-3) (3000 mg, 8.945 mmol) in dichloromethane (45 mL) was added 4.0M hydrogen chloride in dioxane (20 mL, 89.4 mmol) and the reaction was stirred for 18 hours at room temperature. After 18 hours, the reaction was concentrated under reduced pressure yielding of an oil. Ethyl acetate (20 mL) was added to the crude mixture and the resulting mixture was stirred. Heptane (20 mL) was added and the mixture was stirred for 2 hours at room temperature. The material was filtered and the filter cake was washed with ethyl acetate and dried by pulling vacuum for 2 hours yielding the title compound (2140 mg, 88%). $^1$H NMR (METHANOL-$d_4$) δ: 4.25 (s, 6H), 3.72 (s, 6H), 2.97 (s, 3H).

benzyl [6-({1,3-bis(prop-2-yn-1-yloxy)-2-[(prop-2-yn-1-yloxy)methyl]propan-2-yl}amino)-6-oxohexyl]carbamate (I-q-1)

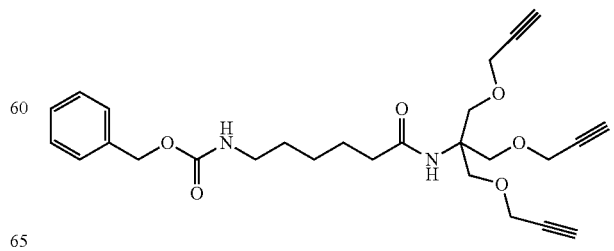

To a solution of 6-{[(benzyloxy)carbonyl]amino}hexanoic acid

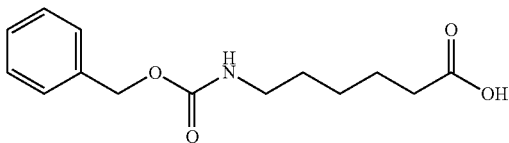 [SMILES: O=C(O)CCCCCNC(=O)OCc1ccccc1]

(2910 mg, 11.0 mmol) in N,N-dimethylformamide (4 mL) and tetrahydrofuran (20.0 mL) was added N-(3-dimethylaminopropyl)-N'-ethylcarbodiimide hydrochloride (I-p-1) (2150 mg, 11.0 mmol) and 1-hydroxybenzotriazole (1480 mg, 11.0 mmol) and the reaction was allowed to stir at room temperature for 1 hour during which time the reaction became homogeneous. 1,3-bis(prop-2-yn-1-yloxy)-2-[(prop-2-yn-1-yloxy)methyl]propan-2-amine hydrochloric acid (2130 mg, 7.84 mmol) was added neat in one portion to the stirring reaction mixture followed by the addition of N,N-diisopropylethylamine (5.46 mL, 31.4 mmol) and the reaction was heated to 60° C. for 24 hours. The reaction was allowed to cool to room temperature and was stirred for 24 hours. The reaction was quenched with water (150 mL) and extracted with ethyl acetate. The aqueous layer was washed an additional time with ethyl acetate. The combined organic layers were washed with brine, dried over sodium sulfate, filtered and concentrated under reduced pressure. The crude material was purified using the CombiFlash Rf (RediSep 80 g silica gel column) and eluting with a gradient of 0-100% ethyl acetate/heptane yielding the title compound as an oil which solidified upon standing (3250 mg, 86%). Method C: MassLynx\Acid_3.0Min.olp—LRMS [M+1=483]. $^1$H NMR (METHANOL-$d_4$) δ: 7.10-7.46 (m, 5H), 5.06 (s, 2H), 4.14 (d, J=2.0 Hz, 6H), 3.79 (s, 6H), 3.03-3.20 (m, 2H), 2.83 (t, J=2.1 Hz, 3H), 2.18 (t, J=7.2 Hz, 2H), 1.59 (quin, J=7.3 Hz, 2H), 1.44-1.54 (m, 2H), 1.28-1.40 (m, 2H)

6-(pyridin-2-yldisulfanyl)hexanoic acid (I-r-1)

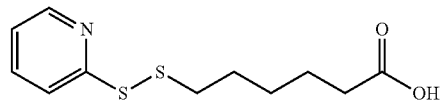 [SMILES: O=C(O)CCCCCSSc1ccccn1]

To a solution of 2,2'-disulfanediyldipyridine

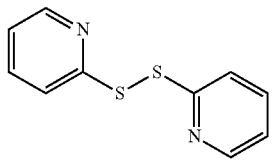 [SMILES: c1ccc(SSc2ccccn2)nc1]

(1490 mg, 6.75 mmol) in a mixture of ethanol (12.0 mL) and acetic acid (0.291 mL) was stirred under nitrogen followed by the drop wise addition of 6-sulfanylhexanoic acid

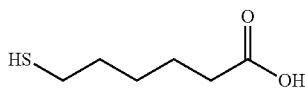

(1000.0 mg, 6.75 mmol) in ethyl acetate (6.0 mL). The reaction was allowed to stir for 2 hours at room temperature. After 2 hours, the reaction was concentrated under reduced pressure. The crude material was purified using the CombiFlash Rf (RediSep Gold 40 g silica gel column) and eluting with a gradient of 0-100% ethyl acetate (2% acetic acid modifier)/heptane yielding crude title compound (1170 mg). The crude material was purified again using the CombiFlash Rf (RediSep Gold 40 g silica gel column) and eluting with a gradient of 0-100% ethyl acetate (2% acetic acid modifier)/heptane yielding the title compound as an oil (544 mg, 31%).

1-{[6-(pyridin-2-yldisulfanyl)hexanoyl]oxy}pyrrolidine-2,5-dione (I-s-1)

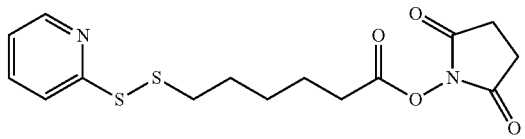 [SMILES: O=C(CCCCCSSc1ccccn1)ON1C(=O)CCC1=O]

To a solution of 6-(pyridin-2-yldisulfanyl)hexanoic acid (I-r-1) (705 mg, 2.2 mmol) in N,N-dimethylformamide (4 mL) was added N-Hydroxysuccinimide (306 mg, 2.66 mmol) followed by N-(3-dimethylaminopropyl)-N-ethylcarbodimiimide hydrochloride (520 mg, 2.66 mmol). The reaction was allowed to stir at room temperature overnight. The following morning, the reaction was quenched with water and extracted three times with dichloromethane. The combined organic layers were washed with saturated sodium bicarbonate, brine, dried over sodium sulfate, filtered and concentrated under reduced pressure. The crude material was purified using the CombiFlash Rf (RediSep 40 g gold column) and eluting with a gradient of 0-100% ethyl acetate/heptane yielding the title compound (364 mg, 47%). Method C: 1.5 minute run LRMS [M+1=355]. $^1$H NMR (METHANOL-$d_4$) δ: 8.39 (d, J=4.7 Hz, 1H), 7.85-7.90 (m, 1H), 7.77-7.84 (m, 1H), 7.21 (dd, J=6.6, 5.5 Hz, 1H), 2.77-2.90 (m, 6H), 2.61 (t, J=7.2 Hz, 2H), 1.63-1.83 (m, 4H), 1.46-1.59 (m, 2H)

N-{1,3-bis(prop-2-yn-1-yloxy)-2-[(prop-2-yn-1-yloxy)methyl]propan-2-yl}-6-(pyridin-2-yldisulfanyl)hexanamide (I-t-1)

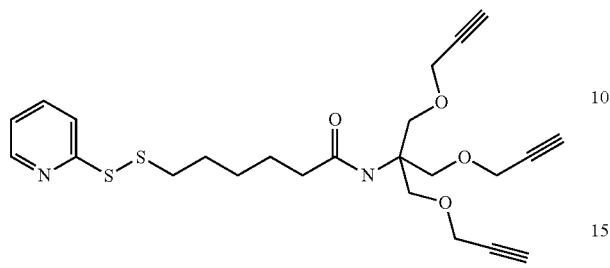

To a solution of 1,3-bis(prop-2-yn-1-yloxy)-2-[(prop-2-yn-1-yloxy)methyl]propan-2-amine hydrochloric acid (I-p-1) (100.0 mg, 0.324 mmol) in N,N-dimethylformamide (2.0 mL) was added N,N-diisopropylethylamine (0.339 mL, 1.95 mmol) and was allowed to stir for 10 minutes before adding 1-{[6-(pyridin-2-yldisulfanyl)hexanoyl]oxy}pyrrolidine-2,5-dione (I-s-1) (138 mg, 0.389 mmol) in one portion and the reaction was then heated to 60° C. for 16 hours. After 16 hours, the reaction was diluted with water and extracted with three times with ethyl acetate. The combined organic layers were washed with water, brine, dried over sodium sulfate, filtered and concentrated under reduced pressure. The crude material was purified using the CombiFlash Rf (RediSep 12 g silica gel column) and eluting with a gradient of 0-100% ethyl acetate/heptane yielding the title compound as a gum (66.7 mg, 43%). Method C: 1.5 minute run LRMS [M+Na=497]. $^1$H NMR (METHANOL-$d_4$) δ: 8.39 (d, J=4.7 Hz, 1H), 7.85-7.90 (m, 1H), 7.78-7.84 (m, 1H), 7.19-7.25 (m, 1H), 4.06-4.23 (m, 6H), 3.72-3.84 (m, 6H), 2.78-2.87 (m, 5H), 2.12-2.20 (m, 2H), 1.71 (quin, J=7.3 Hz, 2H), 1.57 (quin, J=7.3 Hz, 2H), 1.36-1.50 (m, 2H)

1-{[4-(benzyloxy)butanoyl]oxy}pyrrolidine-2,5-dione (I-u-1)

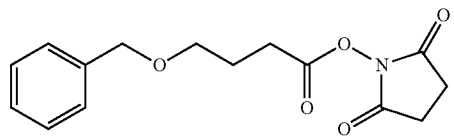 [SMILES: O=C(CCCOCc1ccccc1)ON1C(=O)CCC1=O]

To a solution of 4-(Benzyloxy)butanoic acid (1000 mg, 3.77 mmol) in N,N-dimethylformamide (7.54 mL) was added N-Hydroxysuccinimide (521 mg, 4.52 mmol) followed by N-(3-dimethylaminopropyl)-N-ethylcarbodiimide hydrochloride (885 mg, 4.52 mmol). The reaction was allowed to stir at room temperature overnight. The following morning, the reaction was quenched with water and extracted three times with dichloromethane. The combined organic layers were washed with saturated sodium bicarbonate, brine, dried over sodium sulfate, filtered and concentrated under reduced pressure. The crude material was purified using the CombiFlash Rf (RediSep 40 g gold column) and eluting with a gradient of 0-100% ethyl acetate/heptane yielding the title compound (1098 mg, 100%). Method C: 1.5 minute run LRMS [M+Na=314]. $^1$H NMR (METHANOL-$d_4$) δ: 7.11-7.50 (m, 5H), 4.51 (s, 2H), 3.56 (t, J=6.0 Hz, 2H), 2.81 (s, 4H), 2.73 (t, J=7.2 Hz, 2H), 1.99 (quin, J=6.6 Hz, 2H)

4-(benzyloxy)-N-{1,3-bis(prop-2-yn-1-yloxy)-2-[(prop-2-yn-1-yloxy)methyl]propan-2-yl}butanamide (I-v-1)

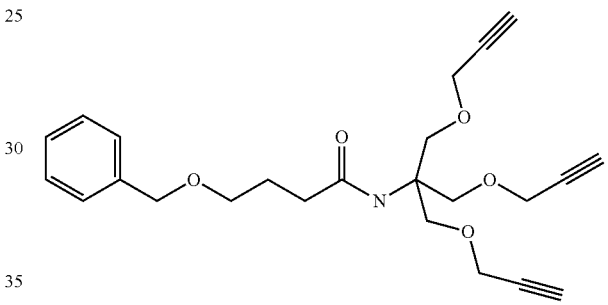

To a solution of 1,3-bis(prop-2-yn-1-yloxy)-2-[(prop-2-yn-1-yloxy)methyl]propan-2-amine trifluoroacetic acid (I-p-1) (750.0 mg, 1.62 mmol) in N,N-dimethylformamide (5 mL) was added N,N-diisopropylethylamine (1.69 mL, 9.71 mmol) and was allowed to stir for 10 minutes before the addition of 1-{[4-(benzyloxy)butanoyl]oxy}pyrrolidine-2,5-dione (I-u-1) (566 mg, 1.94 mmol) in N,N-dimethylformamide (1 mL) and the reaction was then heated to 60° C. for 72 hours. After 72 hours, the reaction was diluted with water and extracted with three times with ethyl acetate. The combined organic layers were washed with water, brine, dried over sodium sulfate, filtered and concentrated under reduced pressure. The crude material was purified using the CombiFlash Rf (RediSep 24 g silica gel column) and eluting with a gradient of 0-100% ethyl acetate/heptane yielding the title compound as a gum (495 mg, None, 74%). Method C: 1.5 minute run LRMS [M+1=412]. $^1$H NMR (METHANOL-$d_4$) δ: 7.21-7.41 (m, 5H), 4.51 (s, 2H), 4.12 (d, J=2.3 Hz, 6H), 3.78 (s, 6H), 3.51 (t, J=6.2 Hz, 2H), 2.82 (t, J=2.3 Hz, 3H), 2.28 (t, J=7.2 Hz, 2H), 1.79-1.94 (m, 2H)

tert-butyl (1,3-bis[(1-{1-[(1S,2R,6R,7R,8S)-7-(acetylamino)-4,4-dimethyl-3,5,9,11-tetraoxatricyclo [6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)carbamate (I-w-1)

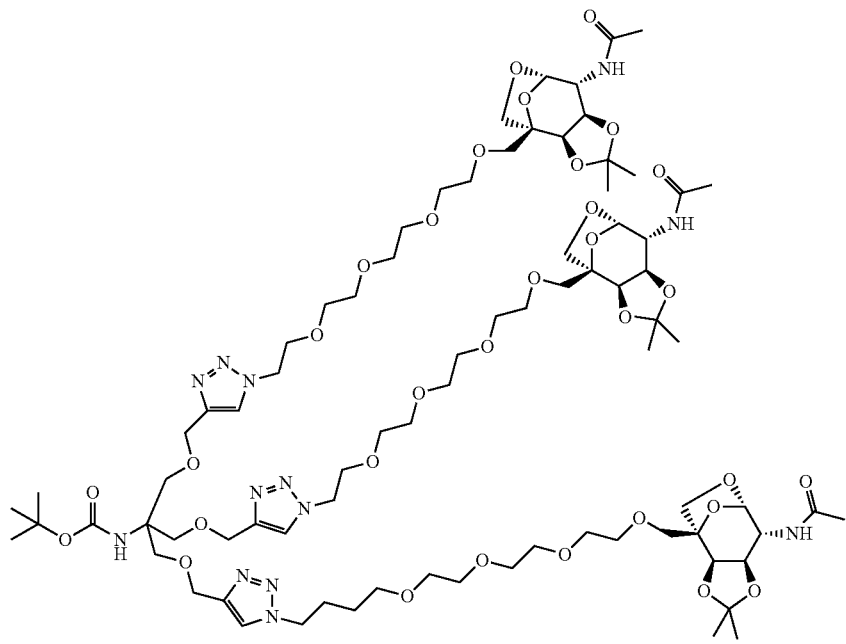 [SMILES: CC(=O)N[C@H]1[C@H]2OC[C@](COCCOCCOCCOCCCCn3cc(COCC(COCc4cn(CCOCCOCCOCCOC[C@@]56CO[C@@H](O5)[C@H](NC(C)=O)[C@H]5OC(C)(C)O[C@H]56)nn4)(COCc4cn(CCOCCOCCOCCOC[C@@]56CO[C@@H](O5)[C@H](NC(C)=O)[C@H]5OC(C)(C)O[C@H]56)nn4)NC(=O)OC(C)(C)C)nn3)(O2)[C@@H]2OC(C)(C)O[C@H]12]

A 50 mL round bottom flask equipped with stir bar was charged with tert-butyl {1,3-bis(prop-2-yn-1-yloxy)-2-[(prop-2-yn-1-yloxy)methyl]propan-2-yl}carbamate (I-f-3) (305.0 mg, 0.909 mmol) was added N-[(1S,2R,6R,7R,8S)-1-(13-azido-2,5,8,11-tetraoxatridec-1-yl)-4,4-dimethyl-3,5,9,11-tetraoxatricyclo[6.2.1.0~2,6~]undec-7-yl]acetamide (1-e-2) (1433.0 mg, 3.020 mmol) in t-butanol (12 mL) followed by the addition of water (5 mL) followed by the addition of sodium ascorbate (1840 mg, 9.09 mmol) neat and the reaction was purged with nitrogen for 10 minutes. Copper (II) sulfate (147 mg, 0.909 mmol) was added in 1 mL of water (deionized) and stirred at room temperature for 24 hours. After 24 hours, the reaction was quenched by adding the reaction mixture to a saturated ammonium chloride (30 mL) and conc. ammonium hydroxide (3 mL) and extracted three times with dichloromethane (20 mL). The combined organic layers were dried over magnesium sulfate, filtered and concentrated under reduced pressure. The crude material was purified using the CombiFlash Rf (RediSep 80 g gold silica gel column) and eluting with a gradient of 0-20% methanol/dichloromethane yielding the title compound as a white foam (789.0 mg, None, 49.3%). Method C: 1.5 minute run LRMS [M+45−1=1804]. $^1$H NMR (METHANOL-$d_4$) δ: 8.00 (s, 3H), 5.23 (d, J=1.6 Hz, 3H), 4.51-4.63 (m, 12H), 4.29 (d, J=5.9 Hz, 3H), 4.16 (t, J=6.4 Hz, 3H), 3.87-3.96 (m, 12H), 3.84 (d, J=7.8 Hz, 3H), 3.73-3.80 (m, 6H), 3.64-3.72 (m, 12H), 3.54-3.63 (m, 30H), 1.98 (s, 9H), 1.48 (s, 9H), 1.40 (s, 9H), 1.33 (s, 9H)

N-(1,3-bis[(1-{1-[(1S,2R,6R,7R,8S)-7-(acety-lamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)-6-(pyridin-2-yldisulfanyl)hexanamide (I-x-1)

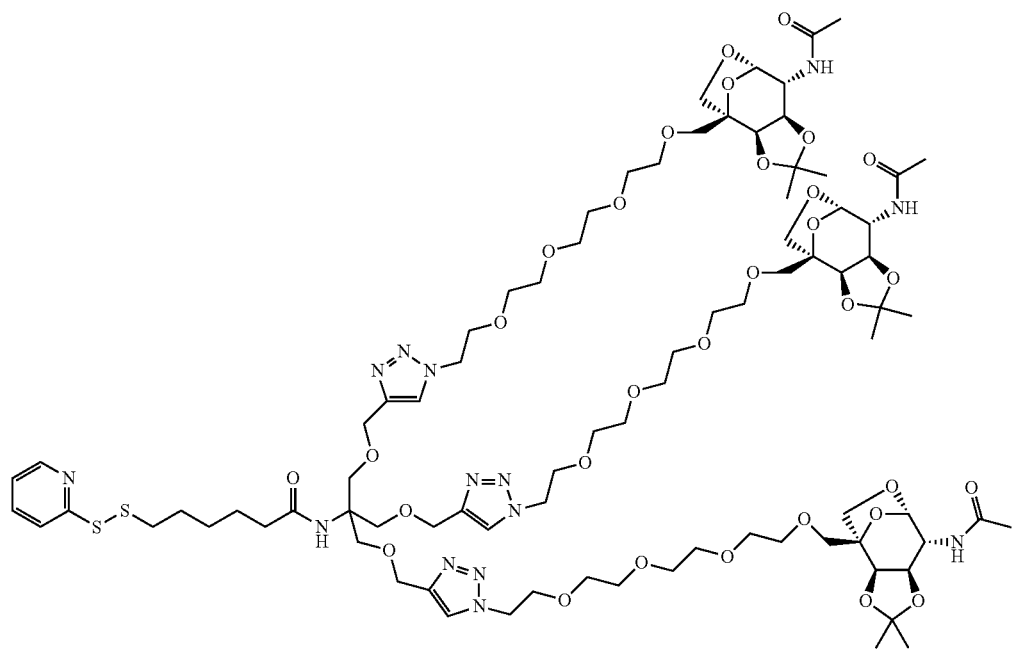 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@H]5OC(C)(C)O[C@H]56)nn4)(COCc4cn(CCOCCOCCOCCOC[C@@]56CO[C@@H](O5)[C@H](NC(C)=O)[C@H]5OC(C)(C)O[C@H]56)nn4)NC(=O)CCCCCSSc4ccccn4)nn3)(O2)[C@@H]2OC(C)(C)O[C@H]12]

To a solution of N-{1,3-bis(prop-2-yn-1-yloxy)-2-[(prop-2-yn-1-yloxy)methyl]propan-2-yl}-6-(pyridin-2-yldisulfanyl)hexanamide (I-t-1) (66.0 mg, 0.14 mmol) and N-[(1S,2R,6R,7R,8S)-1-(13-azido-2,5,8,11-tetraoxatridec-1-yl)-4,4-dimethyl-3,5,9,11-tetraoxatricyclo[6.2.1.0~2,6~]undec-7-yl]acetamide (I-e-2) (219 mg, 0.459 mmol) in t-butanol (2 mL) was added water (0.5 mL, deionized water). Sodium ascorbate (84.3 mg, 0.417 mmol) was added as a solid and the reaction mixture was purged with nitrogen for 5 minutes before the addition of copper (II) sulfate (6.73 mg, 0.0417 mmol) in water (0.5 mL, deionized water) and stirred at room temperature for 24 hours. The reaction was quenched by adding the reaction mixture to a saturated ammonium chloride (20 mL) and conc. ammonium hydroxide (2 mL) and extracted three times with dichloromethane (15 mL). The combined organic layers were washed with brine, dried over magnesium sulfate, filtered and concentrated under reduced pressure. The crude material was purified using the CombiFlash Rf (RediSep 12 g gold silica gel column) and eluting with a gradient of 0-20% methanol/dichloromethane yielding the impure title compound (105.0 mg, None, 40%). The crude (105.0 mg) was purified again using the CombiFlash Rf (RediSep 4 g Gold silica gel column) and eluting with a gradient of 0-20% methanol/dichloromethane yielding the title compound as a gum (94.5 mg, 36%). Method C: MassLynx\Acid_3.0Min.olp—LRMS [M+Na=1921]. $^1$H NMR (METHANOL-d$_4$) δ: 8.38 (d, J=4.7 Hz, 1H), 7.97 (s, 3H), 7.82-7.88 (m, 1H), 7.78-7.81 (m, 1H), 7.20 (t, J=5.9 Hz, 1H), 5.23 (s, 3H), 4.52-4.62 (m, 12H), 4.29 (d, J=5.9 Hz, 3H), 4.15 (t, J=6.4 Hz, 3H), 3.86-3.96 (m, 12H), 3.81-3.85 (m, 3H), 3.72-3.80 (m, 12H), 3.54-3.71 (m, 36H), 2.79 (t, J=7.2 Hz, 2H), 2.16 (t, J=7.2 Hz, 2H), 1.98 (s, 9H), 1.64-1.73 (m, 2H), 1.50-1.57 (m, 2H), 1.48 (s, 9H), 1.42 (d, J=6.6 Hz, 2H), 1.32 (s, 9H)

benzyl {6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}carbamate (I-y-1)

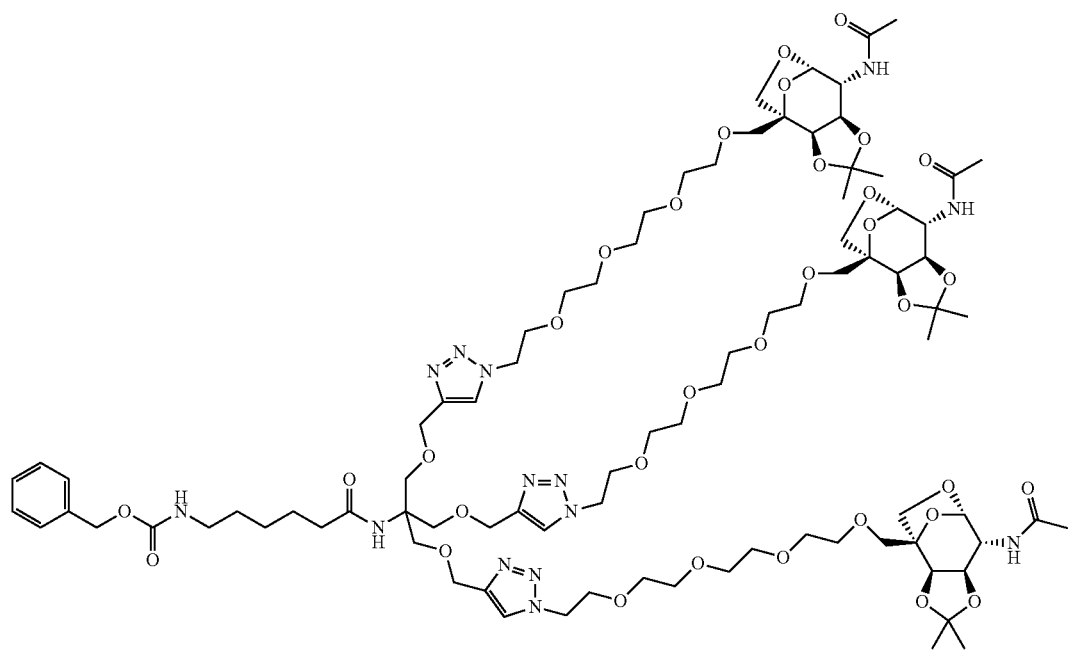 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@H]5OC(C)(C)O[C@H]56)nn4)(COCc4cn(CCOCCOCCOCCOC[C@@]56CO[C@@H](O5)[C@H](NC(C)=O)[C@H]5OC(C)(C)O[C@H]56)nn4)NC(=O)CCCCCNC(=O)OCc4ccccc4)nn3)(O2)[C@@H]2OC(C)(C)O[C@H]12]

A 250 mL round bottom flask equipped with stir bar was charged with benzyl [6-({1,3-bis(prop-2-yn-1-yloxy)-2-[(prop-2-yn-1-yloxy)methyl]propan-2-yl}amino)-6-oxohexyl]carbamate (I-q-1) (880.0 mg, 1.82 mmol) was added N-[(1S,2R,6R,7R,8S)-1-(13-azido-2,5,8,11-tetraoxatridec-1-yl)-4,4-dimethyl-3,5,9,11-tetraoxatricyclo[6.2.1.0~2,6~]undec-7-yl]acetamide (I-e-2) (3075.0 mg, 6.8 mmol) in t-butanol (26 mL) followed by the addition of water (12 mL) followed by the addition of sodium ascorbate (3690 mg, 18.2 mmol) neat and the reaction was purged with nitrogen for 10 minutes. Copper (II) sulfate (294 mg, 1.82 mmol) was added in 1 mL of water and stirred at room temperature for 24 hours. After 24 hours, the reaction was quenched by adding the reaction mixture to a saturated ammonium chloride (50 mL) and conc. ammonium hydroxide (5 mL) and extracted three times with dichloromethane (45 mL). The combined organic layers were dried over magnesium sulfate, filtered and concentrated under reduced pressure. The crude material was purified using the CombiFlash Rf (RediSep 80 g gold silica gel column) and eluting with a gradient of 0-20% methanol/dichloromethane yielding the title compound as a solid (1890.0 mg, 54.4%) and impure title compound. The crude (1270.0 mg, 36.5%) was purified using the CombiFlash Rf (RediSep 80 g gold silica gel column) and eluting with a gradient of 0-20% methanol/dichloromethane yielding the title compound (607.0 mg, 17.5%). Total yield of title compound 2.497 g (72%). Method C: 3 minute run LRMS [M+1=1907]. $^1$H NMR (METHANOL-$d_4$) δ: 7.99 (s, 3H), 7.21-7.47 (m, 5H), 5.25 (d, J=1.6 Hz, 3H), 5.07 (s, 2H), 4.53-4.62 (m, 12H), 4.31 (d, J=5.9 Hz, 3H), 4.18 (t, J=6.4 Hz, 3H), 3.88-3.98 (m, 12H), 3.85 (d, J=7.8 Hz, 3H), 3.74-3.81 (m, 12H), 3.53-3.71 (m, 36H), 3.10 (q, J=6.2 Hz, 2H), 2.18 (t, J=7.2 Hz, 2H), 2.00 (s, 9H), 1.53-1.65 (m, 2H), 1.50 (s, 11H), 1.34 (s, 11H)

N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)-6-(pyridin-2-yldisulfanyl)hexanamide (41)

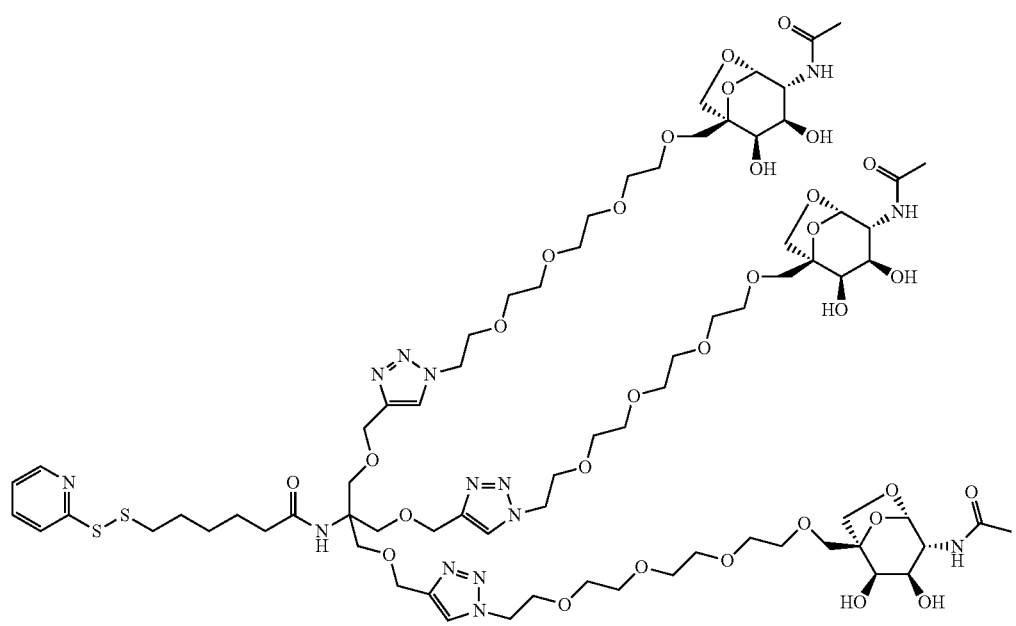 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCSSc4ccccn4)nn3)(O2)[C@H](O)[C@@H]1O]

A solution of N-(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)-6-(pyridin-2-yldisulfanyl)hexanamide (I-x-1) (94.5 mg, 0.0498 mmol) in acetic acid (4 mL), methanol (1 mL) and water (1.0 mL) was heated to 70° C. for 64 hours. After 64 hours, the reaction was cooled to room temperature and concentrated under reduced pressure. The crude material was diluted with toluene and concentrated under reduced pressure. The crude material was diluted with toluene a second time and concentrated under reduced pressure yielding impure title compound as a gum (85.3 mg). The crude material was purified using reverse phase chromatography using the conditions below yielding the title compound as a gum (47.6 mg, 53.8%).

Purification Conditions:

The residue was dissolved in dimethyl sulfoxide (1 mL) and purified by reversed-phase HPLC. Column: Waters Sunfire C18 19×100, 5 u; Mobile phase A: 0.05% TFA in water (v/v); Mobile phase B: 0.05% TFA in acetonitrile (v/v); Gradient: 80.0% H2O/20.0% Acetonitrile linear to 65% H2O/35% Acetonitrile in 8.5 min to 0% H2O/100% MeCN to 9.0 min, Hold at 0% H2O/100% Acetonitrile from 9.0 to 10.0 min. Flow: 25 mL/min. Yielding 47.6 mg of the title compound as a gum (retention time 2.87, mass observed=890.4376).

QC Conditions:

Column: Waters Atlantis dC18 4.6×50, 5 u; Mobile phase A: 0.05% TFA in water (v/v); Mobile phase B: 0.05% TFA in acetonitrile (v/v); 95.0% H2O/5.0% Acetonitrile linear to 50% H2O/50% Acetonitrile in 3.75 min, to 5% H2O/95% Acetonitrile to 4.0 min, Hold at 5% H2O/95% Acetonitrile from 4.0 min to 5.0 min. Flow: 2 mL/min. Retention time=2.87; Mass observed=890.4376. Method C: 3 minute run LRMS [½M=889]. $^1$H NMR (METHANOL-$d_4$) δ: 8.41 (d, J=4.7 Hz, 1H), 7.99 (s, 3H), 7.84-7.91 (m, 2H), 7.26 (t, J=5.9 Hz, 1H), 5.21 (s, 3H), 4.58 (t, J=5.0 Hz, 6H), 4.56 (s, 6H), 3.95 (t, J=8.8 Hz, 6H), 3.89 (t, J=5.0 Hz, 6H), 3.86-3.88 (m, 3H), 3.74-3.78 (m, 9H), 3.71 (dd, J=9.4, 4.1 Hz, 3H), 3.54-3.67 (m, 42H), 2.80 (t, J=7.0 Hz, 2H), 2.16 (t, J=7.3 Hz, 2H), 1.99 (s, 9H), 1.68 (quin, J=7.3 Hz, 2H), 1.50-1.57 (m, 2H), 1.35-1.44 (m, 2H)

N-[(1S,2R,3R,4R,5S)-1-(13-{4-[(3-[(1-{1-[(1S,2R, 3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl) methoxy]methyl}-2-aminopropoxy)methyl]-1H-1,2, 3-triazol-1-yl}-2,5,8,11-tetraoxatridec-1-yl)-2,3-dihydroxy-6,8-dioxabicyclo[3.2.1]oct-4-yl] acetamide-hydrochloric acid salt (42)

A solution of tert-butyl (1,3-bis[(1-{1-[(1S,2R,6R,7R, 8S)-7-(acetylamino)-4,4-dimethyl-3,5,9,11-tetraoxatricyclo [6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R, 7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy] methyl}propan-2-yl)carbamate (I-w-1) (210 mg, 0.119 mmol) in acetic acid (8.0 mL), methanol (2.0 mL) and Water (2.0 mL) was heated to 70° C. overnight. After 18 hours, the reaction was cooled to room temperature and concentrated under reduced pressure. The crude material was diluted with toluene and methanol and concentrated under reduced pressure. The crude material was diluted with toluene a second time and concentrated under reduced pressure. The crude material was diluted with dichloromethane (10 mL) and methanol (4 mL) to which was added 4.0M hydrogen chloride in dioxane (2.0 mL, 8 mmol). The reaction mixture was stirred at room temperature overnight After 18 hours, the reaction was concentrated under reduced pressure. The crude material was diluted with ethyl acetate (1 mL) and to which was added heptane (10 mL) and concentrated under reduced pressure. The material was then placed under high vacuum for 18 hours yielding the title compound as a solid (198.8 mg, 106%). Method C: 3 minute run LRMS [M+Na=1561]. $^1$H NMR (METHANOL-$d_4$) δ: 8.13-8.21 (m, 3H), 5.22 (s, 3H), 4.71 (s, 9H), 4.65 (d, J=4.7 Hz, 6H), 3.92-4.00 (m, 12H), 3.90 (d, J=4.3 Hz, 3H), 3.58-3.80 (m, 51H), 2.02 (s, 9H) 6-azido-N-(1,3-bis[(1-{1-[(1S,2R,3R,4R, 5S)-4-(acetylamino)-2,3-dihydroxy-6,8-dioxabicyclo[3.2.1] oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl) methoxy]methyl}propan-2-yl)hexanamide (43)

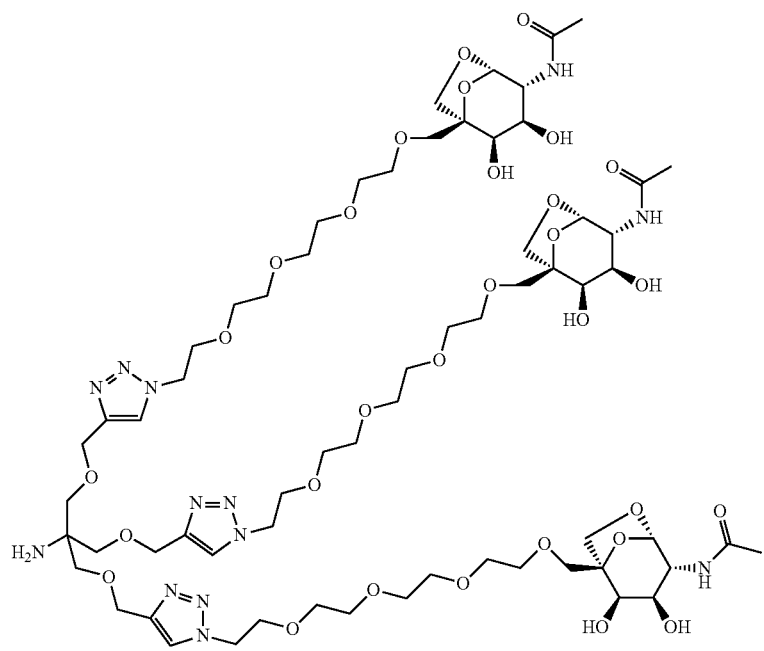 [SMILES: CC(=O)N[C@H]1[C@H]2OC[C@](COCCOCCOCCOCCn3cc(COCC(N)(COCc4cn(CCOCCOCCOCCOC[C@@]56CO[C@@H](O5)[C@H](NC(C)=O)[C@@H](O)[C@H]6O)nn4)COCc4cn(CCOCCOCCOCCOC[C@@]56CO[C@@H](O5)[C@H](NC(C)=O)[C@@H](O)[C@H]6O)nn4)nn3)(O2)[C@H](O)[C@@H]1O]

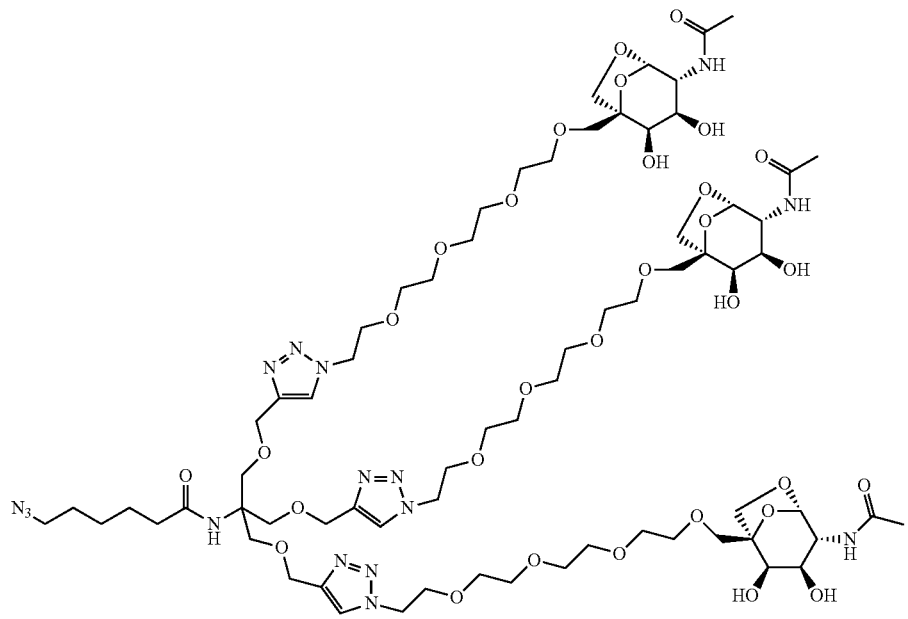 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCN=[N+]=[N-])nn3)(O2)[C@H](O)[C@@H]1O]

To a solution of N-[(1S,2R,3R,4R,5S)-1-(13-{4-[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}-2-aminopropoxy)methyl]-1H-1,2,3-triazol-1-yl}-2,5,8,11-tetraoxatridec-1-yl)-2,3-dihydroxy-6,8-dioxabicyclo[3.2.1]oct-4-yl]acetamide-hydrochloric acid salt (42) (25 mg, 0.016 mmol) in N,N-dimethylformamide (0.5 mL) was added N,N-diisopropylethylamine (0.0111 mL, 0.0635 mmol) and was allowed to stir for 10 minutes before being added to neat 1-[(6-azidohexanoyl)oxy]pyrrolidine-2,5-dione

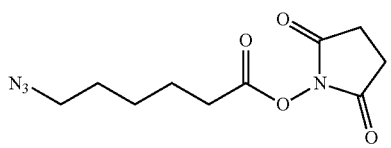 [SMILES: [N-]=[N+]=NCCCCCC(=O)ON1C(=O)CCC1=O]

(see PCT Int. Appl., 2011034951, 24 Mar. 2011, 6.05 mg, 0.0238 mmol) and the reaction was allowed to stir at room temperature for 18 hours. The reaction was then heated to 60° C. for 32 hours. After 32 hours, the reaction was concentrated under reduced pressure. The crude material was diluted with dimethylsulfoxide (1 mL) and passed through a syringe filter and the crude material was purified using reverse-phase chromatography using the conditions seen below yielding the title compound as a gum (6.2 mg, 23%).

Purification Conditions

The residue was dissolved in dimethyl sulfoxide (1 mL) and purified by reversed-phase HPLC (Column: Waters Sunfire C18 19×100, 5 u; Mobile phase A: 0.05% TFA in water (v/v); Mobile phase B: 0.05% TFA in acetonitrile (v/v); 90.0% H2O/10.0% Acetonitrile linear to 70% H2O/30% Acetonitrile in 10.5 min, 70% H2O/30% Acetonitrile linear to 0% H2O/100% MeCN in 0.5 min, Hold at 0% H2O/100% Acetonitrile from 11.0 min to 12.0 min. Flow: 25 mL/min.

QC Conditions

Column: Waters Atlantis dC18 4.6×50, 5 u; Mobile phase A: 0.05% TFA in water (v/v); MobCe phase B: 0.05% TFA in acetonitrile (v/v); 95.0% H2O/5.0% Acetonitrile linear to 5% H2O/95% Acetonitrile in 4.0 min, Hold at 5% H2O/95% Acetonitrile from 4.0 min to 5.0 min. Flow: 2 mL/min.; Retention time=1.77 minutes; Mass observed=839.7097. Method C: 3 minute run LRMS [M+1=1678]. $^1$H NMR (METHANOL-$d_4$) δ: 8.00 (s, 3H), 5.21 (s, 3H), 4.58 (t, J=4.7 Hz, 6H), 4.57 (s, 6H), 3.95 (t, J=10.0 Hz, 6H), 3.85-3.92 (m, 9H), 3.74-3.80 (m, 9H), 3.71 (dd, J=10.0, 4.1 Hz, 3H), 3.55-3.68 (m, 42H), 3.25 (t, J=6.5 Hz, 2H), 2.19 (t, J=7.3 Hz, 2H), 1.99 (s, 9H), 1.52-1.62 (m, 4H), 1.33-1.41 (m, 2H)

N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hept-6-enamide (44)

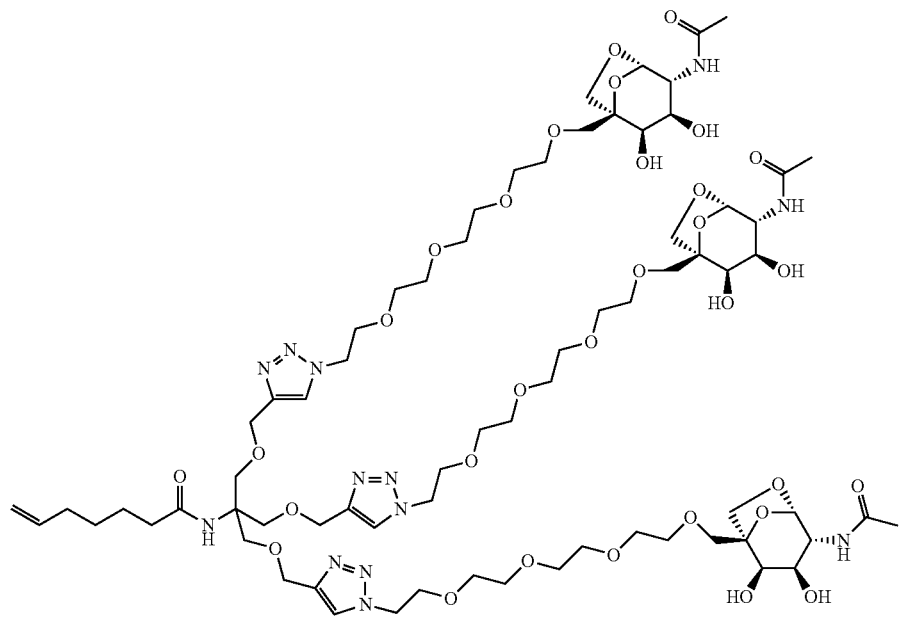 [SMILES: C=CCCCCC(=O)NC(COCc1cn(CCOCCOCCOCCOC[C@@]23CO[C@@H](O2)[C@H](NC(C)=O)[C@@H](O)[C@H]3O)nn1)(COCc1cn(CCOCCOCCOCCOC[C@@]23CO[C@@H](O2)[C@H](NC(C)=O)[C@@H](O)[C@H]3O)nn1)COCc1cn(CCOCCOCCOCCOC[C@@]23CO[C@@H](O2)[C@H](NC(C)=O)[C@@H](O)[C@H]3O)nn1]

To a solution of N-[(1S,2R,3R,4R,5S)-1-(13-{4-[(3-[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}-2-aminopropoxy)methyl]-1H-1,2,3-triazol-1-yl}-2,5,8,11-tetraoxatridec-1-yl)-2,3-dihydroxy-6,8-dioxabicyclo[3.2.1]oct-4-yl]acetamide-hydrochloric acid salt (42) (25 mg, 0.016 mmol) in N,N-dimethylformamide (0.5 mL) was added N,N-diisopropylethylamine (0.0111 mL, 0.0635 mmol) and was allowed to stir for 10 minutes before being added to neat 1-(hept-6-enoyloxy)pyrrolidine-2,5-dione (see Angewandte Chemie, International Edition, 51(25), 6144-6148, S6144/1-S6144/53; 2012, 5.36 mg, 0.0238 mmol) and the reaction was allowed to stir at room temperature for 18 hours. The reaction was then heated to 60° C. for 32 hours. After 32 hours, the reaction was concentrated under reduced pressure. The crude material was diluted with dimethylsulfoxide (1 mL) and passed through a syringe filter and the crude material was purified using reverse-phase chromatography using the conditions seen below yielding the title compound as a gum (4.9 mg, 19%).

Purification Conditions:

The residue was dissolved in dimethyl sulfoxide (1 mL) and purified by reversed-phase HPLC (Column: Waters Sunfire C18 19×100, 5 u; Mobile phase A: 0.05% TFA in water (v/v); Mobile phase B: 0.05% TFA in acetonitrile (v/v); 95.0% H2O/5.0% Acetonitrile linear to 55% H2O/45% Acetonitrile in 10.5 min, 55% H2O/45% Acetonitrile linear to 0% H2O/100% MeCN in 0.5 min, Hold at 0% H2O/100% Acetonitrile from 11.0 min to 12.0 min. Flow: 25 mL/min.

QC Conditions:

Column: Waters Atlantis dC18 4.6×50, 5 u; Mobile phase A: 0.05% TFA in water (v/v); Mobile phase B: 0.05% TFA in acetonitrile (v/v); 95.0% H2O/5.0% Acetonitrile linear to 5% H2O/95% Acetonitrile in 4.0 min, Hold at 5% H2O/95% Acetonitrile from 4.0 min to 5.0 min. Flow: 2 mL/min.; Retention time=1.81; mass observed=825.2381). Method C: 3 minute run LRMS [M−1=1647]. $^1$H NMR (METHANOL-$d_4$) δ: 7.99 (s, 3H), 5.69-5.88 (m, 1H), 5.21 (s, 3H), 4.95 (m, 2H), 4.51-4.63 (m, 12H), 3.95 (t, J=9.7 Hz, 6H), 3.85-3.91 (m, 9H), 3.74-3.81 (m, 9H), 3.71 (dd, J=9.4, 4.1 Hz, 3H), 3.54-3.68 (m, 42H), 2.17 (t, J=7.3 Hz, 2H), 2.01-2.09 (m, 2H), 1.99 (s, 9H), 1.52-1.61 (m, 2H), 1.39 (quin, J=7.5 Hz, 2H)

N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hept-6-ynamide (45)

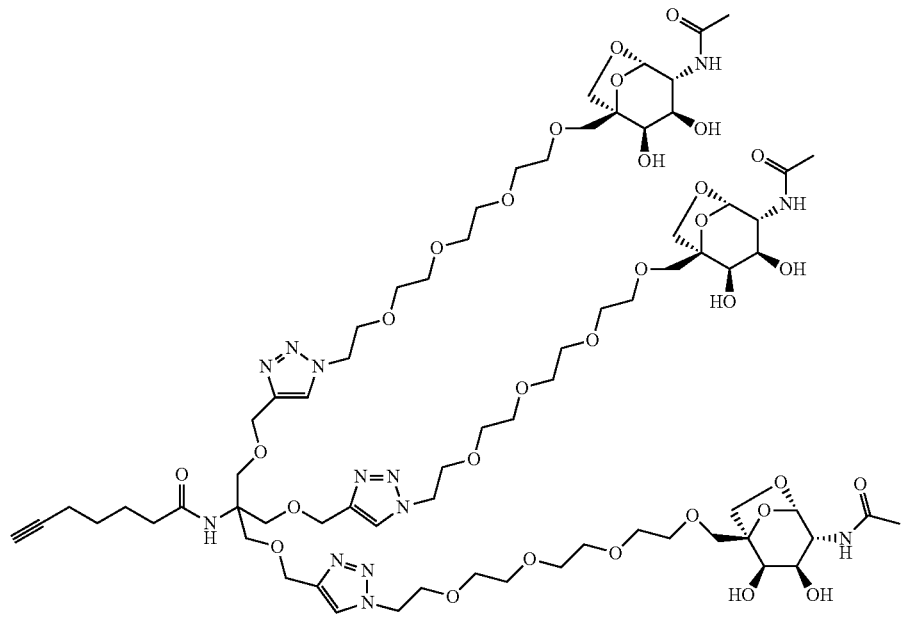 [SMILES: C#CCCCCC(=O)NC(COCc1cn(CCOCCOCCOCCOC[C@@]23CO[C@@H](O2)[C@H](NC(C)=O)[C@@H](O)[C@H]3O)nn1)(COCc1cn(CCOCCOCCOCCOC[C@@]23CO[C@@H](O2)[C@H](NC(C)=O)[C@@H](O)[C@H]3O)nn1)COCc1cn(CCOCCOCCOCCOC[C@@]23CO[C@@H](O2)[C@H](NC(C)=O)[C@@H](O)[C@H]3O)nn1]

To a solution of N-[(1S,2R,3R,4R,5S)-1-(13-{4-[(3-[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}-2-aminopropoxy)methyl]-1H-1,2,3-triazol-1-yl}-2,5,8,11-tetraoxatridec-1-yl)-2,3-dihydroxy-6,8-dioxabicyclo[3.2.1]oct-4-yl]acetamide-hydrochloric acid salt (42) (25 mg, 0.016 mmol) in N,N-dimethylformamide (0.5 mL) was added N,N-diisopropylethylamine (0.0111 mL, 0.0635 mmol) and was allowed to stir for 10 minutes before being added to neat 1-(hept-6-ynoyloxy)pyrrolidine-2,5-dione

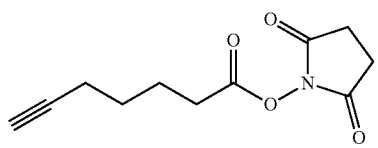 [SMILES: C#CCCCCC(=O)ON1C(=O)CCC1=O]

(see PCT Int. Appl., 2007056389, 18 May 2007, 5.31 mg, 0.0238 mmol) and the reaction was allowed to stir at room temperature for 18 hours. The reaction was then heated to 60° C. for 32 hours. After 32 hours, the reaction was concentrated under reduced pressure. The crude material was diluted with dimethylsulfoxide (1 mL) and passed through a syringe filter and the crude material was purified using reverse-phase chromatography using the conditions seen below yielding the title compound as a gum (5 mg, 19%).

Purification Conditions:

The residue was dissolved in dimethyl sulfoxide (1 mL) and purified by reversed-phase HPLC (Column: Waters Sunfire C18 19×100, 5 u; Mobile phase A: 0.05% TFA in water (v/v); Mobile phase B: 0.05% TFA in acetonitrile (v/v); 95.0% H2O/5.0% Acetonitrile linear to 55% H2O/45% Acetonitrile in 10.5 min, 55% H2O/45% Acetonitrile linear to 0% H2O/100% MeCN in 0.5 min, Hold at 0% H2O/100% Acetonitrile from 11.0 min to 12.0 min. Flow: 25 mL/min.

QC Conditions:

Column: Waters Atlantis dC18 4.6×50, 5 u; Mobile phase A: 0.05% TFA in water (v/v); Mobile phase B: 0.05% TFA in acetonitrile (v/v); 95.0% H2O/5.0% Acetonitrile linear to 5% H2O/95% Acetonitrile in 4.0 min, Hold at 5% H2O/95% Acetonitrile from 4.0 min to 5.0 min. Flow: 2 mL/min.; Retention time=1.68; Mass observed=824.2237. Method C: 3 minute run LRMS [½M=823]. $^1$H NMR (METHANOL-$d_4$) δ: 7.99 (s, 3H), 5.21 (s, 3H), 4.59 (t, J=5.0 Hz, 6H), 4.56 (s, 6H), 3.95 (t, J=10.0 Hz, 6H), 3.85-3.92 (m, 9H), 3.74-3.79 (m, 9H), 3.71 (dd, J=10.0, 4.1 Hz, 3H), 3.54-3.67 (m, 41H), 2.13-2.24 (m, 6H), 1.99 (s, 9H), 1.66 (quin, J=7.5 Hz, 2H), 1.50 (quin, J=7.3 Hz, 2H)

ethyl 7-[(2,5-dioxopyrrolidin-1-yl)oxy]-7-oxoheptanoate (I-z-1)

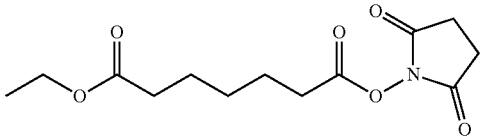 [SMILES: CCOC(=O)CCCCCC(=O)ON1C(=O)CCC1=O]

To a solution of 7-ethoxy-7-oxoheptanoic acid

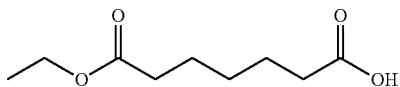

(448 mg, 2.38 mmol) in N,N-dimethylformamide (6.0 mL) was added N-Hydroxysuccinimide (329 mg, 2.86 mmol) followed by N-(3-dimethylaminopropyl)-N'-ethylcarbodiimide hydrochloride (559 mg, 2.86 mmol). The reaction was allowed to stir at room for 72 hours. After 72 hours, the reaction was quenched with water and extracted three times with dichloromethane. The combined organic layers were washed with saturated sodium bicarbonate, brine, dried over sodium sulfate, filtered and concentrated under reduced pressure. The crude material was purified using the CombiFlash Rf (RediSep 40 g gold column) and eluting with a gradient of 0-100% ethyl acetate/heptane yielding the title compound as a gum (426 mg, 63%). Method C: 1.5 minute run LRMS [M+Na=308]. $^1$H NMR (METHANOL-d$_4$) δ: 4.12 (q, J=7.0 Hz, 2H), 2.83 (s, 4H), 2.64 (t, J=7.2 Hz, 2H), 2.33 (t, J=7.2 Hz, 2H), 1.74 (quin, J=7.4 Hz, 2H), 1.58-1.68 (m, 2H), 1.40-1.53 (m, 2H), 1.24 (t, J=7.0 Hz, 3H).

7-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-7-oxoheptanoic acid (Sodium salt) (46)

To a solution of N-[(1S,2R,3R,4R,5S)-1-(13-{4-[(3-[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo [3.2.1]oct-1-yl]-2,5,8,11-tetraoxatridecan-13-yl}-1H-1,2,3-triazol-4-yl)methoxy]methyl]-2-aminopropoxy)methyl]-1H-1,2,3-triazol-1-yl]-2,5,8,11-tetraoxatridec-1-yl)-2,3-dihydroxy-6,8-dioxabicyclo[3.2.1]oct-4-yl]acetamide-hydrochloric acid salt (42) (30.0 mg, 0.019 mmol) in N,N-dimethylformamide (0.5 mL) was added N,N-diisopropylethylamine (0.0133 mL, 0.0762 mmol) and was allowed to stir for 10 minutes before being added to neat ethyl 7-[(2,5-dioxopyrrolidin-1-yl)oxy]-7-oxoheptanoate (I-z-1) (7.4 mg, 0.026 mmol) and the reaction was allowed to stir at room temperature for 18 hours. The reaction was then heated to 60° C. for 32 hours. After 32 hours, the reaction was cooled to room temperature and concentrated under reduced pressure. The crude material was diluted with ethanol (1 mL) and water (0.03 mL) followed by the addition of 12.5M sodium hydroxide aqueous solution (0.015 mL, 0.190 mmol). The reaction was allowed to stir for 3 hours at room temperature. After 3 hours, the reaction was concentrated under reduced pressure. The crude material was diluted with dimethylsulfoxide (1 mL) and filtered through a syringe filter. The solution was purified using reverse-phase chromatography using the conditions below yielding the title compound as a gum (3.7 mg, 11%).

Purification Conditions le;3qThe residue was dissolved in dimethyl sulfoxide (1 mL) and purified by reversed-phase HPLC (Column: Waters Sunfire C18 19×100, 5 u; Mobile phase A: 0.05% TFA in water (v/v); Mobile phase B: 0.05% TFA in acetonitrile (v/v); 90.0% H2O/10.0% Acetonitrile linear to 70% H2O/30% Acetonitrile in 10.5 min, 70% H2O/30% Acetonitrile linear to 0% H2O/100% MeCN in 0.5 min, Hold at 0% H2O/100% Acetonitrile from 11.0 min to 12.0 min. Flow: 25 mL/min.

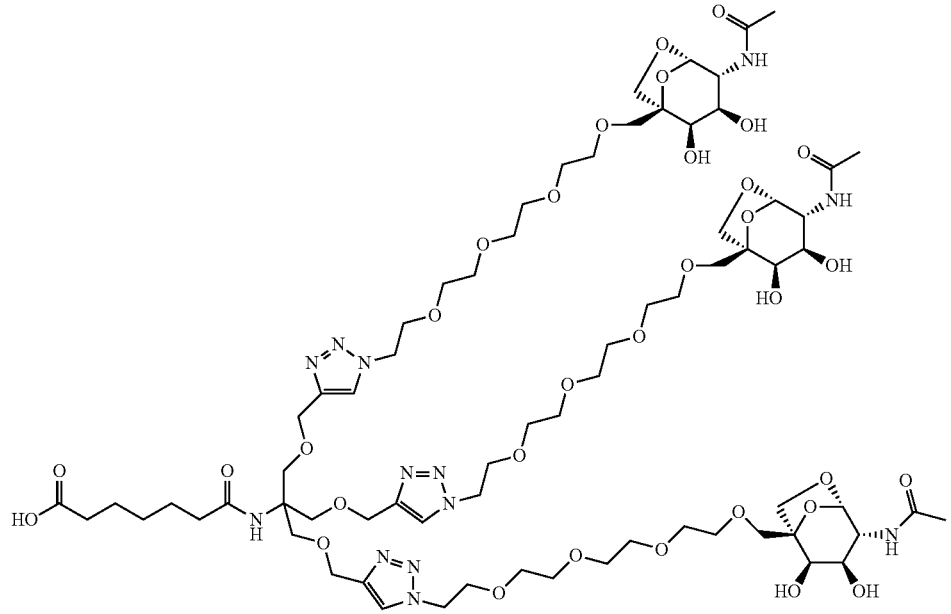 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCC(=O)O)nn3)(O2)[C@H](O)[C@@H]1O]

QC Conditions

Column: Waters Atlantis dC18 4.6×50, 5 u; Mobile phase A: 0.05% TFA in water (v/v); Mobile phase B: 0.05% TFA in acetonitrile (v/v); 95.0% H2O/5.0% Acetonitrile linear to 5% H2O/95% Acetonitrile in 4.0 min, Hold at 5% H2O/95% Acetonitrile from 4.0 min to 5.0 min. Flow: 2 mL/min.;

retention time=1.58 minutes; Mass observed=839.7097). Method C: MassLynx\Acid_3.0Min.olp—LRMS [M+1=1681]. $^1$H NMR (METHANOL-$d_4$) δ: 7.99 (s, 3H), 5.21 (s, 3H), 4.58 (t, J=4.7 Hz, 6H), 4.56 (s, 6H), 3.95 (t, J=9.7 Hz, 6H), 3.89 (dt, J=9.8, 4.8 Hz, 9H), 3.74-3.79 (m, 9H), 3.71 (dd, J=10.0, 4.1 Hz, 3H), 3.53-3.67 (m, 42H), 2.25 (t, J=7.3 Hz, 2H), 2.17 (t, J=7.3 Hz, 2H), 1.99 (s, 9H), 1.58 (dquin, J=14.3, 7.3 Hz, 4H), 1.31-1.39 (m, 2H)

benzyl {6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}carbamate (47)

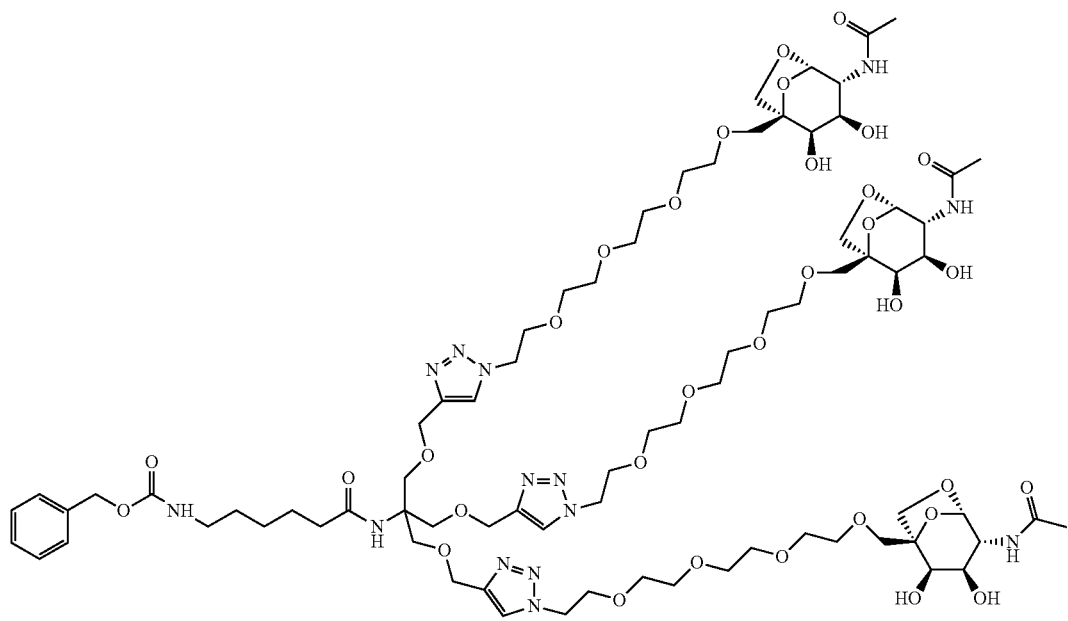 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCNC(=O)OCc4ccccc4)nn3)(O2)[C@H](O)[C@@H]1O]

A solution of benzyl {6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}carbamate (I-y-1) (308 mg, 0.162 mmol) in acetic acid (6 mL), methanol (1.5 mL) and water (1.5 mL) was heated to 70° C. for 64 hours. After 64 hours, the reaction was cooled to room temperature and concentrated under reduced pressure. The crude material was diluted with toluene and concentrated under reduced pressure. The crude material was diluted with toluene a second time and concentrated under reduced pressure yielding the title compound (286 mg, None, 99%). Method C: 1.5 minute run LRMS [M+1=1787]. $^1$H NMR (METHANOL-$d_4$) δ: 7.98 (s, 3H), 7.19-7.43 (m, 5H), 5.21 (s, 3H), 5.06 (s, 2H), 4.50-4.66 (m, 12H), 3.95 (dd, J=9.6, 5.7 Hz, 6H), 3.86-3.91 (m, 9H), 3.74-3.78 (m, 9H), 3.71 (dd, J=10.0, 4.1 Hz, 3H), 3.54-3.67 (m, 42H), 3.03-3.12 (m, 2H), 2.11-2.24 (m, 2H), 1.98 (s, 9H), 1.51-1.63 (m, 2H), 1.43-1.51 (m, 2H), 1.33 (d, J=6.6 Hz, 2H).

6-amino-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl) hexanamide acetate salt (48)

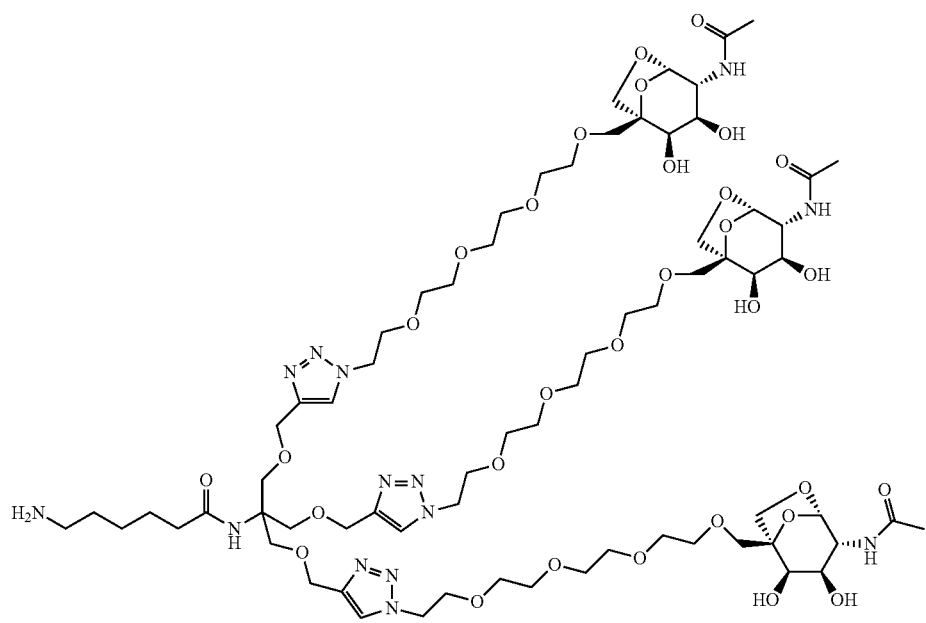 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCN)nn3)(O2)[C@H](O)[C@@H]1O]

Benzyl {6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}carbamate (47) (640 mg, 0.358 mmol) was dissolved in methanol (20.0 mL) and acetic acid (0.041 mL, 0.717 mmol). The solution was then passed through the H-cube using a 10% palladium on carbon (small cartridge) using the following parameters (temperature=50° C., flow rate=1.0 mL/min., pressure=Full $H_2$ (1 bar)). The solution was collected and concentrated under reduced pressure yielding the title compound as white foam (572 mg, 93%). Method C: 3 minute run LRMS [M+1=1652]. $^1$H NMR (METHANOL-$d_4$) δ: 8.00 (s, 3H), 5.21 (s, 3H), 4.59 (t, J=4.9 Hz, 6H), 4.56 (s, 6H), 3.95 (d, J=9.8 Hz, 6H), 3.85-3.92 (m, 9H), 3.74-3.79 (m, 9H), 3.69-3.74 (m, 3H), 3.55-3.69 (m, 42H), 2.91 (t, J=7.6 Hz, 2H), 2.20 (t, J=7.2 Hz, 2H), 1.99 (s, 9H), 1.90 (s, 3H), 1.52-1.68 (m, 4H), 1.34-1.43 (m, 2H)

N-{6-[(1,3-bis[(1-{1-[(1S,2R,3R,4R,5 S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}-6-(2,5-dioxo-2,5-dihydro-1H-pyrrol-1-yl)hexanamide (49)

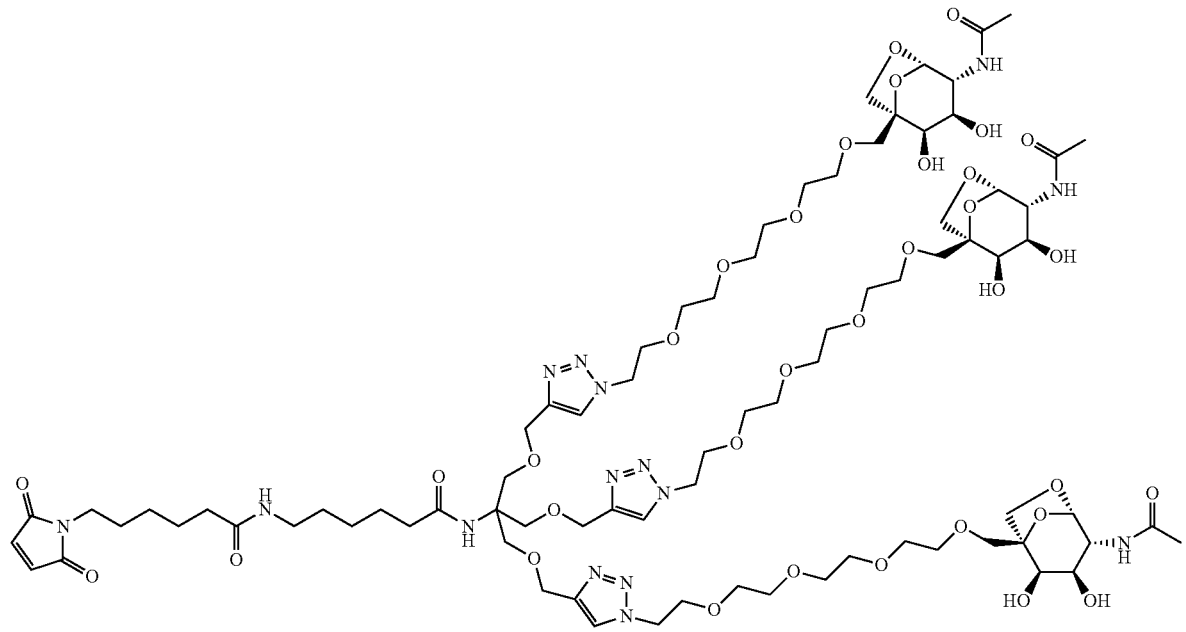 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCNC(=O)CCCCCN4C(=O)C=CC4=O)nn3)(O2)[C@H](O)[C@@H]1O]

To a solution of 6-amino-N-(1,3-bis[(1-{1-[(1 S,2R,3R,4R,5 S)-4-(acetylamino)-2,3-dihydroxy-6, 8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hexanamide (48) (60 mg, 0.036 mmol) in N,N-dimethylformamide (0.5 mL) and tetrahydrofuran (0.5 mL) was added N,N-diisopropylethylamine (0.0253 mL, 0.145 mmol) and 1-{6-[(2,5-dioxopyrrolidin-1-yl)oxy]-6-oxohexyl}-1H-pyrrole-2,5-dione

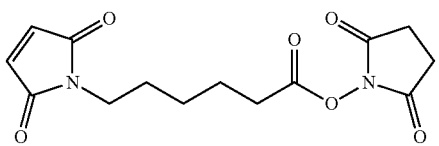 [SMILES: O=C(CCCCCN1C(=O)C=CC1=O)ON1C(=O)CCC1=O]

(12.3 mg, 0.040 mmol) room temperature 16 hours. After 16 hours, the reaction was concentrated under reduced pressure. The crude material was purified using reverse-phase chromatography using the conditions below yielding title compound as a gum (15.4 mg, 23%).

Purification Conditions

The residue was dissolved in dimethyl sulfoxide (1 mL) and purified by reversed-phase HPLC Column: Waters Sunfire C18 19×100, 5 u; Mobile phase A: 0.05% TFA in water (v/v); Mobile phase B: 0.05% TFA in acetonitrile (v/v); Gradient: 80.0% H2O/20.0% Acetonitrile linear to 75% H2O/25% Acetonitrile in 10.5 min to 0% H2O/100% MeCN to 11.0 min, Hold at 0% H2O/100% Acetonitrile from 11.0 to 12.0 min. Flow: 25 mL/min.

QC Conditions

Column: Waters Atlantis dC18 4.6×50, 5 u; Mobile phase A: 0.05% TFA in water (v/v); Mobile phase B: 0.05% TFA in acetonitrile (v/v); Gradient: 95.0% H2O/5.0% Acetonitrile linear to 5% H2O/95% Acetonitrile in 4.0 min, Hold at 5% H2O/95% Acetonitrile from 4.0 min to 5.0 min. Flow: 2 mL/min.; Retention time=1.69 minutes; mass observed=923.4907. Method C: 3 minute run LRMS [M–1=1843]. $^1$H NMR (METHANOL-$d_4$) δ: 8.00 (s, 3H), 6.80 (s, 2H), 5.21 (s, 3H), 4.59 (t, J=5.0 Hz, 6H), 4.56 (s, 6H), 3.95 (t, J=9.7 Hz, 6H), 3.90 (t, J=5.0 Hz, 6H), 3.88 (d, J=4.1 Hz, 3H), 3.74-3.79 (m, 9H), 3.71 (dd, J=10.0, 4.1 Hz, 3H), 3.55-3.68 (m, 42H), 3.48 (t, J=7.0 Hz, 2H), 3.12 (t, J=7.0 Hz, 2H), 2.11-2.23 (m, 4H), 1.99 (s, 9H), 1.53-1.66 (m, 6H), 1.48 (quin, J=7.2 Hz, 2H), 1.24-1.36 (m, 4H)

N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}-6-[(bromoacetyl)amino]hexanamide (50)

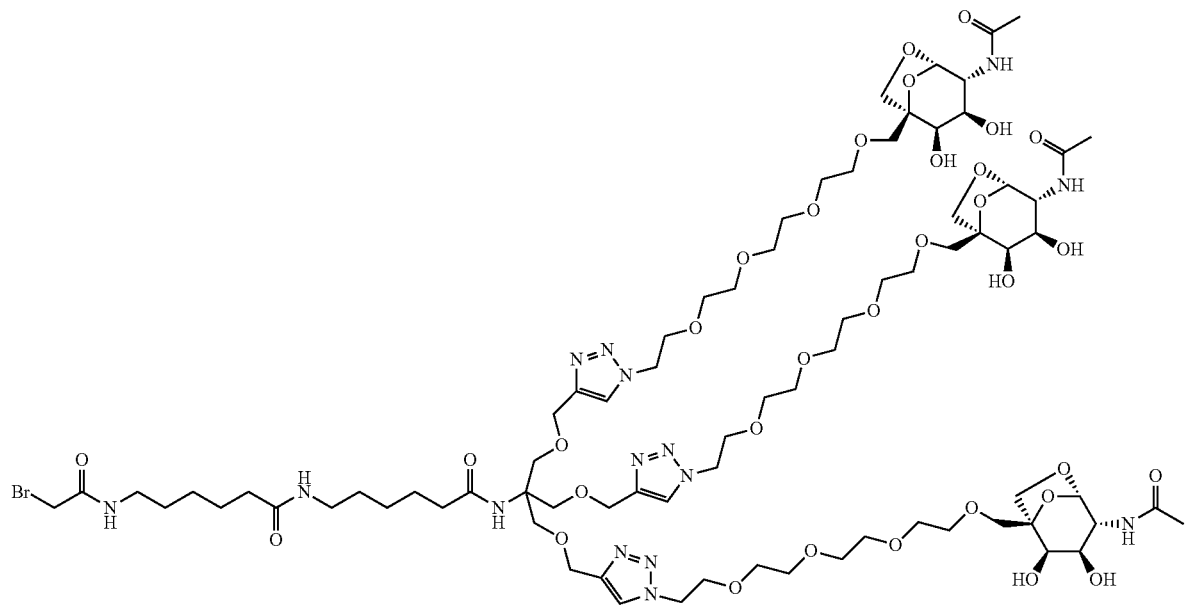 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCNC(=O)CCCCCNC(=O)CBr)nn3)(O2)[C@H](O)[C@@H]1O]

To a solution of 6-amino-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hexanamide (48) (60 mg, 0.036 mmol) in N,N-dimethylformamide (0.5 mL) and tetrahydrofuran (0.5 mL) was added N,N-diisopropylethylamine (0.0253 mL, 0.145 mmol) and pentafluorophenyl 6-[(bromoacetyl)amino]hexanoate

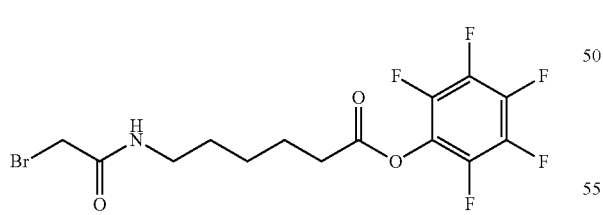

(see Chemistry—A European Journal, 14(16), 4939-4947; 2008, 16.7 mg, 0.0400 mmol) room temperature 16 hours. After 16 hours, the reaction was concentrated under reduced pressure. The crude material was purified using reverse-phase chromatography using the conditions below yielding the title compound as a gum (4.4 mg, 6.4%). Mass observed: 944.1543

Purification Conditions

The residue was dissolved in dimethyl sulfoxide (1 mL) and purified by reversed-phase HPLC Column: Waters Sunfire C18 19×100, 5 u; Mobile phase A: 0.05% TFA in water (v/v); Mobile phase B: 0.05% TFA in acetonitrile (v/v); Gradient: 80.0% H2O/20.0% Acetonitrile linear to 75% H2O/25% Acetonitrile in 10.5 min to 0% H2O/100% MeCN to 11.0 min, Hold at 0% H2O/100% Acetonitrile from 11.0 to 12.0 min. Flow: 25 mL/min.

QC Conditions

Column: Waters Atlantis dC18 4.6×50, 5 u; Mobile phase A: 0.05% TFA in water (v/v); Mobile phase B: 0.05% TFA in acetonitrile (v/v); Gradient: 95.0% H2O/5.0% Acetonitrile linear to 5% H2O/95% Acetonitrile in 4.0 min, Hold at 5% H2O/95% Acetonitrile from 4.0 min to 5.0 min. Flow: 2 mL/min.; Retention time=1.64 minutes; mass observed=944.1543. Method C: 3 minute run LRMS [M+1=1886]. $^1$H NMR (METHANOL-$d_4$) δ: 7.99 (s, 3H), 5.21 (s, 3H), 4.57-4.62 (m, 6H), 4.56 (s, 6H), 3.92-3.98 (m, 6H), 3.83-3.91 (m, 10H), 3.80 (s, 2H), 3.69-3.79 (m, 12H), 3.54-3.68 (m, 43H), 3.13 (t, J=6.7 Hz, 2H), 2.18 (d, J=6.5 Hz, 4H), 1.98 (s, 9H), 1.59-1.67 (m, 2H), 1.51-1.59 (m, 4H), 1.48 (br. s., 2H), 1.27-1.41 (m, 4H)

9H-fluoren-9-ylmethyl {(1S)-1-cyclopentyl-2-[(2,5-dioxopyrrolidin-1-yl)oxy]-2-oxoethyl}carbamate (I-aa-1)

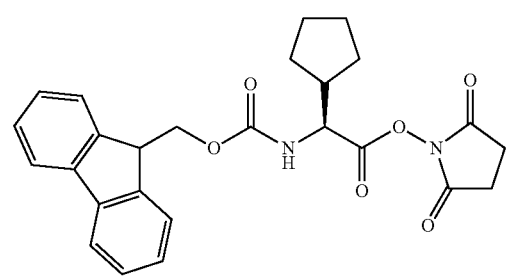 [SMILES: O=C(N[C@H](C(=O)ON1C(=O)CCC1=O)C1CCCC1)OCC1c2ccccc2-c2ccccc21]

N,N'-Dicyclohexylcarbodiimide (247 mg, 1.2 mmol) was added portionwise to a solution of (2S)-cyclopentyl{[(9H-fluoren-9-ylmethoxy)carbonyl]amino}ethanoic acid

181

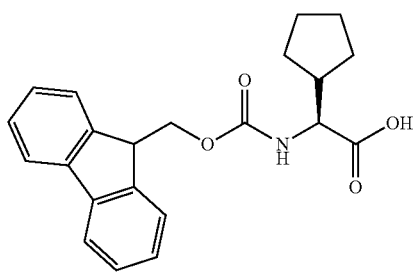 [SMILES: O=C(N[C@H](C(=O)O)C1CCCC1)OCC1c2ccccc2-c2ccccc21]

(380 mg, 1.04 mmol) and N-Hydroxysuccinimide (137.6 mg, 1.2 mmol) in dry tetrahydrofuran (40 mL) at 5-10° C. After the addition, the mixture was stirred at room temperature overnight. The mixture was cooled to −20° C., then filtered to remove by-product. The filter cake was washed by cold tetrahydrofuran, the filtrate was concentrated to dryness, purified by flash column (eluted with petroleum ether: ethyl acetate from 100:10 to 100:50) to afford the title compound (380 mg, 79%).

N~5~-carbamoyl-N~2~-[(2S)-2-cyclopentyl-2-{[(9H-fluoren-9-ylmethoxy)carbonyl]amino}acetyl]-L-ornithine (I-ab-1)

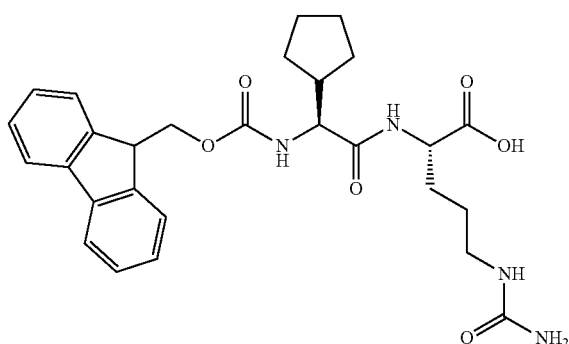

To the solution of (2S)-2-amino-5-(carbamoylamino)pentanoic acid (151 mg, 0.86 mmol) and sodium bicarbonate (72.5 mg, 0.86 mmol) in water (15 mL) was added tetrahydrofuran (10 mL) at 0° C. To the resulted mixture was added a solution of 9H-fluoren-9-ylmethyl {(1S)-1-cyclopentyl-2-[(2,5-dioxopyrrolidin-1-yl)oxy]-2-oxoethyl}carbamate (I-aa-1) (380 mg, 0.82 mmol) in 1,2-dimethoxy-ethane (15 mL) dropwise under nitrogen. After addition, the mixture was stirred at room temperature overnight. The reaction mixture was washed by methyl-tertbutyl ether (50 mL) 4 times. The organic phase was discarded and the aqueous layer was acidified to pH=3-4 by aqueous hydrochloric acid (1 M). The solution was extracted using chloroform/isopropyl alcohol (4:1) (50 mL) 6 times. Combined organic layer was dried over sodium sulfate, concentrated to dryness to afford the title compound (403 mg, 93.7%) as white solid.

182

9H-fluoren-9-ylmethyl [(1S)-2-{[(2S)-5-(carbamoylamino)-1-{[4-(hydroxymethyl)phenyl]amino}-1-oxopentan-2-yl]amino}-1-cyclopentyl-2-oxoethyl] carbamate (I-ac-1)

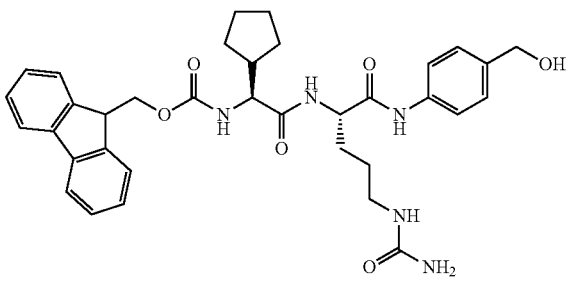 [SMILES: NC(=O)NCCC[C@H](NC(=O)[C@@H](NC(=O)OCC1c2ccccc2-c2ccccc21)C1CCCC1)C(=O)Nc1ccc(CO)cc1]

To the solution of N~5~-carbamoyl-N~2~-[(2S)-2-cyclopentyl-2-{[(9H-fluoren-9-ylmethoxy)carbonyl]amino}acetyl]-L-ornithine (I-ab-1) (500 mg, 0.95 mmol) and 4-aminobenzyl alcohol (470 mg, 3.82 mmol) in dichloromethane/methanol (30 mL/15 mL) was added N-Ethoxycarbonyl-2-ethoxy-1,2-dihydroquinoline (708 mg, 2.86 mmol). Then the reaction mixture was stirred at room temperature overnight in darkness. The following morning, the reaction was concentrated under reduced pressure and the residue was washed by methyl tert-butyl ether (100 mL×3). Then the filter cake was purified by prep-HPLC (see conditions below) to give the title compound as yellow solid (31 mg, 5.1%). 1H NMR (400 MHz, DMSO): δ 9.95 (s, 1H), 8.09 (d, 1H), 7.90-7.88 (d, 2H), 7.73-7.71 (t, 2H), 7.55-7.53 (t, 2H), 7.41 (t, 2H), 7.34-7.30 (t, 2H), 7.24-7.22 (d, 2H), 5.96 (t, 1H), 5.39 (s, 2H), 5.11-5.08 (t, 1H), 4.44-4.42 (d, 3H), 4.32-4.23 (m, 3H), 3.96-3.92 (t, 1H), 3.01-3.00 (m, 3H), 2.15-2.13 (m, 1H), 1.66-1.24 (m, 12H), m/z for C35H41N5O6: 628.4 (M+H)+, Retention time: 4.213 min Purification Conditions:

Column: DIKMA Diamonsil (2) C18 200*20 mm*5 um; mobile phase: from 30% acetonitrile in water (0.1% TFA) to 50% acetonitrile in water (0.1% TFA); wavelength=220 nm; workup: concentrated and lyophilized.

QC Conditions:

Column: Ultimate XB-C18, 3*50 mm, 3 um; Retention time: 4.33 min; Mobile phase: A, water (2.7 mL TFA in 4 L water) B, acetonitrile (2.5 mL TFA in 4 L acetonitrile) elution gradient 1%-100%; Wavelength: 220 nm; ee value: 100%. Column: Chiralcel OD-3 50*4.6 mm I.D., 3 um; retention time: 1.923 minutes; Mobile phase: ethanol (0.05% DEA) in CO2 from 5% to 40%; flow rate: 2.5 mL/minutes; Wavelength: 254 nm; ee value=100%. Column: AD-3 50*4.6 mm I.D., 3 um; retention time: 1.981 min.; Mobile phase: ethanol (0.05% DEA) in CO2 from 5% to 40%; Flow rate: 2.5 mL/min.; wavelength: 220 nm

N~2~-[(2S)-2-amino-2-cyclopentylacetyl]-N~5~-carbamoyl-N-[4-(hydroxymethyl)phenyl]-L-ornithinamide (I-ad-1)

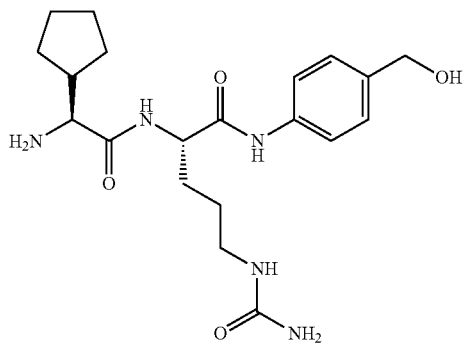 [SMILES: NC(=O)NCCC[C@H](NC(=O)[C@@H](N)C1CCCC1)C(=O)Nc1ccc(CO)cc1]

To a stirred solution of 9H-fluoren-9-ylmethyl [(1S)-2-{[(2S)-5-(carbamoylamino)-1-{[4-(hydroxymethyl)phenyl]amino}-1-oxopentan-2-yl]amino}-1-cyclopentyl-2-oxoethyl]carbamate (I-ac-1) (500 mg, 0.797 mmol) in N,N-dimethylformamide (10 mL) was added drop wise piperidine (4 mL) at 5° C. under nitrogen. The mixture was stirred at room temperature for 1.5 hours. The reaction was concentrated to dryness. The crude product was washed with dichloromethane (20 mL), filtered and filter cake was dried in vacuum to give the title compound (300 mg, 93.1%) as solid which was used for next step without purification.

N-[(1S)-2-{[(2S)-5-(carbamoylamino)-1-{[4-(hydroxymethyl)phenyl]amino}-1-oxopentan-2-yl]amino}-1-cyclopentyl-2-oxoethyl]-6-(2,5-dioxo-2,5-dihydro-1H-pyrrol-1-yl)hexanamide (I-ae-1)

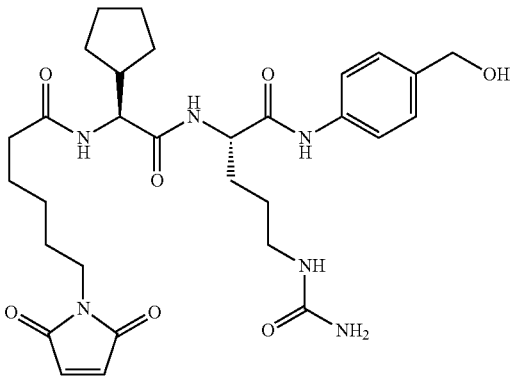 [SMILES: NC(=O)NCCC[C@H](NC(=O)[C@@H](NC(=O)CCCCCN1C(=O)C=CC1=O)C1CCCC1)C(=O)Nc1ccc(CO)cc1]

To a stirred solution of N~2~-[(2S)-2-amino-2-cyclopentylacetyl]-N~5~-carbamoyl-N-[4-(hydroxymethyl)phenyl]-L-ornithinamide (I-ad-1) (300 mg, 0.74 mmol) in N,N-dimethylformamide (12 mL) was added 1-{6-[(2,5-dioxopyrrolidin-1-yl)oxy]-6-oxohexyl}-1H-pyrrole-2,5-dione (272 mg, 0.889 mmol) at 3° C. under nitrogen. The mixture was stirred at room temperature for 2 hours. The reaction was added drop wise into methyl tert-butyl ether (250 mL), stirred at room temperature for 20 min, filtered and filter cake was concentrated to dryness to give the title compound (300 mg, 67.8%) as solid which was used for next step without purification.

N~5~-carbamoyl-N~2~-[(2S)-2-cyclopentyl-2-{[6-(2,5-dioxo-2,5-dihydro-1H-pyrrol-1-yl)hexanoyl]amino}acetyl]-N-[4-({[(4-nitrophenoxy)carbonyl]oxy}methyl)phenyl]-ornithinamide (I-af-1)

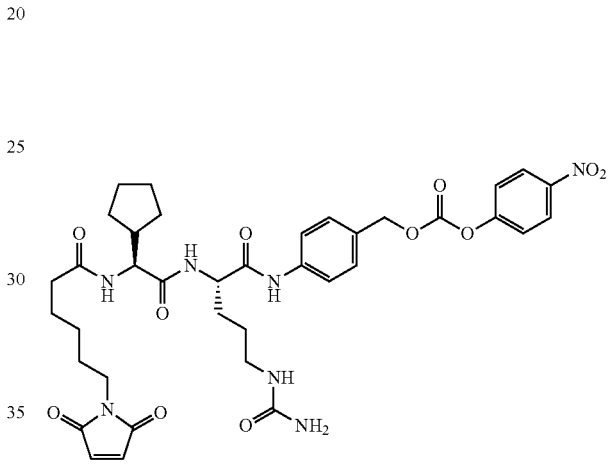

To a stirred solution of N-[(1S)-2-{[(2S)-5-(carbamoylamino)-1-{[4-(hydroxymethyl)phenyl]amino}-1-oxopentan-2-yl]amino}-1-cyclopentyl-2-oxoethyl]-6-(2,5-dioxo-2,5-dihydro-1H-pyrrol-1-yl)hexanamide (I-ae-1) (300 mg, 0.740 mmol) in N,N-dimethylformamide (12 mL) was added bis(4-nitrophenyl) carbonate (900 mg, 2.96 mmol) and N,N-diisopropylethylamine (390 mg, 2.96 mmol) at 3° C. under nitrogen. The reaction was stirred at room temperature for overnight. The reaction was added drop wise into methyl tert-butyl ether (60 mL), stirred at room temperature for 20 min, filtered and filter cake was washed with methyl tert-butyl ether (100 mL). The crude product was dried in vacuum to dryness. The crude product was purified by flash column eluted with dichloromethane:methanol from 100:1 to 94:6 to afford the title compound (50 mg, 17.7%) as solid. 1H NMR (400 MHz, DMSO): δ 10.09 (br, 1H), 8.33 (d, 2H), 8.13 (d, 1H), 7.93 (d, 1H), 7.67-7.41 (m, 6H), 7.01 (s, 2H), 5.98 (br, 1H), 5.43 (s, 2H), 5.25 (s, 2H), 4.39 (m, 1H), 4.23-4.19 (m, 1H), 3.37 (m, 1H), 3.03-2.96 (m, 2H), 2.14-2.11 (m, 3H), 1.70-1.19 (m, 19H). LC-MS: m/z for C37H45N7O11: 764.3 (M+H)+; Retention time: 0.823 min.

4-{[(2R)-5-(carbamoylamino)-2-{[(2R)-2-cyclopentyl-2-{[6-(2,5-dioxo-2,5-dihydro-1H-pyrrol-1-yl)hexanoyl]amino}acetyl]amino}pentanoyl]amino}benzyl {6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}carbamate (51)

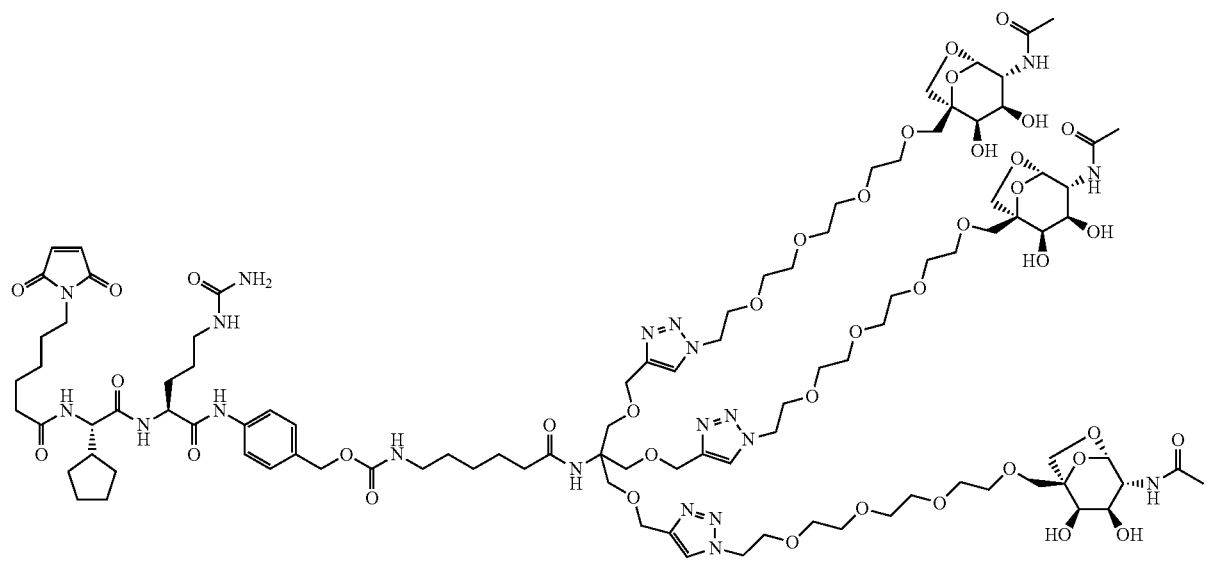 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCNC(=O)OCc4ccc(NC(=O)[C@H](CCCNC(N)=O)NC(=O)[C@@H](NC(=O)CCCCCN5C(=O)C=CC5=O)C5CCCC5)cc4)nn3)(O2)[C@H](O)[C@@H]1O]

To a solution of 6-amino-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hexanamide (48) (45 mg, 0.027 mmol) in N,N-dimethylformamide (0.5 mL) and tetrahydrofuran (0.3 mL) was added N,N-diisopropylethyl amine (0.019 mL, 0.109 mmol) and N~5~-carbamoyl-N~2~-[(2S)-2-cyclopentyl-2-{[6-(2,5-dioxo-2,5-dihydro-1H-pyrrol-1-yl)hexanoyl]amino}acetyl]-N-[4-({[(4-nitrophenoxy)carbonyl]oxy}methyl)phenyl]-L-ornithinamide (I-af-1) (20.8 mg, 0.0272 mmol) room temperature 18 hours. After 18 hours, a sample was removed and the UPLC showed the formation of the desired product. The crude reaction mixture was concentrated under reduced pressure. The resulting crude material was purified by reverse-phase chromatography using the conditions below yielding the title compound as a gum (21.7 mg, 35%).

Purification Conditions:
The residue was dissolved in dimethyl sulfoxide (1 mL) and purified by reversed-phase HPLC Column: Waters Sunfire C18 19×100, 5 u; Mobile phase A: 0.05% TFA in water (v/v); Mobile phase B: 0.05% TFA in acetonitrile (v/v); Gradient: 75.0% H2O/25.0% Acetonitrile linear to 65% H2O/35% Acetonitrile in 10.5 min to 0% H2O/100% MeCN to 11.0 min, Hold at 0% H2O/100% Acetonitrile from 11.0 to 12.0 min. Flow: 25 mL/min.

QC Conditions:
Column: Waters Atlantis dC18 4.6×50, 5 u; Mobile phase A: 0.05% TFA in water (v/v); Mobile phase B: 0.05% TFA in acetonitrile (v/v); 95.0% H2O/5.0% Acetonitrile linear to 5% H2O/95% Acetonitrile in 4.0 min, Hold at 5% H2O/95% Acetonitrile from 4.0 min to 5.0 min. Flow: 2 mL/min.; retention time=1.99 minutes; Retention time=1.99 minutes; Mass observed=1139.1254. Method C: 1.5 minute run LRMS [½M=1138]. $^1$H NMR (METHANOL-$d_4$) δ: 7.99 (s, 3H), 7.57 (d, J=8.2 Hz, 2H), 7.30 (d, J=8.2 Hz, 2H), 6.79 (s, 2H), 5.21 (s, 3H), 5.01 (s, 2H), 4.55-4.64 (m, 12H), 4.51 (dd, J=9.0, 5.1 Hz, 1H), 4.43 (q, J=7.2 Hz, 1H), 4.16 (d, J=9.4 Hz, 1H), 3.95 (d, J=9.8 Hz, 6H), 3.85-3.91 (m, 9H), 3.74-3.79 (m, 9H), 3.71 (dd, J=9.8, 4.3 Hz, 3H), 3.54-3.67 (m, 41H), 3.47 (t, J=7.0 Hz, 2H), 3.16-3.26 (m, 1H), 3.10-3.16 (m, 1H), 3.07 (t, J=6.8 Hz, 2H), 2.24 (q, J=7.7 Hz, 3H), 2.16 (t, J=7.4 Hz, 2H), 1.99 (s, 9H), 1.85-1.95 (m, 1H), 1.42-1.84 (m, 16H), 1.37 (t, J=7.0 Hz, 2H), 1.23-1.34 (m, 5H)

N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)-3,19-dioxo-1-(pyridin-2-yldisulfanyl)-7,10,13,16-tetraoxa-4,20-diazahexacosan-26-amide (52)

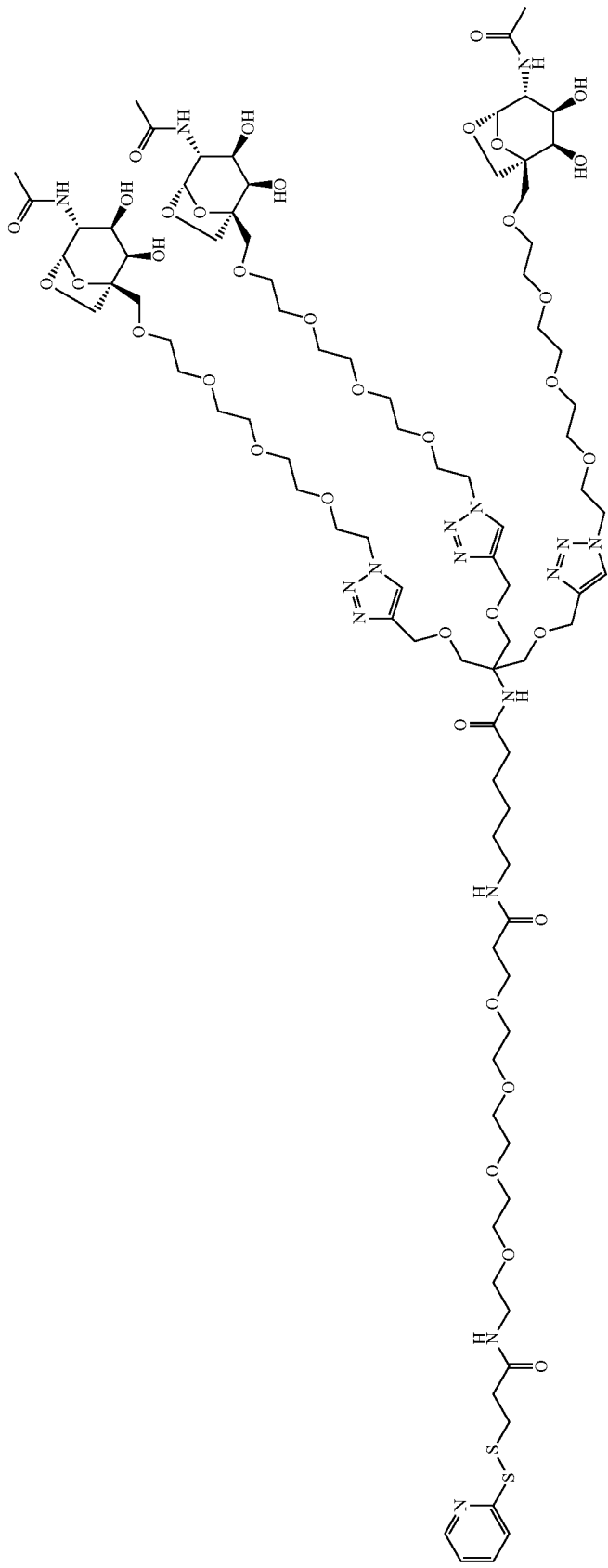

To a solution of 6-amino-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hexanamide acetate salt (48) (70.0 mg, 0.041 mmol) and N-{15-[(2,5-dioxopyrrolidin-1-yl)oxy]-15-oxo-3,6,9,12-tetraoxapentadec-1-yl}-3-(pyridin-2-yldisulfanyl)propanamide

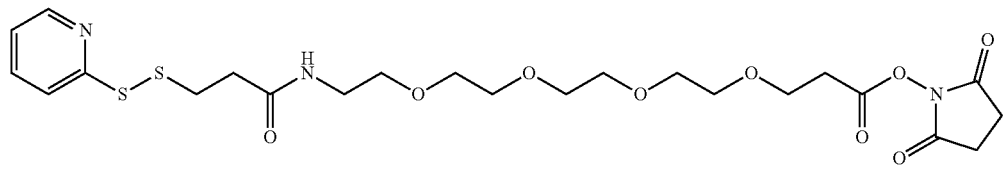 [SMILES: O=C(CCSSc1ccccn1)NCCOCCOCCOCCOCCC(=O)ON1C(=O)CCC1=O]

(27.5 mg, 0.0491 mmol) in N,N-dimethylformamide (0.6 mL) and tetrahydrofuran (0.6 mL) was added N,N-diisopropylethylamine (0.0285 mL, 0.164 mmol). The reaction was allowed to stir at room temperature 18 hours. After 18 hours, the reaction was concentrated under reduced pressure. The crude material was purified using reverse-phase chromatography using the conditions below yielding the title compound as a gum (47.7 mg, 56%). Method C: 3 minute run LRMS [⅓M+1=699]. $^1$H NMR (METHANOL-$d_4$) δ: 8.47 (d, J=4.7 Hz, 1H), 8.01 (s, 3H), 7.93 (d, J=3.5 Hz, 2H), 7.30-7.38 (m, 1H), 5.21 (s, 3H), 4.57-4.62 (m, 6H), 4.57 (s, 6H), 3.92-3.99 (m, 6H), 3.89 (dd, J=10.7, 4.9 Hz, 9H), 3.74-3.80 (m, 9H), 3.72 (dd, J=9.8, 4.7 Hz, 6H), 3.51-3.68 (m, 55H), 3.35-3.41 (m, 2H), 3.14 (t, J=7.0 Hz, 2H), 3.10 (t, J=6.8 Hz, 2H), 2.64 (t, J=7.0 Hz, 2H), 2.43 (t, J=6.0 Hz, 2H), 2.17 (t, J=7.4 Hz, 2H), 1.99 (s, 9H), 1.52-1.61 (m, 2H), 1.43-1.51 (m, 2H), 1.27-1.38 (m, 2H)

Purification Conditions

The residue was dissolved in dimethyl sulfoxide (1 mL) and purified by reversed-phase HPLC Column: Waters Sunfire C18 19×100, 5 u; Mobile phase A: 0.05% TFA in water (v/v); Mobile phase B: 0.05% TFA in acetonitrile (v/v); Gradient: 80.0% H2O/20.0% Acetonitrile linear to 70% H2O/30% Acetonitrile in 8.5 min to 0% H2O/100% MeCN to 9.0 min, Hold at 0% H2O/100% Acetonitrile from 9.0 to 10.0 min. Flow: 25 mL/min.

QC Conditions

Column: Waters Atlantis dC18 4.6×50, 5 u; Mobile phase A: 0.05% TFA in water (v/v); Mobile phase B: 0.05% TFA in acetonitrile (v/v); Gradient: 95.0% H2O/5.0% Acetonitrile linear to 5% H2O/95% Acetonitrile in 4.0 min, Hold at 5% H2O/95% Acetonitrile from 4.0 min to 5.0 min. Flow: 2 mL/min.; Retention time=1.78 minutes; mass observed=699.6404

N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)-3,31-dioxo-1-(pyridin-2-yldisulfanyl)-7,10,13,16,19,22,25,28-octaoxa-4,32-diazaoctatriacontan-38-amide (53)

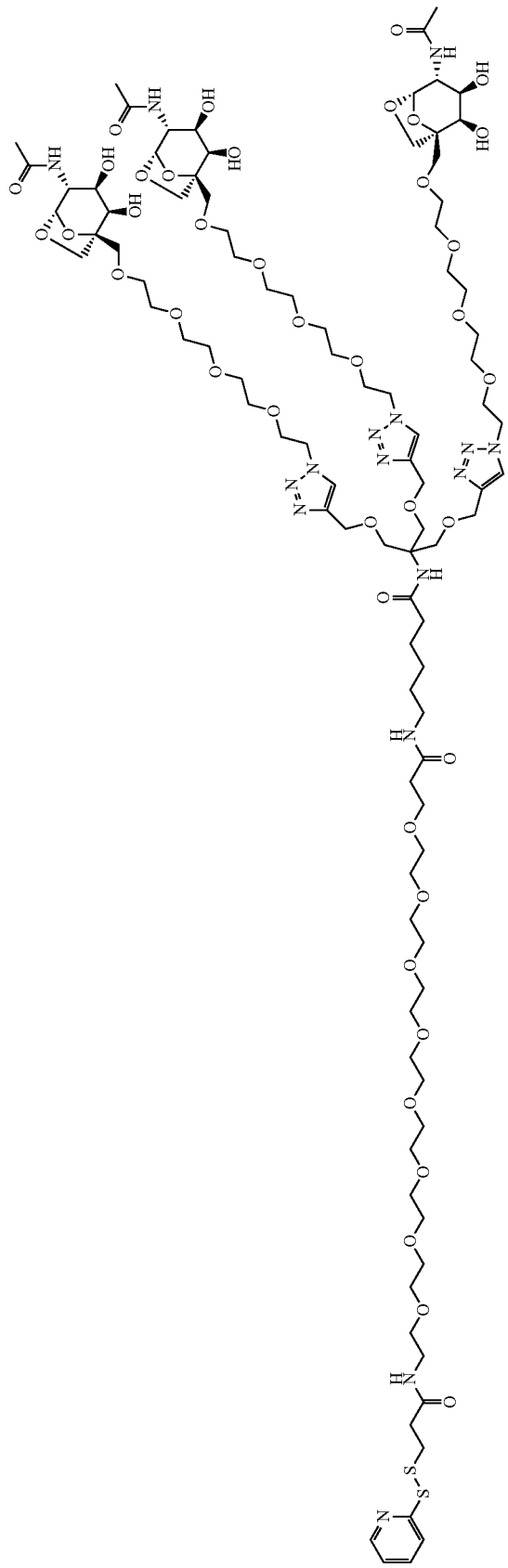

To a solution of 6-amino-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hexanamide acetate salt (48) (70.0 mg, 0.041 mmol) and N-{27-[(2,5-dioxopyrrolidin-1-yl)oxy]-27-oxo-3,6,9,12,15,18,21,24-octaoxaheptacos-1-yl}-3-(pyridin-2-yldisulfanyl)propanamide Gradient: 80.0% H2O/20.0% Acetonitrile linear to 70% H2O/30% Acetonitrile in 8.5 min to 0% H2O/100% MeCN to 9.0 min, Hold at 0% H2O/100% Acetonitrile from 9.0 to 10.0 min. Flow: 25 mL/min.

QC Conditions

Column: Waters Atlantis dC18 4.6×50, 5 u; Mobile phase A: 0.05% TFA in water (v/v); Mobile phase B: 0.05% TFA in acetonitrile (v/v); Gradient: 95.0% H2O/5.0% Acetonitrile linear to 5% H2O/95% Acetonitrile in 4.0 min, Hold at

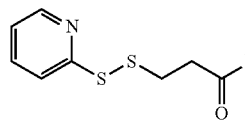

(30.1 mg, 0.041 mmol) in N,N-dimethylformamide (0.6 mL) and tetrahydrofuran (0.6 mL) was added N,N-diisopropylethylamine (0.0285 mL, 0.164 mmol). The reaction was allowed to stir at room temperature 18 hours. After 18 hours, the reaction was concentrated under reduced pressure. The crude material was purified using reverse-phase chromatography using the conditions below yielding the title compound as a gum (59.2 mg, 64%). Method C: 3 minute run LRMS [⅓M=757]. $^1$H NMR (METHANOL-$d_4$) δ: 8.47 (d, J=5.1 Hz, 1H), 8.01 (s, 3H), 7.92 (d, J=3.5 Hz, 2H), 7.30-7.39 (m, 1H), 5.21 (s, 3H), 4.57-4.62 (m, 6H), 4.57 (s, 6H), 3.92-3.99 (m, 6H), 3.86-3.92 (m, 9H), 3.77 (s, 9H), 3.69-3.74 (m, 6H), 3.50-3.68 (m, 73H), 3.14 (t, J=7.0 Hz, 2H), 3.10 (t, J=7.0 Hz, 2H), 2.64 (t, J=6.8 Hz, 2H), 2.43 (t, J=6.0 Hz, 2H), 2.17 (t, J=7.4 Hz, 2H), 1.99 (s, 9H), 1.53-1.63 (m, 2H), 1.42-1.52 (m, 2H), 1.32 (dt, J=15.1, 7.5 Hz, 2H)

5% H2O/95% Acetonitrile from 4.0 min to 5.0 min. Flow: 2 mL/min.; retention time=1.85 minutes; mass observed=758.405

6-amino-N-(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)hexanamide (I-ag-1)

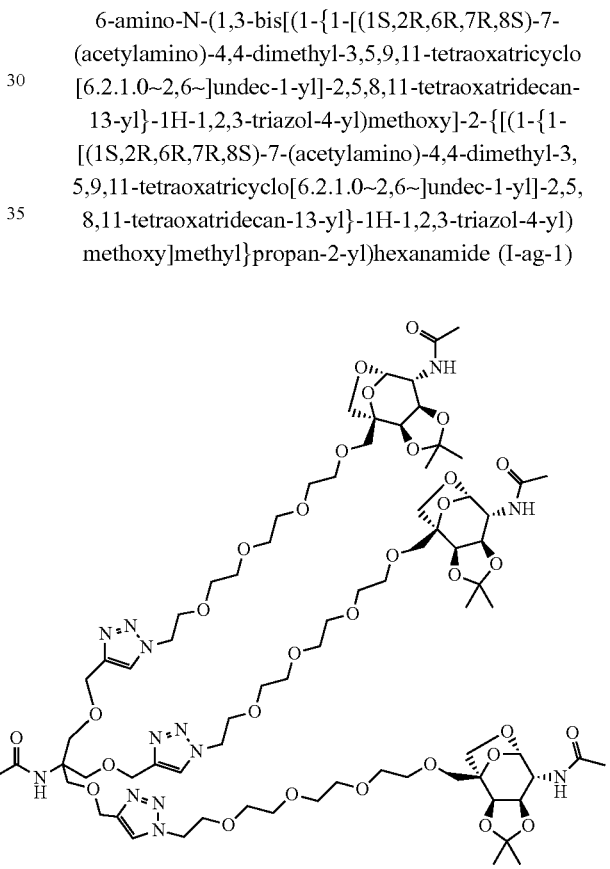

Purification Conditions

The residue was dissolved in dimethyl sulfoxide (1 mL) and purified by reversed-phase HPLC Column: Waters Sunfire C18 19×100, 5 u; Mobile phase A: 0.05% TFA in water (v/v); Mobile phase B: 0.05% TFA in acetonitrile (v/v);

benzyl {6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo

[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}carbamate (I-y-1) (1200 mg, 0.63 mmol) was dissolved in methanol (30 mL). The solution was then passed through the H-cube using a 10% palladium on carbon (small cartridge) using the following parameters (temperature=50° C., flow rate=1.0 mL/min., pressure=Full $H_2$ (1 bar)). The solution was collected. A sample was removed and the UPLC showed starting material remaining. The reaction was passed through the H-cube a second time using the above parameters. The collected solution was concentrated under reduced pressure yielding the title compound as white foam (1039 mg, 93%). Method C: 1.5 minute run LRMS [½M=886]. $^1$H NMR (METHANOL-$d_4$) δ: 7.99 (s, 3H), 5.23 (d, J=1.6 Hz, 3H), 4.45-4.62 (m, 12H), 4.29 (d, J=5.9 Hz, 3H), 4.16 (t, J=6.4 Hz, 3H), 3.87-3.98 (m, 12H), 3.73-3.85 (m, 15H), 3.54-3.70 (m, 36H), 2.87 (t, J=7.6 Hz, 2H), 2.20 (t, J=7.2 Hz, 2H), 1.98 (s, 9H), 1.53-1.69 (m, 4H), 1.48 (s, 9H), 1.34-1.41 (m, 2H), 1.33 (s, 9H)

N-{6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}-6-(pyridin-2-yldisulfanyl)hexanamide (I-ag-2)

To a solution of 6-amino-N-(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)hexanamide (I-ag-1) (105.0 mg, 0.0593 mmol) in N,N-dimethylformamide (0.5 mL) and tetrahydrofuran (0.5 mL) was added N,N-diisopropylethylamine (0.031 mL, 0.178 mmol) and was allowed to stir for 10 minutes before being added to 1-{[6-(pyridin-2-yldisulfanyl)hexanoyl]oxy}pyrrolidine-2,5-dione (I-s-1) (25.2 mg, 0.0711 mmol) and the reaction was then heated to room temperature for 16 hours. After 16 hours, the reaction was diluted with water (15 mL) and brine (5 mL) and extracted three times with dichloromethane (20 mL). The combined organic layers were washed with water (20 mL), brine (20 mL), dried over magnesium sulfate, filtered and concentrated under reduced pressure. The crude material was purified using the CombiFlash Rf (RediSep 12 g silica gel column) and eluting with a gradient of 0-20% methanol/dichloromethane yielding the title compound (59.6 mg, 50%). Method C: MassLynx\Acid_3.0Min.olp—LRMS [½M+1=1006]. $^1$H NMR (METHANOL-$d_4$) δ: 8.39 (d, J=4.7 Hz, 1H), 7.98 (s, 3H), 7.83-7.87 (m, 1H), 7.77-7.83 (m, 1H), 7.21 (t, J=5.9 Hz, 1H), 5.23 (d, J=1.6 Hz, 3H), 4.50-4.64 (m, 12H), 4.29 (d, J=5.9 Hz, 3H), 4.16 (t, J=6.4 Hz, 3H), 3.87-3.96 (m, 12H), 3.84 (d, J=7.8 Hz, 3H), 3.71-3.79 (m, 15H), 3.54-3.70 (m, 31H), 3.18-3.28 (m, 2H), 3.13 (q, J=6.5 Hz, 2H), 2.82 (t, J=7.2 Hz, 2H), 2.12-2.23 (m, 4H), 1.98 (s, 9H), 1.71 (quin, J=7.3 Hz, 2H), 1.51-1.64 (m, 6H), 1.44-1.51 (m, 11H), 1.28-1.34 (m, 11H)

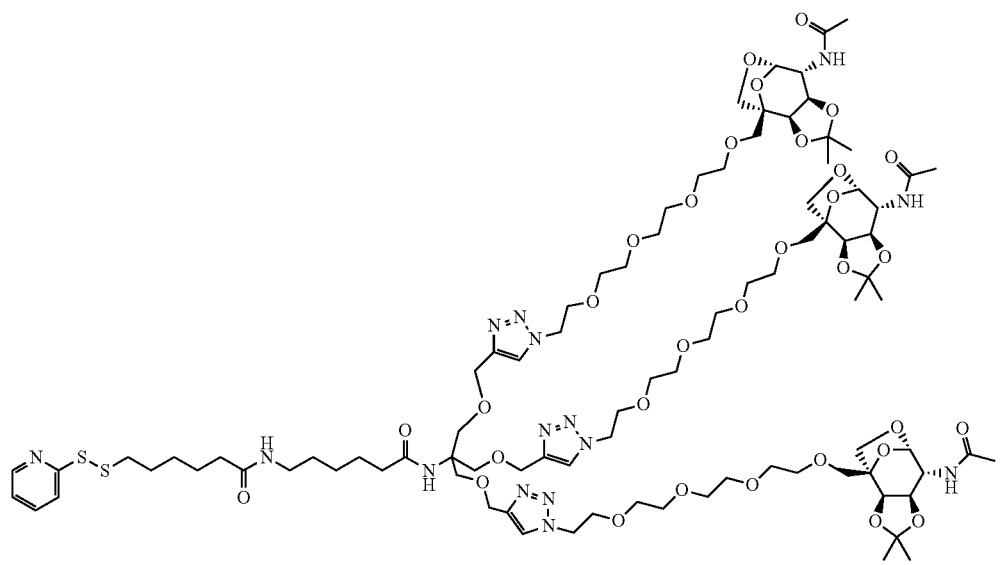 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@H]5OC(C)(C)O[C@H]56)nn4)(COCc4cn(CCOCCOCCOCCOC[C@@]56CO[C@@H](O5)[C@H](NC(C)=O)[C@H]5OC(C)(C)O[C@H]56)nn4)NC(=O)CCCCCNC(=O)CCCCCSSc4ccccn4)nn3)(O2)[C@@H]2OC(C)(C)O[C@H]12]

N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6, 8-dioxabicyclo[3.2.1]oct-1-yl]-2,5, 8,11-tetraoxatridecan-13-yl}-1H-1,2,3-triazol-4-yl)methoxy]methyl}propan-2-yl)amino]-6-oxohexyl}-6-(pyridin-2-yldisulfanyl)hexanamide (54)

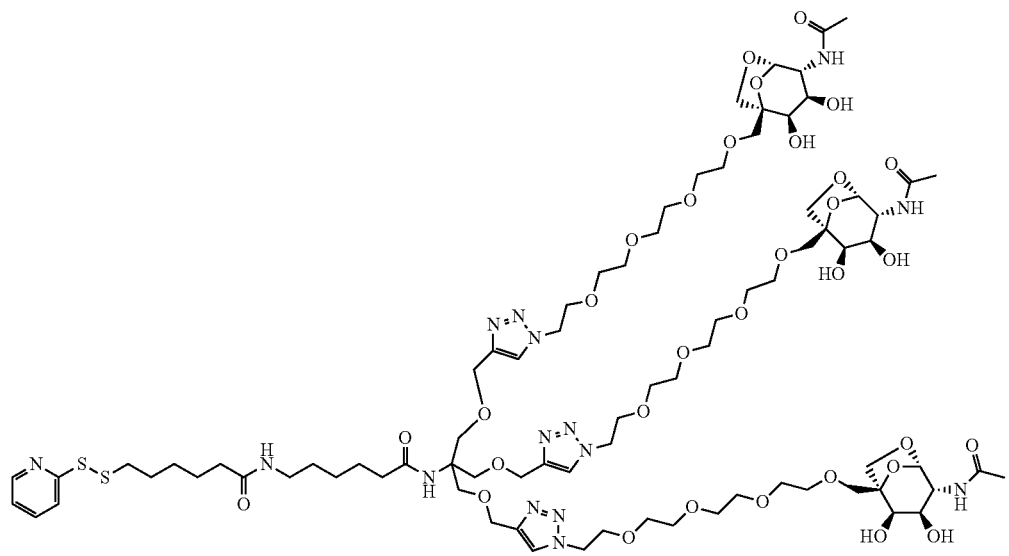 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCNC(=O)CCCCCSSc4ccccn4)nn3)(O2)[C@H](O)[C@@H]1O]

A solution of N-{6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}-6-(pyridin-2-yldisulfanyl)hexanamide (I-ag-2) (59 mg, 0.029 mmol) in acetic acid (4 mL), methanol (1 mL) and water (1 mL) was heated to 70° C. for 24 hours. After 24 hours, the reaction was cooled to room temperature and concentrated under reduced pressure. The crude material was diluted with toluene and concentrated under reduced pressure. The crude material was diluted with toluene a second time and concentrated under reduced pressure yielding the crude title compound (50.5 mg, 91%). The crude material was purified using reverse-phase chromatography using the conditions below and yielding the title compound as a gum (25.2 mg, 45%)

Purification Conditions:

The residue was dissolved in dimethyl sulfoxide (1 mL) and purified by reversed-phase HPLC Column: Waters Sunfire C18 19×100, 5 u; Mobile phase A: 0.05% TFA in water (v/v); Mobile phase B: 0.05% TFA in acetonitrile (v/v); Gradient: 80.0% H2O/20.0% Acetonitrile linear to 70% H2O/30% Acetonitrile in 10.5 min to 0% H2O/100% MeCN to 11.0 min, Hold at 0% H2O/100% Acetonitrile from 11.0 to 12.0 min. Flow: 25 mL/min.

QC Conditions:

Column: Waters Atlantis dC18 4.6×50, 5 u; Mobile phase A: 0.05% TFA in water (v/v); Mobile phase B: 0.05% TFA in acetonitrile (v/v); 95.0% H2O/5.0% Acetonitrile linear to 5% H2O/95% Acetonitrile in 4.0 min, Hold at 5% H2O/95% Acetonitrile from 4.0 min to 5.0 min. Flow: 2 mL/min.; Retention time=1.96 minutes; mass observed=946.5137. Method C: MassLynx\Acid_3.0Min.olp—LRMS [½M+1=946]. $^1$H NMR (METHANOL-$d_4$) δ: 8.45 (d, J=5.1 Hz, 1H), 8.01 (s, 3H), 7.94 (d, J=3.1 Hz, 2H), 7.29-7.36 (m, 1H), 5.21 (s, 3H), 4.57-4.62 (m, 6H), 4.57 (s, 6H), 3.92-4.00 (m, 6H), 3.89 (dd, J=10.7, 4.9 Hz, 9H), 3.74-3.80 (m, 9H), 3.71 (dd, J=10.1, 4.3 Hz, 3H), 3.53-3.68 (m, 42H), 3.13 (t, J=6.8 Hz, 2H), 2.85 (t, J=7.2 Hz, 2H), 2.17 (t, J=7.2 Hz, 4H), 1.99 (s, 9H), 1.71 (quin, J=7.4 Hz, 2H), 1.52-1.64 (m, 4H), 1.45 (td, J=15.0, 7.8 Hz, 4H), 1.26-1.37 (m, 2H)

2-(pyridin-2-yldisulfanyl)ethyl {6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}carbamate (I-ag-3)

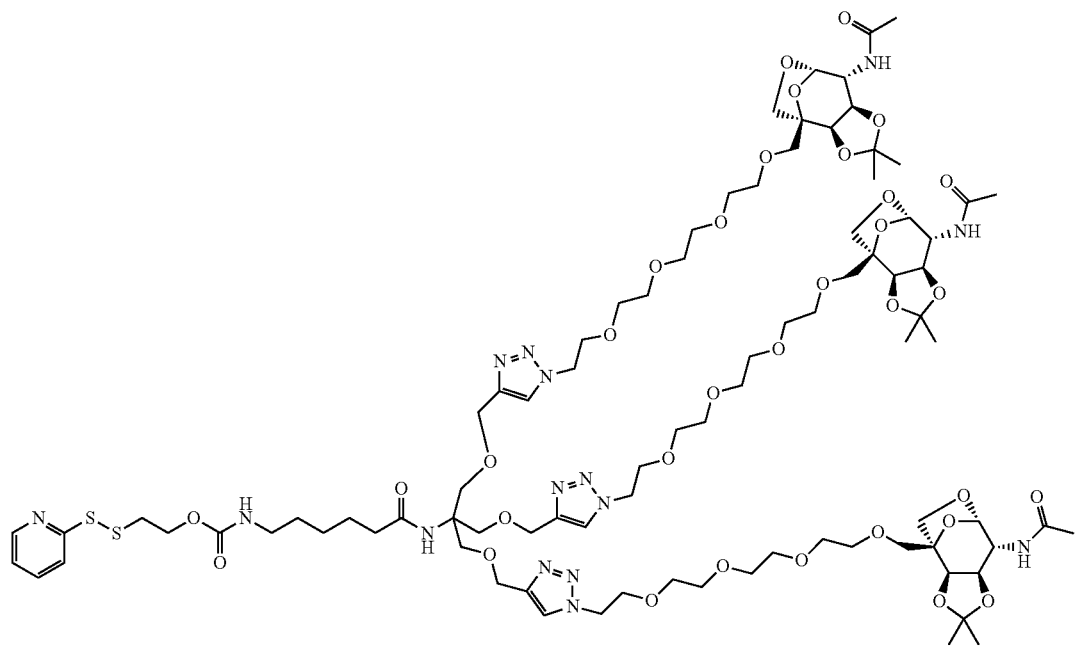 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@H]5OC(C)(C)O[C@H]56)nn4)(COCc4cn(CCOCCOCCOCCOC[C@@]56CO[C@@H](O5)[C@H](NC(C)=O)[C@H]5OC(C)(C)O[C@H]56)nn4)NC(=O)CCCCCNC(=O)OCCSSc4ccccn4)nn3)(O2)[C@@H]2OC(C)(C)O[C@H]12]

To a solution of 6-amino-N-(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)hexanamide (I-ag-1) (61.4 mg, 0.0347 mmol) in N,N-dimethylformamide (0.3 mL) and tetrahydrofuran (0.3 mL) was added N,N-diisopropylethylamine (0.0241 mL, 0.139 mmol) and 4-nitrophenyl 2-(pyridin-2-yldisulfanyl)ethyl carbonate

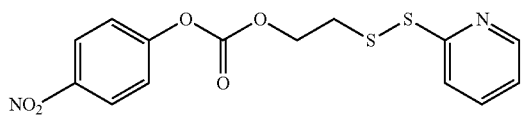 [SMILES: O=C(OCCSSc1ccccn1)Oc1ccc([N+](=O)[O-])cc1]

(see European Journal of Medicinal Chemistry, 82, 355-362; 2014, 18.0 mg, 0.051 mmol) room temperature 16 hours. After 16 hours, the reaction mixture was concentrated under reduced pressure. The crude material was purified using the CombiFlash Rf (RediSep 4 g Gold silica gel column) and eluting with a gradient of 0-20% methanol/dichloromethane yielding the title compound as a gum (57.4 mg, None, 83%). Method C: MassLynx\Acid_3.0Min.olp—LRMS [½M+1=993]. $^1$H NMR (METHANOL-$d_4$) δ: 8.40 (d, J=4.3 Hz, 1H), 7.98 (s, 3H), 7.83-7.89 (m, 1H), 7.75-7.83 (m, 1H), 7.15-7.25 (m, 1H), 5.22 (d, J=1.2 Hz, 3H), 4.51-4.64 (m, 12H), 4.29 (d, J=5.9 Hz, 3H), 4.23 (t, J=6.2 Hz, 2H), 4.15 (t, J=6.4 Hz, 3H), 3.86-3.97 (m, 12H), 3.83 (d, J=7.8 Hz, 3H), 3.72-3.79 (m, 12H), 3.53-3.69 (m, 36H), 3.05 (t, J=5.7 Hz, 4H), 2.17 (t, J=7.0 Hz, 2H), 1.98 (s, 9H), 1.51-1.61 (m, 2H), 1.48 (s, 11H), 1.33 (s, 11H)

2-(pyridin-2-yldisulfanyl)ethyl {6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}carbamate (55)

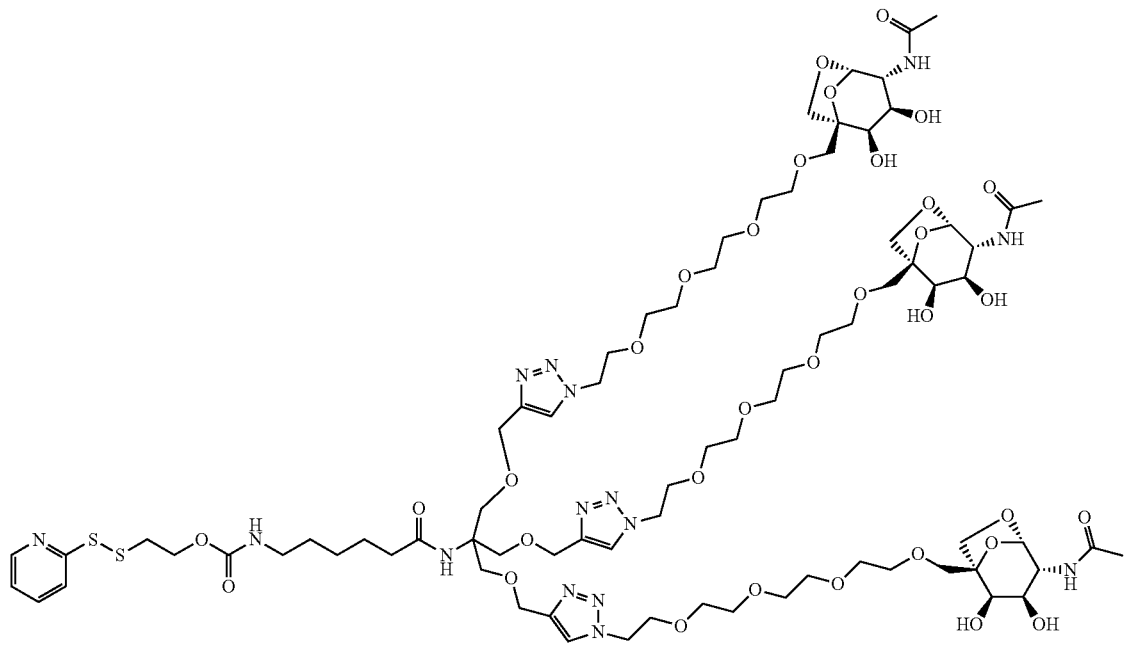 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCNC(=O)OCCSSc4ccccn4)nn3)(O2)[C@H](O)[C@@H]1O]

A solution of 2-(pyridin-2-yldisulfanyl)ethyl {6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}carbamate (I-ag-3) (57.4 mg, 0.0289 mmol) in acetic acid (4.0 mL), methanol (1.0 mL) and water (1.0 mL) was heated to 70° C. for 24 hours. After 24 hours, the reaction was cooled to room temperature and concentrated under reduced pressure. The crude material was diluted with toluene and concentrated under reduced pressure. The crude material was purified using reverse-phase chromatography using the conditions below yielding the title compound as a gum (29.8 mg, 55%)

Purification Conditions:

The residue was dissolved in dimethyl sulfoxide (1 mL) and purified by reversed-phase HPLC Column: Waters Sunfire C18 19×100, 5 u; Mobile phase A: 0.05% TFA in water (v/v); Mobile phase B: 0.05% TFA in acetonitrile (v/v); Gradient: 80.0% H2O/20.0% Acetonitrile linear to 70% H2O/30% Acetonitrile in 10.5 min to 0% H2O/100% MeCN to 11.0 min, Hold at 0% H2O/100% Acetonitrile from 11.0 to 12.0 min. Flow: 25 mL/min.

QC Conditions:

Column: Waters Atlantis dC18 4.6×50, 5 u; Mobile phase A: 0.05% TFA in water (v/v); Mobile phase B: 0.05% TFA in acetonitrile (v/v); 95.0% H2O/5.0% Acetonitrile linear to 5% H2O/95% Acetonitrile in 4.0 min, Hold at 5% H2O/95% Acetonitrile from 4.0 min to 5.0 min. Flow: 2 mL/min.; Retention time=1.91 minutes; mass observed=933.4313. Method C: MassLynx\Acid_3.0Min.olp—LRMS [½M+1=933]. ¹H NMR (METHANOL-d₄) δ: 8.46 (d, J=4.7 Hz, 1H), 8.01 (s, 3H), 7.86-7.97 (m, 2H), 7.32 (t, J=5.3 Hz, 1H), 5.21 (s, 3H), 4.55-4.62 (m, 12H), 4.24 (t, J=6.0 Hz, 2H), 3.92-3.99 (m, 6H), 3.85-3.92 (m, 9H), 3.74-3.79 (m, 9H), 3.71 (dd, J=9.8, 4.3 Hz, 3H), 3.52-3.68 (m, 42H), 2.99-3.15 (m, 4H), 2.17 (t, J=7.2 Hz, 2H), 1.99 (s, 9H), 1.56 (quin, J=7.4 Hz, 2H), 1.42-1.50 (m, 2H), 1.24-1.38 (m, 2H)

1-{[6-(4,4,5,5-tetramethyl-1,3,2-dioxaborolan-2-yl)hexanoyl]oxy}pyrrolidine-2,5 (I-ah-1)

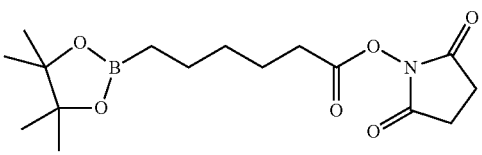 [SMILES: CC1(C)OB(CCCCCC(=O)ON2C(=O)CCC2=O)OC1(C)C]

A solution of chlorotris(Triphenylphosphine)Rhodium (I), Wilkinson's catalyst (39.7 mg, 0.0429 mmol) in dichloromethane (5.0 mL) purged with nitrogen for 10 minutes before the drop wise addition of 4,4,5,5-tetramethyl-1,3,2-dioxaborolane (299 mg, 2.34 mmol, 0.340 mL). The reaction was allowed to stir for 10 minutes at room temperature. 2,5-dioxopyrrolidin-1-yl hex-5-enoate

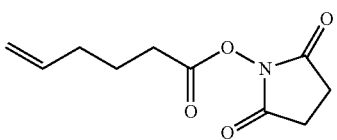

(see Journal of the American Chemical Society, 132(35), 12197-12199; 2010, 412 mg, 1.95 mmol) was dissolved in dichloromethane (1.0 mL) and added drop wise. The reaction was allowed to stir for 18 hours at room temperature. The following morning, the reaction was diluted with dichloromethane and washed with water. The organic layer was dried over magnesium sulfate, filtered and concentrated under reduced pressure. The crude material was purified using the CombiFlash Rf (RediSep 24 g Gold silica gel column) and eluting with a gradient of 0-100% ethyl acetate/heptane yielding crude title compound (366 mg). The crude title compound was purified using the CombiFlash Rf (RediSep 24 g gold silica gel column) and eluting with a gradient of 0-100% ethyl acetate/heptane yielding the title compound as an oil (271.0 mg, None, 41.0%). $^1$H NMR (METHANOL-d$_4$) δ: 2.83 (s, 4H), 2.61 (t, J=7.4 Hz, 2H), 1.71 (quin, J=7.1 Hz, 2H), 1.38-1.50 (m, 4H), 1.24 (s, 12H), 0.75 (t, J=6.8 Hz, 2H).

N-{6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}-6-(4,4,5,5-tetramethyl-1,3,2-dioxaborolan-2-yl)hexanamide (I-ag-4)

To a solution of 6-amino-N-(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)hexanamide (I-ag-1) (200 mg, 0.113 mmol) in N,N-dimethylformamide (0.6 mL) and tetrahydrofuran (0.6 mL) was added N,N-diisopropylethylamine (0.0786 mL, 0.451 mmol) followed by the addition 1-{[6-(4,4,5,5-tetramethyl-1,3,2-dioxaborolan-2-yl)hexanoyl]oxy}pyrrolidine-2,5-dione (I-ah-1) (57.4 mg, 0.169 mmol) and the reaction was allowed to stir at room temperature for 24 hours. After 24 hours, the reaction was concentrated under reduced pressure. The crude material was purified using the CombiFlash Rf (RediSep 12 g gold silica gel column) and eluting with a gradient of 0-20% methanol/dichloromethane yielding the title compound as a gum (209.0 mg, None, 93%). Method C: 3 minute run LRMS [½M=998]. $^1$H NMR (METHANOL-d$_4$) δ: 7.98 (s, 3H), 5.23 (d, J=1.6 Hz, 3H), 4.52-4.62 (m, 12H), 4.29 (d, J=5.9 Hz, 3H), 4.16 (t, J=6.4 Hz, 3H), 3.87-3.97 (m, 12H), 3.84 (d, J=8.2 Hz, 3H), 3.72-3.79 (m, 12H), 3.54-3.69 (m, 36H), 3.13 (q, J=6.6 Hz, 2H), 2.16 (q, J=7.3 Hz, 4H), 1.98 (s, 9H), 1.52-1.66 (m, 4H), 1.44-1.51 (m, 11H), 1.35-1.43 (m, 2H), 1.27-1.35 (m, 13H), 1.18-1.25 (m, 12H), 0.73 (t, J=7.6 Hz, 2H)

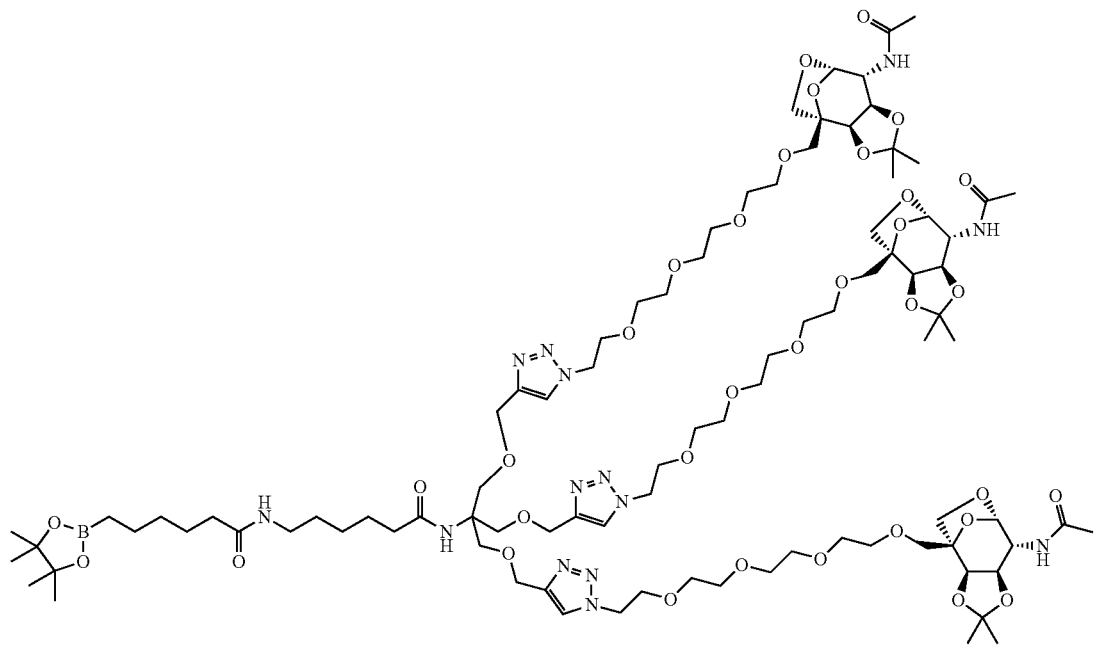 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@H]5OC(C)(C)O[C@H]56)nn4)(COCc4cn(CCOCCOCCOCCOC[C@@]56CO[C@@H](O5)[C@H](NC(C)=O)[C@H]5OC(C)(C)O[C@H]56)nn4)NC(=O)CCCCCNC(=O)CCCCCB4OC(C)(C)C(C)(C)O4)nn3)(O2)[C@@H]2OC(C)(C)O[C@H]12]

N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}-6-(4,4,5,5-tetramethyl-1,3,2-dioxaborolan-2-yl)hexanamide (56)

QC Conditions
Column: Waters Atlantis dC18 4.6×50, 5 u; Mobile phase A: 0.05% TFA in water (v/v); Mobile phase B: 0.05% TFA in acetonitrile (v/v); Gradient: 95.0% H2O/5.0% Acetonitrile linear to 5% H2O/95% Acetonitrile in 4.0 min, Hold at 5% H2O/95% Acetonitrile from 4.0 min to 5.0 min. Flow: 2 mL/min.; Retention time=2 minutes; Mass observed=938.9628). $^1$H NMR (METHANOL-$d_4$) δ: 8.01 (s, 3H), 5.21 (s, 3H), 4.51-4.66 (m, 12H), 3.95 (dd, J=9.4, 5.9 Hz, 6H), 3.89 (dd, J=11.7, 4.7 Hz, 9H), 3.74-3.81 (m,

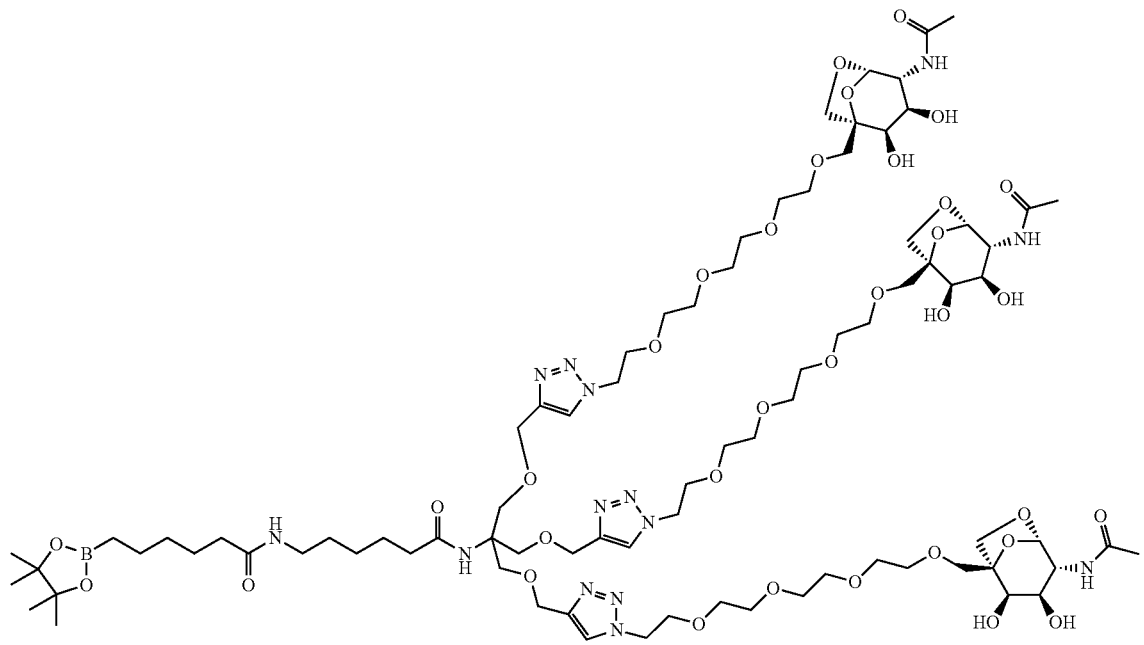 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCNC(=O)CCCCCB4OC(C)(C)C(C)(C)O4)nn3)(O2)[C@H](O)[C@@H]1O]

A solution of N-{6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}-6-(4,4,5,5-tetramethyl-1,3,2-dioxaborolan-2-yl)hexanamide (I-ag-4) (104.0 mg, 0.0521 mmol) in acetic acid (4 mL), methanol (1 mL) and water (1 mL) was heated to 70° C. for 24 hours. After 24 hours, the reaction was cooled to room temperature and concentrated under reduced pressure. The crude material was diluted with toluene and concentrated under reduced pressure. The crude material was diluted with toluene a second time and concentrated under reduced pressure yielding crude title compound (112.0 mg, 115%). A portion of the crude title compound (52.7 mg) was purified using reverse-phase chromatography yielding the title compound as a gum (18.2 mg, 19%)

Purification Conditions
The residue was dissolved in dimethyl sulfoxide (1 mL) and purified by reversed-phase HPLC Column: Waters Sunfire C18 19×100, 5 u; Mobile phase A: 0.05% TFA in water (v/v); Mobile phase B: 0.05% TFA in acetonitrile (v/v); Gradient: 80.0% H2O/20.0% Acetonitrile linear to 65% H2O/35% Acetonitrile in 8.5 min to 0% H2O/100% MeCN to 9.0 min, Hold at 0% H2O/100% Acetonitrile from 9.0 to 10.0 min. Flow: 25 mL/min.

9H), 3.71 (dd, J=9.8, 4.3 Hz, 3H), 3.52-3.68 (m, 42H), 3.13 (t, J=6.8 Hz, 2H), 2.17 (q, J=7.0 Hz, 4H), 1.99 (s, 9H), 1.53-1.66 (m, 4H), 1.45-1.52 (m, 2H), 1.36-1.44 (m, 2H), 1.27-1.35 (m, 4H), 1.23 (s, 12H), 0.73 (t, J=7.6 Hz, 2H)

ethyl 7[(1,3-dihydroxypropan-2-yl)amino]-7-oxo-heptanoate (I-ai-1)

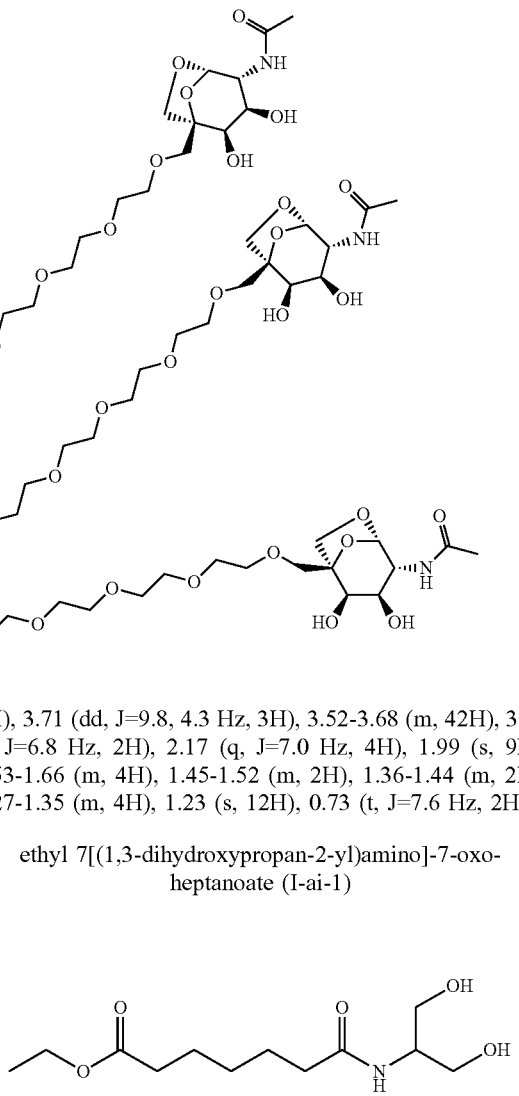

To a solution of ethyl 7-[(2,5-dioxopyrrolidin-1-yl)oxy]-7-oxoheptanoate (I-z-1) (228.0 mg, 0.799 mmol) in N,N-dimethylformamide (1.0 mL) was added N,N-diisopropylethylamine (0.557 mL, 3.20 mmol) and was allowed to stir for 10 minutes before the addition of 2-aminopropane-1,3-diol (72.8 mg, 0.799 mmol) and the reaction was stirred at room temperature for 72 hours. After 72 hours, the reaction was diluted with water and extracted 3 times with dichloromethane. The combined organic layers were washed with brine, dried over magnesium sulfate, filtered and concentrated under reduced pressure yielding crude title compound (89.0 mg, None, 43%). The aqueous layer was concentrated under reduced pressure. The crude concentrated aqueous layer was diluted with methanol (5 mL) and dichloromethane (10 mL). The mixture was decanted and combined with crude title compound from the first extraction. The solution was concentrated under reduced pressure. The combined crude material was purified using the CombiFlash Rf (RediSep 12 g silica gel column) and eluting with a gradient of 0-20% methanol/dichloromethane yielding the title compound (183.0 mg, 88%). Method C: 3 minute run LRMS [M+1=262]. $^1$H NMR (METHANOL-d$_4$) δ: 4.11 (q, J=7.2 Hz, 2H), 3.83-3.99 (m, 1H), 3.60 (d, J=5.5 Hz, 4H), 2.31 (t, J=7.2 Hz, 2H), 2.23 (t, J=7.4 Hz, 2H), 1.63 (quin, J=7.5 Hz, 4H), 1.30-1.45 (m, 2H), 1.24 (t, J=7.0 Hz, 3H)

ethyl 7-[(2,2-dimethyl-1,3-dioxan-5-yl)amino]-7-oxoheptanoate (I-aj-1)

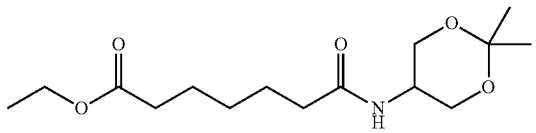 [SMILES: CCOC(=O)CCCCCC(=O)NC1COC(C)(C)OC1]

To a solution of ethyl 7-[(1,3-dihydroxypropan-2-yl)amino]-7-oxoheptanoate (I-ai-1) (180.0 mg, 0.689 mmol) in N,N-dimethylformamide (2 mL) was added 2,2-dimethoxypropane (0.53 mL, 4.13 mmol) followed by (1S)-(+)-10-Camphorsulfonic acid (64.0 mg, 0.276 mmol). The reaction was heated to 70° C. for 72 hours. After 72 hours, the reaction was cooled to room temperature and partitioned between water (20 mL) and ethyl acetate (10 mL). The layers were extracted and the layers were separated. The aqueous layer was washed two additional times with ethyl acetate (10 mL). The combined organic layers were washed with water, brine, dried over sodium sulfate, filtered and concentrated under reduced pressure yielding the crude title compound (94.0 mg, None, 45%).

7-[(2,2-dimethyl-1,3-dioxan-5-yl)amino]-7-oxoheptanoic acid (I-ak-1)

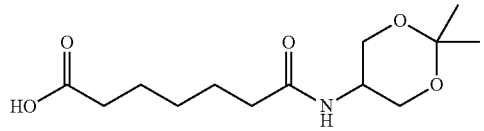 [SMILES: CC1(C)OCC(NC(=O)CCCCCC(=O)O)CO1]

To a solution of ethyl 7-[(2,2-dimethyl-1,3-dioxan-5-yl)amino]-7-oxoheptanoate (I-aj-1) (94.0 mg, 0.31 mmol) in ethanol (5 mL) was added 1.0M sodium hydroxide aqueous (1.5 mL, 1.5 mmol) and the reaction was allowed to stir at room temperature overnight. The following morning, the reaction was concentrated under reduced pressure. The resulting crude material was diluted with 1N hydrochloric acid (3.0 mL) and ethyl acetate. The layers were separated and the organic layer was extracted two additional times with ethyl acetate. The combined organic layers were washed with brine, dried over sodium sulfate, filtered and concentrated under reduced pressure yielding the crude title compound (29.4 mg, None, 34%).

N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}-N'-(1,3-dihydroxypropan-2-yl)heptanediamide (57)

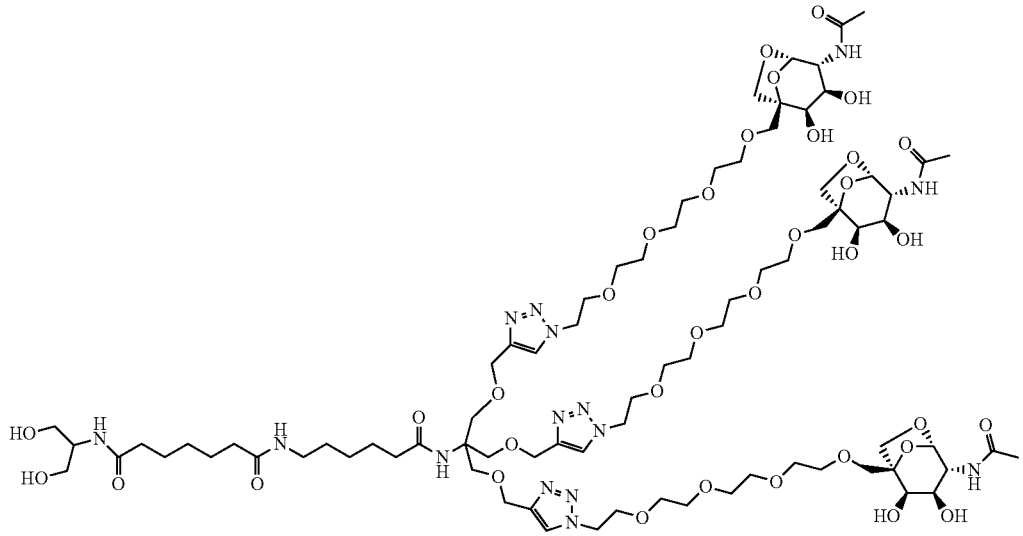 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCNC(=O)CCCCCC(=O)NC(CO)CO)nn3)(O2)[C@H](O)[C@@H]1O]

To a solution of 7-[(2,2-dimethyl-1,3-dioxan-5-yl)amino]-7-oxoheptanoic acid (I-ak-1) (18.8 mg, 0.0688 mmol) in N,N-dimethylformamide (0.3 mL) and tetrahydrofuran (0.3 mL) was added 1-Hydroxybenzotriazole (10.3 mg, 0.0762 mmol) and N-(3-dimethylaminopropyl)-N'-ethylcarbodimiimide hydrochloride (14.9 mg, 0.0762 mmol) and the reaction was allowed to stir for 1 hour at room temperature. The reaction mixture was added to 6-amino-N-(1,3-bis[(1-{1-[(1S,2R,6R,7R,8S)-7-(acetylamino)-4,4- dimethyl-3,5,9,11-tetraoxatricyclo[6.2.1.0~2,6~]undec-1-yl]-2,5,8,11-tetraoxatridecan-13-yl}-1H-1,2,3-triazol-4-yl) methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl) methoxy]methyl}propan-2-yl)hexanamide (I-ag-1) (75.0 mg, 0.042 mmol) followed by the addition of N,N-diisopropylethylamine (0.0295 mL, 0.169 mmol) and the reaction was allowed to stir at room temperature for 16 hours. After 16 hours, the reaction was concentrated under reduced pressure. The crude material was dissolved in acetic acid (4.0 mL), methanol (1 mL), and Water (1.0 mL) was heated to 70° C. for 24 hours. After 24 hours, the reaction was cooled to room temperature and concentrated under reduced pressure. The crude material was diluted with toluene and concentrated under reduced pressure yielding crude title compound (175.0 mg, 220%). The crude title compound was purified by revered-phase chromatography using the conditions below yielding the title compound as a gum (10.9 mg, 14%)

Purification Conditions:

The residue was dissolved in dimethyl sulfoxide (1 mL) and purified by reversed-phase HPLC Column: Waters Sunfire C18 19×100, 5 u; Mobile phase A: 0.05% TFA in water (v/v); Mobile phase B: 0.05% TFA in acetonitrile (v/v); Gradient: 85.0% H2O/15.0% Acetonitrile linear to 75% H2O/25% Acetonitrile in 8.5 min to 0% H2O/100% MeCN to 9.0 min, Hold at 0% H2O/100% Acetonitrile from 9.0 to 10.0 min. Flow: 25 mL/min.

QC Conditions:

Column: Waters Atlantis dC18 4.6×50, 5 u; Mobile phase A: 0.05% TFA in water (v/v); Mobile phase B: 0.05% TFA in acetonitrile (v/v); 95.0% H2O/5.0% Acetonitrile linear to 5% H2O/95% Acetonitrile in 4.0 min, Hold at 5% H2O/95% Acetonitrile from 4.0 min to 5.0 min. Flow: 2 mL/min.; Retention time=1.53 minutes; mass observed=934.548. Method C: 3 minute run LRMS [M+Na=1889]. $^1$H NMR (METHANOL-$d_4$) δ: 8.00 (s, 3H), 5.21 (s, 3H), 4.52-4.62 (m, 12H), 3.95 (t, J=9.4 Hz, 6H), 3.85-3.91 (m, 9H), 3.74-3.79 (m, 9H), 3.71 (dd, J=10.0, 4.1 Hz, 3H), 3.55-3.67 (m, 47H), 3.12 (t, J=6.7 Hz, 2H), 2.22 (t, J=7.3 Hz, 2H), 2.17 (t, J=7.3 Hz, 4H), 1.98 (s, 9H), 1.58-1.69 (m, 4H), 1.51-1.57 (m, 2H), 1.48 (quin, J=7.2 Hz, 2H), 1.26-1.40 (m, 4H)

6-azido-N-{6-[(1,3-bis[(1-{1-[(1S,2R,6R,7R,8S)-7-(acetylamino)-4,4-dimethyl-3,5,9,11-tetraoxatricyclo [6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl) methoxy]methyl}propan-2-yl)amino]-6-oxohexyl}hexanamide (I-ag-5)

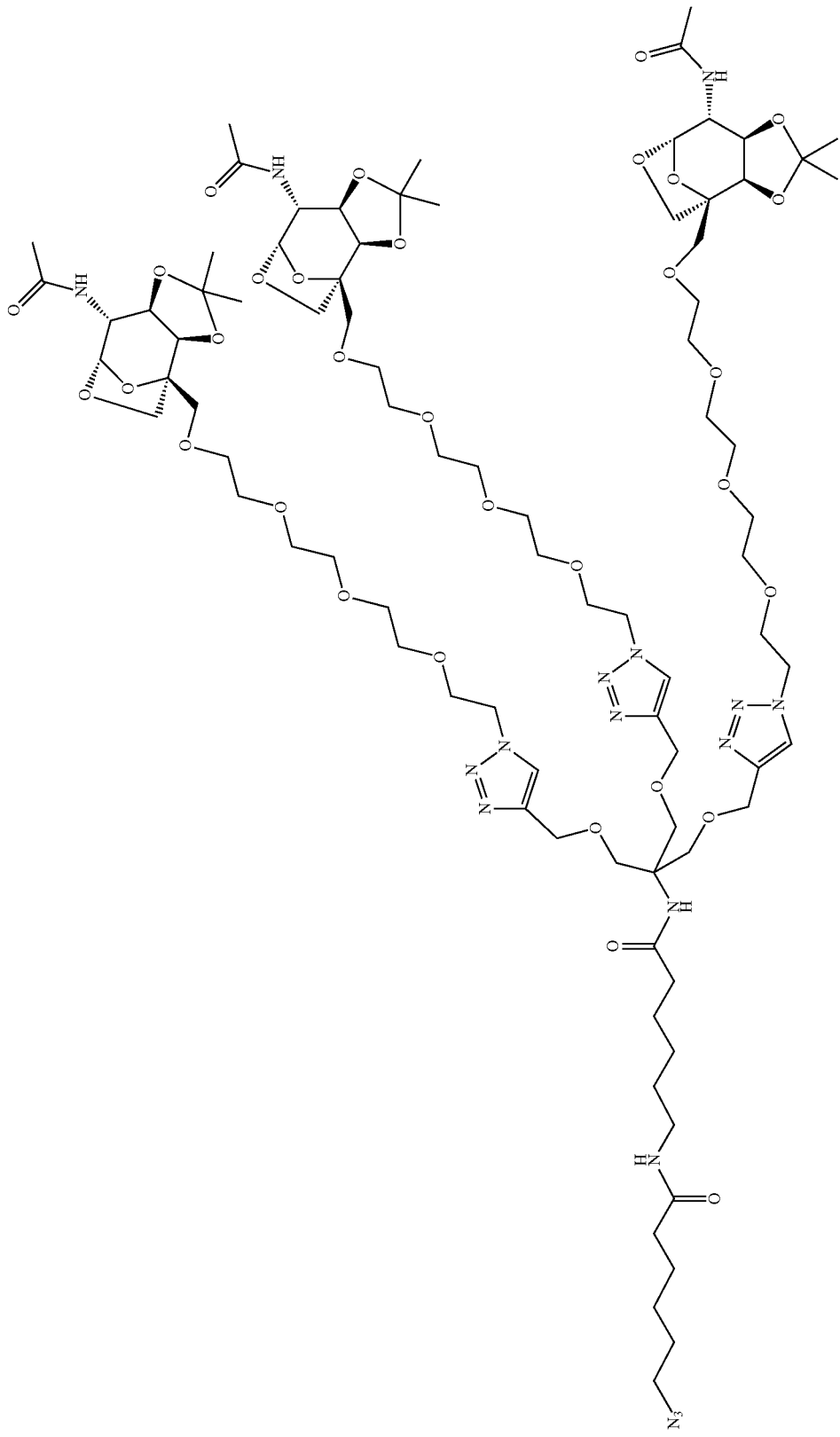

To a solution of 6-amino-N-(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)hexanamide (I-ag-1) (300 mg, 0.169 mmol) in N,N-dimethylformamide (0.6 mL) and tetrahydrofuran (0.6 mL) was added N,N-diisopropylethylamine (0.118 mL, 0.677 mmol) and 1-[(6-azidohexanoyl)oxy]pyrrolidine-2,5-dione (56.0 mg, 0.220 mmol). The reaction was allowed to stir at room temperature for 24 hours. After 24 hours, the reaction was concentrated under reduced pressure. The crude reaction mixture was purified using the CombiFlash Rf (RediSep 24 g gold silica gel column) and eluting with a gradient of 0-20% methanol/dichloromethane yielding the title compound as a gum (269 mg, 83%). Method C: 3 minute run LRMS [½M+1=956]. $^1$H NMR (METHANOL-$d_4$) δ: 7.98 (s, 3H), 5.22 (s, 3H), 4.50-4.65 (m, 12H), 4.29 (d, J=5.9 Hz, 3H), 4.16 (t, J=6.5 Hz, 3H), 3.87-3.95 (m, 12H), 3.83 (d, J=7.6 Hz, 3H), 3.73-3.79 (m, 12H), 3.55-3.71 (m, 36H), 3.26-3.30 (m, 2H), 3.14 (q, J=6.5 Hz, 2H), 2.18 (q, J=7.6 Hz, 4H), 1.98 (s, 9H), 1.53-1.68 (m, 6H), 1.45-1.51 (m, 11H), 1.36-1.43 (m, 2H), 1.29-1.36 (m, 11H)

6-azido-N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}hexanamide (58)

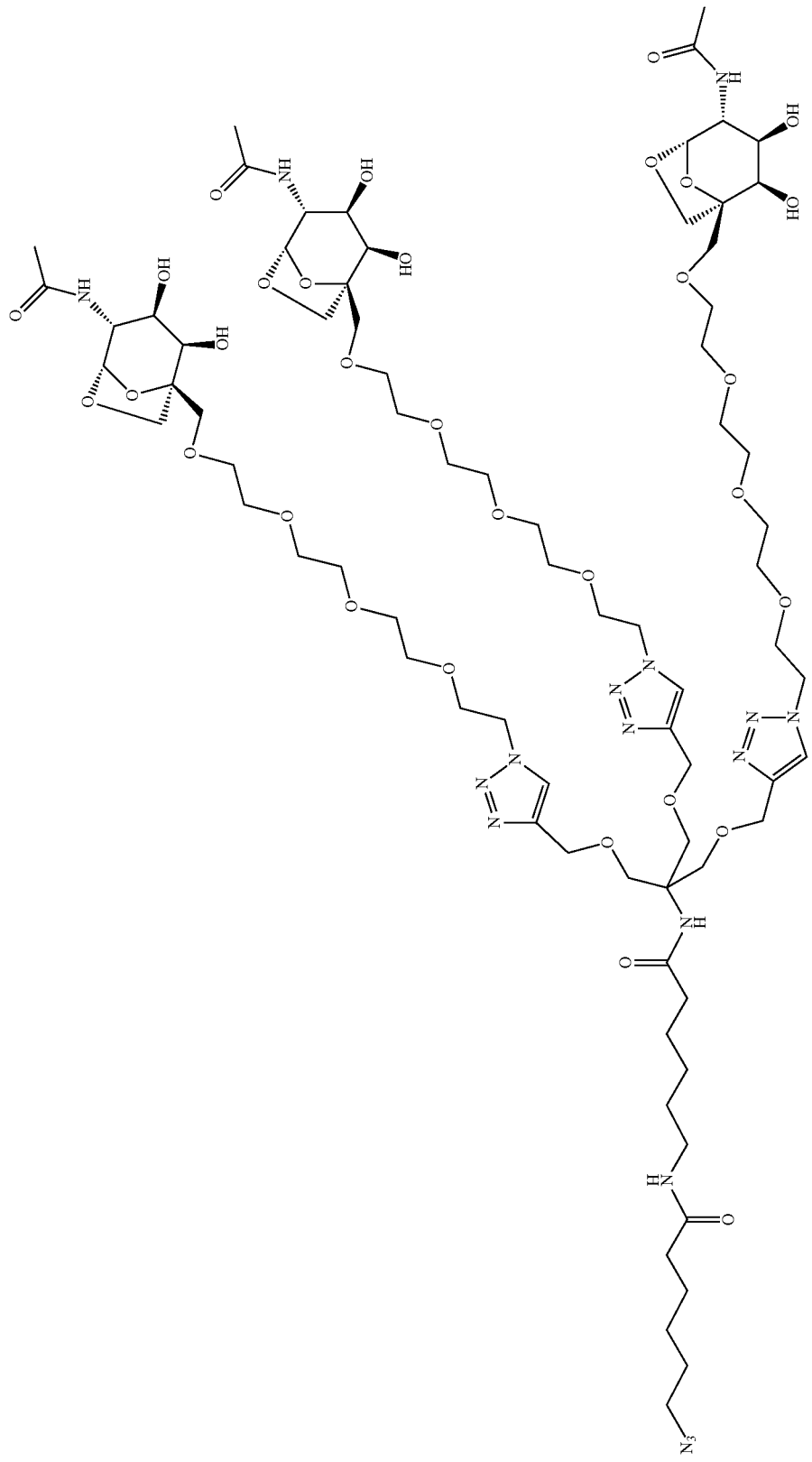

A solution of 6-azido-N-{6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}hexanamide (I-ag-5) (25.0 mg, 0.013 mmol) in acetic acid (3 mL), methanol (0.75 mL) and water (0.75 mL) was heated to 70° C. for 24 hours. After 24 hours, the reaction was cooled to room temperature and concentrated under reduced pressure. The crude material was diluted with toluene and concentrated under reduced pressure yielding the title compound as a gum (22.7 mg, 97%). Method C: 3 minute run LRMS [M+1=1791]. $^1$H NMR (METHANOL-$d_4$) δ: 7.99 (s, 3H), 5.21 (s, 3H), 4.51-4.66 (m, 12H), 3.92-4.01 (m, 6H), 3.89 (dd, J=10.1, 4.7 Hz, 9H), 3.74-3.81 (m, 9H), 3.71 (dd, J=10.0, 4.1 Hz, 3H), 3.52-3.68 (m, 42H), 3.25-3.30 (m, 2H), 3.08-3.19 (m, 2H), 2.13-2.23 (m, 4H), 1.99 (s, 9H), 1.54-1.69 (m, 6H), 1.49 (dt, J=14.4, 7.2 Hz, 2H), 1.36-1.44 (m, 2H), 1.32 (dd, J=14.8, 6.2 Hz, 2H)

1-{[6-(benzyloxy)hexanoyl]oxy}pyrrolidine-2,5-dione (I-al-1)

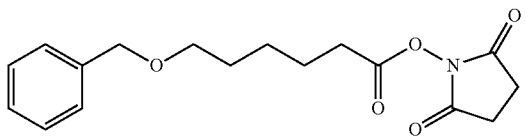 [SMILES: O=C(CCCCCOCc1ccccc1)ON1C(=O)CCC1=O]

To a solution of 6-(benzyloxy)hexanoic acid

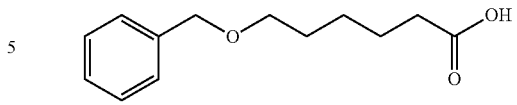

(see Synlett, (4), 693-697; 2004, 1400.0 mg, 6.298 mmol) in N,N-dimethylformamide (20 mL) was added N-Hydroxysuccinimide (870 mg, 7.56 mmol) followed by N-(3-dimethylaminopropyl)-N'-ethylcarbodiimide hydrochloride (1480 mg, 7.56 mmol). The reaction was allowed to stir at room temperature overnight. The following morning, the reaction was quenched with water and extracted three times with dichloromethane. The combined organic layers were washed with saturated sodium bicarbonate, brine, dried over sodium sulfate, filtered and concentrated under reduced pressure. The crude material was purified using the CombiFlash Rf (RediSep 40 g gold column) and eluting with a gradient of 0-100% ethyl acetate/heptane yielding the title compound as a gum (715 mg, 36%). Method C: 1.5 minute run LRMS [M+Na=342]. $^1$H NMR (METHANOL-$d_4$) δ: 7.22-7.42 (m, 5H), 4.51 (s, 2H), 3.53 (t, J=6.4 Hz, 2H), 2.85 (s, 4H), 2.65 (t, J=7.4 Hz, 2H), 1.76 (quin, J=7.5 Hz, 2H), 1.61-1.71 (m, 2H), 1.47-1.59 (m, 2H)

6-(benzyloxy)-N-{6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}hexanamide (I-ag-6)

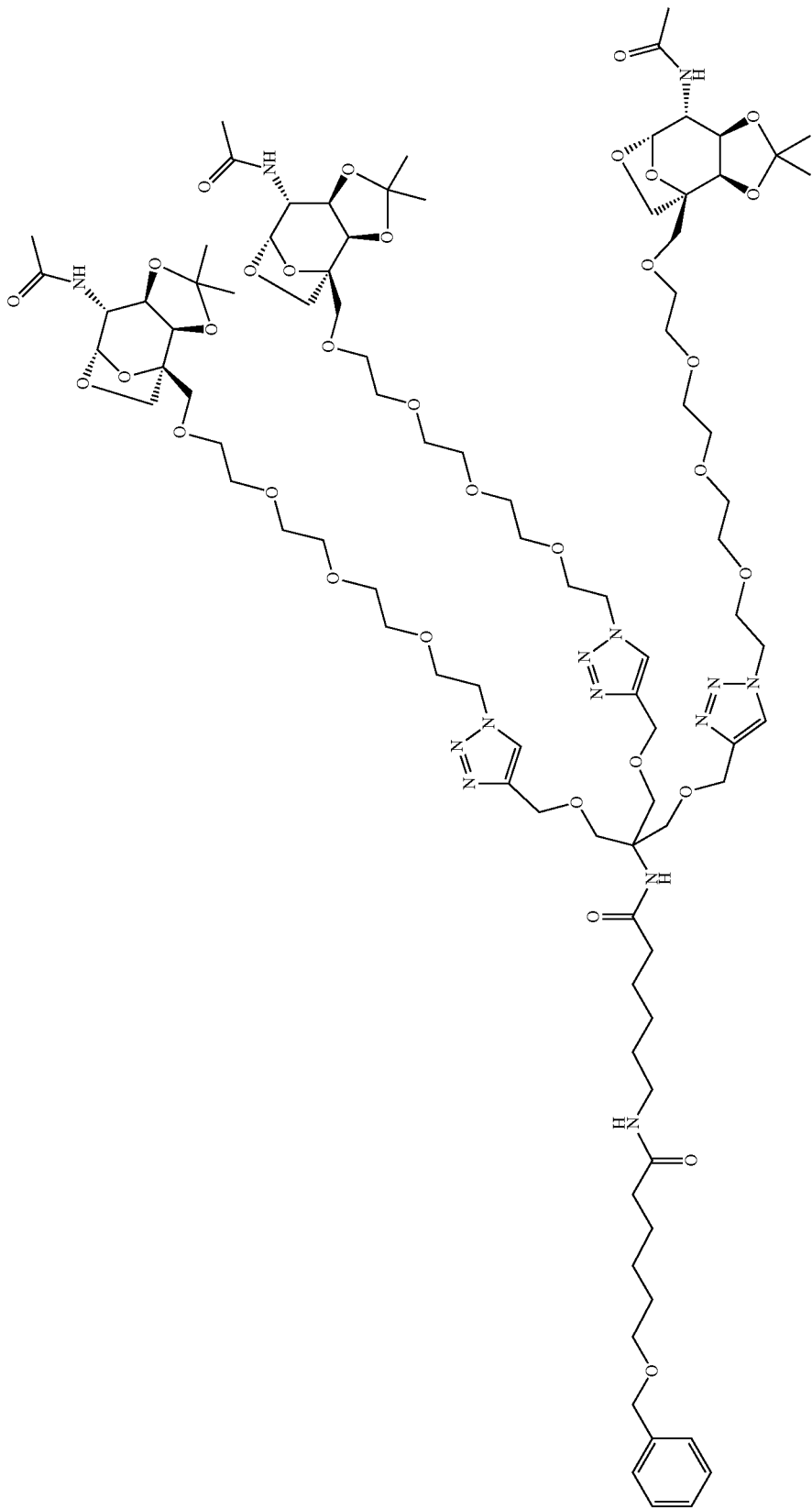

To a solution of 6-amino-N-(1,3-bis[(1-{1-[(1S,2R,6R, 7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R, 6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy] methyl}propan-2-yl)hexanamide (I-ag-1) (200 mg, 0.113 mmol) in N,N-dimethylformamide (0.6 mL) and tetrahydrofuran (0.6 mL) was added N,N-diisopropylethylamine (0.0786 mL, 0.451 mmol) and 1-{[6-(benzyloxy)hexanoyl] oxy}pyrrolidine-2,5-dione (I-al-1) (46.9 mg, 0.147 mmol) and the reaction was allowed to stir at room temperature for 24 hours. After 24 hours, the reaction was concentrated under reduced pressure. The crude material was purified using the CombiFlash Rf (RediSep 12 g gold silica gel column) and eluting with a gradient of 0-20% methanol/ dichloromethane yielding the title compound as gum (203 mg, 91%). $^1$H NMR (METHANOL-$d_4$) δ: 7.98 (s, 3H), 7.19-7.38 (m, 5H), 5.23 (d, J=1.2 Hz, 3H), 4.52-4.64 (m, 12H), 4.48 (s, 2H), 4.29 (d, J=5.9 Hz, 3H), 4.15 (t, J=6.4 Hz, 3H), 3.86-3.96 (m, 12H), 3.83 (d, J=7.8 Hz, 3H), 3.72-3.80 (m, 12H), 3.54-3.70 (m, 36H), 3.49 (t, J=6.4 Hz, 2H), 3.08-3.15 (m, 2H), 2.12-2.26 (m, 4H), 1.98 (s, 9H), 1.51-1.68 (m, 6H), 1.48 (s, 11H), 1.37-1.44 (m, 2H), 1.33 (s, 11H)

6-(benzyloxy)-N-{6-[(1,3-bis[(1-{1-[(1S,2R,3R,4R, 5S)-4-(acetylamino)-2,3-dihydroxy-6,8-dioxabicyclo [3.2.1]oct-1-yl]-2,5,8,11-tetraoxatridecan-13-yl}-1H-1,2,3-triazol-4-yl)methoxy]-2-{[(1-{1-[(1S,2R,3R, 4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl) methoxy]methyl}propan-2-yl)amino]-6-oxohexyl}hexanamide (59)

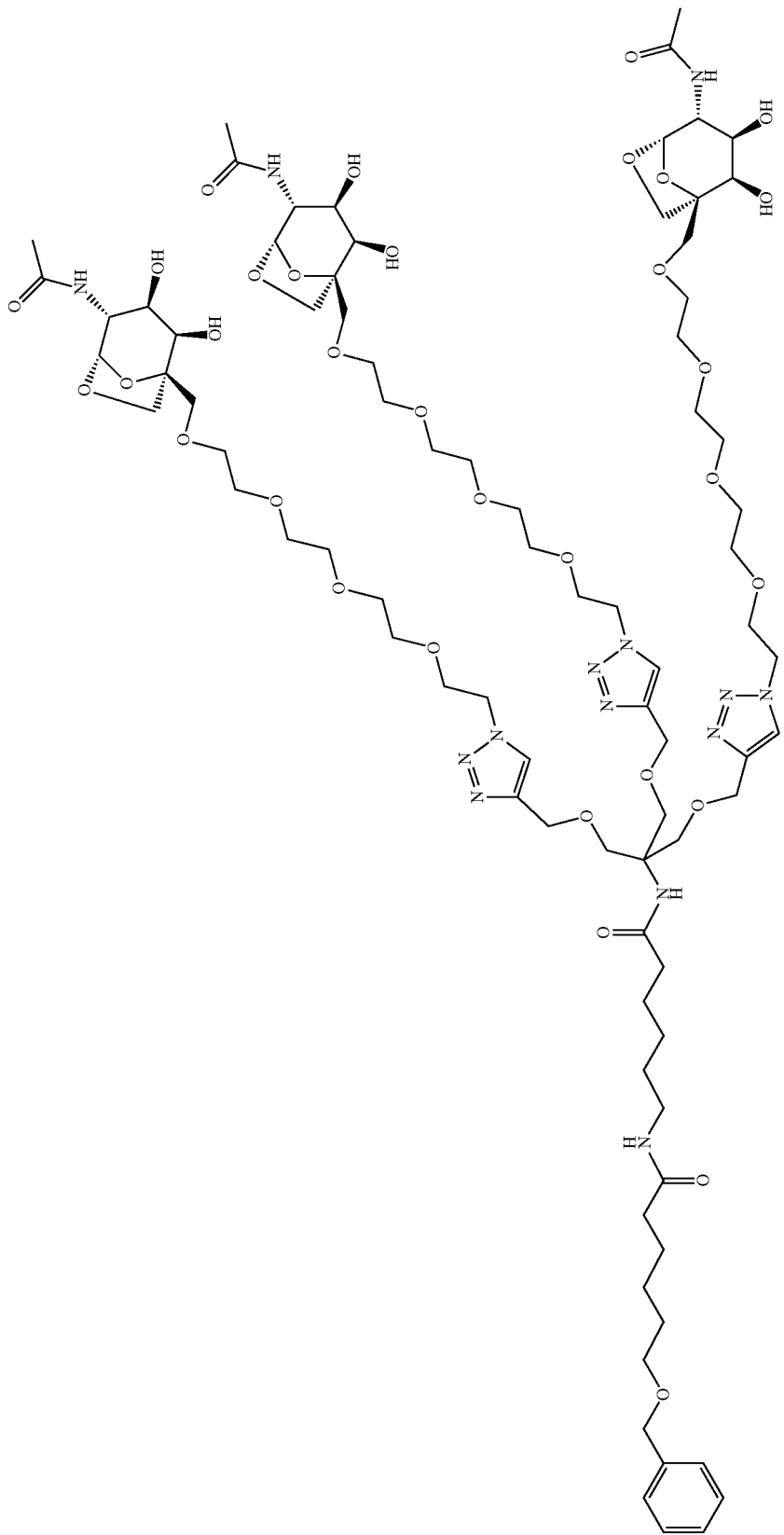

A solution of 6-(benzyloxy)-N-{6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}hexanamide (I-ag-6) (180.0 mg, 0.0911 mmol) in acetic acid (6.0 mL), methanol (1.5 mL) and water (1.5 mL) was heated to 70° C. for 24 hours. After 24 hours, the reaction was cooled to room temperature and concentrated under reduced pressure. The crude material was diluted with toluene and concentrated under reduced pressure. The crude material was diluted with toluene a second time and concentrated under reduced pressure yielding the title compound as a gum (164.0 mg, 97.0%). Method C: 3 minute run LRMS [½M=928]. $^1$H NMR (METHANOL-$d_4$) δ: 7.99 (s, 3H), 7.25-7.39 (m, 5H), 5.21 (s, 3H), 4.52-4.66 (m, 12H), 4.48 (s, 2H), 3.92-3.99 (m, 6H), 3.84-3.91 (m, 9H), 3.74-3.81 (m, 9H), 3.71 (dd, J=9.8, 4.3 Hz, 3H), 3.54-3.67 (m, 42H), 3.49 (t, J=6.4 Hz, 2H), 3.08-3.17 (m, 2H), 2.13-2.22 (m, 4H), 1.99 (s, 9H), 1.51-1.68 (m, 6H), 1.48 (t, J=7.4 Hz, 2H), 1.39 (dt, J=15.3, 7.8 Hz, 2H), 1.26-1.35 (m, 2H)

(1S,2R,3R,4R,5S)-4-(acetylamino)-2-(acetyloxy)-1-{13-[4-(4,4-bis{[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]methyl}-6,13-dioxo-20-phenyl-2,19-dioxa-5,12-diazaicos-1-yl)-1H-1,2,3-triazol-1-yl]-2,5,8,11-tetraoxatridec-1-yl}-6,8-dioxabicyclo[3.2.1]oct-3-yl acetate (I-am-1)

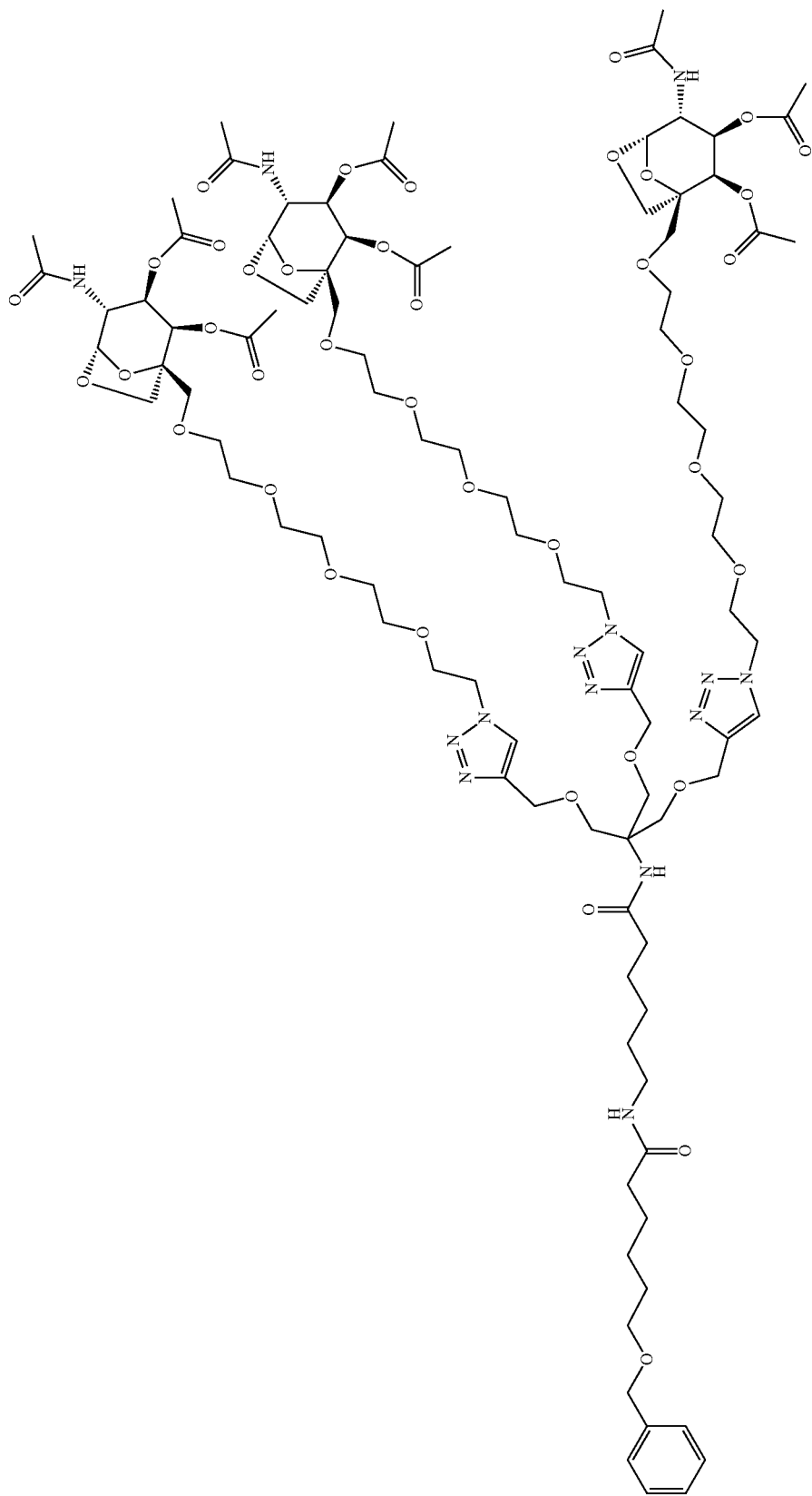

6-(benzyloxy)-N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}hexanamide (59) (130 mg, 0.07 mmol) was dissolved in (3 mL, 40 mmol) and to which was added acetic anhydride (0.198 mL, 2.10 mmol) at room temperature. The reaction was then heated to 50° C. overnight. The following morning, the reaction was concentrated under reduced pressure. The crude material was purified using the CombiFlash Rf (RediSep 12 g gold silica gel column) and eluting with a gradient of 0-20% methanol/dichloromethane yielding the title compound as a gum (130.0 mg, 88%). Method C: 3 minute run LRMS [½M=1054]. $^1$H NMR (METHANOL-$d_4$) δ: 7.98 (s, 3H), 7.16-7.39 (m, 5H), 5.44 (d, J=4.3 Hz, 3H), 5.32 (s, 3H), 5.10 (dd, J=10.5, 4.3 Hz, 3H), 4.52-4.60 (m, 12H), 4.48 (s, 2H), 4.18 (d, J=10.5 Hz, 3H), 3.99 (d, J=8.2 Hz, 3H), 3.89 (t, J=5.1 Hz, 6H), 3.70-3.81 (m, 12H), 3.52-3.67 (m, 39H), 3.49 (t, J=6.2 Hz, 2H), 3.13 (q, J=6.6 Hz, 2H), 2.13-2.21 (m, 13H), 1.94 (d, J=1.6 Hz, 18H), 1.51-1.68 (m, 6H), 1.45-1.50 (m, 2H), 1.37-1.43 (m, 2H), 1.28-1.35 (m, 2H)

N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6, 8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}-6-hydroxyhexanamide (I-an-1)

231 232
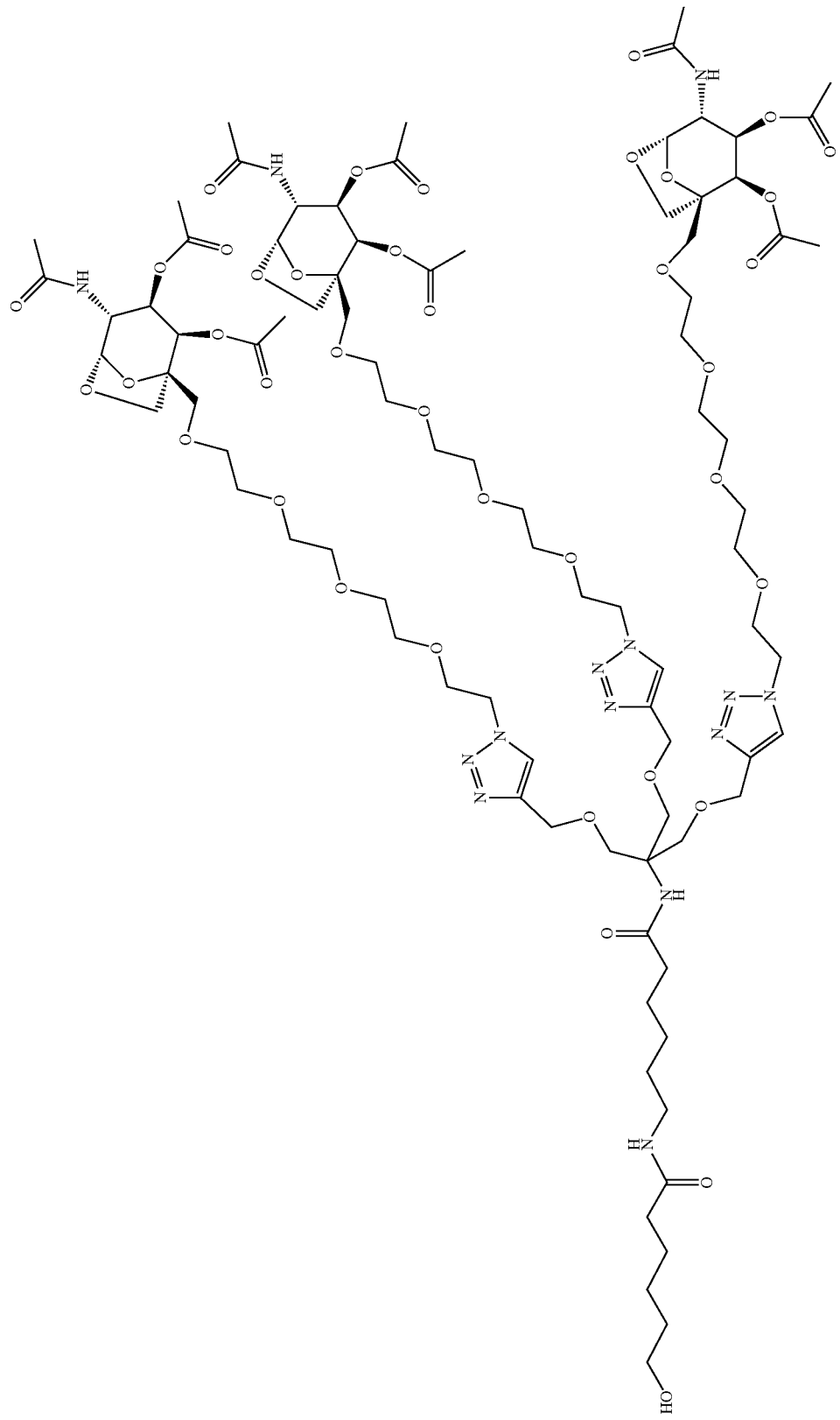

(1S,2R,3R,4R,5S)-4-(acetylamino)-2-(acetyloxy)-1-{13-[4-(4,4-bis{[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]methyl}-6,13-dioxo-20-phenyl-2,19-dioxa-5,12-diazaicos-1-yl)-1H-1,2,3-triazol-1-yl]-2,5,8,11-tetraoxatridec-1-yl}-6,8-dioxabicyclo[3.2.1]oct-3-yl acetate (I-am-1) (110 mg, 0.0522 mmol) was dissolved in methanol (10.0 mL) and the solution was then passed through the H-cube using a 10% palladium on carbon (small cartridge) using the following parameters (Temperature—60° C., Flow rate—1.0 mL/min., pressure—Full H2 (1 bar)). The solution was collected and concentrated under reduced pressure yielding the title compound as a gum (91.6 mg, 87%). Method C: 3 minute run LRMS [½M=1009]. $^1$H NMR (METHANOL-$d_4$) δ: 7.98 (s, 3H), 5.44 (d, J=4.3 Hz, 3H), 5.32 (s, 3H), 5.10 (dd, J=10.5, 4.3 Hz, 3H), 4.50-4.64 (m, 12H), 4.18 (d, J=10.5 Hz, 3H), 3.99 (d, J=8.2 Hz, 3H), 3.90 (t, J=4.9 Hz, 6H), 3.71-3.82 (m, 9H), 3.44-3.66 (m, 44H), 3.08-3.19 (m, 2H), 2.16-2.22 (m, 4H), 2.15 (s, 9H), 1.94 (d, J=1.2 Hz, 18H), 1.44-1.68 (m, 8H), 1.27-1.42 (m, 4H)

(1S,2R,3R,4R,5S)-4-(acetylamino)-1-{13-[4-({3-[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]methyl}-2-({6 [(6hydroxyhexanoyl)amino]hexanoyl}amino)propoxy}methyl)-1H-1,2,3-triazol-1-yl]-2,5,8,11-tetraoxatridec-1-yl}-3-(acetyloxy)-6,8-dioxabicyclo[3.2.1]oct-2-yl acetate (60)

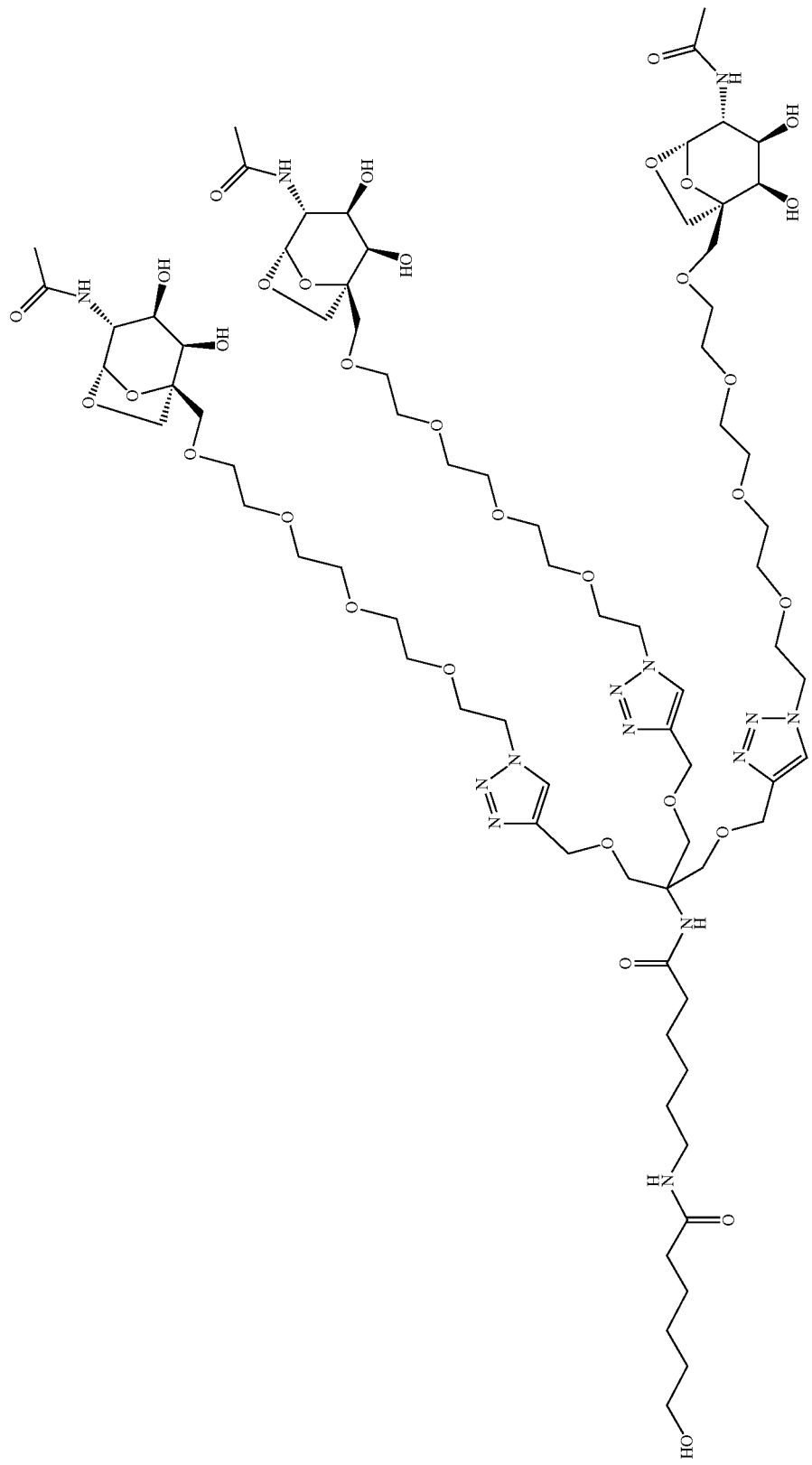

6-(benzyloxy)-N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}hexanamide (I-an-1) (31.0 mg, 0.017 mmol) was dissolved in methanol (5 mL) and the solution was then passed through the H-cube using a 10% palladium on carbon (small cartridge) using the following parameters (Temperature—60° C., Flow rate—1.0 mL/min., pressure—Full H₂ (1 bar)). The solution was collected and concentrated under reduced pressure yielding the title compound as a gum (7.9 mg, 27%). Method C: 3 minute run LRMS [M+1=1766]. ¹H NMR (METHANOL-$d_4$) δ: 7.99 (s, 3H), 5.21 (s, 3H), 4.49-4.63 (m, 12H), 3.92-4.00 (m, 6H), 3.89 (dd, J=10.3, 4.5 Hz, 9H), 3.74-3.79 (m, 9H), 3.71 (dd, J=9.8, 4.3 Hz, 3H), 3.53-3.67 (m, 44H), 3.02-3.16 (m, 2H), 2.18 (td, J=7.3, 3.3 Hz, 4H), 1.99 (s, 9H), 1.44-1.72 (m, 8H), 1.25-1.42 (m, 4H)

S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl} amino)-6-oxohexyl]carbamate (I-ag-7)

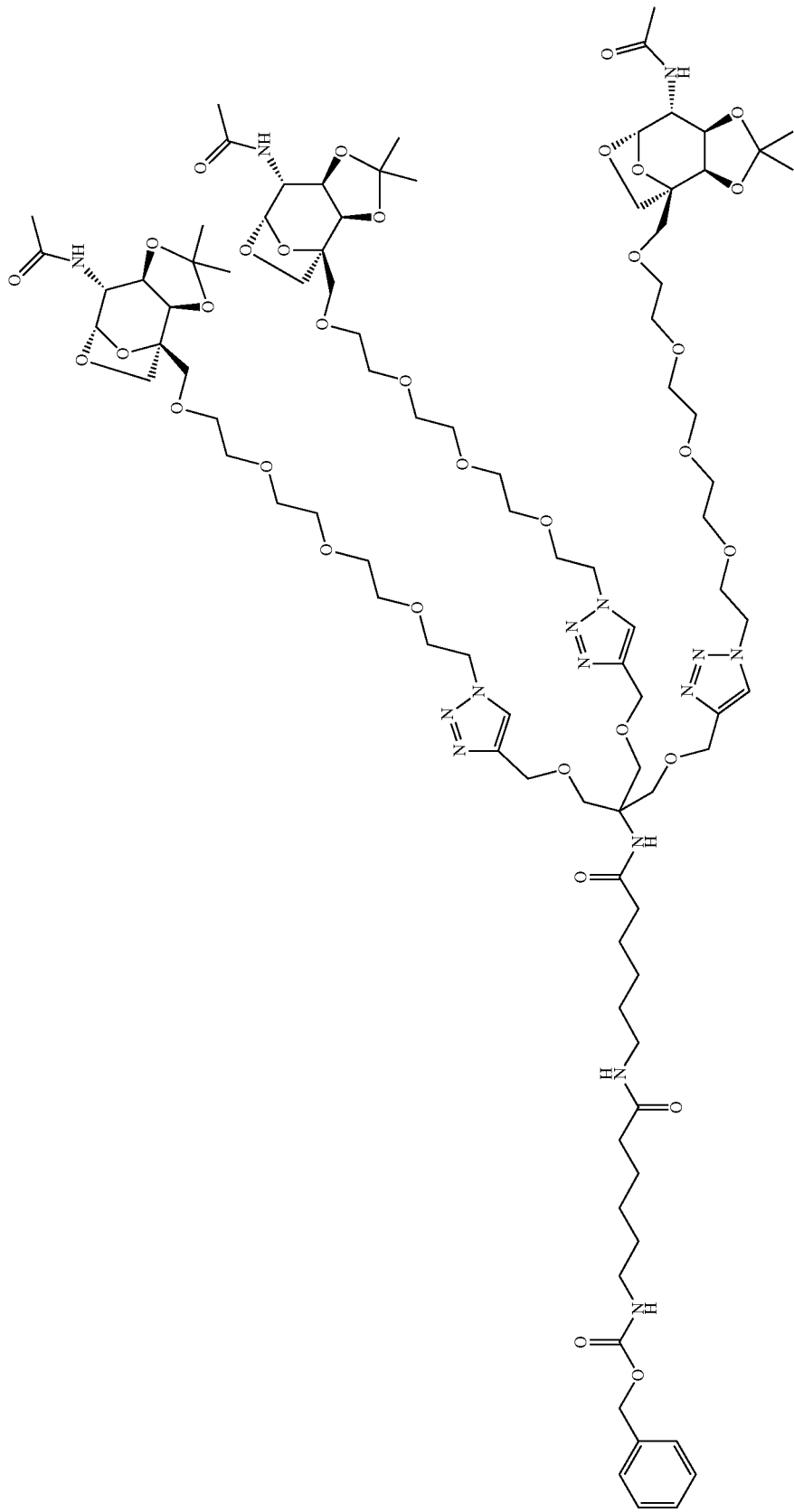

To a solution of 6-amino-N-(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)hexanamide (I-ag-1) (222 mg, 0.125 mmol) in N,N-dimethylformamide (1.5 mL) and tetrahydrofuran (1.0 mL) was added N,N-diisopropylethylamine (0.0873 mL, 0.501 mmol) and benzyl {6-[(2,5-dioxopyrrolidin-1-yl)oxy]-6-oxohexyl}carbamate

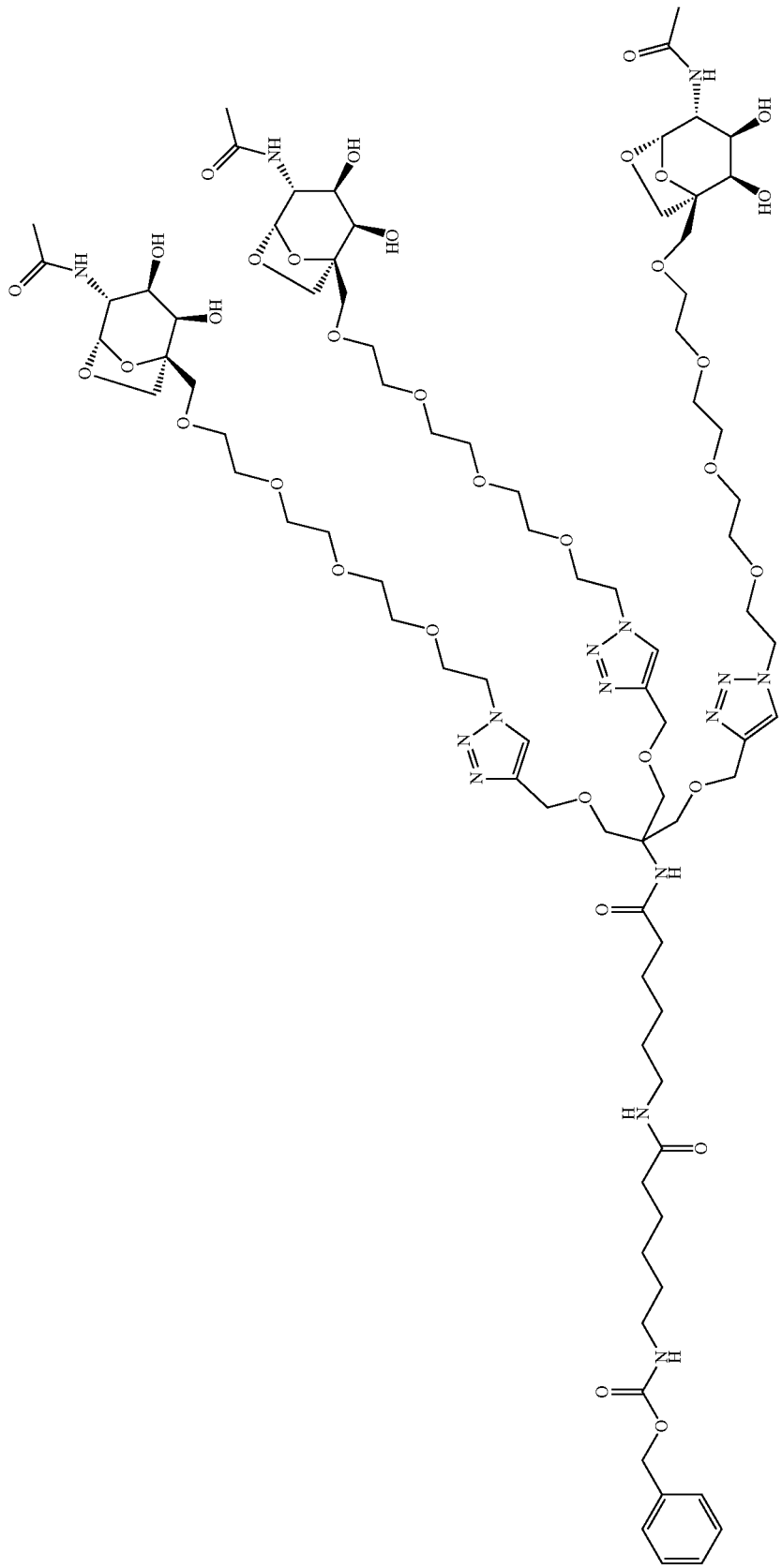

(see Journal of Heterocyclic Chemistry, 23(3), 901-3; 1986, 68.1 mg, 0.188 mmol). The reaction was allowed to stir at room temperature for 24 hours. After 24 hours, the reaction was concentrated under reduced pressure. The crude reaction mixture was purified using the CombiFlash Rf (RediSep 12 g gold silica gel column) and eluting with a gradient of 0-20% methanol/dichloromethane yielding the title compound as a gum (250 mg, 99%). Method C: 3 minute run LRMS [½M+1=1010]. $^1$H NMR (METHANOL-$d_4$) δ: 7.98 (s, 3H), 7.22-7.40 (m, 5H), 5.22 (d, J=1.2 Hz, 3H), 5.06 (s, 2H), 4.51-4.61 (m, 12H), 4.29 (d, J=5.9 Hz, 3H), 4.16 (t, J=6.4 Hz, 3H), 3.86-3.96 (m, 12H), 3.83 (d, J=7.8 Hz, 3H), 3.73-3.79 (m, 12H), 3.53-3.70 (m, 36H), 3.04-3.19 (m, 4H), 2.17 (t, J=7.4 Hz, 4H), 1.98 (s, 9H), 1.58 (td, J=14.5, 7.6 Hz, 4H), 1.48 (s, 13H), 1.33 (s, 13H)

benzyl [6-({6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}amino)-6-oxohexyl]carbamate (61)

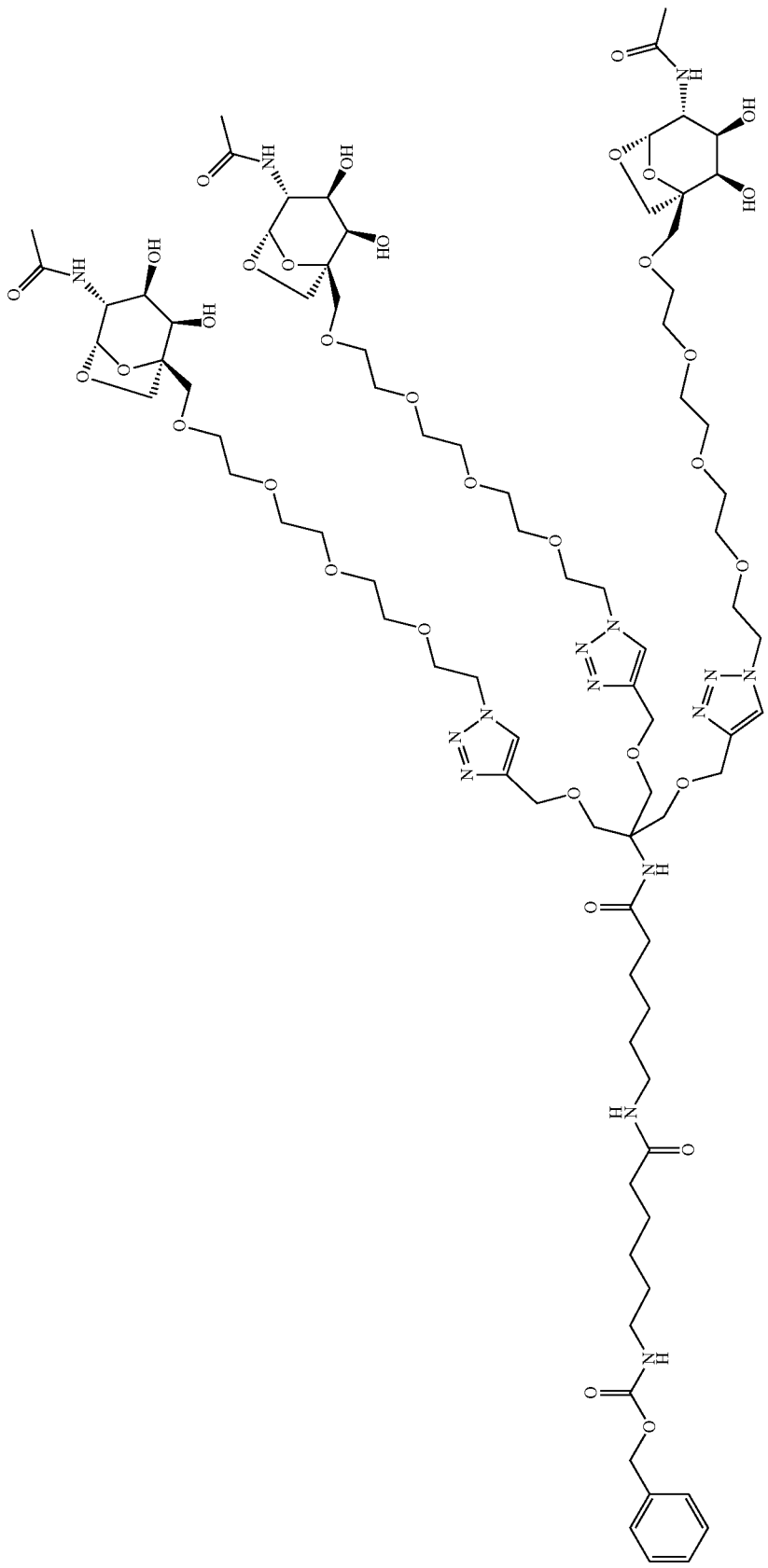

A solution of benzyl [6-({6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}amino)-6-oxohexyl]carbamate (I-ag-7) (250.0 mg, 0.124 mmol) in acetic acid (8 mL), methanol (2 mL) and water (2 mL) was heated to 70° C. for 36 hours. After 36 hours, the reaction was cooled to room temperature and concentrated under reduced pressure. The crude material was diluted with toluene and concentrated under reduced pressure. The crude material was diluted with toluene a second time and concentrated under reduced pressure yielding the title compound as a gum (225 mg, 96%). Method C: 3 minute run LRMS [½M+1=950]. $^1$H NMR (METHANOL-$d_4$) δ: 7.98 (s, 3H), 7.22-7.41 (m, 5H), 5.21 (s, 3H), 5.05 (s, 2H), 4.57 (t, J=5.0 Hz, 6H), 4.55 (s, 6H), 3.92-4.00 (m, 6H), 3.83-3.91 (m, 9H), 3.73-3.78 (m, 9H), 3.68-3.72 (m, J=10.0, 4.1 Hz, 3H), 3.52-3.68 (m, 42H), 3.05-3.17 (m, 4H), 2.16 (t, J=7.3 Hz, 4H), 1.98 (s, 9H), 1.57-1.65 (m, 2H), 1.53-1.57 (m, 2H), 1.43-1.52 (m, 4H), 1.24-1.39 (m, 4H)

6-amino-N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}hexanamide acetate (6)

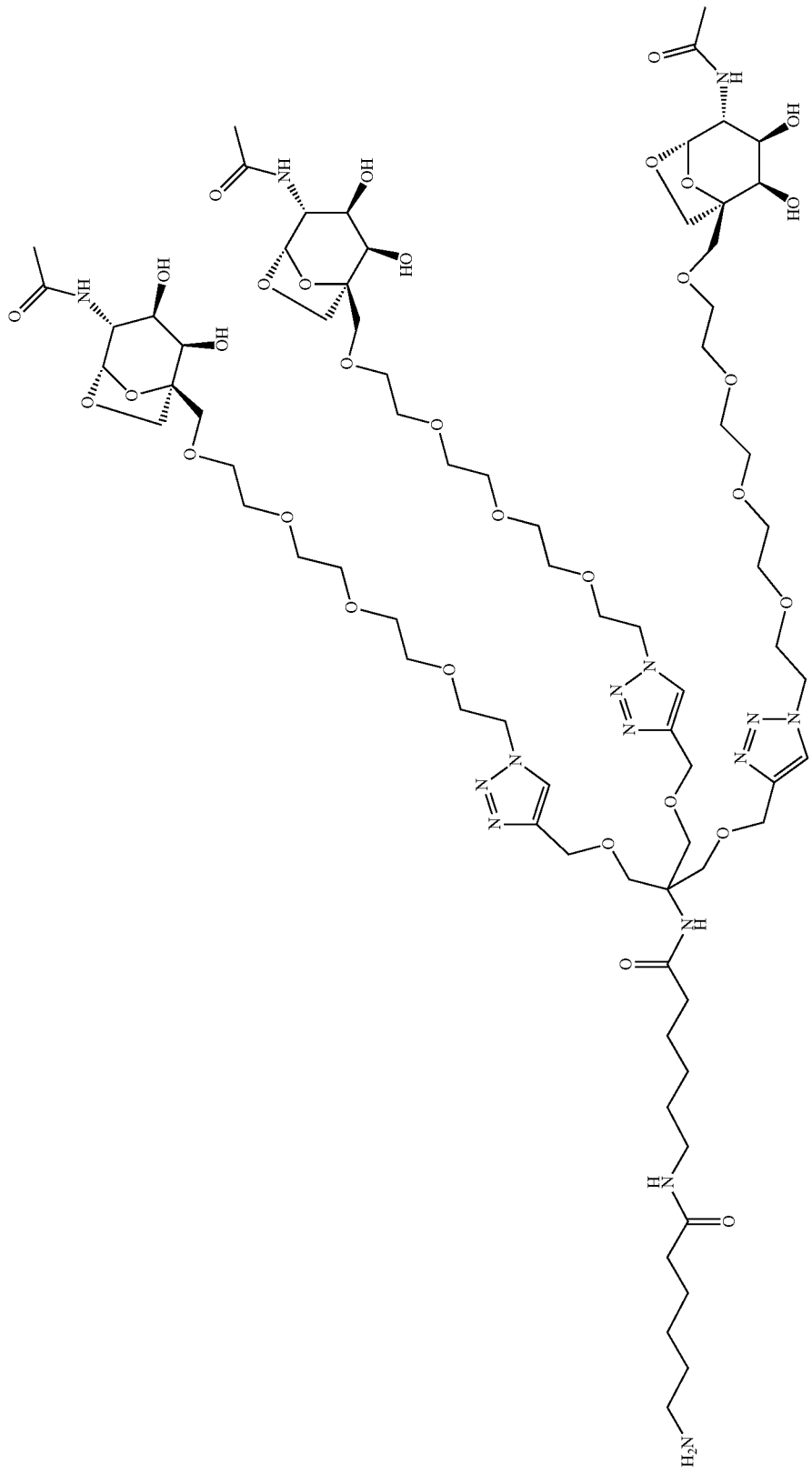

benzyl [6-({6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}amino)-6-oxohexyl]carbamate (61) (200 mg, 0.105 mmol) was dissolved in methanol (20 mL) and acetic acid (0.024 mL, 0.421 mmol) and the solution was then passed through the H-cube using a 10% palladium on carbon (small cartridge) using the following parameters (Temperature—50° C., Flow rate—1.0 mL/min., pressure—Full H2 (1 bar)). The solution was collected and concentrated under reduced pressure yielding the title compound as a gum (148 mg, 77%). Method C: 3 minute run LRMS [M+45 (formic acid)=1809].

trated under reduced pressure. The crude material was purified using the CombiFlash Rf (RediSep 80 g Gold silica gel column) and eluting with a gradient of 0-20% methanol/dichloromethane yielding impure title compound. The crude material was purified using the CombiFlash Rf (RediSep 40 g Gold silica gel column) and eluting with a gradient of 0-100% ethyl acetate/heptane yielding the title compound (2419 mg, 81%). $^1$H NMR (METHANOL-$d_4$) δ: 5.42 (d, J=1.6 Hz, 1H), 4.34-4.43 (m, 2H), 3.88-3.98 (m, 3H), 3.81-3.87 (m, 1H), 3.37 (dd, J=6.2, 1.6 Hz, 1H), 1.54 (s, 3H), 1.42 (s, 3H)

(1S,2R,6R,7R,8S)-7-azido-4,4-dimethyl-1-(15-phenyl-2,5,8,11,14-pentaoxapentadec-1-yl)-3,5,9,11-tetraoxatricyclo[6.2.1.0~2,6~]undecane (I-d-2)

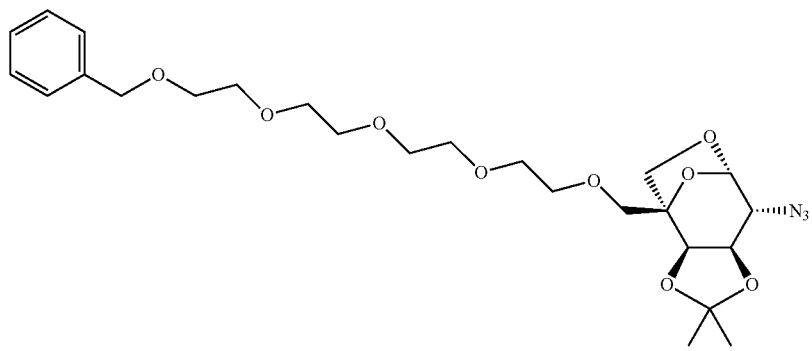

$^1$H NMR (METHANOL-$d_4$) δ: 8.02 (s, 3H), 5.23 (s, 3H), 4.59-4.63 (m, 6H), 4.58 (s, 6H), 3.97 (dd, J=9.6, 5.3 Hz, 6H), 3.91 (dd, J=11.3, 4.7 Hz, 9H), 3.76-3.82 (m, 9H), 3.73 (dd, J=10.1, 4.3 Hz, 3H), 3.56-3.70 (m, 42H), 3.16 (t, J=6.8 Hz, 2H), 2.93 (t, J=7.6 Hz, 2H), 2.16-2.29 (m, 4H), 2.01 (s, 9H), 1.92 (s, 3H), 1.62-1.74 (m, 4H), 1.54-1.61 (m, 2H), 1.46-1.53 (m, 2H), 1.39-1.45 (m, 2H), 1.29-1.38 (m, 2H)

[(1S,2R,6R,7R,8S)-7-azido-4,4-dimethyl-3,5,9,11-tetraoxatricyclo[6.2.1.0~2,6~]undec-1-yl]methanol (I-d-1)

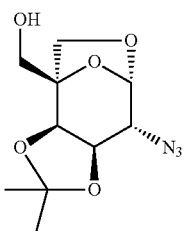 [SMILES: CC1(C)O[C@@H]2[C@@H](N=[N+]=[N-])[C@H]3OC[C@](CO)(O3)[C@@H]2O1]

To a solution of (1S,2R,3R,4R,5S)-4-azido-1-(hydroxymethyl)-6,8-dioxabicyclo[3.2.1]octane-2,3-diol (1) (2.52 g, 11.61 mmol) in N,N-dimethylformamide (21 mL) was added 2 2-dimethoxypropane (9.0 mL, 69.6 mmol) followed by (1S)-(+)-10-Camphorsulfonic acid (1.08 g, 4.65 mmol). The reaction was heated to 70° C. over 24 hours. After 24 hours, the reaction was cooled to room temperature before the addition of methanol (5 mL) was added followed by the addition of triethylamine (0.22 mL, 1.55 mmol) and the solution was stirred for 10 minutes before being concen- To a solution of [(1S,2R,6R,7R,8S)-7-azido-4,4-dimethyl-3,5,9,11-tetraoxatricyclo[6.2.1.0~2,6~]undec-1-yl]methanol (I-d-1) (490 mg, 1.90 mmol) in tetrahydrofuran (5 mL) was added sodium hydride 60% dispersion in mineral oil (127 mg, 3.2 mmol) at room temperature. The reaction was allowed to stir under nitrogen for 30 minutes before the addition of 13-iodo-1-phenyl-2,5,8,11-tetraoxatridecane (1130 mg, 2.86 mmol) in tetrahydrofuran (2 mL). The reaction was allowed to stir overnight at room temperature. The following morning (18 hours), the reaction was quenched with water and extracted with ethyl acetate. The aqueous layer was washed with ethyl acetate two additional times. The combined organic layers were washed with water, brine, dried over sodium sulfate, filtered and concentrated under reduced pressure. The crude material was purified using the CombiFlash Rf (ISCO RediSep Gold 40 g silica gel column) and eluting with a gradient of 0-100% ethyl acetate/heptane yielding the title compound as a gum (336.0 mg, 34%). Method C: 1.5 minute run LRMS [M+Na=546]. $^1$H NMR (METHANOL-$d_4$) δ: 7.17-7.47 (m, 5H), 5.35 (d, J=1.6 Hz, 1H), 4.55 (s, 2H), 4.32-4.37 (m, 1H), 4.25-4.32 (m, 1H), 3.92 (d, J=10.1 Hz, 1H), 3.88 (d, J=8.2 Hz, 1H), 3.73-3.80 (m, 2H), 3.55-3.71 (m, 17H), 1.49 (s, 3H), 1.36 (s, 3H)

tert-butyl [(1S,2R,6R,7R,8S)-1-(13-hydroxy-2,5,8,11-tetraoxatridec-1-yl)-4,4-dimethyl-3,5,9,11-tetraoxatricyclo[6.2.1.0~2,6~]undec-7-yl]carbamate (I-ao-1)

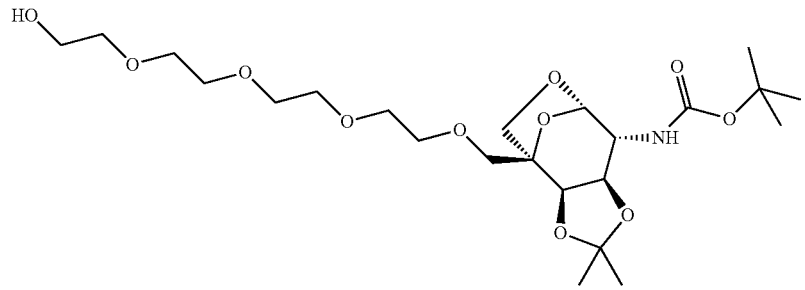 [SMILES: CC(C)(C)OC(=O)N[C@H]1[C@H]2OC[C@](COCCOCCOCCOCCO)(O2)[C@@H]2OC(C)(C)O[C@H]12]

The starting material (1S,2R,6R,7R,8S)-7-azido-4,4-dimethyl-1-(15-phenyl-2,5,8,11,14-pentaoxapentadec-1-yl)-3,5,9,11-tetraoxatricyclo[6.2.1.0~2,6~]undecane (I-d-2) (310.0 mg, 0.592 mmol) was dissolved in methanol (6 mL) followed by the addition of di-tert-butyl-dicarbonate (162 mg, 0.74 mmol) and 10% palladium on carbon (50% wet wt/wt., 100.0 mg, 0.940 mmol) in a 50 mL reactor. The reactor was sealed and the reaction was purged three times with nitrogen (50 psi) and then purged two times with hydrogen (50 psi) and filled to 50 psi with hydrogen and stirred overnight. The following morning (24 hours), the reaction was filtered through a celite plug and washed with methanol. The filtrate was concentrated under reduced pressure. The crude material was purified using the CombiFlash Rf (RediSep 12 g silica gel column) and eluting with a gradient of 0-20% methanol/dichloromethane yielding the title compound as an gum (304 mg, 100%). Method C: 3 minute run LRMS [M+Na=530]. $^1$H NMR (METHANOL-d$_4$) δ: 5.22 (s, 1H), 4.28 (d, J=5.9 Hz, 1H), 4.11 (t, J=6.4 Hz, 1H), 3.93 (d, J=10.1 Hz, 1H), 3.80-3.85 (m, 1H), 3.76 (d, J=6.2 Hz, 1H), 3.74 (d, J=3.9 Hz, 1H), 3.60-3.71 (m, 15H), 3.53-3.59 (m, 2H), 1.50 (s, 3H), 1.45 (s, 9H), 1.34 (s, 3H)

1-{(1S,2R,6R,7R,8S)-7-[(tert-butoxycarbonyl)amino]-4,4-dimethyl-3,5,9,11-tetraoxatricyclo[6.2.1.0~2,6~]undec-1-yl}-2,5,8,11-tetraoxatridecan-13-yl methanesulfonate (I-ap-1)

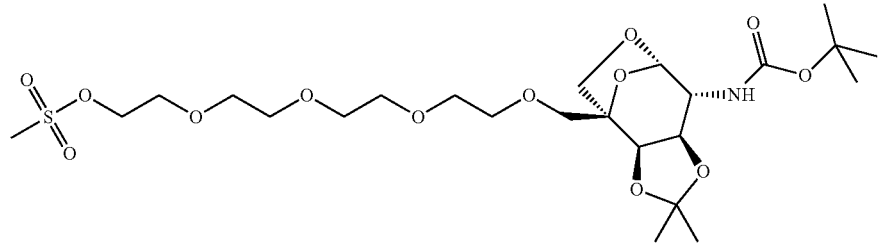 [SMILES: CC(C)(C)OC(=O)N[C@H]1[C@H]2OC[C@](COCCOCCOCCOCCOS(C)(=O)=O)(O2)[C@@H]2OC(C)(C)O[C@H]12]

To a solution of tert-butyl [(1S,2R,6R,7R,8S)-1-(13-hydroxy-2,5,8,11-tetraoxatridec-1-yl)-4,4-dimethyl-3,5,9,11-tetraoxatricyclo[6.2.1.0~2,6~]undec-7-yl]carbamate (I-ao-1) (300.0 mg, 0.591 mmol) in dichloromethane (2 mL) was added triethyl amine (0.332 mL, 2.36 mmol) and cooled to 0° C. using an ice bath followed by the addition of methanesulphonyl chloride (0.055 mL, 0.71 mmol). The reaction was allowed to warm slowly to room temperature and stirred at room temperature for 20 hours. After 20 hours, the reaction was quenched with water and extracted. The layers were separated and the aqueous layer was extracted an additional time with dichloromethane. The combined organic layers were washed with brine, dried over magnesium sulfate, filtered and concentrated under reduced pressure yielding the title compound as an oil (339 mg, 98%). Method C: 3 minute run LRMS [M+Na=608]. $^1$H NMR (METHANOL-d$_4$) δ: 5.22 (s, 1H), 4.33-4.43 (m, 2H), 4.28 (d, J=5.9 Hz, 1H), 4.11 (t, J=6.4 Hz, 1H), 3.93 (d, J=10.1 Hz, 1H), 3.80-3.86 (m, 1H), 3.72-3.79 (m, 4H), 3.61-3.70 (m, 12H), 3.58 (d, J=5.9 Hz, 1H), 3.11 (s, 3H), 1.50 (s, 3H), 1.45 (s, 9H), 1.34 (s, 3H)

tert-butyl [(1S,2R,6R,7R,8S)-1-(13-azido-2,5,8,11-tetraoxatridec-1-yl)-4,4-dimethyl-3,5,9,11-tetraoxatricyclo[6.2.1.0~2,6~]undec-7-yl]carbamate (I-aq-1)

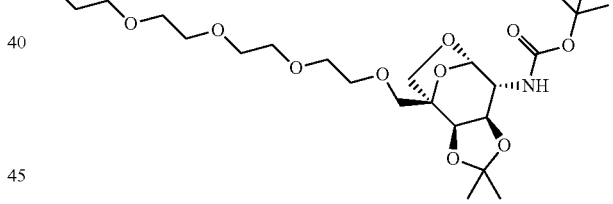

To a solution of 1-{(1S,2R,6R,7R,8S)-7-[(tert-butoxycarbonyl)amino]-4,4-dimethyl-3,5,9,11-tetraoxatricyclo[6.2.1.0~2,6~]undec-1-yl}-2,5,8,11-tetraoxatridecan-13-yl methanesulfonate (I-ap-1) (339 mg, 0.579 mmol) in N,N-dimethylformamide (1.5 mL) was added sodium azide (67.7 mg, 1.04 mmol) and the reaction was heated to 100° C.

overnight in a sealed 5 mL microwave vial. After 18 hours, the reaction was cooled to room temperature and the reaction was diluted with water and extracted with ethyl acetate three times. The combined organic layers were washed with water, brine, dried over sodium sulfate, filtered and concentrated under reduced pressure yielding The crude material was purified using the CombiFlash Rf (RediSep 12 g Gold silica gel column) and eluting with a gradient of 0-20% methanol/dichloromethane yielding the title compound as a gum (246 mg, 80%). $^1$H NMR (METHANOL-$d_4$) δ: 5.24 (s, 1H), 4.30 (d, J=5.9 Hz, 1H), 4.13 (t, J=6.4 Hz, 1H), 3.95 (d, J=9.8 Hz, 1H), 3.82-3.88 (m, 1H), 3.75-3.80 (m, 2H), 3.53-3.74 (m, 15H), 3.39 (t, J=4.9 Hz, 2H), 1.52 (s, 3H), 1.47 (s, 9H), 1.36 (s, 3H)

tert-butyl {(1S,2R,6R,7R,8S)-1-[13-(4-{[2-{[4-(benzyloxy)butanoyl]amino}-3-{[1-(1-{(1S,2R,6R,7R,8S)-7-[(tert-butoxycarbonyl)amino]-4,4-dimethyl-3,5,9,11-tetraoxatricyclo[6.2.1.0~2,6~]undec-1-yl}-2,5,8,11-tetraoxatridecan-13-yl)-1H-1,2,3-triazol-4-yl]methoxy}-2-({[1-(1-{(1S,2R,6R,7R,8S)-7-[(tert-butoxycarbonyl)amino]-4,4-dimethyl-3,5,9,11-tetraoxatricyclo[6.2.1.0~2,6~]undec-1-yl}-2,5,8,11-tetraoxatridecan-13-yl)-1H-1,2,3-triazol-4-yl]methoxy}methyl)propoxy]methyl}-1H-1,2,3-triazol-1-yl)-2,5,8,11-tetraoxatridec-1-yl]-4,4-dimethyl-3,5,9,11-tetraoxatricyclo[6.2.1.0~2,6~]undec-7-yl}carbamate (I-ar-1)

A 20 mL vial equipped with stir bar was charged with 4-(benzyloxy)-N-{1,3-bis(prop-2-yn-1-yloxy)-2-[(prop-2-yn-1-yloxy)methyl]propan-2-yl}butanamide (I-v-1) (45.0 mg, 0.11 mmol) and to which was added tert-butyl [(1S,2R,6R,7R,8S)-1-(13-azido-2,5,8,11-tetraoxatridec-1-yl)-4,4-dimethyl-3,5,9,11-tetraoxatricyclo[6.2.1.0~2,6~]undec-7-yl]carbamate (I-aq-1) (192 mg, 0.361 mmol) in t-butanol (3 mL) and water (1.5 mL, deionized water). The reaction was purged with nitrogen for 5 minutes before the addition of sodium ascorbate (66.3 mg, 0.328 mmol) and the drop wise addition of a solution of copper (II) sulfate (5.24 mg, 0.0328 mmol) in water (500 uL, deionized water). The reaction was stirred at room temperature for 20 hours. After 20 hours, the reaction was cooled to room temperature and the reaction was quenched by adding the reaction mixture to a saturated ammonium chloride (30 mL) and conc. ammonium hydroxide (2 mL) and extracted three times with dichloromethane (15 mL). The combined organic layers were dried over sodium sulfate, filtered and concentrated under reduced pressure. The crude material was purified using the CombiFlash Rf (RediSep 12 g Gold silica gel column) and eluting with a gradient of 0-20% methanol/dichloromethane yielding the title compound as a gum (165 mg, None, 75%). Method C: 3 minute run LRMS [½M+1=1005]. $^1$H NMR (METHANOL-$d_4$) δ: 7.97 (s, 3H), 7.17-7.43 (m, 5H), 5.21 (s, 3H), 4.52-4.60 (m, 12H), 4.45 (s, 2H), 4.25 (d, J=5.9 Hz, 3H), 4.10 (t, J=6.2 Hz, 3H), 3.85-3.93 (m, 9H), 3.71-3.82 (m, 15H), 3.63-3.69 (m, 6H), 3.53-3.62 (m, 33H), 3.48 (t, J=6.2 Hz, 2H), 2.27 (t, J=7.2 Hz, 2H), 1.74-1.96 (m, 2H), 1.49 (s, 9H), 1.45 (s, 27H), 1.32 (s, 9H)

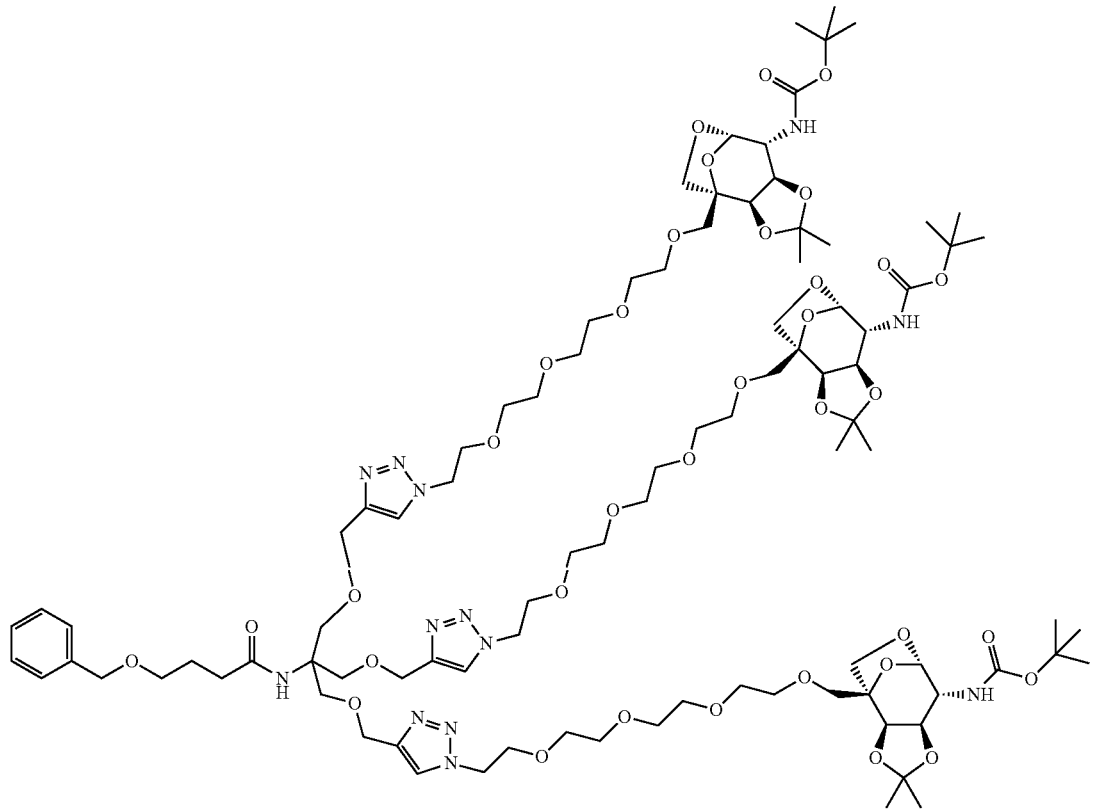 [SMILES: CC(C)(C)OC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(=O)OC(C)(C)C)[C@H]5OC(C)(C)O[C@H]56)nn4)(COCc4cn(CCOCCOCCOCCOC[C@@]56CO[C@@H](O5)[C@H](NC(=O)OC(C)(C)C)[C@H]5OC(C)(C)O[C@H]56)nn4)NC(=O)CCCOCc4ccccc4)nn3)(O2)[C@@H]2OC(C)(C)O[C@H]12]

4-(benzyloxy)-N-(1,3-bis[(1-{1-[(1S,2R,3R,4R,5S)-4-amino-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-amino-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl) butanamide (63)

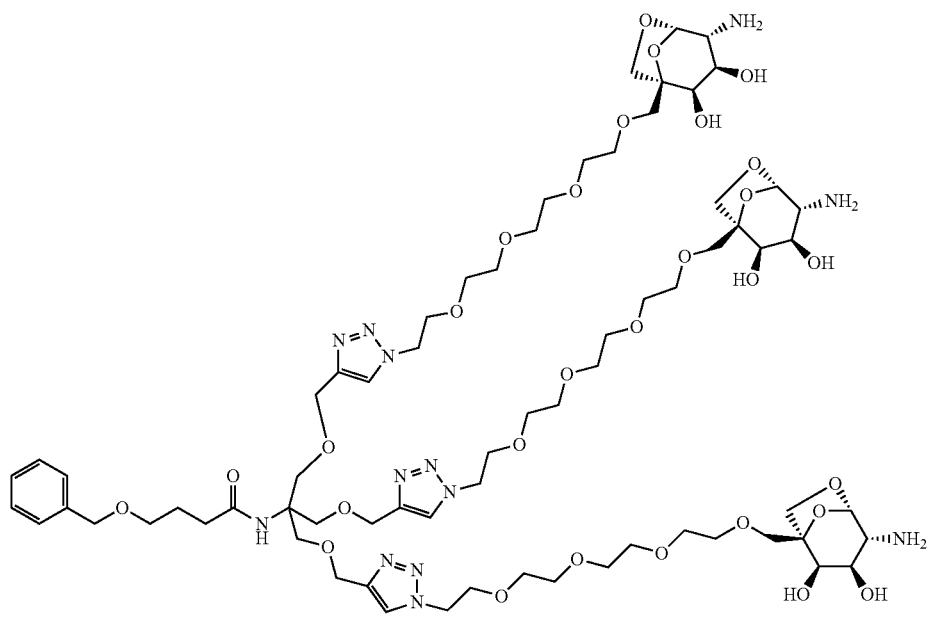 [SMILES: N[C@H]1[C@H]2OC[C@](COCCOCCOCCOCCn3cc(COCC(COCc4cn(CCOCCOCCOCCOC[C@@]56CO[C@@H](O5)[C@H](N)[C@@H](O)[C@H]6O)nn4)(COCc4cn(CCOCCOCCOCCOC[C@@]56CO[C@@H](O5)[C@H](N)[C@@H](O)[C@H]6O)nn4)NC(=O)CCCOCc4ccccc4)nn3)(O2)[C@H](O)[C@@H]1O]

A solution of tert-butyl {(1S,2R,6R,7R,8S)-1-[13-(4-{[2-{[4-(benzyloxy)butanoyl]amino}-3-{[1-(1-{(1S,2R,6R,7R,8S)-7-[(tert-butoxycarbonyl)amino]-4,4-dimethyl-3,5,9,11-tetraoxatricyclo[6.2.1.0~2,6~]undec-1-yl}-2,5,8,11-tetraoxatridecan-13-yl)-1H-1,2,3-triazol-4-yl]methoxy}-2-({[1-(1-{(1S,2R,6R,7R,8S)-7-[(tert-butoxycarbonyl)amino]-4,4-dimethyl-3,5,9,11-tetraoxatricyclo[6.2.1.0~2,6~]undec-1-yl}-2,5,8,11-tetraoxatridecan-13-yl)-1H-1,2,3-triazol-4-yl]methoxy}methyl)propoxy]methyl}-1H-1,2,3-triazol-1-yl)-2,5,8,11-tetraoxatridec-1-yl]-4,4-dimethyl-3,5,9,11-tetraoxatricyclo[6.2.1.0~2,6~]undec-7-yl}carbamate (I-ar-1) (150.0 mg, 0.0747 mmol) in acetic acid (5 mL), methanol (1.5 mL) and water (1.5 mL) was heated to 70° C. for 18 hours. After 18 hours, the reaction was cooled to room temperature and concentrated under reduced pressure. The crude material was diluted with dichloromethane (10 mL) and methanol (4 mL) to which was added 4.0M hydrogen chloride in dioxane (2.0 mL, 8 mmol). The reaction mixture was stirred at room temperature overnight. After 18 hours, the reaction was concentrated under reduced pressure. The crude material was diluted with ethyl acetate (1 mL) and to which was added heptane (10 mL) and concentrated under reduced pressure. The material was then placed under high vacuum for 18 hours yielding the title compound (139.0 mg, 103%). Method C: 3 minute run LRMS [½M+1=795]. $^1$H NMR (METHANOL-d$_4$) δ: 8.09 (s, 3H), 7.27-7.39 (m, 5H), 5.48 (s, 3H), 4.57-4.66 (m, 12H), 4.47 (s, 2H), 3.98 (d, J=9.8 Hz, 3H), 3.90-3.95 (m, 9H), 3.82-3.89 (m, 6H), 3.79 (s, 6H), 3.76 (d, J=8.2 Hz, 3H), 3.71 (d, J=9.8 Hz, 3H), 3.57-3.69 (m, 36H), 3.50 (t, J=6.2 Hz, 2H), 3.21 (d, J=9.4 Hz, 3H), 2.29 (t, J=7.2 Hz, 2H), 1.85 (quin, J=6.8 Hz, 2H)

(1S,2R,3R,4R,5S)-4-(acetylamino)-1-(13-{4-[(3-[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]methyl}-2-{[4-(benzyloxy)butanoyl]amino}propoxy)methyl]-1H-1,2,3-triazol-1-yl}-2,5,8,11-tetraoxatridec-1-yl)-3-(acetyloxy)-6,8-dioxabicyclo[3.2.1]oct-2-yl acetate
(I-as-1)

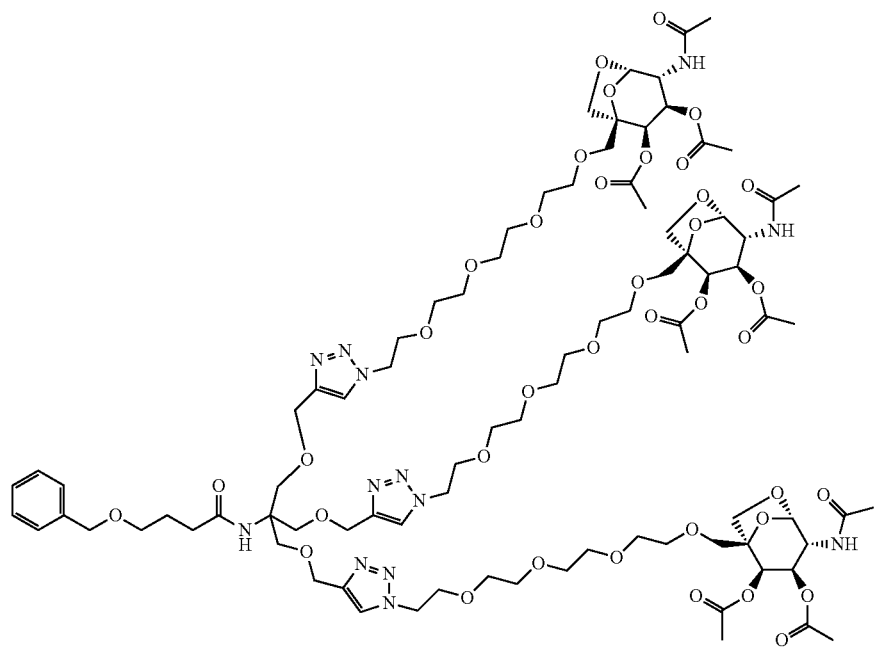 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](OC(C)=O)[C@H]6OC(C)=O)nn4)(COCc4cn(CCOCCOCCOCCOC[C@@]56CO[C@@H](O5)[C@H](NC(C)=O)[C@@H](OC(C)=O)[C@H]6OC(C)=O)nn4)NC(=O)CCCOCc4ccccc4)nn3)(O2)[C@H](OC(C)=O)[C@@H]1OC(C)=O]

4-(benzyloxy)-N-(1,3-bis[(1-{1-[(1S,2R,3R,4R,5S)-4-amino-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-amino-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)butanamide (63) (80 mg, 0.044 mmol) was dissolved in pyridine (anhydrous) (1.5 mL, 19 mmol) and to which was added acetic anhydride (0.125 mL, 1.33 mmol) at room temperature. The reaction was then heated to 50° C. overnight. The following morning, the reaction was concentrated under reduced pressure. The crude material was purified using the CombiFlash Rf (RediSep 12 g gold silica gel column) and eluting with a gradient of 0-20% methanol/dichloromethane yielding crude title compound. The crude title compound was purified using the CombiFlash Rf (RediSep 4 g gold silica gel column) and eluting with a gradient of 0-20% methanol/dichloromethane yielding the title compound as a gum (54.0 mg, 62%). Method C: 1.5 minute run LRMS [½M+1=984]. $^1$H NMR (METHANOL-$d_4$) δ: 7.97 (s, 3H), 7.19-7.42 (m, 5H), 5.44 (d, J=4.3 Hz, 3H), 5.31 (s, 3H), 5.10 (dd, J=10.3, 4.1 Hz, 3H), 4.51-4.64 (m, 12H), 4.45 (s, 2H), 4.18 (d, J=10.1 Hz, 3H), 3.99 (d, J=8.6 Hz, 3H), 3.88 (t, J=4.9 Hz, 6H), 3.68-3.82 (m, 12H), 3.52-3.64 (m, 39H), 3.48 (t, J=6.2 Hz, 2H), 2.26 (t, J=7.4 Hz, 2H), 2.15 (s, 9H), 1.94 (d, J=1.2 Hz, 18H), 1.84 (t, J=6.8 Hz, 2H).

(1S,2R,3R,4R,5S)-4-(acetylamino)-1-{13-[4-({3-[(1-
{1-[(1S,2R,3R,4R,5S)-4-(acetylamino)-2,3-bis
(acetyloxy)-6,8-dioxabicyclo[3.2.1]oct-1-yl]-2,5,8,
11-tetraoxatridecan-13-yl}-1H-1,2,3-triazol-4-yl)
methoxy]-2-{[(1-{1-[(1S,2R,3R,4R,5S)-4-
(acetylamino)-2,3-bis(acetyloxy)-6,8-dioxabicyclo
[3.2.1]oct-1-yl]-2,5,8,11-tetraoxatridecan-13-yl}-1H-
1,2,3-triazol-4-yl)methoxy]methyl}-2-[(4-
hydroxybutanoyl)amino]propoxy}methyl)-1H-1,2,3-
triazol-1-yl]-2,5,8,11-tetraoxatridec-1-yl}-3-
(acetyloxy)-6,8-dioxabicyclo[3.2.1]oct-2-yl acetate
(I-at-1)

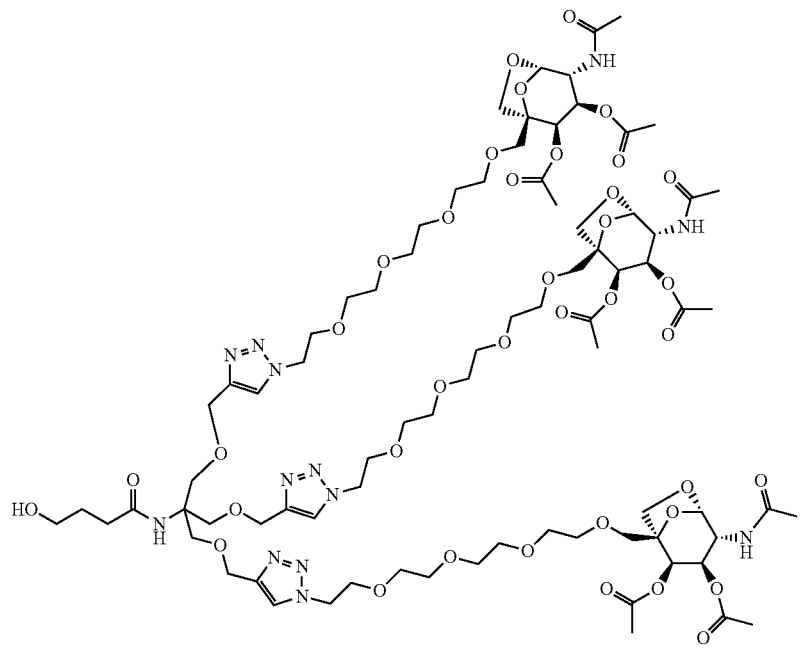 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](OC(C)=O)[C@H]6OC(C)=O)nn4)(COCc4cn(CCOCCOCCOCCOC[C@@]56CO[C@@H](O5)[C@H](NC(C)=O)[C@@H](OC(C)=O)[C@H]6OC(C)=O)nn4)NC(=O)CCCO)nn3)(O2)[C@H](OC(C)=O)[C@@H]1OC(C)=O]

(1S,2R,3R,4R,5S)-4-(acetylamino)-1-(13-{4-[(3-[(1-{1-
[(1S,2R,3R,4R,5S)-4-(acetylamino)-2,3-bis(acetyloxy)-6,8-
dioxabicyclo[3.2.1]oct-1-yl]-2,5,8,11-tetraoxatridecan-13-
yl}-1H-1,2,3-triazol-4-yl)methoxy]-2-{[(1-{1-[(1S,2R,3R,
4R,5S)-4-(acetylamino)-2,3-bis(acetyloxy)-6,8-
dioxabicyclo[3.2.1]oct-1-yl]-2,5,8,11-tetraoxatridecan-13-
yl}-1H-1,2,3-triazol-4-yl)methoxy]methyl}-2-{[4-
(benzyloxy)butanoyl]amino}propoxy)methyl]-1H-1,2,3-
triazol-1-yl}-2,5,8,11-tetraoxatridec-1-yl)-3-(acetyloxy)-6,
8-dioxabicyclo[3.2.1]oct-2-yl acetate (I-as-1) (54.0 mg,
0.027 mmol) was dissolved in methanol (10.0 mL) and the
solution was then passed through the H-cube using a 10%
palladium on carbon (small cartridge) using the following
parameters (Temperature—60° C., Flow rate—1.0 mL/min.,
pressure—Full H$_2$ (1 atm)). The solution was collected and
concentrated under reduced pressure yielding the title compound as a gum (51.0 mg, 99%). Method C: 3 minute run
LRMS [M+Na=1899]. $^1$H NMR (METHANOL-d$_4$) δ: 7.98
(s, 3H), 5.44 (d, J=4.3 Hz, 3H), 5.32 (s, 3H), 5.10 (dd,
J=10.5, 3.9 Hz, 3H), 4.41-4.66 (m, 12H), 4.18 (d, J=10.5 Hz,
3H), 3.99 (d, J=8.6 Hz, 3H), 3.90 (t, J=5.1 Hz, 6H),
3.68-3.83 (m, 12H), 3.51-3.67 (m, 41H), 2.24 (t, J=7.6 Hz,
2H), 2.15 (s, 9H), 1.94 (s, 18H), 1.69-1.83 (m, 2H)

N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)-4-hydroxybutanamide (64)

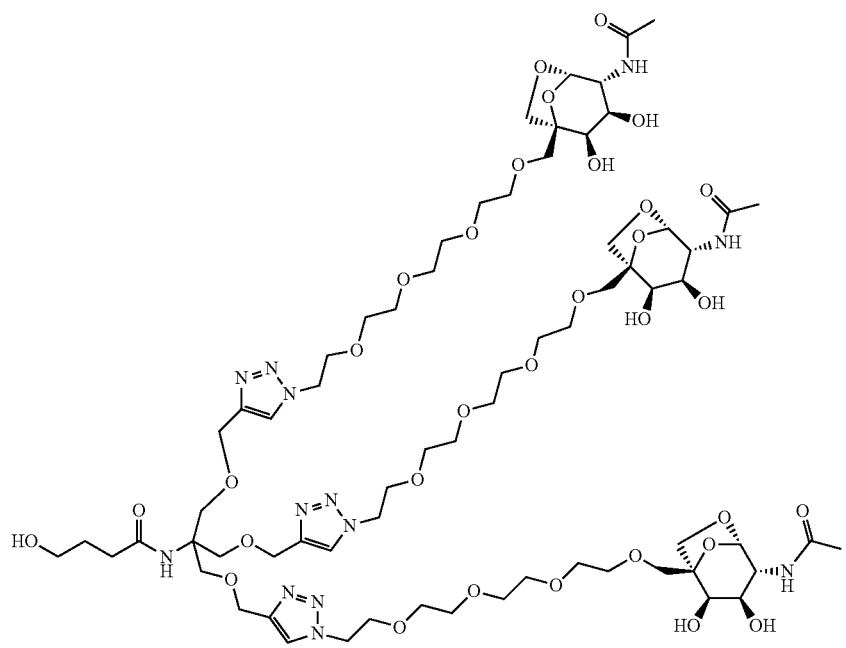 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCO)nn3)(O2)[C@H](O)[C@@H]1O]

To a solution of (1S,2R,3R,4R,5S)-4-(acetylamino)-1-{13-[4-({3-[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]methyl}-2-[(4-hydroxybutanoyl)amino]propoxy}methyl)-1H-1,2,3-triazol-1-yl]-2,5,8,11-tetraoxatridec-1-yl}-3-(acetyloxy)-6,8-dioxabicyclo[3.2.1]oct-2-yl acetate (I-at-1) (8.5 mg, 0.0045 mmol) in methanol (1 mL) was added 0.5M sodium methoxide in methanol (0.154 mL mg, 0.0770 mmol) and the reaction was allowed to stir at room temperature for 3 hours. After 3 hours, the reaction was neutralized by the addition of triple methanol rinsed Amberlyst 15 ion exchange resin (CAS #=39389-20-3, RS-106008) to a pH=5. The reaction mixture was filtered and the resin was rinsed two times with methanol. The filtrate was concentrated under reduced pressure yielding the title compound as a gum (1.5 mg, 20%). Method C: 3 minute run LRMS [M+45(formic acid)=1668]. $^1$H NMR (METHANOL-$d_4$) δ: 8.00 (s, 3H), 5.21 (s, 3H), 4.53-4.65 (m, 12H), 3.92-4.00 (m, 6H), 3.89 (dd, J=11.1, 4.9 Hz, 9H), 3.74-3.79 (m, 9H), 3.71 (dd, J=9.8, 4.3 Hz, 3H), 3.52-3.69 (m, 44H), 2.24 (t, J=7.4 Hz, 2H), 1.99 (s, 9H), 1.76 (quin, J=6.9 Hz, 2H).

The ortho ester linker exemplified by compound (66) in Scheme 4b and described generically in Scheme 3b could be synthesized by one skilled in the art utilizing (I-aw-1) (see H. Bruyère et al, Bioorg. Med. Chem. Lett., 20, 2200-2203, (2010)) and an appropriate alcohol such as (I-an-1), the appropriate acid such as pyridinium p-toluene sulfonate in an appropriate solvent such as toluene under refluxing conditions to produce (I-ax-1). Deprotection of (I-ax-1) could be accomplished under basic conditions known to one skilled in the art (such as catalytic potassium carbonate in methanol) which would result in compound (65). Further functionalization of (65) could be accomplished to produce additional compounds claimed in the present invention. Thus, treatment of (65) with an appropriate acid and coupling agent (known to those skilled in the art) or an activated ester (such as hydroxysuccinamide) such as (I-s-1) in an appropriate solvent such as N,N-dimethylformamide using an appropriate base such as N,N-diisopropylethylamine could produce compound (66).

Scheme 3b.
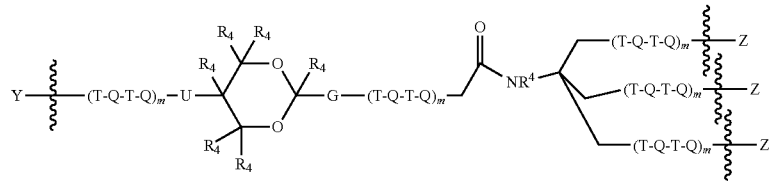
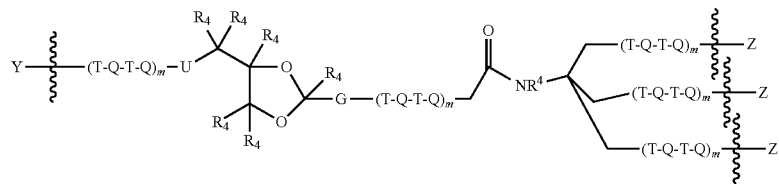
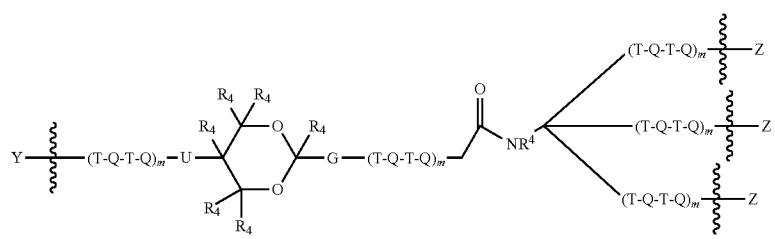
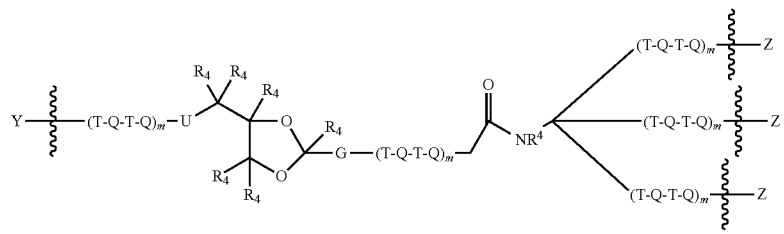
G = O, NR⁴, S
U = O, NR⁴, S, CH₂
Scheme 4b.
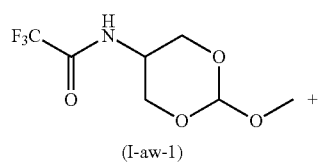
(I-aw-1)

-continued
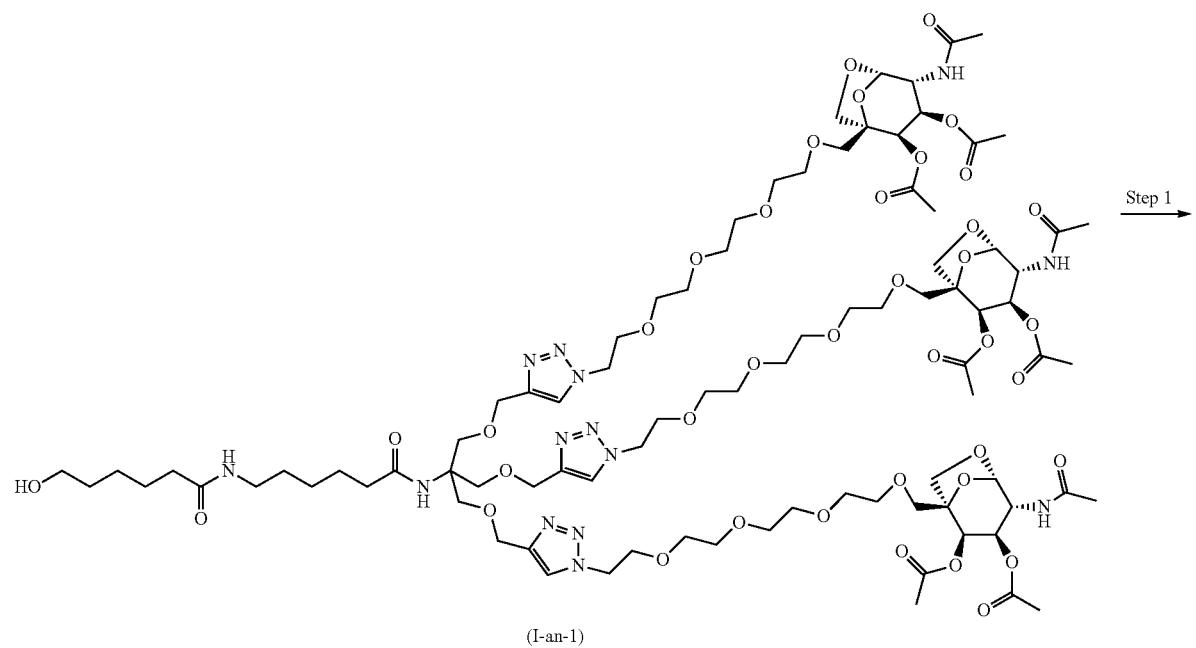
(I-an-1)
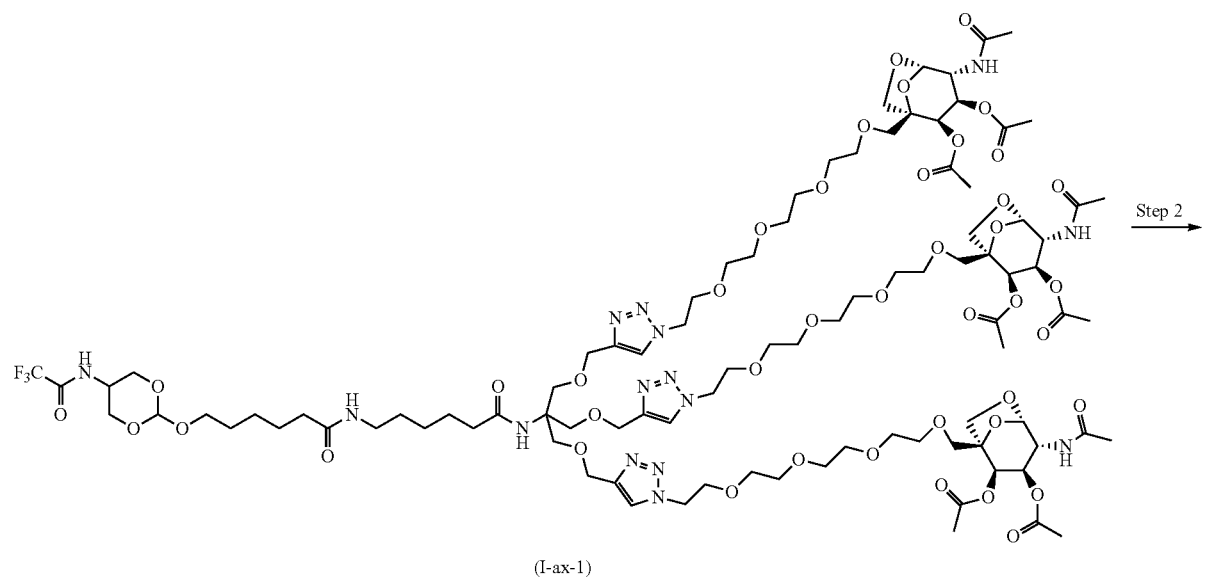
(I-ax-1)

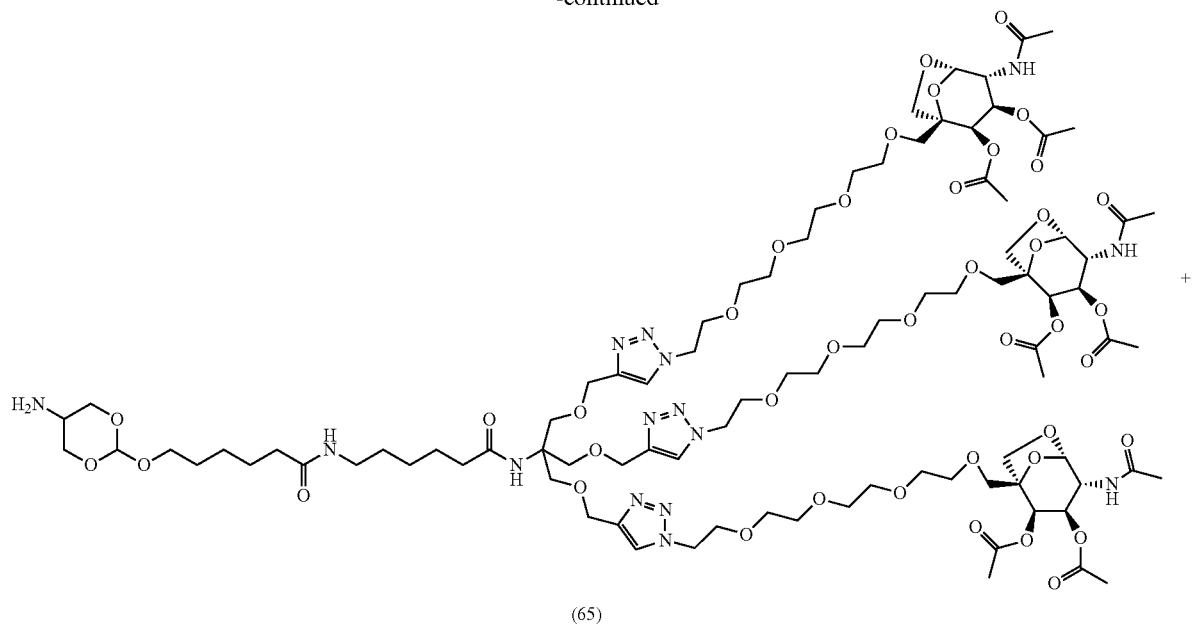
(65)
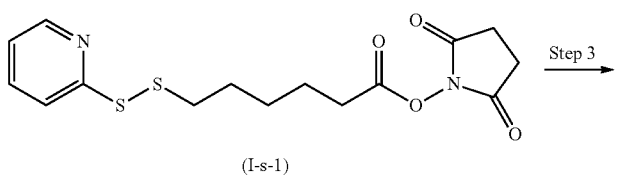
(I-s-1)
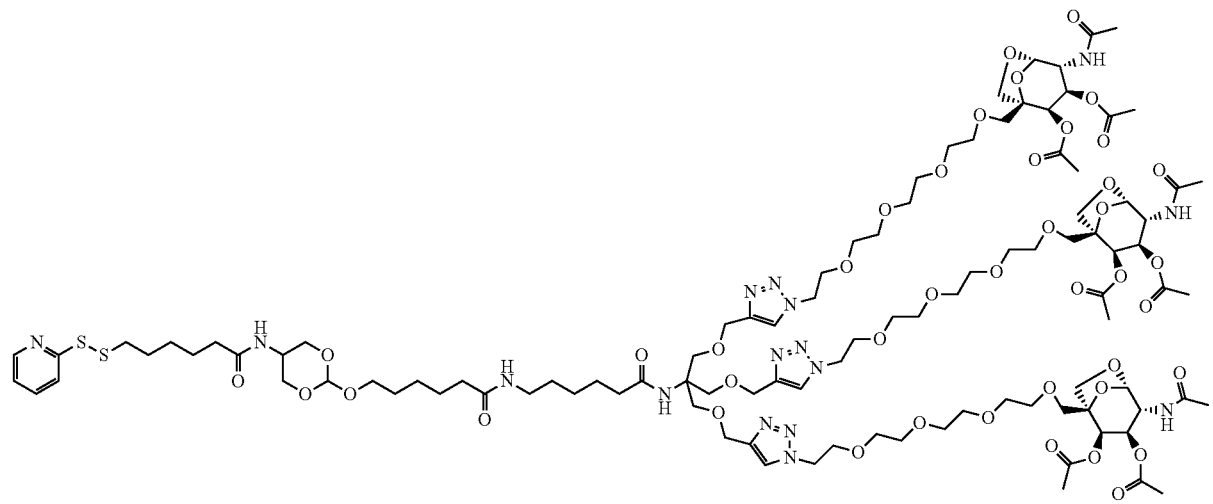
66
In a similar fashion, as shown in Scheme 5b, compound (66) could also be synthesized by one skilled in the art utilizing (I-av-1) and an appropriate alcohol such as (I-an-1) using reaction conditions described previously for Scheme 4b.

Scheme 5b.
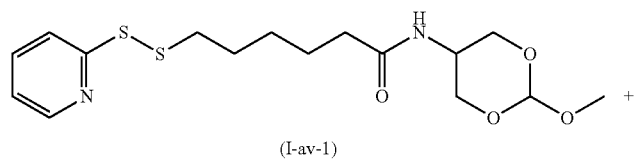
(I-av-1)
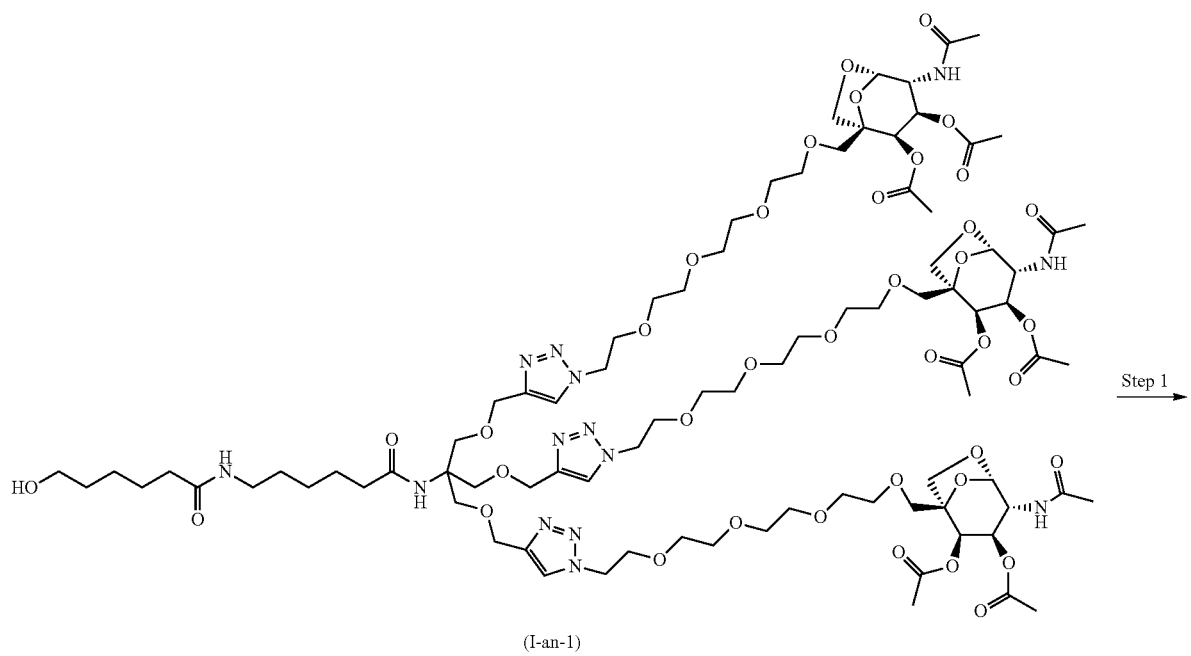
(I-an-1)
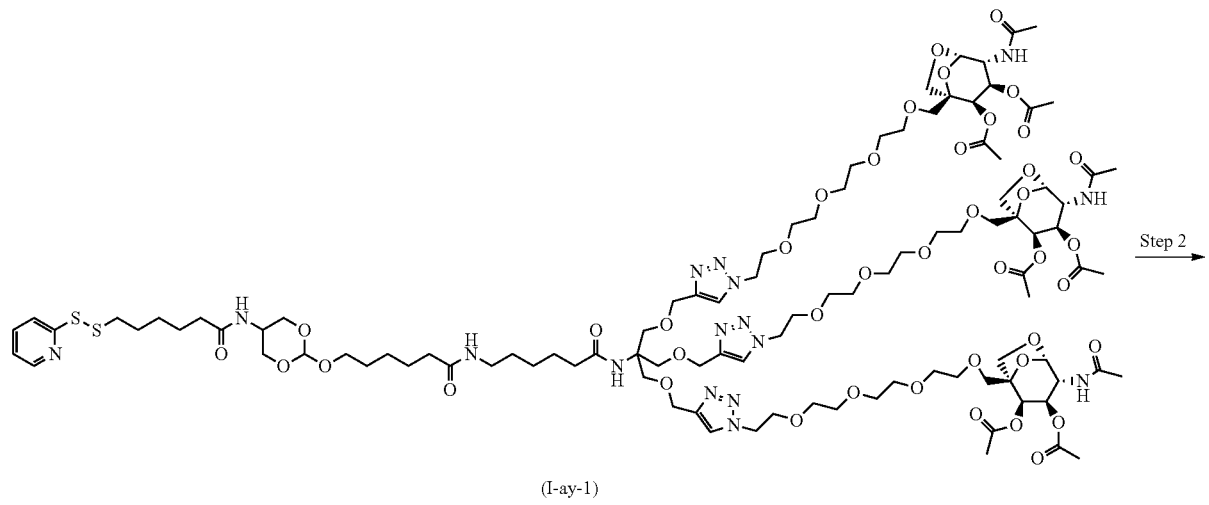
(I-ay-1)

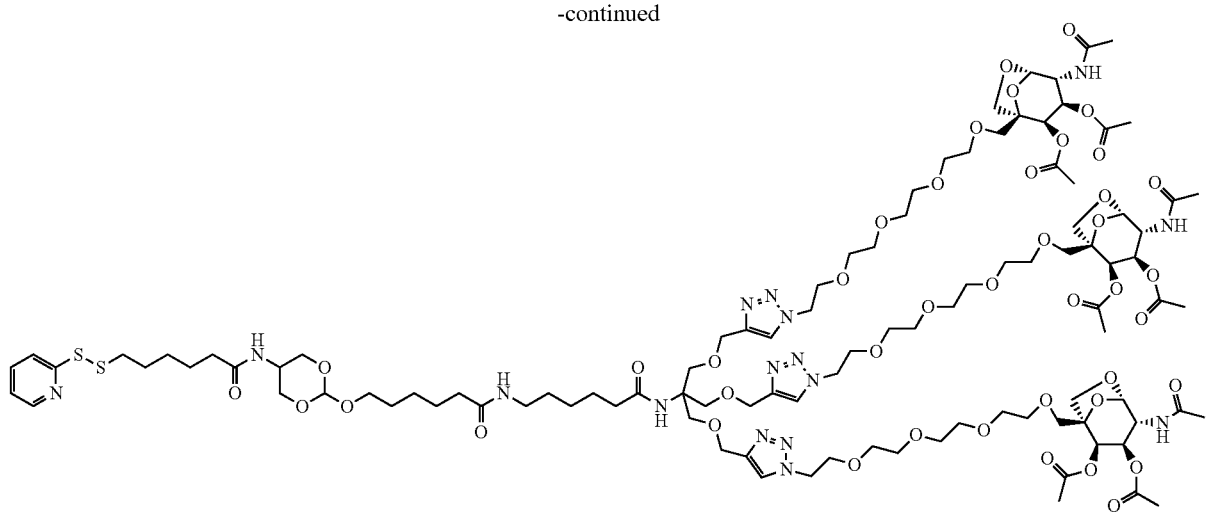

66

N-(1,3-dihydroxypropan-2-yl)-6-(pyridin-2-yldisulfanyl)hexanamide (I-au-1)

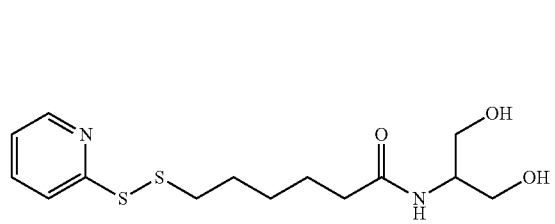 [SMILES: O=C(CCCCCSSc1ccccn1)NC(CO)CO]

To a solution of 1-{[6-(pyridin-2-yldisulfanyl)hexanoyl]oxy}pyrrolidine-2,5-dione (I-s-1) (518 mg, 2.01 mmol) in N,N-dimethylformamide (7 mL) was added N-(3-dimethylaminopropyl)-N-ethylcarbodimiimide hydrochloride (463 mg, 2.42 mmol) and 1-hydroxybenzotriazole (326 mg, 2.42 mmol) and stirred for 1 hour at room temperature. After 1 hour, 2-aminopropane-1,3-diol (183 mg, 2.01 mmol) was added followed by N,N-diisopropylethylamine (1.05 mL, 6.04 mmol). The reaction was allowed to stir overnight at room temperature. After 18 hours, the reaction was diluted with water and extracted with three times with dichloromethane. The combined organic layers were washed with brine, dried over magnesium sulfate, filtered and concentrated under reduced pressure. The crude material was purified using the CombiFlash Rf (RediSep 24 g silica gel column) and eluting with a gradient of 0-20% methanol/dichloromethane yielding the title compound (368 mg, 55%). Method C: 1.5 minute run LRMS [M+45(formic acid)=375]. $^1$H NMR (METHANOL-d$_4$) δ: 8.38 (d, J=4.3 Hz, 1H), 7.84-7.89 (m, 1H), 7.77-7.83 (m, 1H), 7.21 (t, J=5.7 Hz, 1H), 3.92 (quin, J=5.5 Hz, 1H), 3.51-3.70 (m, 4H), 2.82 (t, J=7.2 Hz, 2H), 2.21 (t, J=7.4 Hz, 2H), 1.71 (quin, J=7.3 Hz, 2H), 1.60 (quin, J=7.5 Hz, 2H), 1.37-1.51 (m, 2H)

N-(2-methoxy-1,3-dioxan-5-yl)-6-(pyridin-2-yldisulfanyl)hexanamide (I-av-1)

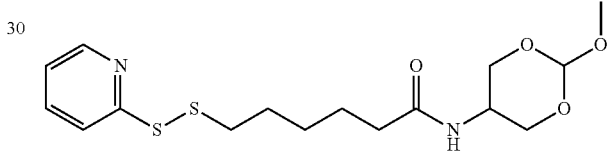

To a mixture of N-(1,3-dihydroxypropan-2-yl)-6-(pyridin-2-yldisulfanyl)hexanamide (I-au-1) (280 mg, 0.847 mmol) in dichloromethane (0.605 mL) and trimethylorthoformate (0.5 mL, 5 mmol) was added p-toluenesulfonic acid monohydrate (1.78 mg, 0.00847 mmol). The reaction was allowed to stir at room temperature for 3 hours. After 3 hours, the TLC showed the almost complete consumption of the starting material. The reaction was diluted with dichloromethane and washed with saturated sodium bicarbonate aqueous (3×1 mL), brine (1 mL), dried over anhydrous potassium carbonate, filtered and concentrated under reduced pressure yielding the crude title compound (263.0 mg, 83.3%). Method C: 3 minute run (basic mode: Column: Base: Waters Acquity UPLC BEH, 2.1 mm×50 mm, C18, 1.8 μm; Mobile phase: A: 0.1% ammonia in water (v/v); B: 0.1% ammonia in acetonitrile (v/v)) LRMS [M+45=417]. 1:1 mixture of cis/trans isomers:

Isomer 1: $^1$H NMR (METHANOL-d$_4$) δ: 8.41 (d, J=4.7 Hz, 1H), 7.86-7.92 (m, 1H), 7.80-7.86 (m, 1H), 7.20-7.27 (m, 1H), 5.31 (s, 1H), 4.29 (d, J=2.7 Hz, 1H), 3.92-3.96 (m, 1H), 3.83 (br. s., 1H), 3.63 (d, J=5.1 Hz, 1H), 3.59 (dd, J=11.5, 3.7 Hz, 1H), 3.42 (s, 3H), 2.85 (t, J=7.2 Hz, 2H), 2.21-2.30 (m, 2H), 1.68-1.80 (m, 2H), 1.56-1.67 (m, 2H), 1.39-1.53 (m, 2H)

Isomer 2: $^1$H NMR (METHANOL-d$_4$) δ: 8.41 (d, J=4.7 Hz, 1H), 7.86-7.92 (m, 1H), 7.80-7.86 (m, 1H), 7.20-7.27 (m, 1H), 5.27 (s, 1H), 4.26 (d, J=2.7 Hz, 1H), 3.92-3.96 (m, 2H), 3.86-3.91 (m, 1H), 3.59 (dd, J=11.5, 3.7 Hz, 1H), 3.38 (s, 3H), 2.85 (t, J=7.2 Hz, 2H), 2.21-2.30 (m, 2H), 1.68-1.80 (m, 2H), 1.56-1.67 (m, 2H), 1.39-1.53 (m, 2H).

(1S,2R,3R,4R,5S)-4-(acetylamino)-2-(acetyloxy)-1-{13-[4-(12,12-bis{[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]methyl}-3,10-dioxo-1-phenyl-2,14-dioxa-4,11-diazapentadecan-15-yl)-1H-1,2,3-triazol-1-yl]-2,5,8,11-tetraoxatridec-1-yl}-6,8-dioxabicyclo[3.2.1]oct-3-yl acetate (I-az-1)

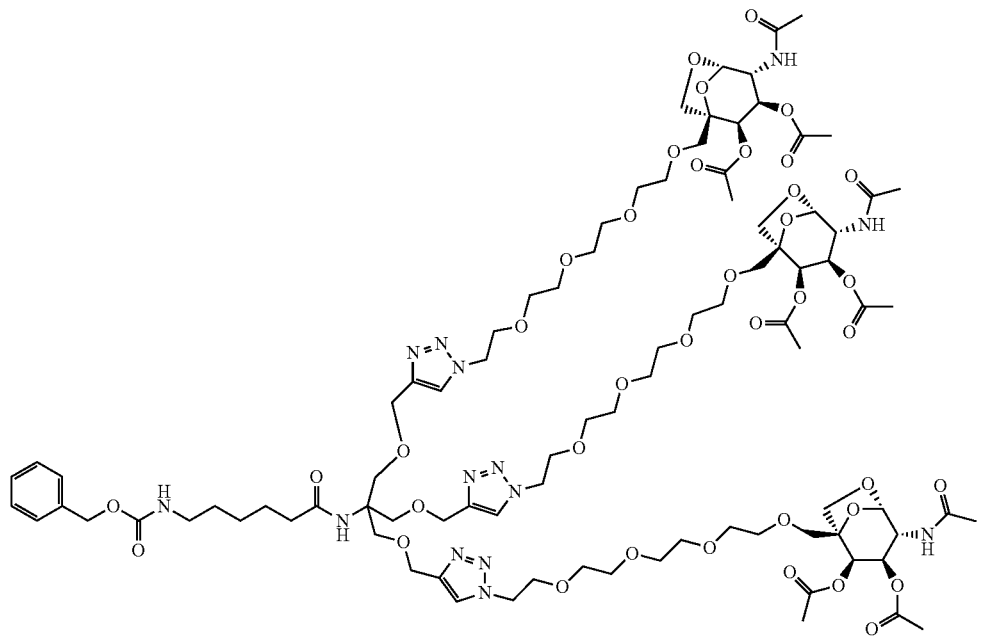 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](OC(C)=O)[C@H]6OC(C)=O)nn4)(COCc4cn(CCOCCOCCOCCOC[C@@]56CO[C@@H](O5)[C@H](NC(C)=O)[C@@H](OC(C)=O)[C@H]6OC(C)=O)nn4)NC(=O)CCCCCNC(=O)OCc4ccccc4)nn3)(O2)[C@H](OC(C)=O)[C@@H]1OC(C)=O]

benzyl {6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}carbamate (47) (1690.0 mg, 0.9463 mmol) was dissolved in anhydrous pyridine (20 mL, 250 mmol) and to which was added acetic anhydride (2.68 mL, 28.4 mmol) at room temperature. The reaction was then heated to 50° C. overnight. The following morning, the reaction was concentrated under reduced pressure. The crude material was purified using the CombiFlash Rf (RediSep 40 g gold silica gel column) and eluting with a gradient of 0-20% methanol/dichloromethane yielding the title compound as a gum (1172 mg, 62.8%). Method C: 3 minute run LRMS [½M+1=1020]. $^1$H NMR (METHANOL-$d_4$) δ: 7.97 (s, 3H), 7.22-7.40 (m, 5H), 5.44 (d, J=3.9 Hz, 3H), 5.32 (s, 3H), 5.10 (dd, J=10.5, 4.3 Hz, 3H), 5.05 (s, 2H), 4.56-4.60 (m, 6H), 4.55 (s, 6H), 4.18 (d, J=10.5 Hz, 3H), 3.99 (d, J=8.6 Hz, 3H), 3.89 (t, J=5.1 Hz, 6H), 3.71-3.80 (m, 12H), 3.51-3.65 (m, 39H), 3.09 (q, J=6.2 Hz, 2H), 2.16-2.19 (m, 2H), 2.15 (s, 9H), 1.94 (d, J=1.6 Hz, 18H), 1.52-1.61 (m, 2H), 1.42-1.52 (m, 2H), 1.33 (d, J=7.0 Hz, 2H)

(1S,2R,3R,4R,5S)-4-(acetylamino)-1-{13-[4-({3-[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]methyl}-2-[(6-aminohexanoyl)amino]propoxy}methyl)-1H-1,2,3-triazol-1-yl]-2,5,8,11-tetraoxatridec-1-yl}-3-(acetyloxy)-6,8-dioxabicyclo[3.2.1]oct-2-yl acetate
(I-ba-1)

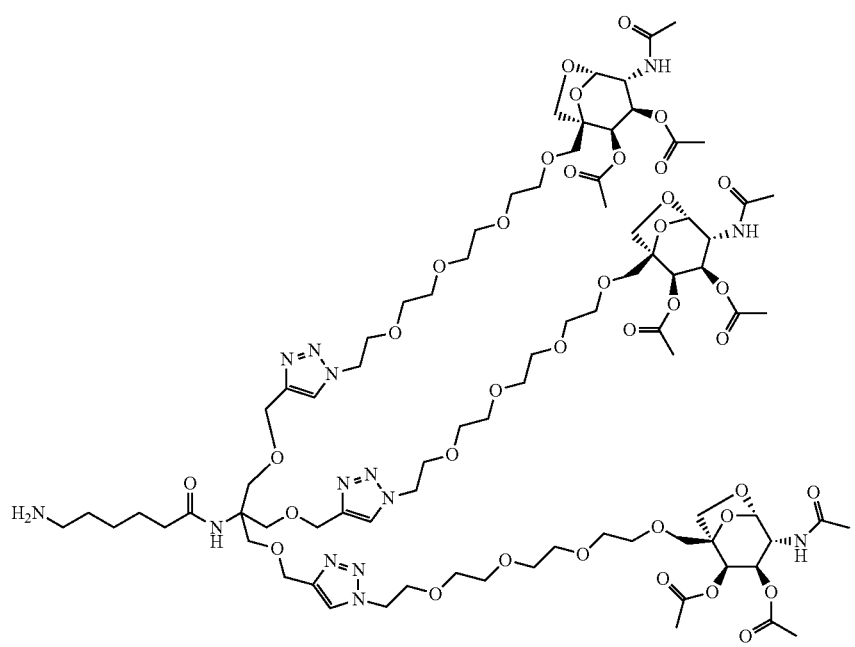 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](OC(C)=O)[C@H]6OC(C)=O)nn4)(COCc4cn(CCOCCOCCOCCOC[C@@]56CO[C@@H](O5)[C@H](NC(C)=O)[C@@H](OC(C)=O)[C@H]6OC(C)=O)nn4)NC(=O)CCCCCN)nn3)(O2)[C@H](OC(C)=O)[C@@H]1OC(C)=O]

A solution of (1S,2R,3R,4R,5S)-4-(acetylamino)-2-(acetyloxy)-1-{13-[4-(12,12-bis{[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]methyl}-3,10-dioxo-1-phenyl-2,14-dioxa-4,11-diazapentadecan-15-yl)-1H-1,2,3-triazol-1-yl]-2,5,8,11-tetraoxatridec-1-yl}-6,8-dioxabicyclo[3.2.1]oct-3-yl acetate (I-az-1) (930.0 mg, 0.456 mmol) in methanol (40 mL) was passed through the H-cube using a 10% palladium on carbon (small cartridge) using the following parameters (temperature=50° C., flow rate=1.0 mL/min., pressure=Full H$_2$ (1 bar)). The solution was collected and was concentrated under reduced pressure yielding the title compound as a gum (837 mg, 96%). Method C: 3 minute run LRMS [M+45 (formic acid)−1=1948]. $^1$H NMR (METHANOL-d$_4$) δ: 7.99 (s, 3H), 5.44 (d, J=4.3 Hz, 3H), 5.32 (s, 3H), 5.10 (dd, J=10.5, 4.3 Hz, 3H), 4.59 (t, J=5.1 Hz, 6H), 4.56 (s, 6H), 4.18 (d, J=10.1 Hz, 3H), 3.99 (d, J=8.2 Hz, 3H), 3.90 (t, J=5.1 Hz, 6H), 3.71-3.82 (m, 12H), 3.53-3.66 (m, 39H), 2.76 (t, J=7.4 Hz, 2H), 2.16-2.23 (m, 2H), 2.15 (s, 9H), 1.94 (s, 18H), 1.48-1.64 (m, 4H), 1.29-1.43 (m, 2H)

ethyl 7-({6-[(1,3-bis[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}amino)-7-oxoheptanoate (I-bb-1)

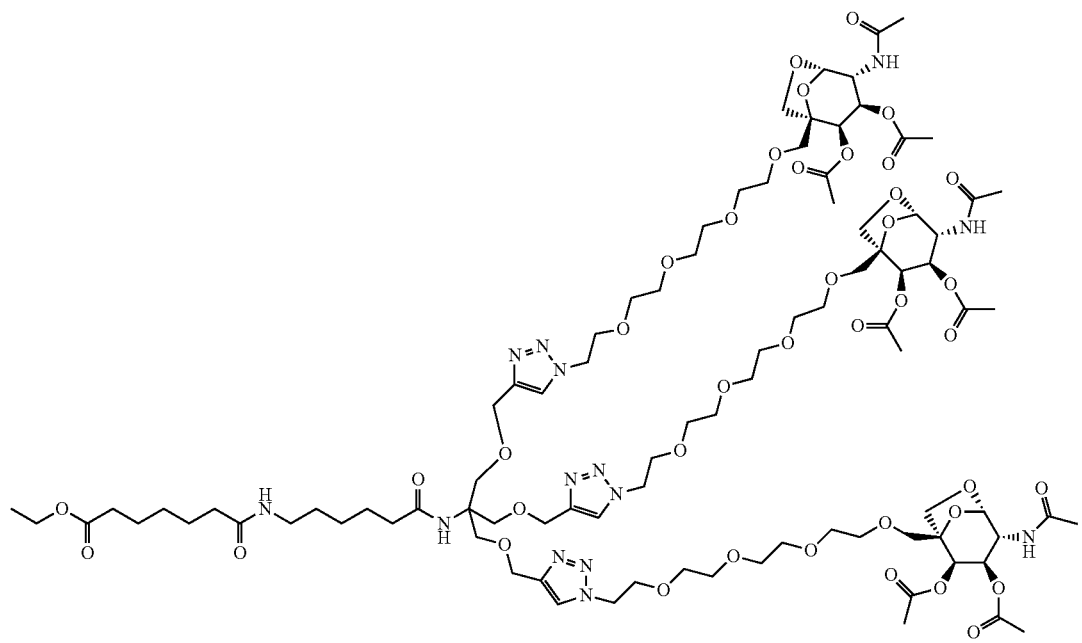 [SMILES: CCOC(=O)CCCCCC(=O)NCCCCCC(=O)NC(COCc1cn(CCOCCOCCOCCOC[C@@]23CO[C@@H](O2)[C@H](NC(C)=O)[C@@H](OC(C)=O)[C@H]3OC(C)=O)nn1)(COCc1cn(CCOCCOCCOCCOC[C@@]23CO[C@@H](O2)[C@H](NC(C)=O)[C@@H](OC(C)=O)[C@H]3OC(C)=O)nn1)COCc1cn(CCOCCOCCOCCOC[C@@]23CO[C@@H](O2)[C@H](NC(C)=O)[C@@H](OC(C)=O)[C@H]3OC(C)=O)nn1]

To a solution of (1S,2R,3R,4R,5S)-4-(acetylamino)-1-{13-[4-({3-[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]methyl}-2-[(6-aminohexanoyl)amino]propoxy}methyl)-1H-1,2,3-triazol-1-yl]-2,5,8,11-tetraoxatridec-1-yl}-3-(acetyloxy)-6,8-dioxabicyclo[3.2.1]oct-2-yl acetate (I-ba-1) (200.0 mg, 0.105 mmol) in N,N-dimethylformamide (2 mL) and tetrahydrofuran (2 mL) was added ethyl 7-[(2,5-dioxopyrrolidin-1-yl)oxy]-7-oxoheptanoate

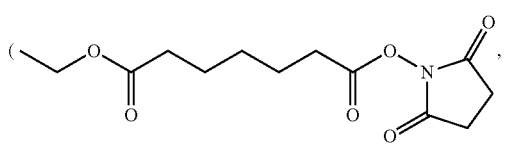 [SMILES: CCOC(=O)CCCCCC(=O)ON1C(=O)CCC1=O]

40.3 mg, 0.126 mmol) and N,N-diisopropylethylamine (0.0732 mL, 0.420 mmol) and the reaction was allowed to stir at room temperature for 24 hours. After 24 hours, the reaction was concentrated under reduced pressure. The crude material was purified using the CombiFlash Rf (RediSep 12 g gold silica gel column) and eluting with a gradient of 0-20% methanol/dichloromethane yielding the title compound as a gum (140.0 mg, 64.3%). Method C: 3 minute run LRMS [½M+1=1038]. $^1$H NMR (METHANOL-$d_4$) δ: 7.98 (s, 3H), 5.44 (d, J=4.3 Hz, 3H), 5.32 (s, 3H), 5.10 (dd, J=10.5, 4.3 Hz, 3H), 4.57-4.61 (m, 6H), 4.56 (s, 6H), 4.18 (d, J=9.8 Hz, 3H), 4.11 (q, J=7.2 Hz, 2H), 3.99 (d, J=8.6 Hz, 3H), 3.90 (t, J=4.9 Hz, 6H), 3.71-3.83 (m, 12H), 3.53-3.65 (m, 39H), 3.08-3.17 (m, 2H), 2.31 (t, J=7.4 Hz, 2H), 2.16-2.22 (m, 4H), 2.15 (s, 9H), 1.94 (d, J=1.6 Hz, 18H), 1.53-1.66 (m, 6H), 1.43-1.52 (m, 2H), 1.28-1.40 (m, 4H), 1.24 (t, J=7.2 Hz, 3H)

7-({6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}amino)-7-oxoheptanoic acid (67)

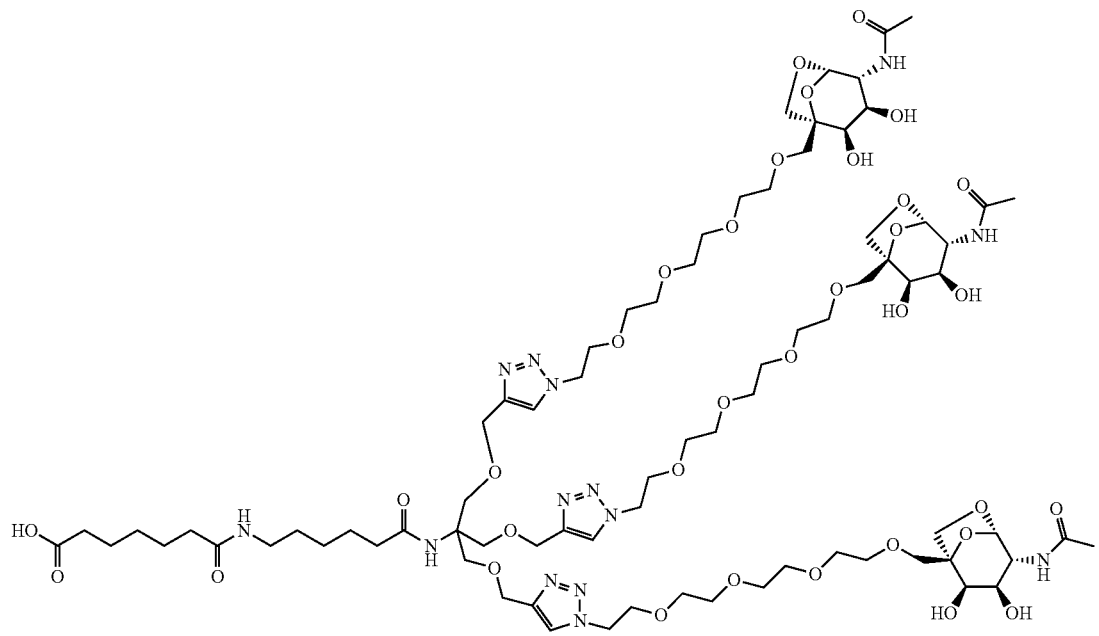 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCNC(=O)CCCCCC(=O)O)nn3)(O2)[C@H](O)[C@@H]1O]

To a solution of ethyl 7-({6-[(1,3-bis[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}amino)-7-oxoheptanoate (I-bb-1) (140.0 mg, 0.0675 mmol) in ethanol (2 mL) and tetrahydrofuran (2 mL) was added 5M sodium hydroxide (0.135 mL, 0.675 mmol). The reaction was allowed to stir overnight at room temperature. The following morning, the reaction was neutralized using the acidic resin and filtered. The resin was washed with ethanol and the filtrate was concentrated under reduced pressure. The material was diluted with ethanol (8 mL) and passed through a syringe filter. The filtrate was then concentrated under reduced pressure yielding the title compound as a gum (110 mg, 90.8%). Method C: 3 minute run LRMS [½M+1=898]. $^1$H NMR (METHANOL-$d_4$) δ: 7.99 (s, 3H), 5.21 (d, J=1.2 Hz, 3H), 4.57-4.62 (m, 6H), 4.56 (s, 6H), 3.92-3.99 (m, 6H), 3.89 (dd, J=10.7, 4.9 Hz, 9H), 3.69-3.80 (m, 12H), 3.54-3.68 (m, 42H), 3.12 (t, J=7.0 Hz, 2H), 2.16 (q, J=7.3 Hz, 6H), 1.99 (s, 9H), 1.53-1.67 (m, 6H), 1.49 (dt, J=14.7, 7.7 Hz, 2H), 1.27-1.41 (m, 4H)

S-[1-(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)-4,4-bis{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}-6,13-dioxo-2,16,19,22,25-pentaoxa-5,12-diazaheptacosan-27-yl] ethanethioate (68)

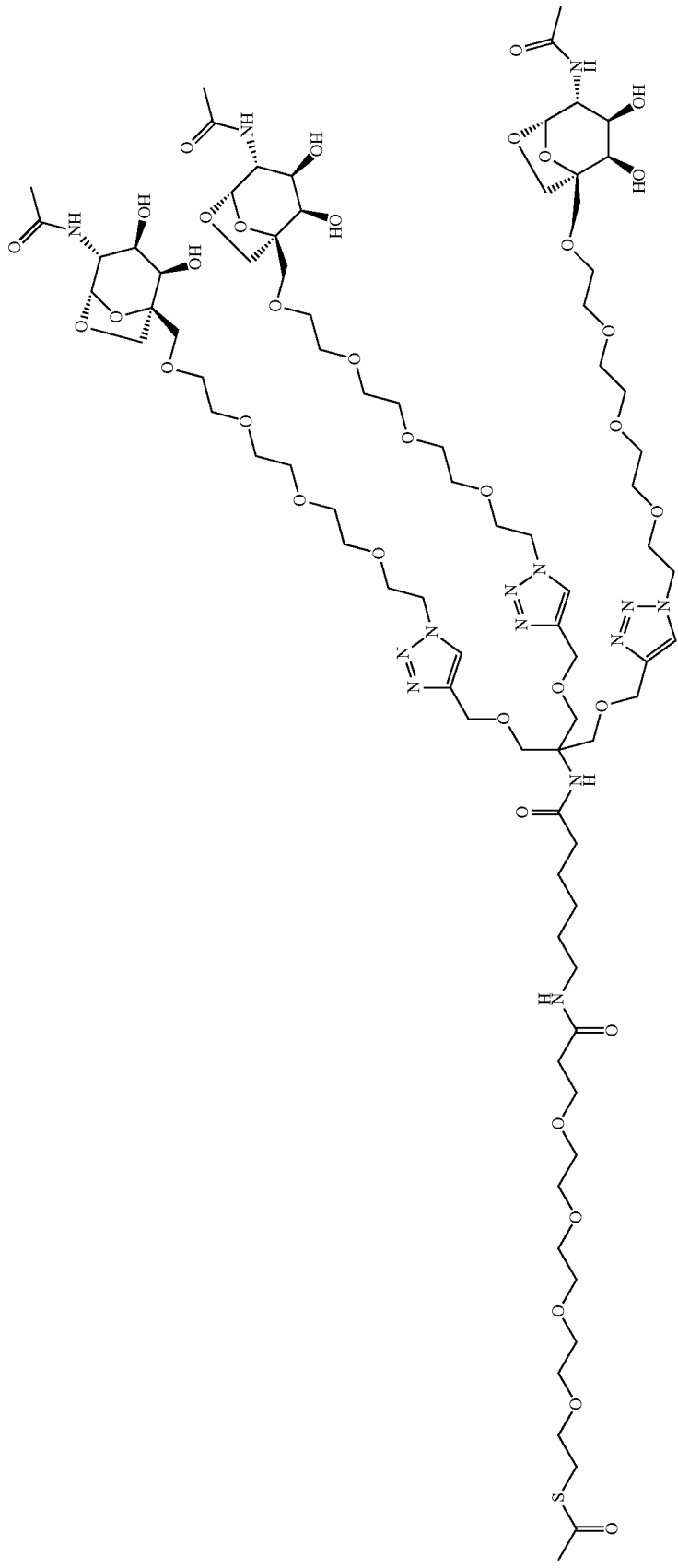

A solution of 6-amino-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hexanamide (48) (200.5 mg, 0.117 mmol), S-{15-[(2,5-dioxopyrrolidin-1-yl)oxy]-15-oxo-3,6,9,12-tetraoxapentadec-1-yl} ethanethioate (60 mg, 0.14 mmol), and N,N-diisopropylethylamine (0.1 mL, 0.59 mmol) in N,N-dimethylformamide (1 mL) and tetrahydrofuran (1 mL) was stirred at room temperature for 20 hours. The reaction mixture was concentrated under reduced pressure. The crude title compound was purified by revered-phase chromatography using the conditions below yielding the title compound as a colorless gum (99 mg, 43%). MS [⅓M+1]=653.7. ¹H NMR (METHANOL-$d_4$) δ: 8.01 (s, 3H), 5.21 (s, 3H), 4.52-4.64 (m, 12H), 3.95 (t, J=9.7 Hz, 6H), 3.85-3.91 (m, 9H), 3.74-3.80 (m, 9H), 3.68-3.73 (m, 6H), 3.54-3.67 (m, 55H), 3.14 (t, J=7.0 Hz, 2H), 3.06 (t, J=6.5 Hz, 2H), 2.43 (t, J=6.2 Hz, 2H), 2.31 (s, 3H), 2.17 (t, J=7.3 Hz, 2H), 1.98 (s, 9H), 1.56 (quin, J=7.5 Hz, 2H), 1.49 (quin, J=7.3 Hz, 2H), 1.28-1.40 (m, 2H)

Purification Conditions

The residue was dissolved in dimethyl sulfoxide (1 mL) and purified by reversed-phase HPLC (Column: Waters Sunfire C18 19×100, 5 u; Mobile phase A: 0.05% TFA in water (v/v); Mobile phase B: 0.05% TFA in acetonitrile (v/v); 80.0% H₂O/20.0% Acetonitrile linear to 60.0% H₂O/40.0% Acetonitrile in 10.5 min, 60.0% H2O/40.0% Acetonitrile linear to 0% H₂O/100% Acetonitrile in 0.5 min HOLD at 0% H₂O/100% Acetonitrile from 11.0 to 12.0 min. Flow: 25 mL/min.

QC Conditions:

Column: Waters Atlantis dC18 4.6×50, 5 u; Mobile phase A: 0.05% TFA in water (v/v); Mobile phase B: 0.05% TFA in acetonitrile (v/v); 95.0% H₂O/5.0% Acetonitrile linear to 5% H₂O/95% Acetonitrile in 4.0 min, HOLD at 5% H₂O/95% Acetonitrile to 5.0 min. Flow: 2 mL/min.

N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)-6-{[3-(4-methyl-2,5-dioxo-2,5-dihydrofuran-3-yl)propanoyl]amino}hexanamide (69)

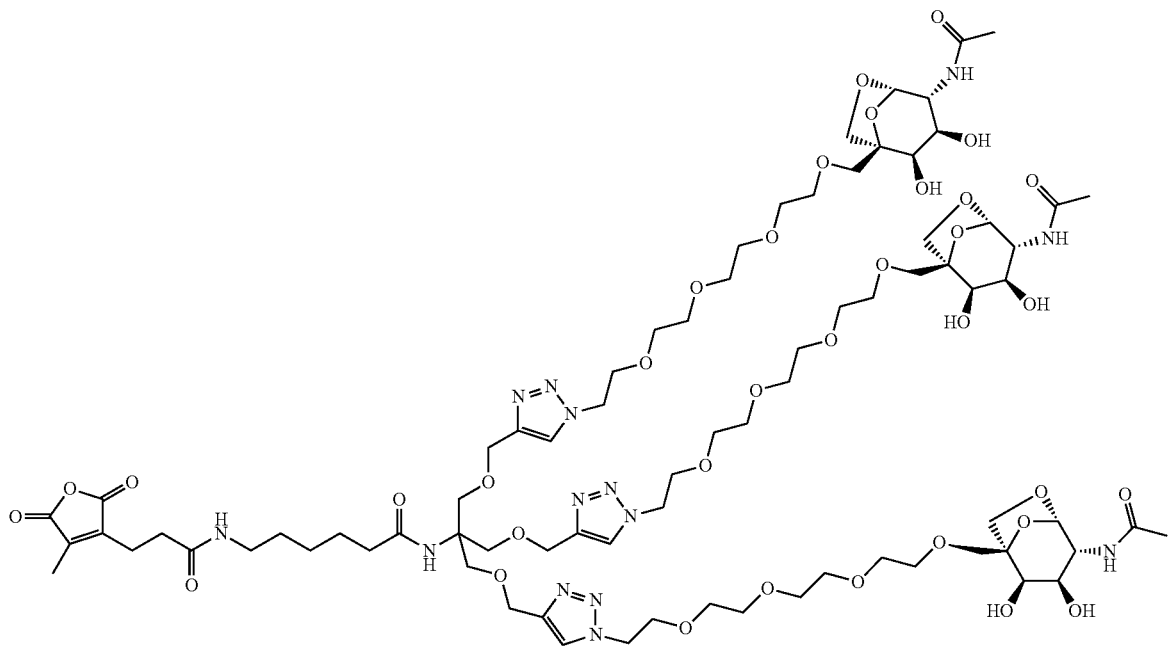 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCNC(=O)CCC4=C(C)C(=O)OC4=O)nn3)(O2)[C@H](O)[C@@H]1O]

To a solution of 3-(4-methyl-2,5-dioxo-2,5-dihydrofuran-3-yl)propanoyl chloride (I-bc-1) (15 mg, 0.074 mmol, See Tetrahedron, 1994, 50, 8969,

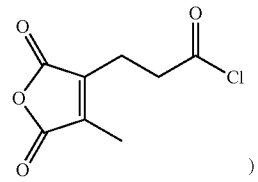

in dichloromethane (0.1 mL) was added 6-amino-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hexanamide acetic acid salt (48) (126.0 mg, 0.0736 mmol) in dichloromethane (0.9 mL), N,N-dimethylformamide (0.1 mL), and anhydrous pyridine (0.024 mL, 0.30 mmol). The reaction was allowed to stir at room temperature overnight. After 18 hours, an additional 4 equiv. of pyridine (0.024 mL, 0.30 mmol) was added followed by an additional 1.0 equivalent of acid chloride (I-bc-1) (15 mg, 0.074 mmol). The reaction was allowed to stir overnight at room temperature. The following morning, an additional 2 equivalents of acid chloride (I-bc-1) was added (30 mg, 0.148 mmol) and the reaction was allowed to stir at room temperature for 4 days. After 4 days, the reaction was concentrated under reduced pressure. The crude title compound was purified by revered-phase chromatography using the conditions below yielding the title compound as a gum (16.1 mg, 12%). Method C: 3 minute run LRMS [½M+1=910]. $^1$H NMR (METHANOL-$d_4$) δ: 8.00 (s, 3H), 5.21 (s, 3H), 4.52-4.62 (m, 12H), 3.92-3.99 (m, 6H), 3.89 (dd, J=11.3, 4.7 Hz, 9H), 3.74-3.79 (m, 9H), 3.71 (dd, J=10.1, 4.3 Hz, 3H), 3.54-3.68 (m, 42H), 3.11 (t, J=7.0 Hz, 2H), 2.75 (t, J=7.2 Hz, 2H), 2.46-2.53 (m, 2H), 2.16 (t, J=7.4 Hz, 2H), 2.05 (s, 3H), 1.99 (s, 9H), 1.55 (dt, J=14.9, 7.6 Hz, 2H), 1.46 (quin, J=7.2 Hz, 2H), 1.24-1.34 (m, 2H)

Purification Conditions

The residue was dissolved in dimethyl sulfoxide (1 mL) and purified by reversed-phase HPLC (Column: Waters Sunfire C18 19×100, 5 u; Mobile phase A: 0.05% TFA in water (v/v); Mobile phase B: 0.05% TFA in acetonitrile (v/v); 75.0% H$_2$O/25.0% Acetonitrile linear to 65.0% H$_2$O/35.0% Acetonitrile in 10.5 min, 65.0% H$_2$O/35.0% Acetonitrile linear to 0% H$_2$O/100% Acetonitrile in 0.5 min HOLD at 0% H$_2$O/100% Acetonitrile from 11.0 to 12.0 min. Flow: 25 mL/min.

QC Conditions

Column: Waters Atlantis dC18 4.6×50, 5 u; Mobile phase A: 0.05% TFA in water (v/v); Mobile phase B: 0.05% TFA in acetonitrile (v/v); 95.0% H$_2$O/5.0% Acetonitrile linear to 5% H$_2$O/95% Acetonitrile in 4.0 min, HOLD at 5% H$_2$O/95% Acetonitrile to 5.0 min. Flow: 2 mL/min.; retention time=1.82 minutes; mass observed=909.8649; mass target—909.2.

tert-butyl [(5S)-5-({6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}carbamoyl)-7,35-dioxo-37-(pyridin-2-yldisulfanyl)-10,13,16,19,22,25,28,31-octaoxa-6,34-diazaheptatriacont-1-yl]carbamate (I-bd-1)

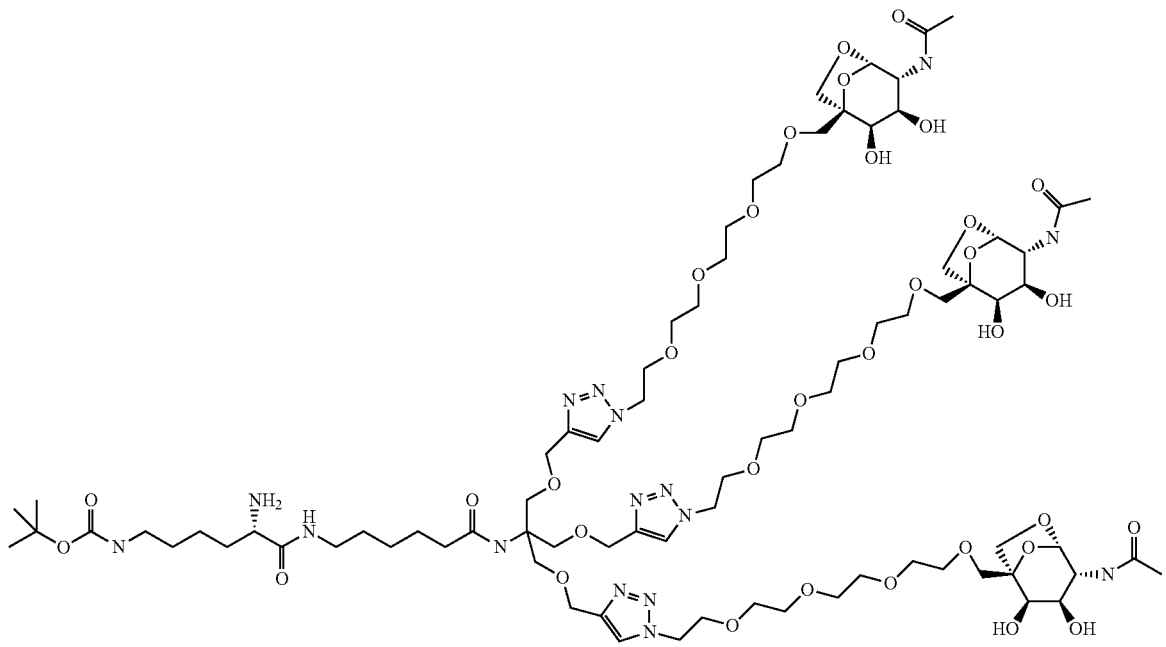 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@@H](O)[C@H]6O)nn4)(COCc4cn(CCOCCOCCOCCOC[C@@]56CO[C@@H](O5)[C@H](NC(C)=O)[C@@H](O)[C@H]6O)nn4)NC(=O)CCCCCNC(=O)[C@@H](N)CCCCNC(=O)OC(C)(C)C)nn3)(O2)[C@H](O)[C@@H]1O]

To a solution of N~6~-(tert-butoxycarbonyl)-N~2~-[(9H-fluoren-9-ylmethoxy)carbonyl]-L-lysine (70.9 mg, 0.151 mmol,

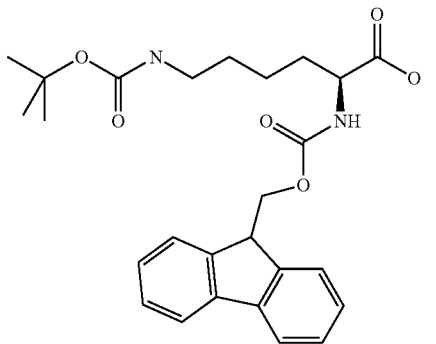

in tetrahydrofuran (2.0 mL) and anhydrous N,N-dimethylformamide (2.0 mL) was added 1-hydroxybenzotriazole (24.5 mg, 0.182 mmol) and N-(3-dimethylaminopropyl)-N-ethylcarbodiimide hydrochloride (35.5 mg, 0.182 mmol) and the reaction was allowed to stir for 1 hour at room temperature. The starting amine To a solution of 6-amino-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy- 6,8-dioxabicyclo[3.2.1]oct-1-yl]-2,5,8,11-tetraoxatridecan-13-yl}-1H-1,2,3-triazol-4-yl)methoxy]methyl}propan-2-yl)hexanamide (48) (250.0 mg, 0.151 mmol) was added to the above solution as a solid followed by the addition of N,N-diisopropylethylamine (0.105 mL, 0.605 mmol) the reaction was allowed to stir at room temperature for 18 hours. After 18 hours, Piperidine (900 mg, 10 mmol, 0.6 mL) was added to the reaction and was allowed to stir at room temperature for 3 hours. After 3 hours, the reaction was concentrated under reduced pressure yielding (450.0 mg, 158%) crude gum.

tert-butyl [(5S)-5-({6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}carbamoyl)-7,35-dioxo-37-(pyridin-2-yldisulfanyl)-10,13,16,19,22,25,28,31-octaoxa-6,34-diazaheptatriacont-1-yl]carbamate (70)

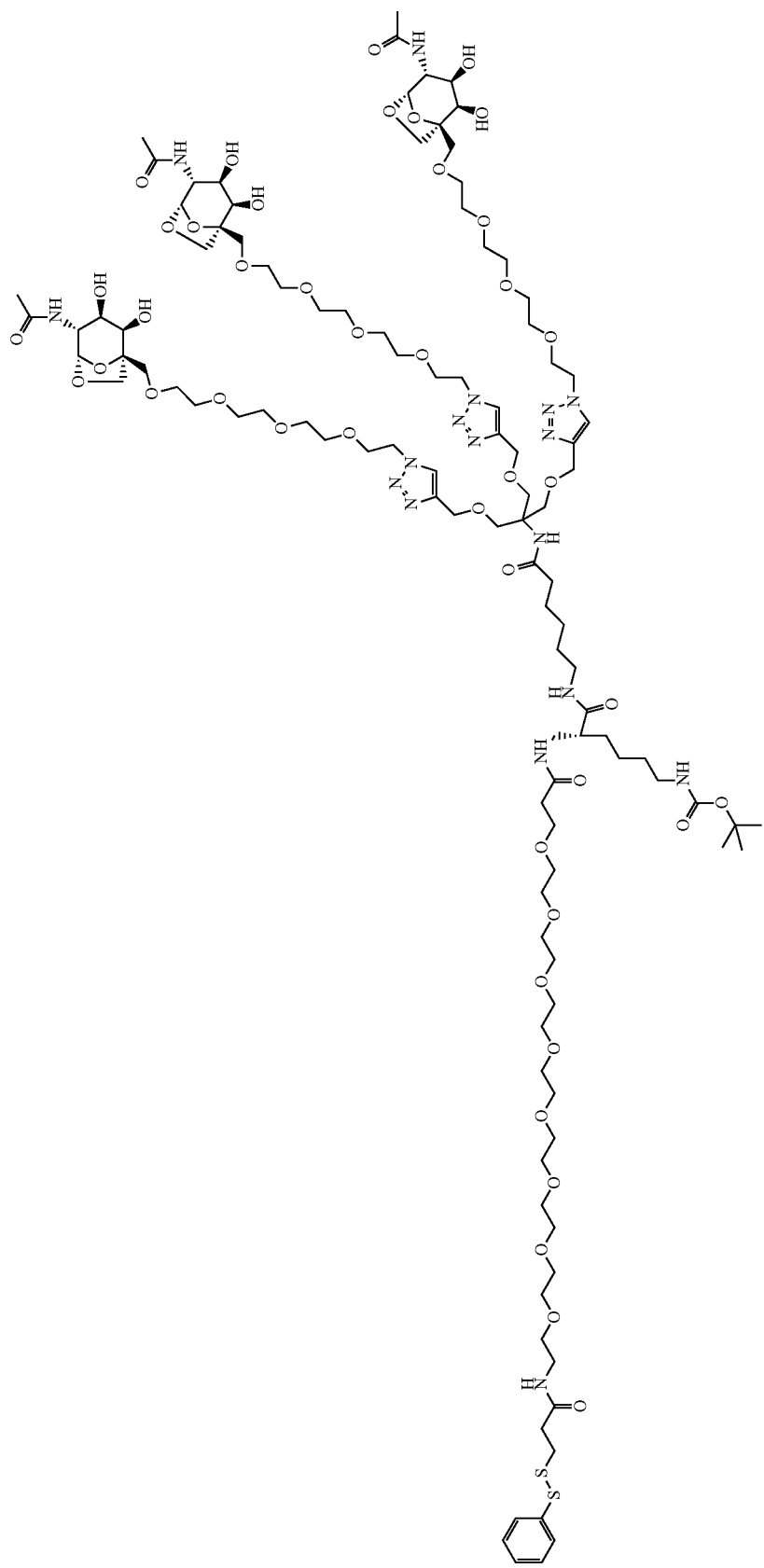

To a solution of tert-butyl [(5S)-5-({6-[(1,3-bis[(1-{1-[(1S, 2R,3R,4R,5S)-4-(acetylamino)-2,3-dihydroxy-6,8-dioxabi-cyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}carbamoyl)-7,35-dioxo-37-(pyridin-2-yldisulfanyl)-10,13,16,19,22,25,28,31-octaoxa-6,34-diazaheptatriacont-1-yl]carbamate (I-bd-1) (225 mg, 0.120 mmol) and N-{27-[(2,5-dioxopyrrolidin-1-yl)oxy]-27-oxo-3,6,9,12,15,18,21,24-octaoxaheptacos-1-yl}-3-(pyridin-2-yldisulfanyl)propanamide (111 mg, 0.151 mmol,

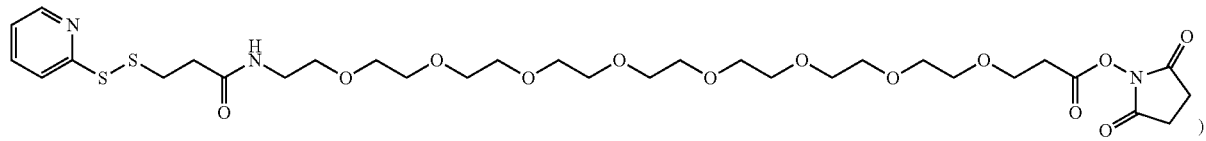 [SMILES: O=C(CCSSc1ccccn1)NCCOCCOCCOCCOCCOCCOCCOCCOCCC(=O)ON1C(=O)CCC1=O]
)

in N,N-dimethylformamide (1 mL) and tetrahydrofuran (2 mL) was added N,N-diisopropylethylamine (0.10 mL, 0.574 mmol). The reaction was allowed to stir at room temperature 3 days. After 3 days, the reaction was concentrated under reduced pressure. A sample of the crude title compound was purified by revered-phase chromatography using the conditions below yielding the title compound as a gum (13.8 mg, 4.6%).

Purification Conditions

The residue was dissolved in dimethyl sulfoxide (1 mL) and purified by reversed-phase HPLC (Column: Waters XBridge C18 19×100, 5 u; Mobile phase A: 0.03% NH4OH in water (v/v); Mobile phase B: 0.03% NH4OH in acetonitrile (v/v); 75.0% $H_2O$/25.0% Acetonitrile linear to 45% $H_2O$/55% Acetonitrile in 8.5 min, 45% $H_2O$/55% Acetonitrile linear to 0% $H_2O$/100% MeCN in 0.5 min, HOLD at 0% $H_2O$/100% Acetonitrile from 9.0 to 10.0 min. Flow: 25 mL/min.

QC Conditions

Column: Waters Atlantis dC18 4.6×50, 5 u; Mobile phase A: 0.05% TFA in water (v/v); Mobile phase B: 0.05% TFA in acetonitrile (v/v); 95.0% $H_2O$/5.0% Acetonitrile linear to 5% $H_2O$/95% Acetonitrile in 4.0 min, HOLD at 5% $H_2O$/95% Acetonitrile to 5.0 min. Flow: 2 mL/min.; retention time=2.06 minutes; mass observed=834.5669, mass target=833.4)

(33S)-33-(4-aminobutyl)-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)-3,31,34-trioxo-1-(pyridin-2-yldisulfanyl)-7,10,13,16,19,22,25,28-octaoxa-4,32,35-triazahentetracontan-41-amide (71)

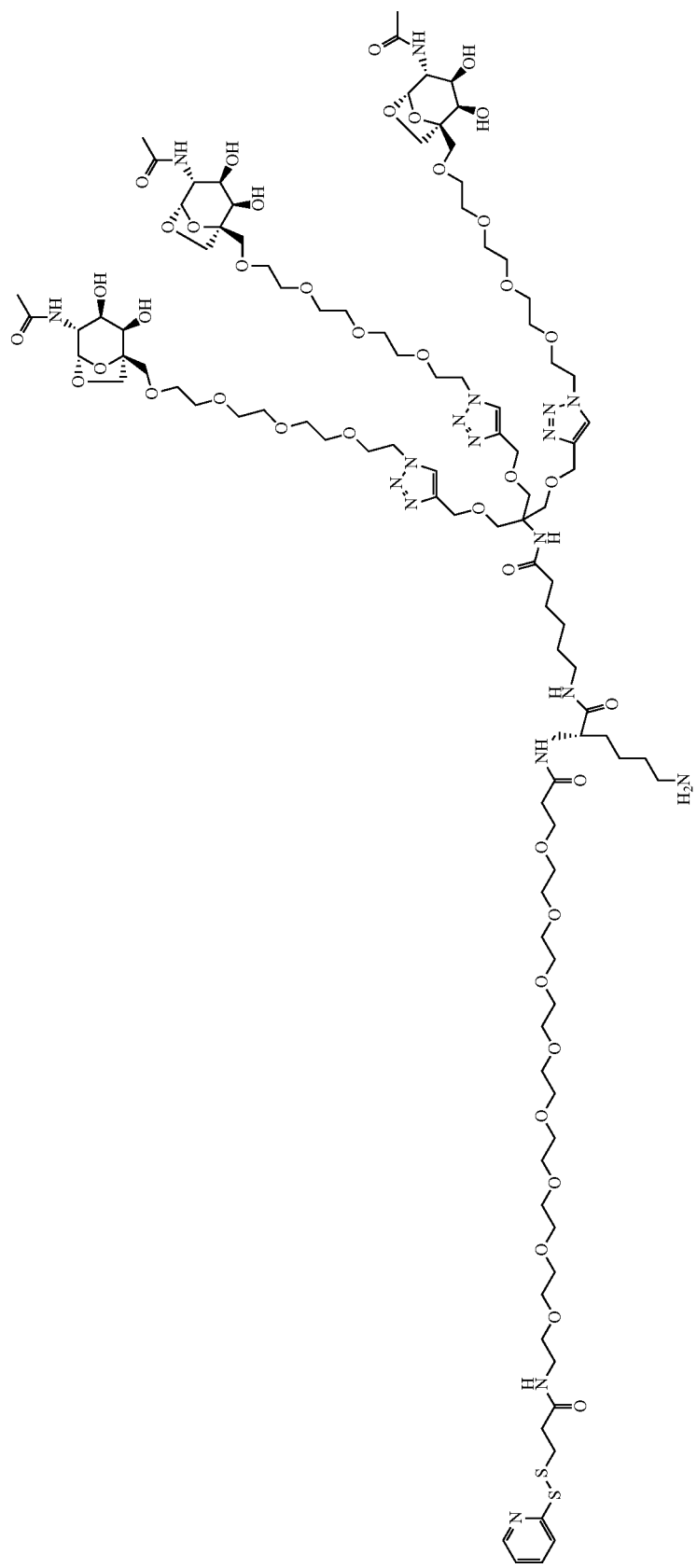

The remaining crude tert-butyl [(5S)-5-({6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}carbamoyl)-7,35-dioxo-37-(pyridin-2-yldisulfanyl)-10,13,16,19,22,25,28,31-octaoxa-6,34-diazaheptatriacont-1-yl]carbamate (70) was diluted in methanol (3 mL) and to which was added 4.0M hydrogen chloride in dioxane (0.898 mL, 3.59 mmol) and the reaction was stirred at room temperature for 18 hours. After 18 hours, the reaction was concentrated under reduced pressure. The crude title compound was purified by revered-phase chromatography using the conditions below yielding the title compound as a gum (78.9 mg, 27%).

Purification Conditions

The residue was dissolved in dimethyl sulfoxide (1 mL) and purified by reversed-phase HPLC (Column: Waters Sunfire C18 19×100, 5 u; Mobile phase A: 0.05% TFA in water (v/v); Mobile phase B: 0.05% TFA in acetonitrile (v/v); 80.0% H₂O/20.0% Acetonitrile linear to 45% H₂O/55% Acetonitrile in 8.5 min, 45% H₂O/55% Acetonitrile linear to 0% H₂O/100% MeCN in 0.5 min, HOLD at 0% H₂O/100% Acetonitrile from 9.0 to 10.0 min. Flow: 25 mL/min.

QC Conditions

Column: Waters Atlantis dC18 4.6×50, 5 u; Mobile phase A: 0.05% TFA in water (v/v); Mobile phase B: 0.05% TFA in acetonitrile (v/v); 95.0% H₂O/5.0% Acetonitrile linear to 5% H₂O/95% Acetonitrile in 4.0 min, HOLD at 5% H₂O/95% Acetonitrile to 5.0 min. Flow: 2 mL/min.; retention time=1.7544 minutes; mass observed=601.159 (¼M+1), Mass target=600.3)

LCMS Method E:

ESI (m/z) with MaxEnt deconvolution software
[Column: Acquity BEH300 C4 1.7 um
Mobile phase: A=0.1% formic acid in water; B=0.1% formic acid in ACN
Gradient: 97% A to 5% A in 2 mins. Hold at 5% A for 0.75 min. Then back to starting conditions.
Temperature: 70 C
MS Detection=ESI 0-2000 daltons, using MaxEnt to deconvolve higher MW species 9H-fluoren-9-ylmethyl [(2S)-1-({6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}amino)-1-oxopent-4-yn-2-yl]carbamate (I-be-1)

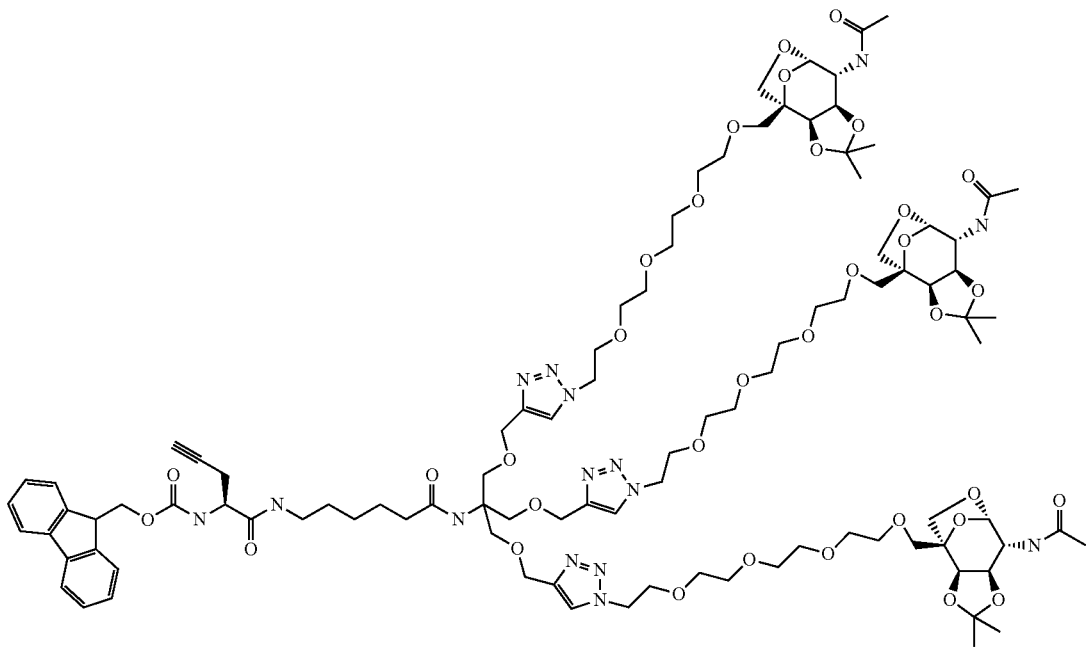 [SMILES: C#CC[C@H](NC(=O)OCC1c2ccccc2-c2ccccc21)C(=O)NCCCCCC(=O)NC(COCc1cn(CCOCCOCCOCCOC[C@@]23CO[C@@H](O2)[C@H](NC(C)=O)[C@H]2OC(C)(C)O[C@H]23)nn1)(COCc1cn(CCOCCOCCOCCOC[C@@]23CO[C@@H](O2)[C@H](NC(C)=O)[C@H]2OC(C)(C)O[C@H]23)nn1)COCc1cn(CCOCCOCCOCCOC[C@@]23CO[C@@H](O2)[C@H](NC(C)=O)[C@H]2OC(C)(C)O[C@H]23)nn1]

To a vial was added (2S)-2-{[(9H-fluoren-9-ylmethoxy)carbonyl]amino}pent-4-ynoic acid (51.7 mg, 0.154 mmol), HBTU (58.0 mg, 0.18 mmol) and anhydrous N,N-dimethylformamide (0.5 ml) and tetrahydrofuran (0.5 mL) followed by the addition of N,N-diisopropylethylamine (0.10 mL, 0.593 mmol) stirred the mixture for 5 minutes. This mixture is added to a solution of 6-amino-N-(1,3-bis[(1-{1-[(1S,2R,6R,7R,8S)-7-(acetylamino)-4,4-dimethyl-3,5,9,11- tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)hexanamide (I-ag-1) (210 mg, 0.119 mmol) in anhydrous N,N-dimethylformamide (0.75 ml) drop wise. Reaction is stirred at room temperature until it's complete by LCMS. Concentrated down using the Gene vac to a crude oil and purified on silica gel column using a 0-20% MeOH/DCM gradient. Isolated fraction is concentrated down to obtain 205 mg (82% yield) as a white form of the titled compound. Method C: LRMS (½M+1=1045.7) The NMR spectrum showed rotomers (1:4 ratio) which are reported as partial hydrogens.

$^1$H NMR (METHANOL-$d_4$) δ: 7.96 (s, 3H), 7.85 (d, J=8.2 Hz, 0.4H), 7.79 (d, J=7.6 Hz, 1.6H), 7.73 (d, J=8.2 Hz, 0.4H), 7.66 (d, J=7.0 Hz, 1.6H), 7.51 (t, J=7.6 Hz, 0.4H), 7.43-7.47 (m, J=7.6 Hz, 0.4H), 7.39 (t, J=7.3 Hz, 1.6H), 7.28-7.32 (m, 1.6H), 5.22 (s, 3H), 4.50-4.62 (m, 12H), 4.38-4.45 (m, 1H), 4.30-4.36 (m, 1H), 4.28 (d, J=5.9 Hz, 3H), 4.19-4.25 (m, 2H), 4.15 (t, J=6.2 Hz, 3H), 3.88-3.94 (m, 6H), 3.87 (t, J=4.7 Hz, 6H), 3.82 (d, J=7.6 Hz, 3H), 3.72-3.78 (m, 12H), 3.48-3.70 (m, 36H), 3.12-3.20 (m, 2H), 2.65 (br. s., 1H), 2.54-2.61 (m, 1H), 2.40 (br. s., 1H), 2.15 (t, J=6.7 Hz, 2H), 1.97 (s, 9H), 1.47 (s, 9H), 1.43-1.59 (m, 4H), 1.31 (s, 9H), 1.36 (s, 2H)

tert-butyl (4S)-5-({6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}amino)-4-{[(9H-fluoren-9-ylmethoxy)carbonyl]amino}-5-oxopentanoate (I-bf-1)

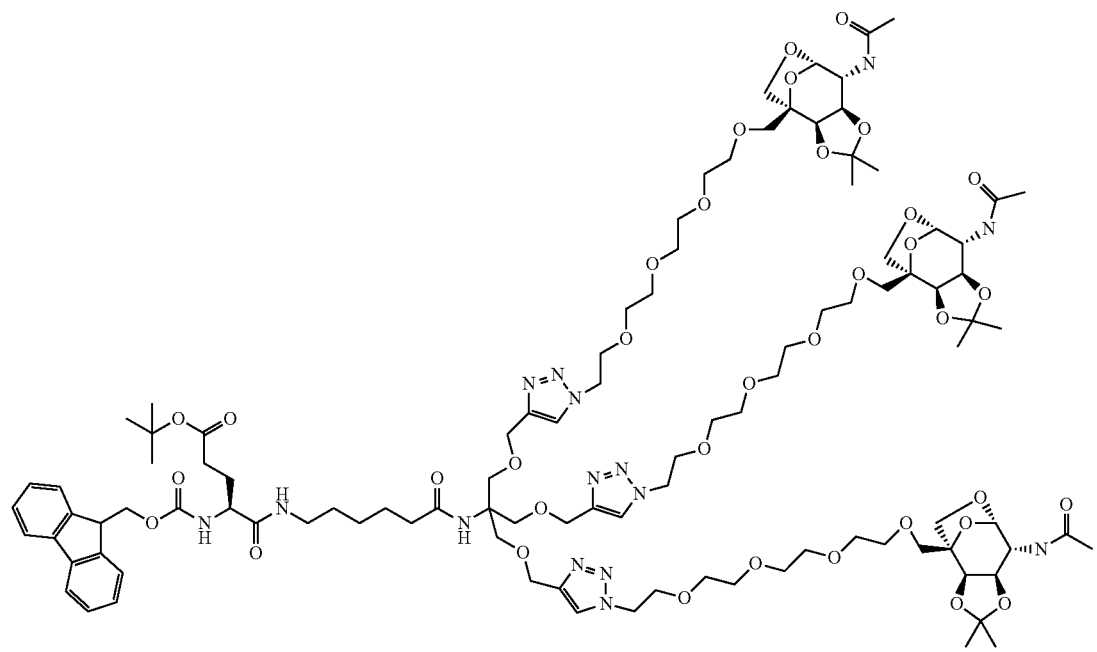 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@H]5OC(C)(C)O[C@H]56)nn4)(COCc4cn(CCOCCOCCOCCOC[C@@]56CO[C@@H](O5)[C@H](NC(C)=O)[C@H]5OC(C)(C)O[C@H]56)nn4)NC(=O)CCCCCNC(=O)[C@H](CCC(=O)OC(C)(C)C)NC(=O)OCC4c5ccccc5-c5ccccc54)nn3)(O2)[C@@H]2OC(C)(C)O[C@H]12]

The above titled compound was synthesized in an analogous manner to (I-be-1), using (2S)-5-tert-butoxy-2-{[(9H-fluoren-9-ylmethoxy)carbonyl]amino}-5-oxopentanoic acid (63.1 mg, 0.148 mmol) to provide 204 mg (82% yield) of the titled compound as a white form. Method C: LRMS (½M+1=1090.7) The NMR spectrum showed rotomers (1:4 ratio) which are reported as partial hydrogens. $^1$H NMR (METHANOL-d$_4$) δ: 7.96 (s, 3H), 7.86 (d, J=8.2 Hz, 0.4H), 7.80 (d, J=7.6 Hz, 1.6H), 7.73 (d, J=8.2 Hz, 0.4H), 7.66 (t, J=6.5 Hz, 1.6H), 7.51 (t, J=7.6 Hz, 0.4H), 7.43-7.47 (m, J=8.2 Hz, 0.4H), 7.39 (t, J=7.3 Hz, 1.6H), 7.28-7.33 (m, 1.6H), 5.23 (s, 3H), 4.50-4.61 (m, 12H), 4.38-4.46 (m, 1H), 4.31-4.38 (m, 1H), 4.28 (d, J=5.9 Hz, 3H), 4.22 (t, J=6.7 Hz, 1H), 4.15 (t, J=6.2 Hz, 3H), 4.04-4.11 (m, 1H), 3.85-3.96 (m, 12H), 3.82 (d, J=7.6 Hz, 3H), 3.71-3.78 (m, 12H), 3.51-3.70 (m, 36H), 3.10-3.19 (m, 2H), 2.29 (t, J=7.3 Hz, 2H), 2.15 (t, J=7.0 Hz, 2H), 2.01-2.10 (m, 1H), 1.98 (s, 9H), 1.78-1.90 (m, 1H), 1.51-1.59 (m, 2H), 1.47 (s, 11H), 1.44 (s, 9H), 1.32 (s, 11H)

9H-fluoren-9-ylmethyl [(2S)-3-azido-1-({6-[(1,3-bis[(1-{1-[(1S,2R,6R,7R,8 S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}amino)-1-oxopropan-2-yl]carbamate (I-bg-1)

The above titled compound was synthesized in an analogous manner to (I-be-1), using 3-azido-N-[(9H-fluoren-9-ylmethoxy)carbonyl]-L-alanine (51.6 mg, 0.148 mmol) to provide 191 mg (68% yield) of the titled compound as a white form. Method C: LRMS (½M+1=1054.1) The NMR spectrum showed rotomers (1:4 ratio) which are reported as partial hydrogens. $^1$H NMR (METHANOL-d$_4$) δ: 7.97 (s, 3H), 7.85 (d, J=8.2 Hz, 0.4H), 7.80 (d, J=7.0 Hz, 1.6H), 7.73 (d, J=8.2 Hz, 0.4H), 7.67 (d, J=7.0 Hz, 1.6H), 7.50 (d, J=7.6 Hz, 0.4H), 7.45 (d, J=7.6 Hz, 0.4H), 7.39 (t, J=7.3 Hz, 1.6H), 7.29-7.33 (m, 1.6H), 5.22 (s, 3H), 4.52-4.62 (m, 12H), 4.41-4.47 (m, 1H), 4.34-4.40 (m, 1H), 4.28 (d, J=5.9 Hz, 3H), 4.21-4.26 (m, 1H), 4.15 (t, J=6.5 Hz, 3H), 3.89-3.95 (m, 6H), 3.87 (t, J=5.0 Hz, 6H), 3.82 (d, J=7.6 Hz, 3H), 3.72-3.79 (m, 12H), 3.49-3.69 (m, 39H), 3.06-3.23 (m, 2H), 2.13-2.23 (m, 2H), 1.98 (s, 9H), 1.50-1.63 (m, 4H), 1.47 (s, 9H), 1.32 (s, 9H), 1.28-1.40 (m, 2H)

9H-fluoren-9-ylmethyl [(2S)-1-({6-[(1,3-bis[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]-2-{[(1-{1-[(1S,2R,6R,7R,8S)-7-(acetylamino)-4,4-dimethyl-3,5,9,11-tetraoxatricyclo[6.2.1.0~2,6~]undec-1-yl]-2,5,8,11-tetraoxatridecan-13-yl}-1H-1,2,3-triazol-4-yl)methoxy]methyl}propan-2-yl)amino]-6-oxohexyl}amino)-3-(1-{15-[(2,5-dioxopyrrolidin-1-yl)oxy]-15-oxo-3,6,9,12-tetraoxapentadec-1-yl}-1H-1,2,3-triazol-4-yl)-1-oxopropan-2-yl]carbamate (I-bh-1)

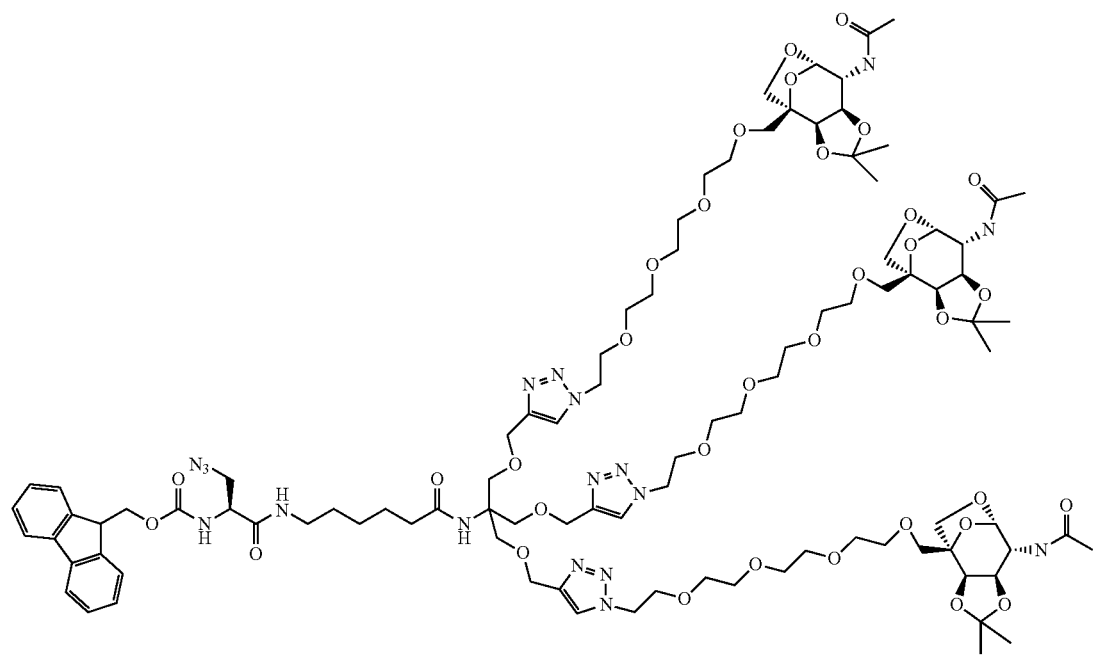 [SMILES: CC(=O)N[C@H]1[C@H]2OC[C@](COCCOCCOCCOCCn3cc(COCC(COCc4cn(CCOCCOCCOCCOC[C@@]56CO[C@@H](O5)[C@H](NC(C)=O)[C@H]5OC(C)(C)O[C@H]56)nn4)(COCc4cn(CCOCCOCCOCCOC[C@@]56CO[C@@H](O5)[C@H](NC(C)=O)[C@H]5OC(C)(C)O[C@H]56)nn4)NC(=O)CCCCCNC(=O)[C@H](CN=[N+]=[N-])NC(=O)OCC4c5ccccc5-c5ccccc54)nn3)(O2)[C@@H]2OC(C)(C)O[C@H]12]

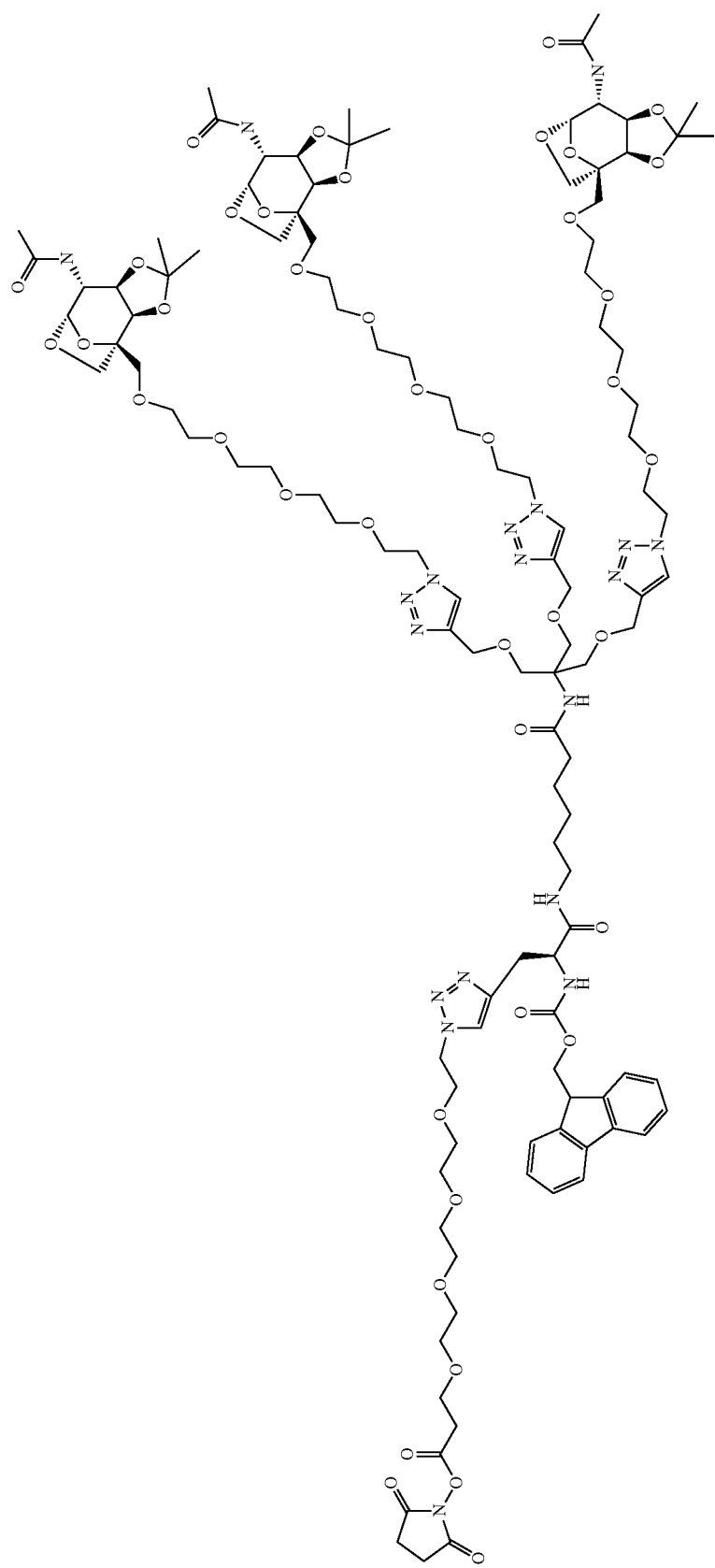

Charged the alkyne from example (I-be-1) (36.5 mg, 0.0175 mmol), 1-[(1-azido-15-oxo-3,6,9,12-tetraoxapentadecan-15-yl)oxy]pyrrolidine-2,5-dione (11.0 mg, 0.0283 mmol) and sodium ascorbate (4.0 mg, 0.020 mmol) in tert-butanol (1 ml) to obtain a clear solution. Freshly prepared solution of copper sulfate (0.93 mg, 0.0058 mmol) in water (0.4 ml) is added to the reaction flask. The reaction turned creamy then light greenish/blue after stirring 1 hour at room temperature. After 1 hour, the reaction was extracted three times with dichloromethane (2 ml). The combined organic layers were dried organic layer with anhydrous sodium sulfate and concentrated down to give a crude solid. Method E: M/Z=2478.0

S-{15-[(2S,4R)-2-{[bis(4-methoxyphenyl)(phenyl)methoxy]methyl}-4-hydroxypyrrolidin-1-yl]-15-oxo-3,6,9,12-tetraoxapentadec-1-yl} ethanethioate
(I-bi-1)

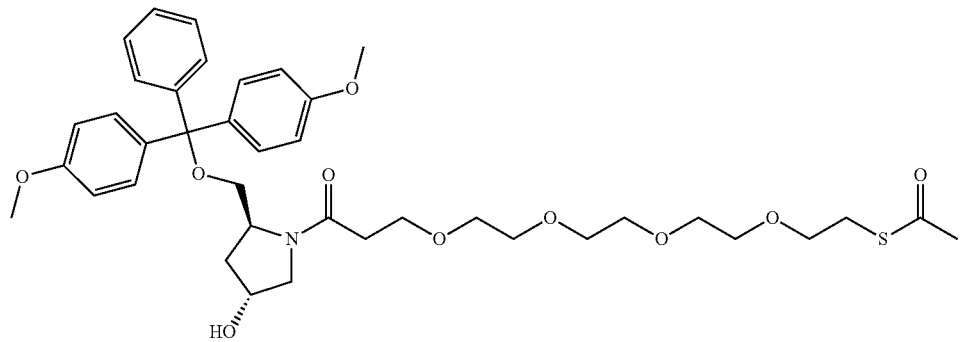 [SMILES: COc1ccc(C(OC[C@@H]2C[C@@H](O)CN2C(=O)CCOCCOCCOCCOCCSC(C)=O)(c2ccccc2)c2ccc(OC)cc2)cc1]

(3R,5S)-5-{[bis(4-methoxyphenyl)(phenyl)methoxy]methyl}pyrrolidin-3-ol was prepared according to a published procedure (Prakash, T. P. et al. 8796-8807 *Nucleic Acids Res.*, 2014, 42, 8796.) A solution of (3R,5S)-5-{[bis(4-methoxyphenyl)(phenyl)methoxy]methyl}pyrrolidin-3-ol (0.18 g, 0.43 mmol) S-{15-[(2,5-dioxopyrrolidin-1-yl)oxy]-15-oxo-3,6,9,12-tetraoxapentadec-1-yl} ethanethioate (0.20 g, 0.48 mmol), and N,N-diisopropylethylamine (0.28 g, 2.2 mmol) in N,N-dimethylformamide (1 mL) and tetrahydrofuran (1 mL) was stirred at room temperature for 5 days. The reaction mixture was diluted with water (10 mL) and extracted with ethyl acetate (3×5 mL). The combined organics were dried over sodium sulfate, filtered and concentrated. The crude residue was purified by column chromatography (0-7% methanol in dichloromethane) to afford the title compound as a colorless oil (0.19 g, 62%).

Method F: 3.0 minute run LRMS (low resolution mass spectroscopy): Waters Acquity UPLC BEH, 2.1 mm×50 mm, C18, 1.8 μm; Column Temperature 60° C.; Mobile Phase: A: 0.1% ammonia in water (v/v); Mobile phase B: 0.1% ammonia in acetonitrile (v/v); Flow-1.25 ml/minute; Initial conditions: A—95%:B—5%; hold at initial from 0.0-0.1 minute; Linear Ramp to A—5%:B—95% over 0.1-2.6 minute; hold at A—5%:B—95% from 2.6-2.95 minute; return to initial conditions 2.95-3.0 minute.

Method D: 3 minute method LRMS [M+1=726.6]. The NMR spectrum was confounded by the presence of rotomers in a 2:1 mixture and is reported as seen. $^1$H NMR (600 MHz, METHANOL-$d_4$) δ: 7.34-7.42 (m, 2H), 7.23-7.32 (m, 6H), 7.16-7.23 (m, 1H), 6.81-6.90 (m, 4H), 4.52-4.62 (m, 0.66H), 4.48 (dt, J=9.7, 5.1 Hz, 0.33H), 4.22-4.34 (m, 1H), 3.67-3.84 (m, 8H), 3.40-3.64 (m, 16H), 3.22 (m, J=5.6, 5.6 Hz, 0.66H), 3.13 (dd, J=9.4, 2.3 Hz, 0.66H), 3.01-3.10 (m, 1.66H), 2.54-2.68 (m, 1.66H), 2.26-2.37 (m, 3.33H), 2.17-2.25 (m, 1H), 2.02-2.11 (m, 0.33H), 1.91-2.00 (m, 0.66H).

N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}-7-[(2S,4R)-2-{[bis(4-methoxyphenyl)(phenyl)methoxy]methyl}-4-hydroxypyrrolidin-1-yl]-7-oxoheptanamide (72)

additional 2 days. The reaction mixture was concentrated under reduced pressure and purified using the below conditions.

Purification Conditions

The residue was dissolved in dimethyl sulfoxide (1 mL) and purified by reversed-phase HPLC (Column: Waters XBridge C18 19×100, 5 u; Mobile phase A: 0.03% NH$_4$OH in water (v/v); Mobile phase B: 0.03% NH$_4$OH in acetonitrile (v/v);

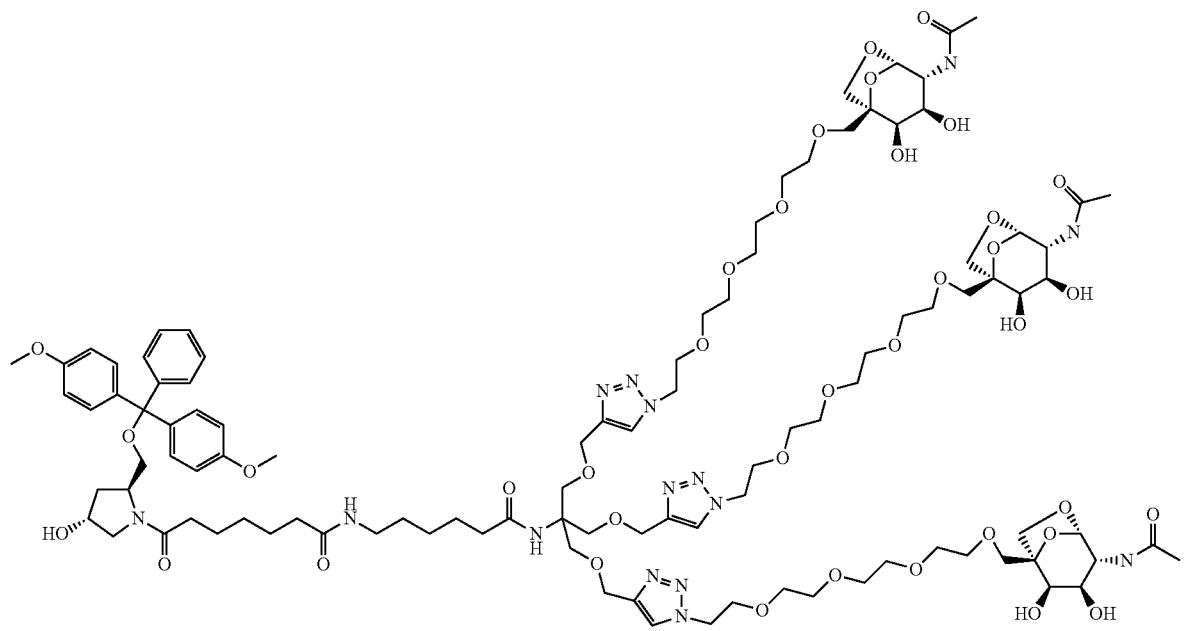 [SMILES: COc1ccc(C(OC[C@@H]2C[C@@H](O)CN2C(=O)CCCCCC(=O)NCCCCCC(=O)NC(COCc2cn(CCOCCOCCOCCOC[C@@]34CO[C@@H](O3)[C@H](NC(C)=O)[C@@H](O)[C@H]4O)nn2)(COCc2cn(CCOCCOCCOCCOC[C@@]34CO[C@@H](O3)[C@H](NC(C)=O)[C@@H](O)[C@H]4O)nn2)COCc2cn(CCOCCOCCOCCOC[C@@]34CO[C@@H](O3)[C@H](NC(C)=O)[C@@H](O)[C@H]4O)nn2)(c2ccccc2)c2ccc(OC)cc2)cc1]

A solution of (3R,5S)-5-{[bis(4-methoxyphenyl)(phenyl)methoxy]methyl}pyrrolidin-3-ol (14 mg, 0.034 mmol) in N,N-dimethylformamide (0.11 mL) was added so a solution of 7-({6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}amino)-7-oxoheptanoic acid (I-bb-1) (61 mg, 0.034 mmol), TBTU (16 mg, 0.049 mmol), and N,N-diisopropylethylamine (22 mg, 0.17 mmol) in N,N-dimethylformamide (0.23 mL) and the reaction was stirred at room temperature for 5 days. (3R,5S)-5-{[bis(4-methoxyphenyl)(phenyl)methoxy]methyl}pyrrolidin-3-ol (14 mg, 0.034 mmol), TBTU (16 mg, 0.049 mmol), and N,N-diisopropylethylamine (22 mg, 0.17 mmol) were then added and the reaction stirred for an 60.0% H$_2$O/40.0% Acetonitrile linear to 40% H$_2$O/60% Acetonitrile in 10.5 min, HOLD at 0% H$_2$O/100% Acetonitrile to 12.0 min. Flow: 25 mL/min.

The title compound was obtained as a colorless residue (1 mg, 1%). Method F: 3 minute method LRMS [½M−1]= 1097.2. $^1$H NMR (600 MHz, METHANOL-d$_4$) δ: 7.99 (s, 3H), 7.40 (d, J=7.6 Hz, 2H), 7.24-7.32 (m, 6H), 7.16-7.22 (m, 1H), 6.85 (d, J=8.8 Hz, 4H), 5.21 (s, 3H), 4.52-4.64 (m, 12H), 4.39-4.47 (m, 1H), 4.21 (br. s., 1H), 3.95 (t, J=9.7 Hz, 6H), 3.85-3.92 (m, 9H), 3.44-3.83 (m, 65H), 3.09-3.17 (m, 2H), 2.24-2.49 (m, 2H), 2.12-2.23 (m, 4H), 1.93-2.11 (m, 10H), 1.53-1.70 (m, 6H), 1.44-1.52 (m, 2H), 1.22-1.42 (m, 4H)

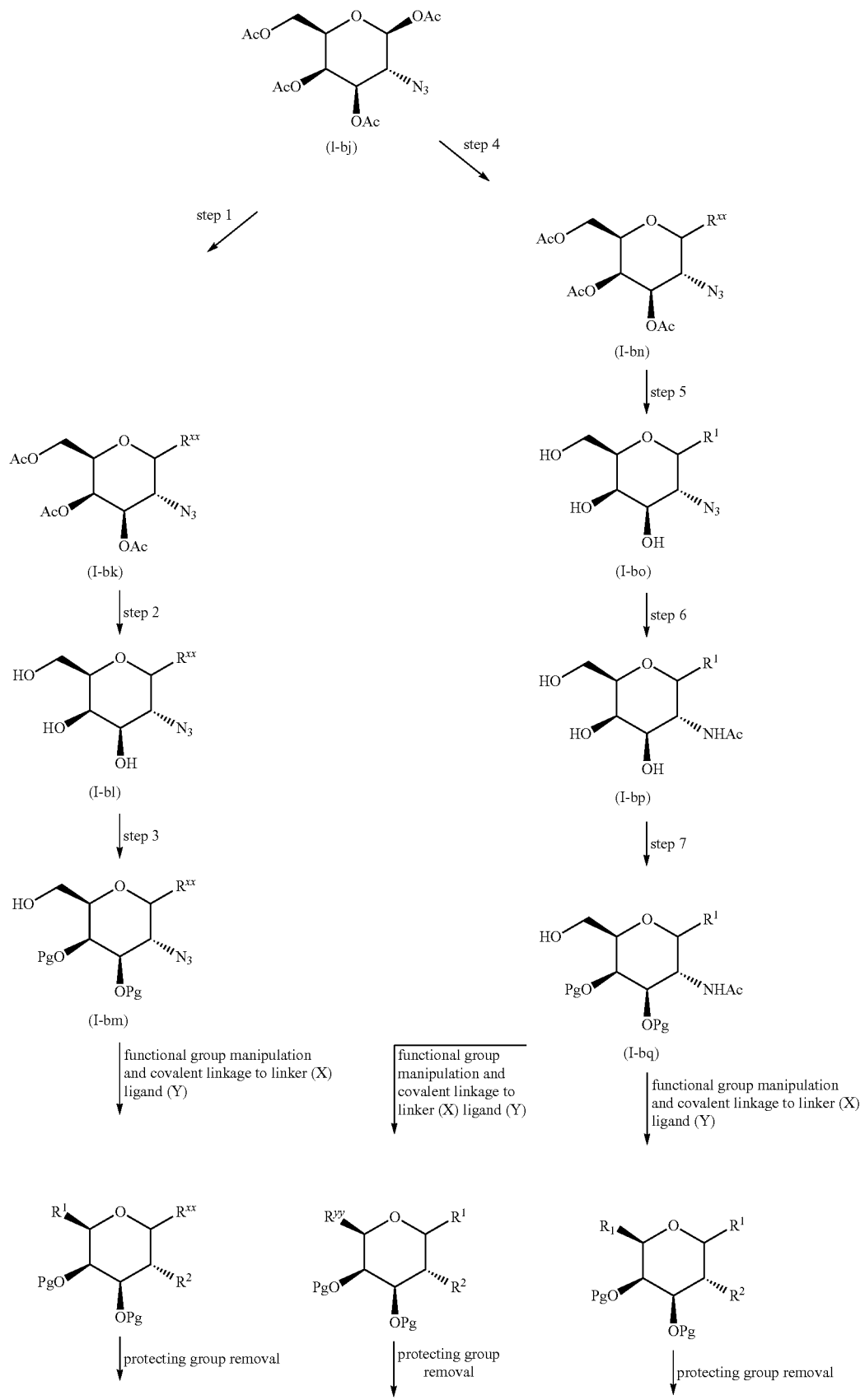

313
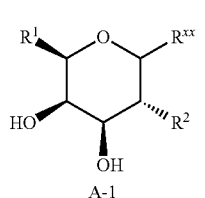
A-1
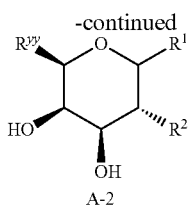
A-2
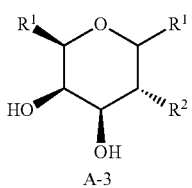
A-3
314
-continued
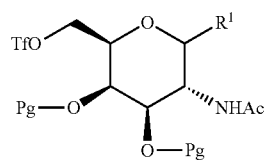
(III-bo-1)
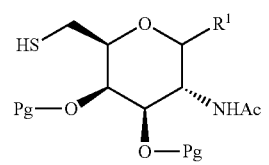
(III-bo-2)
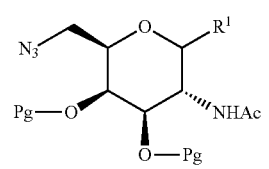
(III-bo-3)
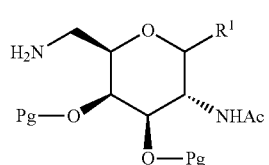
(III-bo-4)
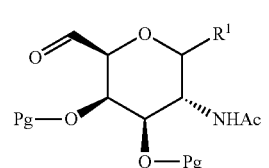
(III-bo-5)
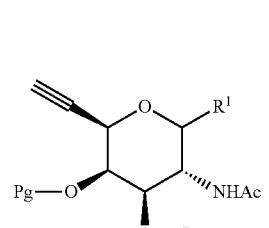
(III-bo-6)
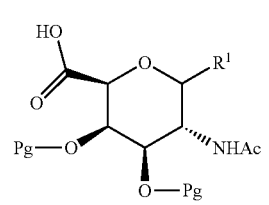
(III-bo-7)
-continued
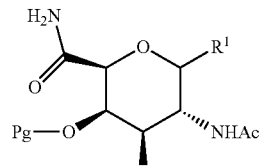
(III-bo-8)
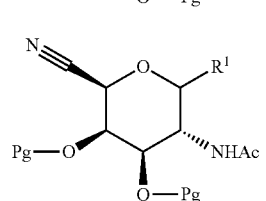
(III-bo-9)
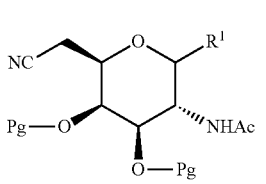
(III-bo-10)
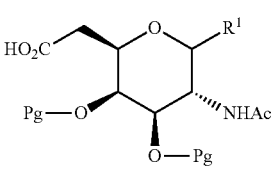
(III-bo-11)
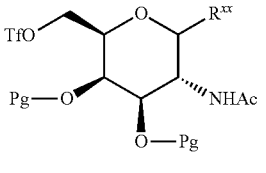
(III-bo-12)
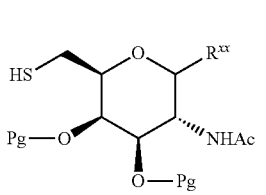
(III-bo-13)
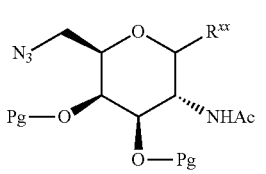
(III-bo-14)

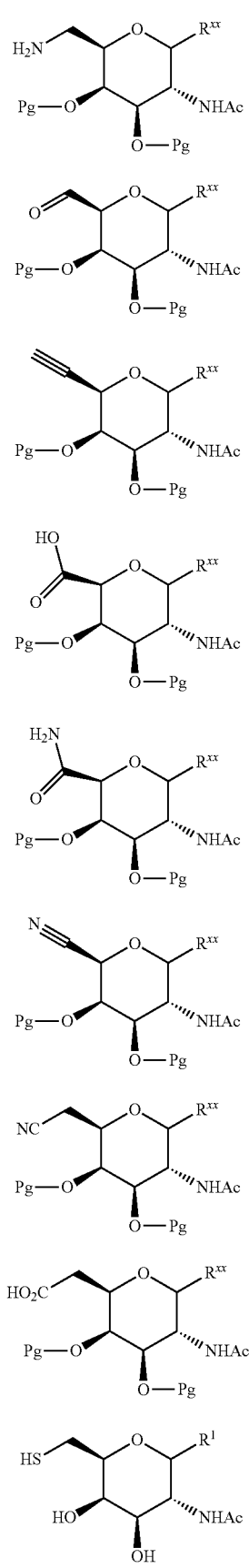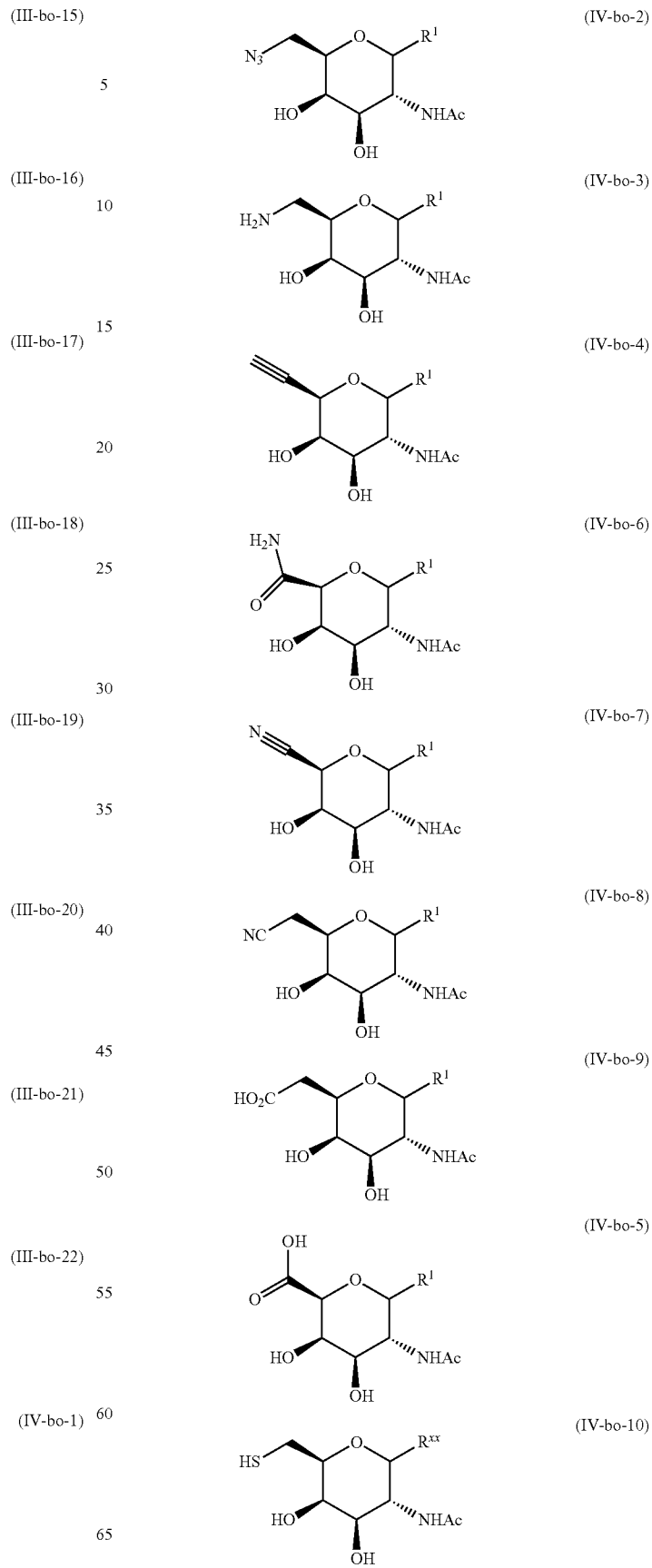

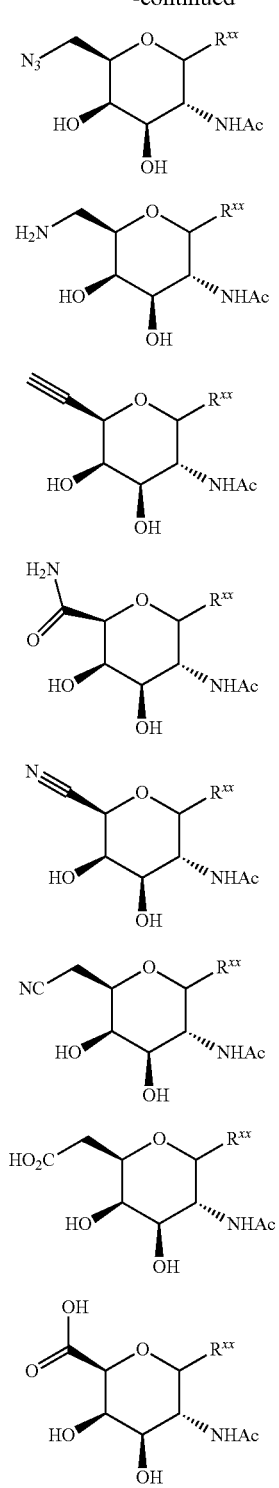

Scheme 9 outlines the general procedures one could use to provide compounds of the present invention. In steps 1 and 4 of Scheme 9, synthetic intermediate (I-bj), that can be prepared by procedures described by H. Paulsen and M. Paal in Carbohydrate Research, 135, 53 (1984), can be glycosylated (using protocols well known by those skilled in the art, such as using an appropriate lewis acid (e.g. diethylether boron trifluoride complex), an appropriate organic solvent like dichloromethane and the appropriate alcohol such as those described by Takao Aoki et al WO 2006028129 A1 Mar. 16, 2006) to produce intermediates such as (I-bk) and (I-bn). In steps 2 and 5 of Scheme 9, treatment of intermediates (I-bk) and (I-bn) in presence of an alkoxide (e.g., sodium methoxide) in a solvent, or mixture of solvents, such as an alcoholic solvent or tetrahydrofuran at a temperature ranging from about 0 to room temperature provides intermediates such as (I-bl) and (I-bo). In step 3 of Scheme 9, secondary hydroxyl groups in compound such as (I-bl) can be further protected by a suitable protecting group (e.g., as a cyclic ketal upon treatment with 2,2-dimethoxypropane under acidic conditions in a solvent such as N,N-dimethylformamide at a temperature ranging from about room temperature to about 90 degrees Celsius) to access intermediates such as (I-bm). Additionally, in step 6 of Scheme 9, compound (I-bo) can be treated with a reducing agent known to reduce azido groups to the corresponding amine (e.g., transition-metal mediated catalytic hydrogenation, use of triphenylphosphine in water under classical experimental conditions well known by those skilled in the art). Subsequent treatment in presence of an acylating agent (e.g., acetic anhydride or acetyl chloride in presence of pyridine or triethylamine in a solvent such as dichloromethane or tetrahydrofuran at a temperature ranging from 0 to 80 degrees Celsius). The subsequent addition of an alkoxide (e.g., sodium methoxide) in a solvent, or mixture of solvents, such as an alcoholic solvent or tetrahydrofuran at a temperature ranging from about 0 to room temperature provides compounds such as (I-bp). In step 7 of Scheme 9, secondary hydroxyl groups in compound (I-bp) can be further protected by a suitable protecting group (e.g., as a cyclic ketal upon treatment with 2,2-dimethoxypropane under acidic conditions in a solvent such as N,N-dimethylformamide at a temperature ranging from about room temperature to about 90 degrees Celsius) to access intermediates such as (I-bq). In turn, using synthetic transformations and functional and protecting groups manipulations well known by those skilled in the art, similarly described for (I-d) and (I-e) can be employed for (I-bm) and (I-bq) which are primed for further functionalization and derivatization of the primary hydroxyl group to link the desired linker X and ligand Y of interest to produce the XY-containing compounds claimed in the present invention. Removal of the protecting groups (e.g., Pg), using reagents and conditions well known to those skilled in the art (e.g., in the case where the two Pg form a cyclic ketal such as an acetonide, it can be removed under acidic conditions using an acid such as acetic acid in a solvent or mixture of solvents such as acetic acid, an alcoholic solvent, water, tetrahydrofuran at a temperature ranging from room temperature to about 80 degrees Celsius), to reveal the secondary hydroxyl groups leads to XY-containing compounds claimed in the present invention. For example, alkylation of the primary hydroxyl group in (I-bq) can lead to, after protecting group manipulation and removal, the corresponding ether-linked XY-containing compounds claimed in this invention. Ester-linked, carbonate-linked and carbamate-linked XY-containing compounds claimed in the present invention can also be conveniently accessed from intermediates such as (I-bm) or (I-bq) using the appropriate reactants and reagents well known by those skilled in the art. Further manipulations of (I-bq) similar to those described previously for (I-e) will allow access to intermediates such as (III-bo-1) through (III-bo-22) and (IV-bo-1) through (IV-bo-18) in similar manner to one skilled in the art for intermediates (III-e-1) through (III-e-11) and (IV-e-1) through (IV-e-9).

2-{2-[2-(2-azidoethoxy)ethoxy]ethoxy}ethyl 3,4,6-tri-O-acetyl-2-(acetylamino)-2-deoxy-beta-D-galactopyranoside (I-br-1)

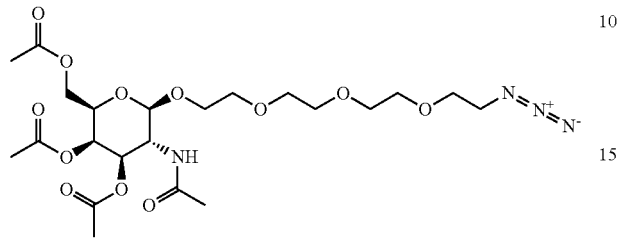

2-{2-[2-(2-azidoethoxy)ethoxy]ethoxy}ethyl 2-(acetylamino)-2-deoxy-beta-D-galactopyranoside (WO 2006028129 A1 Mar. 16, 2006, 1600 mg, 3.78 mmol) was dissolved in anhydrous pyridine (3.0 mL, 38 mmol) and to which was added acetic anhydride (5.36 mL, 56.8 mmol) at room temperature. The reaction was then heated to 50° C. overnight. The following morning, the reaction was concentrated under reduced pressure. The crude material was purified using the CombiFlash Rf (Redi Sep 40 g silica gel column) and eluting with a gradient of 0-20% methanol/dichloromethane yielding the title compound as a gum (1800 mg, 87%). 3 minute run LRMS [M+1=549.3]

benzyl (6-{[1,3-bis{[1-(2-{2-[2-(2-{[3,4,6-tri-O-acetyl-2-(acetylamino)-2-deoxy-beta-D-galactopyranosyl]oxy}ethoxy)ethoxy]ethoxy}ethyl)-1H-1,2,3-triazol-4-yl]methoxy}-2-({[1-(2-{2-[2-(2-{[3,4,6-tri-O-acetyl-2-(acetylamino)-2-deoxy-beta-D-galactopyranosyl]oxy}ethoxy)ethoxy]ethoxy}ethyl)-1H-1,2,3-triazol-4-yl]methoxy}methyl)propan-2-yl]amino}-6-oxohexyl)carbamate (I-bs-1)

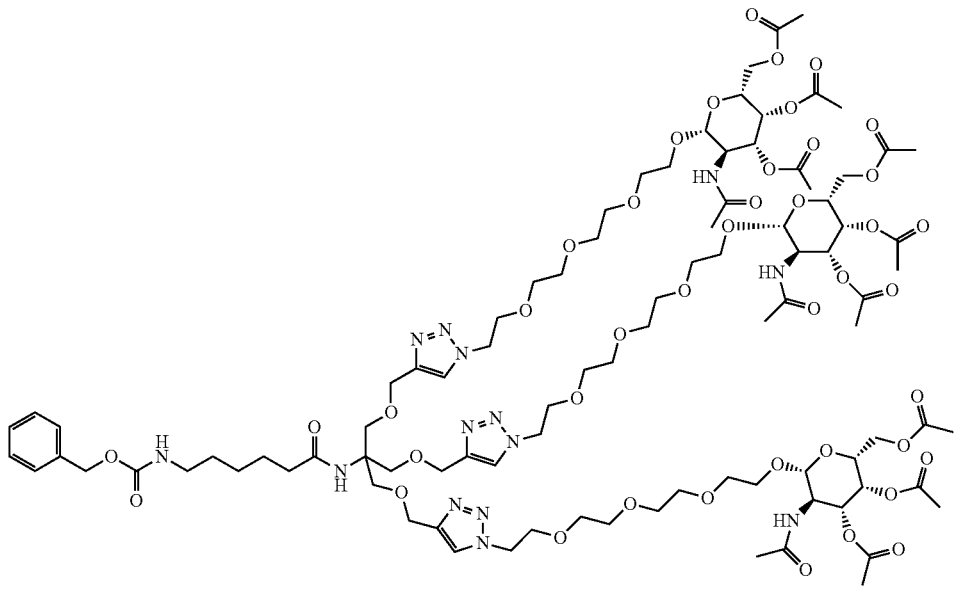 [SMILES: CC(=O)N[C@H]1[C@H](OCCOCCOCCOCCn2cc(COCC(COCc3cn(CCOCCOCCOCCO[C@@H]4O[C@H](COC(C)=O)[C@H](OC(C)=O)[C@H](OC(C)=O)[C@H]4NC(C)=O)nn3)(COCc3cn(CCOCCOCCOCCO[C@@H]4O[C@H](COC(C)=O)[C@H](OC(C)=O)[C@H](OC(C)=O)[C@H]4NC(C)=O)nn3)NC(=O)CCCCCNC(=O)OCc3ccccc3)nn2)O[C@H](COC(C)=O)[C@H](OC(C)=O)[C@@H]1OC(C)=O]

A 50 mL round bottom flask equipped with stir bar was charged with (I-q-1) (250 mg, 0.518 mmol) was added 2-{2-[2-(2-azidoethoxy)ethoxy]ethoxy}ethyl 3,4,6-tri-O-acetyl-2-(acetylamino)-2-deoxy-beta-D-galactopyranoside (I-br-1) (750 mg, 1.37 mmol) in t-butanol (7 mL) followed by the addition of water (3 mL) followed by the addition of sodium ascorbate (1050 mg, 5.18 mmol) neat and the reaction was purged with nitrogen for 30 minutes. Copper sulfate (83.5 mg, 0.518 mmol) was added in 0.5 mL of water (deionized water) and stirred at room temperature for 24 hours. After 24 hours, the reaction was quenched by adding the reaction mixture to a saturated ammonium chloride solution aqueous (20 mL) and conc. ammonium hydroxide (2 mL) and extracted three times with dichloromethane (10 mL). The combined organic layers were dried over magnesium sulfate, filtered and concentrated under reduced pressure. The crude material was purified using the CombiFlash Rf (RediSep 40 g gold silica gel column) and eluting with a gradient of 0-20% methanol/dichloromethane yielding the title compound as a gum (574.0 mg, 52.1%). 3 minute run LRMS [½M+1=1065.2]

6-amino-N-[1,3-bis{[1-(2-{2-[2-(2-{[2-(acetylamino)-2-deoxy-beta-D-galactopyranosyl]oxy}ethoxy)ethoxy]ethoxy}ethyl)-1H-1,2,3-triazol-4-yl]methoxy}-2-({[1-(2-{2-[2-(2-{[2-(acetylamino)-2-deoxy-beta-D-galactopyranosyl]oxy}ethoxy)ethoxy]ethoxy}ethyl)-1H-1,2,3-triazol-4-yl]methoxy}methyl)propan-2-yl]hexanamide (I-bt-1)

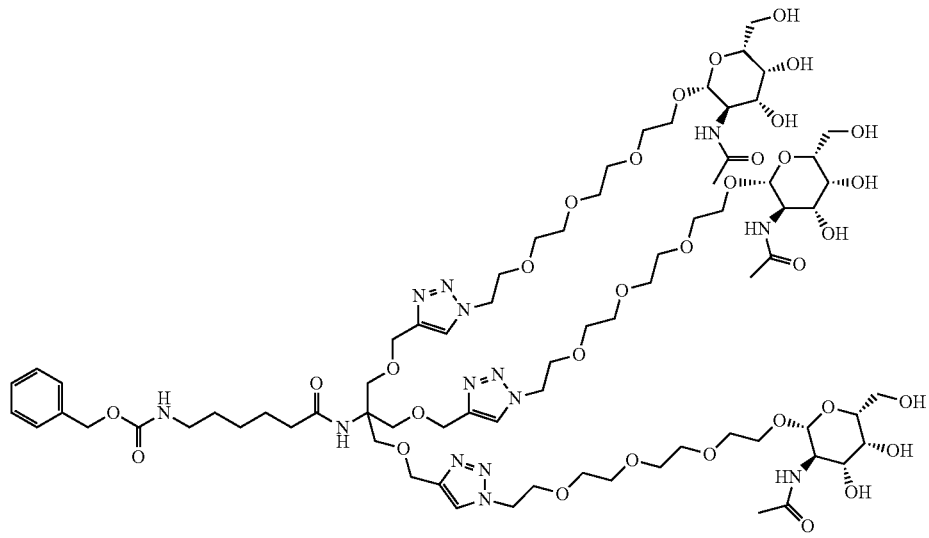 [SMILES: CC(=O)N[C@H]1[C@H](OCCOCCOCCOCCn2cc(COCC(COCc3cn(CCOCCOCCOCCO[C@@H]4O[C@H](CO)[C@H](O)[C@H](O)[C@H]4NC(C)=O)nn3)(COCc3cn(CCOCCOCCOCCO[C@@H]4O[C@H](CO)[C@H](O)[C@H](O)[C@H]4NC(C)=O)nn3)NC(=O)CCCCCNC(=O)OCc3ccccc3)nn2)O[C@H](CO)[C@H](O)[C@@H]1O]

To a solution of benzyl (6-{[1,3-bis{[1-(2-{2-[2-(2-{[3,4,6-tri-O-acetyl-2-(acetylamino)-2-deoxy-beta-D-galactopyranosyl]oxy}ethoxy)ethoxy]ethoxy}ethyl)-1H-1,2,3-triazol-4-yl]methoxy}-2-({[1-(2-{2-[2-(2-{[3,4,6-tri-O-acetyl-2-(acetylamino)-2-deoxy-beta-D-galactopyranosyl]oxy}ethoxy)ethoxy]ethoxy}ethyl)-1H-1,2,3-triazol-4-yl]methoxy}methyl)propan-2-yl]amino}-6-oxohexyl)carbamate (I-bs-1) (274.0 mg, 0.129 mmol) in methanol (10 mL) and tetrahydrofuran (4 mL) was added sodium methoxide, 25% wt. % solution in methanol (0.412 mL, 1.80 mmol) and the reaction was allowed to stir for 20 hours at room temperature. After 20 hours, amberlite IR-120 (H), ion exchange resin (CAS #—78922-04-0, triple rinsed with methanol) until the pH=~6. The mixture was filtered and the resin was washed with methanol (2×15 mL). The filtrate was concentrated under reduced pressure to yielding the title compound as a gum (243.0 mg, 108%). 3 minute run LRMS [M+1=1751.4]

6-amino-N-[1,3-bis{[1-(2-{2-{2-(2-{2-(acety-
lamino)-2-deoxy-beta-D-galactopyranosyl]oxy}
ethoxy]ethoxy}ethyl-1H-1,2,3-triazol-4-yl]
methoxy}-2-({[1-(2-[2-(2-{[2-(acetylamino)-2-
deoxy-beta-D-galactopyranosyl]oxy}ethoxy)ethoxy]
ethoxy}ethyl)-1H-1,2,3-triazol-4-yl]methoxy}
methyl)propan-2-yl]bexanamide acetate(I-bu-1)

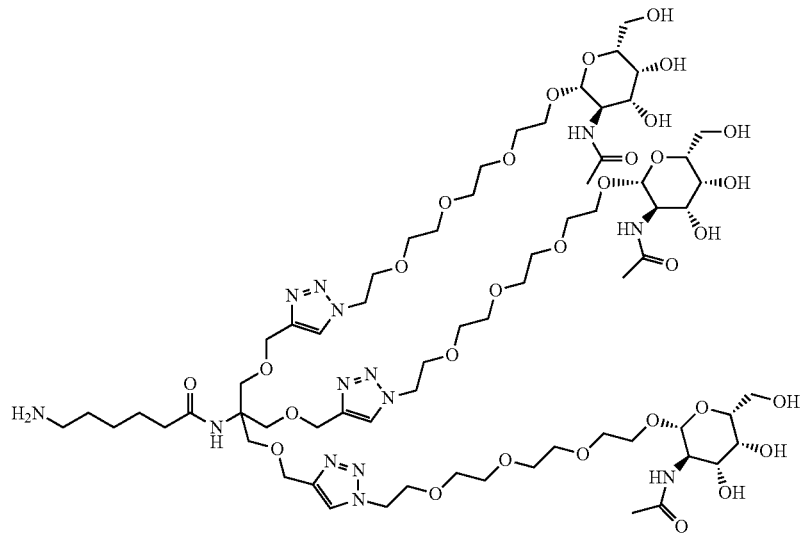 [SMILES: CC(=O)N[C@H]1[C@H](OCCOCCOCCOCCn2cc(COCC(COCc3cn(CCOCCOCCOCCO[C@@H]4O[C@H](CO)[C@H](O)[C@H](O)[C@H]4NC(C)=O)nn3)(COCc3cn(CCOCCOCCOCCO[C@@H]4O[C@H](CO)[C@H](O)[C@H](O)[C@H]4NC(C)=O)nn3)NC(=O)CCCCCN)nn2)O[C@H](CO)[C@H](O)[C@@H]1O]

6-amino-N-[1,3-bis{[1-(2-{2-[2-(2-{[2-(acetylamino)-2-deoxy-beta-D-galactopyranosyl]oxy}ethoxy)ethoxy]ethoxy}ethyl)-1H-1,2,3-triazol-4-yl]methoxy}-2-({[1-(2-{2-[2-(2-{[2-(acetylamino)-2-deoxy-beta-D-galactopyranosyl]oxy}ethoxy)ethoxy]ethoxy}ethyl)-1H-1,2,3-triazol-4-yl]methoxy}methyl)propan-2-yl]hexanamide (I-bt-1) (243 mg, 0.139 mmol) in methanol (13.9 mL) and acetic acid (0.01 mL, 0.2 mmol) was passed through the H-cube using a 10% palladium on carbon (small cartridge) using the following parameters (temperature=50° C., flow rate=1.0 mL/min., pressure=Full H₂ (1 bar)). The solution was collected and was concentrated under reduced pressure yielding the title compound as a gum (187 mg, 80%).

N-[1,3-bis{[1-(2-{2-[2-(2-{[2-(acetylamino)-2-deoxy-beta-D-galactopyranosyl]oxy}ethoxy)ethoxy]ethoxy}ethyl)-1H-1,2,3-triazol-4-yl]methoxy}-2-({[1-(2-{2-[2-(2-{[2-(acetylamino)-2-deoxy-beta-D-galactopyranosyl]oxy}ethoxy)ethoxy]ethoxy}ethyl)-1H-1,2,3-triazol-4-yl]methoxy}methyl)propan-2-yl]-3,31-dioxo-1-(pyridin-2-yldisulfanyl)-7,10,13,16,19,22,25,28-octaoxa-4,32-diazaoctatriacontan-38-amide (73)

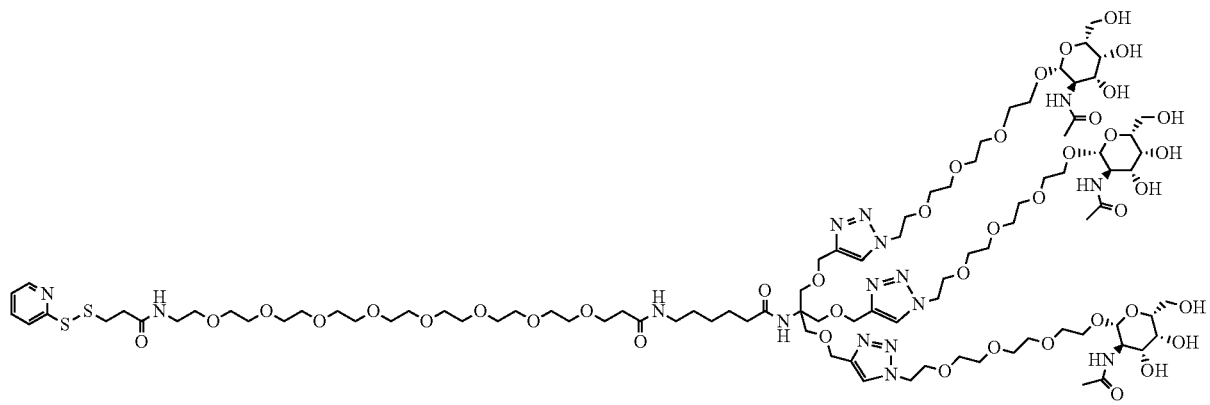 [SMILES: CC(=O)N[C@H]1[C@H](OCCOCCOCCOCCn2cc(COCC(COCc3cn(CCOCCOCCOCCO[C@@H]4O[C@H](CO)[C@H](O)[C@H](O)[C@H]4NC(C)=O)nn3)(COCc3cn(CCOCCOCCOCCO[C@@H]4O[C@H](CO)[C@H](O)[C@H](O)[C@H]4NC(C)=O)nn3)NC(=O)CCCCCNC(=O)CCOCCOCCOCCOCCOCCOCCOCCOCCNC(=O)CCSSc3ccccn3)nn2)O[C@H](CO)[C@H](O)[C@@H]1O]

To a solution of 6-amino-N-[1,3-bis{[1-(2-{2-[2-(2-{[2-(acetylamino)-2-deoxy-beta-D-galactopyranosyl]oxy}ethoxy)ethoxy]ethoxy}ethyl)-1H-1,2,3-triazol-4-yl]methoxy}-2-({[1-(2-{2-[2-(2-{[2-(acetylamino)-2-deoxy-beta-D-galactopyranosyl]oxy}ethoxy)ethoxy]ethoxy}ethyl)-1H-1,2,3-triazol-4-yl]methoxy}methyl)propan-2-yl]hexanamide acetate (I-bu-1) (78.8 mg, 0.047 mmol) and N-{27-[(2,5-dioxopyrrolidin-1-yl)oxy]-27-oxo-3,6,9,12,15,18,21,24-octaoxaheptacos-1-yl}-3-(pyridin-2-yldisulfanyl)propanamide

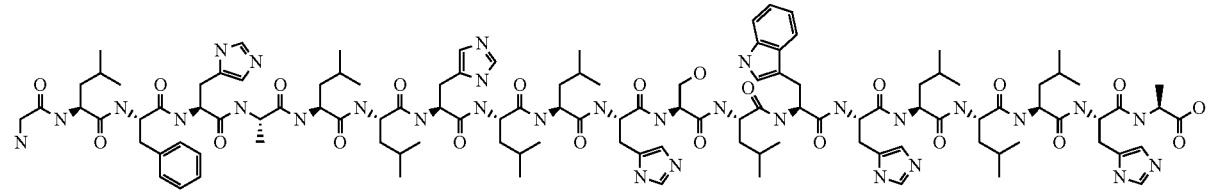 [SMILES: CC(C)C[C@H](NC(=O)CN)C(=O)N[C@@H](Cc1ccccc1)C(=O)N[C@@H](Cc1cnc[nH]1)C(=O)N[C@@H](C)C(=O)N[C@@H](CC(C)C)C(=O)N[C@@H](CC(C)C)C(=O)N[C@@H](Cc1cnc[nH]1)C(=O)N[C@@H](CC(C)C)C(=O)N[C@@H](CC(C)C)C(=O)N[C@@H](Cc1cnc[nH]1)C(=O)N[C@@H](CO)C(=O)N[C@@H](CC(C)C)C(=O)N[C@@H](Cc1c[nH]c2ccccc12)C(=O)N[C@@H](Cc1cnc[nH]1)C(=O)N[C@@H](CC(C)C)C(=O)N[C@@H](CC(C)C)C(=O)N[C@@H](CC(C)C)C(=O)N[C@@H](Cc1cnc[nH]1)C(=O)N[C@@H](C)C(=O)O]

MFCD13185003, 41.5 mg, 0.0564 mmol) in N,N-dimethylformamide (1 mL) and tetrahydrofuran (1 mL) was added N,N-diisopropylethylamine (0.04 mL, 0.2 mmol). The reaction was allowed to stir at room temperature 18 hours. After 18 hours, the reaction was concentrated under reduced pressure. The crude title compound was purified by revered-phase chromatography using the conditions below yielding the title compound as a gum (42.7 mg, 41%).

Purification Conditions

The residue was dissolved in dimethyl sulfoxide (1 mL) and purified by reversed-phase HPLC Column: Waters Sunfire C18 19×100, 5µ; Mobile phase A: 0.05% TFA in water (v/v); Mobile phase B: 0.05% TFA in acetonitrile (v/v); Gradient: 80.0% H$_2$O/20.0% Acetonitrile linear to 65.0% H$_2$O/35.0% Acetonitrile in 10.5 min, 65.0% H$_2$O/35.0% Acetonitrile linear to 0% H$_2$O/100% Acetonitrile in 0.5 min. HOLD at 0% H2O/100% Acetonitrile from 11.0 to 12.0 min. Flow: 25 mL/min.

QC Conditions:

Column: Waters Atlantis dC18 4.6×50, 5µ; Mobile phase A: 0.05% TFA in water (v/v); Mobile phase B: 0.05% TFA in acetonitrile (v/v);
Gradient: 95.0% H$_2$O/5.0% Acetonitrile linear to 5% H$_2$O/95% Acetonitrile in 4.0 min, HOLD at 5% H$_2$O/95% Acetonitrile to 5.0 min. Flow: 2 mL/min., retention time=1.6667 minutes, Mass Observed=746.5042, Mass Target=745.3).

Peptide Experimental Procedures

Purity Check of Peptides:

Unless otherwise stated, pure peptides were analyzed using a HP1090 system with 4.6×150 mm Phenomenox C18 (2), 5 micron 100 A column eluting with a solvent gradient A:B where solvent A=0.1% trifluoroacetic acid in water and B=0.09% trifluoroacetic acid in acetonitrile: water (4:1) over 20 minutes at a flow rate of 1.0 mL/min. The specific retention time, UV purity (220 nm), and solvent gradient are described for final peptides. The hydrogens atoms are omitted from the peptide structures below for clarity of view.

Mass Spectrometry:

An Agilent 6200 series TOF/6500 series Q-TOF or Thermo-LCQ Advantage system was used to collect mass data based on ESI.

ppTG21 and ppTG21 derivatives ppTG21: GLFHALLHLLHSLWHLLLHA (SEQ ID NO: 1012) (74),

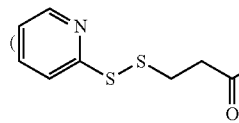 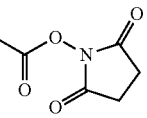

Fmoc-Ala-Wang resin (5 mmol, 10 g) was placed in a peptide reactor, and the resin was swelled in DMF for 2 h. Then, the Fmoc group was removed by addition of a 20% (by volume) solution of piperidine in DMF (150 mL) followed by 1 min of agitation. This treatment was repeated 5 times. A Kaiser ninhydrin test was performed to demonstrate complete deprotection. A solution of Fmoc-His(Trt)-OH (15.0 mmol, 9.29 g) and HBTU (14.3 mmol, 5.42 g) in DMF (~40 mL) was treated with N-methylmorpholine (30 mmol, 3.3 mL) at 0° C., and the mixture was kept at 0° C. for 15 min. This solution was then added to the H-Ala-Wang resin, and mixture was stirred at 25° C. for 1 h, at which point the Kaiser ninhydrin test indicated the reaction was complete. The mixture was filtered, and the solid was washed with DMF (5×150 mL). The resulting Fmoc-His(Trt)-Ala-Wang resin product was used in subsequent step without further treatment.

After Fmoc deprotection of the peptidyl resin, Fmoc-amino acids were coupled to the resin bound peptide sequentially using the standard amide coupling/FMOC cleavage method described above to deliver H-Gly-Leu-Phe-His(Trt)-Ala-Leu-Leu-His(Trt)-Leu-Leu-His(Trt)-Ser(tBu)-Leu-Trp(Boc)-His(Trt)-Leu-Leu-Leu-His(Trt)-Ala-Wang resin (SEQ ID NO: 1052). The peptidyl resin was washed with MeOH (2×150 mL), dichloromethane (2×150 mL) and MeOH (2×150 mL). The resin was dried under vacuum overnight. A solution of TFA:thioanisole:phenol:EDT:H$_2$O (87.5:5:2.5:2.5:2.5, 650 mL) was added to the peptidyl resin, and the resulting suspension was shaken for 2.5 h and filtered. Ether (5 L) was added to the filtrate which afforded a solid. The mixture was centrifuged, and the ether layer was decanted. The resulting solid was washed with ether (3×)

and dried in vacuo overnight. The resulting crude was then purified via reverse phase HPLC, like fractions were combined, and lyophilized to deliver 5.18 g of the desired peptide (TFA salt) as a white solid. UV purity (220 nm)=95.4% (retention time=9.22 min, solvent gradient A:B, 24:76 to 14:86), ESI (m/z) 2341.3430 (M+H)+.

Ac-Cys(NPys)-ppTG21: Ac-Cys(NPys)-GLFHALL-HLLHSLWHLLLHA (SEQ ID NO: 1049) (75), purified via reverse phase HPLC, like fractions were combined, and lyophilized to afford 520 mg (66%) of the desired peptide (TFA salt) as a white solid. UV purity (220 nm)=95.6% (retention time=10.80 min, solvent gradient A:B, 10:90 to 0:100), ESI (m/z) 2640.3345 (M+H)+.

Ac-Cys(NPys)-PEG4-ppTG21: Ac-Cys(NPys)-PEG3-GLFHALLHLLHSLWHLLLHA (SEQ ID NO: 1050) (76),

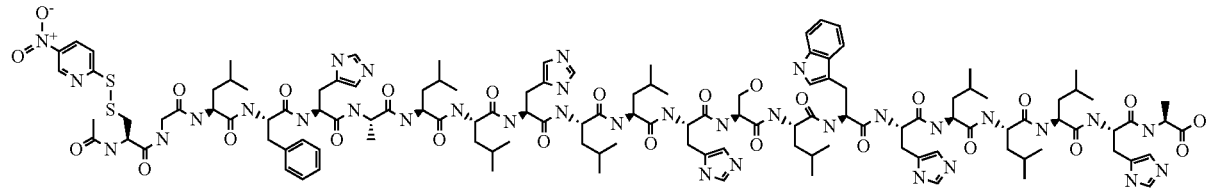 [SMILES: CC(=O)N[C@@H](CSSc1ccc([N+](=O)[O-])cn1)C(=O)NCC(=O)N[C@@H](CC(C)C)C(=O)N[C@@H](Cc1ccccc1)C(=O)N[C@@H](Cc1cnc[nH]1)C(=O)N[C@@H](C)C(=O)N[C@@H](CC(C)C)C(=O)N[C@@H](CC(C)C)C(=O)N[C@@H](Cc1cnc[nH]1)C(=O)N[C@@H](CC(C)C)C(=O)N[C@@H](CC(C)C)C(=O)N[C@@H](Cc1cnc[nH]1)C(=O)N[C@@H](CO)C(=O)N[C@@H](CC(C)C)C(=O)N[C@@H](Cc1c[nH]c2ccccc12)C(=O)N[C@@H](Cc1cnc[nH]1)C(=O)N[C@@H](CC(C)C)C(=O)N[C@@H](CC(C)C)C(=O)N[C@@H](CC(C)C)C(=O)N[C@@H](Cc1cnc[nH]1)C(=O)N[C@@H](C)C(=O)O]

Nearly identical peptide loading and amino acid procedures described above were used to deliver Ac-Cys(Trt)-Gly-Leu-Phe-His(Trt)-Ala-Leu-Leu-His(Trt)-Leu-Leu-His(Trt)-Ser

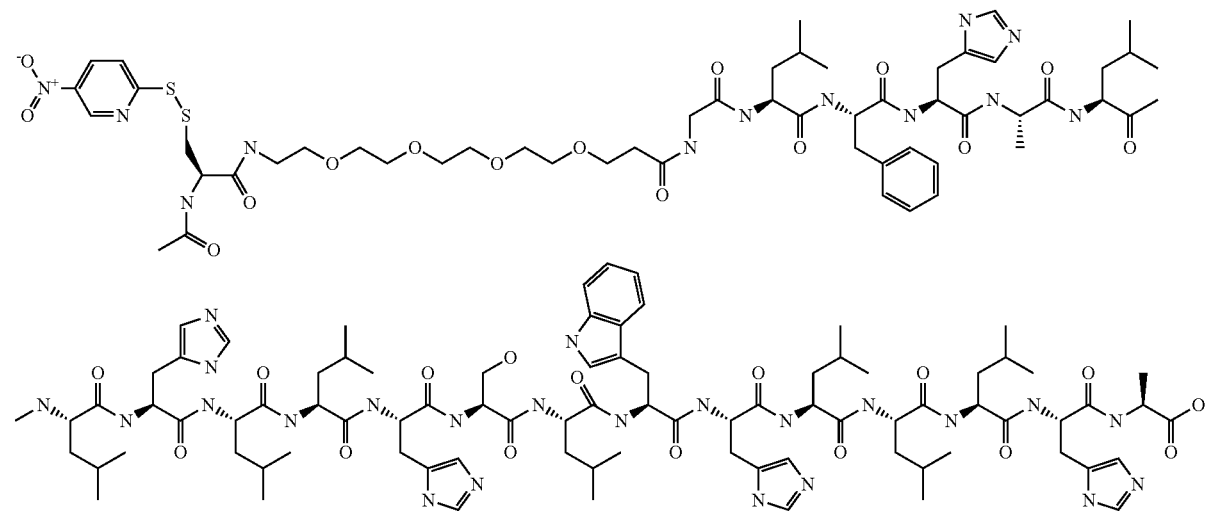

(tBu)-Leu-Trp(Boc)-His(Trt)-Leu-Leu-Leu-His(Trt)-Ala-Wang resin (SEQ ID NO: 1053). The peptidyl resin was washed with methanol (2×150 mL), dichloromethane (2×150 mL) and methanol (2×150 mL). The resin was dried under vacuum overnight. A solution of TFA:thioanisole:phenol:EDT:H$_2$O=87.5:5:2.5:2.5:2.5, 650 mL) was added to the peptidyl resin, and the suspension was shaken for 2.5 h and then filtered. Ether (5 L) was added to the filtrate which afforded a solid. The mixture was centrifuged, and the ether layer was decanted. The resulting solid was washed with ether (3×) and dried in vacuo overnight. The resulting crude peptide was then purified via reverse phase HPLC, like fractions were combined and lyophilized to deliver 800 mg (90% by UV) of Ac-Cys-Gly-Leu-Phe-His-Ala-Leu-Leu-His-Leu-Leu-His-Ser-Leu-Trp-His-Leu-Leu-Leu-His-Ala-OH (SEQ ID NO: 1054). A solution of the peptide in N,N-dimethylformamide (80 mL) was treated with 2,2'-dithiodi(5-nitropyridine) (200 mg, 2 eq) and N,N-diisopropylethylamine (0.23 mL, 4 eq). The mixture was stirred for 1 h. N,N-dimethylformamide was removed in vacuo to give a yellow oil (1.05 g). The resulting crude peptide was To a peptide reactor was placed Fmoc-Ala-wang resin (1.0 mmol, 2 g), the resin was swelled in N,N-dimethylformamide for 2 h. Then, the Fmoc group was cleaved by the addition of a 20 vol % (by volume) solution of piperidine in DMF (30 mL) followed by 1 min of agitation. This treatment was repeated 5 times. A Kaiser ninhydrin test was performed to demonstrate complete deprotection.

A solution of Fmoc-His(Trt)-OH (3 mmol, 1.89 g), HBTU (2.85 mmol, 1.08 g) in N,N-dimethylformamide (~10 mL) was treated with N-methylmorpholine (6 mmol, 0.66 mL) at 0° C., and mixture was kept at 0° C. for 15 min. This solution was then added to the H-Ala-wang resin, and mixture was stirred at 25° C. for 1 h, at which point Kaiser ninhydrin test indicated reaction was complete. The mixture was filtered, and the solid was washed with N,N-dimethylformamide (5×30 mL). The resulting Fmoc-His(Trt)-Ala-CTC resin product was used in the subsequent step without further treatment. After Fmoc deprotection of the peptidyl resin, Fmoc amino acids were coupled to the resin bound peptide sequentially using the standard amide coupling/FMOC cleavage method described above. After Ac-Cys(Trt)-PEG- Gly-Leu-Phe-His(Trt)-Ala-Leu-Leu-His(Trt)-Leu-Leu-His(Trt)-Ser(tBu)-Leu-Trp(Boc)-His(Trt)-Leu-Leu-Leu-His(Trt)-Ala-Wang resin (SEQ ID NO: 1055) was built up. The peptidyl resin was washed with methanol (2×50 mL), dichloromethane (2×50 mL) and methanol (2×50 mL). The resin was dried under vacuum overnight. A solution of TFA:Thioanisole:phenol:EDT:H$_2$O=87.5:5:2.5:2.5:2.5, 150 mL) was added, and the suspension was shaken for 2.5 h and filtered. Ether (1.2 L) was added to the filtrate which afforded a solid. The mixture was centrifuged, and the ether layer was decanted. The resulting solid was washed with ether (3×) and dried in vacuo overnight. The resulting crude peptide was purified via reverse phase HPLC, like fractions were combined, and lyophilized to deliver Ac-Cys-PEG-Gly-Leu-Phe-His-Ala-Leu-Leu-His-Leu-Leu-His-Ser-Leu-Trp-His-Leu-Leu-Leu-His-Ala-OH (SEQ ID NO: 1056). The crude peptide (1.10 g, purity: 85% by HPLC) in N,N-dimethylformamide (110 mL) was treated with 2,2'-dithiodi(5-nitropyridine) (275 mg, 2 eq) and DIPEA (0.32 mL, 4 eq). The mixture was stirred for 1 h, and then DMF was removed under reduced pressure to give a yellow oil. The resulting crude peptide was purified using reverse phase HPLC, like fractions were combined, and lyophilized to afford 270 mg (27%) of the desired peptide (TFA salt) as a white solid. UV purity (220 nm)=95.4% (retention time=9.18 min, solvent gradient A:B, 14:86 to 4:96), ESI (m/z) 2887.4972 (M+H)$^+$.

ppTG21-Cys(NPys)-OH: GLFHALL-HLLHSLWHLLLHA-Cys(NPys)-OH (SEQ ID NO: 1051) (77), treated with N-methylmorpholine (6 mmol, 0.66 mL) at 0° C., and mixture was kept at 0° C. for 15 min. This solution was then was then added to the H-Cys(Trt)-CTC resin, and mixture was stirred at 25° C. for 1 h, at which point Kaiser ninhydrin test indicated the reaction was complete. The mixture was filtered, and the solid was washed with N,N-dimethylformamide (5×30 mL). The Fmoc-Ala-Cys(Trt)-CTC resin was used in subsequent step without further treatment.

The following amino acids were coupled to the resin bound peptide sequentially using the standard amide coupling/FMOC cleavage method described above. After H-Gly-Leu-Phe-His(Trt)-Ala-Leu-Leu-His(Trt)-Leu-Leu-His(Trt)-Ser(tBu)-Leu-Trp(Boc)-His(Trt)-Leu-Leu-Leu-His(Trt)-Ala-Cys(Trt)-CTC resin (SEQ ID NO: 1057) was built up. The peptidyl resin was washed with methanol (2×100 mL), dichloromethane (2×100 mL) and methanol (2×100 mL). The resin was dried under vacuum overnight. A solution TFA:Thioanisole:phenol:EDT:H$_2$O=87.5:5:2.5:2.5:2.5, 150 mL) was added and the suspension was shaken for 2.5 hours and then filtered. Ether (1.2 L) was added to the filtrate to afford a solid. The mixture was centrifuged, and the ether layer was decanted. The crude peptide was washed with ether (3×) and dried in vacuo overnight. The resulting crude was purified by reverse phase HPLC, like fractions were combined and lyophilized to give H-Gly-Leu-Phe-His-Ala-Leu-Leu-His-Leu-Leu-His-Ser-Leu-Trp-His-Leu-Leu-Leu-His-Ala-Cys-OH (SEQ ID NO: 1058). The peptide (1.4 g, purity: 75% by HPLC) was dissolved in N,N-dimethylformamide (140 mL), and was treated with 2,2'-dithiodi(5-nitropyridine) (217 mg, 2 eq) and N,N-diisopropylethylamine (0.25 mL, 4 eq). The mixture was stirred for 1 h, and then

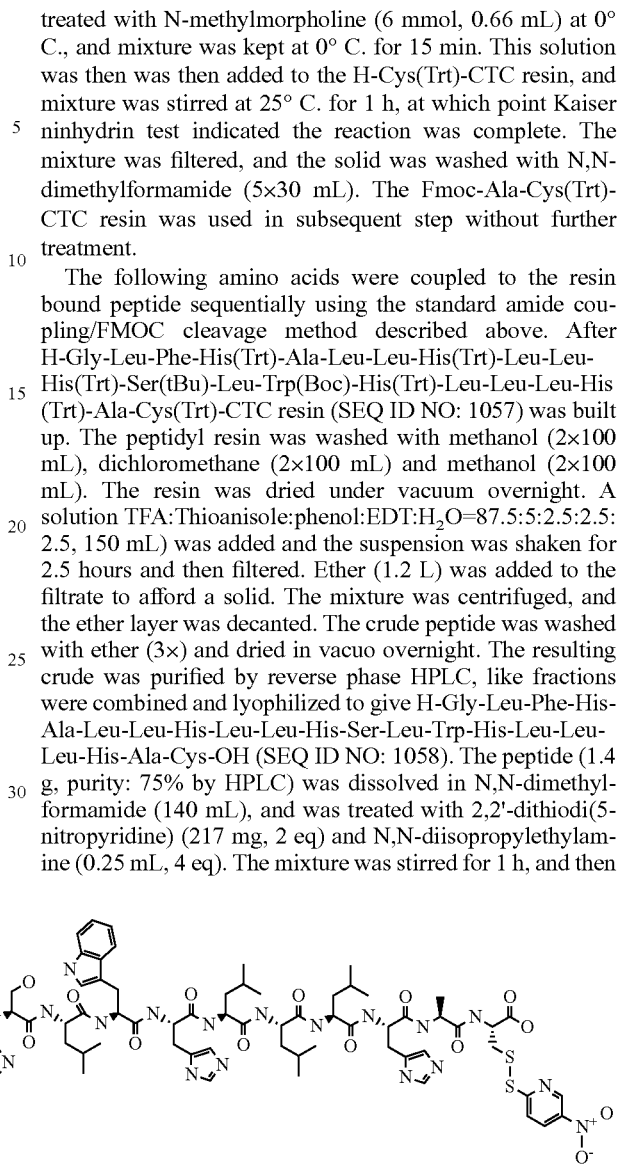

Fmoc-Cys(Trt)-CTC resin (1.0 mmol, 3.3 g) was placed in a peptide reactor. The resin was swelled in N,N-dimethylformamide for 2 hours. Then, the Fmoc group was cleaved using 20% (by volume) solution of piperidine in N,N-dimethylformamide (80 mL) followed by 1 min of agitation. This treatment was repeated 5 times. A Kaiser ninhydrin test was performed to demonstrate complete deprotection. A solution of Fmoc-Ala-OH (3 mmol, 0.93 g), HBTU (2.85 mmol, 1.08 g) in N,N-dimethylformamide (30 mL) was N,N-dimethylformamide was removed under reduced pressure to give a yellow oil. The resulting crude peptide was purified by reverse phase HPLC, like fractions were combined, and lyophilized to give 280 mg (25%) of the desired peptide (TFA salt) as white solid. UV purity (220 nm)=95.3% (retention time=9.88 min, solvent gradient A:B, 11:89 to 1:99), ESI (m/z) 1299.9 (M/2+H)$^+$, 866.7 (M/3+H)$^+$.

Ac-Cys-ppTG21: Ac-CGLFHALLHLLHSLWHLLLHA (SEQ ID NO: 1059) (78),

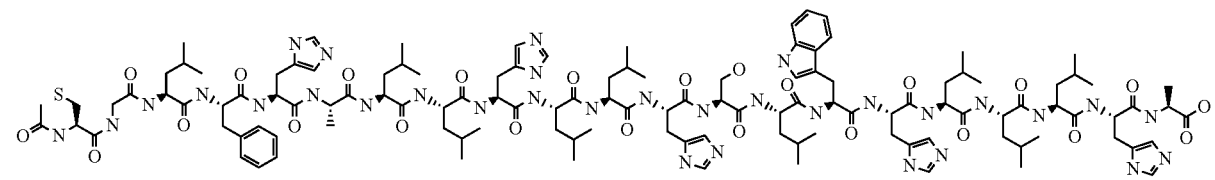 [SMILES: CC(=O)N[C@@H](CS)C(=O)NCC(=O)N[C@@H](CC(C)C)C(=O)N[C@@H](Cc1ccccc1)C(=O)N[C@@H](Cc1cnc[nH]1)C(=O)N[C@@H](C)C(=O)N[C@@H](CC(C)C)C(=O)N[C@@H](CC(C)C)C(=O)N[C@@H](Cc1cnc[nH]1)C(=O)N[C@@H](CC(C)C)C(=O)N[C@@H](CC(C)C)C(=O)N[C@@H](Cc1cnc[nH]1)C(=O)N[C@@H](CO)C(=O)N[C@@H](CC(C)C)C(=O)N[C@@H](Cc1c[nH]c2ccccc12)C(=O)N[C@@H](Cc1cnc[nH]1)C(=O)N[C@@H](CC(C)C)C(=O)N[C@@H](CC(C)C)C(=O)N[C@@H](CC(C)C)C(=O)N[C@@H](Cc1cnc[nH]1)C(=O)N[C@@H](C)C(=O)O]

The peptide was synthesized using similar solid phase peptide synthesis (SPPS) procedures as described in the previous examples. UV purity (220 nm)=95.6% (retention time=10.25 min, solvent gradient A:B, 14:86 to 4:96), ESI (m/z) 2486.3333 (M+H)⁺.

Ac-Cys-dPEG4-ppTG21: Ac-Cys-dPEG4-GLFHALL-HLLHSLWHLLLHA (SEQ ID NO: 1060) (79),

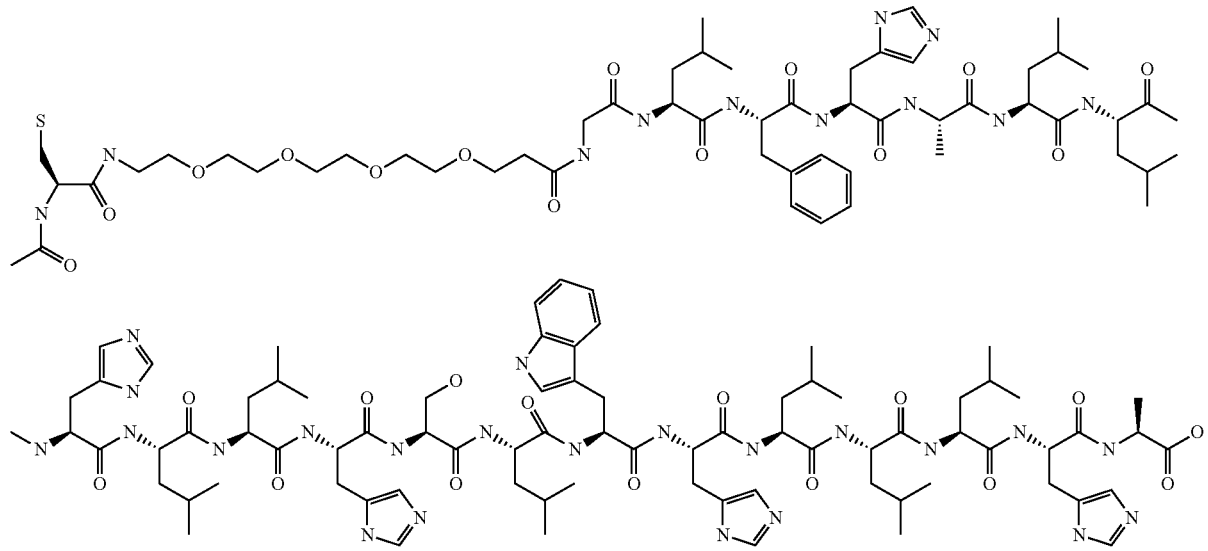

The peptide was synthesized using similar solid phase peptide synthesis (SPPS) procedures as described in the previous examples. UV purity (220 nm)=95.3% (retention time=8.61 min, solvent gradient A:B, 18:82 to 8:92), ESI (m/z) 2733.5157 (M+H)⁺.

ppTG21-Cys: GLFHALLHLLHSLWHLLLHAC (SEQ ID NO: 1061) (80),

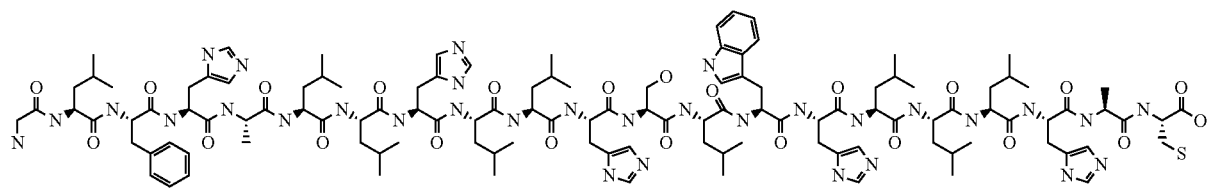 [SMILES: CC(C)C[C@H](NC(=O)CN)C(=O)N[C@@H](Cc1ccccc1)C(=O)N[C@@H](Cc1cnc[nH]1)C(=O)N[C@@H](C)C(=O)N[C@@H](CC(C)C)C(=O)N[C@@H](CC(C)C)C(=O)N[C@@H](Cc1cnc[nH]1)C(=O)N[C@@H](CC(C)C)C(=O)N[C@@H](CC(C)C)C(=O)N[C@@H](Cc1cnc[nH]1)C(=O)N[C@@H](CO)C(=O)N[C@@H](CC(C)C)C(=O)N[C@@H](Cc1c[nH]c2ccccc12)C(=O)N[C@@H](Cc1cnc[nH]1)C(=O)N[C@@H](CC(C)C)C(=O)N[C@@H](CC(C)C)C(=O)N[C@@H](CC(C)C)C(=O)N[C@@H](Cc1cnc[nH]1)C(=O)N[C@@H](C)C(=O)N[C@@H](CS)C(=O)O]

The peptide was synthesized using similar solid phase peptide synthesis (SPPS) procedures as described in the previous examples. UV purity (220 nm)=95.3% (retention time=10.26 min, solvent gradient A:B, 21:79 to 11:89), ESI (m/z) 2444.3673 (M+H)⁺.

Ac-Gly(propargyl)-ppTG21: Ac-Gly(propargyl)-GLF-HALLHLLHSLWHLLLHA (SEQ ID NO: 1062) (81),

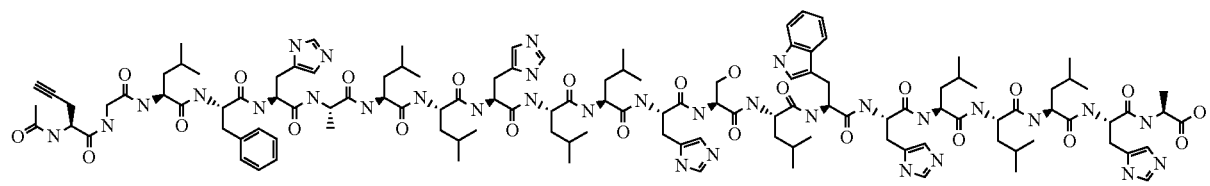 [SMILES: C#CC[C@H](NC(C)=O)C(=O)NCC(=O)N[C@@H](CC(C)C)C(=O)N[C@@H](Cc1ccccc1)C(=O)N[C@@H](Cc1cnc[nH]1)C(=O)N[C@@H](C)C(=O)N[C@@H](CC(C)C)C(=O)N[C@@H](CC(C)C)C(=O)N[C@@H](Cc1cnc[nH]1)C(=O)N[C@@H](CC(C)C)C(=O)N[C@@H](CC(C)C)C(=O)N[C@@H](Cc1cnc[nH]1)C(=O)N[C@@H](CO)C(=O)N[C@@H](CC(C)C)C(=O)N[C@@H](Cc1c[nH]c2ccccc12)C(=O)N[C@@H](Cc1cnc[nH]1)C(=O)N[C@@H](CC(C)C)C(=O)N[C@@H](CC(C)C)C(=O)N[C@@H](CC(C)C)C(=O)N[C@@H](Cc1cnc[nH]1)C(=O)N[C@@H](C)C(=O)O]

The peptide was synthesized using similar solid phase peptide synthesis (SPPS) procedures as described in the previous examples. UV purity (220 nm)=95.4% (retention time=10.56 min, solvent gradient A:B, 14:86 to 4:96), ESI (m/z) 2478.4154 (M+H)⁺.

SPDP-dPEG8-ppTG21: SPDP-dPEG8-GLFHALL-HLLHSLWHLLLHA (SEQ ID NO: 1063) (82)

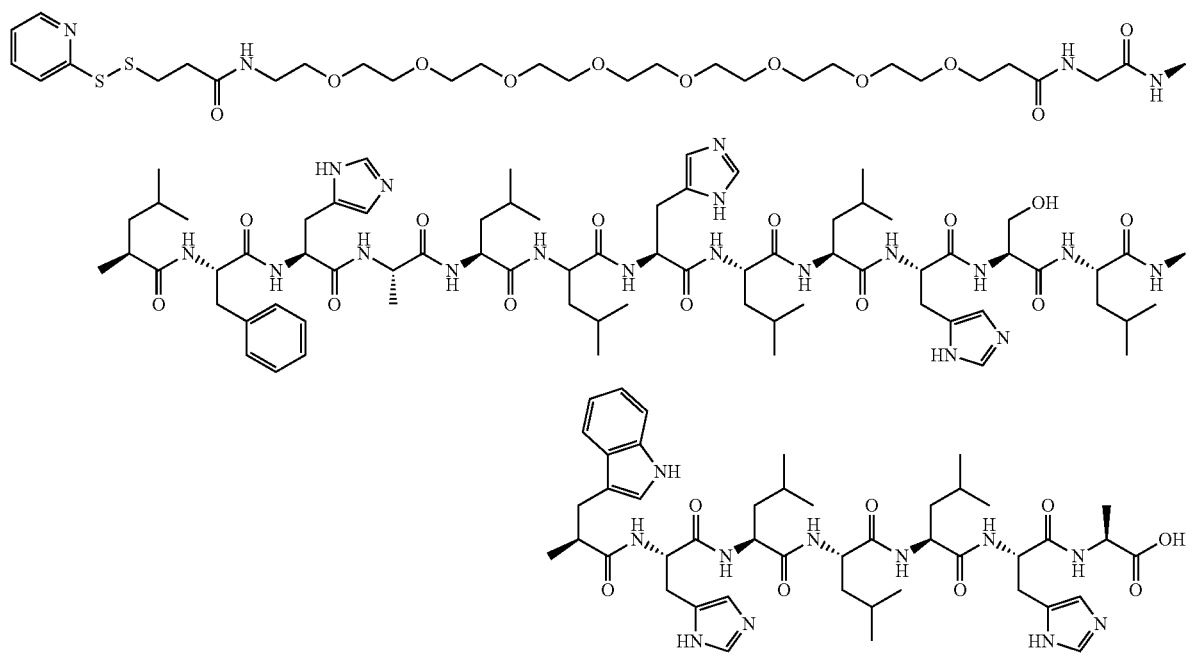

To a solution of ppTG21 (74) Peptide hexatrifluoro acetic acid salt (7.7 mg, 0.0025 mmol) in anhydrous N,N-dimethylformamide (1.0 mL) was added a solution of {27-[(2,5-dioxopyrrolidin-1-yl)oxy]-27-oxo-3,6,9,12,15,18,21,24-octaoxaheptacos-1-yl}-3-(pyridin-2-yldisulfanyl)propanamide

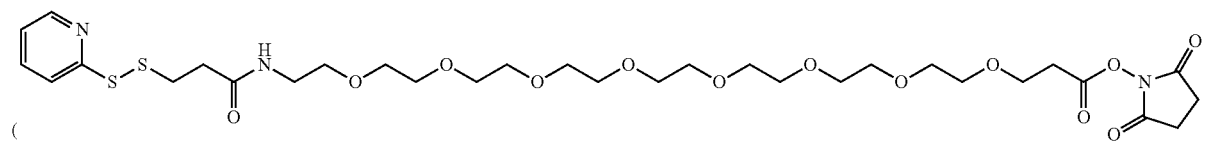 [SMILES: O=C(CCSSc1ccccn1)NCCOCCOCCOCCOCCOCCOCCOCCOCCC(=O)ON1C(=O)CCC1=O]

(FCD13185003, 1.97 mg, 0.0027 mmol) followed by the addition of N,N-diisopropylethylamine (7.0 µL) at room temperature. The reaction was stirred at room temperature for 18 hr and concentrated under reduced pressure using the Genevac. The crude material was purified using reverse-phase chromatography using the conditions below yielding the title compound (3.3 mg, 40%) as a glassy solid.

Purification Conditions

The residue was dissolved in dimethyl sulfoxide (1 mL) and purified by reversed-phase HPLC Column: Waters Sunfire C18 19×100, 5 u; Mobile phase A: 0.05% TFA in water (v/v); Mobile phase B: 0.05% TFA in acetonitrile (v/v); Gradient: 60.0% H₂O/40.0% Acetonitrile linear to 30.0% H₂O/70.0% Acetonitrile in 10.5 min, 30.0% H₂O/70.0% Acetonitrile linear to 0% H₂O/100% Acetonitrile in 0.5 min HOLD at 0% H₂O/100% Acetonitrile from 11.0 to 12.0 min. Flow: 25 mL/min.

QC Conditions

Column: Waters Atlantis dC18 4.6×50, 5 u; Mobile phase A: 0.05% TFA in water (v/v); Mobile phase B: 0.05% TFA in acetonitrile (v/v); Gradient: 75.0% H₂O/25.0% Acetonitrile linear to 5% H₂O/95% Acetonitrile in 4.0 min, HOLD at 5% H₂O/95% Acetonitrile to 5.0 min. Flow: 2 mL/min; retention time=3.33 min Minutes; mass observed M/Z=741.65 Method E: ESI M/Z=2963.0

KALA and KALA Derivatives

KALA: WEAKLAKALAKALAKHLAKALAKALKA-CEA (SEQ ID NO: 869) (83),

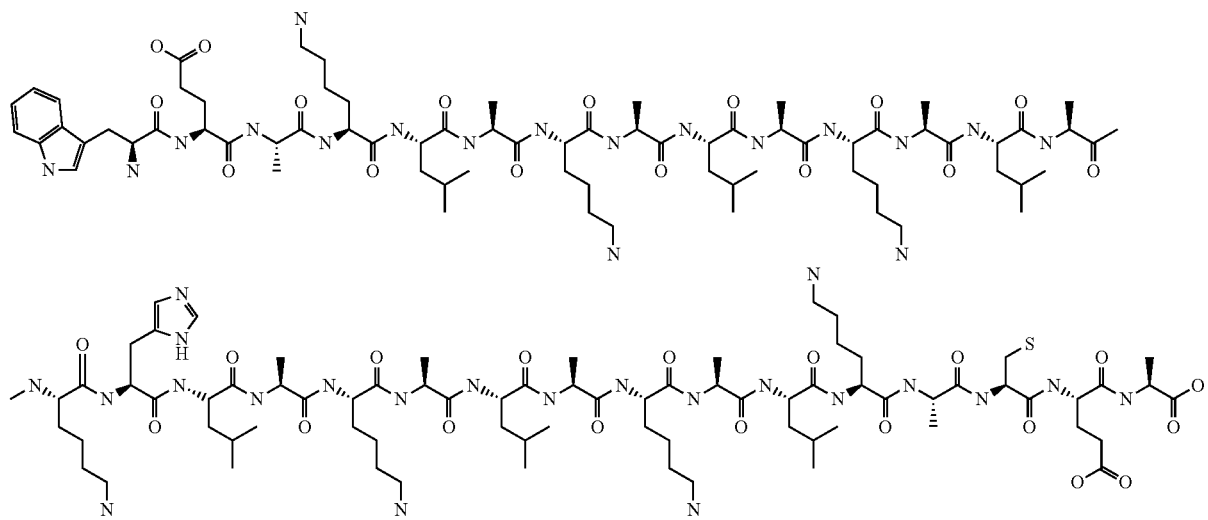

The peptide was synthesized using similar solid phase peptide synthesis (SPPS) procedures as described in the previous examples. UV purity (220 nm)=95.6% (retention time=10.03 min, solvent gradient A:B, 54:46 to 44:56), ESI (m/z) 3130.8272 (M+H)⁺.

Cys-KALA: CWEAKLAKALAKALAKHLAKA-LAKALKACEA (SEQ ID NO: 1064) (84),

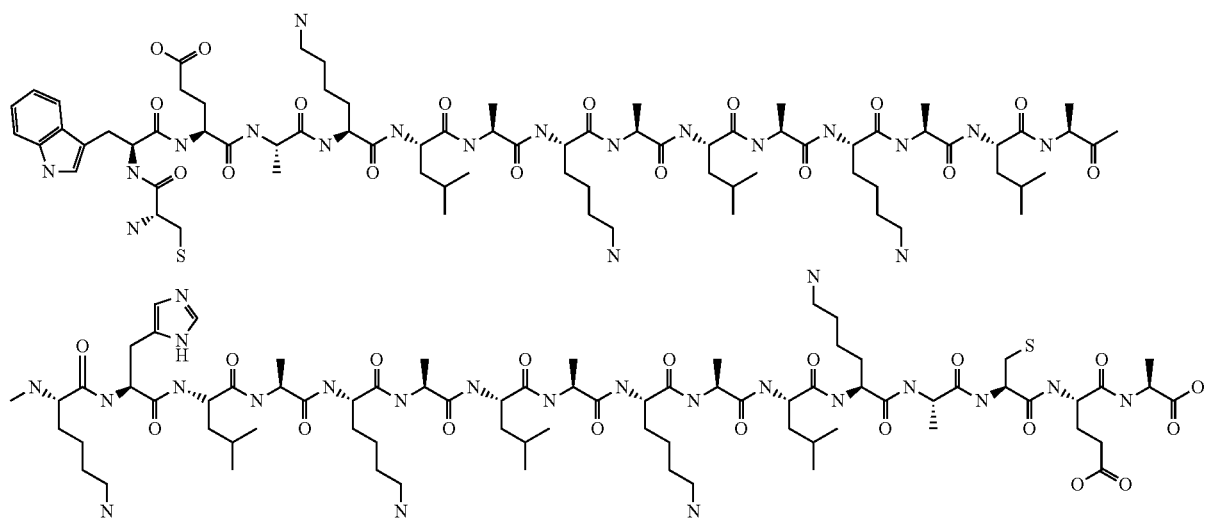

The peptide was synthesized using similar solid phase peptide synthesis (SPPS) procedures as described in the previous examples. UV purity (220 nm)=97.2% (retention time=8.05 min, using a solvent gradient of water (0.1% TFA):acetonitrile/water (4:1, 0.1% TFA); Phenomenex Kinetex (100×4.6 mm), flow rate 1 mL/min. over 10 minutes, ESI (m/z) 1618.6 (M+2H)$^{2+}$, 1079.3 (M+3H)$^{3+}$, 809.8 (M+4H)$^{4+}$.

Serine for Cysteine (KALA)-Cys(NPys)-OH, WEAK-LAKALAKALAKHLAKALAKALKASEA-Cys(NPys)-OH (SEQ ID NO: 1065) (85),

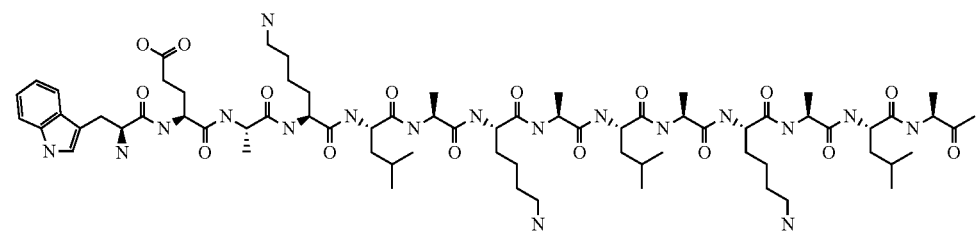

-continued

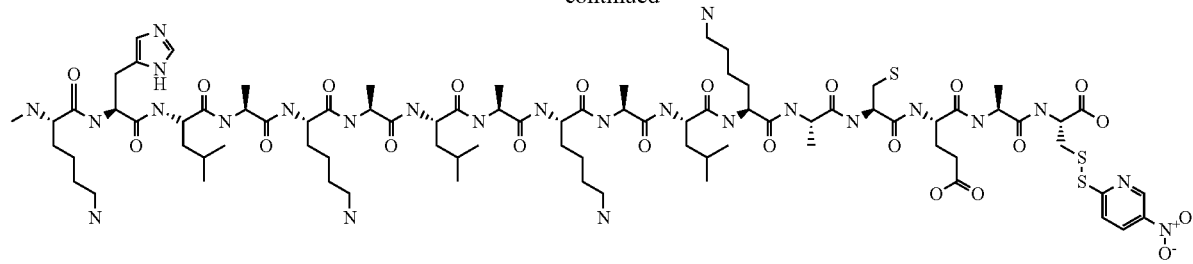

The peptide was synthesized using similar solid phase peptide synthesis (SPPS) procedures as described in the previous examples. UV purity (220 nm)=95.8% (retention time=9.48 min, solvent gradient A:B, 50:50 to 40:60), ESI (m/z) 3372.88 (M+H)⁺.

Ac-Cys(NPys)-Serine (KALA)-OH, Ac-Cys(NPys)-WEAKLAKALAKALAKHLAKALAKALKASEA (SEQ ID NO: 1066) (86),

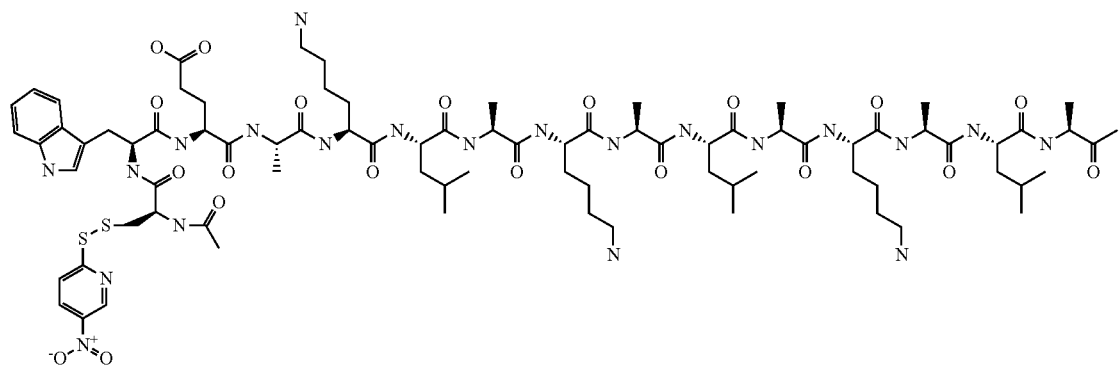

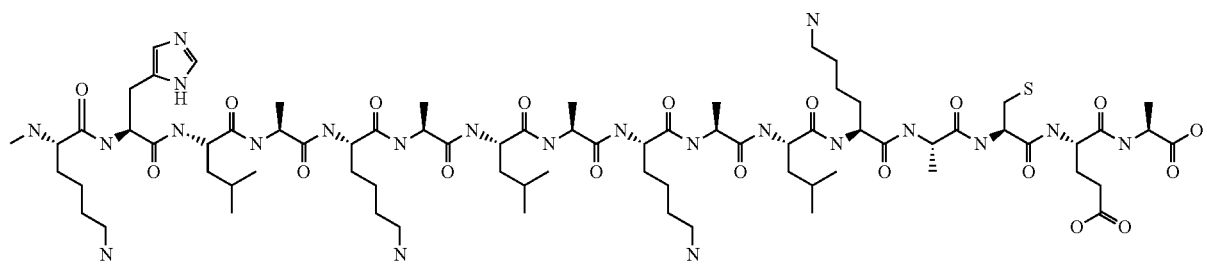

The peptide was synthesized using similar solid phase peptide synthesis (SPPS) procedures as described in the previous examples. UV purity (220 nm)=95.7% (retention time=9.78 min, solvent gradient A:B, 46:54 to 36:64), ESI (m/z) 3414.9079 (M+H)⁺.

Ac-Cys(NPys)-PEG-(KALA) Serine Substituted: Ac-Cys(NPys)-PEG-WEAKLAKALAKALAKHLAKALAKA-LKASEA (SEQ ID NO: 1067) (87),

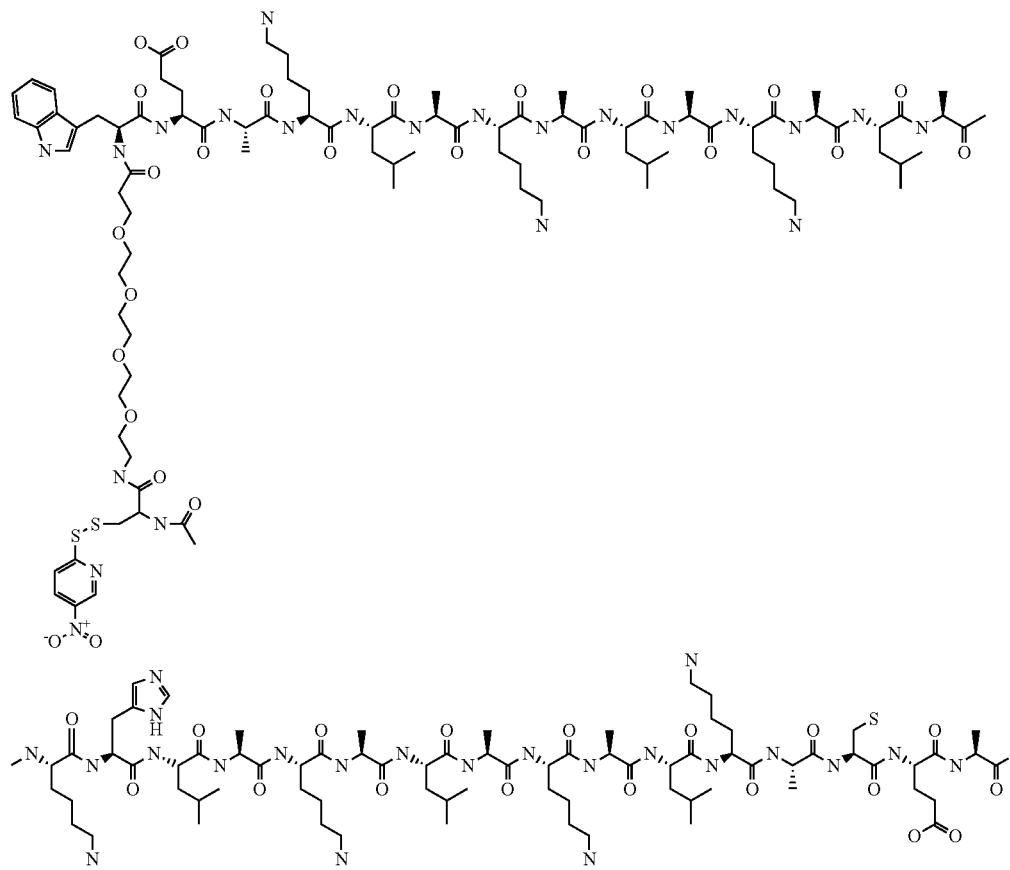

The peptide was synthesized using similar solid phase peptide synthesis (SPPS) procedures as described in the previous examples. UV purity (220 nm)=95.1% (retention time=9.23 min, solvent gradient A:B, 53:47 to 37:63), ESI (m/z) 3662.0715 (M+H)+.

Cas9 Construct and Guide RNA Preparation

Expression and purification of Cas9 constructs and guide RNA was carried out as described in Jinek et al. A programmable dual-RNA-guided DNA endonuclease in adaptive bacterial immunity. Science, 337(6096): p. 816-21 (2012). Briefly, E. coli codon-optimized gene encoding S. pyogenes Cas9 M1C/C80S protein (SEQ ID NO:850) was inserted into a bacterial protein expression plasmid, as fusion protein with hexa-histidine (SEQ ID NO: 1068) and maltose binding protein tags at the N-terminus and either two nuclear localization signals (NLS) (each NLS being PKKKRKV (SEQ ID NO: 830), or three NLS (each NLS being PKKKRKV (SEQ ID NO: 830)) and mCherry (SEQ ID NO: 915), at the C-terminus. The amino acid sequence of the Cas9 construct set forth in SEQ ID NO:1013 is referred to as Y1C80S-2N. The amino acid sequence of the Cas9 construct set forth in SEQ ID NO:1015 is referred to as Cas9 construct Y1C80S-3N-m.

Plasmid was transformed into E. coli Rosetta (DE3). Bacteria was inoculated into Lysogeny broth (LB) media at an optical density at 600 nm ($OD_{600nm}$) of 0.05 and grown at 37° C., 170 rpm. At $OD_{600nm}$ of 0.8, expression was induced by addition of 0.2 mM isopropyl-beta-D-thiogalactopyranoside (IPTG) and bacteria were grown at 16° C. for 16 hours. Bacteria were pelleted, the supernatant discarded and then lysed by sonication in 20 mM 4-(2-hydroxyethyl)-1-piperazineethanesulfonic acid (HEPES), 500 mM potassium chloride (KCl), 5 mM tris(2-carboxyethyl)phosphine (TCEP), 10 mM imidazole pH 7.5. The cleared lysate was captured onto Ni-NTA agarose (Qiagen), washed intensively with 20 mM HEPES, 500 mM KCl, 5 mM TCEP, 10 mM imidazole pH 7.5 and eluted with 20 mM HEPES, 250 mM KCl, 5 mM TCEP, 300 mM imidazole, 10% glycerol pH 7.5. The 6×His-MBP tag ("6×His" disclosed as SEQ ID NO: 1068) was removed by tobacco etch virus (TEV) protease over-night at 4° C., while dialyzing in 20 mM HEPES, 300 mM KCl, 5 mM TCEP, 10% glycerol pH 7.5. Cas9 construct was separated from tags by capture on Heparin SP column (GE healthcare) and linear elution with 300 mM to 1 M KCl. Finally Cas9 construct was further purified on a Superdex 5200 HiLoad column (GE healthcare) in 20 mM HEPES, 150 mM KCl, 10% glycerol pH 7.5. At this point, Cas9 construct was concentrated to about 15-20 mg/ml, concentration determined by UV absorbance, purity assessed by SDS-PAGE, aliquoted and flash-frozen in liquid nitrogen. Aliquots were stored at −80° C.

Figure 3:
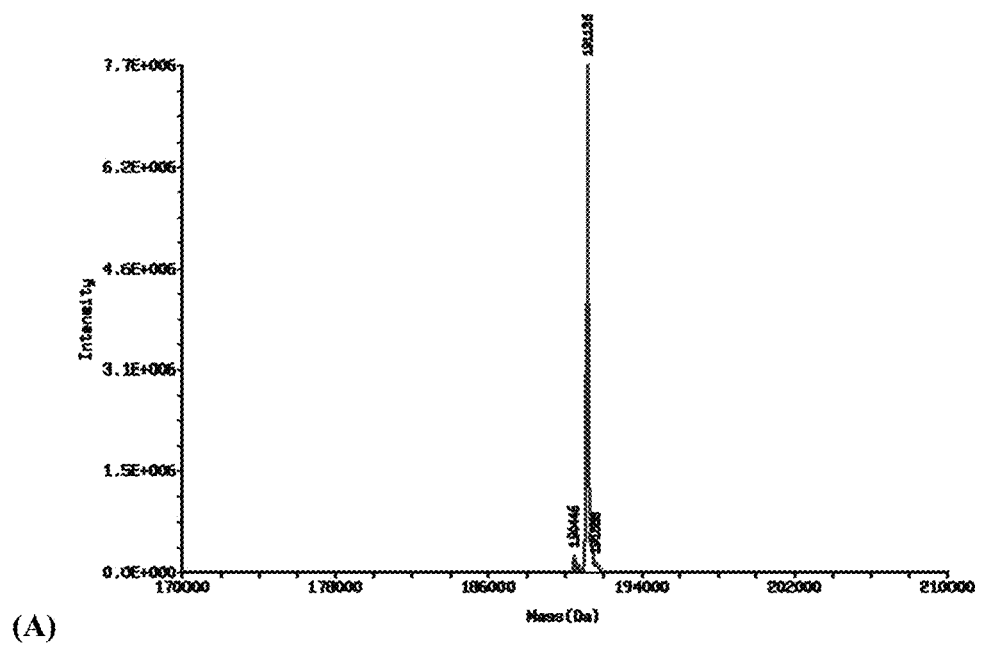
FIG. 3 represents mass spectrometry of Cas9 constructs. Panel A represents a mass spectrometry of Cas9 construct Y1C80S-3N-m. Panel B represents a mass spectrometry of Cas9 construct Y53Aasgprl.
Figure 3:
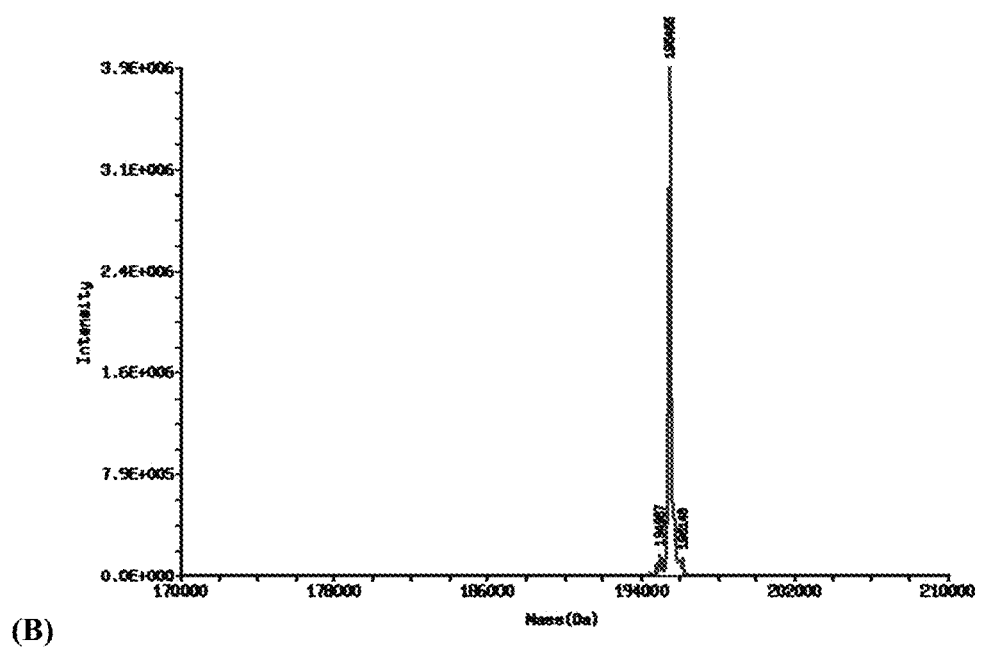

FIG. 3A represents a mass spectrometry of intact Cas9 construct Y1C80S-3N-m.

DNA encoding T7 promoter and guide RNA template was in vitro transcribed using T7 polymerase and ribonucleotide solution mix at 8 mM and pH 7.5 over-night at 37° C. DNA template was then degraded by DNAse for 1 hour at 37° C. and the RNA purified on a denaturing PAGE gel. RNA band was excised from PAGE gel, eluted with 300 mM sodium acetate (NaOAc) pH 5.0 and precipitated with ethanol. RNA pellet was resuspended in 20 mM HEPES, 150 mM KCl, 10% glycerol pH 7.5. Guide RNA was refolded by incubation at 70° C. for 5 minutes, cooled down to room temperature, magnesium chloride (MgCl$_2$) added to 1 mM final, incubated at 50° C. for 5 minutes, and finally cooled down to room temperature. The concentration was determined by UV absorbance and guide RNA stored at −80° C.

Cas9-ASGPR Ligand Conjugate Preparation

Example Y53aASGPRL: ASGPR ligand (compound 53, N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)-3,31-dioxo-1-(pyridin-2-yldisulfanyl)-7,10,13,16,19,22,25,28-octaoxa-4,32-diazaoctatriacontan-38-amide) was reconstituted in dimethyl sulfoxide (DMSO) to 8 mM to provide ligand fragment 53a (shown below). Ligand fragment 53a was subsequently diluted 10-fold in 20 mM HEPES, 150 mM KCl, 10% glycerol pH 7.5, added directly to Cas9 construct (Y1C80S-3N-m) in a 15:1 molar ratio of ligand to protein, and incubated at room temperature for 1 to 2 hours. Labeled Cas9 construct, Y53aASGPRL was then desalted using Zeba Spin columns (Thermo Fisher).

Labeling efficiency was determined by mass spectroscopy on intact Cas9 construct, Y53aASGPRL, using an Agilent 1200 liquid chromatograph (LC) that was equipped with a reversed-phase, C4 column (150 mm×1.0 mm, Restek) and connected in-line with a Thermo LTQ-Orbitrap-XL mass spectrometer equipped with an electrospray ionization (ESI) source. Raw mass spectra were viewed using Xcalibur software (version 2.0.7, Thermo) and mass spectral deconvolution was performed using ProMass software (version 2.5 SR-1, Novatia).

FIG. 3B represents a mass spectrometry of Cas9 construct Y53aASGPRL, which is a Cas9 construct of Y1C80S-3N-m labelled with two copies of fragment 53a, one at each of the cysteines at positions 1 and 574 (addition of 2×2165 Da) via formation of disulfide bond with S atom of cysteine:

S. pyogenes Cas9-mutation C80S (amino acid sequence)—3NLS and mCherry (SEQ ID NO:1026) labelled with compound (53) (12 uL, 80 µM, 960 pmols) [hereby referred to as Y53a-0574-ASGPRL and labelled with compound (53) in a similar manner as described for Cas9 construct Y53aASGPRL] in 20 mM HEPES, 150 mM KCl, 10% glycerol (pH 7.5) buffer was added 3 µl of 5 mM MgCl$_2$ in 20 mM HEPES, 150 mM KCl, 10% glycerol (pH 7.5) buffer to give Cas9 construct Y53a-0574-ASGPRL 15 µL at 64 µM in 1 mM MgCl$_2$, 20 mM HEPES, 150 mM KCl, 10% glycerol (pH 7.5) buffer.

15 µL of the above EMX1 sgRNA guide sequence (SEQ ID NO: 907) solution (15 µl, 76.8 µM, 1152 pmols) was transferred to a separate 2 mL Eppendorf tube and to which was added Y53a-C574-ASGPRL (15 µL, 64 µM, 960 pmols) and pipetted 5 times for mixing to give Y53a-0574-ASGPRL RNP construct (30 µL, 32 µM). This RNP construct is hereby referred to as Y53a-0574-ASGPRL-RNP-EMX1. This reaction mixture was incubated for 10 minutes at 37° C. (waterbath) then used directly in biological or fluorescent microscopy experiments.

Example Y53a-ASGPRL-RNP-PCS1: S. pyogenes Cas9-Mutation M1C & C80S (Amino Acid Sequence)—3NLS and mCherry (SEQ ID NO:1015) Labelled with Compound (53) RNP (PCSK9 Single Guide sgRNA Sequence 1 (SEQ ID NO: 896))

To a solution of PCSK9 single guide sgRNA sequence 1 (SEQ ID NO: 896) (4.04 µL, 96 µM, 388 pmols) in 1 mM MgCl$_2$, 20 mM HEPES, 150 mM KCl, 10% glycerol (pH 7.5) buffer was added 0.96 µL of 1 mM MgCl$_2$, 20 mM HEPES, 150 mM KCl, 10% glycerol (pH 7.5) buffer to give PCSK9 single guide sgRNA sequence 1 (SEQ ID NO: 896) at 5 µL at 76.8 µM.

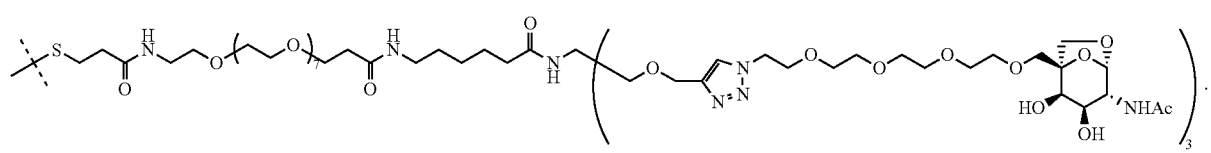

53a

Y1C80S-3N-m (1) and Y53aASGPRL (2) were run on analytical size exclusion chromatography (Superdex S200 10/30 GL), 50 µl at 50 µM, using 20 mM HEPES, 150 mM KCl, 10% glycerol pH 7.5. Elution volume for (1): 11.56 ml; and (2): 11.44 ml.

RNP Assembly and Gene Editing Assays

Example Y53a-0574-ASGPRL-RNP-EMX1: S. pyogenes Cas9-Mutation C80S (Amino Acid Sequence) 3NLS-mcherry (SEQ ID No:1026) Ligated to (53) RNP (EMX1 sgRNA Guide Sequence (SEQ ID NO: 907))

To a solution of EMX1 sgRNA guide sequence (SEQ ID NO: 907) (15.6 µl, 222 µM, 3463 pmols) in 1 mM MgCl$_2$, 20 mM HEPES, 150 mM KCl, 10% glycerol (pH 7.5) buffer was added 29.5 µl of 1 mM MgCl$_2$, 20 mM HEPES, 150 mM KCl, 10% glycerol (pH 7.5) buffer to give EMX1 sgRNA guide sequence (SEQ ID NO: 907) at 45 µl at 76.8 µM.

Cas9 construct Y1C80S-3N-m (4 uL, 80 µM, 320 pmols) in 20 mM HEPES, 150 mM KCl, 10% glycerol (pH 7.5) buffer was added 1 µl of 5 mM MgCl$_2$ in 20 mM HEPES, 150 mM KCl, 10% glycerol (pH 7.5) buffer to give Cas9 construct Y53aASGPRL 5 µL at 64 µM in 1 mM MgCl$_2$, 20 mM HEPES, 150 mM KCl, 10% glycerol (pH 7.5) buffer.

The above solution of Y53aASGPRL (5 uL, 64 µM, 320 pmols) was added to the solution of PCSK9 single guide sgRNA sequence 1 (SEQ ID NO: 896) (5 µl, 76.8 µM, 384 pmols) and pipetted 5 times for mixing to give Y53aASGPRL RNP construct (10 µl at 32 µM), hereby referred to as RNP construct Y53aASGPRL-RNP-PCS1. This reaction mixture was incubated for 10 minutes at 37° C. (waterbath) then used directly in biological or fluorescent microscopy experiments.

Using similar procedures, the following RNPs were prepared:

Example Y53aASGPRL-RNP-EMX1: Using Cas9 Construct Y53aASGPRL and an EMX1 Guide RNA Sequence (SEQ ID NO: 907)

Example Y53aASGPRL-RNP-PCS4: Using Cas9 Construct Y53aASGPRL and a PCSK9 Guide RNA Sequence (SEQ ID NO: 906)

General Protocol:

Gene editing in human hepatocytes was carried out by T7 endonuclease 1 (T7E1) endonuclease assay. Briefly, 80000 HepG2 (ASGPR positive—ATCC nb. HB-8065) or SkHep (ASGRP negative—ATCC nb. HTB-52) cells were seeded in a 24 well plate. Cas9-guide RNA ribonucleoprotein (Cas9 RNP) was assembled by incubating the following Cas9 constructs: Y1C80S-3N-m and Y53aASGPRL, with a guide RNA at a 1:1.2 molar ratio, respectively, for 10 minutes at 37° C.

Cells were treated with 50 pmol of Cas9 RNP, in the presence or absence of ppTG21 endosomolytic agent, by dispensing Cas9 RNP+/−ppTG21 directly into culture media and incubation at 37° C., 5% $CO_2$ in humidified atmosphere. After 48 hours of incubation, culture media was removed and cells lysed with QuickExtract buffer (Epibio) for 5 minutes at room temperature. Transferred supernatant to tubes and heated the samples for 20 minutes at 65° C. followed by 20 minutes at 95° C. Measured genomic DNA concentration by UV absorbance. Amplified genomic locus of interest with specific primers (sequences below) and quantified polymerase chain reaction (PCR) product by visualization on agarose gel relative to a standard. Melted and re-hybridized 200 ng of PCR product and digested it with T7E1 endonuclease for 30 minutes at 37° C. Determined editing efficiency by quantification of the cleaved PCR product.

```
EMX1 locus primers:
Fwd:
                              (SEQ ID NO: 1017)
5'-GCCATCCCCTTCTGTGAATGTTAGAC-3'

Rev:
                              (SEQ ID NO: 1018)
5'-GGAGATTGGAGACACGGAGAGCAG-3'

PCSK9 exon 1 locus primers:
Fwd:
                              (SEQ ID NO: 1019)
5'-CCAGCTCCCAGCCAGGATTC-3'

Rev:
                              (SEQ ID NO: 1020)
5'-ATCGTGCCAAGCGAAGAGC-3'

PCSK9 exons 4&5 locus primers:
Fwd:
                              (SEQ ID NO: 1021)
5'-TGATGGCCTTGGACAGTTACC-3'

Rev:
                              (SEQ ID NO: 1022)
5'-GGTCCAGATGGAGAGAGACCA-3'
```

Figure 4:
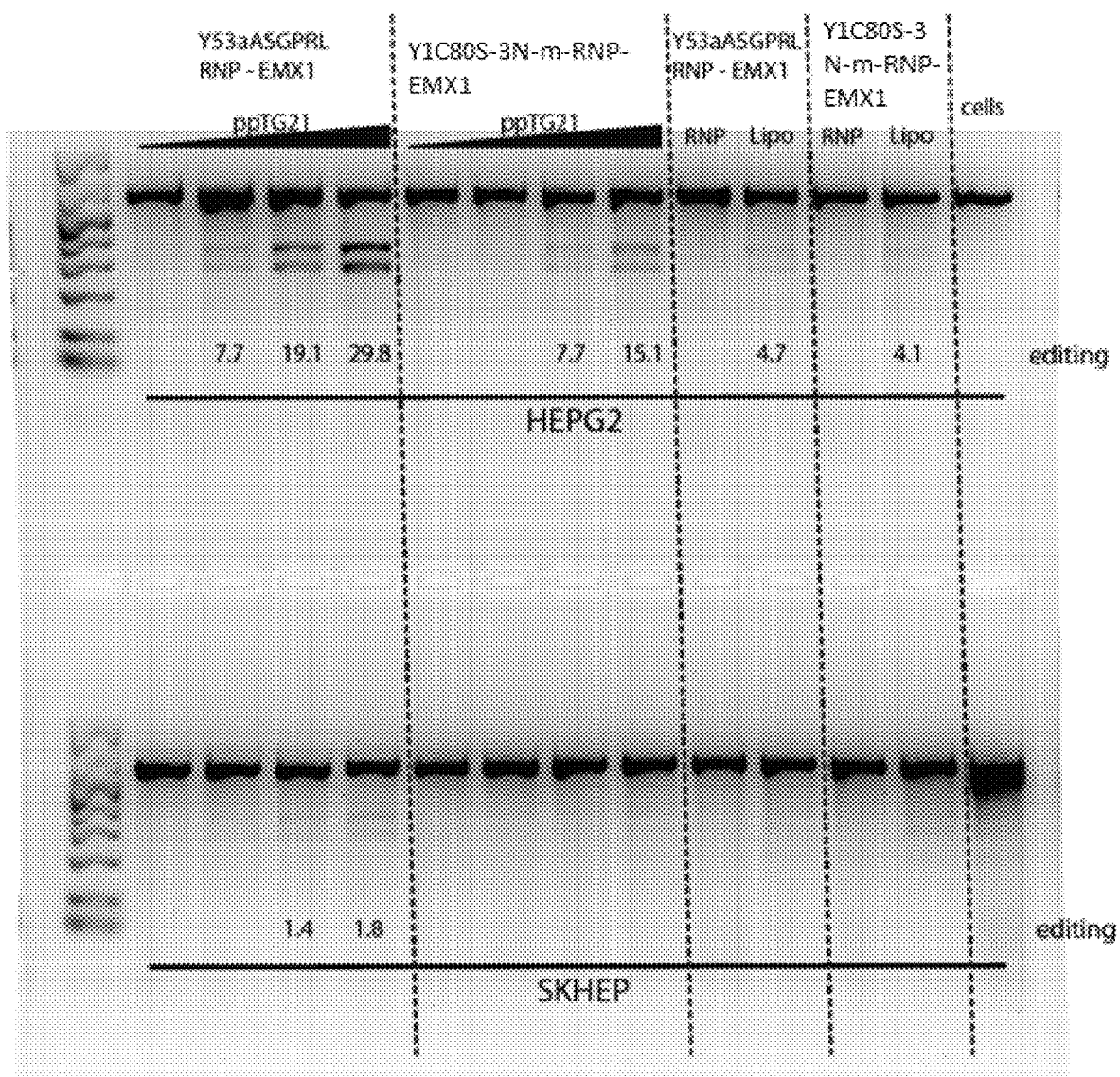
FIG. 4 represents EMX1 editing results in HepG2 and SkHep cells, which were treated with 50 pmol of RNP construct Y53aASGPRL-RNP-EMX1 or Y1C80S-3N-m-RNP-EMX1 and in the presence of (co-incubation) increasing concentrations of ppTG21 endosomolytic peptide (62.5, 250, 1000 and 2000 nM). RNP only treatment and lipofection treatment of the RNP constructs were included as controls.

HepG2 and SkHep cells were treated with 50 pmol of RNP construct Y53aASGPRL-RNP-EMX1Y1C80S-3N-m-RNP-EMX1 and in the presence of (co-incubation) increasing concentrations of ppTG21 endosomolytic peptide (62.5, 250, 1000 and 2000 nM). RNP construct only treatment (without endosomolytic peptide) and lipofection treatment of the RNP construct were used as negative and positive controls respectively. Cells were treated for 48 hours before assessing editing by T7E1 endonuclease assay. Editing efficiencies are annotated in FIG. 4.

Figure 5:
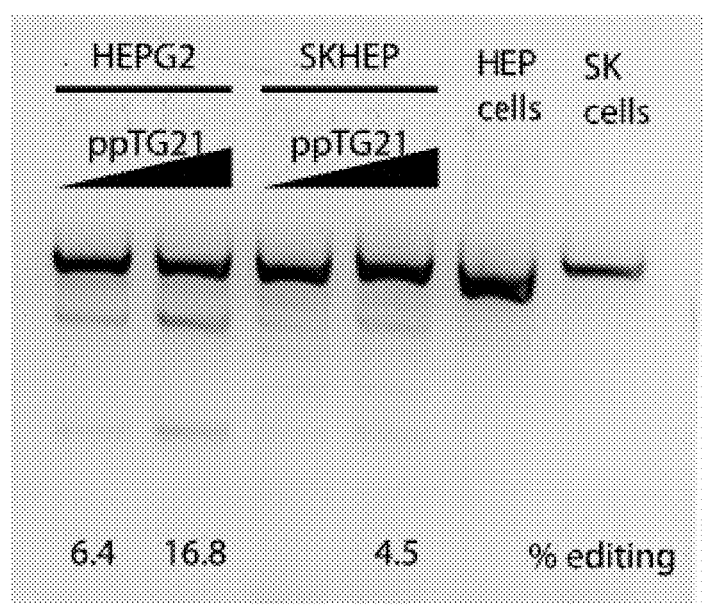
FIG. 5 represents PCSK9 exons 4 and 5 editing results in HepG2 and SkHep cells, which were treated with 50 pmol of RNP construct Y53aASGPRL-RNP-PCS4 and in the presence of (co-incubation) increasing concentrations of ppTG21 endosomolytic peptide (250 and 1000 nM).

HepG2 and SkHep cells were treated with 50 pmol of Cas9 RNP Y53aASGPRL-RNP-PCS4 in the presence of (co-incubation) increasing concentrations of ppTG21 endosomolytic peptide (250 and 1000 nM). Cells were treated for 48 hours before assessing editing by T7E1 endonuclease assay. Editing efficiencies are annotated in FIG. 5

ASGPR-Cas9 Microscopic Imaging Studies

Materials/Reagents:

SKHep cells (ATCC HTB-52)
HepG2 cells (ATCC HB-8065)
Growth media: DMEM high glucose (ThermoFisher 11965-092)
10% Fetal Bovine Serum, heat inactivated (ThermoFisher 16000-044)
1 mM non-essential amino acids (ThermoFisher 11140-$C_{50}$)
2 mM L-glutamine (ThermoFisher 25030-081)
100 unit/mL penicillin/streptomycin (ThermoFisher 10378-016)
MatTek glass bottom wells—(MatTek Corp P35G-1.5-14-C)
Dextran647—(Life Technologies D34682)
Hoechst 3328—(Life Technologies 62249)—use at 1 ug/ml
Collagen—(Life Technologies A10483-01)—use at 5 ug/cm²

Figure 2:
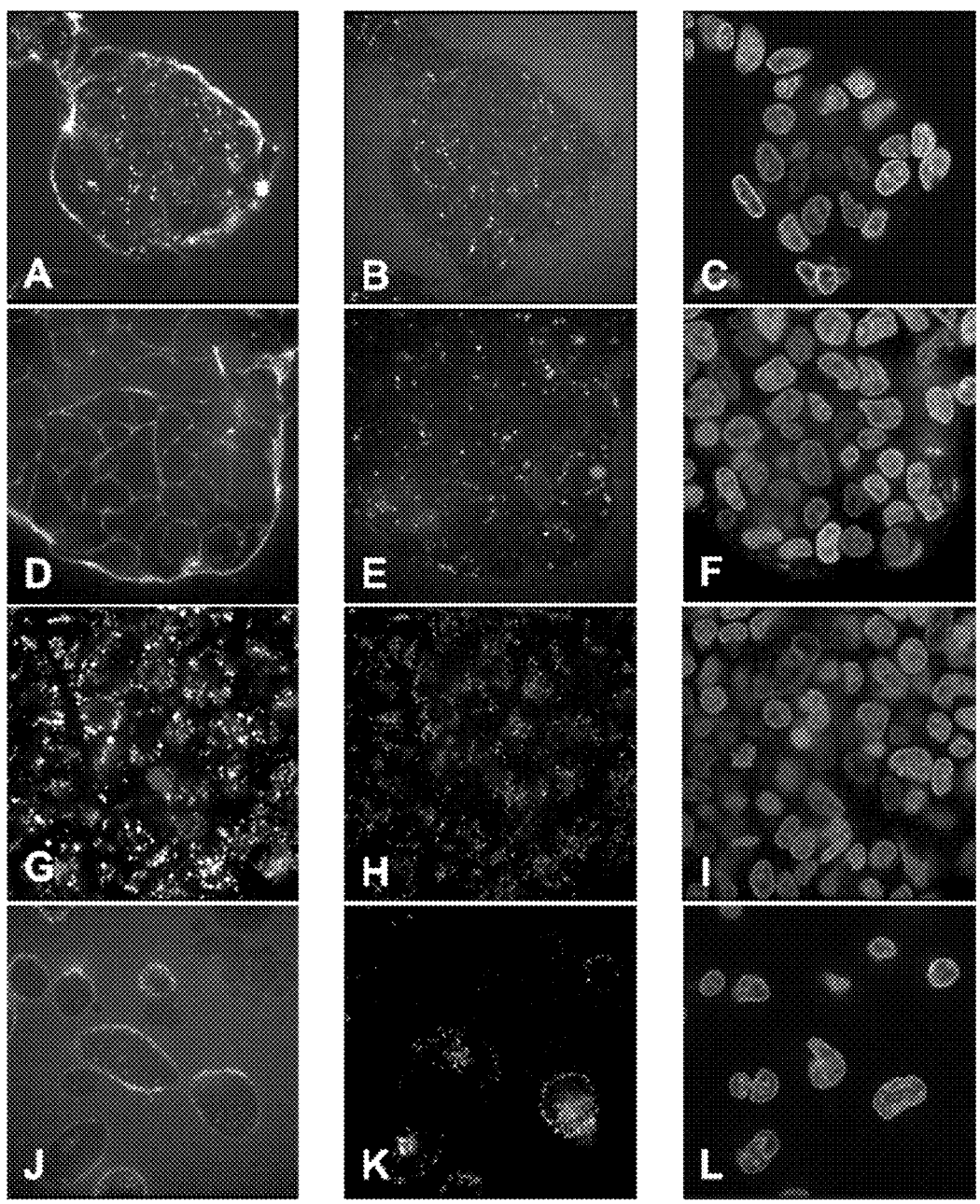
FIG. 2 represents the results of microscopic imaging studies of RNP constructs.
Panels A-C: RNP construct Y53aASGPRL-RNP-EMX1 (A) uptake in HepG2 cells is evident within 60 minutes as indicated by intracellular puncta with some surface binding still evident. Lysosomes are labeled with Dextran-647 (B) and nuclei are labeled with Hoechst (C).
Panels D-F: RNP construct Y1C80S-3N-m-RNP-EMX1 (D) shows only cell surface staining at 60 minutes with no evidence of internalization. Lysosomes are labeled with Dextran-647 (E) and nuclei are labeled with Hoechst (F).
Panels G-I: RNP construct Y53aASGPRL-RNP-EMX1 (G) is completely internalized in HepG2 cells by 20 hours as indicated by intracellular puncta. Lysosomes are labeled with Dextran-647 (H) and nuclei are labeled with Hoechst (I).
Panels J-L: RNP construct Y53aASGPRL-RNP-EMX1 (J) accumulates on the surface of SK-Hep cells within 60 minutes and shows no evidence of internalization. Lysosomes are labeled with Dextran-647 (K) and nuclei are labeled with Hoechst (L).

Y53aASGPRL-RNP-EMX1 and Y1C80S-3N-m-RNP-EMX1 RNP constructs described above were used. The Images are depicted in FIG. 2.

Protocol:

Cells plated onto collagen coated MatTek wells at 40,000/well in growth media
After 24 hours change to fresh media
Treat with Dextran647 (500 ng/ml) for 4 hours
After 4 hours, add Hoechst to media for 5 minutes.
Change to fresh media
Remove media and add Y53ASGPRL-RNP-EMX1 RNP construct at 64 μM or Y1C80S-3N-m-RNP-EMX1 RNP construct at 64 μM.
Image on Zeiss spinning disk microscope under live-cell conditions for 1 hour, collecting images every 5 minutes.
Images were processed in Zen software (Carl Zeiss, Inc)

Pharmacological Data

The practice of the invention for the treatment of diseases modulated by targeting the asialoglycoprotein receptor (ASGPR) using compounds of the invention can be evidenced by activity in one or more of the functional assays described herein below. The source of supply is provided in parenthesis.

SPR Binding Measurements for ASGPr Ligands:

All SPR measurements with compounds were performed using a Biacore 3000 (GE Healthcare) at 25° C. Biotinylated ASGPR was immobilized typically at 2000-3000 resonance units (Ru) using either SA sensor chips (GE Healthcare) or custom sensor chips with Neutravidin (Pierce Biochemical) immobilized by standard amine coupling to CM5 sensor chips (GE Healthcare). The running buffer was HBS (10 mM HEPES, 150 mM NaCl), 20 mM $CaCl_2$, 0.01% p20, 3% DMSO or 50 mM tris, 150 mM NaCl, 50 mM CaCl2, 0.01% p20, 3% DMSO pH 7.5. Compounds were diluted into running buffer at a concentration of 900 uM and serially diluted 3 fold to 3.7 uM. Compound solutions were injected at 50 ul/min for 1 min followed by a 1 min dissociation in duplicate for each concentration. For the multimeric conjugates (dimers, trimers), the conjugates were diluted in running buffer to concentrations of 100 nM or 10 nM and serially diluted. Conjugates were injected for 2 min and off rates were detected for 300 or 600 sec. After completion of off phase data the compounds were displaced using an injection of 900 uM GalNAc returning the receptor surface to the free state. All data was processed using Scrubber2 (Biologic Software, Inc.) to zero, align, reference and correct for excluded volume effects. $K_D$s were determined by fitting the steady state binding responses for the compounds and single conjugated molecules in Scrubber2. $K_D$ for multimeric conjugates showing kinetic responses were processed in Scrubber2 and fit in BiaEval (GE Healthcare) to extract the on and off rate parameters in order to calculate $K_D$. Values reflect standard deviations from multiple experiments.

The following results were obtained for the SPR binding assay wherein each run is separately reported or the number of runs (n) and standard deviation is noted:

| Compound No. | $K_D$ (microM) |
|---|---|
| 3 | 7.18 (n = 54 and std dev = 2.13) |
| II-b | 199 |
|  | 240 |
|  | 260 |
|  | 300 |
| 1 | 9 |
| 18 | 3.1 |
|  | 2.3 |
|  | 2.8 |
|  | 3.8 |
| 17 | 5.3 |
|  | 3.4 |
|  | 2.6 |
| 20 | 2.18 |
|  | 3.8 |
|  | 4.2 |
| 19 | 3.3 |
|  | 3.2 |
|  | 3.2 |
|  | 7.7 |
| 21 | 3.4 |
|  | 1.8 |
| 22 | 5.5 |
|  | 7.2 |
|  | 6.7 |
| 10 | 3.9 |
|  | 4.1 |
| 11 | $1.09 \times 10^{-3}$ |
|  | $0.8 \times 10^{-3}$ |
|  | $1.18 \times 10^{-3}$ |
| 12 | $0.097 \times 10^{-3}$ |
|  | $0.084 \times 10^{-3}$ |
|  | $0.120 \times 10^{-3}$ |
|  | $0.220 \times 10^{-3}$ |
| 25 | 2.2 |
|  | 3.0 |
|  | 2.7 |
|  | 3.2 |
|  | 4.3 |
| 24 | 1.1 |
|  | 2.0 |
|  | 2.3 |
|  | 1.4 |
|  | 0.7 |
|  | 0.8 |
|  | 1.6 |
|  | 1.4 |
| 26 | 60 |
|  | 96 |
|  | 140 |
|  | 110 |
|  | 149 |
|  | 117 |
| 29 | 6.9 |
|  | 11.6 |
|  | 8.8 |
|  | 15.9 |
|  | 11.7 |
|  | 6.4 |
| 30 | 110 |
|  | 83 |
|  | 210 |
|  | 240 |
|  | 132 |
|  | 192 |
| 27 | 0.7 |
|  | 1.9 |
|  | 1.2 |
|  | 1.0 |
|  | 1.5 |
|  | 0.5 |
| 28 | 1.2 |
|  | 1.8 |
|  | 2.1 |
|  | 1.4 |
|  | 2.4 |
|  | 2.9 |
| 31 | 12.3 |
|  | 12.3 |
|  | 14 |
|  | 10.6 |
|  | 15.6 |
|  | 17.3 |

SPR Binding Measurements for RNP Constructs:

SPR:

All experiments were run in a Biacore 3000 (GE Healthcare) using commercially available Streptavidin sensors (Senor Chip SA, GE Healthcare) at 25° C.

Immobilization levels of the ASGPr H1 CRD protein were dependent on the experiment and are noted in the individual experimental protocols. All experiments were run at a flow rate of 50 ul/min. In all experiments, a streptavidin sensor surface was used as reference. All data obtained were processed and fit using Scrubber2 software (BioLogic Software) to zero, x-align, and correct for reference and baseline. Curves were fit using a 1:1 kinetic binding model in Scrubber.

Reagents:

ASGPr H1 CRD: The ASGPr H1 CRD was derivatized using a maleimide-PEG2-biotin (Pierce) reacted with the lone free cysteine as described previously for capture on streptavidin surfaces. For the protein conjugates the surface densities were kept low to reduce crowding on the surface that could result in steric conflicts.

Reagents: ASGPr-Biotin as Described Above

The RNP constructs were supplied as 32 uM stocks in 20 mM HEPES pH 7.5, 150 mM KCl, 20 mM CaCl2, 5 mM MgCl2, 0.01% p20 which served as the running buffer for SPR with these RNPs. For the Cas9-ribonucleoproteins, the stocks were diluted 10-fold in the running buffer and then diluted again to 10 nM as the top concentration. ASGPr was immobilized onto streptavidin sensors at 50 and 200Ru. Single injections of 10 nM concentrations showed clear binding which could largely be competed off by injection of an excess (900 µM) of N-acetyl-galactosamine (GalNAc) as was observed with small molecule conjugates. The control RNP construct that did not contain the ASGPr Ligand (Y1C80S-3N-m-RNP-EMX1) was also injected at the highest concentration (10 nM) but did not show any binding to the immobilized receptor. The proteins were serially diluted 2-fold from 10 nM in running buffer to obtain affinities at both densities. GalNAc at 900 μM was injected between each concentration to remove the RNPs from the receptor. The responses from the concentration series were processed using Scrubber2 as described previously and fit to a 1:1 binding model.

| ASGPr Ru level RNP Construct | 50 Ru KD pM | 200 Ru KD pM |
|---|---|---|
| Y53aASGPRL-RNP-EMX1 | 393 | 120 |
| Y53a-C574-ASGPRL-RNP-EMX1 | 963 | 495 |
| Y1C80S-3N-m-RNP-EMX1 | nd | nd |
| Y53aASGPRL-RNP-PCS1 | 502 | 166 |

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification including the examples be considered as exemplary only, with a true scope and spirit of the invention being indicated by the following claims.

Following are exemplary embodiments:
1. A compound of Formula (A-1), (A-2), or (A-3):

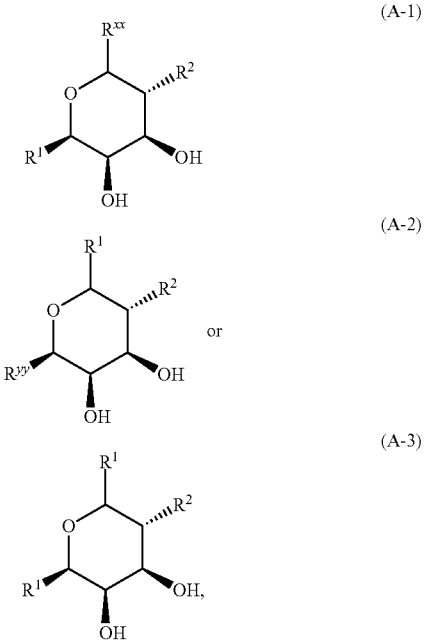

or a pharmaceutically acceptable salt thereof,
wherein:
$R^{xx}$ is —H, -alkyl, -cycloalkyl, -alkenyl, alkynyl, -aryl, -heteroaryl, —$OR^5$, —$N(R^4)$—$R^5$, —$SR^5$, wherein a —$CH_2$— group of said $R^{xx}$ may each be independently replaced with a heteroatom group selected from —O—, —S—, —$N(R^4)$— and wherein a —$CH_3$ of said $R^{xx}$ may be replaced with a heteroatom group selected from —$N(R^4)_2$, —$OR^4$, and —$S(R^4)$ wherein the heteroatom groups are separated by at least 2 carbon atoms, and wherein the alkyl, alkenyl, alkynyl, and cycloalkyl may each be substituted with one or more halo atoms;
$R^{yy}$ is —CN, —$CH_2$—CN, —C≡CH, —$CH_2$—$N_3$, —$CH_2$—$NH_2$, —$CH2$-$N(R^4)$—$S(O)_2$—$R^5$, —$CH_2$—$CO_2H$, —$CO_2H$, —$CH_2$—OH, —$CH_2$—SH, —CH=CH—$R^5$, —$CH_2$—$R^5$, —$CH_2$—S—$R^5$, —$CH_2$—$N(R^4)$—$R^5$, —$CH_2$—$N(R^4)$—C(O)—$R^5$, —$CH_2$—$N(R^4)$—C(O)—O—$R^5$, —$CH_2$—$N(R^4)$—C(O)—$N(R^4)$—$R^5$, —$CH_2$—O—$R^5$, —$CH_2$—O—C(O)—$R^5$, —$CH_2$—O—C(O)—$N(R^4)$—$R^5$, —$CH_2$—O—C(O)—O—$R^5$, —$CH_2$—S(O)—$R^5$, —$CH_2$—$S(O)_2$—$R^5$, —$CH_2$—$S(O)_2$—$N(R^4)$—$R^5$, —C(O)—$NH_2$, —C(O)—O—$R^5$, —C(O)—$N(R^4)$—$R^5$, or aryl or heteroaryl, wherein the aryl or heteroaryl is optionally substituted with $R^5$;
each $R^1$ is independently —CN, —$CH_2$—CN, —C≡CH, —$CH_2$—$N_3$, —$CH_2$—$NH_2$, —$CH_2$—$N(R^4)$—$S(O)_2$—$R^5$, —$CH_2$—$CO_2H$, —$CO_2H$, —$CH_2$—OH, —$CH_2$—SH, —CH=CH—$R^5$, —$CH_2$—$R^5$, —$CH_2$—S—$R^5$, —$CH_2$—$N(R^4)$—$R^5$, —$CH_2$—$N(R^4)$—C(O)—$R^5$, —$CH_2$—$N(R^4)$—C(O)—O—$R^5$, —$CH_2$—$N(R^4)$—C(O)—$N(R^4)$—$R^5$, —$CH_2$—O—$R^5$, —$CH_2$—O—C(O)—$R^5$, —$CH_2$—O—C(O)—$N(R^4)$—$R^5$, —$CH_2$—O—C(O)—O—$R^5$, —$CH_2$—S(O)—$R^5$, —$CH_2$—$S(O)_2$—$R^5$, —$CH_2$—$S(O)_2$—$N(R^4)$—$R^5$, —C(O)—$NH_2$, —C(O)—O—$R^5$, —C(O)—$N(R^4)$—$R^5$, or aryl or heteroaryl, wherein the aryl or heteroaryl is optionally substituted with $R^5$,
or $R^1$ is —Z—X—Y, —Z—Y, —X—Y, —Z—$X^+Y^-$, —$X^+Y^-$, —Z—$X^-Y^+$, —$X^-Y^+$, or —Y;
X is a linker;
$X^+$ is a positively charged linker;
$X^-$ is a negatively charged linker;
Y is a ribonucleoprotein or endonuclease comprising a site-directed modifying polypeptide, or Y is a site-directed modifying polypeptide, or Y is Cas9 ribonucleoprotein, or Y is a Cas9 protein, or Y is a single guide RNA sequence (sgRNA) or Y is a dual guide RNA sequence comprising a CRISPR RNA (crRNA) and a trans-activating crRNA (tracrRNA);
$Y^+$ is a positively charged ribonucleoprotein or endonuclease comprising a site-directed modifying polypeptide, or $Y^+$ a positively charged site-directed modifying polypeptide, or $Y^+$ is a positively charged Cas9 protein;
$Y^-$ is a negatively charged ribonucleoprotein or endonuclease comprising a site-directed modifying polypeptide, or $Y^-$ is a negatively charged site-directed modifying polypeptide, or $Y^-$ is a negatively charged Cas9 ribonucleoprotein, or $Y^-$ is a negatively charged sgRNA, or $Y^-$ is a negatively charged dual guide RNA sequence comprising a CRISPR RNA (crRNA) and a trans-activating crRNA (tracrRNA);
Z is absent or is —C≡C—, —CH=CH—, —$CH_2$—, —$CH_2$—O—, —C(O)—$N(R^4)$—, —$CH_2$—S—, —$CH_2$—S(O)—, —$CH_2$—$S(O)_2$—, —$CH_2$—$S(O)_2$—$N(R^4)$—, —C(O)—O—, —$CH_2$—$N(R^4)$—, —$CH_2$—$N(R^4)$—C(O)—, —$CH_2$—$N(R^4)$—$S(O)_2$—, —$CH_2$—$N(R^4)$—C(O)—O—, —$CH_2$—$N(R^4)$—C(O)—$N(R^4)$—, —$CH_2$—O—C(O)—, —$CH_2$—O—C(O)—$N(R^4)$—, —$CH_2$—O—C(O)—O—, or aryl or heteroaryl, wherein the aryl or heteroaryl is optionally substituted with $R^5$;
$R^2$ is —OH, —$N_3$, —$N(R^3)_2$, —$N(R^3)$—C(O)—$R^3$, —$N(R^3)$—C(O)—$N(R^3)_2$, —$N(R^3)$—C(O)—$OR^3$, —$N(R^3)$—$S(O)_2$—$R^3$, tetrazole, or triazole, wherein the tetrazole and triazole are optionally substituted with $R^3$;
each $R^3$ is independently —H, —$(C_1$-$C_5)$alkyl, halo-substituted $(C_1$-$C_5)$alkyl, halo substituted $(C_3$-$C_6)$cycloalkyl, —(C$_1$-C$_5$)alkenyl, —(C$_1$-C$_5$)alkynyl, halo substituted —(C$_1$-C$_5$)alkenyl, halo substituted —(C$_1$-C$_5$)alkynyl, or (C$_3$-C$_6$)cycloalkyl, wherein a —CH$_2$— group of the alkyl or cycloalkyl may each be independently replaced with a heteroatom group selected from —O—, —S—, and —N(R$^4$)— and —CH$_3$ of the alkyl may each be independently replaced with a heteroatom group selected from —N(R$^4$)$_2$, —OR$^4$, and —S(R$^4$) wherein the heteroatom groups are separated by at least 2 carbon atoms;

each R$^4$ is independently —H, —(C$_1$-C$_{20}$)alkyl, —(C$_1$-C$_{20}$)alkenyl, —(C$_1$-C$_{20}$)alkynyl, or (C$_3$-C$_6$)cycloalkyl wherein one to six —CH$_2$— groups of the alkyl or cycloalkyl separated by at least two carbon atoms may each be independently replaced with a heteroatom independently selected from —O—, —S—, or —N(R$^4$)—, and —CH$_3$ of the alkyl may each be independently replaced with a heteroatom group selected from —N(R$^4$)$_2$, —OR$^4$, and —S(R$^4$) wherein the heteroatom groups are separated by at least 2 carbon atoms; and wherein the alkyl, alkenyl, alkynyl, and cycloalkyl may be substituted with halo atoms;

each R$^5$ is independently —H, (C$_3$-C$_{20}$)cycloalkyl, —(C$_1$-C$_{60}$)alkenyl, —(C$_1$-C$_{60}$)alkynyl, or (C$_1$-C$_{60}$)alkyl wherein one to six —CH$_2$— groups of the cycloalkyl or one to 20 —CH$_2$— groups of the alkyl may each be independently replaced with heteroatoms independently selected from —O—, —S—, and —N(R$^4$)— wherein the heteroatoms are separated by at least two carbon atoms, and —CH$_3$ of the alkyl may each be independently replaced with a heteroatom group selected from —N(R$^4$)$_2$, —OR$^4$, and —S(R$^4$) wherein the heteroatom groups are separated by at least 2 carbon atoms; and wherein the alkyl, alkenyl, alkynyl, and cycloalkyl may be substituted with halo atoms.

2. A compound of Formula (B):

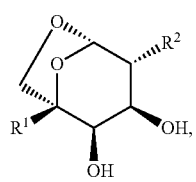

(B)

or a pharmaceutically acceptable salt thereof, wherein:

R$^1$ is —Z—X—Y, —Z—Y, —X—Y, —Z—X$^+$Y$^-$, —X$^+$Y$^-$, —Z—X$^-$Y$^+$, —X$^-$Y$^+$, or —Y;

X is a linker;

X$^+$ is a positively charged linker;

X$^-$ is a negatively charged linker;

Y is a ribonucleoprotein or endonuclease comprising a site-directed modifying polypeptide, or Y is a site-directed modifying polypeptide, or Y is Cas9 ribonucleoprotein, or Y is a Cas9 protein, or Y is a single guide RNA sequence (sgRNA) or Y is a dual guide RNA sequence comprising a CRISPR RNA (crRNA) and a trans-activating crRNA (tracrRNA);

Y$^+$ is a positively charged ribonucleoprotein or endonuclease comprising a site-directed modifying polypeptide, or Y$^+$ a positively charged site-directed modifying polypeptide, or Y$^+$ is a positively charged Cas9 protein;

Y$^-$ is a negatively charged ribonucleoprotein or endonuclease comprising a site-directed modifying polypeptide, or Y$^-$ is a negatively charged site-directed modifying polypeptide, or Y$^-$ is a negatively charged Cas9 ribonucleoprotein, or Y$^-$ is a negatively charged sgRNA, or Y$^-$ is a negatively charged dual guide RNA sequence comprising a CRISPR RNA (crRNA) and a trans-activating crRNA (tracrRNA);

Z is absent or is —C≡C—, —CH=CH—, —CH$_2$—, —CH$_2$—O—, —C(O)—N(R$^4$)—, —CH$_2$—S—, —CH$_2$—S(O)—, —CH$_2$—S(O)$_2$—, —CH$_2$—S(O)$_2$—N(R$^4$)—, —C(O)—O—, —CH$_2$—N(R$^4$)—, —CH$_2$—N(R$^4$)—C(O)—, —CH$_2$—N(R$^4$)—S(O)$_2$—, —CH$_2$—N(R$^4$)—C(O)—O—, —CH$_2$—N(R$^4$)—C(O)—N(R$^4$)—, —CH$_2$—O—C(O)—, —CH$_2$—O—C(O)—N(R$^4$)—, —CH$_2$—O—C(O)—O—, or aryl or heteroaryl, wherein the aryl or heteroaryl is optionally substituted with R$^5$;

R$^2$ is —OH, —N$_3$, —N(R$^3$)$_2$, —N(R$^3$)—C(O)—R$^3$, —N(R$^3$)—C(O)—N(R$^3$)$_2$, —N(R$^3$)—C(O)—OR$^3$, —N(R$^3$)—S(O)$_2$—R$^3$, tetrazole, or triazole, wherein the tetrazole and triazole are optionally substituted with R$^3$;

each R$^3$ is independently —H, —(C$_1$-C$_5$)alkyl, halo-substituted (C$_1$-C$_5$)alkyl, halo substituted (C$_3$-C$_6$)cycloalkyl, —(C$_1$-C$_5$)alkenyl, —(C$_1$-C$_5$)alkynyl, halo substituted —(C$_1$-C$_5$)alkenyl, halo substituted —(C$_1$-C$_5$)alkynyl, or (C$_3$-C$_6$)cycloalkyl, wherein a —CH$_2$— group of the alkyl or cycloalkyl may each be independently replaced with a heteroatom group selected from —O—, —S—, and —N(R$^4$)— and —CH$_3$ of the alkyl may each be independently replaced with a heteroatom group selected from —N(R$^4$)$_2$, —OR$^4$, and —S(R$^4$) wherein the heteroatom groups are separated by at least 2 carbon atoms;

each R$^4$ is independently —H, —(C$_1$-C$_{20}$)alkyl, —(C$_1$-C$_{20}$)alkenyl, —(C$_1$-C$_{20}$)alkynyl, or (C$_3$-C$_6$)cycloalkyl wherein one to six —CH$_2$— groups of the alkyl or cycloalkyl separated by at least two carbon atoms may each be independently replaced with a heteroatom independently selected from —O—, —S—, or —N(R$^4$)—, and —CH$_3$ of the alkyl may each be independently replaced with a heteroatom group selected from —N(R$^4$)$_2$, —OR$^4$, and —S(R$^4$) wherein the heteroatom groups are separated by at least 2 carbon atoms; and wherein the alkyl, alkenyl, alkynyl, and cycloalkyl may be substituted with halo atoms;

each R$^5$ is independently —H, (C$_3$-C$_{20}$)cycloalkyl, —(C$_1$-C$_{60}$)alkenyl, —(C$_1$-C$_{60}$)alkynyl, or (C$_1$-C$_{60}$)alkyl wherein one to six —CH$_2$— groups of the cycloalkyl or one to 20 —CH$_2$— groups of the alkyl may each be independently replaced with heteroatoms independently selected from —O—, —S—, and —N(R$^4$)— wherein the heteroatoms are separated by at least two carbon atoms, and —CH$_3$ of the alkyl may each be independently replaced with a heteroatom group selected from —N(R$^4$)$_2$, —OR$^4$, and —S(R$^4$) wherein the heteroatom groups are separated by at least 2 carbon atoms; and wherein the alkyl, alkenyl, alkynyl, and cycloalkyl may be substituted with halo atoms.

3. The compound according to embodiment 1 or 2, wherein R2 is —NH—C(O)—CH3.

4. The compound according to any one of embodiments 1-3, where R1 is —Z—X+Y-.

5. The compound according to any one of embodiments 1-3, where R1 is —Z—X-Y+.

6. The compound according to any one of embodiments 1-3, where R1 is —Z—X—Y.

7. The compound according to embodiment 6, wherein R$^1$ is —Z—X—Y that is selected from the group consisting of L1 to L10:

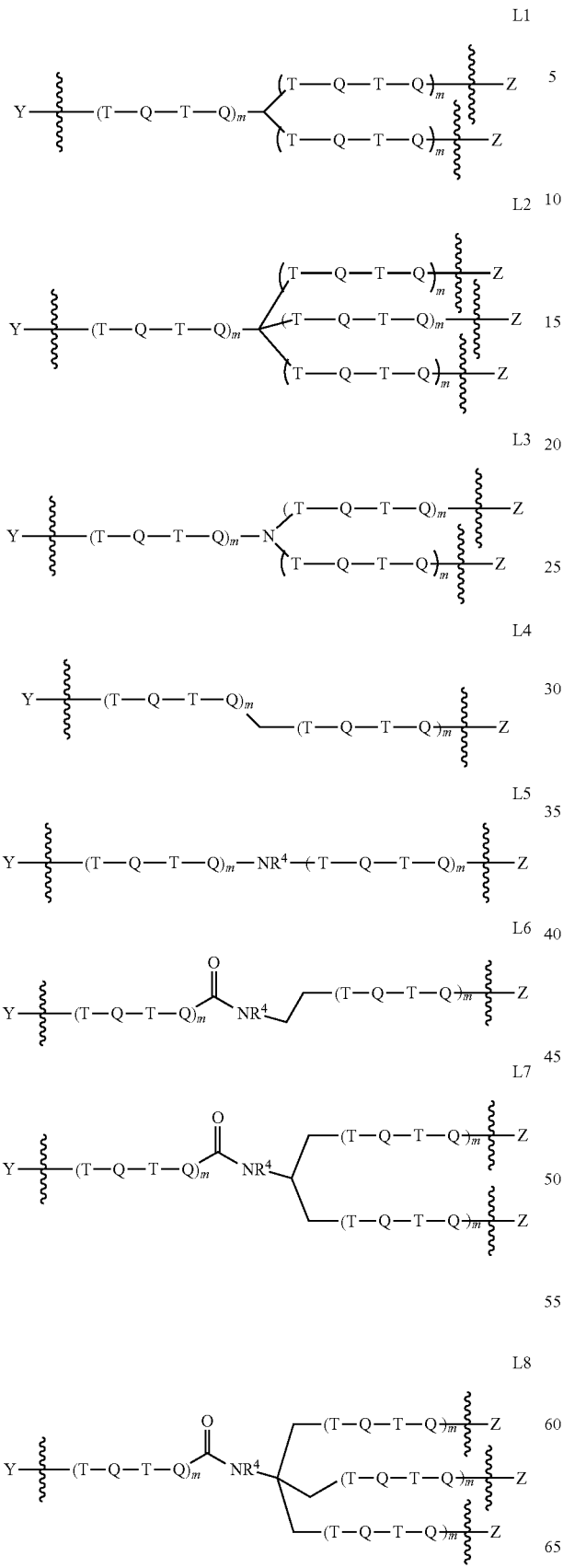

wherein each T is independently absent or is $(C_1$-$C_{10})$ alkylene, $(C_2$-$C_{10})$ alkenylene, or $(C_2$-$C_{10})$ alkynylene, wherein one or more carbon groups of said T may each independently be replaced with a heteroatom group independently selected from —O—, —S—, and —N($R^4$)— wherein the heteroatom groups are separated by at least 2 carbon atoms, and wherein alkylene, alkenylene, and alkynylene may each be independently substituted with one or more halo atoms;

each Q is independently absent or is C(O), C(O)—$NR^4$, $NR^4$—C(O), O—C(O)—$NR^4$, $NR^4$—C(O)—O, —$CH_2$—, a heteroaryl, or a heteroatom group selected from O, S, S—S, S(O), S(O)$_2$, and $NR^4$, wherein at least two carbon atoms separate the heteroatom groups O, S, S—S, S(O), S(O)$_2$ and $NR^4$ from any other heteroatom group;

each $R^4$ is independently —H, —$(C_1$-$C_{20})$alkyl, or $(C_3$-$C_6)$ cycloalkyl wherein one to six —$CH_2$— groups of the alkyl or cycloalkyl separated by at least two carbon atoms may each be independently replaced with —O—, —S—, or —N($R^4$)—, and —$CH_3$ of the alkyl may be replaced with a heteroatom group selected from —N($R^4$)2, —$OR^4$, and —S($R^4$) wherein the heteroatom groups are separated by at least 2 carbon atoms; and wherein the alkyl and cycloalkyl may be substituted with halo atoms; and each m is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40.

8. The compound according to embodiment 7, wherein each occurrence of said Q is independently a heteroaryl selected from 1H-1,2,3-triazolyl, pyridinyl, and 1,2,3,4-tetrazolyl.

9. The compound according to embodiment 7 or 8, wherein said X comprises a disulfide bond.

10. The compound according to embodiment 1, wherein said compound has a formula of Formula (C-1), (C-2), (C-3) or (C4):

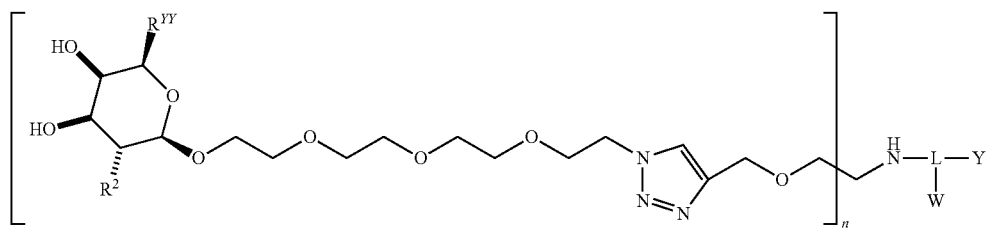

(C-1)

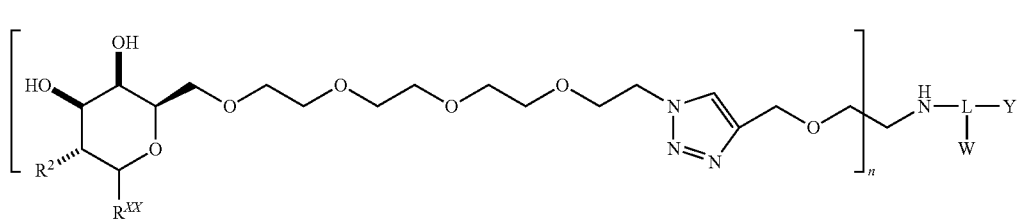

(C-2)

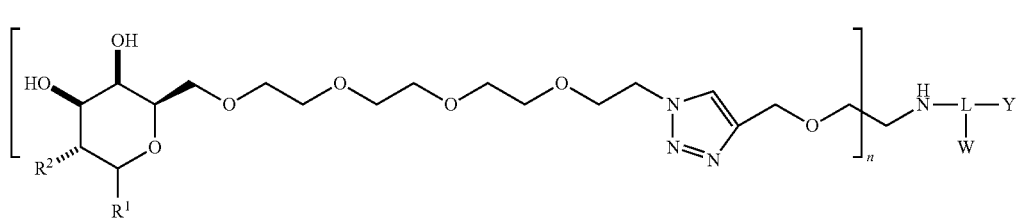

(C-3)

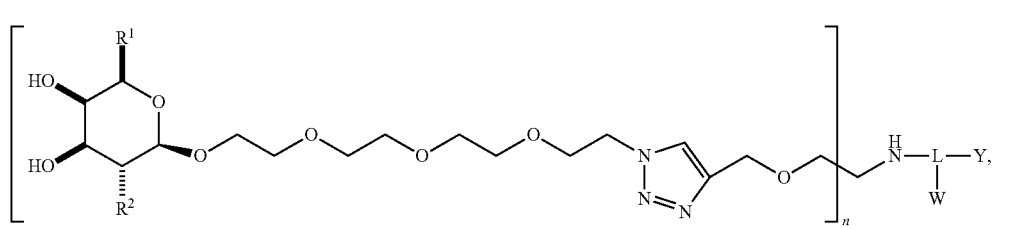

(C-4)

or a pharmaceutically acceptable salt thereof,
wherein:

n is 1, 2, or 3;

W is absent or a peptide;

L is -(T-Q-T-Q)$_m$-, wherein:

each T is independently absent or is (C$_1$-C$_{10}$) alkylene, (C$_2$-C$_{10}$) alkenylene, or (C$_2$-C$_{10}$) alkynylene, wherein one or more carbon groups of said T may each independently be replaced with a heteroatom group independently selected from —O—, —S—, and —N(R$^4$)— wherein the heteroatom groups are separated by at least 2 carbon atoms, and wherein alkylene, alkenylene, and alkynylene may each be independently substituted with one or more halo atoms;

each Q is independently absent or is C(O), C(O)—NR$^4$, NR$^4$—C(O), O—C(O)—NR$^4$, NR$^4$—C(O)—O, —CH$_2$—, a heteroaryl, or a heteroatom group selected from O, S, S—S, S(O), S(O)$_2$, and NR$^4$, wherein at least two carbon atoms separate the heteroatom groups O, S, S—S, S(O), S(O)$_2$ and NR$^4$ from any other heteroatom group;

each R$^4$ is independently —H, —(C$_1$-C$_{20}$)alkyl, or (C$_3$-C$_6$) cycloalkyl wherein one to six —CH$_2$— groups of the alkyl or cycloalkyl separated by at least two carbon atoms may be replaced with —O—, —S—, or —N(R$^4$)—, and —CH$_3$ of the alkyl may each be independently replaced with a heteroatom group selected from —N(R$^4$)$_2$, —OR$^4$, and —S(R$^4$) wherein the heteroatom groups are separated by at least 2 carbon atoms; and wherein the alkyl and cycloalkyl may be substituted with halo atoms; and each m is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40.

11. The compound according to embodiment 1, wherein said compound has a formula of Formula (D-1) or (D-2):

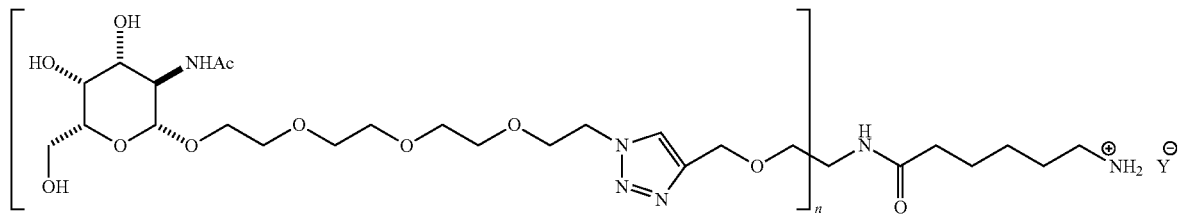

(D-1)

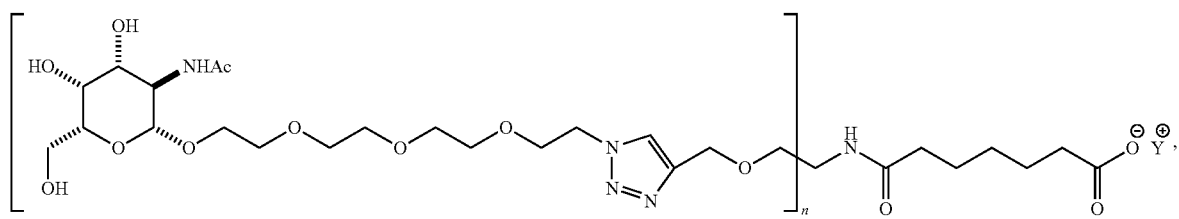

(D-2)

or a pharmaceutically acceptable salt thereof,
wherein:
n is from 1, 2 or 3.

12. The compound according to embodiment 2, wherein said compound has a formula of Formulae (E):

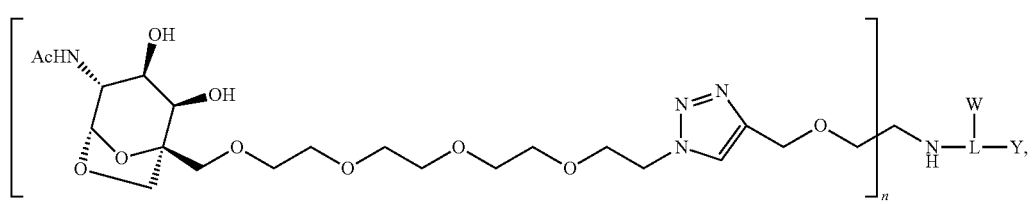

(E)

or a pharmaceutically acceptable salt thereof,
wherein:
n is 1, 2 or 3;
W is absent or is a peptide;
L is -(T-Q-T-Q)$_m$-, wherein:
  each T is independently absent or is ($C_1$-$C_{10}$) alkylene, ($C_2$-$C_{10}$) alkenylene, or ($C_2$-$C_{10}$) alkynylene, wherein one or more carbon groups of said T may each independently be replaced with a heteroatom group independently selected from —O—, —S—, and —N($R^4$)— wherein the heteroatom groups are separated by at least 2 carbon atoms;
  each Q is independently absent or is C(O), C(O)—$NR^4$, $NR^4$—C(O), O—C(O)—$NR^4$, $NR^4$—C(O)—O, —$CH_2$—, a heteroaryl, or a heteroatom group selected from O, S, S—S, S(O), S(O)$_2$, and $NR^4$, wherein at least two carbon atoms separate the heteroatom groups O, S, S—S, S(O), S(O)$_2$ and $NR^4$ from any other heteroatom group;
  each $R^4$ is independently —H, —($C_1$-$C_{20}$)alkyl, or ($C_3$-$C_6$)cycloalkyl wherein one to six —$CH_2$— groups of the alkyl or cycloalkyl separated by at least two carbon atoms may each be independently replaced with —O—, —S—, or —N($R^4$)—, and —$CH_3$ of the alkyl may be replaced with a heteroatom group selected from —N($R^4$)$_2$, —$OR^4$, and —S($R^4$) wherein the heteroatom groups are separated by at least 2 carbon atoms; and wherein the alkyl and cycloalkyl may be substituted with halo atoms; and each m is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40.

13. The compound according to embodiment 2, wherein said compound has a formula of Formula (F-1) or (F-2):

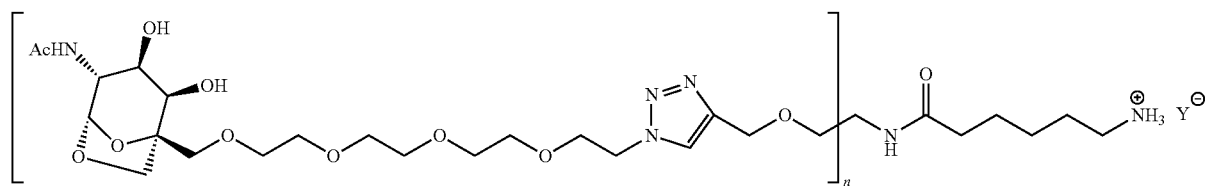
(F-1)
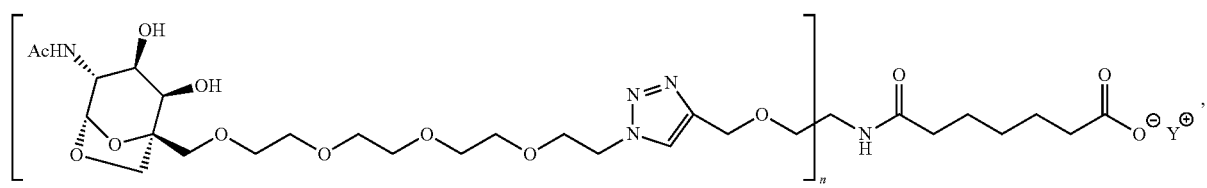
(F-2)
or a pharmaceutically acceptable salt thereof,
wherein:
n is selected from 1, 2 and 3.
14. The compound according to any one of embodiments 10-13, wherein n is 3.
15. The compound according to embodiment 12, wherein said compound has the formula

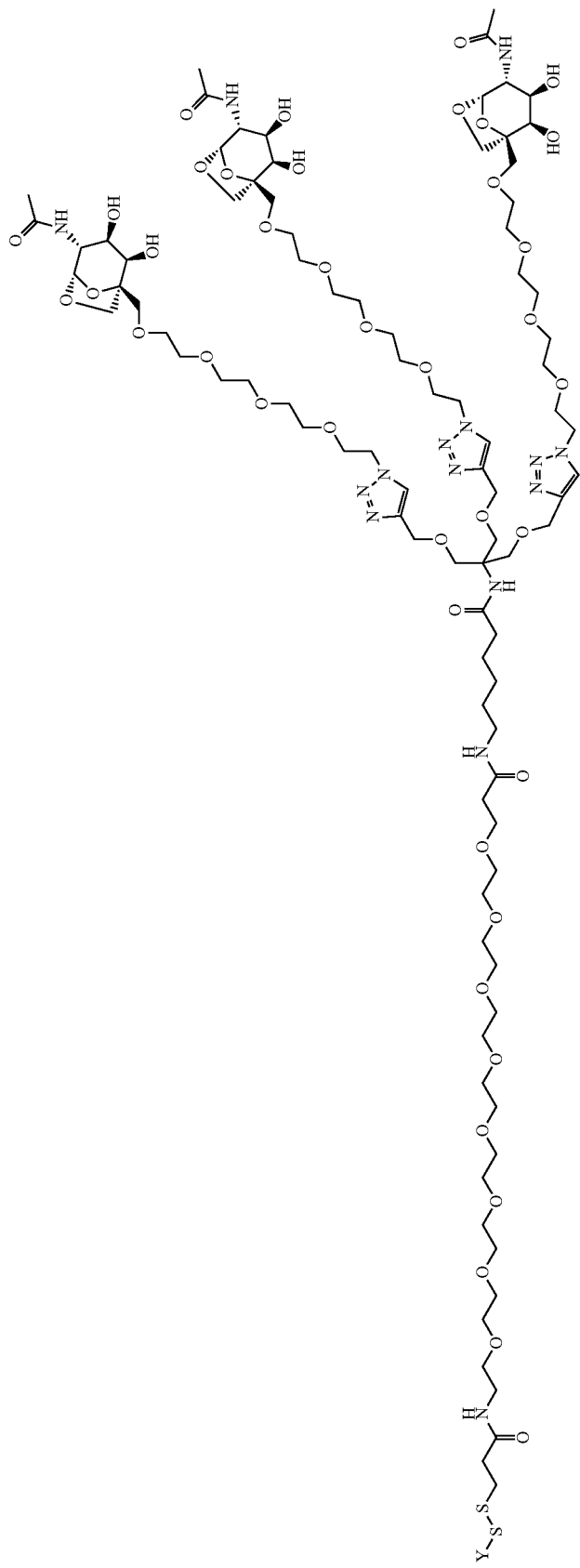

or a pharmaceutically acceptable salt thereof.
16. The compound according to embodiment 10 or 12, wherein W is a peptide that is an endosomolytic peptide or a nuclear localization peptide.
17. The compound according to any one of the preceding embodiments, wherein Y is a Cas9 ribonucleoprotein comprising:
    (1) a first element comprising a recognition element comprising either a dual guide RNA sequence comprising a CRISPR RNA (crRNA) and a trans-activating crRNA (tracrRNA), or a single guide RNA sequence (sgRNA), wherein when expressed, the guide sequence directs sequence-specific binding of the Cas9 ribonucleoprotein to a target sequence, and the first element optionally comprises one or more endosomal escape agents, and
    (2) a second element comprising a Cas9 protein and optionally one or more nuclear localization sequences (NLSs) and optionally one or more fluorescent proteins, and one or more endosomal escape agents;
    wherein said first element is associated with said second element.
18. The compound according to embodiment 17, wherein said target sequence is a eukaryotic cell target sequence.
19. The compound according to embodiment 17, wherein the first element comprises a dual guide RNA sequence comprising a CRISPR RNA (crRNA) and a trans-activating crRNA (tracrRNA), wherein the remainder of the compound is linked to said Cas9 ribonucleoprotein via one or more interactions each independently to the tracrRNA sequence or to the crRNA.
20. The compound according to embodiment 19, wherein said tracrRNA is optionally chemically modified.
21. The compound according to embodiment 19 or 20, wherein the tracrRNA comprises a sequence that is at least about 75 percent, at least about 80 percent, at least about 85 percent, at least about 90 percent, at least about 95 percent, at least about 96 percent, at least about 97 percent, at least about 98 percent, at least about 99 percent or 100 percent nucleotide sequence identity to the sequence of: CAGCAUAGCAAGUUAAAAUAAGGC-UAGUCCGUUAUCAACUUGAAAAAGUGGC ACCGAGUCGGUGCUUUU (SEQ ID NO:1028), wherein said sequence optionally contains 2'-O-methyl or 2'-F modifications at the first 3 bases.
22. The compound according to any one of embodiments 19-21, wherein said crRNA is optionally chemically modified.
23. The compound according to any one of embodiments 19-21, wherein the crRNA comprises a sequence that is at least about 75 percent, at least about 80 percent, at least about 85 percent, at least about 90 percent, at least about 95 percent, at least about 96 percent, at least about 97 percent, at least about 98 percent, at least about 99 percent or 100 percent nucleotide sequence identity to a sequence selected from:

```
PCSK9 crRNA sequence 1:
                                    (SEQ ID NO: 885)
GGUGCUAGCCUUGCGUUCCGGUUUUAGAGCUAUGCUG,
optionally containing 2'-O-methyl or 2'-F
modifications at the first 3 of the last 4 bases
(GCU);

PCSK9 crRNA sequence 2:
                                    (SEQ ID NO: 886)
CGUGCUCGGGUGCUUCGGCCGUUUUAGAGCUAUGCUG,
```

```
-continued
optionally containing 2'-O-methyl or 2'-F
modifications at the first 3 of the last 4 bases
(GCU);

PCSK9 crRNA sequence 3:
                                    (SEQ ID NO: 887)
GCCGUCCUCCUCGGAACGCAGUUUUAGAGCUAUGCUG,
optionally containing 2'-O-methyl or 2'-F
modifications at the first 3 of the last 4 bases
(GCU);

PCSK9 crRNA sequence 4:
                                    (SEQ ID NO: 888)
GGACGAGGACGGCGACUACGGUUUUAGAGCUAUGCUG,
optionally containing 2'-O-methyl or 2'-F
modifications at the first 3 of the last 4 bases
(GCU);

PCSK9 crRNA sequence 5:
                                    (SEQ ID NO: 889)
ACCACCGGGAAAUCGAGGGCGUUUUAGAGCUAUGCUG,
optionally containing 2'-O-methyl or 2'-F
modifications at the first 3 of the last 4 bases
(GCU);

PCSK9 crRNA sequence 6:
                                    (SEQ ID NO: 890)
CGACUUCGAGAAUGUGCCCGGUUUUAGAGCUAUGCUG,
optionally containing 2'-O-methyl or 2'-F
modifications at the first 3 of the last 4 bases
(GCU);

PCSK9 crRNA sequence 7:
                                    (SEQ ID NO: 891)
GAGUGACCACCGGGAAAUCGGUUUUAGAGCUAUGCUG,
optionally containing 2'-O-methyl or 2'-F
modifications at the first 3 of the last 4 bases
(GCU);

PCSK9 crRNA sequence 8:
                                    (SEQ ID NO: 892)
CUCGGGCACAUUCUCGAAGUGUUUUAGAGCUAUGCUG,
optionally containing 2'-O-methyl or 2'-F
modifications at the first 3 of the last 4 bases
(GCU);

PCSK9 crRNA sequence 9:
                                    (SEQ ID NO: 893)
GGAAGCCAGGAAGAAGGCCAGUUUUAGAGCUAUGCUG,
optionally containing 2'-O-methyl or 2'-F
modifications at the first 3 of the last 4 bases
(GCU);

PCSK9 crRNA sequence 10:
                                    (SEQ ID NO: 894)
UCUUUGCCCAGAGCAUCCCGGUUUUAGAGCUAUGCUG,
optionally containing 2'-O-methyl or 2'-F
modifications at the first 3 of the last 4 bases
(GCU);

PCSK9 crRNA sequence 11:
                                    (SEQ ID NO: 895)
CUAGGAGAUACACCUCCACCGUUUUAGAGCUAUGCUG,
optionally containing 2'-O-methyl or 2'-F
modifications at the first 3 of the last 4 bases
(GCU).
```

24. The compound according to embodiment 17, wherein the first element comprises a single guide RNA sequence (sgRNA), wherein the remainder of the compound is linked to said Cas9 ribonucleoprotein via one or more interactions to the sgRNA.
25. The compound according to embodiment 24, wherein said sgRNA comprises at least 20 nucleotides.
26. The compound according to embodiment 24, wherein said sgRNA comprises at least 8 nucleotides.
27. The compound according to embodiment 24, wherein the degree of complementarity between the sgRNA and its corresponding target sequence, when optimally aligned using a suitable alignment algorithm, is at least 50%, 60%, 70%, 75%, 80%, 85%, 86%, 87%, 88%, 89%, 90%, 91%, 92%, 93%, 94%, 95%, 96%, 97%, 98%, 99%, or 100%.

28. The compound according to any one of embodiments 24, wherein said sgRNA has at least about 75 percent, at least about 80 percent, at least about 85 percent, at least about 90 percent, at least about 95 percent, at least about 96 percent, at least about 97 percent, at least about 98 percent, at least about 99 percent or 100 percent nucleotide sequence identity to the sequence selected from the group consisting of:

```
PCSK9 single guide RNA sequence 1:
                                          (SEQ ID NO: 896)
GGUGCUAGCCUUGCGUUCCGGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

PCSK9 single guide RNA sequence 2:
                                          (SEQ ID NO: 897)
CGUGCUCGGGUGCUUCGGCCGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

PCSK9 single guide RNA sequence 3:
                                          (SEQ ID NO: 898)
GCCGUCCUCCUCGGAACGCAGUUUAAGAGCUAUGCUGGAAACAGCAUAGC

AAGUUUAAAUAAGGCUAGUCCGUUAUCAACUUGAAAAAGUGGCACCGAGU

CGGUGCUUUUUUU;

PCSK9 single guide RNA sequence 4:
                                          (SEQ ID NO: 899)
GGACGAGGACGGCGACUACGGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;

PCSK9 single guide RNA sequence 5:
                                          (SEQ ID NO: 900)
ACCACCGGGAAAUCGAGGGCGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;

PCSK9 single guide RNA sequence 6:
                                          (SEQ ID NO: 901)
CGACUUCGAGAAUGUGCCCGGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;

PCSK9 single guide RNA sequence 7:
                                          (SEQ ID NO: 902)
GAGUGACCACCGGGAAAUCGGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;

PCSK9 single guide RNA sequence 8:
                                          (SEQ ID NO: 903)
CUCGGGCACAUUCUCGAAGUGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;

PCSK9 single guide RNA sequence 9:
                                          (SEQ ID NO: 904)
GGAAGCCAGGAAGAAGGCCAGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;

PCSK9 single guide RNA sequence 10:
                                          (SEQ ID NO: 905)
UCUUUGCCCAGAGCAUCCCGGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;

PCSK9 single guide RNA sequence 11:
                                          (SEQ ID NO: 906)
CUAGGAGAUACACCUCCACCGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;

EMX1 single guide RNA sequence:
                                          (SEQ ID NO: 907)
GUCACCUCCAAUGACUAGGGGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;

ROSA26 single guide RNA sequence:
                                          (SEQ ID NO: 908)
CGAACCCUACACAUUCAACGGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;
``` wherein said sequence is optionally chemically modified.

29. The compound according to any one of embodiments 24-28, wherein said Y comprises a sgRNA that is optionally chemically modified.
30. The compound according to any one of the preceding embodiments, wherein said Y further comprises a fluorescent probe.
31. The compound according to embodiment 30, wherein said fluorescent probe is the mCherry sequence (SEQ ID NO:915).
32. The compound according to any one of the preceding embodiments, wherein said Y comprises one or more NLSs.
33. The compound according to embodiment 32, wherein each of said NLS comprises an amino acid sequence selected from the group consisting of:

```
                                          (SEQ ID NO: 830)
PKKKRKV;

(SEQ ID NO: 831)
KRPAATKKAGQAKKKK;

(SEQ ID NO: 832)
PAAKRVKLD;

(SEQ ID NO: 833)
RQRRNELKRSP;

(SEQ ID NO: 834)
NQSSNFGPMKGGNFGGRSSGPYGGGGQYFAKPRNQGGY;

(SEQ ID NO: 835)
RMRIXFKNKGKDTAELRRRRVEVSVELRKAKKDEQILKRRNV;

(SEQ ID NO: 836)
```

-continued

```
VSRKRPRP;

(SEQ ID NO: 837)
PPKKARED;

(SEQ ID NO: 838)
PQPKKKPL;

(SEQ ID NO: 839)
SALIKKKKMAP;

(SEQ ID NO: 840)
DRLRR;

(SEQ ID NO: 841)
PKQKKRK;

(SEQ ID NO: 842)
RKLKKKIKKL;

(SEQ ID NO: 843)
REKKKFLKRR;

(SEQ ID NO: 844)
KRKGDEVDGVDEVAKKKSKK;

(SEQ ID NO: 845)
RKCLQAGMNLEARKTKK;

(SEQ ID NO: 1035)
MAPKKKRKVGIHRGVP;
and (SEQ ID NO: 1036)
PKKKRKVEDPKKKRKVD.
```

34. The compound according to embodiment 33, wherein each of said NLSs comprises the amino acid sequence PKKKRKV (SEQ ID NO: 830).

35. The compound according to embodiment 34, wherein said compound comprises two NLSs each comprising the amino acid sequence PKKKRKV (SEQ ID NO: 830).

36. The compound according to any one of the preceding embodiments, wherein said Y comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to a Cas9 protein derived from *S. aureus*, *S. pneumoniae*, *S. pyogenes*, *S. thermophilus*, *N. meningitidis* or *A. ebreus*.

37. The compound according to any one of the preceding embodiments, wherein said Y comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to a Type II Cas9 protein.

38. The compound according to any one of the preceding embodiments, wherein said Y comprises a Cas9 protein that is at least about 75 percent, at least about 80 percent, at least about 85 percent, at least about 90 percent, at least about 95 percent, at least about 99 percent or 100 percent amino acid sequence identity to the amino acids at positions 7 to 166 or 731 to 1003 of SEQ ID NO:8 or the corresponding amino acids of those set forth in SEQ ID NOs:1-7, 9-829.

39. The compound according to any one of the preceding embodiments, wherein said Y comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to the amino acids at positions 7 to 166 or 731 to 1003 of SEQ ID NO:8.

40. The compound according to any one of the preceding embodiments, wherein said Y comprises a Cas9 protein having at least 4 motifs within the sequence which have at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to the motifs 1, 2, 3, and 4 of the Cas9 amino acid sequence of any of SEQ ID NOs: 260-263.

41. The compound according to any one of the preceding embodiments, wherein said Y comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to a sequence selected from: *S. pyogenes* Cas9 (wild type) (SEQ ID NO:848), *S. pyogenes* Cas9-mutation M1C (SEQ ID NO:849), *S. pyogenes* Cas9-mutation M1C & C80S (SEQ ID NO:850), *S. pyogenes* Cas9 nickase-mutation D10A (SEQ ID NO:851), *S. pyogenes* Cas9 nickase-mutation H840A (SEQ ID NO:852), *S. pyogenes* Cas9 nickase-mutations E923P & T924P (SEQ ID NO:853), *Acidovorax ebreus* Cas9 (SEQ ID NO:854), Acid mine drainage bacteria Ga0052161_JGI Cas9 (SEQ ID NO:855), *S. pyogenes* Cas9 null-mutation D10A& H840A (SEQ ID NO:1027), and Uranium mine bacteria FW106_JGI Cas9 (SEQ ID NO:856).

42. The compound according to any one of the preceding embodiments, wherein the compound is capable of binding to a receptor present on a hepatocyte.

43. The compound according to embodiment 42, wherein the receptor presents on a hepatocyte is an asialoglycoprotein receptor.

44. The compound according to any one of the preceding embodiments, wherein said compound further comprises an endosomal escape agent.

45. The compound according to any one of the preceding embodiments, wherein said Y further comprises an endosomal escape agent.

46. The compound according to embodiment 44 or 45, wherein said endosomal escape agent is selected from the group consisting of: a lysosomotropic agent, a cell penetrating peptide, a fusogenic peptide, a pore forming agent, and a proton sponge agent.

47. The compound according to embodiment 46, wherein said endosomal escape agent is peptide ppTG21: GLF-HALLHLLHSLWHLLLHA (SEQ ID NO: 1012).

48. A composition comprising a compound according to any one of embodiments 1-47 and an endosomal escape agent, wherein said compound and the endosomal escape agent are co-incubated to form the composition.

49. The composition according to embodiment 48, wherein said endosomal escape agent is selected from the group consisting of: a lysosomotropic agent, a cell penetrating peptide, a fusogenic peptide, a pore forming agent, and a proton sponge agent.

50. The composition according to embodiment 49, wherein said endosomal escape agent is peptide ppTG21: GLF-HALLHLLHSLWHLLLHA (SEQ ID NO: 1012).

51. A pharmaceutical composition comprising a compound of any one of the preceding embodiments and a pharmaceutically acceptable carrier, excipient or diluent.
52. A method of treating a liver disease or condition or a liver modulated disease or condition in a subject, comprising administering to said subject a therapeutically effective amount of a pharmaceutical composition according to embodiment 51.
53. The method according to embodiment 52, wherein the disease or condition is selected from the group consisting of: hereditary angioedema, familial tyrosinemia type I, Alagille syndrome, Alpha-1-antitrypsin deficiency, Bile acid synthesis and metabolism defects, Biliary Atresia, Cystic Fibrosis liver disease, Idiopathic neonatal hepatitis, Mitochondrial hepatopathies, Progressive familial intrahepatic cholestasis, Primary sclerosing cholangitis, Transthyretin amyloidosis, Hemophilia, Homozygous familial hypercholesterolemia, familial chylomicronemia, hyperlipidemia, steatohepatitis, non-alcoholic steatohepatitis (NASH), non-alcoholic fatty liver disease (NAFLD), hyperglycemia, and diseases involving abnormally high hepatic glucose production similar to Type II diabetes mellitus.
54. The method according to embodiment 53, wherein the disease or condition is hyperlipidemia, non-alcoholic steatohepatitis (NASH), or non-alcoholic fatty liver disease (NAFLD).
55. A method of selectively modulating transcription of a target DNA in a liver cell of a subject, comprising administering to said subject a pharmaceutical composition according to embodiment 51.
56. The method according to embodiment 55, wherein the target DNA is associated with a disease or condition is selected from the group consisting of: hereditary angioedema, familial tyrosinemia type I, Alagille syndrome, Alpha-1-antitrypsin deficiency, Bile acid synthesis and metabolism defects, Biliary Atresia, Cystic Fibrosis liver disease, Idiopathic neonatal hepatitis, Mitochondrial hepatopathies, Progressive familial intrahepatic cholestasis, Primary sclerosing cholangitis, Transthyretin amyloidosis, Hemophilia, Homozygous familial hypercholesterolemia, familial chylomicronemia, hyperlipidemia, steatohepatitis, non-alcoholic steatohepatitis (NASH), non-alcoholic fatty liver disease (NAFLD), hyperglycemia, and diseases involving abnormally high hepatic glucose production similar to Type II diabetes mellitus.
57. The method according to embodiment 55, wherein said target DNA is the PCSK9 gene.
58. A method of editing a nucleic acid molecule encoding a protein associated with a liver disease or condition in a subject, comprising administering to said subject a pharmaceutical composition according to embodiment 48.
59. The method of embodiment 57, wherein said protein is associated with a liver disease or condition is selected from the group consisting of: hereditary angioedema, familial tyrosinemia type I, Alagille syndrome, Alpha-1-antitrypsin deficiency, Bile acid synthesis and metabolism defects, Biliary Atresia, Cystic Fibrosis liver disease, Idiopathic neonatal hepatitis, Mitochondrial hepatopathies, Progressive familial intrahepatic cholestasis, Primary sclerosing cholangitis, Transthyretin amyloidosis, Hemophilia, Homozygous familial hypercholesterolemia, familial chylomicronemia, hyperlipidemia, steatohepatitis, non-alcoholic steatohepatitis (NASH), non-alcoholic fatty liver disease (NAFLD), hyperglycemia, and diseases involving abnormally high hepatic glucose production similar to Type II diabetes mellitus.
60. A method of modulating the expression of level of at least one gene product associated with a liver disease or condition in a subject, comprising administering to said subject a pharmaceutical composition according to embodiment 51.
61. The method according to embodiment 60, wherein said gene product is associated with a liver disease or condition is selected from the group consisting of: hereditary angioedema, familial tyrosinemia type I, Alagille syndrome, Alpha-1-antitrypsin deficiency, Bile acid synthesis and metabolism defects, Biliary Atresia, Cystic Fibrosis liver disease, Idiopathic neonatal hepatitis, Mitochondrial hepatopathies, Progressive familial intrahepatic cholestasis, Primary sclerosing cholangitis, Transthyretin amyloidosis, Hemophilia, Homozygous familial hypercholesterolemia, familial chylomicronemia, hyperlipidemia, steatohepatitis, non-alcoholic steatohepatitis (NASH), non-alcoholic fatty liver disease (NAFLD), hyperglycemia, and diseases involving abnormally high hepatic glucose production similar to Type II diabetes mellitus.
62. The method according to embodiment 61, wherein said method modulates the level of low-density lipoproteins (LDLs).
63. The method of embodiment 61, wherein said method modulates the level of cholesterol in the blood of said subject.
64. The method of embodiment 63, wherein said method reduces the blood cholesterol level in said subject.
65. A composition comprising a ribonucleoprotein and an endosomal escape agent.
66. The composition of embodiment 65, wherein said ribonucleoprotein is a Cas9 ribonucleoprotein or a Cpf1 ribonucleoprotein.
67. The composition of embodiment 66, wherein said ribonucleoprotein is a Cas9 ribonucleoprotein.
68. The composition according to embodiment 67, wherein said Cas9 ribonucleoprotein and said endosomal escape agent are co-incubated.
69. The composition according to embodiment 67 or 68, wherein said Cas9 ribonucleoprotein comprises:
    (1) a first element comprising a recognition element comprising either a dual guide RNA sequence comprising a CRISPR RNA (crRNA) and a trans-activating crRNA (tracrRNA), or a single guide RNA sequence (sgRNA), wherein when expressed, the guide sequence directs sequence-specific binding of the Cas9 ribonucleoprotein to a target sequence, and the first element optionally comprises one or more endosomal escape agents, and
    (2) a second element comprising a Cas9 protein and optionally one or more nuclear localization sequences (NLSs) and optionally one or more fluorescent proteins, and one or more endosomal escape agents;
    wherein said first element is associated with said second element.
70. The composition according to embodiment 69, wherein said target sequence is a eukaryotic cell target sequence.
71. The composition according to embodiment 69, wherein the first element comprises a dual guide RNA sequence comprising a CRISPR RNA (crRNA) and a trans-activating crRNA (tracrRNA).
72. The composition according to embodiment 71, wherein said tracrRNA is optionally chemically modified.
73. The composition according to embodiment 71 or 72, wherein the tracrRNA comprises a sequence that is at least about 75 percent, at least about 80 percent, at least about 85 percent, at least about 90 percent, at least about 95 percent, at least about 96 percent, at least about 97 percent, at least about 98 percent, at least about 99 percent or 100 percent nucleotide sequence identity to the sequence of: CAGCAUAGCAAGUUAAAAUAAGGC-UAGUCCGUUAUCAACUUGAAAAAGUGGC ACCGAGUCGGUGCUUUU (SEQ ID NO:1028), wherein said sequence optionally contains 2'-O-methyl or 2'-F modifications at the first 3 bases.

74. The composition according to any one of embodiments 71-73, wherein said crRNA is optionally chemically modified.

75. The composition according to any one of embodiments 71-73, wherein the crRNA comprises a sequence that is at least about 75 percent, at least about 80 percent, at least about 85 percent, at least about 90 percent, at least about 95 percent, at least about 96 percent, at least about 97 percent, at least about 98 percent, at least about 99 percent or 100 percent nucleotide sequence identity to a sequence selected from:

```
PCSK9 crRNA sequence 1:
                                    (SEQ ID NO: 885)
GGUGCUAGCCUUGCGUUCCGGUUUUAGAGCUAUGCUG,
optionally containing 2'-O-methyl or 2'-F
modifications at the first 3 of the last 4 bases
(GCU);

PCSK9 crRNA sequence 2:
                                    (SEQ ID NO: 886)
CGUGCUCGGGUGCUUCGGCCGUUUUAGAGCUAUGCUG,
optionally containing 2'-O-methyl or 2'-F
modifications at the first 3 of the last 4 bases
(GCU);

PCSK9 crRNA sequence 3:
                                    (SEQ ID NO: 887)
GCCGUCCUCCUCGGAACGCAGUUUUAGAGCUAUGCUG,
optionally containing 2'-O-methyl or 2'-F
modifications at the first 3 of the last 4 bases
(GCU);

PCSK9 crRNA sequence 4:
                                    (SEQ ID NO: 888)
GGACGAGGACGGCGACUACGGUUUUAGAGCUAUGCUG,
optionally containing 2'-O-methyl or 2'-F
modifications at the first 3 of the last 4 bases
(GCU);

PCSK9 crRNA sequence 5:
                                    (SEQ ID NO: 889)
ACCACCGGGAAAUCGAGGGCGUUUUAGAGCUAUGCUG,
optionally containing 2'-O-methyl or 2'-F
modifications at the first 3 of the last 4 bases
(GCU);

PCSK9 crRNA sequence 6:
                                    (SEQ ID NO: 890)
CGACUUCGAGAAUGUGCCCGGUUUUAGAGCUAUGCUG,
optionally containing 2'-O-methyl or 2'-F
modifications at the first 3 of the last 4 bases
(GCU);

PCSK9 crRNA sequence 7:
                                    (SEQ ID NO: 891)
GAGUGACCACCGGGAAAUCGGUUUUAGAGCUAUGCUG,
optionally containing 2'-O-methyl or 2'-F
modifications at the first 3 of the last 4 bases
(GCU);

PCSK9 crRNA sequence 8:
                                    (SEQ ID NO: 892)
CUCGGGCACAUUCUCGAAGUGUUUUAGAGCUAUGCUG,
optionally containing 2'-O-methyl or 2'-F
modifications at the first 3 of the last 4 bases
(GCU);

PCSK9 crRNA sequence 9:
                                    (SEQ ID NO: 893)
GGAAGCCAGGAAGAAGGCCAGUUUUAGAGCUAUGCUG,
optionally containing 2'-O-methyl or 2'-F
modifications at the first 3 of the last 4 bases
(GCU);

PCSK9 crRNA sequence 10:
                                    (SEQ ID NO: 894)
UCUUUGCCCAGAGCAUCCCGGUUUUAGAGCUAUGCUG,
optionally containing 2'-O-methyl or 2'-F
modifications at the first 3 of the last 4 bases
(GCU);

PCSK9 crRNA sequence 11:
                                    (SEQ ID NO: 895)
CUAGGAGAUACACCUCCACCGUUUUAGAGCUAUGCUG,
optionally containing 2'-O-methyl or 2'-F
modifications at the first 3 of the last 4 bases
(GCU).
```

76. The composition according to embodiment 69, wherein the first element comprises a single guide RNA sequence (sgRNA).

77. The composition according to embodiment 76, wherein said sgRNA comprises at least 20 nucleotides.

78. The composition according to embodiment 76, wherein said sgRNA comprises at least 8 nucleotides.

79. The composition according to embodiment 76, wherein the degree of complementarity between the sgRNA and its corresponding target sequence, when optimally aligned using a suitable alignment algorithm, is at least 50%, 60%, 70%, 75%, 80%, 85%, 86%, 87%, 88%, 89%, 90%, 91%, 92%, 93%, 94%, 95%, 96%, 97%, 98%, 99%, or 100%.

80. The composition according to embodiment 76, wherein said sgRNA has at least about 75 percent, at least about 80 percent, at least about 85 percent, at least about 90 percent, at least about 95 percent, at least about 96 percent, at least about 97 percent, at least about 98 percent, at least about 99 percent or 100 percent nucleotide sequence identity to the sequence selected from the group consisting of:

```
PCSK9 guide RNA sequence 1:
                                    (SEQ ID NO: 896)
GGUGCUAGCCUUGCGUUCCGGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;

PCSK9 guide RNA sequence 2:
                                    (SEQ ID NO: 897)
CGUGCUCGGGUGCUUCGGCCGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;

PCSK9 guide RNA sequence 3:
                                    (SEQ ID NO: 898)
GCCGUCCUCCUCGGAACGCAGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUUU;

PCSK9 guide RNA sequence 4:
                                    (SEQ ID NO: 899)
GGACGAGGACGGCGACUACGGUUUAAGAGCUAUGCUGGAAACAGCAUAG

CAAGUUUAAAUAAGGCUAGUCCGUUAUCAACUUGAAAAAGUGGCACCGA
```

-continued

```
GUCGGUGCUUUUUU;

PCSK9 guide RNA sequence 5:
                                              (SEQ ID NO: 900)
ACCACCGGGAAAUCGAGGGCGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUU;

PCSK9 guide RNA sequence 6:
                                              (SEQ ID NO: 901)
CGACUUCGAGAAUGUGCCCGGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUU;

PCSK9 guide RNA sequence 7:
                                              (SEQ ID NO: 902)
GAGUGACCACCGGGAAAUCGGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUU;

PCSK9 guide RNA sequence 8:
                                              (SEQ ID NO: 903)
CUCGGGCACAUUCUCGAAGUGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUU;

PCSK9 guide RNA sequence 9:
                                              (SEQ ID NO: 904)
GGAAGCCAGGAAGAAGGCCAGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUU;

PCSK9 guide RNA sequence 10:
                                              (SEQ ID NO: 905)
UCUUUGCCCAGAGCAUCCCGGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUU;

PCSK9 guide RNA sequence 11:
                                              (SEQ ID NO: 906)
CUAGGAGAUACACCUCCACCGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUU;

EMX1 guide RNA sequence:
                                              (SEQ ID NO: 907)
GUCACCUCCAAUGACUAGGGGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUU;

ROSA26 guide RNA sequence:
                                              (SEQ ID NO: 908)
CGAACCCUACACAUUCAACGGUUUAAGAGCUAUGCUGGAAACAGCAUAG

CAAGUUUAAAUAAGGCUAGUCCGUUAUCAACUUGAAAAAGUGGCACCGA

GUCGGUGCUUUUUU;
```
wherein said sequence is optionally chemically modified.

81. The composition according to any one of embodiments 76-80, wherein the sgRNA is optionally chemically modified.

82. The composition according to any one of embodiments 67-81, wherein said Cas9 ribonucleoprotein further comprises a fluorescent probe.

83. The composition according to embodiment 82, wherein said fluorescent probe is the mCherry sequence (SEQ ID NO:915).

84. The composition according any one of embodiments 67-83, wherein said composition comprises one or more NLSs.

85. The composition according any one of embodiments 67-83, wherein said Cas9 ribonucleoprotein comprises one or more NLSs.

86. The composition according to embodiment 84 or 85, wherein each of said NLS comprises an amino acid sequence selected from the group consisting of:

```
                                              (SEQ ID NO: 830)
PKKKRKV;

(SEQ ID NO: 831)
KRPAATKKAGQAKKKK;

(SEQ ID NO: 832)
PAAKRVKLD;

(SEQ ID NO: 833)
RQRRNELKRSP;

(SEQ ID NO: 834)
NQSSNFGPMKGGNFGGRSSGPYGGGGQYFAKPRNQGGY;

(SEQ ID NO: 835)
RMRIXFKNKGKDTAELRRRRVEVSVELRKAKKDEQILKRRNV;

(SEQ ID NO: 836)
VSRKRPRP;

(SEQ ID NO: 837)
PPKKARED;

(SEQ ID NO: 838)
PQPKKKPL;

(SEQ ID NO: 839)
SALIKKKKMAP;

(SEQ ID NO: 840)
DRLRR;

(SEQ ID NO: 841)
PKQKKRK;

(SEQ ID NO: 842)
RKLKKKIKKL;

(SEQ ID NO: 843)
REKKKFLKRR;

(SEQ ID NO: 844)
KRKGDEVDGVDEVAKKKSKK;

(SEQ ID NO: 845)
RKCLQAGMNLEARKTKK;

(SEQ ID NO: 1035)
MAPKKKRKVGIHRGVP;
and (SEQ ID NO: 1036)
PKKKRKVEDPKKKRKVD.
```

87. The composition according to embodiment 86, wherein each of said NLSs comprises the amino acid sequence PKKKRKV (SEQ ID NO: 830).

88. The composition according to embodiment 87, wherein said composition comprises two NLSs each comprising the amino acid sequence PKKKRKV (SEQ ID NO: 830).

89. The composition according to any one of embodiments 67-88, wherein said Cas9 ribonucleoprotein comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to a Cas9 protein derived from *S. aureus, S. pneumoniae, S. pyogenes, S. thermophilus,* or *N. meningitidis*.

90. The composition according to any one of embodiments 67-89, wherein said Cas9 ribonucleoprotein comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to a Type II Cas9 protein.

91. The composition according to any one of embodiments 67-90, wherein said Cas9 ribonucleoprotein comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to the amino acids at positions 7 to 166 or 731 to 1003 of SEQ ID NO:8 or the corresponding amino acids of those set forth in SEQ ID NOs:1-7, 9-829.

92. The composition according to embodiment 91, wherein said Cas9 ribonucleoprotein comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to the amino acids at positions 7 to 166 or 731 to 1003 of SEQ ID NO:8.

93. The composition according to embodiment 92, wherein said Cas9 ribonucleoprotein comprises a Cas9 protein having at least 4 motifs within the sequence which have at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to the motifs 1, 2, 3, and 4 of the Cas9 amino acid sequence of any of SEQ ID NOs:260-263.

94. The composition according to any one of embodiments 67-93, wherein said Cas9 ribonucleoprotein comprises a Cas9 protein that is at least about 75 percent, at least about 80 percent, at least about 85 percent, at least about 90 percent, at least about 95 percent, at least about 96 percent, at least about 97 percent, at least about 98 percent, at least about 99 percent or 100 percent amino acid sequence identity to a sequence selected from: *S. pyogenes* Cas9 (wild type) (SEQ ID NO:848), *S. pyogenes* Cas9-mutation M1C (SEQ ID NO:849), *S. pyogenes* Cas9-mutation M1C & C80S (SEQ ID NO:850), *S. pyogenes* Cas9 nickase-mutation D10A (SEQ ID NO:851), *S. pyogenes* Cas9 nickase-mutation H840A (SEQ ID NO:852), *S. pyogenes* Cas9 nickase-mutations E923P & T924P (SEQ ID NO:853), *Acidovorax ebreus* Cas9 (SEQ ID NO:854), Acid mine drainage bacteria Ga0052161_JGI Cas9 (SEQ ID NO:855), *S. pyogenes* Cas9 null-mutation D10A& H840A (SEQ ID NO:1027), and Uranium mine bacteria FW106_JGI Cas9 (SEQ ID NO:856).

95. The composition according to any one of embodiments 67-94, wherein said endosomal escape agent is selected from the group consisting of: a lysosomotropic agent, a cell penetrating peptide, a fusogenic peptide, a pore forming agent, and a proton sponge agent.

96. The composition according to embodiment 95, wherein said endosomal escape agent is peptide ppTG21: GLF-HALLHLLHSLWHLLLHA (SEQ ID NO.:1012).

97. A pharmaceutical composition comprising a composition according to any one of embodiments 65-96 and a pharmaceutically acceptable carrier, excipient or diluent.

98. A method of treating a disease or condition in a subject, comprising administering to said subject a therapeutically effective amount of a pharmaceutical composition according to embodiment 97.

99. The method according to embodiment 98, wherein the disease or condition is selected from the group consisting of: blood disorders, cell dysregulation or oncology diseases and disorders, inflammation and immune related diseases, metabolic, liver, kidney and protein diseases and disorders, muscular or skeletal diseases, neurological and neuronal diseases and disorders, and ocular diseases and disorders.

100. A method of selectively modulating transcription of a target DNA in a cell of a subject, comprising administering to said subject a pharmaceutical composition according to embodiment 97.

101. The method according to embodiment 100, wherein said target DNA is associated with a disorder or disease selected from the group consisting of: blood disorders, cell dysregulation or oncology diseases and disorders, inflammation and immune related diseases, metabolic, liver, kidney and protein diseases and disorders, muscular or skeletal diseases, neurological and neuronal diseases and disorders, and ocular diseases and disorders.

102. A method of editing a nucleic acid molecule encoding a protein associated with a disease or condition in a subject, comprising administering to said subject a pharmaceutical composition according to embodiment 97.

103. The method of embodiment 102, wherein said protein is associated with a disease or condition that is selected from the group consisting of blood disorders, cell dysregulation or oncology diseases and disorders, inflammation and immune related diseases, metabolic, liver, kidney and protein diseases and disorders, muscular or skeletal diseases, neurological and neuronal diseases and disorders, and ocular diseases and disorders 104. A method of modulating the expression of level of at least one gene product associated with a disease or condition in a subject, comprising administering to said subject a pharmaceutical composition according to embodiment 97.

105. The method according to embodiment 104, wherein said gene product is associated with a disease or condition selected from the group consisting of: blood disorders, cell dysregulation or oncology diseases and disorders, inflammation and immune related diseases, metabolic, liver, kidney and protein diseases and disorders, muscular or skeletal diseases, neurological and neuronal diseases and disorders, and ocular diseases and disorders.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10851367B2). An electronic copy of the "Sequence Listing" will also be available from the USPTO upon request and payment of the fee set forth in 37 CFR 1.19(b)(3).

What is claimed is:

1. A compound of any one of Formulas (A-1), (A-2), or (A-3):

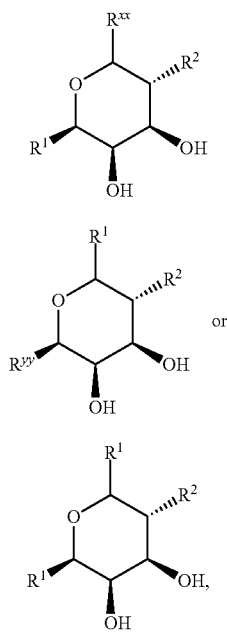

or a pharmaceutically acceptable salt thereof, wherein:

$R^{xx}$ is H, alkyl, cycloalkyl, alkenyl, alkynyl, aryl, heteroaryl, —$OR^5$, —$N(R^4)R^5$, or —$SR^5$, wherein any one or more —$CH_2$— groups of said $R^{xx}$ are each optionally replaced independently with a first heteroatom group selected from the group consisting of —O—, —S—, —$N(R^4)$—; wherein any one or more —$CH_3$ groups of said $R^{xx}$ are each optionally replaced independently with a second heteroatom group selected from the group consisting of —$N(R^4)2$, —$OR^4$, and —$SR^4$, wherein any two of said second heteroatom groups are separated by at least two carbon atoms; and wherein said alkyl, alkenyl, alkynyl, or cycloalkyl is optionally substituted with one or more halogen atoms;

$R^{yy}$ is —CN, —$CH_2CN$, —C≡CH, —$CH_2N_3$, —$CH_2NH_2$—$CH_2N(R^4)SO_2R^5$, —$CH_2CO_2H$, —$CO_2H$, —$CH_2OH$, —$CH_2SH$, —CH=C(H)$R^5$, —$CH_2R^5$, —$CH_2SR^5$, —$CH_2N(R^4)R^5$, —$CH_2N(R^4)C(O)R^5$, —$CH_2N(R^4)CO_2R^5$, —$CH_2N(R^4)C(O)N(R^4)$ $R^5$, —$CH_2OR^5$, —$CH_2OC(O)R^5$, —$CH_2OC(O)N(R^4)$ $R^5$, —$CH_2OCO_2R^5$, —$CH_2S(O)R^5$, —$CH_2SO_2R^5$, —$CH_2SO_2N(R^4)R^5$, —$C(O)NH_2$, —$CO_2R^5$, —$C(O)N(R^4)R^5$, aryl, or heteroaryl, wherein said aryl or heteroaryl is optionally substituted with $R^5$;

each $R^1$ is independently —CN, —$CH_2CN$, —C≡CH, —$CH_2N_3$, —$CH_2NH_2$, —$CH_2N(R^4)SO_2R^5$, —$CH_2CO_2H$, —$CO_2H$, —$CH_2SH$, —CH=$CHR^5$, —$CH_2R^5$, —$CH_2SR^5$, —$CH_2N(R^4)R^5$, $CH_2N(R^4)C(O)R^5$, $CH_2N(R^4)CO_2R^5$, —$CH_2N(R^4)C(O)N(R^4)R^5$, —$CH_2OR^5$, —$CH_2OC(O)R^5$, —$CH_2OC(O)N(R^4)R^5$, —$CH_2OCO_2R^5$, —$CH_2S(O)R^5$, —$CH_2SO_2R^5$, —$CH_2SO_2N(R^4)$ $R^5$, —$C(O)NH_2$, —$C(O)N(R^4)R^5$, aryl, or heteroaryl, wherein the aryl or heteroaryl is optionally substituted with $R^5$, or $R^1$ is —Z—X—Y, —Z—Y, —X—Y, —Z—$X^+Y^-$, —$X^+Y^-$, —$X^-Y^+$, or —Y;

X is a linker;

$X^+$ is a positively charged linker;

$X^-$ is a negatively charged linker;

Y is selected from the group consisting of a ribonucleoprotein comprising a site-directed modifying polypeptide, an endonuclease comprising a site-directed modifying polypeptide, a site-directed modifying polypeptide, a single guide RNA sequence (sgRNA), and a dual guide RNA sequence comprising a CRISPR RNA (crRNA) and a trans-activating crRNA (tracrRNA), optionally wherein Y is a Cas9 ribonucleoprotein or a Cas9 protein;

$Y^+$ is selected from the group consisting of a positively charged ribonucleoprotein comprising a site-directed modifying polypeptide, a positively charged endonuclease comprising a site-directed modifying polypeptide, and a positively charged site-directed modifying polypeptide, optionally wherein r is a positively charged Cas9 protein;

$Y^-$ is selected from the group consisting of a negatively charged ribonucleoprotein comprising a site-directed modifying polypeptide, a negatively charged endonuclease comprising a site-directed modifying polypeptide, a negatively charged site-directed modifying polypeptide, a negatively charged sgRNA, and a negatively charged dual guide RNA sequence comprising a CRISPR RNA (crRNA) and a trans-activating crRNA (tracrRNA), optionally wherein $Y^-$ is a negatively charged Cas9 ribonucleoprotein;

Z is a covalent bond, —C≡C—, —CH=CH—, —$CH_2$—, —$CH_2O$—, —$C(O)N(R^4)$—, —$CH_2S$—, —$CH_2S(O)$—, —$CH_2SO_2$—, —$CH_2SO_2N(R^4)$—, —$CO_2$—, —$CH_2N(R^4)$—, —$CH_2N(R^4)C(O)$—, —$CH_2N(R^4)SO_2$—, —$CH_2N(R^4)CO_2$—, —$CH_2N(R^4)C(O)N(R^4)$—, —$CH_2OC(O)$—, —$CH_2OC(O)N(R^4)$—, —$CH_2OCO_2$—, aryl, or heteroaryl, wherein said aryl or heteroaryl is optionally substituted with $R^5$;

$R^2$ is —OH, —$N_3$, —$N(R^3)_2$, —$N(R^3)C(O)R^3$, —$N(R^3)C(O)N(R^3)_2$, —$N(R^3)CO_2R^3$, —$N(R^3)SO_2R^3$, tetrazole, or triazole, wherein said tetrazole or triazole is optionally substituted with $R^3$;

each $R^3$ is independently H, $(C_1-C_5)$alkyl, halo-substituted $(C_1-C_5)$alkyl, halo-substituted $(C_3-C_6)$cycloalkyl, $(C_1-C_5)$alkenyl, $(C_1-C_5)$alkynyl, halo-substituted $(C_1-C_5)$alkenyl, halo-substituted $(C_1-C_5)$alkynyl, or $(C_3-C_6)$cycloalkyl, wherein any one or more —$CH_2$— groups of said $(C_1-C_5)$alkyl, halo-substituted $(C_1-C_5)$alkyl, halo-substituted $(C_3-C_6)$cycloalkyl, and $(C_3-C_6)$cycloalkyl are each optionally replaced independently with a first heteroatom group selected from the group consisting of —O—, —S— and —N($R^4$)—, wherein any two of said first heteroatom groups are separated by at least two carbon atoms; and wherein any one or more —$CH_3$ groups of said $(C_1-C_5)$alkyl and halo-substituted $(C_1-C_5)$alkyl are each optionally replaced independently with a second heteroatom group selected from the group consisting of —N($R^4$)$_2$, —O$R^4$, and —S$R^4$, wherein any two of said second heteroatom groups are separated by at least two carbon atoms;

each $R^4$ is independently H, $(C_1-C_{20})$alkyl, $(C_1-C_{20})$alkenyl, $(C_1-C_{20})$alkynyl, or $(C_3-C_6)$cycloalkyl, wherein one to six —$CH_2$— groups of said $(C_1-C_{20})$alkyl and $(C_3-C_6)$cycloalkyl are each optionally replaced independently with a heteroatom group that is —O— or —S; and wherein any two of said heteroatom groups are separated by at least two carbon atoms; and wherein said $(C_1-C_{20})$alkyl, $(C_1-C_{20})$alkenyl, $(C_1-C_{20})$alkynyl, or $(C_3-C_6)$cycloalkyl is optionally substituted with one or more halogen atoms;

each $R^5$ is independently $(C_3-C_{20})$cycloalkyl, $(C_1-C_{60})$alkenyl, $(C_1-C_{60})$alkynyl, or $(C_1-C_{60})$alkyl, wherein one to six —$CH_2$— groups of said $(C_3-C_{20})$cycloalkyl or one to 20 —$CH_2$— groups of the $(C_1-C_{60})$alkyl are each optionally replaced independently with a first heteroatom group selected from the group consisting of —O—, —S—, and —N($R^4$)—, wherein any two of said first heteroatom groups are separated by at least two carbon atoms; wherein any one or more —$CH_3$ groups of said $(C_1-C_{60})$alkyl are each optionally replaced independently with a second heteroatom group selected from the group consisting of —N($R^4$)$_2$, —O$R^4$, and —S($R^4$), wherein any two of said second heteroatom groups are separated by at least two carbon atoms; and wherein said $(C_3-C_{20})$cycloalkyl, $(C_1-C_{60})$alkenyl, $(C_1-C_{60})$alkynyl, or $(C_1-C_{60})$alkyl is optionally substituted with one or more halogen atoms.

2. A compound of Formula (B):

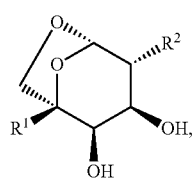

(B)

or a pharmaceutically acceptable salt thereof, wherein:

$R^1$ is —Z—X—Y, —Z—Y, —X—Y, —Z—$X^+Y^-$, —$X^+Y^-$, —Z—$X^-Y^+$, —$X^-Y^+$, or —Y;

X is a linker;

$X^+$ is a positively charged linker;

$X^-$ is a negatively charged linker;

Y is selected from the group consisting of a ribonucleoprotein comprising a site-directed modifying polypeptide, an endonuclease comprising a site-directed modifying polypeptide, a site-directed modifying polypeptide, a single guide RNA sequence (sgRNA), and a dual guide RNA sequence comprising a CRISPR RNA (crRNA) and a trans-activating crRNA (tracrRNA), optionally wherein Y is Cas9 ribonucleoprotein or a Cas9 protein, and wherein Y further comprises an endosomal escape agent selected from the group consisting of a lysosomotropic agent, a cell penetrating peptide, a fusogenic peptide, an endosomolytic peptide, a pore forming agent, and a proton sponge agent;

$Y^+$ is selected from the group consisting of a positively charged ribonucleoprotein comprising a site-directed modifying polypeptide, a positively charged endonuclease comprising a site-directed modifying polypeptide, and a positively charged site-directed modifying polypeptide, optionally wherein or $Y^+$ is a positively charged Cas9 protein, and wherein $Y^+$ further comprises an endosomal escape agent selected from the group consisting of a lysosomotropic agent, a cell penetrating peptide, a fusogenic peptide, an endosomolytic peptide, a pore forming agent, and a proton sponge agent;

$Y^-$ is selected from the group consisting of a negatively charged ribonucleoprotein comprising a site-directed modifying polypeptide, a negatively charged endonuclease comprising a site-directed modifying polypeptide, a negatively charged site-directed modifying polypeptide, negatively charged sgRNA, and a negatively charged dual guide RNA sequence comprising a CRISPR RNA (crRNA) and a trans-activating crRNA (tracrRNA), optionally wherein $Y^-$ is a negatively charged Cas9 ribonucleoprotein, and wherein $Y^-$ further comprises an endosomal escape agent selected from the group consisting of a lysosomotropic agent, a cell penetrating peptide, a fusogenic peptide, an endosomolytic peptide, a pore forming agent, and a proton sponge agent;

Z is a covalent bond, —C≡C—, —CH=CH—, —$CH_2$—, —$CH_2$O—, —C(O)N($R^4$)—, —$CH_2$S—, —$CH_2$S(O)—, —$CH_2SO_2$—, —$CH_2SO_2$N($R^4$)—, —$CO_2$—, —$CH_2$N($R^4$)—, —$CH_2$N($R^4$)C(O)—, —$CH_2$N($R^4$)$SO_2$—, —$CH_2$N($R^4$)$CO_2$—, —$CH_2$N($R^4$)C(O)N($R^4$)—, —$CH_2$OC(O)—, —$CH_2$OC(O)N($R^4$)—, —$CH_2OCO_2$—, aryl, or heteroaryl, wherein said aryl or heteroaryl is optionally substituted with $R^5$;

$R^2$ is —OH, —$N_3$, —N($R^3$)$_2$, —N($R^3$)C(O)$R^3$, —N($R^3$)C(O)N($R^3$)$_2$, —N($R^3$)$CO_2R^3$, —N($R^3$)$SO_2R^3$, tetrazole, or triazole, wherein said tetrazole or triazole is optionally substituted with $R^3$;

each $R^3$ is independently H, $(C_1-C_5)$alkyl, halo-substituted $(C_1-C_5)$alkyl, halo-substituted $(C_3-C_6)$cycloalkyl, $(C_1-C_5)$alkenyl, $(C_1-C_5)$alkynyl, halo-substituted $(C_1-C_5)$alkenyl, halo-substituted $(C_1-C_5)$alkynyl, or $(C_3-C_6)$cycloalkyl, wherein any one or more —$CH_2$— groups of said $(C_1-C_5)$alkyl, halo-substituted $(C_1-C_5)$alkyl, halo-substituted $(C_3-C_6)$cycloalkyl, and $(C_3-C_6)$cycloalkyl are each optionally replaced independently with a first heteroatom group selected from the group consisting of —O—, —S—, and —N($R^4$)—; and wherein any one or more —$CH_3$ groups of said $(C_1-C_5)$alkyl and halo-substituted $(C_1-C_5)$alkyl are each optionally replaced independently with a second heteroatom group selected from —N($R^4$)$_2$, —O$R^4$, and —SR⁴, wherein any two of said heteroatom groups are separated by at least two carbon atoms;

each R⁴ is independently H, $(C_1\text{-}C_{20})$alkyl, $(C_1\text{-}C_{20})$alkenyl, $(C_1\text{-}C_{20})$alkynyl, or $(C_3\text{-}C_6)$cycloalkyl, wherein one to six —CH₂— groups of said $(C_1\text{-}C_{20})$alkyl and $(C_3\text{-}C_6)$cycloalkyl are each optionally replaced independently with a heteroatom group that is —O— or —S—, wherein any two of said heteroatom groups are separated by at least two carbon atoms; and wherein said $(C_1\text{-}C_{20})$alkyl, $(C_1\text{-}C_{20})$alkenyl, $(C_1\text{-}C_{20})$alkynyl, or $(C_3\text{-}C_6)$cycloalkyl is optionally substituted with one or more halogen atoms;

each R⁵ is independently H, $(C_3\text{-}C_{20})$cycloalkyl, $(C_1\text{-}C_{60})$alkenyl, $(C_1\text{-}C_{60})$alkynyl, or $(C_1\text{-}C_{60})$alkyl, wherein one to six —CH₂— groups of said $(C_3\text{-}C_{20})$cycloalkyl or one to 20 —CH₂— groups of the $(C_1\text{-}C_{60})$alkyl are each optionally replaced independently with a first heteroatom group selected from the group consisting of —O—, —S—, and —N(R⁴)—, wherein any two of said first heteroatom groups are separated by at least two carbon atoms; wherein any one or more —CH₃ groups of said $(C_1\text{-}C_{60})$alkyl are each optionally replaced independently with a second heteroatom group selected from the group consisting of —N(R⁴)₂, —OR⁴, and —SR⁴, wherein any two of said second heteroatom groups are separated by at least two carbon atoms; and wherein said $(C_3\text{-}C_{20})$cycloalkyl, $(C_1\text{-}C_{60})$alkenyl, $(C_1\text{-}C_{60})$alkynyl, or $(C_1\text{-}C_{60})$alkyl is optionally substituted with one or more halogen atoms.

3. The compound according to claim 1 or 2, wherein R² is —NHC(O)CH₃.

4. The compound according to claim 1 or 2, where R¹ is —Z—X-Y.

5. The compound according to claim 4, wherein R¹ is —Z—X-Y that is selected from the group consisting of L1 to L10:

L1
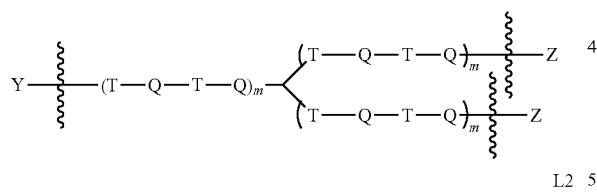

L2
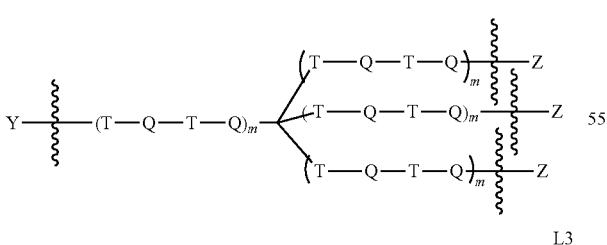

L3
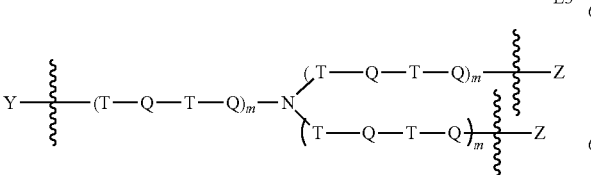

L4
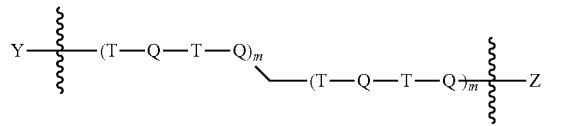

L5
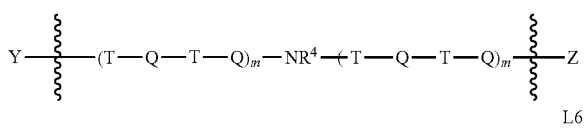

L6
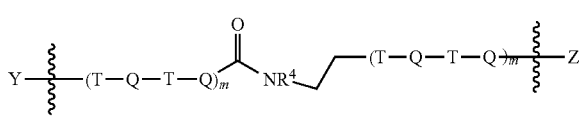

L7
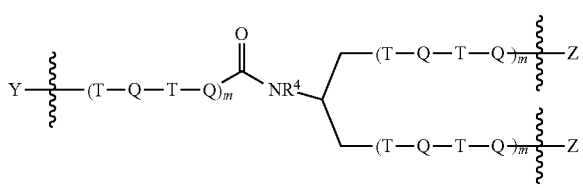

L8
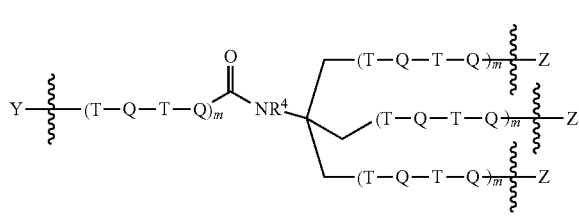

L9
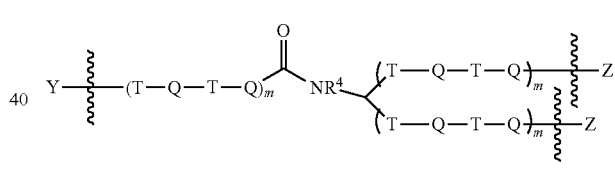

L10
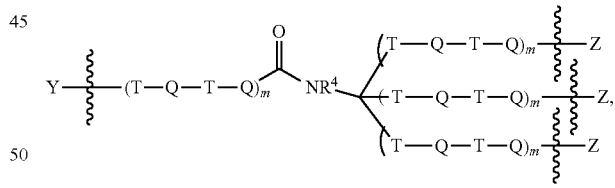

wherein each T is independently a covalent bond, $(C_1\text{-}C_{10})$alkylene, $(C_2\text{-}C_{10})$alkenylene, or $(C_2\text{-}C_{10})$alkynylene, wherein any one or more —CH₂— groups of said T are each optionally replaced independently with a heteroatom group selected from the group consisting of —O—, —S—, and —N(R⁴)—, wherein any two of said heteroatom groups are separated by at least two carbon atoms; and wherein said $(C_1\text{-}C_{10})$alkylene, $(C_2\text{-}C_{10})$alkenylene, or $(C_2\text{-}C_{10})$alkynylene is optionally substituted with one or more halogen atoms;

each Q is independently a covalent bond, —C(O)—, —C(O)N(R⁴)—, —N(R⁴)C(O)—, —OC(O)N(R⁴)—, —N(R⁴)—, —CO₂—, —CH₂—, heteroaryl, or a heteroatom group selected from the group consisting of —O—, —S—, —S—S—, —S(O)—, —SO₂—, and —N($R^4$)—, wherein any two of said heteroatom groups are separated by at least two carbon atoms;

each $R^4$ is independently H, ($C_1$-$C_{20}$)alkyl, or ($C_3$-$C_6$)cycloalkyl, wherein one to six —$CH_2$— groups of said ($C_1$-$C_{20}$)alkyl and ($C_3$-$C_0$)cycloalkyl are each optionally replaced independently with a heteroatom group that is —O— or —S—, wherein any two of said heteroatom groups are separated by at least two carbon atoms; and wherein said ($C_1$-$C_{20}$)alkyl, or ($C_3$-$C_6$)cycloalkyl is optionally substituted with one or more halogen atoms; and each m is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40.

6. The compound according to claim 5, wherein said X comprises a disulfide bond.

7. The compound according to claim 1, wherein said compound has a formula of Formula (C-1), (C-2), (C-3) or (C-4):

—O—, —S—, and —N($R^4$)—, wherein any two of said heteroatom groups are separated by at least two carbon atoms; and wherein said ($C_1$-$C_{10}$)alkylene, ($C_2$-$C_{10}$)alkenylene, or ($C_2$-$C_{10}$)alkynylene is optionally substituted with one or more halogen atoms;

each Q is independently a covalent bond, —C(O)—, —C(O)N($R^4$)—, —N($R^4$)C(O)—, —OC(O)N($R^4$)—, —N($R^4$)—, —$CO_2$—, —$CH_2$—, a heteroaryl, or a heteroatom group selected from the group consisting of —O—, —S—, —S—S—, —S(O)—, —$SO_2$—, and —N($R^4$)—, wherein any two of said heteroatom groups are separated by at least two carbon atoms;

each $R^4$ is independently H, ($C_1$-$C_{20}$)alkyl, or ($C_3$-$C_6$)cycloalkyl, wherein one to six —$CH_2$— groups of said ($C_1$-$C_{20}$)alkyl and ($C_3$-$C_6$)cycloalkyl are each optionally replaced independently with a heteroatom group that is —O— or —S—, wherein any two of said heteroatom groups are separated by at least two carbon

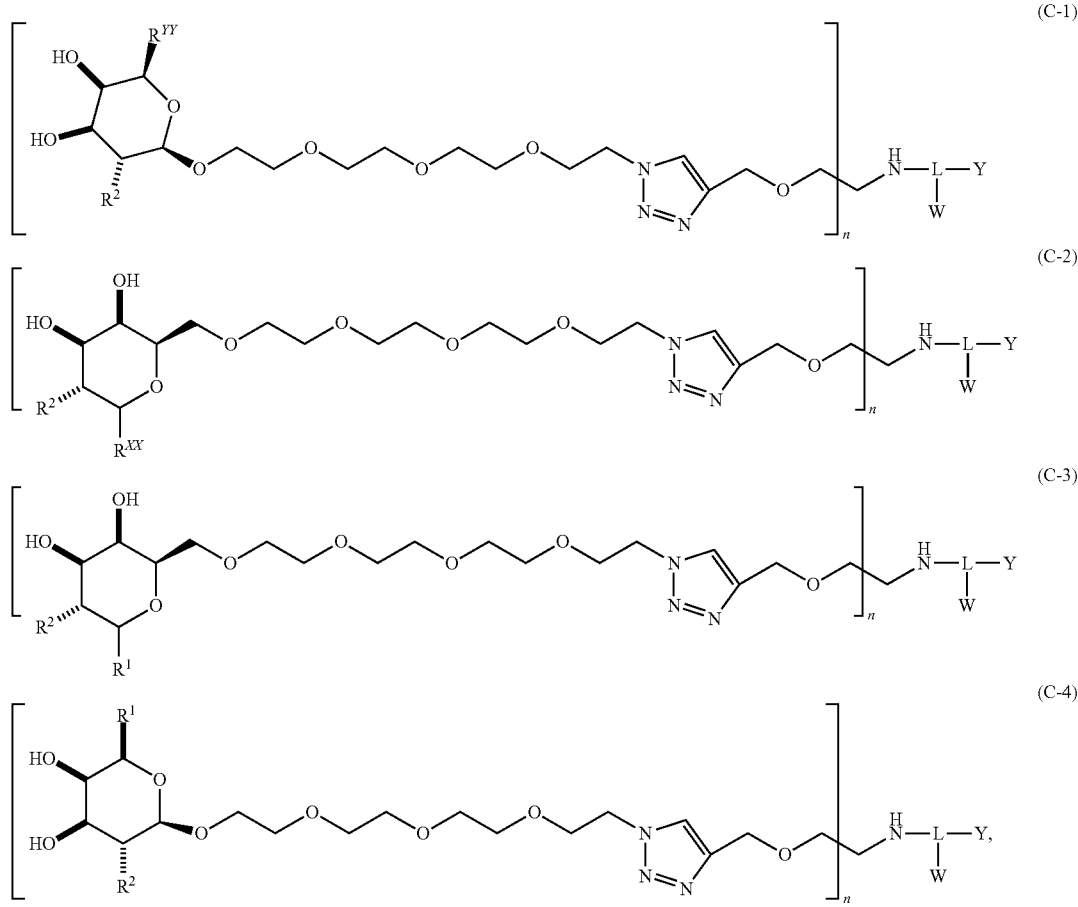

or a pharmaceutically acceptable salt thereof, wherein:

n is 1, 2, or 3;

W is absent or a peptide;

L is -(T-Q-T-Q)$_m$-, wherein:

each T is independently a covalent bond, ($C_1$-$C_{10}$)alkylene, ($C_2$-$C_{10}$)alkenylene, or ($C_2$-$C_{10}$)alkynylene, wherein one or more —$CH_2$— groups of said T are each optionally replaced independently with a heteroatom group selected from the group consisting of atoms; and wherein said ($C_1$-$C_{20}$)alkyl or ($C_3$-$C_6$)cycloalkyl is optionally substituted with one or more halogen atoms; and each m is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40.

8. The compound according to claim 2, wherein said compound has a formula of Formula (E):

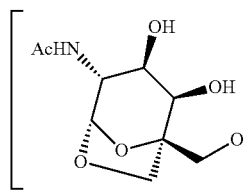 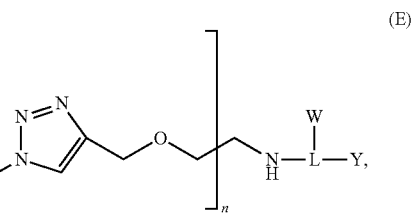 (E)

or a pharmaceutically acceptable salt thereof,
wherein:
n is 1, 2 or 3;
W is absent or is a peptide;
L is -(T-Q-T-Q)$_m$-, wherein:
each T is independently a covalent bond, $(C_1-C_{10})$alkylene, $(C_2-C_{10})$alkenylene, or $(C_2-C_{10})$alkynylene, wherein one or more —CH$_2$— groups of said T are each optionally replaced independently with a heteroatom group selected from the group consisting of —O—, —S—, and —N(R$^4$)—, wherein any two of said heteroatom groups are separated by at least two carbon atoms;
each Q is independently a covalent bond, —C(O)—, —C(O)N(R$^4$)—, —N(R$^4$)C(O)—, —OC(O)N(R$^4$), —N(R$^4$)CO$_2$—, —CH$_2$—, a heteroaryl, or a heteroatom group selected from the group consisting of —O—, —S—, —S—S—, —S(O)—, —SO$_2$—, and —N(R$^4$)—, wherein any two of said heteroatom groups are separated by at least two carbon atoms;
each R$^4$ is independently H, $(C_1-C_{20})$alkyl, or $(C_3-C_6)$cycloalkyl, wherein one to six —CH$_2$— groups of said $(C_1-C_{20})$alkyl and $(C_3-C_6)$cycloalkyl are each optionally replaced independently with a heteroatom group that is —O— or —S—, wherein any two of said heteroatom groups are separated by at least two carbon atoms; and wherein said $(C_1-C_{20})$alkyl or $(C_3-C_6)$cycloalkyl is optionally substituted with one or more halogen atoms; and
each m is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40.

9. The compound according to claim 8, wherein said compound has the formula

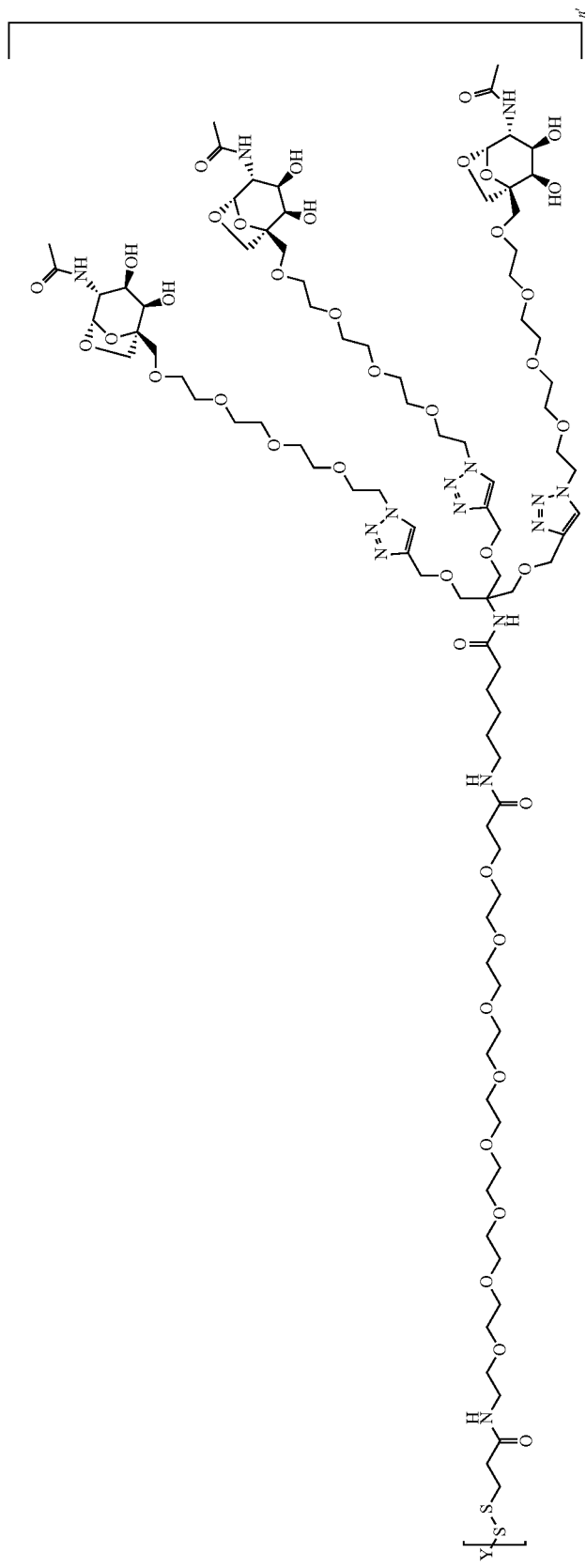

wherein n' is 1 or 2 or a pharmaceutically acceptable salt thereof.

10. The compound according to claim 1 or 2, wherein Y is a Cas9 ribonucleoprotein comprising: (1) a first element comprising a recognition element comprising either a dual guide RNA sequence comprising a CRISPR RNA (crRNA) and a trans-activating crRNA (tracrRNA), or a single guide RNA sequence (sgRNA), wherein when expressed, the guide sequence directs sequence-specific binding of the Cas9 ribonucleoprotein to a target sequence, and the first element optionally comprises one or more endosomal escape agents, and (2) a second element comprising a Cas9 protein and optionally one or more nuclear localization sequences (NLSs) and optionally one or more fluorescent proteins, and one or more endosomal escape agents;

wherein said first element is associated with said second element.

11. The compound according to claim 10, wherein Y comprises one or two NLSs and each of said NLSs comprises the amino acid sequence PKKKRKV (SEQ ID NO: 830).

12. The compound according to claim 1 or 2, wherein said Y comprises a Cas9 protein that is at least 75 percent amino acid sequence identity to a Cas9 protein derived from *S. aureus, S. pneumoniae, S. pyogenes, S. thermophilus, N. meningitidis* or *A. ebreus*.

13. The compound according to claim 1 or 2, wherein said Y comprises a Cas9 protein that is at least 75 percent amino acid sequence identity to a sequence selected from: *S. pyogenes* Cas9 (wild type) (SEQ ID NO: 848), *S. pyogenes* Cas9-mutation M1C (SEQ ID NO: 849), *S. pyogenes* Cas9—mutation M1C & C8OS (SEQ ID NO: 850), *S. pyogenes* Cas9 nickase—mutation D10A (SEQ ID NO: 851), *S. pyogenes* Cas9 nickase—mutation H840A (SEQ ID NO: 852), *S. pyogenes* Cas9 nickase—mutations E923P & T924P (SEQ ID NO: 853), *Acidovorax ebreus* Cas9 (SEQ ID NO: 854), Acid mine drainage bacteria Ga0052161-JGI Cas9 (SEQ ID NO: 855), *S. pyogenes* Cas9 null—mutation D10A& H840A (SEQ ID NO: 1027), and Uranium mine bacteria FW106-JGI Cas9 (SEQ ID NO: 856).

14. The compound according to claim 1, wherein said compound further comprises an endosomal escape agent.

15. The compound according to claim 14, wherein said endosomal escape agent is peptide ppTG21: GLFHALL-HLLHSLWHLLLHA (SEQ ID NO: 1012).

16. A composition comprising a compound according to claim 1 and an endosomal escape agent, wherein said compound and the endosomal escape agent are co-incubated to form the composition.

17. A pharmaceutical composition comprising a compound of claim 1 or 2 and a pharmaceutically acceptable carrier, excipient or diluent.

18. The compound according to claim 2, wherein said endosomal escape agent is peptide ppTG21: GLFHALL-HLLHSLWHLLLHA (SEQ ID NO: 1012).

19. The compound according to claim 2, wherein said endosomal escape agent is peptide KALA: WEAKLAKA-LAKALAKHLAKALAKALKACEA (SEQ ID NO: 869).

20. The compound according to claim 14, wherein said endosomal escape agent is peptide KALA: WEAKLAKA-LAKALAKHLAKALAKALKACEA (SEQ ID NO: 869).

* * * * *

UNITED STATES PATENT AND TRADEMARK OFFICE
CERTIFICATE OF CORRECTION

PATENT NO.         : 10,851,367 B2
APPLICATION NO.    : 15/347339
DATED              : December 1, 2020
INVENTOR(S)        : Spiros Liras et al.

Page 1 of 1

It is certified that error appears in the above-identified patent and that said Letters Patent is hereby corrected as shown below:

In the Claims

Column 375, Line 55: Please change "–N(R$^4$)2" to -- –N(R$^4$)$_2$ --

Column 376, Lines 46-47: Please change "optionally wherein r is a positively charged Cas9 protein" to -- optionally wherein Y$^+$ is a positively charged Cas9 protein --

Column 381, Line 5: Please change "(C$_3$-C$_0$)cycloalkyl" to -- (C$_3$-C$_6$)cycloalkyl --

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*